(12) United States Patent
Barlaam et al.

(10) Patent No.: US 8,017,611 B2
(45) Date of Patent: Sep. 13, 2011

(54) PYRIDINE AND PYRAZINE DERIVATIVES -083

(75) Inventors: Bernard Christophe Barlaam, Reims (FR); Craig Steven Harris, Reims (FR); Christine Marie Paul Lambert, Reims (FR); Gilles Ouvry, Reims (FR); Justin Fairfield Bower, Macclesfield (GB); Benedicte Delouvrie, Macclesfield (GB); Gary Fairley, Macclesfield (GB); Jon James Gordon Winter, Macclesfield (GB)

(73) Assignee: AstraZeneca AB, Sodertalje (SE)

( * ) Notice: Subject to any disclaimer, the term of this patent is extended or adjusted under 35 U.S.C. 154(b) by 426 days.

(21) Appl. No.: 12/256,739

(22) Filed: Oct. 23, 2008

(65) Prior Publication Data

US 2009/0118305 A1    May 7, 2009

(30) Foreign Application Priority Data

Oct. 25, 2007   (EP) ..................... 07301491
Dec. 21, 2007   (EP) ..................... 07305005
May 19, 2008   (EP) ..................... 08305180

(51) Int. Cl.
*A61K 31/497*   (2006.01)
*C07D 413/14*   (2006.01)

(52) U.S. Cl. .................. 514/252.11; 544/357

(58) Field of Classification Search ............. 514/252.11; 544/357
See application file for complete search history.

(56) References Cited

FOREIGN PATENT DOCUMENTS

| WO | 03/066629 A2 | 8/2003 |
|---|---|---|
| WO | 03/080610 A1 | 10/2003 |
| WO | 03/093297 | 11/2003 |
| WO | 2004/016600 A1 | 2/2004 |
| WO | 2004/069160 A2 | 8/2004 |
| WO | 2004/084813 A2 | 10/2004 |
| WO | 2006/021881 A2 | 3/2006 |
| WO | 2006/063167 A1 | 6/2006 |
| WO | 2007/111904 A2 | 10/2007 |
| WO | 2007/147874 A1 | 12/2007 |
| WO | 2008/025820 A1 | 3/2008 |
| WO | 2008/038010 A1 | 4/2008 |
| WO | 2008/074997 A1 | 6/2008 |
| WO | 2009126003 A9 | 10/2009 |

OTHER PUBLICATIONS

Bamford et. al. (1H-Imidazo[4,5-c]pyridin-2-yl)-1,2,5-oxadiazol-3-ylamine derivatives: A novel class of potent MSK-1-inhibitors Bioorganic & Medicinal Chemistry Letters (2005), 3402-3406, 15.

*Primary Examiner* — Joseph Kosack
*Assistant Examiner* — Matthew Coughlin

(57) ABSTRACT

The invention concerns pyridine and pyrazine derivatives of Formula I

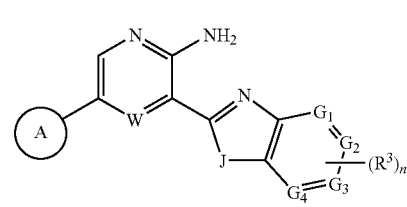

or a pharmaceutically-acceptable salt thereof, wherein each of W, $G_1$, $G_2$, $G_3$, $G_4$, J, Ring A, n and $R^3$ has any of the meanings defined hereinbefore in the description; processes for their preparation, pharmaceutical compositions containing them and their use in the manufacture of a medicament for use in the treatment of cell proliferative disorders.

4 Claims, No Drawings

PYRIDINE AND PYRAZINE DERIVATIVES -083

This application claims the benefit under 35 U.S.C. §119 (a)-(d) of Application No EP07301491.2 filed on 25 Oct. 2007 and Application No EP07305005.6 filed on 21 Dec. 2007 and Application No EP08305180.5 filed on 19 May 2008.

The invention concerns certain novel pyridine and pyrazine derivatives, or pharmaceutically-acceptable salts thereof, which possess anti-cancer activity and are accordingly useful in methods of treatment of the human or animal body. The invention also concerns processes for the manufacture of said pyridine and pyrazine derivatives, pharmaceutical compositions containing them and their use in therapeutic methods, for example in the manufacture of medicaments for use in the prevention or treatment of cancers in a warm-blooded animal such as man, including use in the prevention or treatment of solid tumour disease.

Receptor tyrosine kinases (RTKs) are cell surface receptors that transmit signals from the extracellular environment to control growth, differentiation and survival of cells. All RTKs contain an extracellular ligand binding domain and a conserved protein tyrosine kinase cytoplasmic domain. RTKs are activated by growth factors, which promote receptor dimerisation and autophosphorylation of tyrosine residues in the kinase domain (Schlessinger, Cell, 2000, 103, 211).

RTKs can be classified into distinct subfamilies on the basis of sequence similarities. The Axl receptor subfamily is one of these subfamilies and includes Axl (also called Ark, Ufo and Tyro7), Tyro3 (also called Rse, Brt, Sky and Dtk) and Mer (also called Nyk and Tyro12). This RTK family is characterized by an extracellular domain consisting of two immunoglobulin-like and two fibronectin type 3-like domains. The Axl family RTKs are activated by the vitamin K-dependent protein known as growth arrest specific gene 6 (Gas6). The affinity of Gas6 for these receptors is Axl>Tyro3>Mer (Nagata et al., *J. Biol. Chem.*, 1996, 271, 30022).

The gene encoding for the Axl protein was originally identified as a transforming gene in chronic myeloid leukemia (O'Bryan et al., *Mol. Cell. Biol.*, 1991, 11, 5031). The Axl receptor has been shown to be overexpressed in primary colon (Craven et al, *Int. J. Cancer*, 1995, 60, 791), gastric (Sawabu et al., *Mol. Carcinog.*, 2007, 46, 155), oesophageal (Nemoto et al., *Pathobiology*, 1997, 65, 195), melanoma (Quong et al., *Melanoma Res.*, 1994, 4, 313), ovarian (Sun et al., *Oncology*, 2004, 66, 450), renal (Chung et al., *DNA Cell Biol.*, 2003, 22, 533), endometrial (Sun et al, *Ann. Oncol.*, 2003, 14, 898), and thyroid (Ito et al, *Thyroid*, 1999, 9, 563) cancers. The presence of the Axl receptor is highly correlated with lymph node status and stage in lung cancer and ER expression in breast cancer (Berclaz et al., *Ann. Oncol.*, 2001, 12, 819).

Gas6/Axl signalling has been shown to have roles in proliferation, protection from apoptosis, angiogenesis and invasion. The gene encoding for Axl has been shown to transform both NIH-3T3 fibroblasts, enabling them to grow as xenografts in nude mice (O'Bryan et al., *Mol. Cell. Biol.*, 1991, 11, 5031), and IL-3 dependent hematopoietic 32D cells, enabling IL-3 independent growth (McCloskey et al., *Cell Growth Differ.*, 1994, 5, 1105).

The anti-apoptotic effects of Gas6/Axl signalling have been demonstrated in NIH-3T3 cells (Bellosta et al., *Oncogene*, 1997, 15, 2387), human oligodendrocytes (Shankar et al., *J. Neurosci.*, 2006, 26, 5638) and in the uveal melanoma cell line Mel 290 (Van Ginkel et al., *Cancer Res.*, 2004, 64, 128). Gas6/Axl signalling has also been shown to have a weak mitogenic effect in mouse NIH-3T3 fibroblasts (Goruppi et al., *Oncogene*, 1996, 12, 471), human C57MG mammary carcinoma cells (Goruppi et al., *Mol. Cell. Biol.*, 2001, 21, 902) and human DU145 and PC3 prostate carcinoma cells (Sainaghi et al., *J. Cell. Physiol.*, 2005, 204, 36).

The depletion of Axl protein has been shown to disrupt CL1-5 human lung adenocarcinoma cell invasion (Shieh et al, *Neoplasia*, 2005, 7, 1058) and primary human umbilical vein endothelial cells (HUVEC) cell migration and tube formation (Holland et al., *Cancer Res.*, 2005, 65, 9294). Furthermore, inhibition of the Axl protein by either knockdown of protein levels (Holland et al., *Cancer Res.*, 2005, 65, 9294) or transfection of a dominant negative Axl mutant gene (Vajkoczy et al., *Proc. Natl. Acad. Sci. USA*, 2006, 103, 5799) has been shown to suppress xenograft growth in vivo.

Axl RTKs have also been shown to have roles in immunity (Lu et al., *Science*, 2001, 293, 306), platelet function (Angelillo-Scherrer et al., *Nat. Med.*, 2001, 7, 215), spermatogenesis (Lu et al., *Nature*, 1999, 398, 723), vascular calcification (Son et al., *Eur. J. Pharmacol.*, 2007, 556, 1), thrombin induced vascular smooth muscle cell (VSMC) proliferation (Nakano et al., *J. Biol. Chem.*, 1995, 270, 5702), and various kidney diseases, for example acute and chronic glomerulonephritis, diabetic nephropathy and chronic allograft rejection (Yanagita et al., *J. Clin. Invest.*, 2002, 110, 239).

Accordingly, antagonism of the activity of Axl receptor kinases is expected to be beneficial in the treatment of a number of cell proliferative disorders such as cancer (comprising solid tumours such as carcinomas, sarcomas and the leukaemia and lymphoid malignancies), as well as vascular disease (including but not limited to thrombosis, atherosclerosis and restenosis), kidney disease (including but not limited to acute and chronic glomerulonephritis, diabetic nephropathy and transplant rejection), and diseases where deregulated angiogenesis is important (including but not limited to diabetic retinopathy, retinopathy, psoriasis, rheumatoid arthritis, atheroma, Kaposi's sarcoma and haemangioma).

c-Met is also a receptor tyrosine kinase which acts as the cellular receptor for hepatocyte growth factor (HGF/scatter factor), a dimeric glycoprotein that is synthesized as a single-chain precursor called pro-HGF and comprises a 50 kDa α-chain and a 145 kDa β-chain. When HGF non-covalently binds to the extracellular domain of c-Met, receptor oligomerisation occurs. This results in phosphorylation of a number of sites within c-Met such as tyrosine residue $Y^{1234/5}$ that lies within the c-Met activation loop (a flexible region of amino acids whose conformation controls kinase activity) and tyrosine residue $Y^{1349/56}$ which forms part of a structurally unique protein docking site. Phosphorylation within the activation loop causes an increase in c-Met kinase activity, whilst phosphorylation of the docking site is essential for binding and subsequent activation of classical intracellular tyrosine kinase effecter proteins such as p85, Gab1 and Grb2 (Ponzetto, C., et al. (1994), *Cell* 77, 261-271).

A variety of proteins from different signalling pathways can bind to and be phosphorylated by activated c-Met (Giordano, S., et al. (2000), *FASEB J.* 14, 401-408 and Giordano, S., et al. (1997), *Proc. Natl. Acad. Sci. USA* 94, 13868-13872) with the result that c-Met activity is required for signal transmission via several signalling pathways. For example, c-Met-Gab1-Shp2 association results in sustained stimulation of the Erk pathway, thus stimulating cell transformation and proliferation (Maroun, C., et al. (2000), *Mol. Cell. Biol.* 20, 8513-8525; Schaeper, U., et al. (2000), *J. Cell. Biol.* 149, 1419-1432; and Paumelle, R., et al. (2002) *Oncogene* 21, 2309-2319). However, c-Met-p85 association stimulates the PI3K pathway thus promoting cell migration and protecting cells from apoptosis following cellular damage (Ponzetto, C., et al (1993), *Mol. Cell. Biol.* 13, 4600-4608; and Xiao, G., (2001) *Proc. Natl. Acad. Sci. USA* 98, 247-252). The role of c-Met on these different pathways, means that it is involved in the regulation of a range of different cellular processes such as proliferation, apoptosis, morphogenesis, and migration (Bardelli, A., et al. (1999) *Oncogene* 18, 1139-1146).

c-Met and HGF are expressed in numerous tissues. c-Met expression is normally restricted to cells of endothelial and epithelial origin. HGF is usually expressed in cells of mesenchymal origin and is therefore considered to be a paracrine acting growth factor which induces proliferative, morphogenic and motile responses in proximal target cells (Birchmeier, C., et al. (2003), *Nature Rev. Mol. Cell. Biol.* 4, 915-925).

A significant number of clinical studies have shown that both c-Met and HGF are frequently aberrantly expressed in aggressive carcinomas, in other types of human solid tumours, and in their metastases (reviewed in Truslino et al.; Birchmeier et al.; Maulik, G., et al. (2002), *Cytokine & Growth Factor Rev.* 13, 41-59; and Danilkovitch-Miagkova, A. & Zbar, B. (2002) *J. Clin. Invest.* 109, 863-867. Further, the presence of c-Met or HGF in clinical samples often correlates with poor patient prognosis (reviewed in Truslino et al.) suggesting that c-Met activation promotes tumour growth and metastatic spread.

Activation of c-Met in cancer cells is most commonly driven by ligand-dependent mechanisms, for example, tumour carcinoma or tumour endothelial cells express c-Met but not HGF, which is produced by the surrounding stroma. However, in other tumours, cells may express c-Met and HGF resulting in autocrine c-Met activation. Ligand independent activation is also possible and is observed in cells that express very high levels of c-Met or which harbour activating mutations (Birchmeier et al.). Activating mutations of c-Met have been discovered in sporadic and inherited forms of human renal papillary carcinoma (reviewed in Maulik et al and Danilkovitch-Miagkova et al.) and, at present, 21 mutations have been described. The majority are localised within the kinase domain and are believed to convert c-Met into a constitutively active form. More recently, a number of additional mutations have been found in other types of primary cancer and metastatic lesions (Lorenzato, A., et al. (2002), *Canc. Res.* 62, 7025-7030).

Consequently, a considerable body of evidence supports the theory that primary cancer growth, angiogenesis, local tumour invasion and distant metastasis formation are driven or enhanced by inappropriate c-Met activation. The role of c-Met in angiogenesis has been demonstrated by experiments involving HGF stimulation of new blood vessel growth in rat corneal and mouse matrigel models (Rosen, E.m et al. (1997) *Ciba Found. Symp.* 212, 215-9 and Rosen, E. & Goldberg, I. (1995) *Adv. Cancer Res.* 67, 257-279). Mouse and human cell lines that ectopically overexpress either HGF or c-Met, or both, have been observed to become tumorigenic in nude mice and frequently such cells acquire an invasive phenotype that enables them to form metastases in distant organs (reviewed in Truslino, L. and Comoglio, P. (2002), *Nature Rev. Canc.* 2, 289-300 and Birchmeier et al). Downregulation of c-Met/HGF signalling in human tumour cells (either by biological or small molecule approaches) has also been shown to substantially decrease the cells' tumorigenic potential through a decrease in proliferation, angiogenesis and invasion (Abounader, R., et al. (2002), *FASEB J.* 16, 108-110 and Christensen, J., et al. (2003), *Canc. Res.* 63, 7345-7355). Finally, it has also been reported that mouse models expressing c-Met or HGF as a transgene in specific tissues ultimately develop a broad array of aggressively invasive tumours and metastatic lesions (Wang, R., et al. (2001), *J. Cell Biol.* 153, 1023-1034; Gallego, M., et al. (2003), *Oncogene* 22, 8498-8508; and Takayama, H., et al. (1997), *Proc. Natl. Acad. Sci. USA* 94, 701-706) indicating that activation of c-Met is sufficient to initiate tumour formation and promote angiogenesis and invasion (Rosen et al.).

c-Met therefore represents an attractive target in the pursuit of therapies for the treatment of cancer, and an inhibitor of c-Met activity would be expected to have anti-tumour activity and in particular anti-proliferative, anti-angiogenic and anti-invasive properties. Additionally, the role of c-Met and HGF in tissue remodelling, particularly in the lungs and liver has also been demonstrated (Michalopoulos, G. & DeFrances, M. (1997) *Science* 276, 60-6621), and elevated levels of c-Met or HGF have been observed in patients suffering from liver cirrhosis, chronic hepatitis and pulmonary fibrosis. It is therefore further expected that inhibitors of c-Met will be of therapeutic use in the treatment of a number of inflammatory diseases (Funakoshi, H. & Nakamura, T. (2003) *Clin. Chim. Acta* 327, 1-23).

We have now found that surprisingly certain novel pyridine and pyrazine derivatives possess potent activity against cell proliferative disorders. Without wishing to imply that the compounds disclosed in the present invention possess pharmacological activity only by virtue of an effect on one or two biological processes, it is believed that the compounds provide a useful treatment of cell proliferative disorders, for example to provide an anti-tumour effect, by way of a contribution from inhibition of Axl and/or c-Met receptor tyrosine kinases.

International Patent Application WO 2008/025820 is concerned with certain aminopyridine derivatives that possess inhibitory kinase activity, in particular against the tyrosine kinase Itk. The compounds in WO 2008/025820 are stated to be useful in the treatment or prophylaxis of immunological, inflammatory or allergic disorders or other diseases or disorders associated with Itk kinase.

International Patent Application WO 2008/074997 is concerned with certain pyridine and pyrazine benzamide compounds which, inter alia, possess inhibitory kinase activity against the serine/threonine kinase Protein Kinase D (PKD). The compounds in WO 2008/074997 are stated to be useful in the treatment diseases mediated by PKD, including proliferative conditions such as cancer.

There is no mention of Axl or c-Met receptor tyrosine kinases in either WO 2008/025820 or WO 2008/074997. Furthermore, it is believed that, in general, the compounds now being claimed exhibit improved potency against Axl and/or c-Met receptor tyrosine kinases over compounds disclosed in WO 2008/025820.

According to one aspect of the invention there is provided a pyridine or pyrazine derivative of the Formula I

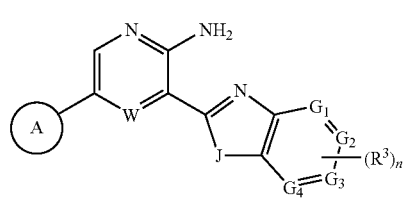

in which:
W is CH or N;
J is O or S;

each of $G_1$, $G_2$, $G_3$ and $G_4$ is selected from CH and N provided that not more than two of $G_1$, $G_2$, $G_3$ and $G_4$ represent N;
Ring A is selected from:
  (i) phenyl substituted by $R^1$ and optionally substituted by up to three $R^2$ groups; or
  (ii) a 5- or 6-membered monocyclic heteroaryl ring with up to three ring heteroatoms selected from oxygen, nitrogen and sulphur, said ring being substituted by $R^1$ and optionally substituted by up to three $R^2$ groups; or
  (iii) a 8-, 9- or 10-membered bicyclic ring system, wherein said bicyclic ring system optionally contains up to three ring heteroatoms selected from oxygen, nitrogen and sulphur and is optionally substituted by $R^1$ and optionally substituted by up to three $R^2$ groups;
$R^1$ is a group of the formula:

$$R^4-X^1-$$

wherein $X^1$ is a direct bond or is selected from O, S, SO, $SO_2$, $N(R^5)$, CO, $CH(OR^5)$, $CON(R^5)$, $N(R^5)CO$, $N(R^5)CON(R^5)$, $SO_2N(R^5)$, $N(R^5)SO_2$, $C(R^5)_2O$, $OC(R^5)_2$, $C(R^5)_2S$, $SC(R^5)_2$, $C(R^5)_2$, $C(R^5)_2N(R^5)$ and $N(R^5)C(R^5)_2$, wherein each $R^5$ is independently selected from hydrogen, (1-8C)alkyl, hydroxy-(1-6C)alkyl, (1-6C)alkoxy-(1-6C)alkyl, cyano-(1-6C)alkyl, halogeno-(1-6C)alkyl, di-[(1-6C)alkyl]amino-(1-6C)alkyl, (1-6C)alkylamino-(1-6C)alkyl or amino-(1-6C)alkyl, and when $X^1$ is a direct bond or is selected from $CH(OR^5)$, $C(R^5)_2O$, $C(R^5)_2S$, $C(R^5)_2$ or $C(R^5)_2N(R^5)$, wherein $R^5$ has any of the meanings defined hereinbefore, $R^4$ is hydroxy-(1-6C)alkyl, (1-6C)alkoxy-(1-6C)alkyl, $R^5-S$, $R^5-S(O)$, $R^5-SO_2$, $R^5-SO_2-O$, $R^5-S-(1-6C)$alkyl, $R^5-S(O)-(1-6C)$alkyl, $R^5-SO_2-(1-6C)$alkyl, N,N-di-$(R^5)$sulphamoyl, N,N-di-$(R^5)$sulphamoyl-(1-6C)alkyl, $R^5-SO_2N(R^5)$, $R^5-SO_2N(R^5)-(1-6C)$alkyl, $R^5-CON(R^5)$, $R^5O-CON(R^5)$, $R^5-CON(R^5)-(1-6C)$alkyl, $R^5O-CON(R^5)-(1-6C)$alkyl, $(R^5)_2N-SO_2N(R^5)$, $(R^5)_2N-SO_2N(R^5)-(1-6C)$alkyl, $(R^5)_2N-CON(R^5)$, $(R^5)_2N-CON(R^5)-(1-6C)$alkyl, $R^5-CO$, $R^5-CO-(1-6C)$alkyl, $R^5O-CO-(1-6C)$alkyl, $(R^5)_2NCO$, $(R^5)_2NCO-(1-6C)$alkyl, $(R^5)_2N-COO$, $(R^5)_2NCOO-(1-6C)$alkyl, cyano, amino, $(R^6)$-amino, di-$(R^6)$-amino, amino-(1-6C)alkyl, $(R^6)$-amino-(1-6C)alkyl or di-$(R^6)$-amino-(1-6C)alkyl, wherein each $R^6$ present is (1-6C)alkyl optionally substituted by 1, 2 or 3 substituents independently selected from halogeno, cyano, hydroxy and (1-6C)alkoxy;
and when $X^1$ is selected from O, S, SO, $SO_2$, $N(R^5)$, CO, $CON(R^5)$, $N(R^5)CO$, $N(R^5)CON(R^5)$, $SO_2N(R^5)$, $N(R^5)SO_2$, $OC(R^5)_2$, $SC(R^5)_2$ and $N(R^5)C(R^5)_2$, wherein $R^5$ has any of the meanings defined hereinbefore, $R^4$ is hydroxy-(1-6C)alkyl, (1-6C)alkoxy-(1-6C)alkyl, $R^5-S-(1-6C)$alkyl, $R^5-S(O)-(1-6C)$alkyl, $R^5-SO_2-(1-6C)$alkyl, N,N-di-$(R^5)$sulphamoyl-(1-6C)alkyl, $R^5-SO_2N(R^5)-(1-6C)$alkyl, $R^5-CON(R^5)-(1-6C)$alkyl, $R^5O-CON(R^5)-(1-6C)$alkyl, $(R^5)_2N-SO_2N(R^5)-(1-6C)$alkyl, $(R^5)_2N-CON(R^5)-(1-6C)$alkyl, $R^5-CO$, $R^5-CO-(1-6C)$alkyl, $R^{50}-CO$, $R^5O-CO-(1-6C)$alkyl, $(R^5)_2NCO$, $(R^5)_2NCO-(1-6C)$alkyl, $(R^5)_2NCOO-(1-6C)$alkyl, amino-(1-6C)alkyl, $(R^6)$-amino-(1-6C)alkyl or di-$(R^6)$-amino-(1-6C)alkyl, wherein each $R^6$ present is (1-6C)alkyl optionally substituted by 1, 2 or 3 substituents independently selected from halogeno, cyano, hydroxy and (1-6C)alkoxy; or $R^1$ is a group of the formula:

$$Q^1-X^2-$$

wherein $X^2$ is a direct bond or is selected from O, S, SO, $SO_2$, $N(R^7)$, $N[C(O)R^7]$, $N[C(O)N(R^7)_2]$, $N[C(O)OR^7]$, $N[SO_2-N(R^7)_2]$, CO, $CH(OR^7)$, $CON(R^7)$, $N(R^7)CO$, $N(R^7)CON(R^7)$, $SO_2N(R^7)$, $N(R^7)SO_2$, $O-SO_2$, $SO_2-O$, $C(R^7)_2O$, $OC(R^7)_2$, $C(R^7)_2S$, $SC(R^7)_2$, $C(R^7)_2$, $C(R^7)_2N(R^7)$ and $N(R^7)C(R^7)_2$, wherein each $R^7$ is independently selected from hydrogen, (1-8C)alkyl, hydroxy-(1-6C)alkyl, (1-6C)alkoxy-(1-6C)alkyl, cyano-(1-6C)alkyl, halogeno-(1-6C)alkyl, di-$(R^8)$amino-(1-6C)alkyl, $(R^8)$-amino-(1-6C)alkyl or amino-(1-6C)alkyl, wherein $R^8$ is (1-6C)alkyl optionally substituted by 1, 2 or 3 substituents independently selected from halogeno, cyano, hydroxy and (1-6C)alkoxy; and $Q^1$ is aryl, aryl-(1-6C)alkyl, (3-8C)cycloalkyl, (3-8C)cycloalkyl-(1-6C)alkyl, heterocyclyl, heterocyclyl-(1-6C)alkyl, heteroaryl or heteroaryl-(1-6C)alkyl, wherein any aryl or (3-8C)cycloalkyl group within a $R^1$ substituent bears 1, 2 or 3 substituents and any heterocyclyl or heteroaryl group within a $R^1$ substituent optionally bears 1, 2 or 3 substituents, wherein said substituents are independently selected from halogeno, trifluoromethyl, cyano, nitro, hydroxy, amino, carboxy, carbamoyl, ureido, (1-8C)alkyl, (2-8C)alkenyl, (2-8C)alkynyl, (1-6C)alkoxy, halogeno-(1-6C)alkoxy, hydroxy-(1-6C)alkyl, (1-6C)alkoxy-(1-6C)alkyl, (1-6C)alkylsulphonyl-(1-6C)alkyl, cyano-(1-6C)alkyl, halogeno-(1-6C)alkyl, amino-(1-6C)alkyl, (1-6C)alkylamino-(1-6C)alkyl, di-[(1-6C)alkyl]amino-(1-6C)alkyl, (2-6C)alkenyloxy, (2-6C)alkynyloxy, (1-6C)alkylthio, (1-6C)alkylsulphinyl, (1-6C)alkylsulphonyl, (1-6C)alkylamino, di-[(1-6C)alkyl]amino, (1-6C)alkoxycarbonyl, (2-6C)alkanoyl, hydroxy-(2-6C)alkanoyl, (1-6C)alkoxy-(2-6C)alkanoyl, (2-6C)alkanoyloxy, N-(1-6C)alkylcarbamoyl, N,N-di-[(1-6C)alkyl]carbamoyl, carbamoyl-(1-6C)alkyl, N-(1-6C)alkylcarbamoyl-(1-6C)alkyl, N,N-di-[(1-6C)alkyl]carbamoyl-(1-6C)alkyl, (1-6C)alkanoylamino, N-(1-6C)alkyl-(1-6C)alkanoylamino, N-(1-6C)alkylureido, N'-(1-6C)alkylureido, N',N'-di-[(1-6C)alkyl]ureido, N,N'-di-[(1-6C)alkyl]ureido, N,N',N'-tri-[(1-6C)alkyl]ureido, N-(1-6C)alkylsulphamoyl, N,N-di-[(1-6C)alkyl]sulphamoyl, (1-6C)alkanesulphonylamino, N-(1-6C)alkyl-(1-6C)alkanesulphonylamino, (1-6C)alkoxy-(1-6C)alkoxycarbonyl, (1-6C)alkylamino-(2-6C)alkanoyl, di-[(1-6C)alkyl]amino-(2-6C)alkanoyl, (1-6C)alkanoylamino-(2-6C)alkanoyl, (1-6C)alkoxy-(1-6C)alkoxy-(2-6C)alkanoyl, heterocyclyl, heterocyclyl-(1-6C)alkyl, heteroaryl or heteroaryl-(1-6C)alkyl and any heterocyclyl group within a $R^1$ substituent optionally bears 1 or 2 oxo substituents; wherein, any CH, $CH_2$, or $CH_3$ in any alkyl group present in the definition of $R^4$ that is connected to $X^1$ or present in the definition of $Q^1$ that is connected to $X^2$, optionally bears a hydroxy or cyano group and optionally bears up to three halogeno groups, and can optionally be replaced by an atom selected from O, S or N or a $SO_2$ group and adjacent carbon atoms in an alkyl chain can optionally be separated by the insertion into the chain of a C≡C group; each $R^2$ group may be the same or different and is selected from halogeno, cyano, hydroxy, amino, (1-8C)alkyl, (2-8C)alkenyl, (2-8C)alkynyl, (1-6C)alkoxy, (2-6C)alkenyloxy, (2-6C)alkynyloxy, halogeno-(1-6C)alkoxy, (1-6C)alkylthio, (1-6C)alkylsulphinyl, (1-6C)alkylsulphonyl, (1-6C)alkylamino, di-[(1-6C)alkyl]amino, (1-6C)alkoxycarbonyl, (2-6C)alkanoyl, (2-6C)alkanoyloxy, carbamoyl, N-(1-6C)alkylcarbamoyl, N,N-di-[(1-6C)alkyl]carbamoyl, (1-6C)alkanoylamino, N-(1-6C)alkyl-(1-6C)alkanoylamino, (1-6C)alkoxy-(1-6C)alkyl, hydroxy-(1-6C)alkyl, amino-(1-6C)alkyl, (1-6C)alkylamino-(1-6C)alkyl, di-[(1-6C)alkyl]amino-(1-6C)alkyl, (1-6C)alkoxy-(1-6C)alkoxy, hydroxy-(1-6C)alkoxy, amino-(1-6C)alkoxy, (1-6C)alkylamino-(1-6C)alkoxy and di-[(1-6C)alkyl]amino-(1-6C)alkoxy;
n is 0, 1, 2 or 3 and, when n is 2 or 3, each $R^3$ group may be the same or different, and each $R^3$ group present is selected from hydrogen, halogeno, amino, cyano, sulphamoyl, $OR^9$, N-(1-6C)alkylsulphamoyl, N,N-di-[(1-6C)alkyl]sulphamoyl, trifluoromethyl, (1-8C)alkyl, (2-8C)alkenyl, (2-8C)alkynyl, (1-6C)alkoxy, (1-6C)alkoxycarbonyl, halogeno-(1-6C)alkoxy, carbamoyl, N-(1-6C)alkylcarbamoyl, N,N-di-[(1-6C)alkyl]carbamoyl, (1-6C)alkanoylamino, (1-6C)alkylthio, (1-6C)alkylsulphinyl, (1-6C)alkylsulphonyl, hydroxy-(1-6C)alkyl, (1-6C)alkoxy-(1-6C)alkyl, (2-6C)alkanoyl, (1-6C)alkanesulphonylamino, amino-(1-6C)alkyl, (1-6C)alkylamino-(1-6C)alkyl, di-[(1-6C)alkyl]amino-(1-6C)alkyl, (1-6C)alkoxy-(1-6C)alkoxy, hydroxy-(1-6C)alkoxy, amino-(1-6C)alkoxy, (1-6C)alkylamino-(1-6C)alkoxy and di-[(1-6C)alkyl]amino-(1-6C)alkoxy, wherein $R^9$ is fluoro-(1-6C)alkyl, aryl, aryl-(1-6C)alkyl, heterocyclyl, heterocyclyl-(1-6C)alkyl, heteroaryl or heteroaryl-(1-6C)alkyl, wherein any aryl, heterocyclyl or heteroaryl group within the definition of $R^9$ optionally bears 1, 2 or 3 substituents independently selected from halogeno, fluoro-(1-6C)alkyl, oxo, cyano, hydroxy, amino, carboxy, carbamoyl, (1-8C)alkyl, (2-8C)alkenyl, (2-8C)alkynyl or (1-6C)alkoxy; or a pharmaceutically-acceptable salt thereof.

According to a further aspect of the invention there is provided a pyridine or pyrazine derivative of the Formula I

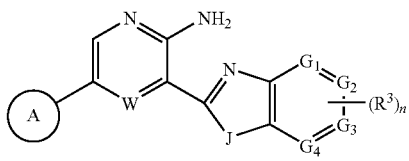

in which:
W is CH or N;
J is O or S;
each of $G_1$, $G_2$, $G_3$ and $G_4$ is selected from CH and N provided that not more than two of $G_1$, $G_2$, $G_3$ and $G_4$ represent N;
Ring A is selected from:
  (i) phenyl substituted by $R^1$ and optionally substituted by up to three $R^2$ groups; or
  (ii) a 5- or 6-membered monocyclic heteroaryl ring with up to three ring heteroatoms selected from oxygen, nitrogen and sulphur, said ring being substituted by $R^1$ and optionally substituted by up to three $R^2$ groups; or
  (iii) a 8-, 9- or 10-membered bicyclic ring system, wherein said bicyclic ring system optionally contains up to three ring heteroatoms selected from oxygen, nitrogen and sulphur and is optionally substituted by $R^1$ and optionally substituted by up to three $R^2$ groups;
$R^1$ is a group of the formula:

$$R^4-X^1-$$

wherein $X^1$ is a direct bond or is selected from O, S, SO, $SO_2$, $N(R^5)$, CO, $CH(OR^5)$, $CON(R^5)$, $N(R^5)CO$, $N(R^5)CON(R^5)$, $SO_2N(R^5)$, $N(R^5)SO_2$, $C(R^5)_2O$, $OC(R^5)_2$, $C(R^5)_2S$, $SC(R^5)_2$, $C(R^5)_2$, $C(R^5)_2N(R^5)$ and $N(R^5)C(R^5)_2$, wherein each $R^5$ is independently selected from hydrogen, (1-8C)alkyl, hydroxy-(1-6C)alkyl, (1-6C)alkoxy-(1-6C)alkyl, cyano-(1-6C)alkyl, halogeno-(1-6C)alkyl, di-[(1-6C)alkyl]amino-(1-6C)alkyl, (1-6C)alkylamino-(1-6C)alkyl or amino-(1-6C)alkyl,
and when $X^1$ is a direct bond or is selected from $CH(OR^5)$, $C(R^5)_2O$, $C(R^5)_2S$, $C(R^5)_2$ or $C(R^5)_2N(R^5)$, wherein $R^5$ has any of the meanings defined hereinbefore, $R^4$ is hydroxy-(1-6C)alkyl, (1-6C)alkoxy-(1-6C)alkyl, $R^5$—S, $R^5$—S(O), $R^5$—$SO_2$, $R^5$—$SO_2$—O, $R^5$—S-(1-6C)alkyl, $R^5$—S(O)-(1-6C)alkyl, $R^5$—$SO_2$-(1-6C)alkyl, N,N-di-($R^5$)sulphamoyl, N,N-di-($R^5$)sulphamoyl-(1-6C)alkyl, $R^5$—$SO_2N(R^5)$, $R^5$—$SO_2N(R^5)$-(1-6C)alkyl, $R^5$—$CON(R^5)$, $R^5O$—CON($R^5$), $R^5$—$CON(R^5)$-(1-6C)alkyl, $R^5O$—$CON(R^5)$-(1-6C)alkyl, $(R^5)_2N$—$SO_2N(R^5)$, $(R^5)_2N$—$SO_2N(R^5)$-(1-6C)alkyl, $(R^5)_2N$—$CON(R^5)$, $(R^5)_2N$—$CON(R^5)$-(1-6C)alkyl, $R^5$—CO, $R^5$—CO-(1-6C)alkyl, $R^5O$—CO-(1-6C)alkyl, $(R^5)_2$ NCO, $(R^5)_2NCO$-(1-6C)alkyl, $(R^5)_2N$—COO, $(R^5)_2$NCOO-(1-6C)alkyl, cyano, amino, $(R^6)$-amino, di-$(R^6)$-amino, amino-(1-6C)alkyl, $(R^6)$-amino-(1-6C)alkyl or di-$(R^6)$-amino-(1-6C)alkyl, wherein each $R^6$ present is (1-6C)alkyl optionally substituted by 1, 2 or 3 substituents independently selected from halogeno, cyano, hydroxy and (1-6C)alkoxy;
and when $X^1$ is selected from O, S, SO, $SO_2$, $N(R^5)$, CO, $CON(R^5)$, $N(R^5)CO$, $N(R^5)CON(R^5)$, $SO_2N(R^5)$, $N(R^5)SO_2$, $OC(R^5)_2$, $SC(R^5)_2$ and $N(R^5)C(R^5)_2$, wherein $R^5$ has any of the meanings defined hereinbefore, $R^4$ is hydroxy-(1-6C)alkyl, (1-6C)alkoxy-(1-6C)alkyl, $R^5$—S-(1-6C)alkyl, $R^5$—S(O)-(1-6C)alkyl, $R^5$—$SO_2$-(1-6C)alkyl, N,N-di-($R^5$)sulphamoyl-(1-6C)alkyl, $R^5$—$SO_2N(R^5)$-(1-6C)alkyl, $R^5$—$CON(R^5)$-(1-6C)alkyl, $R^5$—$CON(R^5)$-(1-6C)alkyl, $(R^5)_2N$—$SO_2N(R^5)$-(1-6C)alkyl, $(R^5)_2N$—$CON(R^5)$-(1-6C)alkyl, $R^5$—CO, $R^5$—CO-(1-6C)alkyl, $R^{5O}$—CO, $R^5O$—CO-(1-6C)alkyl, $(R^5)_2NCO$, $(R^5)_2NCO$-(1-6C)alkyl, $(R^5)_2$ NCOO-(1-6C)alkyl, amino-(1-6C)alkyl, $(R^6)$-amino-(1-6C)alkyl or di-$(R^6)$-amino-(1-6C)alkyl, wherein each $R^6$ present is (1-6C)alkyl optionally substituted by 1, 2 or 3 substituents independently selected from halogeno, cyano, hydroxy and (1-6C)alkoxy; or $R^1$ is a group of the formula:

$$Q^1-X^2-$$

wherein $X^2$ is a direct bond or is selected from O, S, SO, $SO_2$, $N(R^7)$, $N[C(O)R^7]$, $N[C(O)N(R^7)_2]$, $N[C(O)OR^7]$, $N[SO_2-N(R^7)_2]$, CO, $CH(OR^7)$, $CON(R^7)$, $N(R^7)CO$, $N(R^7)CON(R^7)$, $SO_2N(R^7)$, $N(R^7)SO_2$, O—$SO_2$, $SO_2$—O, $C(R^7)_2O$, $OC(R^7)_2$, $C(R^7)_2S$, $SC(R^7)_2$, $C(R^7)_2$, $C(R^7)_2N(R^7)$ and $N(R^7)C(R^7)_2$, wherein each $R^7$ is independently selected from hydrogen, (1-8C)alkyl, hydroxy-(1-6C)alkyl, (1-6C)alkoxy-(1-6C)alkyl, cyano-(1-6C)alkyl, halogeno-(1-6C)alkyl, di-($R^8$)amino-(1-6C)alkyl, $(R^8)$-amino-(1-6C)alkyl or amino-(1-6C)alkyl, wherein $R^5$ is (1-6C)alkyl optionally substituted by 1, 2 or 3 substituents independently selected from halogeno, cyano, hydroxy and (1-6C)alkoxy;
and $Q^1$ is aryl, aryl-(1-6C)alkyl, (3-8C)cycloalkyl, (3-8C)cycloalkyl-(1-6C)alkyl, heterocyclyl, heterocyclyl-(1-6C)alkyl, heteroaryl or heteroaryl-(1-6C)alkyl, wherein any aryl or (3-8C)cycloalkyl group within a $R^1$ substituent bears 1, 2 or 3 substituents and any heterocyclyl or heteroaryl group within a $R^1$ substituent optionally bears 1, 2 or 3 substituents, wherein said substituents are independently selected from halogeno, trifluoromethyl, cyano, nitro, hydroxy, amino, carboxy, carbamoyl, ureido, (1-8C)alkyl, (2-8C)alkenyl, (2-8C)alkynyl, (1-6C)alkoxy, halogeno-(1-6C)alkoxy, hydroxy-(1-6C)alkyl, (1-6C)alkoxy-(1-6C)alkyl, (1-6C)alkylsulphonyl-(1-6C)alkyl, cyano-(1-6C)alkyl, halogeno-(1-6C)alkyl, amino-(1-6C)alkyl, (1-6C)alkylamino-(1-6C)alkyl, di-[(1-6C)alkyl]amino-(1-6C)alkyl, (2-6C)alkenyloxy, (2-6C)alkynyloxy, (1-6C)alkylthio, (1-6C)alkylsulphinyl, (1-6C)alkylsulphonyl, (1-6C)alkylamino, di-[(1-6C)alkyl]amino, (1-6C)alkoxycarbonyl, (2-6C)alkanoyl, hydroxy-(2-6C)alkanoyl, (1-6C)alkoxy-(2-6C)alkanoyl, (2-6C)alkanoyloxy, N-(1-6C)alkylcarbamoyl, N,N-di-[(1-6C)alkyl]carbamoyl, carbamoyl-(1-6C)alkyl, N-(1-6C)alkylcarbamoyl-(1-6C)alkyl, N,N-di-[(1-6C)alkyl]carbamoyl-(1-6C)alkyl, (1-6C)alkanoylamino, N-(1-6C)alkyl-(1-6C)alkanoylamino, N-(1-6C)alkylureido, N'-(1-6C)alkylureido, N',N'-di-[(1-6C)alkyl]ureido, N,N'-di-[(1-6C)alkyl]ureido, N,N',N'-tri-[(1-6C)alkyl]ureido, N-(1-6C)alkylsulphamoyl, N,N-di-[(1-6C)

alkyl]sulphamoyl, (1-6C)alkanesulphonylamino, N-(1-6C)alkyl-(1-6C)alkanesulphonylamino, heterocyclyl, heterocyclyl-(1-6C)alkyl, heteroaryl or heteroaryl-(1-6C)alkyl and any heterocyclyl group within a $R^1$ substituent optionally bears 1 or 2 oxo substituents;
wherein, any CH, $CH_2$, or $CH_3$ in any alkyl group present in the definition of $R^4$ that is connected to $X^1$ or present in the definition of $Q^1$ that is connected to $X^2$, optionally bears a hydroxy or cyano group and optionally bears up to three halogeno groups, and can optionally be replaced by an atom selected from O, S or N or a $SO_2$ group and adjacent carbon atoms in an alkyl chain can optionally be separated by the insertion into the chain of a C≡C group;
each $R^2$ group may be the same or different and is selected from halogeno, cyano, hydroxy, amino, (1-8C)alkyl, (2-8C)alkenyl, (2-8C)alkynyl, (1-6C)alkoxy, (2-6C)alkenyloxy, (2-6C)alkynyloxy, halogeno-(1-6C)alkoxy, (1-6C)alkylthio, (1-6C)alkylsulphinyl, (1-6C)alkylsulphonyl, (1-6C)alkylamino, di-[(1-6C)alkyl]amino, (1-6C)alkoxycarbonyl, (2-6C)alkanoyl, (2-6C)alkanoyloxy, N-(1-6C)alkylcarbamoyl, N,N-di-[(1-6C)alkyl]carbamoyl, (1-6C)alkanoylamino, N-(1-6C)alkyl-(1-6C)alkanoylamino, (1-6C)alkoxy-(1-6C)alkyl, hydroxy-(1-6C)alkyl, amino-(1-6C)alkyl, (1-6C)alkylamino-(1-6C)alkyl, di-[(1-6C)alkyl]amino-(1-6C)alkyl, (1-6C)alkoxy-(1-6C)alkoxy, hydroxy-(1-6C)alkoxy, amino-(1-6C)alkoxy, (1-6C)alkylamino-(1-6C)alkoxy and di-[(1-6C)alkyl]amino-(1-6C)alkoxy;
n is 0, 1, 2 or 3 and, when n is 2 or 3, each $R^3$ group may be the same or different, and each $R^3$ group present is selected from hydrogen, halogeno, amino, cyano, sulphamoyl, $OR^9$, N-(1-6C)alkylsulphamoyl, N,N-di-[(1-6C)alkyl]sulphamoyl, trifluoromethyl, (1-8C)alkyl, (2-8C)alkenyl, (2-8C)alkynyl, (1-6C)alkoxy, (1-6C)alkoxycarbonyl, halogeno-(1-6C)alkoxy, carbamoyl, N-(1-6C)alkylcarbamoyl, N,N-di-[(1-6C)alkyl]carbamoyl, (1-6C)alkanoylamino, (1-6C)alkylthio, (1-6C)alkylsulphinyl, (1-6C)alkylsulphonyl, hydroxy-(1-6C)alkyl, (1-6C)alkoxy-(1-6C)alkyl, (2-6C)alkanoyl, (1-6C)alkanesulphonylamino, amino-(1-6C)alkyl, (1-6C)alkylamino-(1-6C)alkyl, di-[(1-6C)alkyl]amino-(1-6C)alkyl, (1-6C)alkoxy-(1-6C)alkoxy, hydroxy-(1-6C)alkoxy, amino-(1-6C)alkoxy, (1-6C)alkylamino-(1-6C)alkoxy and di-[(1-6C)alkyl]amino-(1-6C)alkoxy, wherein $R^9$ is fluoro-(1-6C)alkyl, aryl, aryl-(1-6C)alkyl, heterocyclyl, heterocyclyl-(1-6C)alkyl, heteroaryl or heteroaryl-(1-6C)alkyl, wherein any aryl, heterocyclyl or heteroaryl group within the definition of $R^9$ optionally bears 1, 2 or 3 substituents independently selected from halogeno, fluoro-(1-6C)alkyl, oxo, cyano, hydroxy, amino, carboxy, carbamoyl, (1-8C)alkyl, (2-8C)alkenyl, (2-8C)alkynyl or (1-6C)alkoxy; or a pharmaceutically-acceptable salt thereof.

According to yet a further aspect of the invention there is provided a pyridine or pyrazine derivative of the Formula I

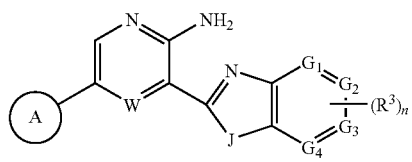

in which:
W is CH or N;
J is O or S;
each of $G_1$, $G_2$, $G_3$ and $G_4$ is selected from CH and N provided that not more than two of $G_1$, $G_2$, $G_3$ and $G_4$ represent N;

Ring A is selected from:
(i) phenyl substituted by $R^1$ and optionally substituted by up to three $R^2$ groups; or
(ii) a 5- or 6-membered monocyclic heteroaryl ring with up to three ring heteroatoms selected from oxygen, nitrogen and sulphur, said ring being substituted by $R^1$ and optionally substituted by up to three $R^2$ groups; or
(iii) a 8-, 9- or 10-membered bicyclic ring system, wherein said bicyclic ring system optionally contains up to three ring heteroatoms selected from oxygen, nitrogen and sulphur and is optionally substituted by $R^1$ and optionally substituted by up to three $R^2$ groups;
$R^1$ is a group of the formula:

$R^4—X^1—$ wherein $X^1$ is a direct bond or is selected from O, S, SO, $SO_2$, $N(R^5)$, CO, $CH(OR^5)$, $CON(R^5)$, $N(R^5)CO$, $N(R^5)CON(R^5)$, $SO_2N(R^5)$, $N(R^5)SO_2$, $C(R^5)_2O$, $OC(R^5)_2$, $C(R^5)_2S$, $SC(R^5)_2$, $C(R^5)_2$, $C(R^5)_2N(R^5)$ and $N(R^5)C(R^5)_2$, wherein each $R^5$ is independently selected from hydrogen, (1-8C)alkyl, hydroxy-(1-6C)alkyl, (1-6C)alkoxy-(1-6C)alkyl, cyano-(1-6C)alkyl, halogeno-(1-6C)alkyl, di-[(1-6C)alkyl]amino-(1-6C)alkyl, (1-6C)alkylamino-(1-6C)alkyl or amino-(1-6C)alkyl,
and when $X^1$ is a direct bond or is selected from $CH(OR^5)$, $C(R^5)_2O$, $C(R^5)_2S$, $C(R^5)_2$ or $C(R^5)_2N(R^5)$, wherein $R^5$ has any of the meanings defined hereinbefore, $R^4$ is hydroxy-(1-6C)alkyl, (1-6C)alkoxy-(1-6C)alkyl, $R^5—S$, $R^5—S(O)$, $R^5—SO_2$, $R^5—SO_2—O$, $R^5—S$-(1-6C)alkyl, $R^5—S(O)$-(1-6C)alkyl, $R^5—SO_2$-(1-6C)alkyl, N,N-di-($R^5$)sulphamoyl, N,N-di-($R^5$)sulphamoyl-(1-6C)alkyl, $R^5—SO_2N(R^5)$, $R^5—SO_2N(R^5)$-(1-6C)alkyl, $R^5—CON(R^5)$, $R^5O—CON(R^5)$, $R^5—CON(R^5)$-(1-6C)alkyl, $R^5O—CON(R^5)$-(1-6C)alkyl, $(R^5)_2N—SO_2N(R^5)$, $(R^5)_2N—SO_2N(R^5)$-(1-6C)alkyl, $(R^5)_2N—CON(R^5)$, $(R^5)_2N—CON(R^5)$-(1-6C)alkyl, $R^5—CO$, $R^5O—CO$-(1-6C)alkyl, $R^5O—CO$-(1-6C)alkyl, $(R^5)_2NCO$, $(R^5)_2NCO$-(1-6C)alkyl, $(R^5)_2N—COO$, $(R^5)_2NCOO$-(1-6C)alkyl, cyano, amino, $(R^6)$-amino, di-$(R^6)$-amino, amino-(1-6C)alkyl, $(R^6)$— amino-(1-6C)alkyl or di-$(R^6)$-amino-(1-6C)alkyl, wherein each $R^6$ present is (1-6C)alkyl optionally substituted by 1, 2 or 3 substituents independently selected from halogeno, cyano, hydroxy and (1-6C)alkoxy;
and when $X^1$ is selected from O, S, SO, $SO_2$, $N(R^5)$, CO, $CON(R^5)$, $N(R^5)CO$, $N(R^5)CON(R^5)$, $SO_2N(R^5)$, $N(R^5)SO_2$, $OC(R^5)_2$, $SC(R^5)_2$ and $N(R^5)C(R^5)_2$, wherein $R^5$ has any of the meanings defined hereinbefore, $R^4$ is hydroxy-(1-6C)alkyl, (1-6C)alkoxy-(1-6C)alkyl, $R^5—S$-(1-6C)alkyl, $R^5—S(O)$-(1-6C)alkyl, $R^5—SO_2$-(1-6C)alkyl, N,N-di-($R^5$)sulphamoyl-(1-6C)alkyl, $R^5—SO_2N(R^5)$-(1-6C)alkyl, $R^5—CON(R^5)$-(1-6C)alkyl, $R^5O—CON(R^5)$-(1-6C)alkyl, $(R^5)_2N—SO_2N(R^5)$-(1-6C)alkyl, $(R^5)_2N—CON(R^5)$-(1-6C)alkyl, $R^5—CO$, $R^5—CO$-(1-6C)alkyl, $R^{5O}—CO$, $R^5O—CO$-(1-6C)alkyl, $(R^5)_2NCO$, $(R^5)_2NCO$-(1-6C)alkyl, $(R^5)_2NCOO$-(1-6C)alkyl, amino-(1-6C)alkyl, $(R^6)$-amino-(1-6C)alkyl or di-$(R^6)$-amino-(1-6C)alkyl, wherein each $R^6$ present is (1-6C)alkyl optionally substituted by 1, 2 or 3 substituents independently selected from halogeno, cyano, hydroxy and (1-6C)alkoxy;
or $R^1$ is a group of the formula:

$Q^1-X^2—$ wherein $X^2$ is a direct bond or is selected from O, S, SO, $SO_2$, $N(R^7)$, $N[C(O)R^7]$, $N[C(O)N(R^7)_2]$, $N[C(O)OR^7]$, $N[SO_2—N(R^7)_2]$, CO, $CH(OR^7)$, $CON(R^7)$, $N(R^7)CO$, $N(R^7)CON(R^7)$, $SO_2N(R^7)$, $N(R^7)SO_2$, $O—SO_2$, $SO_2—O$, $C(R^7)_2O$, $OC(R^7)_2$, $C(R^7)_2S$, $SC(R^7)_2$, $C(R^7)_2$, $C(R^7)_2N(R^7)$ and $N(R^7)$ C($R^7$)$_2$, wherein each $R^7$ is independently selected from hydrogen, (1-8C)alkyl, hydroxy-(1-6C)alkyl, (1-6C)alkoxy-(1-6C)alkyl, cyano-(1-6C)alkyl, halogeno-(1-6C)alkyl, di-($R^8$)amino-(1-6C)alkyl, ($R^8$)-amino-(1-6C)alkyl or amino-(1-6C)alkyl, wherein $R^8$ is (1-6C)alkyl optionally substituted by 1, 2 or 3 substituents independently selected from halogeno, cyano, hydroxy and (1-6C)alkoxy;

and $Q^1$ is aryl, aryl-(1-6C)alkyl, (3-8C)cycloalkyl, (3-8C)cycloalkyl-(1-6C)alkyl, heterocyclyl, heterocyclyl-(1-6C)alkyl, heteroaryl or heteroaryl-(1-6C)alkyl, wherein any aryl or (3-8C)cycloalkyl group within a $R^1$ substituent bears 1, 2 or 3 substituents and any heterocyclyl or heteroaryl group within a $R^1$ substituent optionally bears 1, 2 or 3 substituents, wherein said substituents are independently selected from halogeno, trifluoromethyl, cyano, nitro, hydroxy, amino, carboxy, carbamoyl, ureido, (1-8C)alkyl, (2-8C)alkenyl, (2-8C)alkynyl, (1-6C)alkoxy, halogeno-(1-6C)alkoxy, hydroxy-(1-6C)alkyl, (1-6C)alkoxy-(1-6C)alkyl, (1-6C)alkylsulphonyl-(1-6C)alkyl, cyano-(1-6C)alkyl, halogeno-(1-6C)alkyl, amino-(1-6C)alkyl, (1-6C)alkylamino-(1-6C)alkyl, di-[(1-6C)alkyl]amino-(1-6C)alkyl, (2-6C)alkenyloxy, (2-6C)alkynyloxy, (1-6C)alkylthio, (1-6C)alkylsulphinyl, (1-6C)alkylsulphonyl, (1-6C)alkylamino, di-[(1-6C)alkyl]amino, (1-6C)alkoxycarbonyl, (2-6C)alkanoyl, (2-6C)alkanoyloxy, N-(1-6C)alkylcarbamoyl, N,N-di-[(1-6C)alkyl]carbamoyl, (1-6C)alkanoylamino, N-(1-6C)alkyl-(1-6C)alkanoylamino, N-(1-6C)alkylureido, N'-(1-6C)alkylureido, N',N'-di-[(1-6C)alkyl]ureido, N,N'-di-[(1-6C)alkyl]ureido, N,N',N'-tri-[(1-6C)alkyl]ureido, N-(1-6C)alkylsulphamoyl, N,N-di-[(1-6C)alkyl]sulphamoyl, (1-6C)alkanesulphonylamino, N-(1-6C)alkyl-(1-6C)alkanesulphonylamino or heterocyclyl-(1-6C)alkyl, and any heterocyclyl group within a $R^1$ substituent optionally bears 1 or 2 oxo substituents;

each $R^2$ group may be the same or different and is selected from halogeno, cyano, hydroxy, amino, (1-8C)alkyl, (2-8C)alkenyl, (2-8C)alkynyl, (1-6C)alkoxy, (2-6C)alkenyloxy, (2-6C)alkynyloxy, halogeno-(1-6C)alkoxy, (1-6C)alkylthio, (1-6C)alkylsulphinyl, (1-6C)alkylsulphonyl, (1-6C)alkylamino, di-[(1-6C)alkyl]amino, (1-6C)alkoxycarbonyl, (2-6C)alkanoyl, (2-6C)alkanoyloxy, N-(1-6C)alkylcarbamoyl, N,N-di-[(1-6C)alkyl]carbamoyl, (1-6C)alkanoylamino, N-(1-6C)alkyl-(1-6C)alkanoylamino, (1-6C)alkoxy-(1-6C)alkyl, hydroxy-(1-6C)alkyl, amino-(1-6C)alkyl, (1-6C)alkylamino-(1-6C)alkyl, di-[(1-6C)alkyl]amino-(1-6C)alkyl, (1-6C)alkoxy-(1-6C)alkoxy, hydroxy-(1-6C)alkoxy, amino-(1-6C)alkoxy, (1-6C)alkylamino-(1-6C)alkoxy and di-[(1-6C)alkyl]amino-(1-6C)alkoxy;

n is 0, 1, 2 or 3 and, when n is 2 or 3, each $R^3$ group may be the same or different, and each $R^3$ group present is selected from hydrogen, halogeno, amino, cyano, sulphamoyl, $OR^9$, N-(1-6C)alkylsulphamoyl, N,N-di-[(1-6C)alkyl]sulphamoyl, trifluoromethyl, (1-8C)alkyl, (2-8C)alkenyl, (2-8C)alkynyl, (1-6C)alkoxy, (1-6C)alkoxycarbonyl, halogeno-(1-6C)alkoxy, carbamoyl, N-(1-6C)alkylcarbamoyl, N,N-di-[(1-6C)alkyl]carbamoyl, (1-6C)alkanoylamino, (1-6C)alkylthio, (1-6C)alkylsulphinyl, (1-6C)alkylsulphonyl, hydroxy-(1-6C)alkyl, (1-6C)alkoxy-(1-6C)alkyl, (2-6C)alkanoyl, (1-6C)alkanesulphonylamino, amino-(1-6C)alkyl, (1-6C)alkylamino-(1-6C)alkyl, di-[(1-6C)alkyl]amino-(1-6C)alkyl, (1-6C)alkoxy-(1-6C)alkoxy, hydroxy-(1-6C)alkoxy, amino-(1-6C)alkoxy, (1-6C)alkylamino-(1-6C)alkoxy and di-[(1-6C)alkyl]amino-(1-6C)alkoxy, wherein $R^9$ is fluoro-(1-6C)alkyl, aryl, aryl-(1-6C)alkyl, heterocyclyl, heterocyclyl-(1-6C)alkyl, heteroaryl or heteroaryl-(1-6C)alkyl, wherein any aryl, heterocyclyl or heteroaryl group within the definition of $R^9$ optionally bears 1, 2 or 3 substituents independently selected from halogeno, fluoro-(1-6C)alkyl, oxo, cyano, hydroxy, amino, carboxy, carbamoyl, (1-8C)alkyl, (2-8C)alkenyl, (2-8C)alkynyl or (1-6C)alkoxy; or a pharmaceutically-acceptable salt thereof.

According to yet a further aspect of the invention there is provided a pyridine or pyrazine derivative of the Formula I

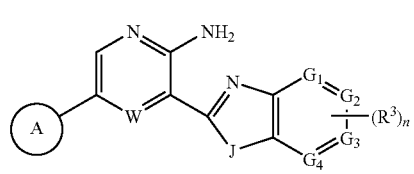

in which:
W is CH or N;
J is O or S;
each of $G_1$, $G_2$, $G_3$ and $G_4$ is selected from CH and N provided that not more than two of $G_1$, $G_2$, $G_3$ and $G_4$ represent N;
Ring A is selected from:
 (i) phenyl substituted by $R^1$ and optionally substituted by up to three $R^2$ groups; or
 (ii) a 5- or 6-membered monocyclic heteroaryl ring with up to three ring heteroatoms selected from oxygen, nitrogen and sulphur, said ring being substituted by $R^1$ and optionally substituted by up to three $R^2$ groups; or
 (iii) a 8-, 9- or 10-membered bicyclic ring system, wherein said bicyclic ring system optionally contains up to three ring heteroatoms selected from oxygen, nitrogen and sulphur and is optionally substituted by $R^1$ and optionally substituted by up to three $R^2$ groups;
$R^1$ is a group of the formula:

$R^4$—$X^1$— wherein $X^1$ is a direct bond or is selected from O, S, SO, $SO_2$, N($R^5$), CO, CH($OR^5$), CON($R^5$), N($R^5$)CO, N($R^5$)CON($R^5$), $SO_2$N($R^5$), N($R^5$)$SO_2$, C($R^5$)$_2$O, OC($R^5$)$_2$, C($R^5$)$_2$S, SC($R^5$)$_2$, C($R^5$)$_2$, C($R^5$)$_2$N($R^5$) and N($R^5$)C($R^5$)$_2$, wherein each $R^5$ is independently selected from hydrogen, (1-8C)alkyl, hydroxy-(1-6C)alkyl, (1-6C)alkoxy-(1-6C)alkyl, cyano-(1-6C)alkyl, halogeno-(1-6C)alkyl, di-[(1-6C)alkyl]amino-(1-6C)alkyl, (1-6C)alkylamino-(1-6C)alkyl or amino-(1-6C)alkyl, and when $X^1$ is a direct bond or is selected from CH($OR^5$), C($R^5$)$_2$O, C($R^5$)$_2$S, C($R^5$)$_2$ or C($R^5$)$_2$N($R^5$), wherein $R^5$ has any of the meanings defined hereinbefore, $R^4$ is hydroxy-(1-6C)alkyl, (1-6C)alkoxy-(1-6C)alkyl, $R^5$—S, $R^5$—S(O), $R^5$—$SO_2$, $R^5$—S-(1-6C)alkyl, $R^5$—S(O)-(1-6C)alkyl, $R^5$—$SO_2$-(1-6C)alkyl, N,N-di-($R^5$)sulphamoyl, N,N-di-($R^5$)sulphamoyl-(1-6C)alkyl, $R^5$—$SO_2$N($R^5$), $R^5$—$SO_2$N($R^5$)-(1-6C)alkyl, $R^5$—CON($R^5$), $R^5$O—CON($R^5$), $R^5$—CON($R^5$)-(1-6C)alkyl, $R^5$O—CON($R^5$)-(1-6C)alkyl, ($R^5$)$_2$N—$SO_2$N($R^5$), ($R^5$)$_2$N—$SO_2$N($R^5$)-(1-6C)alkyl, ($R^5$)$_2$N—CON($R^5$), ($R^5$)$_2$N—CON($R^5$)-(1-6C)alkyl, $R^5$—CO, $R^5$—CO-(1-6C)alkyl, $R^5$O—CO-(1-6C)alkyl, ($R^5$)$_2$NCO, ($R^5$)$_2$NCO-(1-6C)alkyl, ($R^5$)$_2$N—COO, ($R^5$)$_2$NCOO-(1-6C)alkyl, cyano, amino, ($R^6$)-amino, di-($R^6$)-amino, amino-(1-6C)alkyl, ($R^6$)—amino-(1-6C)alkyl or di-($R^6$)-amino-(1-6C)alkyl, wherein each $R^6$ present is (1-6C)alkyl optionally substituted by 1, 2 or 3 substituents independently selected from halogeno, cyano, hydroxy and (1-6C)alkoxy;

and when $X^1$ is selected from O, S, SO, $SO_2$, N($R^5$), CO, CON($R^5$), N($R^5$)CO, N($R^5$)CON($R^5$), $SO_2$N($R^5$), N($R^5$)$SO_2$, OC($R^5$)$_2$, SC($R^5$)$_2$, C($R^5$)$_2$ and N($R^5$)C($R^5$)$_2$, wherein $R^5$ has any of the meanings defined hereinbefore, $R^4$ is hydroxy-(1-6C)alkyl, (1-6C)alkoxy-(1-6C)alkyl, $R^5$—S-(1-6C)alkyl, R⁵—S(O)-(1-6C)alkyl, R⁵—SO₂-(1-6C)alkyl, N,N-di-(R⁵) sulphamoyl-(1-6C)alkyl, R⁵—SO₂N(R⁵)-(1-6C)alkyl, R⁵—CON(R⁵)-(1-6C)alkyl, R⁵O—CON(R⁵)-(1-6C)alkyl, (R⁵)₂N—SO₂N(R⁵)-(1-6C)alkyl, (R⁵)₂N—CON(R⁵)-(1-6C)alkyl, R⁵—CO, R⁵—CO-(1-6C)alkyl, R⁵⁰—CO, R⁵O—CO-(1-6C)alkyl, (R⁵)₂NCO, (R⁵)₂NCO-(1-6C)alkyl, (R⁵)₂NCOO-(1-6C)alkyl, amino-(1-6C)alkyl, (R⁶)-amino-(1-6C)alkyl or di-(R⁶)-amino-(1-6C)alkyl, wherein each R⁶ present is (1-6C)alkyl optionally substituted by 1, 2 or 3 substituents independently selected from halogeno, cyano, hydroxy and (1-6C)alkoxy; or R¹ is a group of the formula:

Q¹-X²— wherein X² is a direct bond or is selected from O, S, SO, SO₂, N(R⁷), N[C(O)R⁷], N[C(O)N(R⁷)₂], N[C(O)OR⁷], N[SO₂—N(R⁷)₂], CO, CH(OR⁷), CON(R⁷), N(R⁷)CO, N(R⁷)CON(R⁷), SO₂N(R⁷), N(R⁷)SO₂, O—SO₂, SO₂—O, C(R⁷)₂O, OC(R⁷)₂, C(R⁷)₂S, SC(R⁷)₂, C(R⁷)₂, C(R⁷)₂N(R⁷) and N(R⁷)C(R⁷)₂, wherein each R⁷ is independently selected from hydrogen, (1-8C)alkyl, hydroxy-(1-6C)alkyl, (1-6C)alkoxy-(1-6C)alkyl, cyano-(1-6C)alkyl, halogeno-(1-6C)alkyl, di-(R⁸)amino-(1-6C)alkyl, (R⁸)-amino-(1-6C)alkyl or amino-(1-6C)alkyl, wherein R⁸ is (1-6C)alkyl optionally substituted by 1, 2 or 3 substituents independently selected from halogeno, cyano, hydroxy and (1-6C)alkoxy;

and Q¹ is aryl, aryl-(1-6C)alkyl, (3-8C)cycloalkyl, (3-8C)cycloalkyl-(1-6C)alkyl, heterocyclyl, heterocyclyl-(1-6C)alkyl, heteroaryl or heteroaryl-(1-6C)alkyl, wherein any aryl or (3-8C)cycloalkyl group within a R¹ substituent bears 1, 2 or 3 substituents and any heterocyclyl or heteroaryl group within a R¹ substituent optionally bears 1, 2 or 3 substituents, wherein said substituents are independently selected from halogeno, trifluoromethyl, cyano, nitro, hydroxy, amino, carboxy, carbamoyl, ureido, (1-8C)alkyl, (2-8C)alkenyl, (2-8C)alkynyl, (1-6C)alkoxy, halogeno-(1-6C)alkoxy, hydroxy-(1-6C)alkyl, (1-6C)alkoxy-(1-6C)alkyl, (1-6C)alkylsulphonyl-(1-6C)alkyl, cyano-(1-6C)alkyl, halogeno-(1-6C)alkyl, amino-(1-6C)alkyl, (1-6C)alkylamino-(1-6C)alkyl, di-[(1-6C)alkyl]amino-(1-6C)alkyl, (2-6C)alkenyloxy, (2-6C)alkynyloxy, (1-6C)alkylthio, (1-6C)alkylsulphinyl, (1-6C)alkylsulphonyl, (1-6C)alkylamino, di-[(1-6C)alkyl]amino, (1-6C)alkoxycarbonyl, (2-6C)alkanoyl, (2-6C)alkanoyloxy, N-(1-6C)alkylcarbamoyl, N,N-di-[(1-6C)alkyl]carbamoyl, (1-6C)alkanoylamino, N-(1-6C)alkyl-(1-6C)alkanoylamino, N-(1-6C)alkylureido, N'-(1-6C)alkylureido, N',N'-di-[(1-6C)alkyl]ureido, N,N'-di-[(1-6C)alkyl]ureido, N,N',N'-tri-[(1-6C)alkyl]ureido, N-(1-6C)alkylsulphamoyl, N,N-di-[(1-6C)alkyl]sulphamoyl, (1-6C)alkanesulphonylamino, N-(1-6C)alkyl-(1-6C)alkanesulphonylamino or heterocyclyl-(1-6C)alkyl, and any heterocyclyl group within a R¹ substituent optionally bears 1 or 2 oxo substituents;

each R² group may be the same or different and is selected from halogeno, cyano, hydroxy, amino, (1-8C)alkyl, (2-8C)alkenyl, (2-8C)alkynyl, (1-6C)alkoxy, (2-6C)alkenyloxy, (2-6C)alkynyloxy, halogeno-(1-6C)alkoxy, (1-6C)alkylthio, (1-6C)alkylsulphinyl, (1-6C)alkylsulphonyl, (1-6C)alkylamino, di-[(1-6C)alkyl]amino, (1-6C)alkoxycarbonyl, (2-6C)alkanoyl, (2-6C)alkanoyloxy, N-(1-6C)alkylcarbamoyl, N,N-di-[(1-6C)alkyl]carbamoyl, (1-6C)alkanoylamino, N-(1-6C)alkyl-(1-6C)alkanoylamino, (1-6C)alkoxy-(1-6C)alkyl, hydroxy-(1-6C)alkyl, amino-(1-6C)alkyl, (1-6C)alkylamino-(1-6C)alkyl, di-[(1-6C)alkyl]amino-(1-6C)alkyl, (1-6C)alkoxy-(1-6C)alkoxy, hydroxy-(1-6C)alkoxy, amino-(1-6C)alkoxy, (1-6C)alkylamino-(1-6C)alkoxy and di-[(1-6C)alkyl]amino-(1-6C)alkoxy;

n is 0, 1, 2 or 3 and, when n is 2 or 3, each R³ group may be the same or different, and each R³ group present is selected from hydrogen, halogeno, amino, cyano, sulphamoyl, OR⁹, N-(1-6C)alkylsulphamoyl, N,N-di-[(1-6C)alkyl]sulphamoyl, trifluoromethyl, (1-8C)alkyl, (2-8C)alkenyl, (2-8C)alkynyl, (1-6C)alkoxy, (1-6C)alkoxycarbonyl, halogeno-(1-6C)alkoxy, carbamoyl, N-(1-6C)alkylcarbamoyl, N,N-di-[(1-6C)alkyl]carbamoyl, (1-6C)alkanoylamino, (1-6C)alkylthio, (1-6C)alkylsulphinyl, (1-6C)alkylsulphonyl, hydroxy-(1-6C)alkyl, (1-6C)alkoxy-(1-6C)alkyl, (2-6C)alkanoyl, (1-6C)alkanesulphonylamino, amino-(1-6C)alkyl, (1-6C)alkylamino-(1-6C)alkyl, di-[(1-6C)alkyl]amino-(1-6C)alkyl, (1-6C)alkoxy-(1-6C)alkoxy, hydroxy-(1-6C)alkoxy, amino-(1-6C)alkoxy, (1-6C)alkylamino-(1-6C)alkoxy and di-[(1-6C)alkyl]amino-(1-6C)alkoxy, wherein R⁹ is fluoro-(1-6C)alkyl, aryl, aryl-(1-6C)alkyl, heterocyclyl, heterocyclyl-(1-6C)alkyl, heteroaryl or heteroaryl-(1-6C)alkyl, wherein any aryl, heterocyclyl or heteroaryl group within the definition of R⁹ optionally bears 1, 2 or 3 substituents independently selected from halogeno, fluoro-(1-6C)alkyl, oxo, cyano, hydroxy, amino, carboxy, carbamoyl, (1-8C)alkyl, (2-8C)alkenyl, (2-8C)alkynyl or (1-6C)alkoxy; or a pharmaceutically-acceptable salt thereof.

In this specification the generic term "(1-8C)alkyl" includes both straight-chain and branched-chain alkyl groups such as propyl, isopropyl and tert-butyl, and also (3-8C)cycloalkyl groups such as cyclopropyl, cyclobutyl, cyclopentyl, cyclohexyl and cycloheptyl, and also (3-6C)cycloalkyl-(1-2C)alkyl groups such as cyclopropylmethyl, 2-cyclopropylethyl, cyclobutylmethyl, 2-cyclobutylethyl, cyclopentylmethyl, 2-cyclopentylethyl, cyclohexylmethyl and 2-cyclohexylethyl. However references to individual alkyl groups such as "propyl" are specific for the straight-chain version only, references to individual branched-chain alkyl groups such as "isopropyl" are specific for the branched-chain version only and references to individual cycloalkyl groups such as "cyclopentyl" are specific for that 5-membered ring only. An analogous convention applies to other generic terms, for example (1-6C)alkoxy includes (3-6C)cycloalkyloxy groups and cycloalkyl-alkoxy groups having 4 to 6 carbon atoms, for example methoxy, ethoxy, propoxy, isopropoxy, cyclopropyloxy, cyclobutyloxy, cyclopentyloxy, cyclohexyloxy, cyclopropylmethoxy, 2-cyclopropylethoxy, cyclobutylmethoxy, 2-cyclobutylethoxy and cyclopentylmethoxy; (1-6C)alkylamino includes (3-6C)cycloalkylamino groups and N-(cycloalkylalkyl)amino groups having 4 to 6 carbon atoms, for example methylamino, ethylamino, propylamino, cyclopropylamino, cyclobutylamino, cyclohexylamino, cyclopropylmethylamino, 2-cyclopropylethylamino, cyclobutylmethylamino, 2-cyclobutylethylamino and cyclopentylmethylamino; and di-[(1-6Calkyl]amino includes di-[(3-6C)cycloalkyl]amino groups and di-[cycloalkylalkyl]amino groups in which the cycloalkylalkyl moiety has 4 to 6 carbon atoms, for example dimethylamino, diethylamino, dipropylamino, N-cyclopropyl-N-methylamino, N-cyclobutyl-N-methylamino, N-cyclohexyl-N-ethylamino, N-cyclopropylmethyl-N-methylamino, N-(2-cyclopropylethyl)-N-methylamino and N-cyclopentylmethyl-N-methylamino. An analogous convention also applies to other generic groups used within the specification, such as for example (1-6C)alkylthio, (1-6C)alkylsulphinyl, (1-6C)alkylsulphonyl, N-(1-6C)alkylsulphamoyl, N,N-di-[(1-6C)alkyl]sulphamoyl, N,N-di-(R⁵)sulphamoyl, R⁵—SO₂N(R⁵), (1-6C)alkyl-SO₂N(R⁵), R⁵—CON(R⁵), (1-6C)alkyl-CON(R⁵), N-(1-6C)alkylcarbamoyl, (R⁵)₂NCO and N,N-di-[(1-6C)alkyl]carbamoyl.

A person skilled in the art will appreciate that the terms "(1-6C)alkyl", "(1-4C)alkyl", "(1-3C)alkyl" and "(1-2C)alkyl" that are used herein refer to any of the alkyl groups defined above that possesses 1 to 6, 1 to 4, 1 to 3 and 1 to 2 carbon atoms respectively. The same convention applies to other terms used herein, such as, for example, "(1-6C)alkoxy", "(1-4C)alkoxy", "(1-3C)alkoxy" and "(1-2C)alkoxy".

In this specification, unless otherwise specified, the term "heterocyclyl" is to be understood as being, for example, a non-aromatic saturated or partially saturated 3 to 12 membered monocyclic or bicyclic ring with up to five heteroatoms selected from oxygen, nitrogen and sulphur, wherein a ring sulphur or nitrogen atom is optionally oxidised to form the N or S-oxide(s). It is to be understood that the definition of heterocyclyl includes bridged ring systems and spiro ring systems. Suitable examples include oxiranyl, oxetanyl, tetrahydrofuranyl, tetrahydropyranyl, oxepanyl, tetrahydrothienyl, 1,1-dioxotetrahydrothienyl, tetrahydrothiopyranyl, 1,1-dioxotetrahydrothiopyranyl, aziridinyl, azetidinyl, pyrrolinyl, pyrrolidinyl, imidazolinyl, imidazolidinyl, pyrazolinyl, pyrazolidinyl, morpholinyl, tetrahydro-1,4-thiazinyl, 1,1-dioxotetrahydro-1,4-thiazinyl, piperidinyl, homopiperidinyl, piperazinyl, homopiperazinyl, 2-azabicyclo[2.2.1]heptyl, quinuclidinyl, chromanyl, isochromanyl, indolinyl, isoindolinyl, dihydropyridinyl, tetrahydropyridinyl, dihydropyrimidinyl, tetrahydropyrimidinyl or 1,4-dioxa-8-azaspiro[4.5]decanyl.

In this specification, unless otherwise specified, the term "heteroaryl" is to be understood as being, for example an aromatic 5- or 6-membered monocyclic ring or a 9- or 10-membered bicyclic ring with up to five ring heteroatoms selected from oxygen, nitrogen and sulphur, wherein a ring sulphur or nitrogen atom is optionally oxidised to form the N or S-oxide(s), for example furyl, pyrrolyl, thienyl, oxazolyl, isoxazolyl, imidazolyl, pyrazolyl, thiazolyl, isothiazolyl, oxadiazolyl, thiadiazolyl, triazolyl, tetrazolyl, pyridyl, pyridazinyl, pyrimidinyl, pyrazinyl, 1,3,5-triazenyl, benzofuranyl, indolyl, benzothienyl, benzoxazolyl, benzimidazolyl, benzothiazolyl, indazolyl, benzofurazanyl, quinolyl, isoquinolyl, quinazolinyl, quinoxalinyl, cinnolinyl or naphthyridinyl.

It is to be understood that, insofar as certain of the compounds of Formula I defined above may exist in optically active or racemic forms by virtue of one or more asymmetric carbon atoms, the invention includes in its definition any such optically active or racemic form which possesses the above-mentioned activity. The synthesis of optically active forms may be carried out by standard techniques of organic chemistry well known in the art, for example by synthesis from optically active starting materials or by resolution of a racemic form. Similarly, the above-mentioned activity may be evaluated using the standard laboratory techniques.

It is to be understood that certain compounds of Formula I defined above may exhibit the phenomenon of tautomerism. It is to be understood that the present invention includes in its definition any such tautomeric form, or a mixture thereof, which possesses the above-mentioned activity and is not to be limited merely to any one tautomeric form utilised within the formulae drawings or named in the Examples. In general, just one of any such tautomeric forms is named in the Examples that follow hereinafter or is presented in any relevant formulae drawings that follow hereinafter.

For the avoidance of doubt, it will be appreciated that when any of $G_1$, $G_2$, $G_3$ and $G_4$ is CH and an $R^3$ group is present, the $G_1$, $G_2$, $G_3$ and $G_4$ groups that are CH can be substituted by the $R^3$ group to give $C(R^3)$.

In structural Formula I, it is to be understood that any CH, $CH_2$, or $CH_3$ in any alkyl group present in the definition of $R^4$ that is connected to $X^1$ or present in the definition of $Q^1$ that is connected to $X^2$, optionally bears a hydroxy or cyano group and optionally bears up to three halogeno groups, preferably fluoro groups. For example, where $Q^1$ is heterocyclyl-propyl-, any $CH_2$ within the propyl group can be substituted, to give, for example, heterocyclyl-$CH_2CH(OH)CH_2$— or heterocyclyl-$CH_2C(F)_2CH_2$— and where $Q^1$ is heterocyclyl-butyl-, any CH, $CH_2$, or $CH_3$ within the butyl group can be substituted, to give, for example, heterocyclyl-$CH_2CH(CF_3)CH_2$—. A further example would be where $R^4$ is hydroxy-propyl-, in which case any $CH_2$ in the propyl group can be substituted, to give, for example, hydroxy-$CH_2C(F)_2CH_2$—.

In structural Formula I, it is to be understood that any CH, $CH_2$, or $CH_3$ in any alkyl group present in the definition of $R^4$ that is connected to $X^1$ or present in the definition of $Q^1$ that is connected to $X^2$, optionally can be replaced by an atom selected from O, S or N or a group such as $SO_2$. For example, where $Q^1$ is heterocyclyl-butyl-, any $CH_2$ within the butyl group can be replaced, to give, for example, heterocyclyl-$CH_2OCH_2CH_2$—, heterocyclyl-$OCH_2CH_2CH_2$— or heterocyclyl-$SO_2CH_2CH_2CH_2$—. A further example would be where $R^4$ is hydroxy-butyl-, in which case any $CH_2$ in the butyl group can be replaced, to give for example hydroxy-$CH_2OCH_2CH_2$—. It is also to be understood that adjacent carbon atoms in any alkyl group present in the definition of $R^4$ that is connected to $X^1$ or present in the definition of $Q^1$ that is connected to $X^2$, optionally may be separated by the insertion into the chain of a group such as C≡C. For example, insertion of a C≡C group into the ethylene chain within a heterocyclyl-ethyl- group would give rise to a group such as heterocyclyl-but-2-ynyl.

Suitable values for the generic radicals referred to above include those set out below.

A suitable value for Ring A when it is a 5- or 6-membered monocyclic heteroaryl ring with up to three ring heteroatoms selected from oxygen, nitrogen and sulphur is, for example, furyl, pyrrolyl, thienyl, oxazolyl, isoxazolyl, imidazolyl, pyrazolyl, thiazolyl, isothiazolyl, oxadiazolyl, thiadiazolyl, triazolyl, pyridyl, pyridazinyl, pyrimidinyl, pyrazinyl or 1,3,5-triazinyl. In a particular group of compounds of the Formula I, Ring A is a pyrazolyl or pyridinyl ring. In a particular group of compounds of the Formula I, Ring A is a pyrazol-4-yl, or pyridin-3-yl ring. In a particular group of compounds of the Formula I, Ring A is a pyrazolyl, pyridinyl or thienyl ring. In a particular group of compounds of the Formula I, Ring A is a pyrazol-4-yl, pyridin-3-yl or thien-2-yl ring. In yet a further particular group of compounds, Ring A is a pyrazolyl, pyridinyl, thienyl, thiazolyl or 1H-1,2,3-triazolyl ring and especially a pyrazol-4-yl, pyridin-3-yl, thien-2-yl, thiazol-5-yl, 1H-1,2,3-triazol-4-yl or 3H-1,2,3-triazol-5-yl ring. In yet a further particular group of compounds, Ring A is a pyrazolyl ring and, especially, a pyrazol-4-yl ring.

A suitable value for Ring A when it is a 8-, 9- or 10-membered bicyclic ring system with up to three ring heteroatoms selected from oxygen, nitrogen and sulphur is, for example, naphthyl, benzofuranyl, indolyl, benzothienyl, benzoxazolyl, benzimidazolyl, benzothiazolyl, indazolyl, benzofurazanyl, quinolyl, isoquinolyl, quinazolinyl, quinoxalinyl, cinnolinyl, naphthyridinyl, 2,3-dihydro-1,4-benzodioxinyl, 1,3-benzodioxolyl or thienopyrrolyl. In a particular group of compounds of the Formula I, Ring A is naphthyl. In a further particular group of compounds of the Formula I, Ring A is a quinolyl, 2,3-dihydro-1,4-benzodioxinyl, 1H-indazolyl, 1H-indolyl or 1,3-benzodioxolyl ring. In yet a further particular group of compounds of the Formula I, Ring A is a quinol-8-yl, quinol-3-yl, quinol-4-yl, 2,3-dihydro-1,4-benzodioxin-6-yl, 1H-indazol-5-yl, 1H-indol-5-yl, 1H-indol-6-yl or 1,3-benzodioxol-5-yl ring.

A suitable value for the heterocyclyl group within the $R^1$ group is, for example, a non-aromatic saturated or partially saturated 3 to 12 membered monocyclic or bicyclic ring with up to five heteroatoms selected from oxygen, nitrogen and sulphur, wherein a ring sulphur or nitrogen atom is optionally oxidised to form the N or S-oxide(s). It is to be understood that the definition of heterocyclyl includes bridged ring systems and spiro ring systems. Suitable examples include oxiranyl, oxetanyl, tetrahydrofuranyl, tetrahydropyranyl, oxepanyl, azepanyl, tetrahydrothienyl, 1,1-dioxotetrahydrothienyl, tetrahydrothiopyranyl, 1,1-dioxotetrahydrothiopyranyl, aziridinyl, azetidinyl, pyrrolinyl, pyrrolidinyl, imidazolinyl, imidazolidinyl, pyrazolinyl, pyrazolidinyl, morpholinyl, tetrahydro-1,4-thiazinyl, 1,1-dioxotetrahydro-1,4-thiazinyl, piperidinyl, homopiperidinyl, piperazinyl, homopiperazinyl, 2-azabicyclo[2.2.1]heptyl, quinuclidinyl, chromanyl, isochromanyl, indolinyl, isoindolinyl, dihydropyridinyl, tetrahydropyridinyl, dihydropyrimidinyl, tetrahydropyrimidinyl or 1,4-dioxa-8-azaspiro[4.5]decanyl. When $Q^1$ is an optionally substituted heterocyclyl, heterocyclyl-(1-6C)alkyl or heterocyclyl-(1-3C)alkyl, particular examples of the heterocyclyl ring include piperidinyl, pyrrolidinyl, morpholinyl, piperazinyl and especially piperidin-4-yl, piperidin-1-yl, pyrrolidin-1-yl, morpholin-4-yl and piperazin-1-yl. In a particular group of compounds, when $Q^1$ is an optionally substituted heterocyclyl, heterocyclyl-(1-6C)alkyl or heterocyclyl-(1-3C) alkyl, particular examples of the heterocyclyl ring include piperidinyl, pyrrolidinyl, morpholinyl, piperazinyl, tetrahydro-2H-pyranyl, azetidinyl, 1,1-dioxotetrahydro-1,4-thiazinyl, imidazolinyl, azepanyl, 1H-imidazolyl, 1,4-diazepanyl, (1R,5S)-8-azabicyclo[3.2.1]octanyl, quinuclidinyl, (3R)-quinuclidinyl, 3,4,4a,5,6,7,8,8a-octahydro-2H-quinolinyl, 3,4,6,7,8,8a-hexahydro-1H-pyrrolo[2,1-c]pyrazinyl and especially piperidin-4-yl, piperidin-1-yl, pyrrolidin-1-yl, morpholin-4-yl, piperazin-1-yl, tetrahydro-2H-pyran-2-yl, piperidin-3-yl, azetidin-3-yl, 1,1-dioxotetrahydro-1,4-thiazin-4-yl, pyrrolidin-2-yl, pyrrolidin-3-yl, imidazolin-1-yl, azepan-1-yl, morpholin-2-yl, 1H-imidazol-1-yl, 1,4-diazepan-1-yl, (1R,5S)-8-azabicyclo[3.2.1]octan-3-yl, quinuclidin-3-yl, (3R)-quinuclidin-3-yl, 3,4,4a,5,6,7,8,8a-octahydro-2H-quinolin-4-yl and 3,4,6,7,8,8a-hexahydro-1H-pyrrolo[2,1-c]pyrazin-2-yl. In a particular group of compounds, when $Q^1$ is an optionally substituted heterocyclyl, heterocyclyl-(1-6C)alkyl or heterocyclyl-(1-3C)alkyl, particular examples of the heterocyclyl ring include piperidinyl, pyrrolidinyl, morpholinyl, piperazinyl, tetrahydro-2H-pyranyl, azetidinyl, 1,1-dioxotetrahydro-1,4-thiazinyl, imidazolinyl, azepanyl, 1H-imidazolyl, 1,4-diazepanyl, (1R,5S)-8-azabicyclo[3.2.1]octanyl, quinuclidinyl, (3R)-quinuclidinyl, 3,4,4a,5,6,7,8,8a-octahydro-2H-quinolinyl, 3,4,6,7,8,8a-hexahydro-1H-pyrrolo[2,1-c]pyrazinyl, 3,8-diazaspiro[5.5]undecanyl, 2,8-diazaspiro[4.5]decanyl, 4,9-diazaspiro[5.5]undecanyl, 2,3,3a,4,6,6a-hexahydro-1H-pyrrolo[3,4-c]pyrrolyl, 3,9-diazaspiro[5.5]undecanyl, (1S,4S)-3,6-diazabicyclo[2.2.1]heptanyl and especially piperidin-4-yl, piperidin-1-yl, piperidin-2-yl, pyrrolidin-1-yl, pyrrolidin-2-yl, morpholin-4-yl, piperazin-1-yl, tetrahydro-2H-pyran-2-yl, tetrahydro-2H-pyran-4-yl, piperidin-3-yl, azetidin-3-yl, 1,1-dioxotetrahydro-1,4-thiazin-4-yl, pyrrolidin-2-yl, pyrrolidin-3-yl, imidazolin-1-yl, azepan-1-yl, azepan-4-yl, morpholin-2-yl, 1H-imidazol-1-yl, 1,4-diazepan-1-yl, (1R,5S)-8-azabicyclo[3.2.1]octan-3-yl, quinuclidin-3-yl, (3R)-quinuclidin-3-yl, 3,4,4a,5,6,7,8,8a-octahydro-2H-quinolin-4-yl, 3,4,6,7,8,8a-hexahydro-1H-pyrrolo[2,1-c]pyrazin-2-yl, 3,8-diazaspiro[5.5]undecan-3-yl, 2,8-diazaspiro[4.5]decan-8-yl, 4,9-diazaspiro[5.5]undecan-4-yl, 2,3,3a,4,6,6a-hexahydro-1H-pyrrolo[3,4-c]pyrrol-5-yl, 3,9-diazaspiro[5.5]undecan-3-yl and (1S,4S)-3,6-diazabicyclo[2.2.1]heptan-6-yl. When $Q^1$ comprises a heterocyclyl or heterocyclyl-(1-6C)alkyl substituent group on the heterocyclyl, heterocyclyl-(1-6C)alkyl, heteroaryl or heteroaryl-(1-6C)alkyl ring, particular values for the heterocyclyl substituent group include piperidinyl, morpholinyl, pyrrolidinyl, azepanyl and piperazinyl and especially piperidin-1-yl, piperidin-2-yl, morpholin-4-yl, pyrrolidin-1-yl, azepan-1-yl and piperazin-1-yl. In a particular group of compounds, when $Q^1$ comprises a heterocyclyl or heterocyclyl-(1-6C)alkyl substituent group on the heterocyclyl, heterocyclyl-(1-6C)alkyl, heteroaryl or heteroaryl-(1-6C)alkyl ring, particular values for the heterocyclyl substituent group include piperidinyl, morpholinyl, pyrrolidinyl, azepanyl and piperazinyl and especially piperidin-1-yl, piperidin-2-yl, piperidin-4-yl, morpholin-4-yl, pyrrolidin-1-yl, azepan-1-yl and piperazin-1-yl.

A suitable value for the heteroaryl group within the $R^1$ or $R^3$ group is, for example, an aromatic 5- or 6-membered monocyclic ring or a 9- or 10-membered bicyclic ring with up to five ring heteroatoms selected from oxygen, nitrogen and sulphur, wherein a ring sulphur or nitrogen atom is optionally oxidised to form the N or S-oxide(s), for example furyl, pyrrolyl, thienyl, oxazolyl, isoxazolyl, imidazolyl, pyrazolyl, thiazolyl, isothiazolyl, oxadiazolyl, thiadiazolyl, triazolyl, tetrazolyl, pyridyl, pyridazinyl, pyrimidinyl, pyrazinyl, 1,3,5-triazenyl, benzofuranyl, indolyl, benzothienyl, benzoxazolyl, benzimidazolyl, benzothiazolyl, indazolyl, benzofurazanyl, quinolyl, isoquinolyl, quinazolinyl, quinoxalinyl, cinnolinyl or naphthyridinyl. When $Q^1$ is an optionally substituted heteroaryl, heteroaryl-(1-6C)alkyl or heteroaryl-(1-3C)alkyl, particular examples of the heteroaryl ring include pyrazolyl and especially pyrazol-3-yl. In a particular group of compounds, when $Q^1$ is an optionally substituted heteroaryl, heteroaryl-(1-6C)alkyl or heteroaryl-(1-3C)alkyl, particular examples of the heteroaryl ring include pyrazolyl and thienyl and especially pyrazol-3-yl and thien-2-yl. When $Q^1$ comprises a heteroaryl or heteroaryl-(1-6C)alkyl substituent group on the heterocyclyl, heterocyclyl-(1-6C)alkyl, heteroaryl or heteroaryl-(1-6C)alkyl ring, particular values for the heteroaryl substituent group are pyridinyl and especially pyridin-3-yl or pyridin-4-yl. In a particular group of compounds, when $Q^1$ comprises a heteroaryl or heteroaryl-(1-6C) alkyl substituent group on the heterocyclyl, heterocyclyl-(1-6C)alkyl, heteroaryl or heteroaryl-(1-6C)alkyl ring, particular values for the heteroaryl substituent group include pyridinyl and especially pyridin-3-yl, pyridin-4-yl or pyridin-2-yl.

A suitable value for the aryl group within any $R^1$ or $R^3$ group is, for example, phenyl or naphthyl, conveniently phenyl.

A suitable value for the (3-8C)cycloalkyl group within any $R^1$ group is, for example, cyclopropyl, cyclobutyl, cyclopentyl, cyclohexyl, cycloheptyl, bicyclo[2.2.1]heptyl or cyclooctyl.

A suitable value for a heterocyclyl-(1-6C)alkyl is, for example, heterocyclylmethyl, 2-heterocyclylethyl and 3-heterocyclylpropyl. The invention comprises corresponding suitable values when, for example, rather than a heterocyclyl-(1-6C)alkyl group, a heteroaryl-(1-6C)alkyl, an aryl-(1-6C) alkyl or a (3-8C)cycloalkyl-(1-6C)alkyl group is present.

A suitable value for any heterocyclyl group within the $R^3$ group is, for example, a non-aromatic saturated or partially saturated 3 to 12 membered monocyclic or bicyclic ring with up to five heteroatoms selected from oxygen, nitrogen and sulphur, wherein a ring sulphur or nitrogen atom is optionally oxidised to form the N or S-oxide(s). It is to be understood that the definition of heterocyclyl includes bridged ring systems and spiro ring systems. Suitable examples include oxiranyl, oxetanyl, tetrahydrofuranyl, tetrahydropyranyl, oxepanyl, tetrahydrothienyl, 1,1-dioxotetrahydrothienyl, tetrahydrothiopyranyl, 1,1-dioxotetrahydrothiopyranyl, aziridinyl, azetidinyl, pyrrolinyl, pyrrolidinyl, imidazolinyl, imidazolidinyl, pyrazolinyl, pyrazolidinyl, morpholinyl, tetrahydro-1,4-thiazinyl, 1,1-dioxotetrahydro-1,4-thiazinyl, piperidinyl, homopiperidinyl, piperazinyl, homopiperazinyl, 2-azabicyclo[2.2.1]heptyl, quinuclidinyl, chromanyl, isochromanyl, indolinyl, isoindolinyl, dihydropyridinyl, tetrahydropyridinyl, dihydropyrimidinyl, tetrahydropyrimidinyl or 1,4-dioxa-8-azaspiro[4.5]decanyl.

Suitable values for any of the 'R' groups ($R^1$ to $R^3$), or for various groups such as $R^4$ to $R^8$ within an $R^1$ substituent or for various groups such as $R^9$ within a $R^3$ group include, for example:—

| | |
|---|---|
| for halogeno | fluoro, chloro, bromo and iodo; |
| for (1-8C)alkyl: | methyl, ethyl, propyl, isopropyl, tert-butyl, cyclobutyl, cyclohexyl, cyclohexylmethyl and 2-cyclopropylethyl; |
| for (2-8C)alkenyl: | vinyl, isopropenyl, allyl and but-2-enyl; |
| for (2-8C)alkynyl: | ethynyl, 2-propynyl and but-2-ynyl; |
| for (1-6C)alkoxy: | methoxy, ethoxy, propoxy, isopropoxy and butoxy; |
| for (2-6C)alkenyloxy: | vinyloxy and allyloxy; |
| for (2-6C)alkynyloxy: | ethynyloxy and 2-propynyloxy; |
| for (1-6C)alkylthio: | methylthio, ethylthio and propylthio; |
| for (1-6C)alkylsulphinyl: | methylsulphinyl and ethylsulphinyl; |
| for (1-6C)alkylsulphonyl: | methylsulphonyl and ethylsulphonyl; |
| for (1-6C)alkylamino: | methylamino, ethylamino, propylamino, isopropylamino and butylamino; |
| for di-[(1-6C)alkyl]amino: | dimethylamino, diethylamino, N-ethyl-N-methylamino and diisopropylamino; |
| for (1-6C)alkoxycarbonyl: | methoxycarbonyl, ethoxycarbonyl, propoxycarbonyl and tert-butoxycarbonyl; |
| for N-(1-6C)alkylcarbamoyl: | N-methylcarbamoyl, N-ethylcarbamoyl and N-propylcarbamoyl; |
| for N,N-di-[(1-6C)alkyl]carbamoyl: | N,N-dimethylcarbamoyl, N-ethyl-N-methylcarbamoyl and N,N-diethylcarbamoyl; |
| for (2-6C)alkanoyl: | acetyl, propionyl and isobutyryl; |
| for (2-6C)alkanoyloxy: | acetoxy and propionyloxy; |
| for (1-6C)alkanoylamino: | formamido, acetamido and propionamido; |
| for N-(1-6C)alkyl-(1-6C)alkanoylamino: | N-methylformamido, N-methylacetamido and N-methylpropionamido; |
| for N'-(1-6C)alkylureido: | N'-methylureido and N'-ethylureido; |
| for N',N'-di-[(1-6C)alkyl]ureido: | N',N'-dimethylureido and N'-methyl-N'-ethylureido; |
| for N-(1-6C)alkylureido: | N-methylureido and N-ethylureido; |
| for N,N'-di-[(1-6C)alkyl]ureido: | N,N'-dimethylureido, N-methyl-N'-ethylureido and N-ethyl-N'-methylureido; |
| for N,N',N'-tri-[(1-6C)alkyl]ureido: | N,N',N'-trimethylureido, N-ethyl-N',N'-dimethylureido and N-methyl-N',N'-diethylureido; |
| for N-(1-6C)alkylsulphamoyl: | N-methylsulphamoyl and N-ethylsulphamoyl; |
| for N,N-di-[(1-6C)alkyl]sulphamoyl: | N,N-dimethylsulphamoyl; |
| for (1-6C)alkanesulphonylamino: | methanesulphonylamino and ethanesulphonylamino; |
| for N-(1-6C)alkyl-(1-6C)alkanesulphonlylamino: | N-methylmethanesulphonylamino and N-methylethanesulphonylamino; |
| for halogeno-(1-6C)alkyl: | chloromethyl, 2-fluoroethyl, 2-chloroethyl, 1-chloroethyl, 2,2-difluoroethyl, 2,2,2-trifluoroethyl, 3-fluoropropyl, 3-chloropropyl, 3,3-difluoropropyl and 3,3,3-trifluoropropyl; |
| for fluoro-(1-6C)alkyl: | fluoromethyl, difluoromethyl, trifluoromethyl, 2-fluoroethyl, 1-fluoroethyl, 2,2-difluoroethyl, 2,2,2-trifluoroethyl, 3-fluoropropyl, 3,3-difluoropropyl and 3,3,3-trifluoropropyl; |
| for halogeno-(1-6C)alkoxy | fluoromethoxy, chloroethoxy, trifluoromethoxy, 2,2,2-trifluoroethoxy, 3,3-difluoropropoxy, 3,3,3-trifluoropropoxy |
| for hydroxy-(1-6C)alkyl: | hydroxymethyl, 2-hydroxyethyl, 1-hydroxyethyl and 3-hydroxypropyl; |
| for (1-6C)alkoxy-(1-6C)alkyl: | methoxymethyl, ethoxymethyl, 1-methoxyethyl, 2-methoxyethyl, 2-ethoxyethyl and 3-methoxypropyl; |
| for (1-6C)alkylsulphonyl-(1-6C)alkyl: | methylsulphonylmethyl, ethylsulphonylmethyl, 2-methylsulphonylethyl, 1-methylsulphonylethyl and 3-methylsulphonylpropyl; |
| for cyano-(1-6C)alkyl: | cyanomethyl, 2-cyanoethyl, 1-cyanoethyl and 3-cyanopropyl; |
| for amino-(1-6C)alkyl: | aminomethyl, 2-aminoethyl, 1-aminoethyl, 3-aminopropyl and 1-aminopropyl; |
| for (1-6C)alkylamino-(1-6C)alkyl: | methylaminomethyl, ethylaminomethyl, 1-methylaminoethyl, 2-methylaminoethyl, 2-ethylaminoethyl and 3-methylaminopropyl; |
| for di-[(1-6C)alkyl]amino-(1-6C)alkyl: | dimethylaminomethyl, diethylaminomethyl, 1-dimethylaminoethyl, 2-dimethylaminoethyl and 3-dimethylaminopropyl; |

-continued

| | |
|---|---|
| for (1-6C)alkoxy-(1-6C)alkoxy: | methoxymethoxy, ethoxymethoxy, 1-methoxyethoxy, 2-methoxyethoxy, 2-ethoxyethoxy and 3-methoxypropoxy; |
| for hydroxy-(1-6C)alkoxy: | hydroxymethoxy, 2-hydroxyethoxy, 1-hydroxyethoxy and 3-hydroxypropoxy; |
| for amino-(1-6C)alkoxy: | aminomethoxy, 2-aminoethoxy, 1-aminoethoxy, 3-aminopropoxy and 1-aminopropoxy; |
| for (1-6C)alkylamino-(1-6C)alkoxy: | methylaminomethoxy, ethylaminomethoxy, 1-methylaminoethoxy, 2-methylaminoethoxy, 2-ethylaminoethoxy and 3-methylaminopropoxy; |
| for di-[(1-6C)alkyl]amino-(1-6C)alkoxy: | dimethylaminomethoxy, diethylaminomethoxy, 1-dimethylaminoethoxy, 2-dimethylaminoethoxy and 3-dimethylaminopropoxy; |
| for hydroxy-(2-6C)alkanoyl: | 2-hydroxyacetyl, 2-hydroxypropionyl, 3-hydroxypropionyl, 2-hydroxyisobutyryl and 3-hydroxyisobutyryl; |
| for (1-6C)alkoxy-(2-6C)alkanoyl: | 2-methoxyacetyl, 2-methoxypropionyl, 3-methoxypropionyl, 2-methoxyisobutyryl and 3-methoxyisobutyryl; |
| for carbamoyl-(1-6C)alkyl: | carbamoylmethyl, 1-carbamoylethyl, 2-carbamoylethyl and 3-carbamoylpropyl; |
| for N-(1-6C)alkylcarbamoyl-(1-6C)alkyl: | N-methylcarbamoylmethyl, N-ethylcarbamoylmethyl, N-propylcarbamoylmethyl, 1-(N-methylcarbamoyl)ethyl, 1-(N-ethylcarbamoyl)ethyl, 2-(N-methylcarbamoyl)ethyl, 2-(N-ethylcarbamoyl)ethyl and 3-(N-methylcarbamoyl)propyl; |
| for N,N-di-[(1-6C)alkyl]carbamoyl-(1-6C)alkyl: | N,N-dimethylcarbamoylmethyl, N-ethyl-N-methylcarbamoylmethyl, N,N-diethylcarbamoylmethyl, 1-(N,N-dimethylcarbamoyl)ethyl, 1-(N,N-diethylcarbamoyl)ethyl, 2-(N,N-dimethylcarbamoyl)ethyl, 2-(N,N-diethylcarbamoyl)ethyl, 3-(N,N-dimethylcarbamoyl)propyl and 4-(N,N-dimethylcarbamoyl)butyl; |
| for (1-6C)alkoxy-(1-6C)alkoxycarbonyl: | methoxymethoxycarbonyl, 2-methoxyethoxycarbonyl, 3-methoxypropoxycarbonyl, ethoxymethoxycarbonyl, 2-ethoxyethoxycarbonyl; |
| for (1-6C)alkylamino-(2-6C)alkanoyl: | methylaminoacetyl, 3-methylaminopropionyl, ethylaminoacetyl, 3-ethylaminopropionyl, propylaminoacetyl, 3-propylaminopropionyl, butylaminoacetyl, 3-butylaminopropionyl, isopropylaminoacetyl, 3-isopropylaminopropionyl,; |
| for di-[(1-6C)alkyl]amino-(2-6C)alkanoyl: | dimethylaminoacetyl, 3-dimethylaminopropionyl, diethylaminoacetyl, 3-diethylaminopropionyl, (N-ethyl-N-methylamino)acetyl, 3-(N-ethyl-N-methylamino)propionyl, diisopropylaminoacetyl and 3-diisopropylaminopropionyl; |
| for (1-6C)alkanoylamino-(2-6C)alkanoyl: | formamidoacetyl, 3-formamidopropionyl, acetamidoacetyl, 3-acetamidopropionyl, propionamidoacetyl and 3-propionamidopropionyl; |
| for (1-6C)alkoxy-(1-6C)alkoxy-(2-6C)alkanoyl: | methoxymethoxyacetyl, 3-(methoxymethoxy)propionyl, ethoxymethoxyacetyl, 3-(ethoxymethoxy)propionyl, 1-methoxyethoxyacetyl, 3-(1-methoxyethoxy)propionyl, 2-methoxyethoxyacetyl, 3-(2-methoxyethoxy)propionyl, 3-methoxypropoxy acetyl and 3-(3-methoxypropoxy)propionyl. |

When, as defined hereinbefore, an $R^1$ group forms a group of the formula $R^4$—$X^1$— and, for example, $X^1$ is a $OC(R^5)_2$ linking group, it is the carbon atom, not the oxygen atom, of the $OC(R^5)_2$ linking group which is attached to Ring A and the oxygen atom is attached to the $R^4$ group. Similarly, when, as defined hereinbefore, an $R^1$ group forms a group of the formula $Q^1$-$X^2$— and, for example, $X^2$ is a $OC(R^7)_2$ linking group, it is the oxygen atom of the $OC(R^7)_2$ linking group which is attached to the $Q^1$ group.

A suitable value for an $(R^6)$-amino-(1-6C)alkyl group or an $(R^8)$-amino-(1-6C)alkyl group is, for example, trifluoromethylaminomethyl, cyanomethylaminomethyl, 2-cyanoethylaminomethyl, 2-hydroxyethylaminomethyl, 2-methoxyethylaminomethyl, 2-trifluoromethylaminoethyl, 2-(2-hydroxyethylamino)ethyl and 2-(2-methoxyethylamino)ethyl.

A suitable value for a di-$(R^6)$-amino-(1-6C)alkyl group or an di-$(R^8)$-amino-(1-6C)alkyl group is, for example, [(2-hydroxyethyl)(methyl)amino]methyl, di-(2-hydroxyethyl)aminomethyl, di-(2-methoxyethyl)aminomethyl and 1-[(hydroxymethyl)(methyl)amino]ethyl.

A suitable pharmaceutically-acceptable salt of a compound of the Formula I is, for example, an acid-addition salt of a compound of the Formula I, for example an acid-addition salt with an inorganic or organic acid such as hydrochloric, hydrobromic, sulphuric, trifluoroacetic or citric acid; or, for example, a salt of a compound of the Formula I which is sufficiently acidic, for example an alkali or alkaline earth metal salt such as a calcium or magnesium salt, or an ammonium salt, or a salt with an organic base such as methylamine, dimethylamine, trimethylamine, piperidine, morpholine or tris-(2-hydroxyethyl)amine. A further suitable pharmaceutically-acceptable salt of a compound of the Formula I is, for example, a salt formed within the human or animal body after administration of a compound of the Formula I.

It is further to be understood that a suitable pharmaceutically-acceptable solvate of a compound of the Formula I also forms an aspect of the present invention. A suitable pharmaceutically-acceptable solvate is, for example, a hydrate such as a hemi-hydrate, a mono-hydrate, a di-hydrate or a tri-hydrate or an alternative quantity thereof.

It is further to be understood that a suitable pharmaceutically-acceptable pro-drug of a compound of the Formula I also forms an aspect of the present invention. Accordingly, the compounds of the invention may be administered in the form of a pro-drug, that is a compound that is broken down in the human or animal body to release a compound of the invention. A pro-drug may be used to alter the physical properties and/or the pharmacokinetic properties of a compound of the invention. A pro-drug can be formed when the compound of the invention contains a suitable group or substituent to which a property-modifying group can be attached. Examples of pro-drugs include in vivo cleavable ester derivatives that may be formed at a carboxy group or a hydroxy group in a compound of the Formula I and in vivo cleavable amide derivatives that may be formed at a carboxy group or an amino group in a compound of the Formula I.

Accordingly, the present invention includes those compounds of the Formula I as defined hereinbefore when made available by organic synthesis and when made available within the human or animal body by way of cleavage of a pro-drug thereof. Accordingly, the present invention includes those compounds of the Formula I that are produced by organic synthetic means and also such compounds that are produced in the human or animal body by way of metabolism of a precursor compound, that is a compound of the Formula I may be a synthetically-produced compound or a metabolically-produced compound.

A suitable pharmaceutically-acceptable pro-drug of a compound of the Formula I is one that is based on reasonable medical judgement as being suitable for administration to the human or animal body without undesirable pharmacological activities and without undue toxicity.

Various forms of pro-drug have been described, for example in the following documents:— a) *Methods in Enzymology*, Vol. 42, p. 309-396, edited by K. Widder, et al. (Academic Press, 1985);
b) Design of Pro-drugs, edited by H. Bundgaard, (Elsevier, 1985);
c) A Textbook of Drug Design and Development, edited by Krogsgaard-Larsen and H. Bundgaard, Chapter 5 "Design and Application of Pro-drugs", by H. Bundgaard p. 113-191 (1991);
d) H. Bundgaard, *Advanced Drug Delivery Reviews*, 8, 1-38 (1992);
e) H. Bundgaard, et al., *Journal of Pharmaceutical Sciences*, 77, 285 (1988);
f) N. Kakeya, et al., *Chem. Pharm. Bull.*, 32, 692 (1984);
g) T. Higuchi and V. Stella, "Pro-Drugs as Novel Delivery Systems", A.C.S. Symposium Series, Volume 14; and
h) E. Roche (editor), "Bioreversible Carriers in Drug Design", Pergamon Press, 1987.

A suitable pharmaceutically-acceptable pro-drug of a compound of the Formula I that possesses a carboxy group is, for example, an in vivo cleavable ester thereof. An in vivo cleavable ester of a compound of the Formula I containing a carboxy group is, for example, a pharmaceutically-acceptable ester which is cleaved in the human or animal body to produce the parent acid. Suitable pharmaceutically-acceptable esters for carboxy include (1-6C)alkyl esters such as methyl, ethyl and tert-butyl, (1-6C)alkoxymethyl esters such as methoxymethyl esters, (1-6C)alkanoyloxymethyl esters such as pivaloyloxymethyl esters, 3-phthalidyl esters, (3-8C)cycloalkylcarbonyloxy-(1-6C)alkyl esters such as cyclopentylcarbonyloxymethyl and 1-cyclohexylcarbonyloxyethyl esters, 2-oxo-1,3-dioxolenylmethyl esters such as 5-methyl-2-oxo-1,3-dioxolen-4-ylmethyl esters and (1-6C)alkoxycarbonyloxy-(1-6C)alkyl esters such as methoxycarbonyloxymethyl and 1-methoxycarbonyloxyethyl esters.

A suitable pharmaceutically-acceptable pro-drug of a compound of the Formula I that possesses a hydroxy group is, for example, an in vivo cleavable ester or ether thereof. An in vivo cleavable ester or ether of a compound of the Formula I containing a hydroxy group is, for example, a pharmaceutically-acceptable ester or ether which is cleaved in the human or animal body to produce the parent hydroxy compound. Suitable pharmaceutically-acceptable ester forming groups for a hydroxy group include inorganic esters such as phosphate esters (including phosphoramidic cyclic esters). Further suitable pharmaceutically-acceptable ester forming groups for a hydroxy group include (1-10C)alkanoyl groups such as acetyl, benzoyl, phenylacetyl and substituted benzoyl and phenylacetyl groups, (1-10C)alkoxycarbonyl groups such as ethoxycarbonyl, N,N-[di-(1-4C)alkyl]carbamoyl, 2-dialkylaminoacetyl and 2-carboxyacetyl groups. Examples of ring substituents on the phenylacetyl and benzoyl groups include aminomethyl, N-alkylaminomethyl, N,N-dialkylaminomethyl, morpholinomethyl, piperazin-1-ylmethyl and 4-(1-4C)alkylpiperazin-1-ylmethyl. Suitable pharmaceutically-acceptable ether forming groups for a hydroxy group include α-acyloxyalkyl groups such as acetoxymethyl and pivaloyloxymethyl groups.

A suitable pharmaceutically-acceptable pro-drug of a compound of the Formula I that possesses a carboxy group is, for example, an in vivo cleavable amide thereof, for example an amide formed with an amine such as ammonia, a (1-4C)alkylamine such as methylamine, a di-(1-4C)alkylamine such as dimethylamine, N-ethyl-N-methylamine or diethylamine, a (1-4C)alkoxy-(2-4C)alkylamine such as 2-methoxyethylamine, a phenyl-(1-4C)alkylamine such as benzylamine and amino acids such as glycine or an ester thereof.

A suitable pharmaceutically-acceptable pro-drug of a compound of the Formula I that possesses an amino group is, for example, an in vivo cleavable amide derivative thereof. Suitable pharmaceutically-acceptable amides from an amino group include, for example an amide formed with (1-10C)alkanoyl groups such as an acetyl, benzoyl, phenylacetyl and substituted benzoyl and phenylacetyl groups. Examples of ring substituents on the phenylacetyl and benzoyl groups include aminomethyl, N-alkylaminomethyl, N,N-dialkylaminomethyl, morpholinomethyl, piperazin-1-ylmethyl and 4-(1-4C)alkylpiperazin-1-ylmethyl.

The in vivo effects of a compound of the Formula I may be exerted in part by one or more metabolites that are formed within the human or animal body after administration of a compound of the Formula I. As stated hereinbefore, the in vivo effects of a compound of the Formula I may also be exerted by way of metabolism of a precursor compound (a pro-drug).

Particular novel compounds of the invention include, for example, pyridine and pyrazine derivatives of the Formula I, or pharmaceutically-acceptable salts thereof, wherein, unless otherwise stated, each of W, $G_1$, $G_2$, $G_3$, $G_4$, J, Ring A, $R^1$, $R^2$, n and $R^3$ has any of the meanings defined hereinbefore or in paragraphs (a) to (eeee) hereinafter:—

(a) W is CH;
(b) W is N;
(c) J is O;
(d) J is S;
(e) each of $G_1$, $G_2$, $G_3$ and $G_4$ is selected from CH and N provided that not more than one of $G_1$, $G_2$, $G_3$ and $G_4$ represent N;
(f) $G_1$ is N and $G_2$, $G_3$ and $G_4$ are CH;
(g) $G_2$ is N and $G_1$, $G_3$ and $G_4$ are CH;
(h) $G_3$ is N and $G_1$, $G_2$ and $G_4$ are CH;
(i) $G_4$ is N and $G_1$, $G_2$ and $G_3$ are CH;
(j) $G_1$, $G_2$, $G_3$ and $G_4$ are all CH;
(k) Ring A is selected from:
 (i) phenyl substituted by $R^1$ and optionally substituted by an $R^2$ group; or
 (ii) a 5- or 6-membered monocyclic heteroaryl ring with up to three ring heteroatoms selected from oxygen, nitrogen and sulphur, said ring being substituted by $R^1$ and optionally substituted by an $R^2$ group; or
 (iii) a 8-, 9- or 10-membered bicyclic ring system, wherein said bicyclic ring system optionally contains up to three ring heteroatoms selected from oxygen, nitrogen and sulphur and is optionally substituted by $R^1$ and optionally substituted by an $R^2$ group;
(l) Ring A is selected from:
 (i) phenyl substituted by $R^1$ and optionally substituted by an $R^2$ group; or
 (ii) a 5- or 6-membered monocyclic heteroaryl ring with up to three ring nitrogen atoms, said ring being substituted by $R^1$ and optionally substituted by an $R^2$ group; or
 (iii) a 8-, 9- or 10-membered bicyclic ring system, wherein the ring of attachment to the central core pyridinyl ring is a phenyl or a monocyclic heteroaryl ring, and wherein said bicyclic ring system optionally contains up to two ring heteroatoms selected from oxygen and nitrogen and is optionally substituted by $R^1$ and optionally substituted by an $R^2$ group;
(m) Ring A is selected from:
 (i) phenyl substituted by $R^1$ and optionally substituted by an $R^2$ group; or
 (ii) furyl, pyrrolyl, thienyl, oxazolyl, isoxazolyl, imidazolyl, pyrazolyl, thiazolyl, isothiazolyl, oxadiazolyl, thiadiazolyl, triazolyl, pyridyl, pyridazinyl, pyrimidinyl, pyrazinyl or 1,3,5-triazinyl, said ring being substituted by $R^1$ and optionally substituted by an $R^2$ group; or
 (iii) naphthyl, benzofuranyl, indolyl, benzothienyl, benzoxazolyl, benzimidazolyl, benzothiazolyl, indazolyl, benzofurazanyl, quinolyl, isoquinolyl, quinazolinyl, quinoxalinyl, cinnolinyl, naphthyridinyl, 2,3-dihydro-1,4-benzodioxinyl or 1,3-benzodioxolyl, wherein said bicyclic ring system is optionally substituted by $R^1$ and optionally substituted by an $R^2$ group;
(n) Ring A is selected from:
 (i) phenyl substituted by $R^1$ and optionally substituted by an $R^2$ group; or
 (ii) pyrazolyl or pyridinyl, said ring being substituted by $R^1$ and optionally substituted by an $R^2$ group; or
 (iii) naphthyl, quinolyl, 2,3-dihydro-1,4-benzodioxinyl, 1H-indazolyl, 1H-indolyl or 1,3-benzodioxolyl, wherein said bicyclic ring system is optionally substituted by $R^1$ and optionally substituted by an $R^2$ group;
(o) Ring A is selected from:
 (i) phenyl substituted by $R^1$ and optionally substituted by an $R^2$ group; or
 (ii) pyrazol-4-yl or pyridin-3-yl, said ring being substituted by $R^1$ and optionally substituted by an $R^2$ group; or
 (iii) naphthyl, quinol-8-yl, quinol-3-yl, quinol-4-yl, 2,3-dihydro-1,4-benzodioxin-6-yl, 1H-indazol-5-yl, 1H-indol-5-yl, 1H-indol-6-yl or 1,3-benzodioxol-5-yl, wherein said bicyclic ring system is optionally substituted by $R^1$ and optionally substituted by an $R^2$ group;
(p) Ring A is phenyl substituted by $R^1$ and optionally substituted by an $R^2$ group;
(q) Ring A is a 5- or 6-membered monocyclic heteroaryl ring with up to three ring nitrogen atoms, said ring being substituted by $R^1$ and optionally substituted by an $R^2$ group;
(r) Ring A is a 8-, 9- or 10-membered bicyclic ring system, wherein said bicyclic ring system optionally contains up to three ring heteroatoms selected from oxygen, nitrogen and sulphur and is optionally substituted by $R^1$ and optionally substituted by an $R^2$ group;
(s) Ring A is a 8-, 9- or 10-membered bicyclic ring system, wherein the ring of attachment to the central core pyridinyl ring is a phenyl or a monocyclic heteroaryl ring, and wherein said bicyclic ring system optionally contains up to two ring heteroatoms selected from oxygen and nitrogen and is optionally substituted by $R^1$ and optionally substituted by an $R^2$ group;
(t) Ring A is naphthyl optionally substituted by $R^1$ and optionally substituted by an $R^2$ group;
(u) Ring A is quinol-8-yl, quinol-3-yl, quinol-4-yl, 2,3-dihydro-1,4-benzodioxin-6-yl, 1H-indazol-5-yl, 1H-indol-5-yl, 1H-indol-6-yl or 1,3-benzodioxol-5-yl, wherein said bicyclic ring system is optionally substituted by $R^1$ and optionally substituted by an $R^2$ group;
(v) $R^1$ is a group of the formula:

$$R^4-X^1-$$

wherein $X^1$ is a direct bond or is selected from O, SO, $SO_2$, $N(R^5)$, CO, $CON(R^5)$, $N(R^5)CO$, $SO_2N(R^5)$, $N(R^5)SO_2$, $C(R^5)_2O$, $OC(R^5)_2$, $C(R^5)_2$, $C(R^5)_2N(R^5)$ and $N(R^5)C(R^5)_2$, wherein each $R^5$ is independently selected from hydrogen or (1-8C)alkyl;

and when $X^1$ is a direct bond or is selected from $C(R^5)_2O$, $C(R^5)_2$ or $C(R^5)_2N(R^5)$, wherein $R^5$ has any of the meanings defined hereinbefore, $R^4$ is hydroxy-(1-6C)alkyl, (1-6C)alkoxy-(1-6C)alkyl, $R^5$—S, $R^5$—S(O), $R^5$—$SO_2$, $R^5$—S-(1-6C)alkyl, $R^5$—S(O)-(1-6C)alkyl, $R^5$—$SO_2$-(1-6C)alkyl, N,N-di-($R^5$)sulphamoyl, N,N-di-($R^5$)sulphamoyl-(1-6C)alkyl, $R^5$—$SO_2N(R^5)$, $R^5$—$SO_2N(R^5)$-(1-6C)alkyl, $R^5$—$CON(R^5)$, $R^5O$—$CON(R^5)$, $R^5$—$CON(R^5)$-(1-6C)alkyl, $R^5O$—$CON(R^5)$-(1-6C)alkyl, $(R^5)_2N$—$SO_2N(R^5)$, $(R^5)_2N$—$SO_2N(R^5)$-(1-6C)alkyl, $(R^5)_2N$—$CON(R^5)$, $(R^5)_2N$—$CON(R^5)$-(1-6C)alkyl, $R^5$—CO, $R^5$—CO-(1-6C)alkyl, $R^5O$—CO-(1-6C)alkyl, $(R^5)_2NCO$, $(R^5)_2NCO$-(1-6C)alkyl, $(R^5)_2N$—COO, $(R^5)_2NCOO$-(1-6C)alkyl, cyano, amino, $(R^6)$-amino, di-$(R^6)$-amino, amino-(1-6C)alkyl, $(R^6)$-amino-(1-6C)alkyl or di-$(R^6)$-amino-(1-6C)alkyl, wherein each $R^6$ present is (1-6C)alkyl optionally substituted by 1, 2 or 3 substituents independently selected from halogeno, cyano, hydroxy and (1-6C)alkoxy; and when $X^1$ is selected from O, SO, $SO_2$, $N(R^5)$, CO, $CON(R^5)$, $N(R^5)CO$, $SO_2N(R^5)$, $N(R^5)SO_2$, $OC(R^5)_2$ and $N(R^5)C(R^5)_2$, wherein $R^5$ has any of the meanings defined hereinbefore, $R^4$ is hydroxy-(1-6C)alkyl, (1-6C)alkoxy-(1-6C)alkyl, $R^5$—S-(1-6C)alkyl, $R^5$—S(O)-(1-6C)alkyl, $R^5$—$SO_2$-(1-6C)alkyl, N,N-di-$(R^5)$sulphamoyl-(1-6C)alkyl, $R^5$—$SO_2N(R^5)$-(1-6C)alkyl, $R^5$—$CON(R^5)$-(1-6C)alkyl, $R^5O$—$CON(R^5)$-(1-6C)alkyl, $(R^5)_2N$—$SO_2N(R^5)$-(1-6C)alkyl, $(R^5)_2N$—$CON(R^5)$-(1-6C)alkyl, $R^5$—CO, $R^5$—CO-(1-6C)alkyl, $R^{5O}$—Co, $R^5O$—CO-(1-6C)alkyl, $(R^5)_2NCO$, $(R^5)_2NCO$-(1-6C)alkyl, $(R^5)_2NCOO$-(1-6C)alkyl, amino-(1-6C)alkyl, $(R^6)$-amino-(1-6C)alkyl or di-$(R^6)$-amino-(1-6C)alkyl, wherein each $R^6$ present is (1-6C)alkyl optionally substituted by 1, 2 or 3 substituents independently selected from halogeno, cyano, hydroxy and (1-6C)alkoxy;

or $R^1$ is a group of the formula:

$Q^1$-$X^2$— wherein $X^2$ is a direct bond or is selected from O, SO, $SO_2$, $N(R^7)$, $N[C(O)R^7]$, $N[C(O)N(R^7)_2]$, $N[C(O)OR^7]$, $N[SO_2$—$N(R^7)_2]$, CO, $CON(R^7)$, $N(R^7)CO$, $SO_2N(R^7)$, $N(R^7)SO_2$, O—$SO_2$, $SO_2$—O, $C(R^7)_2O$, $OC(R^7)_2$, $C(R^7)_2$, $C(R^7)_2N(R^7)$ and $N(R^7)C(R^7)_2$, wherein each $R^7$ is independently selected from hydrogen or (1-8C)alkyl;

and $Q^1$ is aryl, aryl-(1-6C)alkyl, (3-8C)cycloalkyl, (3-8C)cycloalkyl-(1-6C)alkyl, heterocyclyl, heterocyclyl-(1-6C)alkyl, heteroaryl or heteroaryl-(1-6C)alkyl, wherein any aryl or (3-8C)cycloalkyl group within a $R^1$ substituent bears 1, 2 or 3 substituents and any heterocyclyl or heteroaryl group within a $R^1$ substituent optionally bears 1, 2 or 3 substituents, wherein said substituents are independently selected from halogeno, trifluoromethyl, cyano, nitro, hydroxy, amino, carboxy, carbamoyl, ureido, (1-8C)alkyl, (2-8C)alkenyl, (2-8C)alkynyl, (1-6C)alkoxy, halogeno-(1-6C)alkoxy, hydroxy-(1-6C)alkyl, (1-6C)alkoxy-(1-6C)alkyl, (1-6C)alkylsulphonyl-(1-6C)alkyl, cyano-(1-6C)alkyl, halogeno-(1-6C)alkyl, amino-(1-6C)alkyl, (1-6C)alkylamino-(1-6C)alkyl, di-[(1-6C)alkyl]amino-(1-6C)alkyl, (2-6C)alkenyloxy, (2-6C)alkynyloxy, (1-6C)alkylthio, (1-6C)alkylsulphinyl, (1-6C)alkylsulphonyl, (1-6C)alkylamino, di-[(1-6C)alkyl]amino, (1-6C)alkoxycarbonyl, (2-6C)alkanoyl, (2-6C)alkanoyloxy, N-(1-6C)alkylcarbamoyl, N,N-di-[(1-6C)alkyl]carbamoyl, (1-6C)alkanoylamino, N-(1-6C)alkyl-(1-6C)alkanoylamino, N-(1-6C)alkylureido, N'-(1-6C)alkylureido, N',N'-di-[(1-6C)alkyl]ureido, N,N-di-[(1-6C)alkyl]ureido, N,N',N'-tri-[(1-6C)alkyl]ureido, N-(1-6C)alkylsulphamoyl, N,N-di-[(1-6C)alkyl]sulphamoyl, (1-6C)alkanesulphonylamino, N-(1-6C)alkyl-(1-6C)alkanesulphonylamino or heterocyclyl-(1-6C)alkyl, and any heterocyclyl group within a $R^1$ substituent optionally bears 1 or 2 oxo substituents;

(w) $R^1$ is a group of the formula:

$R^4$—$X^1$— wherein $X^1$ is a direct bond or is selected from O, SO, $SO_2$, $N(R^5)$, CO, $CON(R^5)$, $N(R^5)CO$, $SO_2N(R^5)$, $N(R^5)SO_2$, $C(R^5)_2O$, $OC(R^5)_2$, $C(R^5)_2$, $C(R^5)_2N(R^5)$ and $N(R^5)C(R^5)_2$, wherein each $R^5$ is independently selected from hydrogen or (1-8C)alkyl, and when $X^1$ is a direct bond or is selected from $C(R^5)_2O$, $C(R^5)_2$ or $C(R^5)_2N(R^5)$, wherein $R^5$ has any of the meanings defined hereinbefore, $R^4$ is hydroxy-(1-6C)alkyl, (1-6C)alkoxy-(1-6C)alkyl, $R^5$—S, $R^5$—S(O), $R^5$—$SO_2$, $R^5$—S-(1-6C)alkyl, $R^5$—S(O)-(1-6C)alkyl, $R^5$—$SO_2$-(1-6C)alkyl, N,N-di-$(R^5)$sulphamoyl, N,N-di-$(R^5)$sulphamoyl-(1-6C)alkyl, $R^5$—$SO_2N(R^5)$, $R^5$—$SO_2N(R^5)$-(1-6C)alkyl, $R^5$—$CON(R^5)$, $R^5O$—$CON(R^5)$, $R^5$—$CON(R^5)$-(1-6C)alkyl, $R^5O$—$CON(R^5)$-(1-6C)alkyl, $(R^5)_2N$—$SO_2N(R^5)$, $(R^5)_2N$—$SO_2N(R^5)$-(1-6C)alkyl, $(R^5)_2N$—$CON(R^5)$, $(R^5)_2N$—$CON(R^5)$-(1-6C)alkyl, $R^5$—CO, $R^5$—CO-(1-6C)alkyl, $R^5O$—CO-(1-6C)alkyl, $(R^5)_2NCO$, $(R^5)_2NCO$-(1-6C)alkyl, $(R^5)_2N$—COO, $(R^5)_2NCOO$-(1-6C)alkyl, cyano, amino, $(R^6)$-amino, di-$(R^6)$-amino, amino-(1-6C)alkyl, $(R^6)$-amino-(1-6C)alkyl or di-$(R^6)$-amino-(1-6C)alkyl, wherein each $R^6$ present is (1-6C)alkyl optionally substituted by 1, 2 or 3 substituents independently selected from halogeno, cyano, hydroxy and (1-6C)alkoxy; and when $X^1$ is selected from O, SO, $SO_2$, $N(R^5)$, CO, $CON(R^5)$, $N(R^5)CO$, $SO_2N(R^5)$, $N(R^5)SO_2$, $OC(R^5)_2$ and $N(R^5)C(R^5)_2$, wherein $R^5$ has any of the meanings defined hereinbefore, $R^4$ is hydroxy-(1-6C)alkyl, (1-6C)alkoxy-(1-6C)alkyl, $R^5$—S-(1-6C)alkyl, $R^5$—S(O)-(1-6C)alkyl, $R^5$—$SO_2$-(1-6C)alkyl, N,N-di-$(R^5)$sulphamoyl-(1-6C)alkyl, $R^5$—$SO_2N(R^5)$-(1-6C)alkyl, $R^5$—$CON(R^5)$-(1-6C)alkyl, $R^5O$—$CON(R^5)$-(1-6C)alkyl, $(R^5)_2N$—$SO_2N(R^5)$-(1-6C)alkyl, $(R^5)_2N$—$CON(R^5)$-(1-6C)alkyl, $R^5$—CO, $R^5$—CO-(1-6C)alkyl, $R^5O$—CO, $R^5O$—CO-(1-6C)alkyl, $(R^5)_2NCO$, $(R^5)_2NCO$-(1-6C)alkyl, $(R^5)_2NCOO$-(1-6C)alkyl, amino-(1-6C)alkyl, $(R^6)$-amino-(1-6C)alkyl or di-$(R^6)$-amino-(1-6C)alkyl, wherein each $R^6$ present is (1-6C)alkyl optionally substituted by 1, 2 or 3 substituents independently selected from halogeno, cyano, hydroxy and (1-6C)alkoxy;

or $R^1$ is a group of the formula:

$Q^1$-$X^2$— wherein $X^2$ is a direct bond or is selected from O, SO, $SO_2$, $N(R^7)$, $N[C(O)R^7]$, $N[C(O)N(R^7)_2]$, $N[C(O)OR^7]$, $N[SO_2$—$N(R^7)_2]$, CO, $CON(R^7)$, $N(R^7)CO$, $SO_2N(R^7)$, $N(R^7)SO_2$, O—$SO_2$, $SO_2$—O, $C(R^7)_2O$, $OC(R^7)_2$, $C(R^7)_2$, $C(R^7)_2N(R^7)$ and $N(R^7)C(R^7)_2$, wherein each $R^7$ is independently selected from hydrogen or (1-8C)alkyl;

and $Q^1$ is heterocyclyl, heterocyclyl-(1-6C)alkyl, heteroaryl or heteroaryl-(1-6C)alkyl, wherein any heterocyclyl or heteroaryl group within a $R^1$ substituent optionally bears 1, 2 or 3 substituents, wherein said substituents are independently selected from halogeno, trifluoromethyl, cyano, nitro, hydroxy, amino, carboxy, carbamoyl, ureido, (1-8C)alkyl, (2-8C)alkenyl, (2-8C)alkynyl, (1-6C)alkoxy, halogeno-(1-6C)alkoxy, hydroxy-(1-6C)alkyl, (1-6C)alkoxy-(1-6C)alkyl, cyano-(1-6C)alkyl, halogeno-(1-6C)alkyl, amino-(1-6C)alkyl, (1-6C)alkylamino-(1-6C)alkyl, di-[(1-6C)alkyl]amino-(1-6C)alkyl, (2-6C)alkenyloxy, (2-6C)alkynyloxy, (1-6C)alkylthio, (1-6C)alkylsulphinyl, (1-6C)alkylsulphonyl, (1-6C)alkylamino, di-[(1-6C)alkyl]amino, (1-6C)alkoxycarbonyl, (2-6C)alkanoyl, (2-6C)alkanoyloxy, N-(1-6C)alkylcarbamoyl, N,N-di-[(1-6C)alkyl]carbamoyl, (1-6C)alkanoylamino, N-(1-6C)alkylsulphamoyl, or heterocyclyl-(1-6C)alkyl, and any heterocyclyl group within a $R^1$ substituent optionally bears 1 or 2 oxo substituents;

(x) $R^1$ is a group of the formula:

$R^4$—$X^1$— wherein $X^1$ is a direct bond or is selected from O, SO, $SO_2$, $N(R^5)$, CO, $CON(R^5)$, $N(R^5)CO$, $SO_2N(R^5)$, $N(R^5)SO_2$, $C(R^5)_2O$, $OC(R^5)_2$, $C(R^5)_2$, $C(R^5)_2N(R^5)$ and $N(R^5)C(R^5)_2$, wherein each $R^5$ is independently selected from hydrogen or (1-8C)alkyl, and when $X^1$ is a direct bond or is selected from $C(R^5)_2O$, $C(R^5)_2$ or $C(R^5)_2N(R^5)$, wherein $R^5$ has any of the meanings defined hereinbefore, $R^4$ is hydroxy-(1-6C)alkyl, (1-6C)alkoxy-(1-6C)alkyl, $R^5$—S, $R^5$—S(O), $R^5$—$SO_2$, $R^5$—S-(1-6C)alkyl, $R^5$—S(O)-(1-6C)alkyl, $R^5$—$SO_2$-(1-6C)alkyl, N,N-di-$(R^5)$sulphamoyl, N,N-di-$(R^5)$sulphamoyl-(1-6C)

alkyl, $R^5$—$SO_2N(R^5)$, $R^5$—$SO_2N(R^5)$-(1-6C)alkyl, $R^5$—$CON(R^5)$, $R^5O$—$CON(R^5)$, $R^5$—$CON(R^5)$-(1-6C)alkyl, $R^5O$—$CON(R^5)$-(1-6C)alkyl, $(R^5)_2N$—$SO_2N(R^5)$, $(R^5)_2N$—$SO_2N(R^5)$-(1-6C)alkyl, $(R^5)_2N$—$CON(R^5)$, $(R^5)_2N$—$CON(R^5)$-(1-6C)alkyl, $R^5$—$CO$, $R^5$—$CO$-(1-6C)alkyl, $R^5O$—$CO$-(1-6C)alkyl, $(R^5)_2NCO$, $(R^5)_2NCO$-(1-6C)alkyl, $(R^5)_2N$—$COO$, $(R^5)_2NCOO$-(1-6C)alkyl, cyano, amino, $(R^6)$-amino, di-$(R^6)$-amino, amino-(1-6C)alkyl, $(R^6)$-amino-(1-6C)alkyl or di-$(R^6)$-amino-(1-6C)alkyl, wherein each $R^6$ present is (1-6C)alkyl optionally substituted by 1, 2 or 3 substituents independently selected from halogeno, cyano, hydroxy and (1-6C)alkoxy;

and when $X^1$ is selected from O, SO, $SO_2$, $N(R^5)$, CO, CON $(R^5)$, $N(R^5)CO$, $SO_2N(R^5)$, $N(R^5)SO_2$, $OC(R^5)_2$ and $N(R^5)C$ $(R^5)_2$, wherein $R^5$ has any of the meanings defined hereinbefore, $R^4$ is hydroxy-(1-6C)alkyl, (1-6C)alkoxy-(1-6C)alkyl, $R^5$—S-(1-6C)alkyl, $R^5$—S(O)-(1-6C)alkyl, $R^5$—$SO_2$-(1-6C)alkyl, N,N-di-$(R^5)$sulphamoyl-(1-6C)alkyl, $R^5$—$SO_2N$ $(R^5)$-(1-6C)alkyl, $R^5$—$CON(R^5)$-(1-6C)alkyl, $R^5O$—CON $(R^5)$-(1-6C)alkyl, $(R^5)_2N$—$SO_2N(R^5)$-(1-6C)alkyl, $(R^5)_2$ N—$CON(R^5)$-(1-6C)alkyl, $R^5$—CO, $R^5$—CO-(1-6C)alkyl, $R^5O$—Co, $R^5O$—CO-(1-6C)alkyl, $(R^5)_2NCO$, $(R^5)_2NCO$-(1-6C)alkyl, $(R^5)_2NCOO$-(1-6C)alkyl, amino-(1-6C)alkyl, $(R^6)$-amino-(1-6C)alkyl or di-$(R^6)$-amino-(1-6C)alkyl, wherein each $R^6$ present is (1-6C)alkyl optionally substituted by 1, 2 or 3 substituents independently selected from halogeno, cyano, hydroxy and (1-6C)alkoxy;

or $R^1$ is a group of the formula:

$Q^1$-$X^2$— wherein $X^2$ is a direct bond or is selected from O, SO, $SO_2$, $N(R^7)$, $N[C(O)R^7]$, $N[C(O)N(R^7)_2]$, $N[C(O)OR^7]$, $N[SO_2$—$N(R^7)_2]$, CO, $CON(R^7)$, $N(R^7)CO$, $SO_2N(R^7)$, $N(R^7)SO_2$, O—$SO_2$, $SO_2$—O, $C(R^7)_2O$, $OC(R^7)_2$, $C(R^7)_2$, $C(R^7)_2N(R^7)$ and $N(R^7)C(R^7)_2$, wherein each $R^7$ is independently selected from hydrogen or (1-8C)alkyl;

and $Q^1$ is heterocyclyl, heterocyclyl-(1-6C)alkyl, heteroaryl or heteroaryl-(1-6C)alkyl, wherein any heterocyclyl or heteroaryl group within a $R^1$ substituent optionally bears 1, 2 or 3 substituents, wherein said substituents are independently selected from halogeno, trifluoromethyl, cyano, hydroxy, amino, carboxy, (1-8C)alkyl, (2-8C)alkenyl, (2-8C)alkynyl, (1-6C)alkoxy, halogeno-(1-6C)alkoxy, hydroxy-(1-6C)alkyl, (1-6C)alkoxy-(1-6C)alkyl, halogeno-(1-6C)alkyl, amino-(1-6C)alkyl, (1-6C)alkylamino-(1-6C)alkyl, di-[(1-6C)alkyl]amino-(1-6C)alkyl, (1-6C)alkylamino, di-[(1-6C)alkyl]amino, (1-6C)alkoxycarbonyl, N-(1-6C)alkylcarbamoyl, (1-6C)alkanoylamino or heterocyclyl-(1-6C)alkyl, and any heterocyclyl group within a $R^1$ substituent optionally bears 1 or 2 oxo substituents;

(y) $R^1$ is a group of the formula:

$R^4$—$X^1$— wherein $X^1$ is a direct bond or is selected from O, SO, $SO_2$, $N(R^5)$, CO, $CON(R^5)$, $N(R^5)CO$, $SO_2N(R^5)$, $N(R^5)SO_2$, $C(R^5)_2O$, $OC(R^5)_2$, $C(R^5)_2$, $C(R^5)_2N(R^5)$ and $N(R^5)C(R^5)_2$, wherein each $R^5$ is independently selected from hydrogen or (1-8C)alkyl, and when $X^1$ is a direct bond or is selected from $C(R^5)_2O$, $C(R^5)_2$ or $C(R^5)_2N(R^5)$, wherein $R^5$ has any of the meanings defined hereinbefore, $R^4$ is hydroxy-(1-6C)alkyl, (1-6C)alkoxy-(1-6C)alkyl, $R^5$—S, $R^5$—S(O), $R^5$—$SO_2$, $R^5$—S-(1-6C)alkyl, $R^5$—S(O)-(1-6C)alkyl, $R^5$—$SO_2$-(1-6C)alkyl, N,N-di-$(R^5)$sulphamoyl, N,N-di-$(R^5)$sulphamoyl-(1-6C) alkyl, $R^5$—$SO_2N(R^5)$, $R^5$—$SO_2N(R^5)$-(1-6C)alkyl, $R^5$—$CON(R^5)$, $R^5$—$CON(R^5)$-(1-6C)alkyl, $R^5$—CO, $R^5$—CO-(1-6C)alkyl, $(R^5)_2NCO$, $(R^5)_2NCO$-(1-6C)alkyl, cyano, amino, $(R^6)$-amino, di-$(R^6)$-amino, amino-(1-6C)alkyl, $(R^6)$-amino-(1-6C)alkyl or di-$(R^6)$-amino-(1-6C)alkyl, wherein each $R^6$ present is (1-6C)alkyl;

and when $X^1$ is selected from O, SO, $SO_2$, $N(R^5)$, CO, CON $(R^5)$, $N(R^5)CO$, $SO_2N(R^5)$, $N(R^5)SO_2$, $OC(R^5)_2$ and $N(R^5)C$ $(R^5)_2$, wherein $R^5$ has any of the meanings defined hereinbefore, $R^4$ is hydroxy-(1-6C)alkyl, (1-6C)alkoxy-(1-6C)alkyl, $R^5$—S-(1-6C)alkyl, $R^5$—S(O)-(1-6C)alkyl, $R^5$—$SO_2$-(1-6C)alkyl, $R^5$—$CON(R^5)$-(1-6C)alkyl, $R^5$—CO-(1-6C)alkyl, $(R^5)_2NCO$-(1-6C)alkyl, amino-(1-6C)alkyl, $(R^6)$-amino-(1-6C)alkyl or di-$(R^6)$-amino-(1-6C)alkyl, wherein each $R^6$ present is (1-6C)alkyl;

or $R^1$ is a group of the formula:

$Q^1$-$X^2$— wherein $X^2$ is a direct bond or is selected from O, SO, $SO_2$, $N(R^7)$, $N[C(O)R^7]$, $N[C(O)N(R^7)_2]$, $N[C(O)OR^7]$, $N[SO_2$—$N(R^7)_2]$, CO, $CON(R^7)$, $N(R^7)CO$, $SO_2N(R^7)$, $N(R^7)SO_2$, O—$SO_2$, $SO_2$—O, $C(R^7)_2O$, $OC(R^7)_2$, $C(R^7)_2$, $C(R^7)_2N(R^7)$ and $N(R^7)C(R^7)_2$, wherein each $R^7$ is independently selected from hydrogen or (1-8C)alkyl;

and $Q^1$ is heterocyclyl, heterocyclyl-(1-6C)alkyl, heteroaryl or heteroaryl-(1-6C)alkyl, wherein any heterocyclyl or heteroaryl group within a $R^1$ substituent optionally bears 1, 2 or 3 substituents, wherein said substituents are independently selected from halogeno, trifluoromethyl, cyano, hydroxy, amino, carboxy, (1-8C)alkyl, (2-8C)alkenyl, (2-8C)alkynyl, (1-6C)alkoxy, halogeno-(1-6C)alkoxy, hydroxy-(1-6C)alkyl, (1-6C)alkoxy-(1-6C)alkyl, halogeno-(1-6C)alkyl, amino-(1-6C)alkyl, (1-6C)alkylamino-(1-6C)alkyl, di-[(1-6C)alkyl]amino-(1-6C)alkyl, (1-6C)alkylamino, di-[(1-6C)alkyl]amino, (1-6C)alkoxycarbonyl, N-(1-6C)alkylcarbamoyl, (1-6C)alkanoylamino or heterocyclyl-(1-6C)alkyl, and any heterocyclyl group within a $R^1$ substituent optionally bears 1 or 2 oxo substituents;

(z) $R^1$ is a group of the formula:

$R^4$—$X^1$— wherein $X^1$ is a direct bond or is selected from O, SO, $SO_2$, $N(R^5)$, CO, $CON(R^5)$, $N(R^5)CO$, $SO_2N(R^5)$, $N(R^5)SO_2$, $C(R^5)_2O$, $OC(R^5)_2$, $C(R^5)_2$, $C(R^5)_2N(R^5)$ and $N(R^5)C(R^5)_2$, wherein each $R^5$ is independently selected from hydrogen or (1-8C)alkyl, and when $X^1$ is a direct bond or is selected from $C(R^5)_2O$, $C(R^5)_2$ or $C(R^5)_2N(R^5)$, wherein $R^5$ has any of the meanings defined hereinbefore, $R^4$ is hydroxy-(1-3C)alkyl, (1-6C)alkoxy-(1-3C)alkyl, $R^5$—S, $R^5$—S(O), $R^5$—$SO_2$, $R^5$—S-(1-3C)alkyl, $R^5$—S(O)-(1-3C)alkyl, $R^5$—$SO_2$-(1-3C)alkyl, N,N-di-$(R^5)$sulphamoyl, N,N-di-$(R^5)$sulphamoyl-(1-3C) alkyl, $R^5$—$SO_2N(R^5)$, $R^5$—$SO_2N(R^5)$-(1-3C)alkyl, $R^5$—$CON(R^5)$, $R^5$—$CON(R^5)$-(1-3C)alkyl, $R^5$—CO, $R^5$—CO-(1-3C)alkyl, $(R^5)_2NCO$, $(R^5)_2NCO$-(1-3C)alkyl, cyano, amino, $(R^6)$-amino, di-$(R^6)$-amino, amino-(1-3C)alkyl, $(R^6)$-amino-(1-3C)alkyl or di-$(R^6)$-amino-(1-3C)alkyl, wherein each $R^6$ present is (1-3C)alkyl;

and when $X^1$ is selected from O, SO, $SO_2$, $N(R^5)$, CO, CON $(R^5)$, $N(R^5)CO$, $SO_2N(R^5)$, $N(R^5)SO_2$, $OC(R^5)_2$ and $N(R^5)C$ $(R^5)_2$, wherein $R^5$ has any of the meanings defined hereinbefore, $R^4$ is hydroxy-(1-3C)alkyl, (1-6C)alkoxy-(1-3C)alkyl, $R^5$—S-(1-3C)alkyl, $R^5$—S(O)-(1-3C)alkyl, $R^5$—$SO_2$-(1-3C)alkyl, $R^5$—$CON(R^5)$-(1-3C)alkyl, $R^5$—CO-(1-3C)alkyl, $(R^5)_2NCO$-(1-3C)alkyl, amino-(1-3C)alkyl, $(R^6)$-amino-(1-3C)alkyl or di-$(R^6)$-amino-(1-3C)alkyl, wherein each $R^6$ present is (1-3C)alkyl;

or $R^1$ is a group of the formula:

$Q^1$-$X^2$— wherein $X^2$ is a direct bond or is selected from O, SO, $SO_2$, $N(R^7)$, $N[C(O)R^7]$, $N[C(O)N(R^7)_2]$, $N[C(O)OR^7]$, $N[SO_2—N(R^7)_2]$, CO, $CON(R^7)$, $N(R^7)CO$, $SO_2N(R^7)$, $N(R^7)SO_2$, $O—SO_2$, $SO_2—O$, $C(R^7)_2O$, $OC(R^7)_2$, $C(R^7)_2$, $C(R^7)_2N(R^7)$ and $N(R^7)C(R^7)_2$, wherein each $R^7$ is independently selected from hydrogen or (1-8C)alkyl;

and $Q^1$ is heterocyclyl or heterocyclyl-(1-3C)alkyl, wherein any heterocyclyl group within a $R^1$ substituent optionally bears a halogeno, trifluoromethyl, cyano, hydroxy, amino, carboxy, (1-8C)alkyl, (2-8C)alkenyl, (2-8C)alkynyl, (1-6C)alkoxy, halogeno-(1-6C)alkoxy, hydroxy-(1-6C)alkyl, (1-6C)alkoxy-(1-6C)alkyl, halogeno-(1-6C)alkyl, amino-(1-6C)alkyl, (1-6C)alkylamino-(1-6C)alkyl, di-[(1-6C)alkyl]amino-(1-6C)alkyl, (1-6C)alkylamino, di-[(1-6C)alkyl]amino, (1-6C)alkoxycarbonyl, N-(1-6C)alkylcarbamoyl, (1-6C)alkanoylamino or heterocyclyl-(1-6C)alkyl group, and any heterocyclyl group within a $R^1$ substituent optionally bears 1 or 2 oxo substituents;

(aa) $R^1$ is a group of the formula:

$$R^4—X^1—$$

wherein $X^1$ is a direct bond or is selected from O, SO, $SO_2$, $N(R^5)$, CO, $CON(R^5)$, $N(R^5)CO$, $SO_2N(R^5)$, $N(R^5)SO_2$, $C(R^5)_2O$, $OC(R^5)_2$, $C(R^5)_2$, $C(R^5)_2N(R^5)$ and $N(R^5)C(R^5)_2$, wherein each $R^5$ is independently selected from hydrogen or (1-8C)alkyl, and when $X^1$ is a direct bond or is selected from $C(R^5)_2O$, $C(R^5)_2$ or $C(R^5)_2N(R^5)$, wherein $R^5$ has any of the meanings defined hereinbefore, $R^4$ is hydroxy-(1-3C)alkyl, (1-6C)alkoxy-(1-3C)alkyl, $R^5$—S, $R^5$—S(O), $R^5$—$SO_2$, $R^5$—S-(1-3C)alkyl, $R^5$—S(O)-(1-3C)alkyl, $R^5$—$SO_2$-(1-3C)alkyl, N,N-di-($R^5$)sulphamoyl, N,N-di-($R^5$)sulphamoyl-(1-3C)alkyl, $R^5$—$SO_2N(R^5)$, $R^5$—$SO_2N(R^5)$-(1-3C)alkyl, $R^5$—$CON(R^5)$, $R^5$—$CON(R^5)$-(1-3C)alkyl, $R^5$—CO, $R^5$—CO-(1-3C)alkyl, $(R^5)_2NCO$, $(R^5)_2NCO$-(1-3C)alkyl, cyano, amino, $(R^6)$-amino, di-$(R^6)$— amino, amino-(1-3C)alkyl, $(R^6)$-amino-(1-3C)alkyl or di-$(R^6)$-amino-(1-3C)alkyl, wherein each $R^6$ present is (1-3C)alkyl;

and when $X^1$ is selected from O, SO, $SO_2$, $N(R^5)$, CO, $CON(R^5)$, $N(R^5)CO$, $SO_2N(R^5)$, $N(R^5)SO_2$, $OC(R^5)_2$ and $N(R^5)C(R^5)_2$, wherein $R^5$ has any of the meanings defined hereinbefore, $R^4$ is hydroxy-(1-3C)alkyl, (1-6C)alkoxy-(1-3C)alkyl, $R^5$—S-(1-3C)alkyl, $R^5$—S(O)-(1-3C)alkyl, $R^5$—$SO_2$-(1-3C)alkyl, $R^5$—$CON(R^5)$-(1-3C)alkyl, $R^5$—CO-(1-3C)alkyl, $(R^5)_2NCO$-(1-3C)alkyl, amino-(1-3C)alkyl, $(R^6)$-amino-(1-3C)alkyl or di-$(R^6)$-amino-(1-3C)alkyl, wherein each $R^6$ present is (1-3C)alkyl;

or $R^1$ is a group of the formula:

$$Q^1-X^2—$$

wherein $X^2$ is a direct bond or is selected from O, SO, $SO_2$, $N(R^7)$, $N[C(O)R^7]$, $N[C(O)N(R^7)_2]$, $N[C(O)OR^7]$, $N[SO_2—N(R^7)_2]$, CO, $CON(R^7)$, $N(R^7)CO$, $SO_2N(R^7)$, $N(R^7)SO_2$, $O—SO_2$, $SO_2—O$, $C(R^7)_2O$, $OC(R^7)_2$, $C(R^7)_2$, $C(R^7)_2N(R^7)$ and $N(R^7)C(R^7)_2$, wherein each $R^7$ is independently selected from hydrogen or (1-8C)alkyl;

and $Q^1$ is heterocyclyl or heterocyclyl-(1-3C)alkyl, wherein said heterocyclyl or the heterocyclyl within the heterocyclyl-(1-3C)alkyl group is selected from piperidinyl, pyrrolidinyl, morpholinyl and piperazinyl, each of which optionally bears a halogeno, trifluoromethyl, cyano, hydroxy, amino, carboxy, (1-8C)alkyl, (2-8C)alkenyl, (2-8C)alkynyl, (1-6C)alkoxy, halogeno-(1-6C)alkoxy, hydroxy-(1-6C)alkyl, (1-6C)alkoxy-(1-6C)alkyl, halogeno-(1-6C)alkyl, amino-(1-6C)alkyl, (1-6C)alkylamino-(1-6C)alkyl, di-[(1-6C)alkyl]amino-(1-6C)alkyl, (1-6C)alkylamino, di-[(1-6C)alkyl]amino, (1-6C)alkoxycarbonyl, N-(1-6C)alkylcarbamoyl, (1-6C)alkanoylamino or heterocyclyl-(1-6C)alkyl group, and any heterocyclyl group within a $R^1$ substituent optionally bears 1 or 2 oxo substituents;

(bb) $R^1$ is a group of the formula:

$$Q^1-X^2—$$

wherein $X^2$ is a direct bond or is selected from O, SO, $SO_2$, $N(R^7)$, $N[C(O)R^7]$, $N[C(O)N(R^7)_2]$, $N[C(O)OR^7]$, $N[SO_2—N(R^7)_2]$, CO, $CON(R^7)$, $N(R^7)CO$, $SO_2N(R^7)$, $N(R^7)SO_2$, $O—SO_2$, $SO_2—O$, $C(R^7)_2O$, $OC(R^7)_2$, $C(R^7)_2$, $C(R^7)_2N(R^7)$ and $N(R^7)C(R^7)_2$, wherein each $R^7$ is independently selected from hydrogen or (1-8C)alkyl;

and $Q^1$ is heterocyclyl or heterocyclyl-(1-3C)alkyl, wherein said heterocyclyl or the heterocyclyl within the heterocyclyl-(1-3C)alkyl group is selected from piperidinyl, pyrrolidinyl, morpholinyl and piperazinyl, each of which optionally bears a halogeno, trifluoromethyl, cyano, hydroxy, amino, carboxy, (1-8C)alkyl, (2-8C)alkenyl, (2-8C)alkynyl, (1-6C)alkoxy, halogeno-(1-6C)alkoxy, hydroxy-(1-6C)alkyl, (1-6C)alkoxy-(1-6C)alkyl, halogeno-(1-6C)alkyl, amino-(1-6C)alkyl, (1-6C)alkylamino-(1-6C)alkyl, di-[(1-6C)alkyl]amino-(1-6C)alkyl, (1-6C)alkylamino, di-[(1-6C)alkyl]amino, (1-6C)alkoxycarbonyl, N-(1-6C)alkylcarbamoyl, (1-6C)alkanoylamino or heterocyclyl-(1-6C)alkyl group, and any heterocyclyl group within a $R^1$ substituent optionally bears 1 or 2 oxo substituents;

(cc) $R^1$ is a group of the formula:

$$R^4—X^1—$$

wherein $X^1$ is a direct bond or is selected from O, SO, $SO_2$, $N(R^5)$, CO, $CON(R^5)$, $N(R^5)CO$, $SO_2N(R^5)$, $N(R^5)SO_2$, $C(R^5)_2O$, $OC(R^5)_2$, $C(R^5)_2$, $C(R^5)_2N(R^5)$ and $N(R^5)C(R^5)_2$, wherein each $R^5$ is independently selected from hydrogen or (1-8C)alkyl, and when $X^1$ is a direct bond or is selected from $C(R^5)_2O$, $C(R^5)_2$ or $C(R^5)_2N(R^5)$, wherein $R^5$ has any of the meanings defined hereinbefore, $R^4$ is hydroxy-(1-3C)alkyl, (1-6C)alkoxy-(1-3C)alkyl, $R^5$—S, $R^5$—S(O), $R^5$—$SO_2$, $R^5$—S-(1-3C)alkyl, $R^5$—S(O)-(1-3C)alkyl, $R^5$—$SO_2$-(1-3C)alkyl, N,N-di-($R^5$)sulphamoyl, N,N-di-($R^5$)sulphamoyl-(1-3C)alkyl, $R^5$—$SO_2N(R^5)$, $R^5$—$SO_2N(R^5)$-(1-3C)alkyl, $R^5$—$CON(R^5)$, $R^5$—$CON(R^5)$-(1-3C)alkyl, $R^5$—CO, $R^5$—CO-(1-3C)alkyl, $(R^5)_2NCO$, $(R^5)_2NCO$-(1-3C)alkyl, cyano, amino, $(R^6)$-amino, di-$(R^6)$-amino, amino-(1-3C)alkyl, $(R^6)$-amino-(1-3C)alkyl or di-$(R^6)$-amino-(1-3C)alkyl, wherein each $R^6$ present is (1-3C)alkyl;

and when $X^1$ is selected from O, SO, $SO_2$, $N(R^5)$, CO, $CON(R^5)$, $N(R^5)CO$, $SO_2N(R^5)$, $N(R^5)SO_2$, $OC(R^5)_2$ and $N(R^5)C(R^5)_2$, wherein $R^5$ has any of the meanings defined hereinbefore, $R^4$ is hydroxy-(1-3C)alkyl, (1-6C)alkoxy-(1-3C)alkyl, $R^5$—S-(1-3C)alkyl, $R^5$—S(O)-(1-3C)alkyl, $R^5$—$SO_2$-(1-3C)alkyl, $R^5$—$CON(R^5)$-(1-3C)alkyl, $R^5$—CO-(1-3C)alkyl, $(R^5)_2NCO$-(1-3C)alkyl, amino-(1-3C)alkyl, $(R^6)$-amino-(1-3C)alkyl or di-$(R^6)$-amino-(1-3C)alkyl, wherein each $R^6$ present is (1-3C)alkyl;

(dd) $R^1$ is hydroxymethyl, 2-hydroxyethyl, 3-hydroxypropyl, methoxymethyl, ethoxymethyl, propoxymethyl, 2-methoxyethoxy, 2-ethoxyethoxy, methylsulphonyl, ethylsulphonyl, propylsulphonyl, methylsulphamoyl, ethylsulphamoyl, propylsulphamoyl, dimethylsulphamoyl, diethylsulphamoyl, cyclopropylsulphamoyl, methanesulphonamido, ethanesulphonamido, acetamido, carbamoyl, methylcarbamoyl, ethylcarbamoyl, 2-dimethylaminoethylcarbamoyl, dimethylaminomethylcarbamoyl, cyano, aminomethyl, 2-aminoethyl, 3-aminopropyl, dimethylaminomethyl, diethylaminomethyl, 2-dimethylaminoethyl, 2-diethylaminoethyl, 3-dimethylaminopropoxy, 2-dimethylaminoethoxy, dimethylaminomethoxy, pyrrolidin-1-yl, piperazin-1-yl, piperidin-4-yl, morpholino, pyrrolidin-1-ylmethyl, morpholinomethyl, piperazin-1-ylmethyl, piperidin-4-ylmethyl, 2-(pyrrolidin-1-yl)ethyl, 2-(morpholino)ethyl, 2-(piperazin-1-yl)ethyl, 2-(piperidin-4-yl)ethyl, 4-hydroxypiperidine-1-carbonyl, 1-methyl-4-piperidyl, 1-ethyl-4-piperidyl, 1-isopropyl-4-piperidyl, 1-tert-butoxycarbonyl-4-piperidyl or 1-methyl-1-oxido-piperidin-1-ium-4-yl (ee) $R^1$ is hydroxymethyl, methoxymethyl, 2-methoxyethoxy, ethylsulphonyl, methylsulphamoyl, dimethylsulphamoyl, cyclopropylsulphamoyl, methanesulphonamido, acetamido, carbamoyl, methylcarbamoyl, 2-dimethylaminoethylcarbamoyl, cyano, aminomethyl, dimethylaminomethyl, pyrrolidin-1-yl, piperazin-1-yl, piperidin-4-yl, pyrrolidin-1-ylmethyl, morpholinomethyl, 4-hydroxypiperidine-1-carbonyl, 1-methyl-4-piperidyl, 1-ethyl-4-piperidyl, 1-isopropyl-4-piperidyl, 3-dimethylaminopropoxy, 1-tert-butoxycarbonyl-4-piperidyl or 1-methyl-1-oxido-piperidin-1-ium-4-yl;

(ff) each $R^2$ group may be the same or different and is selected from halogeno, cyano, (gg) (1-8C)alkyl, (2-8C)alkenyl, (2-8C)alkynyl, (1-6C)alkoxy, (2-6C)alkenyloxy, (hh) (2-6C)alkynyloxy, fluoro-(1-6C)alkoxy, (1-6C)alkylthio, (1-6C)alkylsulphinyl, (1-6C)alkylsulphonyl, (1-6C)alkylamino, di-[(1-6C)alkyl]amino, (2-6C)alkanoyl, N-(1-6C)alkylcarbamoyl, N,N-di-[(1-6C)alkyl]carbamoyl, (1-6C)alkanoylamino, N-(1-6C)alkyl-(1-6C)alkanoylamino, (1-6C)alkoxy-(1-6C)alkyl, hydroxy-(1-6C)alkyl, (1-6C)alkoxy-(1-6C)alkoxy or hydroxy-(1-6C)alkoxy;

(ii) each $R^2$ group may be the same or different and is selected from halogeno, cyano, (1-8C)alkyl, (1-6C)alkoxy, (1-6C)alkylthio, (2-6C)alkanoyl, (1-6C)alkoxy-(1-6C)alkyl, hydroxy-(1-6C)alkyl, (1-6C)alkoxy-(1-6C)alkoxy or hydroxy-(1-6C)alkoxy;

(jj) each $R^2$ group is methoxy, ethoxy, propoxy, fluoro, bromo or chloro;

(kk) each $R^2$ group is methoxy;

(ll) n is 0, 1 or 2 and, when n is 2, each $R^3$ group may be the same or different, and each $R^3$ group present is selected from hydrogen, halogeno, cyano, $OR^9$, trifluoromethyl, (1-8C)alkyl, (2-8C)alkenyl, (2-8C)alkynyl, (1-6C)alkoxy, halogeno-(1-6C)alkoxy, carbamoyl, N-(1-6C)alkylcarbamoyl, N,N-di-[(1-6C)alkyl]carbamoyl, (1-6C)alkanoylamino, (1-6C)alkylthio, (1-6C)alkylsulphinyl, (1-6C)alkylsulphonyl, hydroxy-(1-6C)alkyl, (1-6C)alkoxy-(1-6C)alkyl, (2-6C)alkanoyl, (1-6C)alkanesulphonylamino, (1-6C)alkoxy-(1-6C)alkoxy, hydroxy-(1-6C)alkoxy, amino-(1-6C)alkoxy, (1-6C)alkylamino-(1-6C)alkoxy and di-[(1-6C)alkyl]amino-(1-6C)alkoxy, wherein $R^9$ is fluoro-(1-6C)alkyl;

(mm) n is 0, 1 or 2 and, when n is 2, each $R^3$ group may be the same or different, and each $R^3$ group present is selected from hydrogen, halogeno, cyano, $OR^9$, trifluoromethyl, (1-8C)alkyl, (1-6C)alkoxy, (1-6C)alkanoylamino, (1-6C)alkylthio, hydroxy-(1-6C)alkyl, (1-6C)alkoxy-(1-6C)alkyl, (2-6C)alkanoyl, (1-6C)alkoxy-(1-6C)alkoxy, hydroxy-(1-6C)alkoxy, wherein $R^9$ is fluoro-(1-6C)alkyl;

(nn) n is 0, 1 or 2 and, when n is 2, each $R^3$ group may be the same or different, and each $R^3$ group present is selected from hydrogen, halogeno, cyano, $OR^9$, trifluoromethyl, (1-4C)alkyl, methoxy, ethoxy, propoxy, wherein $R^9$ is trifluoromethyl or 2,2,2-trifluoroethyl;

(oo) n is 0, 1 or 2 and, when n is 2, each $R^3$ group may be the same or different, and each $R^3$ group present is selected from hydrogen, halogeno, $OR^9$, trifluoromethyl, (1-4C)alkyl, wherein $R^9$ is trifluoromethyl;

(pp) n is 0, 1 or 2 and, when n is 2, each $R^3$ group may be the same or different, and each $R^3$ group present is selected from hydrogen, fluoro, bromo, chloro, $OR^9$, trifluoromethyl, methyl or propyl, wherein $R^9$ is trifluoromethyl;

(qq) n is 0;

(rr) Ring A is selected from:
(i) phenyl substituted by $R^1$ and optionally substituted by an $R^2$ group; or
(ii) pyrazolyl, thienyl or pyridinyl, said ring being substituted by $R^1$ and optionally substituted by an $R^2$ group; or
(iii) naphthyl, quinolyl, 2,3-dihydro-1,4-benzodioxinyl, 1H-indazolyl, 1H-indolyl or 1,3-benzodioxolyl, wherein said bicyclic ring system is optionally substituted by $R^1$ and optionally substituted by an $R^2$ group;

(ss) Ring A is selected from:
(i) phenyl substituted by $R^1$ and optionally substituted by an $R^2$ group; or
(ii) pyrazol-4-yl, pyridin-3-yl or thien-2-yl, said ring being substituted by $R^1$ and optionally substituted by an $R^2$ group; or
(iii) naphthyl, quinol-8-yl, quinol-3-yl, quinol-4-yl, 2,3-dihydro-1,4-benzodioxin-6-yl, 1H-indazol-5-yl, 1H-indol-5-yl, 1H-indol-6-yl or 1,3-benzodioxol-5-yl, wherein said bicyclic ring system is optionally substituted by $R^1$ and optionally substituted by an $R^2$ group;

(tt) $R^1$ is a group of the formula:

$$R^4-X^1-$$

wherein $X^1$ is a direct bond or is selected from O, SO, $SO_2$, $N(R^5)$, CO, $CON(R^5)$, $N(R^5)CO$, $SO_2N(R^5)$, $N(R^5)SO_2$, $C(R^5)_2O$, $OC(R^5)_2$, $C(R^5)_2$, $C(R^5)_2N(R^5)$ and $N(R^5)C(R^5)_2$, wherein each $R^5$ is independently selected from hydrogen or (1-8C)alkyl;

and when $X^1$ is a direct bond or is selected from $C(R^5)_2O$, $C(R^5)_2$ or $C(R^5)_2N(R^5)$, wherein $R^5$ has any of the meanings defined hereinbefore, $R^4$ is hydroxy-(1-6C)alkyl, (1-6C)alkoxy-(1-6C)alkyl, $R^5-S$, $R^5-S(O)$, $R^5-SO_2$, $R^5-SO_2-O$, $R^5-S$-(1-6C)alkyl, $R^5-S(O)$-(1-6C)alkyl, $R^5-SO_2$-(1-6C)alkyl, N,N-di-($R^5$)sulphamoyl, N,N-di-($R^5$)sulphamoyl-(1-6C)alkyl, $R^5-SO_2N(R^5)$, $R^5-SO_2N(R^5)$-(1-6C)alkyl, $R^5-CON(R^5)$, $R^5O-CON(R^5)$, $R^5-CON(R^5)$-(1-6C)alkyl, $R^5O-CON(R^5)$-(1-6C)alkyl, $(R^5)_2N-SO_2N(R^5)$, $(R^5)_2N-SO_2N(R^5)$-(1-6C)alkyl, $(R^5)_2N-CON(R^5)$, $(R^5)_2N-CON(R^5)$-(1-6C)alkyl, $R^5-CO$, $R^5-CO$-(1-6C)alkyl, $R^5O-CO$-(1-6C)alkyl, $(R^5)_2NCO$, $(R^5)_2NCO$-(1-6C)alkyl, $(R^5)_2N-COO$, $(R^5)_2NCOO$-(1-6C)alkyl, cyano, amino, $(R^6)$-amino, di-$(R^6)$-amino, amino-(1-6C)alkyl, $(R^6)$-amino-(1-6C)alkyl or di-$(R^6)$-amino-(1-6C)alkyl, wherein each $R^6$ present is (1-6C)alkyl optionally substituted by 1, 2 or 3 substituents independently selected from halogeno, cyano, hydroxy and (1-6C)alkoxy;

and when $X^1$ is selected from O, SO, $SO_2$, $N(R^5)$, CO, $CON(R^5)$, $N(R^5)CO$, $SO_2N(R^5)$, $N(R^5)SO_2$, $OC(R^5)_2$ and $N(R^5)C(R^5)_2$, wherein $R^5$ has any of the meanings defined hereinbefore, $R^4$ is hydroxy-(1-6C)alkyl, (1-6C)alkoxy-(1-6C)alkyl, $R^5-S$-(1-6C)alkyl, $R^5-S(O)$-(1-6C)alkyl, $R^5-SO_2$-(1-6C)alkyl, N,N-di-($R^5$)sulphamoyl-(1-6C)alkyl, $R^5-SO_2N(R^5)$-(1-6C)alkyl, $R^5-CON(R^5)$-(1-6C)alkyl, $R^5O-CON(R^5)$-(1-6C)alkyl, $(R^5)_2N-SO_2N(R^5)$-(1-6C)alkyl, $(R^5)_2N-CON(R^5)$-(1-6C)alkyl, $R^5-CO$, $R^5-CO$-(1-6C)alkyl, $R^{50}-Co$, $R^5O-CO$-(1-6C)alkyl, $(R^5)_2NCO$, $(R^5)_2NCO$-(1-6C)alkyl, $(R^5)_2NCOO$-(1-6C)alkyl, amino-(1-6C)alkyl, $(R^6)$-amino-(1-6C)alkyl or di-$(R^6)$-amino-(1-6C)alkyl, wherein each $R^6$ present is (1-6C)alkyl optionally substituted by 1, 2 or 3 substituents independently selected from halogeno, cyano, hydroxy and (1-6C)alkoxy;
or $R^1$ is a group of the formula:

$$Q^1-X^2—$$

wherein $X^2$ is a direct bond or is selected from O, SO, $SO_2$, $N(R^7)$, $N[C(O)R^7]$, $N[C(O)N(R^7)_2]$, $N[C(O)OR^7]$, $N[SO_2-N(R^7)_2]$, CO, $CON(R^7)$, $N(R^7)CO$, $SO_2N(R^7)$, $N(R^7)SO_2$, $O-SO_2$, $SO_2-O$, $C(R^7)_2O$, $OC(R^7)_2$, $C(R^7)_2$, $C(R^7)_2N(R^7)$ and $N(R^7)C(R^7)_2$, wherein each $R^7$ is independently selected from hydrogen or (1-8C)alkyl;
and $Q^1$ is aryl, aryl-(1-6C)alkyl, (3-8C)cycloalkyl, (3-8C)cycloalkyl-(1-6C)alkyl, heterocyclyl, heterocyclyl-(1-6C)alkyl, heteroaryl or heteroaryl-(1-6C)alkyl, wherein any aryl or (3-8C)cycloalkyl group within a $R^1$ substituent bears 1, 2 or 3 substituents and any heterocyclyl or heteroaryl group within a $R^1$ substituent optionally bears 1, 2 or 3 substituents, wherein said substituents are independently selected from halogeno, trifluoromethyl, cyano, nitro, hydroxy, amino, carboxy, carbamoyl, ureido, (1-8C)alkyl, (2-8C)alkenyl, (2-8C)alkynyl, (1-6C)alkoxy, halogeno-(1-6C)alkoxy, hydroxy-(1-6C)alkyl, (1-6C)alkoxy-(1-6C)alkyl, (1-6C)alkylsulphonyl-(1-6C)alkyl, cyano-(1-6C)alkyl, halogeno-(1-6C)alkyl, amino-(1-6C)alkyl, (1-6C)alkylamino-(1-6C)alkyl, di-[(1-6C)alkyl]amino-(1-6C)alkyl, (2-6C)alkenyloxy, (2-6C)alkynyloxy, (1-6C)alkylthio, (1-6C)alkylsulphinyl, (1-6C)alkylsulphonyl, (1-6C)alkylamino, di-[(1-6C)alkyl]amino, (1-6C)alkoxycarbonyl, (2-6C)alkanoyl, (2-6C)alkanoyloxy, N-(1-6C)alkylcarbamoyl, N,N-di-[(1-6C)alkyl]carbamoyl, (1-6C)alkanoylamino, N-(1-6C)alkyl-(1-6C)alkanoylamino, N-(1-6C)alkylureido, N'-(1-6C)alkylureido, N',N'-di-[(1-6C)alkyl]ureido, N,N'-di-[(1-6C)alkyl]ureido, N,N',N'-tri-[(1-6C)alkyl]ureido, N-(1-6C)alkylsulphamoyl, N,N-di-[(1-6C)alkyl]sulphamoyl, (1-6C)alkanesulphonylamino, N-(1-6C)alkyl-(1-6C)alkanesulphonylamino or heterocyclyl-(1-6C)alkyl, and any heterocyclyl group within a $R^1$ substituent optionally bears 1 or 2 oxo substituents;
(uu) $R^1$ is a group of the formula:

$$R^4-X^1—$$

wherein $X^1$ is a direct bond or is selected from O, SO, $SO_2$, $N(R^5)$, CO, $CON(R^5)$, $N(R^5)CO$, $SO_2N(R^5)$, $N(R^5)SO_2$, $C(R^5)_2O$, $OC(R^5)_2$, $C(R^5)_2$, $C(R^5)_2N(R^5)$ and $N(R^5)C(R^5)_2$, wherein each $R^5$ is independently selected from hydrogen or (1-8C)alkyl,
and when $X^1$ is a direct bond or is selected from $C(R^5)_2O$, $C(R^5)_2$ or $C(R^5)_2N(R^5)$, wherein $R^5$ has any of the meanings defined hereinbefore, $R^4$ is hydroxy-(1-6C)alkyl, (1-6C)alkoxy-(1-6C)alkyl, $R^5—S$, $R^5—S(O)$, $R^5—SO_2$, $R^5—SO_2—O$, $R^5—S$-(1-6C)alkyl, $R^5—S(O)$-(1-6C)alkyl, $R^5—SO_2$-(1-6C)alkyl, N,N-di-$(R^5)$sulphamoyl, N,N-di-$(R^5)$sulphamoyl-(1-6C)alkyl, $R^5—SO_2N(R^5)$, $R^5—SO_2N(R^5)$-(1-6C)alkyl, $R^5—CON(R^5)$, $R^5O—CON(R^5)$, $R^5—CON(R^5)$-(1-6C)alkyl, $R^5O—CON(R^5)$-(1-6C)alkyl, $(R^5)_2N—SO_2N(R^5)$, $(R^5)_2N—SO_2N(R^5)$-(1-6C)alkyl, $(R^5)_2N—CON(R^5)$, $(R^5)_2N—CON(R^5)$-(1-6C)alkyl, $R^5—CO$, $R^5—CO$-(1-6C)alkyl, $R^5O—CO$-(1-6C)alkyl, $(R^5)_2NCO$, $(R^5)_2NCO$-(1-6C)alkyl, $(R^5)_2N—COO$, $(R^5)_2NCOO$-(1-6C)alkyl, cyano, amino, $(R^6)$-amino, di-$(R^6)$-amino, amino-(1-6C)alkyl, $(R^6)$-amino-(1-6C)alkyl or di-$(R^6)$-amino-(1-6C)alkyl, wherein each $R^6$ present is (1-6C)alkyl optionally substituted by 1, 2 or 3 substituents independently selected from halogeno, cyano, hydroxy and (1-6C)alkoxy; and when $X^1$ is selected from O, SO, $SO_2$, $N(R^5)$, CO, $CON(R^5)$, $N(R^5)CO$, $SO_2N(R^5)$, $N(R^5)SO_2$, $OC(R^5)_2$ and $N(R^5)C(R^5)_2$, wherein $R^5$ has any of the meanings defined hereinbefore, $R^4$ is hydroxy-(1-6C)alkyl, (1-6C)alkoxy-(1-6C)alkyl, $R^5—S$-(1-6C)alkyl, $R^5—S(O)$-(1-6C)alkyl, $R^5—SO_2$-(1-6C)alkyl, N,N-di-$(R^5)$sulphamoyl-(1-6C)alkyl, $R^5—SO_2N(R^5)$-(1-6C)alkyl, $R^5—CON(R^5)$-(1-6C)alkyl, $R^5O—CON(R^5)$-(1-6C)alkyl, $(R^5)_2N—SO_2N(R^5)$-(1-6C)alkyl, $(R^5)_2N—CON(R^5)$-(1-6C)alkyl, $R^5—CO$, $R^5—CO$-(1-6C)alkyl, $R^5O—CO$, $R^5O—CO$-(1-6C)alkyl, $(R^5)_2NCO$, $(R^5)_2NCO$-(1-6C)alkyl, $(R^5)_2NCOO$-(1-6C)alkyl, amino-(1-6C)alkyl, $(R^6)$-amino-(1-6C)alkyl or di-$(R^6)$-amino-(1-6C)alkyl, wherein each $R^6$ present is (1-6C)alkyl optionally substituted by 1, 2 or 3 substituents independently selected from halogeno, cyano, hydroxy and (1-6C)alkoxy;
or $R^1$ is a group of the formula:

$$Q^1-X^2—$$

wherein $X^2$ is a direct bond or is selected from O, SO, $SO_2$, $N(R^7)$, $N[C(O)R^7]$, $N[C(O)N(R^7)_2]$, $N[C(O)OR^7]$, $N[SO_2-N(R^7)_2]$, CO, $CON(R^7)$, $N(R^7)CO$, $SO_2N(R^7)$, $N(R^7)SO_2$, $O-SO_2$, $SO_2-O$, $C(R^7)_2O$, $OC(R^7)_2$, $C(R^7)_2$, $C(R^7)_2N(R^7)$ and $N(R^7)C(R^7)_2$, wherein each $R^7$ is independently selected from hydrogen or (1-8C)alkyl;
and $Q^1$ is heterocyclyl, heterocyclyl-(1-6C)alkyl, heteroaryl or heteroaryl-(1-6C)alkyl, wherein any heterocyclyl or heteroaryl group within a $R^1$ substituent optionally bears 1, 2 or 3 substituents, wherein said substituents are independently selected from halogeno, trifluoromethyl, cyano, nitro, hydroxy, amino, carboxy, carbamoyl, ureido, (1-8C)alkyl, (2-8C)alkenyl, (2-8C)alkynyl, (1-6C)alkoxy, halogeno-(1-6C)alkoxy, hydroxy-(1-6C)alkyl, (1-6C)alkoxy-(1-6C)alkyl, cyano-(1-6C)alkyl, halogeno-(1-6C)alkyl, amino-(1-6C)alkyl, (1-6C)alkylamino-(1-6C)alkyl, di-[(1-6C)alkyl]amino-(1-6C)alkyl, (2-6C)alkenyloxy, (2-6C)alkynyloxy, (1-6C)alkylthio, (1-6C)alkylsulphinyl, (1-6C)alkylsulphonyl, (1-6C)alkylamino, di-[(1-6C)alkyl]amino, (1-6C)alkoxycarbonyl, (2-6C)alkanoyl, (2-6C)alkanoyloxy, N-(1-6C)alkylcarbamoyl, N,N-di-[(1-6C)alkyl]carbamoyl, (1-6C)alkanoylamino, N-(1-6C)alkylsulphamoyl, or heterocyclyl-(1-6C)alkyl, and any heterocyclyl group within a $R^1$ substituent optionally bears 1 or 2 oxo substituents;
(vv) $R^1$ is a group of the formula:

$$R^4-X^1—$$

wherein $X^1$ is a direct bond or is selected from O, SO, $SO_2$, $N(R^5)$, CO, $CON(R^5)$, $N(R^5)CO$, $SO_2N(R^5)$, $N(R^5)SO_2$, $C(R^5)_2O$, $OC(R^5)_2$, $C(R^5)_2$, $C(R^5)_2N(R^5)$ and $N(R^5)C(R^5)_2$, wherein each $R^5$ is independently selected from hydrogen or (1-8C)alkyl,
and when $X^1$ is a direct bond or is selected from $C(R^5)_2O$, $C(R^5)_2$ or $C(R^5)_2N(R^5)$, wherein $R^5$ has any of the meanings defined hereinbefore, $R^4$ is hydroxy-(1-6C)alkyl, (1-6C)alkoxy-(1-6C)alkyl, $R^5—S$, $R^5—S(O)$, $R^5—SO_2$, $R^5—SO_2—O$, $R^5—S$-(1-6C)alkyl, $R^5—S(O)$-(1-6C)alkyl, $R^5—SO_2$-(1-6C)alkyl, N,N-di-$(R^5)$sulphamoyl, N,N-di-$(R^5)$sulphamoyl-(1-6C)alkyl, $R^5—SO_2N(R^5)$, $R^5—SO_2N(R^5)$-(1-6C)alkyl, $R^5—CON(R^5)$, $R^5O—CON(R^5)$, $R^5—CON(R^5)$-(1-6C)alkyl, $R^5O—CON(R^5)$-(1-6C)alkyl, $(R^5)_2N—SO_2N(R^5)$, $(R^5)_2N—SO_2N(R^5)$-(1-6C)alkyl, $(R^5)_2N—CON(R^5)$, $(R^5)_2N—CON(R^5)$-(1-6C)alkyl, $R^5—CO$, $R^5—CO$-(1-6C)alkyl, $R^5O—CO$-(1-6C)alkyl, $(R^5)_2NCO$, $(R^5)_2NCO$-(1-6C)alkyl, $(R^5)_2N—COO$, $(R^5)_2NCOO$-(1-6C)alkyl, cyano, amino, $(R^6)$-amino, di-$(R^6)$-amino, amino-(1-6C)alkyl, $(R^6)$-amino-(1-6C)alkyl or di-$(R^6)$-amino-(1-6C)alkyl, wherein each $R^6$ present is (1-6C)alkyl optionally substituted by 1, 2 or 3 substituents independently selected from halogeno, cyano, hydroxy and (1-6C)alkoxy; and when $X^1$ is selected from O, SO, $SO_2$, $N(R^5)$, CO, $CON(R^5)$, $N(R^5)CO$, $SO_2N(R^5)$, $N(R^5)SO_2$, $OC(R^5)_2$ and $N(R^5)C(R^5)_2$, wherein $R^5$ has any of the meanings defined hereinbefore, $R^4$ is hydroxy-(1-

6C)alkyl, (1-6C)alkoxy-(1-6C)alkyl, $R^5$—S-(1-6C)alkyl, $R^5$—S(O)-(1-6C)alkyl, $R^5$—SO$_2$-(1-6C)alkyl, N,N-di-($R^5$) sulphamoyl-(1-6C)alkyl, $R^5$—SO$_2$N($R^5$)-(1-6C)alkyl, $R^5$—CON($R^5$)-(1-6C)alkyl, $R^5$O—CON($R^5$)-(1-6C)alkyl, ($R^5$)$_2$N—SO$_2$N($R^5$)-(1-6C)alkyl, ($R^5$)$_2$N—CON($R^5$)-(1-6C) alkyl, $R^5$—CO, $R^5$—CO-(1-6C)alkyl, $R^{5O}$—Co, $R^5$O—CO-(1-6C)alkyl, ($R^5$)$_2$NCO, ($R^5$)$_2$NCO-(1-6C)alkyl, ($R^5$)$_2$NCOO-(1-6C)alkyl, amino-(1-6C)alkyl, ($R^6$)-amino-(1-6C)alkyl or di-($R^6$)-amino-(1-6C)alkyl, wherein each $R^6$ present is (1-6C)alkyl optionally substituted by 1, 2 or 3 substituents independently selected from halogeno, cyano, hydroxy and (1-6C)alkoxy;

or $R^1$ is a group of the formula:

$Q^1$-$X^2$— wherein $X^2$ is a direct bond or is selected from O, SO, SO$_2$, N($R^7$), N[C(O)$R^7$], N[C(O)N($R^7$)$_2$], N[C(O)O$R^7$], N[SO$_2$—N($R^7$)$_2$], CO, CON($R^7$), N($R^7$)CO, SO$_2$N($R^7$), N($R^7$)SO$_2$, O—SO$_2$, SO$_2$—O, C($R^7$)$_2$O, OC($R^7$)$_2$, C($R^7$)$_2$, C($R^7$)$_2$N($R^7$) and N($R^7$)C($R^7$)$_2$, wherein each $R^7$ is independently selected from hydrogen or (1-8C)alkyl;

and $Q^1$ is heterocyclyl, heterocyclyl-(1-6C)alkyl, heteroaryl or heteroaryl-(1-6C)alkyl, wherein any heterocyclyl or heteroaryl group within a $R^1$ substituent optionally bears 1, 2 or 3 substituents, wherein said substituents are independently selected from halogeno, trifluoromethyl, cyano, hydroxy, amino, carboxy, (1-8C)alkyl, (2-8C)alkenyl, (2-8C)alkynyl, (1-6C)alkoxy, halogeno-(1-6C)alkoxy, hydroxy-(1-6C)alkyl, (1-6C)alkoxy-(1-6C)alkyl, halogeno-(1-6C)alkyl, amino-(1-6C)alkyl, (1-6C)alkylamino-(1-6C)alkyl, di-[(1-6C)alkyl]amino-(1-6C)alkyl, (1-6C)alkylamino, di-[(1-6C)alkyl]amino, (1-6C)alkoxycarbonyl, N-(1-6C)alkylcarbamoyl, (1-6C)alkanoylamino or heterocyclyl-(1-6C)alkyl, and any heterocyclyl group within a $R^1$ substituent optionally bears 1 or 2 oxo substituents;

(ww) $R^1$ is a group of the formula:

$R^4$—$X^1$— wherein $X^1$ is a direct bond or is selected from O, SO, SO$_2$, N($R^5$), CO, CON($R^5$), N($R^5$)CO, SO$_2$N($R^5$), N($R^5$)SO$_2$, C($R^5$)$_2$O, OC($R^5$)$_2$, C($R^5$)$_2$, C($R^5$)$_2$N($R^5$) and N($R^5$)C($R^5$)$_2$, wherein each $R^5$ is independently selected from hydrogen or (1-8C)alkyl, and when $X^1$ is a direct bond or is selected from C($R^5$)$_2$O, C($R^5$)$_2$ or C($R^5$)$_2$N($R^5$), wherein $R^5$ has any of the meanings defined hereinbefore, $R^4$ is hydroxy-(1-6C)alkyl, (1-6C)alkoxy-(1-6C)alkyl, $R^5$—S, $R^5$—S(O), $R^5$—SO$_2$, $R^5$—SO$_2$—O, $R^5$—S-(1-6C)alkyl, $R^5$—S(O)-(1-6C)alkyl, $R^5$—SO$_2$-(1-6C)alkyl, N,N-di-($R^5$)sulphamoyl, N,N-di-($R^5$)sulphamoyl-(1-6C)alkyl, $R^5$—SO$_2$N($R^5$), $R^5$—SO$_2$N($R^5$)-(1-6C)alkyl, $R^5$—CON($R^5$), $R^5$—CON($R^5$)-(1-6C)alkyl, $R^5$—CO, $R^5$—CO-(1-6C)alkyl, ($R^5$)$_2$NCO, ($R^5$)$_2$NCO-(1-6C)alkyl, cyano, amino, ($R^6$)-amino, di-($R^6$)— amino, amino-(1-6C)alkyl, ($R^6$)-amino-(1-6C)alkyl or di-($R^6$)-amino-(1-6C)alkyl, wherein each $R^6$ present is (1-6C)alkyl;

and when $X^1$ is selected from O, SO, SO$_2$, N($R^5$), CO, CON($R^5$), N($R^5$)CO, SO$_2$N($R^5$), N($R^5$)SO$_2$, OC($R^5$)$_2$ and N($R^5$)C($R^5$)$_2$, wherein $R^5$ has any of the meanings defined hereinbefore, $R^4$ is hydroxy-(1-6C)alkyl, (1-6C)alkoxy-(1-6C)alkyl, $R^5$—S-(1-6C)alkyl, $R^5$—S(O)-(1-6C)alkyl, $R^5$—SO$_2$-(1-6C)alkyl, $R^5$—CON($R^5$)-(1-6C)alkyl, $R^5$—CO-(1-6C)alkyl, ($R^5$)$_2$NCO-(1-6C)alkyl, amino-(1-6C)alkyl, ($R^6$)-amino-(1-6C)alkyl or di-($R^6$)-amino-(1-6C)alkyl, wherein each $R^6$ present is (1-6C)alkyl;

or $R^1$ is a group of the formula:

$Q^1$-$X^2$— wherein $X^2$ is a direct bond or is selected from O, SO, SO$_2$, N($R^7$), N[C(O)$R^7$], N[C(O)N($R^7$)$_2$], N[C(O)O$R^7$], N[SO$_2$—N($R^7$)$_2$], CO, CON($R^7$), N($R^7$)CO, SO$_2$N($R^7$), N($R^7$)SO$_2$, O—SO$_2$, SO$_2$—O, C($R^7$)$_2$O, OC($R^7$)$_2$, C($R^7$)$_2$, C($R^7$)$_2$N($R^7$) and N($R^7$)C($R^7$)$_2$, wherein each $R^7$ is independently selected from hydrogen or (1-8C)alkyl;

and $Q^1$ is heterocyclyl, heterocyclyl-(1-6C)alkyl, heteroaryl or heteroaryl-(1-6C)alkyl, wherein any heterocyclyl or heteroaryl group within a $R^1$ substituent optionally bears 1, 2 or 3 substituents, wherein said substituents are independently selected from halogeno, trifluoromethyl, cyano, hydroxy, amino, carboxy, (1-8C)alkyl, (2-8C)alkenyl, (2-8C)alkynyl, (1-6C)alkoxy, halogeno-(1-6C)alkoxy, hydroxy-(1-6C)alkyl, (1-6C)alkoxy-(1-6C)alkyl, halogeno-(1-6C)alkyl, amino-(1-6C)alkyl, (1-6C)alkylamino-(1-6C)alkyl, di-[(1-6C)alkyl]amino-(1-6C)alkyl, (1-6C)alkylamino, di-[(1-6C)alkyl]amino, (1-6C)alkoxycarbonyl, N-(1-6C)alkylcarbamoyl, (1-6C)alkanoylamino or heterocyclyl-(1-6C)alkyl, and any heterocyclyl group within a $R^1$ substituent optionally bears 1 or 2 oxo substituents;

(xx) $R^1$ is a group of the formula:

$R^4$—$X^1$— wherein $X^1$ is a direct bond or is selected from O, SO, SO$_2$, N($R^5$), CO, CON($R^5$), N($R^5$)CO, SO$_2$N($R^5$), N($R^5$)SO$_2$, C($R^5$)$_2$O, OC($R^5$)$_2$, C($R^5$)$_2$, C($R^5$)$_2$N($R^5$) and N($R^5$)C($R^5$)$_2$, wherein each $R^5$ is independently selected from hydrogen or (1-8C)alkyl, and when $X^1$ is a direct bond or is selected from C($R^5$)$_2$O, C($R^5$)$_2$ or C($R^5$)$_2$N($R^5$), wherein $R^5$ has any of the meanings defined hereinbefore, $R^4$ is hydroxy-(1-3C)alkyl, (1-6C)alkoxy-(1-3C)alkyl, $R^5$—S, $R^5$—S(O), $R^5$—SO$_2$, $R^5$—SO$_2$—O, $R^5$—S-(1-3C)alkyl, $R^5$—S(O)-(1-3C)alkyl, $R^5$—SO$_2$-(1-3C)alkyl, N,N-di-($R^5$)sulphamoyl, N,N-di-($R^5$)sulphamoyl-(1-3C)alkyl, $R^5$—SO$_2$N($R^5$), $R^5$—SO$_2$N($R^5$)-(1-3C)alkyl, $R^5$—CON($R^5$), $R^5$—CON($R^5$)-(1-3C)alkyl, $R^5$—CO, $R^5$—CO-(1-3C)alkyl, ($R^5$)$_2$NCO, ($R^5$)$_2$NCO-(1-3C)alkyl, cyano, amino, ($R^6$)-amino, di-($R^6$)-amino, amino-(1-3C)alkyl, ($R^6$)-amino-(1-3C)alkyl or di-($R^6$)-amino-(1-3C)alkyl, wherein each $R^6$ present is (1-3C)alkyl;

and when $X^1$ is selected from O, SO, SO$_2$, N($R^5$), CO, CON($R^5$), N($R^5$)CO, SO$_2$N($R^5$), N($R^5$)SO$_2$, OC($R^5$)$_2$ and N($R^5$)C($R^5$)$_2$, wherein $R^5$ has any of the meanings defined hereinbefore, $R^4$ is hydroxy-(1-3C)alkyl, (1-6C)alkoxy-(1-3C)alkyl, $R^5$—S-(1-3C)alkyl, $R^5$—S(O)-(1-3C)alkyl, $R^5$—SO$_2$-(1-3C)alkyl, $R^5$—CON($R^5$)-(1-3C)alkyl, $R^5$—CO-(1-3C)alkyl, ($R^5$)$_2$NCO-(1-3C)alkyl, amino-(1-3C)alkyl, ($R^6$)-amino-(1-3C)alkyl or di-($R^6$)-amino-(1-3C)alkyl, wherein each $R^6$ present is (1-3C)alkyl;

or $R^1$ is a group of the formula:

$Q^1$-$X^2$— wherein $X^2$ is a direct bond or is selected from O, SO, SO$_2$, N($R^7$), N[C(O)$R^7$], N[C(O)N($R^7$)$_2$], N[C(O)O$R^7$], N[SO$_2$—N($R^7$)$_2$], CO, CON($R^7$), N($R^7$)CO, SO$_2$N($R^7$), N($R^7$)SO$_2$, O—SO$_2$, SO$_2$—O, C($R^7$)$_2$O, OC($R^7$)$_2$, C($R^7$)$_2$, C($R^7$)$_2$N($R^7$) and N($R^7$)C($R^7$)$_2$, wherein each $R^7$ is independently selected from hydrogen or (1-8C)alkyl;

and $Q^1$ is heterocyclyl or heterocyclyl-(1-3C)alkyl, wherein any heterocyclyl group within a $R^1$ substituent optionally bears a halogeno, trifluoromethyl, cyano, hydroxy, amino, carboxy, (1-8C)alkyl, (2-8C)alkenyl, (2-8C)alkynyl, (1-6C)alkoxy, halogeno-(1-6C)alkoxy, hydroxy-(1-6C)alkyl, (1-6C)alkoxy-(1-6C)alkyl, halogeno-(1-6C)alkyl, amino-(1-6C)alkyl, (1-6C)alkylamino-(1-6C)alkyl, di-[(1-6C)alkyl]amino-(1-6C)alkyl, (1-6C)alkylamino, di-[(1-6C)alkyl]amino, (1-6C)alkoxycarbonyl, N-(1-6C)alkylcarbamoyl, (1-6C)alkanoylamino or heterocyclyl-(1-6C)alkyl group, and any heterocyclyl group within a $R^1$ substituent optionally bears 1 or 2 oxo substituents;

(yy) $R^1$ is a group of the formula:

$$R^4—X^1—$$

wherein $X^1$ is a direct bond or is selected from O, SO, $SO_2$, $N(R^5)$, CO, $CON(R^5)$, $N(R^5)CO$, $SO_2N(R^5)$, $N(R^5)SO_2$, $C(R^5)_2O$, $OC(R^5)_2$, $C(R^5)_2$, $C(R^5)_2N(R^5)$ and $N(R^5)C(R^5)_2$, wherein each $R^5$ is independently selected from hydrogen or (1-8C)alkyl, and when $X^1$ is a direct bond or is selected from $C(R^5)_2O$, $C(R^5)_2$ or $C(R^5)_2N(R^5)$, wherein $R^5$ has any of the meanings defined hereinbefore, $R^4$ is hydroxy-(1-3C)alkyl, (1-6C)alkoxy-(1-3C)alkyl, $R^5$—S, $R^5$—S(O), $R^5$—$SO_2$, $R^5$—$SO_2$—O, $R^5$—S-(1-3C)alkyl, $R^5$—S(O)-(1-3C)alkyl, $R^5$—$SO_2$-(1-3C)alkyl, N,N-di-$(R^5)$sulphamoyl, N,N-di-$(R^5)$sulphamoyl-(1-3C)alkyl, $R^5$—$SO_2N(R^5)$, $R^5$—$SO_2N(R^5)$-(1-3C)alkyl, $R^5$—$CON(R^5)$, $R^5$—$CON(R^5)$-(1-3C)alkyl, $R^5$—CO, $R^5$—CO-(1-3C)alkyl, $(R^5)_2NCO$, $(R^5)_2NCO$-(1-3C)alkyl, cyano, amino, $(R^6)$-amino, di-$(R^6)$-amino, amino-(1-3C)alkyl, $(R^6)$-amino-(1-3C)alkyl or di-$(R^6)$-amino-(1-3C)alkyl, wherein each $R^6$ present is (1-3C)alkyl;

and when $X^1$ is selected from O, SO, $SO_2$, $N(R^5)$, CO, $CON(R^5)$, $N(R^5)CO$, $SO_2N(R^5)$, $N(R^5)SO_2$, $OC(R^5)_2$ and $N(R^5)C(R^5)_2$, wherein $R^5$ has any of the meanings defined hereinbefore, $R^4$ is hydroxy-(1-3C)alkyl, (1-6C)alkoxy-(1-3C)alkyl, $R^5$—S-(1-3C)alkyl, $R^5$—S(O)-(1-3C)alkyl, $R^5$—$SO_2$-(1-3C)alkyl, $R^5$—$CON(R^5)$-(1-3C)alkyl, $R^5$—CO-(1-3C)alkyl, $(R^5)_2NCO$-(1-3C)alkyl, amino-(1-3C)alkyl, $(R^6)$-amino-(1-3C)alkyl or di-$(R^6)$-amino-(1-3C)alkyl, wherein each $R^6$ present is (1-3C)alkyl;

or $R^1$ is a group of the formula:

$$Q^1-X^2—$$

wherein $X^2$ is a direct bond or is selected from O, SO, $SO_2$, $N(R^7)$, $N[C(O)R^7]$, $N[C(O)N(R^7)_2]$, $N[C(O)OR^7]$, $N[SO_2—N(R^7)_2]$, CO, $CON(R^7)$, $N(R^7)CO$, $SO_2N(R^7)$, $N(R^7)SO_2$, O—$SO_2$, $SO_2$—O, $C(R^7)_2O$, $OC(R^7)_2$, $C(R^7)_2$, $C(R^7)_2N(R^7)$ and $N(R^7)C(R^7)_2$, wherein each $R^7$ is independently selected from hydrogen or (1-8C)alkyl;

and $Q^1$ is heterocyclyl, heterocyclyl-(1-3C)alkyl, heteroaryl or heteroaryl-(1-3C)alkyl, wherein said heterocyclyl or the heterocyclyl within the heterocyclyl-(1-3C)alkyl group is selected from piperidinyl, pyrrolidinyl, morpholinyl and piperazinyl, and said heteroaryl or the heteroaryl within the heteroaryl-(1-3C)alkyl group is pyrazolyl, each of which optionally bears a halogeno, trifluoromethyl, cyano, hydroxy, amino, carboxy, (1-8C)alkyl, (2-8C)alkenyl, (2-8C)alkynyl, (1-6C)alkoxy, halogeno-(1-6C)alkoxy, hydroxy-(1-6C)alkyl, (1-6C)alkoxy-(1-6C)alkyl, halogeno-(1-6C)alkyl, amino-(1-6C)alkyl, (1-6C)alkylamino-(1-6C)alkyl, di-[(1-6C)alkyl]amino-(1-6C)alkyl, (1-6C)alkylamino, di-[(1-6C)alkyl]amino, (1-6C)alkoxycarbonyl, N-(1-6C)alkylcarbamoyl, (1-6C)alkanoylamino or heterocyclyl-(1-6C)alkyl group, and any heterocyclyl group within a $R^1$ substituent optionally bears 1 or 2 oxo substituents;

(zz) $R^1$ is a group of the formula:

$$Q^1-X^2—$$

wherein $X^2$ is a direct bond or is selected from O, SO, $SO_2$, $N(R^7)$, $N[C(O)R^7]$, $N[C(O)N(R^7)_2]$, $N[C(O)OR^7]$, $N[SO_2—N(R^7)_2]$, CO, $CON(R^7)$, $N(R^7)CO$, $SO_2N(R^7)$, $N(R^7)SO_2$, O—$SO_2$, $SO_2$—O, $C(R^7)_2O$, $OC(R^7)_2$, $C(R^7)_2$, $C(R^7)_2N(R^7)$ and $N(R^7)C(R^7)_2$, wherein each $R^7$ is independently selected from hydrogen or (1-8C)alkyl;

and $Q^1$ is heterocyclyl, heterocyclyl-(1-3C)alkyl, heteroaryl or heteroaryl-(1-3C)alkyl, wherein said heterocyclyl or the heterocyclyl within the heterocyclyl-(1-3C)alkyl group is selected from piperidinyl, pyrrolidinyl, morpholinyl and piperazinyl, and said heteroaryl or the heteroaryl within the heteroaryl-(1-3C)alkyl group is pyrazolyl, each of which optionally bears a halogeno, trifluoromethyl, cyano, hydroxy, amino, carboxy, (1-8C)alkyl, (2-8C)alkenyl, (2-8C)alkynyl, (1-6C)alkoxy, halogeno-(1-6C)alkoxy, hydroxy-(1-6C)alkyl, (1-6C)alkoxy-(1-6C)alkyl, halogeno-(1-6C)alkyl, amino-(1-6C)alkyl, (1-6C)alkylamino-(1-6C)alkyl, di-[(1-6C)alkyl]amino-(1-6C)alkyl, (1-6C)alkylamino, di-[(1-6C)alkyl]amino, (1-6C)alkoxycarbonyl, N-(1-6C)alkylcarbamoyl, (1-6C)alkanoylamino or heterocyclyl-(1-6C)alkyl group, and any heterocyclyl group within a $R^1$ substituent optionally bears 1 or 2 oxo substituents;

(aaa) $R^1$ is a group of the formula:

$$R^4—X^1—$$

wherein $X^1$ is a direct bond or is selected from O, SO, $SO_2$, $N(R^5)$, CO, $CON(R^5)$, $N(R^5)CO$, $SO_2N(R^5)$, $N(R^5)SO_2$, $C(R^5)_2O$, $OC(R^5)_2$, $C(R^5)_2$, $C(R^5)_2N(R^5)$ and $N(R^5)C(R^5)_2$, wherein each $R^5$ is independently selected from hydrogen or (1-8C)alkyl, and when $X^1$ is a direct bond or is selected from $C(R^5)_2O$, $C(R^5)_2$ or $C(R^5)_2N(R^5)$, wherein $R^5$ has any of the meanings defined hereinbefore, $R^4$ is hydroxy-(1-3C)alkyl, (1-6C)alkoxy-(1-3C)alkyl, $R^5$—S, $R^5$—S(O), $R^5$—$SO_2$, $R^5$—$SO_2$—O, $R^5$—S-(1-3C)alkyl, $R^5$—S(O)-(1-3C)alkyl, $R^5$—$SO_2$-(1-3C)alkyl, N,N-di-$(R^5)$sulphamoyl, N,N-di-$(R^5)$sulphamoyl-(1-3C)alkyl, $R^5$—$SO_2N(R^5)$, $R^5$—$SO_2N(R^5)$-(1-3C)alkyl, $R^5$—$CON(R^5)$, $R^5$—$CON(R^5)$-(1-3C)alkyl, $R^5$—CO, $R^5$—CO-(1-3C)alkyl, $(R^5)_2NCO$, $(R^5)_2NCO$-(1-3C)alkyl, cyano, amino, $(R^6)$-amino, di-$(R^6)$-amino, amino-(1-3C)alkyl, $(R^6)$-amino-(1-3C)alkyl or di-$(R^6)$-amino-(1-3C)alkyl, wherein each $R^6$ present is (1-3C)alkyl;

and when $X^1$ is selected from O, SO, $SO_2$, $N(R^5)$, CO, $CON(R^5)$, $N(R^5)CO$, $SO_2N(R^5)$, $N(R^5)SO_2$, $OC(R^5)_2$ and $N(R^5)C(R^5)_2$, wherein $R^5$ has any of the meanings defined hereinbefore, $R^4$ is hydroxy-(1-3C)alkyl, (1-6C)alkoxy-(1-3C)alkyl, $R^5$—S-(1-3C)alkyl, $R^5$—S(O)-(1-3C)alkyl, $R^5$—$SO_2$-(1-3C)alkyl, $R^5$—$CON(R^5)$-(1-3C)alkyl, $R^5$—CO-(1-3C)alkyl, $(R^5)_2NCO$-(1-3C)alkyl, amino-(1-3C)alkyl, $(R^6)$-amino-(1-3C)alkyl or di-$(R^6)$-amino-(1-3C)alkyl, wherein each $R^6$ present is (1-3C)alkyl;

(bbb) $R^1$ is hydroxymethyl, methoxymethyl, 2-methoxyethoxy, ethylsulphonyl, methylsulphonyl, methylsulphonyloxy, methylsulphamoyl, cyclopropylsulphamoyl, dimethylsulphamoyl, 2-hydroxyethylsulphamoyl, cyclopropylsulphamoyl, methanesulphonamido, acetamido, carbamoyl, methylcarbamoyl, cyclopropylcarbamoyl, 2-hydroxyethylcarbamoyl, dimethylamino, 2-dimethylaminoethylcarbamoyl, 2-diethylaminoethylcarbamoyl, 3-diethylaminopropylcarbamoyl, cyano, cyanomethyl, aminomethyl, dimethylaminomethyl, pyrrolidin-1-yl, piperazin-1-yl, piperidin-4-yl, pyrazol-3-yl, pyrrolidin-1-ylmethyl, morpholino, morpholinomethyl, 2-morpholinoethylcarbamoyl, morpholine-4-carbonyl, morpholinosulphonyl, 4-hydroxypiperidine-1-carbonyl, 2-pyrrolidin-1-ylethylcarbamoyl, piperidin-1-yl, piperidin-4-yl, 1-methyl-4-piperidyl, 1-ethyl-4-piperidyl, 1-isopropyl-4-piperidyl, 1-piperidylmethyl, piperidine-4-carbonylamino, 4-methylpiperazine-1-carbonyl, 4-methylpiperazin-1-yl, 3-dimethylaminopropoxy, 1-tert-butoxycarbonyl-4-piperidyl or 1-methyl-1-oxido-piperidin-1-ium-4-yl;

(ccc) each $R^2$ group is methyl, methoxy, ethoxy, propoxy, fluoro, bromo or chloro;
(ddd) each $R^2$ group is methyl, methoxy or fluoro;
(eee) Ring A is selected from:
  (i) phenyl substituted by $R^1$ and optionally substituted by an $R^2$ group; or
  (ii) pyrazolyl, pyridinyl, thienyl, thiazolyl or 1H-1,2,3-triazolyl, said ring being substituted by $R^1$ and optionally substituted by an $R^2$ group; or
  (iii) naphthyl, quinolyl, 2,3-dihydro-1,4-benzodioxinyl, 1H-indazolyl, 1H-indolyl or 1,3-benzodioxolyl, wherein said bicyclic ring system is optionally substituted by $R^1$ and optionally substituted by an $R^2$ group;
(fff) Ring A is selected from:
  (i) phenyl substituted by $R^1$ and optionally substituted by an $R^2$ group; or
  (ii) pyrazol-4-yl, pyridin-3-yl, thien-2-yl, thiazol-5-yl, 1H-1,2,3-triazol-4-yl or 3H-1,2,3-triazol-5-yl ring, said ring being substituted by $R^1$ and optionally substituted by an $R^2$ group; or
  (iii) naphthyl, quinol-8-yl, quinol-3-yl, quinol-4-yl, 2,3-dihydro-1,4-benzodioxin-6-yl, 1H-indazol-5-yl, 1H-indol-5-yl, 1H-indol-6-yl or 1,3-benzodioxol-5-yl, wherein said bicyclic ring system is optionally substituted by $R^1$ and optionally substituted by an $R^2$ group;
(ggg) $R^1$ is a group of the formula:

$$R^4-X^1-$$

wherein $X^1$ is a direct bond or is selected from O, SO, $SO_2$, $N(R^5)$, CO, $CON(R^5)$, $N(R^5)CO$, $SO_2N(R^5)$, $N(R^5)SO_2$, $C(R^5)_2O$, $OC(R^5)_2$, $C(R^5)_2$, $C(R^5)_2N(R^5)$ and $N(R^5)C(R^5)_2$, wherein each $R^5$ is independently selected from hydrogen or (1-8C)alkyl;
and when $X^1$ is a direct bond or is selected from $C(R^5)_2O$, $C(R^5)_2$ or $C(R^5)_2N(R^5)$, wherein $R^5$ has any of the meanings defined hereinbefore, $R^4$ is hydroxy-(1-6C)alkyl, (1-6C)alkoxy-(1-6C)alkyl, $R^5-S$, $R^5-S(O)$, $R^5-SO_2$, $R^5-SO_2-O$, $R^5-S-(1-6C)$alkyl, $R^5-S(O)-(1-6C)$alkyl, $R^5-SO_2-(1-6C)$alkyl, N,N-di-$(R^5)$sulphamoyl, N,N-di-$(R^5)$sulphamoyl-(1-6C)alkyl, $R^5-SO_2N(R^5)$, $R^5-SO_2N(R^5)$-(1-6C)alkyl, $R^5-CON(R^5)$, $R^5O-CON(R^5)$, $R^5-CON(R^5)$-(1-6C)alkyl, $R^5O-CON(R^5)$-(1-6C)alkyl, $(R^5)_2N-SO_2N(R^5)$, $(R^5)_2N-SO_2N(R^5)$-(1-6C)alkyl, $(R^5)_2N-CON(R^5)$, $(R^5)_2N-CON(R^5)$-(1-6C)alkyl, $R^5-CO$, $R^5-CO$-(1-6C)alkyl, $R^5O-CO$, $R^5O-CO$-(1-6C)alkyl, $(R^5)_2NCO$, $(R^5)_2NCO$-(1-6C)alkyl, $(R^5)_2N-COO$, $(R^5)_2NCOO$-(1-6C)alkyl, cyano, amino, $(R^6)$-amino, di-$(R^6)$-amino, amino-(1-6C)alkyl, $(R^6)$-amino-(1-6C)alkyl or di-$(R^6)$-amino-(1-6C)alkyl, wherein each $R^6$ present is (1-6C)alkyl optionally substituted by 1, 2 or 3 substituents independently selected from halogeno, cyano, hydroxy and (1-6C)alkoxy;
and when $X^1$ is selected from O, SO, $SO_2$, $N(R^5)$, CO, CON$(R^5)$, $N(R^5)CO$, $SO_2N(R^5)$, $N(R^5)SO_2$, $OC(R^5)_2$ and $N(R^5)C(R^5)_2$, wherein $R^5$ has any of the meanings hereinbefore, $R^4$ is hydroxy-(1-6C)alkyl, (1-6C)alkoxy-(1-6C)alkyl, $R^5-S$-(1-6C)alkyl, $R^5-S(O)$-(1-6C)alkyl, $R^5-SO_2$-(1-6C)alkyl, N,N-di-$(R^5)$sulphamoyl-(1-6C)alkyl, $R^5-SO_2N(R^5)$-(1-6C)alkyl, $R^5-CON(R^5)$-(1-6C)alkyl, $R^5O-CON(R^5)$-(1-6C)alkyl, $(R^5)_2N-SO_2N(R^5)$-(1-6C)alkyl, $(R^5)_2N-CON(R^5)$-(1-6C)alkyl, $R^5-CO$, $R^5-CO$-(1-6C)alkyl, $R^5O-CO$, $R^5O-CO$-(1-6C)alkyl, $(R^5)_2NCO$, $(R^5)_2NCO$-(1-6C)alkyl, $(R^5)_2NCOO$-(1-6C)alkyl, amino-(1-6C)alkyl, $(R^6)$-amino-(1-6C)alkyl or di-$(R^6)$-amino-(1-6C)alkyl, wherein each $R^6$ present is (1-6C)alkyl optionally substituted by 1, 2 or 3 substituents independently selected from halogeno, cyano, hydroxy and (1-6C)alkoxy;
or $R^1$ is a group of the formula:

$$Q^1-X^2-$$

wherein $X^2$ is a direct bond or is selected from O, SO, $SO_2$, $N(R^7)$, $N[C(O)R^7]$, $N[C(O)N(R^7)_2]$, $N[C(O)OR^7]$, $N[SO_2-N(R^7)_2]$, CO, $CON(R^7)$, $N(R^7)CO$, $SO_2N(R^7)$, $N(R^7)SO_2$, $O-SO_2$, $SO_2-O$, $C(R^7)_2O$, $OC(R^7)_2$, $C(R^7)_2$, $C(R^7)_2N(R^7)$ and $N(R^7)C(R^7)_2$, wherein each $R^7$ is independently selected from hydrogen or (1-8C)alkyl;
and $Q^1$ is aryl, aryl-(1-6C)alkyl, (3-8C)cycloalkyl, (3-8C)cycloalkyl-(1-6C)alkyl, heterocyclyl, heterocyclyl-(1-6C)alkyl, heteroaryl or heteroaryl-(1-6C)alkyl, wherein any aryl or (3-8C)cycloalkyl group within a $R^1$ substituent bears 1, 2 or 3 substituents and any heterocyclyl or heteroaryl group within a $R^1$ substituent optionally bears 1, 2 or 3 substituents, wherein said substituents are independently selected from halogeno, trifluoromethyl, cyano, nitro, hydroxy, amino, carboxy, carbamoyl, ureido, (1-8C)alkyl, (2-8C)alkenyl, (2-8C)alkynyl, (1-6C)alkoxy, halogeno-(1-6C)alkoxy, hydroxy-(1-6C)alkyl, (1-6C)alkoxy-(1-6C)alkyl, (1-6C)alkylsulphonyl-(1-6C)alkyl, cyano-(1-6C)alkyl, halogeno-(1-6C)alkyl, amino-(1-6C)alkyl, (1-6C)alkylamino-(1-6C)alkyl, di-[(1-6C)alkyl]amino-(1-6C)alkyl, (2-6C)alkenyloxy, (2-6C)alkynyloxy, (1-6C)alkylthio, (1-6C)alkylsulphinyl, (1-6C)alkylsulphonyl, (1-6C)alkylamino, di-[(1-6C)alkyl]amino, (1-6C)alkoxycarbonyl, (2-6C)alkanoyl, hydroxy-(2-6C)alkanoyl, (1-6C)alkoxy-(2-6C)alkanoyl, (2-6C)alkanoyloxy, N-(1-6C)alkylcarbamoyl, N,N-di-[(1-6C)alkyl]carbamoyl, carbamoyl-(1-6C)alkyl, N-(1-6C)alkylcarbamoyl-(1-6C)alkyl, N,N-di-[(1-6C)alkyl]carbamoyl-(1-6C)alkyl, (1-6C)alkanoylamino, N-(1-6C)alkyl-(1-6C)alkanoylamino, N-(1-6C)alkylureido, N'-(1-6C)alkylureido, N',N'-di-[(1-6C)alkyl]ureido, N,N'-di-[(1-6C)alkyl]ureido, N,N',N'-tri-[(1-6C)alkyl]ureido, N-(1-6C)alkylsulphamoyl, N,N-di-[(1-6C)alkyl]sulphamoyl, (1-6C)alkanesulphonylamino, N-(1-6C)alkyl-(1-6C)alkanesulphonylamino, heterocyclyl, heterocyclyl-(1-6C)alkyl, heteroaryl or heteroaryl-(1-6C)alkyl and any heterocyclyl group within a $R^1$ substituent optionally bears 1 or 2 oxo substituents; wherein, any CH, $CH_2$, or $CH_3$ in any alkyl group present in the definition of $R^4$ that is connected to $X^1$ or present in the definition of $Q^1$ that is connected to $X^2$, optionally bears a hydroxy or cyano group and optionally bears up to three halogeno groups, and can optionally be replaced by an atom selected from O, S or N or a $SO_2$ group and adjacent carbon atoms in an alkyl chain can optionally be separated by the insertion into the chain of a $C\equiv C$ group;
(hhh) $R^1$ is a group of the formula:

$$R^4-X^1-$$

wherein $X^1$ is a direct bond or is selected from O, SO, $SO_2$, $N(R^5)$, CO, $CON(R^5)$, $N(R^5)CO$, $SO_2N(R^5)$, $N(R^5)SO_2$, $C(R^5)_2O$, $OC(R^5)_2$, $C(R^5)_2$, $C(R^5)_2N(R^5)$ and $N(R^5)C(R^5)_2$, wherein each $R^5$ is independently selected from hydrogen or (1-8C)alkyl,
and when $X^1$ is a direct bond or is selected from $C(R^5)_2O$, $C(R^5)_2$ or $C(R^5)_2N(R^5)$, wherein $R^5$ has any of the meanings defined hereinbefore, $R^4$ is hydroxy-(1-6C)alkyl, (1-6C)alkoxy-(1-6C)alkyl, $R^5-S$, $R^5-S(O)$, $R^5-SO_2$, $R^5-SO_2-O$, $R^5-S-(1-6C)$alkyl, $R^5-S(O)-(1-6C)$alkyl, $R^5-SO_2-(1-6C)$alkyl, N,N-di-$(R^5)$sulphamoyl, N,N-di-$(R^5)$sulphamoyl-(1-6C)alkyl, $R^5-SO_2N(R^5)$, $R^5-SO_2N(R^5)$-(1-6C)alkyl, $R^5-CON(R^5)$, $R^5-CON(R^5)$-(1-6C)alkyl, $R^5-CO$, $R^5-CO$-(1-6C)alkyl, $(R^5)_2NCO$, $(R^5)_2NCO$-(1-6C)alkyl, cyano, amino, $(R^6)$- amino, di-$(R^6)$-amino, amino-(1-6C)alkyl, $(R^6)$-amino-(1-6C)alkyl or di-$(R^6)$-amino-(1-6C)alkyl, wherein each $R^6$ present is (1-6C)alkyl;

and when X$^1$ is selected from O, SO, SO$_2$, N(R$^5$), CO, CON(R$^5$), N(R$^5$)CO, SO$_2$N(R$^5$), N(R$^5$)SO$_2$, OC(R$^5$)$_2$ and N(R$^5$)C(R$^5$)$_2$, wherein R$^5$ has any of the meanings defined hereinbefore, R$^4$ is hydroxy-(1-6C)alkyl, (1-6C)alkoxy-(1-6C)alkyl, R$^5$—S-(1-6C)alkyl, R$^5$—S(O)-(1-6C)alkyl, R$^5$—SO$_2$-(1-6C)alkyl, R$^5$—CON(R$^5$)-(1-6C)alkyl, R$^5$—CO-(1-6C)alkyl, (R$^5$)$_2$NCO-(1-6C)alkyl, amino-(1-6C)alkyl, (R$^6$)-amino-(1-6C)alkyl or di-(R$^6$)-amino-(1-6C)alkyl, wherein each R$^6$ present is (1-6C)alkyl;

or R$^1$ is a group of the formula:

Q$^1$-X$^2$— wherein X$^2$ is a direct bond or is selected from O, SO, SO$_2$, N(R$^7$), N[C(O)R$^7$], N[C(O)N(R$^7$)$_2$], N[C(O)OR$^7$], N[SO$_2$—N(R$^7$)$_2$], CO, CON(R$^7$), N(R$^7$)CO, SO$_2$N(R$^7$), N(R$^7$)SO$_2$, O—SO$_2$, SO$_2$—O, C(R$^7$)$_2$O, OC(R$^7$)$_2$, C(R$^7$)$_2$, C(R$^7$)$_2$N(R$^7$) and N(R$^7$)C(R$^7$)$_2$, wherein each R$^7$ is independently selected from hydrogen or (1-8C)alkyl;

and Q$^1$ is heterocyclyl, heterocyclyl-(1-6C)alkyl, heteroaryl or heteroaryl-(1-6C)alkyl, wherein any heterocyclyl or heteroaryl group within a R$^1$ substituent optionally bears 1, 2 or 3 substituents, wherein said substituents are independently selected from halogeno, trifluoromethyl, cyano, hydroxy, amino, carboxy, (1-8C)alkyl, (2-8C)alkenyl, (2-8C)alkynyl, (1-6C)alkoxy, halogeno-(1-6C)alkoxy, hydroxy-(1-6C)alkyl, (1-6C)alkoxy-(1-6C)alkyl, halogeno-(1-6C)alkyl, amino-(1-6C)alkyl, (1-6C)alkylamino-(1-6C)alkyl, di-[(1-6C)alkyl]amino-(1-6C)alkyl, (1-6C)alkylamino, di-[(1-6C)alkyl]amino, (1-6C)alkoxycarbonyl, N-(1-6C)alkylcarbamoyl, (1-6C)alkanoylamino, hydroxy-(2-6C)alkanoyl, (1-6C)alkoxy-(2-6C)alkanoyl, carbamoyl-(1-6C)alkyl, N-(1-6C)alkylcarbamoyl-(1-6C)alkyl, N,N-di-[(1-6C)alkyl]carbamoyl-(1-6C)alkyl, heterocyclyl, heterocyclyl-(1-6C)alkyl, heteroaryl or heteroaryl-(1-6C)alkyl, and any heterocyclyl group within a R$^1$ substituent optionally bears 1 or 2 oxo substituents; wherein, any CH, CH$_2$, or CH$_3$ in any alkyl group present in the definition of R$^4$ that is connected to X$^1$ or present in the definition of Q$^1$ that is connected to X$^2$, can optionally be replaced by an O atom or a SO$_2$ group and adjacent carbon atoms in an alkyl chain can optionally be separated by the insertion into the chain of a C≡C group;

(iii) R$^1$ is a group of the formula:

R$^4$—X$^1$— wherein X$^1$ is a direct bond or is selected from O, SO, SO$_2$, N(R$^5$), CO, CON(R$^5$), N(R$^5$)CO, SO$_2$N(R$^5$), N(R$^5$)SO$_2$, C(R$^5$)$_2$O, OC(R$^5$)$_2$, C(R$^5$)$_2$, C(R$^5$)$_2$N(R$^5$) and N(R$^5$)C(R$^5$)$_2$, wherein each R$^5$ is independently selected from hydrogen or (1-8C)alkyl, and when X$^1$ is a direct bond or is selected from C(R$^5$)$_2$O, C(R$^5$)$_2$ or C(R$^5$)$_2$N(R$^5$), wherein R$^5$ has any of the meanings defined hereinbefore, R$^4$ is hydroxy-(1-3C)alkyl, (1-6C)alkoxy-(1-3C)alkyl, R$^5$—S, R$^5$—S(O), R$^5$—SO$_2$, R$^5$—SO$_2$—O, R$^5$—S-(1-3C)alkyl, R$^5$—S(O)-(1-3C)alkyl, R$^5$—SO$_2$-(1-3C)alkyl, N,N-di-(R$^5$)sulphamoyl, N,N-di-(R$^5$)sulphamoyl-(1-3C)alkyl, R$^5$—SO$_2$N(R$^5$), R$^5$—SO$_2$N(R$^5$)-(1-3C)alkyl, R$^5$—CON(R$^5$), R$^5$—CON(R$^5$)-(1-3C)alkyl, R$^5$—CO, R$^5$—CO-(1-3C)alkyl, (R$^5$)$_2$NCO, (R$^5$)$_2$NCO-(1-3C)alkyl, cyano, amino, (R$^6$)-amino, di-(R$^6$)-amino, amino-(1-3C)alkyl, (R$^6$)-amino-(1-3C)alkyl or di-(R$^6$)-amino-(1-3C)alkyl, wherein each R$^6$ present is (1-3C)alkyl;

and when X$^1$ is selected from O, SO, SO$_2$, N(R$^5$), CO, CON(R$^5$), N(R$^5$)CO, SO$_2$N(R$^5$), N(R$^5$)SO$_2$, OC(R$^5$)$_2$ and N(R$^5$)C(R$^5$)$_2$, wherein R$^5$ has any of the meanings defined hereinbefore, R$^4$ is hydroxy-(1-3C)alkyl, (1-6C)alkoxy-(1-3C)alkyl, R$^5$—S-(1-3C)alkyl, R$^5$—S(O)-(1-3C)alkyl, R$^5$—SO$_2$-(1-3C)alkyl, R$^5$—CON(R$^5$)-(1-3C)alkyl, R$^5$—CO-(1-3C)alkyl, (R$^5$)$_2$NCO-(1-3C)alkyl, amino-(1-3C)alkyl, (R$^6$)-amino-(1-3C)alkyl or di-(R$^6$)-amino-(1-3C)alkyl, wherein each R$^6$ present is (1-3C)alkyl;

or R$^1$ is a group of the formula:

Q$^1$-X$^2$— wherein X$^2$ is a direct bond or is selected from O, SO, SO$_2$, N(R$^7$), N[C(O)R$^7$], N[C(O)N(R$^7$)$_2$], N[C(O)OR$^7$], N[SO$_2$—N(R$^7$)$_2$], CO, CON(R$^7$), N(R$^7$)CO, SO$_2$N(R$^7$), N(R$^7$)SO$_2$, O—SO$_2$, SO$_2$—O, C(R$^7$)$_2$O, OC(R$^7$)$_2$, C(R$^7$)$_2$, C(R$^7$)$_2$N(R$^7$) and N(R$^7$)C(R$^7$)$_2$, wherein each R$^7$ is independently selected from hydrogen or (1-8C)alkyl;

and Q$^1$ is heterocyclyl, heterocyclyl-(1-3C)alkyl, heteroaryl or heteroaryl-(1-3C)alkyl, wherein said heterocyclyl or the heterocyclyl within the heterocyclyl-(1-3C)alkyl group is selected from piperidinyl, pyrrolidinyl, morpholinyl, piperazinyl, tetrahydro-2H-pyranyl, azetidinyl, 1,1-dioxotetrahydro-1,4-thiazinyl, imidazolinyl, azepanyl, 1H-imidazolyl, 1,4-diazepanyl, (1R,5S)-8-azabicyclo[3.2.1]octanyl, quinuclidinyl, (3R)-quinuclidinyl, 3,4,4a,5,6,7,8,8a-octahydro-2H-quinolinyl, 3,4,6,7,8,8a-hexahydro-1H-pyrrolo[2,1-c]pyrazinyl, and said heteroaryl or the heteroaryl within the heteroaryl-(1-3C)alkyl group is pyrazolyl, each of which optionally bears a halogeno, trifluoromethyl, cyano, hydroxy, amino, carboxy, (1-8C)alkyl, (2-8C)alkenyl, (2-8C)alkynyl, (1-6C)alkoxy, halogeno-(1-6C)alkoxy, hydroxy-(1-6C)alkyl, (1-6C)alkoxy-(1-6C)alkyl, halogeno-(1-6C)alkyl, amino-(1-6C)alkyl, (1-6C)alkylamino-(1-6C)alkyl, di-[(1-6C)alkyl]amino-(1-6C)alkyl, (1-6C)alkylamino, di-[(1-6C)alkyl]amino, (1-6C)alkoxycarbonyl, N-(1-6C)alkylcarbamoyl, (1-6C)alkanoylamino, hydroxy-(2-6C)alkanoyl, (1-6C)alkoxy-(2-6C)alkanoyl, carbamoyl-(1-6C)alkyl, N-(1-6C)alkylcarbamoyl-(1-6C)alkyl, N,N-di-[(1-6C)alkyl]carbamoyl-(1-6C)alkyl, heterocyclyl, heterocyclyl-(1-6C)alkyl, heteroaryl or heteroaryl-(1-6C)alkyl, and any heterocyclyl group within a R$^1$ substituent optionally bears 1 or 2 oxo substituents; wherein, any CH, CH$_2$, or CH$_3$ in any alkyl group present in the definition of R$^4$ that is connected to X$^1$ or present in the definition of Q$^1$ that is connected to X$^2$, can optionally be replaced by an O atom or a SO$_2$ group and adjacent carbon atoms in an alkyl chain can optionally be separated by the insertion into the chain of a C≡C group;

(jjj) R$^1$ is hydroxymethyl, 2-hydroxyethyl, 3-hydroxypropyl, methoxymethyl, cyanomethyl, acetyl, 2-methoxyacetyl, hydroxyacetyl, 2-hydroxypropionyl, 2-aminoethoxy, 2-methylaminoethoxy, 3-aminopropoxy, 3-methylaminopropoxy, 4-methylaminobutoxy, 2-methoxyethoxy, ethylsulphonyl, methylsulphonyl, methylsulphonyloxy, methylsulphamoyl, cyclopropylsulphamoyl, dimethylsulphamoyl, 2-hydroxyethylsulphamoyl, cyclopropylsulphamoyl, methanesulphonamido, acetamido, carbamoyl, methylcarbamoyl, cyclopropylcarbamoyl, 2-hydroxyethylcarbamoyl, dimethylamino, 2-dimethylaminoethylcarbamoyl, 3-dimethylaminopropylcarbamoyl, 2-diethylaminoethylcarbamoyl, 3-diethylaminopropylcarbamoyl, cyano, cyanomethyl, aminomethyl, dimethylaminomethyl, 2-(dimethylamino)ethoxy, 2-(diethylamino)ethoxy, 3-(dimethylamino)propoxy, 3-(diethylamino)propoxy, pyrrolidin-1-yl, pyrrolidin-3-yl, pyrrolidin-2-yl, piperazin-1-yl, piperidin-4-yl, piperidin-3-yl, pyrazol-3-yl, tetrahydropyran-2-yl, tetrahydropyran-4-yl, azetidinyl, 1,1-dioxotetrahydro-1,4-thiazinyl, imidazolinyl, azepanyl, 1H-imidazolyl, 1,4-diazepanyl, (1R,5S)-8-azabicyclo[3.2.1]octanyl, quinuclidinyl, (3R)-quinuclidinyl, 3,4,4a,5,6,7,8,8a-octahydro-2H-quinolinyl, 3,4,6,7,8,8a-hexahydro-1H-pyrrolo[2,1-c]pyrazinyl, pyrrolidin-1-ylmethyl, piperidin-4-ylmethyl, 1-methylpyrrolidin-3-yl, 1-methylpyrrolidin-3-ylmethyl, 1-methylpyrrolidin-3-ylmethoxy, 1-methylpyrrolidin-3-yloxy, 2-(1-methylpyrrolidin-3-yl)ethoxy, 2-pyrrolidin-1-ylethyl, 3-pyrrolidin-1-ylpropyl, 2-(1-methylpyrrolidin-2-yl)ethoxy, 2-(1-methylpyrrolidin-2-yl)ethylcarbamoyl, piperidin-3-ylmethyl, 1-methyl-piperidin-3-yl, 1-methyl-piperidin-3-ylmethoxy, 1-methyl-piperidin-3-yloxy, piperidin-3-ylmethoxy, 2-(1-methyl-piperidin-3-yl)ethoxy, 3-(1-methyl-piperidin-3-yl)propoxy, piperidin-4-yloxy, 1-methyl-piperidin-4-ylmethoxy, azetidin-3-ylmethyl, 2-azetidinylethyl, 3-azetidinylpropyl, 1-methyl-azetidin-3-yl, 1-methyl-azetidin-3-ylmethyl, 2-(3-hydroxy-pyrrolidin-1-yl)ethyl, 3-(3-hydroxy-pyrrolidin-1-yl)propyl, 3-(3-hydroxymethyl-pyrrolidin-1-yl)propyl, 2-(4-hydroxypiperidin-1-yl)ethyl, 3-(4-hydroxypiperidin-1-yl)propyl, 1-acetylpiperidin-4-yl, 1-methoxyacetylpiperidin-4-yl, 1-hydroxyacetylpiperidin-4-yl, 1-hydroxyacetylpiperidin-4-yl, 1-(2-hydroxypropionyl)piperidin-4-yl, 5-(methylcarbamoyl)-1-methyl-pyrrolidin-3-yl, 3-pyrrolidin-1-ylpropoxy, 2-pyrrolidin-1-ylethoxy, 2-(1-methylpiperidin-2-yl)ethoxy, 3-(1,1-dioxotetrahydro-1,4-thiazin-4-yl)propoxy, 2-(piperazin-1-yl)ethyl, 2-(1-methyl-piperazin-4-yl)ethoxy, 3-(1-methyl-piperazin-4-yl)propoxy, 2-(1-methyl-piperazin-4-yl)ethyl, 3-(1-methyl-piperazin-4-yl)propyl, 3-(1-sulphonyl-piperazin-4-yl)propoxy, 3-(1-methylsulphonylpiperazin-4-yl)-propoxy, 3-(1,1-dioxotetrahydro-1,4-thiazin-4-yl)propoxy, (1R,5S)-8-azabicyclo[3.2.1]octan-3-yloxy, [(2E)-4-(1,1-dioxidothiomorpholin-4-yl)but-2-en-1-yl]oxidanyl, (3R)-quinuclidin-8-ylcarbamoyl, morpholino, morpholinomethyl, 2-morpholinoethyl, 3-morpholinopropyl, 2-morpholinoethoxy, 3-morpholinopropoxy, 2-(2-morpholinoethoxy)ethoxy, 2-piperazin-4-ylethoxy, 2-(piperidin-4-yloxy)ethoxy, 2-(azetidin-3-yloxy)ethoxy, 3-(2,6-dimethylpiperazin-4-yl)propoxy, 1-methylpyrrolidin-3-yl-N-methylcarbamoyl, quinuclidinylcarbonyl, 2-imidazolin-1-ylethylcarbamoyl, 2-(piperidin-1-ylmethyl)piperidin-1-ylcarbonyl, 1-ethoxypiperidin-4-ylcarbamoyl, 2-pyrrolidin-1-ylcyclohex-1-yl-N-methylcarbamoyl, 2-(3-fluoropyrrolidin-1-yl)ethylcarbamoyl, 4-(2-dimethylaminoethyl)piperidin-1-ylcarbonyl, 2-(1-methylpiperidin-2-yl)-pyrrolidin-1-ylcarbonyl, 5-(morpholinylmethyl)pyrrolidin-1-ylcarbonyl, 5-(azepan-1-yl)pyrrolidin-1-ylcarbonyl, 2-(3,3-difluoropyrrolidin-1-yl)ethylcarbamyl, 2-(3-fluoropyrrolidin-1-yl)ethylcarbamyl, 3,4,4a,5,6,7,8,8a-octahydro-2H-quinolin-4-ylcarbamoyl, 1-dimethylaminocyclohex-1-ylmethylcarbamoyl, 2-morpholinoethylcarbamoyl, 2-1H-imidazolylethylcarbamoyl, 1-(pyridin-3-yl)piperazin-4-ylcarbonyl, 1-(pyridin-4-yl)piperazin-4-ylcarbonyl, 1,4-diazepanylcarbonyl, 1-(N-dimethylcarbamoylmethyl)piperazin-4-ylcarbonyl, 1-(carbamoylethyl)piperazin-4-ylcarbonyl, 3,4,6,7,8,8a-hexahydro-1H-pyrrolo[2,1-c]pyrazin-1-ylcarbonyl, morpholine-4-carbonyl, morpholinosulphonyl, 4-hydroxypiperidine-1-carbonyl, 2-pyrrolidin-1-ylethylcarbamoyl, piperidin-1-yl, piperidin-4-yl, 1-methyl-4-piperidyl, 1-methylpiperidin-4-ylmethyl, 1-(2-methoxyethyl)piperidin-4-ylcarbamoyl, 1-ethyl-4-piperidyl, 1-isopropyl-4-piperidyl, 1-piperidylmethyl, piperidine-4-carbonylamino, 4-methylpiperazine-1-carbonyl, 4-methylpiperazin-1-yl, 3-dimethylaminopropoxy, 1-tert-butoxycarbonyl-4-piperidyl or 1-methyl-1-oxido-piperidin-1-ium-4-yl;

(kkk) each $R^2$ group is methyl, methoxy, ethoxy, propoxy, fluoro, bromo, chloro or hydroxymethyl;

(lll) each $R^2$ group is methyl, methoxy, ethoxy, fluoro or hydroxymethyl;

(mmm) n is 0, 1 or 2 and, when n is 2, each $R^3$ group may be the same or different, and each $R^3$ group present is selected from hydrogen, fluoro, bromo, chloro, $OR^9$, trifluoromethyl, methyl or propyl, wherein $R^9$ is methyl or trifluoromethyl;

(nnn) each of $G_1$, $G_2$, $G_3$ and $G_4$ is selected from CH and N provided that one of $G_1$, $G_2$, $G_3$ and $G_4$ represents N;

(ooo) Ring A is pyrazolyl, said ring being substituted by $R^1$ and optionally substituted by an $R^2$ group;

(ppp) Ring A is pyrazol-4-yl, said ring being substituted by $R^1$ and optionally substituted by an $R^2$ group;

(qqq) Ring A is pyrazol-4-yl, said ring being substituted by $R^1$ and being substituted by an $R^2$ group;

(rrr) Ring A is pyrazol-4-yl, said ring being substituted by $R^1$ and being substituted by an $R^2$ group which is located at the 3 position of the pyrazol-4-yl ring;

(sss) Ring A is pyrazol-4-yl, said ring being substituted by $R^1$ and being substituted by an $R^2$ group which is located at the 3 position of the pyrazol-4-yl ring, wherein the $R^2$ is selected from any one of methyl, methoxy, ethoxy, fluoro, hydroxymethyl, methoxymethyl, ethoxymethyl, cyano, 1-hydroxyethyl, dimethylcarbamoyl, dimethylamino, methylcarbamoyl, methylaminomethyl or carbamoyl;

(ttt) Ring A is pyrazol-4-yl, said ring being substituted by $R^1$ and being substituted by an $R^2$ group which is located at the 3-position of the pyrazol-4-yl ring, wherein the $R^2$ is selected from any one of methyl, methoxy, ethoxy, hydroxymethyl, methoxymethyl, cyano or dimethylcarbamoyl;

(uuu) $R^1$ is a group of the formula:

$$R^4—X^1—$$

wherein $X^1$ is a direct bond or is selected from O, SO, $SO_2$, $N(R^5)$, CO, $CON(R^5)$, $N(R^5)CO$, $SO_2N(R^5)$, $N(R^5)SO_2$, $C(R^5)_2O$, $OC(R^5)_2$, $C(R^5)_2$, $C(R^5)_2N(R^5)$ and $N(R^5)C(R^5)_2$, wherein each $R^5$ is independently selected from hydrogen or (1-8C)alkyl;

and when $X^1$ is a direct bond or is selected from $C(R^5)_2O$, $C(R^5)_2$ or $C(R^5)_2N(R^5)$, wherein $R^5$ has any of the meanings defined hereinbefore, $R^4$ is hydroxy-(1-6C)alkyl, (1-6C)alkoxy-(1-6C)alkyl, $R^5—S$, $R^5—S(O)$, $R^5—SO_2$, $R^5—SO_2—O$, $R^5—S-(1-6C)alkyl$, $R^5—S(O)-(1-6C)alkyl$, $R^5—SO_2-(1-6C)alkyl$, N,N-di-$(R^5)$sulphamoyl, N,N-di-$(R^5)$sulphamoyl-(1-6C)alkyl, $R^5—SO_2N(R^5)$, $R^5—SO_2N(R^5)$-(1-6C)alkyl, $R^5—CON(R^5)$, $R^5O—CON(R^5)$, $R^5—CON(R^5)$-(1-6C)alkyl, $R^5O—CON(R^5)$-(1-6C)alkyl, $(R^5)_2N—SO_2N(R^5)$, $(R^5)_2N—SO_2N(R^5)$-(1-6C)alkyl, $(R^5)_2N—CON(R^5)$, $(R^5)_2N—CON(R^5)$-(1-6C)alkyl, $R^5—CO$, $R^5—CO$-(1-6C)alkyl, $R^5O—CO$-(1-6C)alkyl, $(R^5)_2NCO$, $(R^5)_2NCO$-(1-6C)alkyl, $(R^5)_2N—COO$, $(R^5)_2NCOO$-(1-6C)alkyl, cyano, amino, $(R^6)$-amino, di-$(R^6)$-amino, amino-(1-6C)alkyl, $(R^6)$— amino-(1-6C)alkyl or di-$(R^6)$-amino-(1-6C)alkyl, wherein each $R^6$ present is (1-6C)alkyl optionally substituted by 1, 2 or 3 substituents independently selected from halogeno, cyano, hydroxy and (1-6C)alkoxy;

and when $X^1$ is selected from O, SO, $SO_2$, $N(R^5)$, CO, $CON(R^5)$, $N(R^5)CO$, $SO_2N(R^5)$, $N(R^5)SO_2$, $OC(R^5)_2$ and $N(R^5)C(R^5)_2$, wherein $R^5$ has any of the meanings defined hereinbefore, $R^4$ is hydroxy-(1-6C)alkyl, (1-6C)alkoxy-(1-6C)alkyl, $R^5—S$-(1-6C)alkyl, $R^5—S(O)$-(1-6C)alkyl, $R^5—SO_2$-(1-6C)alkyl, N,N-di-$(R^5)$sulphamoyl-(1-6C)alkyl, $R^5—SO_2N(R^5)$-(1-6C)alkyl, $R^5—CON(R^5)$-(1-6C)alkyl, $R^5O—CON(R^5)$-(1-6C)alkyl, $(R^5)_2N—SO_2N(R^5)$-(1-6C)alkyl, $(R^5)_2N—CON(R^5)$-(1-6C)alkyl, $R^5—CO$, $R^5—CO$-(1-6C)alkyl, $R^{5O}—Co$, $R^5O—CO$-(1-6C)alkyl, $(R^5)_2NCO$, $(R^5)_2NCO$-(1-

6C)alkyl, (R⁵)₂NCOO-(1-6C)alkyl, amino-(1-6C)alkyl, (R⁶)-amino-(1-6C)alkyl or di-(R⁶)-amino-(1-6C)alkyl, wherein each R⁶ present is (1-6C)alkyl optionally substituted by 1, 2 or 3 substituents independently selected from halogeno, cyano, hydroxy and (1-6C)alkoxy;

or R¹ is a group of the formula:

Q¹-X²— wherein X² is a direct bond or is selected from O, SO, SO₂, N(R⁷), N[C(O)R⁷], N[C(O)N(R⁷)₂], N[C(O)OR⁷], N[SO₂—N(R⁷)₂], CO, CON(R⁷), N(R⁷)CO, SO₂N(R⁷), N(R⁷)SO₂, O—SO₂, SO₂—O, C(R⁷)₂O, OC(R⁷)₂, C(R⁷)₂, C(R⁷)₂N(R⁷) and N(R⁷)C(R⁷)₂, wherein each R⁷ is independently selected from hydrogen or (1-8C)alkyl;

and Q¹ is aryl, aryl-(1-6C)alkyl, (3-8C)cycloalkyl, (3-8C)cycloalkyl-(1-6C)alkyl, heterocyclyl, heterocyclyl-(1-6C)alkyl, heteroaryl or heteroaryl-(1-6C)alkyl, wherein any aryl or (3-8C)cycloalkyl group within a R¹ substituent bears 1, 2 or 3 substituents and any heterocyclyl or heteroaryl group within a R¹ substituent optionally bears 1, 2 or 3 substituents, wherein said substituents are independently selected from halogeno, trifluoromethyl, cyano, nitro, hydroxy, amino, carboxy, carbamoyl, ureido, (1-8C)alkyl, (2-8C)alkenyl, (2-8C)alkynyl, (1-6C)alkoxy, halogeno-(1-6C)alkoxy, hydroxy-(1-6C)alkyl, (1-6C)alkoxy-(1-6C)alkyl, (1-6C)alkylsulphonyl-(1-6C)alkyl, cyano-(1-6C)alkyl, halogeno-(1-6C)alkyl, amino-(1-6C)alkyl, (1-6C)alkylamino-(1-6C)alkyl, di-[(1-6C)alkyl]amino-(1-6C)alkyl, (2-6C)alkenyloxy, (2-6C)alkynyloxy, (1-6C)alkylthio, (1-6C)alkylsulphinyl, (1-6C)alkylsulphonyl, (1-6C)alkylamino, di-[(1-6C)alkyl]amino, (1-6C)alkoxycarbonyl, (2-6C)alkanoyl, hydroxy-(2-6C)alkanoyl, (1-6C)alkoxy-(2-6C)alkanoyl, (2-6C)alkanoyloxy, N-(1-6C)alkylcarbamoyl, N,N-di-[(1-6C)alkyl]carbamoyl, carbamoyl-(1-6C)alkyl, N-(1-6C)alkylcarbamoyl-(1-6C)alkyl, N,N-di-[(1-6C)alkyl]carbamoyl-(1-6C)alkyl, (1-6C)alkanoylamino, N-(1-6C)alkyl-(1-6C)alkanoylamino, N-(1-6C)alkylureido, N'-(1-6C)alkylureido, N',N'-di-[(1-6C)alkyl]ureido, N,N'-di-[(1-6C)alkyl]ureido, N,N',N'-tri-[(1-6C)alkyl]ureido, N-(1-6C)alkylsulphamoyl, N,N-di-[(1-6C)alkyl]sulphamoyl, (1-6C)alkanesulphonylamino, N-(1-6C)alkyl-(1-6C)alkanesulphonylamino, (1-6C)alkoxy-(1-6C)alkoxycarbonyl, (1-6C)alkylamino-(2-6C)alkanoyl, di-[(1-6C)alkyl]amino-(2-6C)alkanoyl, (1-6C)alkanoylamino-(2-6C)alkanoyl, (1-6C)alkoxy-(1-6C)alkoxy-(2-6C)alkanoyl, heterocyclyl, heterocyclyl-(1-6C)alkyl, heteroaryl or heteroaryl-(1-6C)alkyl and any heterocyclyl group within a R¹ substituent optionally bears 1 or 2 oxo substituents; wherein, any CH, CH₂, or CH₃ in any alkyl group present in the definition of R⁴ that is connected to X¹ or present in the definition of Q¹ that is connected to X², optionally bears a hydroxy or cyano group and optionally bears up to three halogeno groups, and can optionally be replaced by an atom selected from O, S or N or a SO₂ group and adjacent carbon atoms in an alkyl chain can optionally be separated by the insertion into the chain of a C≡C group;

(vvv) R¹ is a group of the formula:

R⁴—X¹— wherein X¹ is a direct bond or is selected from O, SO, SO₂, N(R⁵), CO, CON(R⁵), N(R⁵)CO, SO₂N(R⁵), N(R⁵)SO₂, C(R⁵)₂O, OC(R⁵)₂, C(R⁵)₂, C(R⁵)₂N(R⁵) and N(R⁵)C(R⁵)₂, wherein each R⁵ is independently selected from hydrogen or (1-8C)alkyl, and when X¹ is a direct bond or is selected from C(R⁵)₂O, C(R⁵)₂ or C(R⁵)₂N(R⁵), wherein R⁵ has any of the meanings defined hereinbefore, R⁴ is hydroxy-(1-6C)alkyl, (1-6C)alkoxy-(1-6C)alkyl, R⁵—S, R⁵—S(O), R⁵—SO₂, R⁵—SO₂—O, R⁵—S-(1-6C)alkyl, R⁵—S(O)-(1-6C)alkyl, R⁵—SO₂-(1-6C)alkyl, N,N-di-(R⁵)sulphamoyl, N,N-di-(R⁵)sulphamoyl-(1-6C)alkyl, R⁵—SO₂N(R⁵), R⁵—SO₂N(R⁵)-(1-6C)alkyl, R⁵—CON(R⁵), R⁵—CON(R⁵)-(1-6C)alkyl, R⁵—CO, R⁵—CO-(1-6C)alkyl, (R⁵)₂NCO, (R⁵)₂NCO-(1-6C)alkyl, cyano, amino, (R⁶)-amino, di-(R⁶)-amino, amino-(1-6C)alkyl, (R⁶)-amino-(1-6C)alkyl or di-(R⁶)-amino-(1-6C)alkyl, wherein each R⁶ present is (1-6C)alkyl;

and when X¹ is selected from O, SO, SO₂, N(R⁵), CO, CON(R⁵), N(R⁵)CO, SO₂N(R⁵), N(R⁵)SO₂, OC(R⁵)₂ and N(R⁵)C(R⁵)₂, wherein R⁵ has any of the meanings defined hereinbefore, R⁴ is hydroxy-(1-6C)alkyl, (1-6C)alkoxy-(1-6C)alkyl, R⁵—S-(1-6C)alkyl, R⁵—S(O)-(1-6C)alkyl, R⁵—SO₂-(1-6C)alkyl, R⁵—CON(R⁵)-(1-6C)alkyl, R⁵—CO-(1-6C)alkyl, (R⁵)₂NCO-(1-6C)alkyl, amino-(1-6C)alkyl, (R⁶)-amino-(1-6C)alkyl or di-(R⁶)-amino-(1-6C)alkyl, wherein each R⁶ present is (1-6C)alkyl;

or R¹ is a group of the formula:

Q¹-X²— wherein X² is a direct bond or is selected from O, SO, SO₂, N(R⁷), N[C(O)R⁷], N[C(O)N(R⁷)₂], N[C(O)OR⁷], N[SO₂—N(R⁷)₂], CO, CON(R⁷), N(R⁷)CO, SO₂N(R⁷), N(R⁷)SO₂, O—SO₂, SO₂—O, C(R⁷)₂O, OC(R⁷)₂, C(R⁷)₂, C(R⁷)₂N(R⁷) and N(R⁷)C(R⁷)₂, wherein each R⁷ is independently selected from hydrogen or (1-8C)alkyl;

and Q¹ is heterocyclyl, heterocyclyl-(1-6C)alkyl, heteroaryl or heteroaryl-(1-6C)alkyl, wherein any heterocyclyl or heteroaryl group within a R¹ substituent optionally bears 1, 2 or 3 substituents, wherein said substituents are independently selected from halogeno, trifluoromethyl, cyano, hydroxy, amino, carboxy, (1-8C)alkyl, (2-8C)alkenyl, (2-8C)alkynyl, (1-6C)alkoxy, halogeno-(1-6C)alkoxy, hydroxy-(1-6C)alkyl, (1-6C)alkoxy-(1-6C)alkyl, cyano-(1-6C)alkyl, halogeno-(1-6C)alkyl, amino-(1-6C)alkyl, (1-6C)alkylamino-(1-6C)alkyl, di-[(1-6C)alkyl]amino-(1-6C)alkyl, (1-6C)alkylsulphonyl, (1-6C)alkylamino, di-[(1-6C)alkyl]amino, (1-6C)alkoxycarbonyl, N-(1-6C)alkylcarbamoyl, (1-6C)alkanoylamino, (2-6C)alkanoyl, hydroxy-(2-6C)alkanoyl, (1-6C)alkoxy-(2-6C)alkanoyl, carbamoyl-(1-6C)alkyl, N-(1-6C)alkylcarbamoyl-(1-6C)alkyl, N,N-di-[(1-6C)alkyl]carbamoyl-(1-6C)alkyl, (1-6C)alkoxy-(1-6C)alkoxycarbonyl, (1-6C)alkylamino-(2-6C)alkanoyl, di-[(1-6C)alkyl]amino-(2-6C)alkanoyl, (1-6C)alkanoylamino-(2-6C)alkanoyl, (1-6C)alkoxy-(1-6C)alkoxy-(2-6C)alkanoyl, heterocyclyl, heterocyclyl-(1-6C)alkyl, heteroaryl or heteroaryl-(1-6C)alkyl, and any heterocyclyl group within a R¹ substituent optionally bears 1 or 2 oxo substituents; wherein, any CH, CH₂, or CH₃ in any alkyl group present in the definition of R⁴ that is connected to X¹ or present in the definition of Q¹ that is connected to X², can optionally be replaced by an O atom or a SO₂ group and adjacent carbon atoms in an alkyl chain can optionally be separated by the insertion into the chain of a C≡C group;

(www) R¹ is a group of the formula:

R⁴—X¹— wherein X¹ is a direct bond or is selected from O, SO, SO₂, N(R⁵), CO, CON(R⁵), N(R⁵)CO, SO₂N(R⁵), N(R⁵)SO₂, C(R⁵)₂O, OC(R⁵)₂, C(R⁵)₂, C(R⁵)₂N(R⁵) and N(R⁵)C(R⁵)₂, wherein each R⁵ is independently selected from hydrogen or (1-8C)alkyl, and when X¹ is a direct bond or is selected from C(R⁵)₂O, C(R⁵)₂ or C(R⁵)₂N(R⁵), wherein R⁵ has any of the meanings defined hereinbefore, R⁴ is hydroxy-(1-3C)alkyl, (1-6C)alkoxy-(1-3C)alkyl, R⁵—S, R⁵—S(O), R⁵—SO₂, R⁵—SO₂—O, R⁵—S-(1-3C)alkyl, R⁵—S(O)-(1-3C)alkyl, R⁵—SO₂-(1-3C)alkyl, N,N-di-(R⁵)sulphamoyl, N,N-di-(R⁵) sulphamoyl-(1-3C)alkyl, R⁵—SO₂N(R⁵), R⁵—SO₂N(R⁵)-(1-3C)alkyl, R⁵—CON(R⁵), R⁵—CON(R⁵)-(1-3C)alkyl, R⁵—CO, R⁵—CO-(1-3C)alkyl, (R⁵)₂NCO, (R⁵)₂NCO-(1-3C)alkyl, cyano, amino, (R⁶)-amino, di-(R⁶)-amino, amino-(1-3C)alkyl, (R⁶)-amino-(1-3C)alkyl or di-(R⁶)-amino-(1-3C)alkyl, wherein each R⁶ present is (1-3C)alkyl;

and when X¹ is selected from O, SO, SO₂, N(R⁵), CO, CON(R⁵), N(R⁵)CO, SO₂N(R⁵), N(R⁵)SO₂, OC(R⁵)₂ and N(R⁵)C(R⁵)₂, wherein R⁵ has any of the meanings defined hereinbefore, R⁴ is hydroxy-(1-3C)alkyl, (1-6C)alkoxy-(1-3C)alkyl, R⁵—S-(1-3C)alkyl, R⁵—S(O)-(1-3C)alkyl, R⁵—SO₂-(1-3C)alkyl, R⁵—CON(R⁵)-(1-3C)alkyl, R⁵—CO-(1-3C)alkyl, (R⁵)₂NCO-(1-3C)alkyl, amino-(1-3C)alkyl, (R⁶)-amino-(1-3C)alkyl or di-(R⁶)-amino-(1-3C)alkyl, wherein each R⁶ present is (1-3C)alkyl;

or R¹ is a group of the formula:

Q¹-X²— wherein X² is a direct bond or is selected from O, SO, SO₂, N(R⁷), N[C(O)R⁷], N[C(O)N(R⁷)₂], N[C(O)OR⁷], N[SO₂—N(R⁷)₂], CO, CON(R⁷), N(R⁷)CO, SO₂N(R⁷), N(R⁷)SO₂, O—SO₂, SO₂—O, C(R⁷)₂O, OC(R⁷)₂, C(R⁷)₂, C(R⁷)₂N(R⁷) and N(R⁷)C(R⁷)₂, wherein each R⁷ is independently selected from hydrogen or (1-8C)alkyl;

and Q¹ is heterocyclyl, heterocyclyl-(1-3C)alkyl, heteroaryl or heteroaryl-(1-3C)alkyl, wherein said heterocyclyl or the heterocyclyl within the heterocyclyl-(1-3C)alkyl group is selected from piperidinyl, pyrrolidinyl, morpholinyl, piperazinyl, tetrahydro-2H-pyranyl, azetidinyl, 1,1-dioxotetrahydro-1,4-thiazinyl, imidazolinyl, azepanyl, 1H-imidazolyl, 1,4-diazepanyl, (1R,5S)-8-azabicyclo[3.2.1]octanyl, quinuclidinyl, (3R)-quinuclidinyl, 3,4,4a,5,6,7,8,8a-octahydro-2H-quinolinyl, 3,4,6,7,8,8a-hexahydro-1H-pyrrolo[2,1-c]pyrazinyl, 3,8-diazaspiro[5.5]undecanyl, 2,8-diazaspiro[4.5]decanyl, 4,9-diazaspiro[5.5]undecanyl, 2,3,3a,4,6,6a-hexahydro-1H-pyrrolo[3,4-c]pyrrolyl, 3,9-diazaspiro[5.5]undecanyl and (1S,4S)-3,6-diazabicyclo[2.2.1]heptanyl, and said heteroaryl or the heteroaryl within the heteroaryl-(1-3C)alkyl group is pyrazolyl, each of which optionally bears a halogeno, trifluoromethyl, cyano, hydroxy, amino, carboxy, (1-8C)alkyl, (2-8C)alkenyl, (2-8C)alkynyl, (1-6C)alkoxy, halogeno-(1-6C)alkoxy, hydroxy-(1-6C)alkyl, (1-6C)alkoxy-(1-6C)alkyl, cyano-(1-6C)alkyl, halogeno-(1-6C)alkyl, amino-(1-6C)alkyl, (1-6C)alkylamino-(1-6C)alkyl, di-[(1-6C)alkyl]amino-(1-6C)alkyl, (1-6C)alkylsulphonyl, (1-6C)alkylamino, di-[(1-6C)alkyl]amino, (1-6C)alkoxycarbonyl, N-(1-6C)alkylcarbamoyl, (1-6C)alkanoylamino, (2-6C)alkanoyl, hydroxy-(2-6C)alkanoyl, (1-6C)alkoxy-(2-6C)alkanoyl, carbamoyl-(1-6C)alkyl, N-(1-6C)alkylcarbamoyl-(1-6C)alkyl, N,N-di-[(1-6C)alkyl]carbamoyl-(1-6C)alkyl, (1-6C)alkoxy-(1-6C)alkoxycarbonyl, (1-6C)alkylamino-(2-6C)alkanoyl, di-[(1-6C)alkyl]amino-(2-6C)alkanoyl, (1-6C)alkanoylamino-(2-6C)alkanoyl, (1-6C)alkoxy-(1-6C)alkoxy-(2-6C)alkanoyl, heterocyclyl, heterocyclyl-(1-6C)alkyl, heteroaryl or heteroaryl-(1-6C)alkyl, and any heterocyclyl group within a R¹ substituent optionally bears 1 or 2 oxo substituents; wherein, any CH, CH₂, or CH₃ in any alkyl group present in the definition of R⁴ that is connected to X¹ or present in the definition of Q¹ that is connected to X², can optionally be replaced by an O atom or a SO₂ group and adjacent carbon atoms in an alkyl chain can optionally be separated by the insertion into the chain of a C≡C group;

(xxx) R¹ is hydroxymethyl, 2-hydroxyethyl, 3-hydroxypropyl, methoxymethyl, cyanomethyl, acetyl, 2-methoxyacetyl, 3-methoxypropionyl, 3-methoxy-2-methyl-propionyl, hydroxyacetyl, 2-hydroxypropionyl, 2-aminoethyl, 2-methylaminoethyl, 3-methylaminopropylcarbamoyl, 2-methylaminoethylcarbamoyl, 2-dimethylaminoethyl-N-methylcarbamoyl, 2-aminoethoxy, 2-methylaminoethoxy, 3-aminopropoxy, 3-methylaminopropoxy, 4-methylaminobutoxy, 2-methoxyethoxy, ethylsulphonyl, methylsulphonyl, methylsulphonyloxy, methylsulphamoyl, cyclopropylsulphamoyl, dimethylsulphamoyl, 2-hydroxyethylsulphamoyl, cyclopropylsulphamoyl, methanesulphonamido, acetamido, carbamoyl, methylcarbamoyl, cyclopropylcarbamoyl, 2-hydroxyethylcarbamoyl, dimethylamino, 2-dimethylaminoethylcarbamoyl, 3-dimethylaminopropylcarbamoyl, 2-diethylaminoethylcarbamoyl, 3-diethylaminopropylcarbamoyl, cyano, cyanomethyl, aminomethyl, dimethylaminomethyl, 2-(dimethylamino)ethoxy, 2-(diethylamino)ethoxy, 3-(dimethylamino)propoxy, 3-(diethylamino)propoxy, pyrrolidin-1-yl, pyrrolidin-3-yl, pyrrolidin-2-yl, piperazin-1-yl, piperidin-4-yl, piperidin-3-yl, pyrazol-3-yl, tetrahydropyran-2-yl, tetrahydropyran-4-yl, azetidinyl, 1,1-dioxotetrahydro-1,4-thiazinyl, imidazolinyl, azepanyl, 4-aminoazepan-1-ylcarbonyl, azepan-4-yloxy, 4-(4-piperidyl)piperidin-1-ylcarbonyl, 1H-imidazolyl, 1,4-diazepanyl, (1R,5S)-8-azabicyclo[3.2.1]octanyl, quinuclidinyl, (3R)-quinuclidinyl, 3,4,4a,5,6,7,8,8a-octahydro-2H-quinolinyl, 3,4,6,7,8,8a-hexahydro-1H-pyrrolo[2,1-c]pyrazinyl, 3,8-diazaspiro[5.5]undecan-3-ylcarbonyl, 2,8-diazaspiro[4.5]decan-8-ylcarbonyl, 3,9-diazaspiro[5.5]undecan-3-yl carbonyl, (1S,4S)-3,6-diazabicyclo[2.2.1]heptan-6-ylcarbonyl, 3-aminoazetidin-1-ylcarbonyl, pyrrolidin-1-ylmethyl, (3S)-3-aminopiperidin-1-ylcarbonyl, (2S)-pyrrolidin-2-yl]methylcarbamoyl, 4,9-diazaspiro[5.5]undecan-4-ylcarbonyl, 2,3,3a,4,6,6a-hexahydro-1H-pyrrolo[3,4-c]pyrrol-5-ylcarbonyl, (3R)-3-(2-aminoethyl)-1-piperidylcarbonyl, piperidin-4-ylmethyl, 1-methylpyrrolidin-3-yl, 1-methylpyrrolidin-3-ylmethyl, 1-methylpyrrolidin-3-ylmethoxy, pyrrolidin-3-yloxy, pyrrolidin-2-yloxy, 1-methylpyrrolidin-3-yloxy, 2-(1-methylpyrrolidin-3-yl)ethoxy, 2-pyrrolidin-1-ylethyl, 3-pyrrolidin-1-ylpropyl, 2-(1-methylpyrrolidin-2-yl)ethoxy, 2-(1-methylpyrrolidin-2-yl)ethylcarbamoyl, piperidin-3-ylmethyl, 1-methyl-piperidin-3-yl, 1-methyl-piperidin-3-ylmethoxy, 1-methyl-piperidin-3-yloxy, piperidin-3-ylmethoxy, 2-(1-methyl-piperidin-3-yl)ethoxy, 3-(1-methyl-piperidin-3-yl)propoxy, piperidin-3-ylcarbamoyl, (3R)-piperidin-3-ylmethylcarbamoyl, piperidin-4-yloxy, 1-methyl-piperidin-4-ylmethoxy, azetidin-3-ylmethyl, 2-azetidinylethyl, 3-azetidinylpropyl, 1-methyl-azetidin-3-yl, 1-methyl-azetidin-3-ylmethyl, 2-(3-hydroxy-pyrrolidin-1-yl)ethyl, 3-(3-hydroxy-pyrrolidin-1-yl)propyl, 3-(3-hydroxymethyl-pyrrolidin-1-yl)propyl, 3-(2-hydroxymethyl-pyrrolidin-1-yl)propyl, 2-(2-hydroxymethyl-pyrrolidin-1-yl)ethyl, 2-(4-hydroxypiperidin-1-yl)ethyl, 3-(4-hydroxypiperidin-1-yl)propyl, 1-acetylpiperidin-4-yl, 1-methoxyacetylpiperidin-4-yl, 1-hydroxyacetylpiperidin-4-yl, 1-hydroxyacetylpiperidin-4-yl, 1-(2-hydroxypropionyl)piperidin-4-yl, 5-(methylcarbamoyl)-1-methyl-pyrrolidin-3-yl, 3-pyrrolidin-1-ylpropoxy, 2-pyrrolidin-1-ylethoxy, 2-(1-methylpiperidin-2-yl)ethoxy, 3-(1,1-dioxotetrahydro-1,4-thiazin-4-yl)propoxy, 2-(piperazin-1-yl)ethyl, 2-(1-methyl-piperazin-4-yl)ethoxy, 3-(1-methyl-piperazin-4-yl)propoxy, 2-(1-methyl-piperazin-4-yl)ethyl, 3-(1-methyl-piperazin-4-yl)propyl, (1-methyl-piperazin-4-yl)carbonyl, 3-(1-sulphonyl-piperazin-4-yl)propoxy, 3-(1-methylsulphonylpiperazin-4-yl)-propoxy, 1-(methylsulphonyl)piperidin-4-yl, 1-(cyclopropylsulphonyl)piperidin-4-yl, 1-(methoxycarbonyl)piperidin-4-yl, 1-(methoxymethylcarbonyl)piperidin-4-yl, 3-(1,1-dioxotetrahydro-1,4-thiazin-4-yl)propoxy, (1R,5S)-8-azabicyclo[3.2.1]octan-3-yloxy, [(2E)-4-(1,1-dioxidothiomorpholin-4-yl)but-2-en-1-yl]oxidanyl, (3R)-quinuclidin-8-ylcarbamoyl, morpholino, morpholinomethyl, 2-morpholinoethyl, 3-morpholinopropyl, 2-morpholinoethoxy, 3-morpholinopropoxy, 2-(2-morpholinoethoxy)ethoxy, 3-[(3R,5S)-3,5-dimethylpiperazin-1-yl]propoxy, (3S,5S)-5-(methoxymethyl)pyrrolidin-3-yloxy, (3S,4R)-3-methylaminotetrahydropyran-4-yloxy, 4-(2-pyridylmethyl)piperazin-1-ylcarbonyl, 2-piperazin-4-ylethoxy, 2-(piperidin-4-yloxy)ethoxy, 2-(azetidin-3-yloxy)ethoxy, 3-(2,6-dimethylpiperazin-4-yl)propoxy, 1-methylpyrrolidin-3-yl-N-methylcarbamoyl, quinuclidinylcarbonyl, 2-imidazolin-1-ylethylcarbamoyl, 2-(piperidin-1-ylmethyl)piperidin-1-ylcarbonyl, 1-ethoxypiperidin-4-ylcarbamoyl, 2-pyrrolidin-1-ylcyclohex-1-yl-N-methylcarbamoyl, 2-(3-fluoropyrrolidin-1-yl)ethylcarbamoyl, 4-(2-dimethylaminoethyl)piperidin-1-ylcarbonyl, 2-(1-methylpiperidin-2-yl)-pyrrolidin-1-ylcarbonyl, 5-(morpholinylmethyl)pyrrolidin-1-ylcarbonyl, 5-(azepan-1-yl)pyrrolidin-1-ylcarbonyl, 2-(3,3-difluoropyrrolidin-1-yl)ethylcarbamyl, 2-(3-fluoropyrrolidin-1-yl)ethylcarbamyl, 3,4,4a,5,6,7,8,8a-octahydro-2H-quinolin-4-ylcarbamoyl, 1-dimethylaminocyclohex-1-ylmethylcarbamoyl, 2-morpholinoethylcarbamoyl, 2-1H-imidazolylethylcarbamoyl, 1-(pyridin-3-yl)piperazin-4-ylcarbonyl, 1-(pyridin-4-yl)piperazin-4-ylcarbonyl, 1,4-diazepanylcarbonyl, 1-(N-dimethylcarbamoylmethyl)piperazin-4-ylcarbonyl, 1-(carbamoylethyl)piperazin-4-ylcarbonyl, 3,4,6,7,8,8a-hexahydro-1H-pyrrolo[2,1-c]pyrazin-1-ylcarbonyl, morpholine-4-carbonyl, morpholinosulphonyl, 4-hydroxypiperidine-1-carbonyl, 2-pyrrolidin-1-ylethylcarbamoyl, piperidin-1-yl, 4-(aminomethyl)piperidin-1-ylcarbonyl, 3-aminopyrrolidin-1-ylcarbonyl, 3-methylaminopyrrolidin-1-ylcarbonyl, piperidin-4-yl-N-methylcarbamoyl, 4-methylaminopiperidin-1-ylcarbonyl, 4-(piperazin-1-ylmethyl)piperidin-1-ylcarbonyl, 4-methylaminocyclohexylcarbonyl, pyrrolidin-3-ylcarbamoyl, 4-pyrrolidin-1-ylpiperidin-1-ylcarbonyl, 1-(dimethylcarbamoylmethyl)piperazin-4-ylcarbonyl, 5-(N-methylcarbamoyl)pyrrolidin-3-yl, 1-(N,N-dimethylcarbamoylmethyl)piperidin-4-yl, 1-(methylcarbamoylmethyl)piperidin-4-yl, 1-(carbamoylmethyl)piperidin-4-yl, 1-isopropylpiperidin-4-yl, 1-(2-hydroxyethyl)piperidin-4-yl, 1-(N,N-dimethylaminomethylcarbonyl)piperidin-4-yl, 1-methyl-4-piperidyl, 1-methylpiperidin-4-ylmethyl, 1-(2-methoxyethyl)piperidin-4-ylcarbamoyl, 1-ethyl-4-piperidyl, 1-isopropyl-4-piperidyl, 1-piperidylmethyl, piperidine-4-carbonylamino, 4-methylpiperazine-1-carbonyl, 4-methylpiperazin-1-yl, 1-(4-methylpiperazin-1-ylcarbonyl)piperidin-4-yl, 3-dimethylaminopropoxy, 1-tert-butoxycarbonyl-4-piperidyl or 1-methyl-1-oxidopiperidin-1-ium-4-yl;

(yyy) each $R^2$ group may be the same or different and is selected from halogeno, cyano, (1-8C)alkyl, (2-8C)alkenyl, (2-8C)alkynyl, (1-6C)alkoxy, (2-6C)alkenyloxy, (2-6C)alkynyloxy, fluoro-(1-6C)alkoxy, (1-6C)alkylthio, (1-6C)alkylsulphinyl, (1-6C)alkylsulphonyl, (1-6C)alkylamino, di-[(1-6C)alkyl]amino, (2-6C)alkanoyl, carbamoyl, N-(1-6C)alkylcarbamoyl, N,N-di-[(1-6C)alkyl]carbamoyl, (1-6C)alkanoylamino, N-(1-6C)alkyl-(1-6C)alkanoylamino, (1-6C)alkoxy-(1-6C)alkyl, amino-(1-6C)alkyl, (1-6C)alkylamino-(1-6C)alkyl, di-[(1-6C)alkyl]amino-(1-6C)alkyl, hydroxy-(1-6C)alkyl, (1-6C)alkoxy-(1-6C)alkoxy or hydroxy-(1-6C)alkoxy;

(zzz) each $R^2$ group may be the same or different and is selected from halogeno, cyano, (1-8C)alkyl, (1-6C)alkoxy, (1-6C)alkylthio, (2-6C)alkanoyl, (1-6C)alkylamino, carbamoyl, N-(1-6C)alkylcarbamoyl, N,N-di-[(1-6C)alkyl]carbamoyl, (1-6C)alkoxy-(1-6C)alkyl, hydroxy-(1-6C)alkyl, (1-6C)alkoxy-(1-6C)alkoxy, (1-6C)alkylamino-(1-6C)alkyl or hydroxy-(1-6C)alkoxy;

(aaaa) each $R^2$ group is methyl, methoxy, ethoxy, fluoro, hydroxymethyl, methoxymethyl, ethoxymethyl, cyano, 1-hydroxyethyl, dimethylcarbamoyl, dimethylamino, methylcarbamoyl, methylaminomethyl or carbamoyl;

(bbbb) each $R^2$ group is methyl, methoxy, ethoxy, hydroxymethyl, methoxymethyl, cyano or dimethylcarbamoyl;

(cccc) $R^2$ is selected from any one of methyl, methoxy, ethoxy, fluoro, hydroxymethyl, methoxymethyl, ethoxymethyl, cyano, 1-hydroxyethyl, dimethylcarbamoyl, dimethylamino, methylcarbamoyl, methylaminomethyl or carbamoyl and is located on the 3-position of Ring A;

(dddd) n is 0, 1 or 2 and, when n is 2, each $R^3$ group may be the same or different, and each $R^3$ group present is selected from hydrogen, fluoro, bromo, chloro, cyano, hydroxymethyl, methylcarbamoyl, $OR^9$, trifluoromethyl, methyl or propyl, wherein $R^9$ is methyl or trifluoromethyl; or (eeee) n is 0, 1 or 2 and the $(R^3)_n$ groups are selected from 4-fluoro, 5-fluoro, 6-fluoro, 6-bromo, 6-propan-2-yl, 5-bromo, 4,6-difluoro, 6-chloro, 5-methyl, 6-methyl, 6-trifluoromethoxy, 5-trifluoromethyl, 6-methoxy, 7-methyl, 6,7-difluoro, 7-fluoro, 5-methoxy, 7-methoxy, 4-methoxy, 4-cyano, 7-cyano, 7-hydroxymethyl or 7-methylcarbamoyl.

A further aspect of the invention provides particular compounds in which J is O and Ring A is pyrazol-4-yl, said ring being substituted by $R^1$ and being substituted by an $R^2$ group which is located at the 3-position of the pyrazol-4-yl ring, wherein each of W, $G_1$, $G_2$, $G_3$, $G_4$, $R^1$, $R^2$, n and $R^3$ has any of the meanings defined hereinbefore. A yet further aspect of the invention provides particular compounds in which J is O and Ring A is pyrazol-4-yl, said ring being substituted by $R^1$ and being substituted by an $R^2$ group which is located at the 3-position of the pyrazol-4-yl ring and is selected from any one of methyl, methoxy, ethoxy, fluoro, hydroxymethyl, methoxymethyl, ethoxymethyl, cyano, 1-hydroxyethyl, dimethylcarbamoyl, dimethylamino, methylcarbamoyl, methylaminomethyl or carbamoyl and especially methyl, methoxy, ethoxy, hydroxymethyl, methoxymethyl, cyano or dimethylcarbamoyl, wherein each of W, $G_1$, $G_2$, $G_3$, $G_4$, $R^1$, n and $R^3$ has any of the meanings defined hereinbefore. In a particular group of compounds of the particular aspects of the invention described immediately above, W is CH.

A particular group of compounds of the invention are pyridine and pyrazine derivatives of Formula I above wherein:—
W is CH or N;
J is O or S;
each of $G_1$, $G_2$, $G_3$ and $G_4$ is selected from CH and N provided that not more than one of $G_1$, $G_2$, $G_3$ and $G_4$ represent N;
Ring A is selected from:
(i) phenyl substituted by $R^1$ and optionally substituted by an $R^2$ group; or
(ii) a 5- or 6-membered monocyclic heteroaryl ring with up to three ring heteroatoms selected from oxygen, nitrogen and sulphur, said ring being substituted by $R^1$ and optionally substituted by an $R^2$ group; or
(iii) a 8-, 9- or 10-membered bicyclic ring system, wherein said bicyclic ring system optionally contains up to three ring heteroatoms selected from oxygen, nitrogen and sulphur and is optionally substituted by $R^1$ and optionally substituted by an $R^2$ group;
$R^1$ is a group of the formula:

$$R^4-X^1-$$

wherein $X^1$ is a direct bond or is selected from O, SO, $SO_2$, $N(R^5)$, CO, $CON(R^5)$, $N(R^5)CO$, $SO_2N(R^5)$, $N(R^5)SO_2$, $C(R^5)_2O$, $OC(R^5)_2$, $C(R^5)_2$, $C(R^5)_2N(R^5)$ and $N(R^5)C(R^5)_2$, wherein each $R^5$ is independently selected from hydrogen or (1-8C)alkyl;
and when $X^1$ is a direct bond or is selected from $C(R^5)_2O$, $C(R^5)_2$ or $C(R^5)_2N(R^5)$, wherein $R^5$ has any of the meanings defined hereinbefore, $R^4$ is hydroxy-(1-6C)alkyl, (1-6C)alkoxy-(1-6C)alkyl, $R^5$—S, $R^5$—S(O), $R^5$—$SO_2$, $R^5$—S-(1-6C)alkyl, $R^5$—S(O)-(1-6C)alkyl, $R^5$—$SO_2$-(1-6C)alkyl, N,N-di-($R^5$)sulphamoyl, N,N-di-($R^5$)sulphamoyl-(1-6C)alkyl, $R^5$—$SO_2N(R^5)$, $R^5$—$SO_2N(R^5)$-(1-6C)alkyl, $R^5$—$CON(R^5)$, $R^5O$—$CON(R^5)$, $R^5$—$CON(R^5)$-(1-6C)alkyl, $R^5O$—$CON(R^5)$-(1-6C)alkyl, $(R^5)_2N$—$SO_2N(R^5)$, $(R^5)_2N$—$SO_2N(R^5)$-(1-6C)alkyl, $(R^5)_2N$—$CON(R^5)$, $(R^5)_2N$—$CON(R^5)$-(1-6C)alkyl, $R^5$—CO, $R^5$—CO-(1-6C)alkyl, $R^5O$—CO-(1-6C)alkyl, $(R^5)_2NCO$, $(R^5)_2NCO$-(1-6C)alkyl, $(R^5)_2N$—COO, $(R^5)_2NCOO$-(1-6C)alkyl, cyano, amino, $(R^6)$-amino, di-$(R^6)$-amino, amino-(1-6C)alkyl, $(R^6)$-amino-(1-6C)alkyl or di-$(R^6)$-amino-(1-6C)alkyl, wherein each $R^6$ present is (1-6C)alkyl optionally substituted by 1, 2 or 3 substituents independently selected from halogeno, cyano, hydroxy and (1-6C)alkoxy; and when $X^1$ is selected from O, SO, $SO_2$, $N(R^5)$, CO, $CON(R^5)$, $N(R^5)CO$, $SO_2N(R^5)$, $N(R^5)SO_2$, $OC(R^5)_2$ and $N(R^5)C(R^5)_2$, wherein $R^5$ has any of the meanings defined hereinbefore, $R^4$ is hydroxy-(1-6C)alkyl, (1-6C)alkoxy-(1-6C)alkyl, $R^5$—S-(1-6C)alkyl, $R^5$—S(O)-(1-6C)alkyl, $R^5$—$SO_2$-(1-6C)alkyl, N,N-di-($R^5$)sulphamoyl-(1-6C)alkyl, $R^5$—$SO_2N(R^5)$-(1-6C)alkyl, $R^5$—CON($R^5$)-(1-6C)alkyl, $R^5O$—$CON(R^5)$-(1-6C)alkyl, $(R^5)_2N$—$SO_2N(R^5)$-(1-6C)alkyl, $(R^5)_2N$—$CON(R^5)$-(1-6C)alkyl, $R^5$—CO, $R^5$—CO-(1-6C)alkyl, $R^5O$—CO, $R^5O$—CO-(1-6C)alkyl, $(R^5)_2NCO$, $(R^5)_2NCO$-(1-6C)alkyl, $(R^5)_2NCOO$-(1-6C)alkyl, amino-(1-6C)alkyl, $(R^6)$-amino-(1-6C)alkyl or di-$(R^6)$-amino-(1-6C)alkyl, wherein each $R^6$ present is (1-6C)alkyl optionally substituted by 1, 2 or 3 substituents independently selected from halogeno, cyano, hydroxy and (1-6C)alkoxy;
or $R^1$ is a group of the formula:

$$Q^1-X^2-$$

wherein $X^2$ is a direct bond or is selected from O, SO, $SO_2$, $N(R^7)$, $N[C(O)R^7]$, $N[C(O)N(R^7)_2]$, $N[C(O)OR^7]$, $N[SO_2-N(R^7)_2]$, CO, $CON(R^7)$, $N(R^7)CO$, $SO_2N(R^7)$, $N(R^7)SO_2$, O—$SO_2$, $SO_2$—O, $C(R^7)_2O$, $OC(R^7)_2$, $C(R^7)_2$, $C(R^7)_2N(R^7)$ and $N(R^7)C(R^7)_2$, wherein each $R^7$ is independently selected from hydrogen or (1-8C)alkyl;
and $Q^1$ is aryl, aryl-(1-6C)alkyl, (3-8C)cycloalkyl, (3-8C)cycloalkyl-(1-6C)alkyl, heterocyclyl, heterocyclyl-(1-6C)alkyl, heteroaryl or heteroaryl-(1-6C)alkyl, wherein any aryl or (3-8C)cycloalkyl group within a $R^1$ substituent bears 1, 2 or 3 substituents and any heterocyclyl or heteroaryl group within a $R^1$ substituent optionally bears 1, 2 or 3 substituents, wherein said substituents are independently selected from halogeno, trifluoromethyl, cyano, nitro, hydroxy, amino, carboxy, carbamoyl, ureido, (1-8C)alkyl, (2-8C)alkenyl, (2-8C)alkynyl, (1-6C)alkoxy, halogeno-(1-6C)alkoxy, hydroxy-(1-6C)alkyl, (1-6C)alkoxy-(1-6C)alkyl, (1-6C)alkylsulphonyl-(1-6C)alkyl, cyano-(1-6C)alkyl, halogeno-(1-6C)alkyl, amino-(1-6C)alkyl, (1-6C)alkylamino-(1-6C)alkyl, di-[(1-6C)alkyl]amino-(1-6C)alkyl, (2-6C)alkenyloxy, (2-6C)alkynyloxy, (1-6C)alkylthio, (1-6C)alkylsulphinyl, (1-6C)alkylsulphonyl, (1-6C)alkylamino, di-[(1-6C)alkyl]amino, (1-6C)alkoxycarbonyl, (2-6C)alkanoyl, (2-6C)alkanoyloxy, N-(1-6C)alkylcarbamoyl, N,N-di-[(1-6C)alkyl]carbamoyl, (1-6C)alkanoylamino, N-(1-6C)alkyl-(1-6C)alkanoylamino, N-(1-6C)alkylureido, N'-(1-6C)alkylureido, N',N'-di-[(1-6C)alkyl]ureido, N,N'-di-[(1-6C)alkyl]ureido, N,N',N'-tri-[(1-6C)alkyl]ureido, N-(1-6C)alkylsulphamoyl, N,N-di-[(1-6C)alkyl]sulphamoyl, (1-6C)alkanesulphonylamino, N-(1-6C)alkyl-(1-6C)alkanesulphonylamino or heterocyclyl-(1-6C)alkyl, and any heterocyclyl group within a $R^1$ substituent optionally bears 1 or 2 oxo substituents;
each $R^2$ group may be the same or different and is selected from halogeno, cyano, (1-8C)alkyl, (2-8C)alkenyl, (2-8C)alkynyl, (1-6C)alkoxy, (2-6C)alkenyloxy, (2-6C)alkynyloxy, fluoro-(1-6C)alkoxy, (1-6C)alkylthio, (1-6C)alkylsulphinyl, (1-6C)alkylsulphonyl, (1-6C)alkylamino, di-[(1-6C)alkyl]amino, (2-6C)alkanoyl, N-(1-6C)alkylcarbamoyl, N,N-di-[(1-6C)alkyl]carbamoyl, (1-6C)alkanoylamino, N-(1-6C)alkyl-(1-6C)alkanoylamino, (1-6C)alkoxy-(1-6C)alkyl, hydroxy-(1-6C)alkyl, (1-6C)alkoxy-(1-6C)alkoxy or hydroxy-(1-6C)alkoxy; and
n is 0, 1 or 2 and, when n is 2, each $R^3$ group may be the same or different, and each $R^3$ group present is selected from hydrogen, halogeno, cyano, $OR^9$, trifluoromethyl, (1-8C)alkyl, (2-8C)alkenyl, (2-8C)alkynyl, (1-6C)alkoxy, halogeno-(1-6C)alkoxy, carbamoyl, N-(1-6C)alkylcarbamoyl, N,N-di-[(1-6C)alkyl]carbamoyl, (1-6C)alkanoylamino, (1-6C)alkylthio, (1-6C)alkylsulphinyl, (1-6C)alkylsulphonyl, hydroxy-(1-6C)alkyl, (1-6C)alkoxy-(1-6C)alkyl, (2-6C)alkanoyl, (1-6C)alkanesulphonylamino, (1-6C)alkoxy-(1-6C)alkoxy, hydroxy-(1-6C)alkoxy, amino-(1-6C)alkoxy, (1-6C)alkylamino-(1-6C)alkoxy and di-[(1-6C)alkyl]amino-(1-6C)alkoxy, wherein $R^9$ is fluoro-(1-6C)alkyl; or a pharmaceutically-acceptable salt thereof.

A particular group of compounds of the invention are pyridine and pyrazine derivatives of Formula I above wherein:—
W is CH or N;
J is O or S;
each of $G_1$, $G_2$, $G_3$ and $G_4$ is selected from CH and N provided that not more than one of $G_1$, $G_2$, $G_3$ and $G_4$ represent N;
Ring A is selected from:
(i) phenyl substituted by $R^1$ and optionally substituted by an $R^2$ group; or
(ii) a 5- or 6-membered monocyclic heteroaryl ring with up to three ring heteroatoms selected from oxygen, nitrogen and sulphur, said ring being substituted by $R^1$ and optionally substituted by an $R^2$ group; or
(iii) a 8-, 9- or 10-membered bicyclic ring system, wherein said bicyclic ring system optionally contains up to three ring heteroatoms selected from oxygen, nitrogen and sulphur and is optionally substituted by $R^1$ and optionally substituted by an $R^2$ group;
$R^1$ is a group of the formula:

$$R^4-X^1-$$

wherein $X^1$ is a direct bond or is selected from O, SO, $SO_2$, $N(R^5)$, CO, $CON(R^5)$, $N(R^5)CO$, $SO_2N(R^5)$, $N(R^5)SO_2$, $C(R^5)_2O$, $OC(R^5)_2$, $C(R^5)_2$, $C(R^5)_2N(R^5)$ and $N(R^5)C(R^5)_2$, wherein each $R^5$ is independently selected from hydrogen or (1-8C)alkyl;
and when $X^1$ is a direct bond or is selected from $C(R^5)_2O$, $C(R^5)_2$ or $C(R^5)_2N(R^5)$, wherein $R^5$ has any of the meanings defined hereinbefore, $R^4$ is hydroxy-(1-6C)alkyl, (1-6C)alkoxy-(1-6C)alkyl, $R^5$—S, $R^5$—S(O), $R^5$—$SO_2$, $R^5$—$SO_2$—O, $R^5$—S-(1-6C)alkyl, $R^5$—S(O)-(1-6C)alkyl, $R^5$—$SO_2$-(1-6C)alkyl, N,N-di-($R^5$)sulphamoyl, N,N-di-($R^5$)sulphamoyl-(1-6C)alkyl, $R^5$—$SO_2N(R^5)$, $R^5$—$SO_2N(R^5)$-

(1-6C)alkyl, $R^5$—CON($R^5$), $R^5$O—CON($R^5$), $R^5$—CON($R^5$)-(1-6C)alkyl, $R^5$O—CON($R^5$)-(1-6C)alkyl, $(R^5)_2$N—SO$_2$N($R^5$), $(R^5)_2$N—SO$_2$N($R^5$)-(1-6C)alkyl, $(R^5)_2$N—CON($R^5$), $(R^5)_2$N—CON($R^5$)-(1-6C)alkyl, $R^5$—CO, $R^5$—CO-(1-6C)alkyl, $R^5$O—CO-(1-6C)alkyl, $(R^5)_2$NCO, $(R^5)_2$NCO-(1-6C)alkyl, $(R^5)_2$N—COO, $(R^5)_2$NCOO-(1-6C)alkyl, cyano, amino, $(R^6)$-amino, di-$(R^6)$-amino, amino-(1-6C)alkyl, $(R^6)$-amino-(1-6C)alkyl or di-$(R^6)$-amino-(1-6C)alkyl, wherein each $R^6$ present is (1-6C)alkyl optionally substituted by 1, 2 or 3 substituents independently selected from halogeno, cyano, hydroxy and (1-6C)alkoxy; and when $X^1$ is selected from O, SO, SO$_2$, N($R^5$), CO, CON($R^5$), N($R^5$)CO, SO$_2$N($R^5$), N($R^5$)SO$_2$, OC($R^5$)$_2$ and N($R^5$)C($R^5$)$_2$, wherein $R^5$ has any of the meanings defined hereinbefore, $R^4$ is hydroxy-(1-6C)alkyl, (1-6C)alkoxy-(1-6C)alkyl, $R^5$—S-(1-6C)alkyl, $R^5$—S(O)-(1-6C)alkyl, $R^5$—SO$_2$-(1-6C)alkyl, N,N-di-($R^5$)sulphamoyl-(1-6C)alkyl, $R^5$—SO$_2$N($R^5$)-(1-6C)alkyl, $R^5$—CON($R^5$)-(1-6C)alkyl, $R^5$O—CON($R^5$)-(1-6C)alkyl, $(R^5)_2$N—SO$_2$N($R^5$)-(1-6C)alkyl, $(R^5)_2$N—CON($R^5$)-(1-6C)alkyl, $R^5$—CO, $R^5$—CO-(1-6C)alkyl, $R^{50}$—CO, $R^5$O—CO-(1-6C)alkyl, $(R^5)_2$NCO, $(R^5)_2$NCO-(1-6C)alkyl, $(R^5)_2$NCOO-(1-6C)alkyl, amino-(1-6C)alkyl, $(R^6)$-amino-(1-6C)alkyl or di-$(R^6)$-amino-(1-6C)alkyl, wherein each $R^6$ present is (1-6C)alkyl optionally substituted by 1, 2 or 3 substituents independently selected from halogeno, cyano, hydroxy and (1-6C)alkoxy;

or $R^1$ is a group of the formula:

$$Q^1\text{-}X^2\text{—}$$

wherein $X^2$ is a direct bond or is selected from O, SO, SO$_2$, N($R^7$), N[C(O)$R^7$], N[C(O)N($R^7$)$_2$], N[C(O)O$R^7$], N[SO$_2$—N($R^7$)$_2$], CO, CON($R^7$), N($R^7$)CO, SO$_2$N($R^7$), N($R^7$)SO$_2$, O—SO$_2$, SO$_2$—O, C($R^7$)$_2$O, OC($R^7$)$_2$, C($R^7$)$_2$, C($R^7$)$_2$N($R^7$) and N($R^7$)C($R^7$)$_2$, wherein each $R^7$ is independently selected from hydrogen or (1-8C)alkyl;

and $Q^1$ is aryl, aryl-(1-6C)alkyl, (3-8C)cycloalkyl, (3-8C)cycloalkyl-(1-6C)alkyl, heterocyclyl, heterocyclyl-(1-6C)alkyl, heteroaryl or heteroaryl-(1-6C)alkyl, wherein any aryl or (3-8C)cycloalkyl group within a $R^1$ substituent bears 1, 2 or 3 substituents and any heterocyclyl or heteroaryl group within a $R^1$ substituent optionally bears 1, 2 or 3 substituents, wherein said substituents are independently selected from halogeno, trifluoromethyl, cyano, nitro, hydroxy, amino, carboxy, carbamoyl, ureido, (1-8C)alkyl, (2-8C)alkenyl, (2-8C)alkynyl, (1-6C)alkoxy, halogeno-(1-6C)alkoxy, hydroxy-(1-6C)alkyl, (1-6C)alkoxy-(1-6C)alkyl, (1-6C)alkylsulphonyl-(1-6C)alkyl, cyano-(1-6C)alkyl, halogeno-(1-6C)alkyl, amino-(1-6C)alkyl, (1-6C)alkylamino-(1-6C)alkyl, di-[(1-6C)alkyl]amino-(1-6C)alkyl, (2-6C)alkenyloxy, (2-6C)alkynyloxy, (1-6C)alkylthio, (1-6C)alkylsulphinyl, (1-6C)alkylsulphonyl, (1-6C)alkylamino, di-[(1-6C)alkyl]amino, (1-6C)alkoxycarbonyl, (2-6C)alkanoyl, (2-6C)alkanoyloxy, N-(1-6C)alkylcarbamoyl, N,N-di-[(1-6C)alkyl]carbamoyl, (1-6C)alkanoylamino, N-(1-6C)alkyl-(1-6C)alkanoylamino, N-(1-6C)alkylureido, N'-(1-6C)alkylureido, N',N'-di-[(1-6C)alkyl]ureido, N,N'-di-[(1-6C)alkyl]ureido, N,N',N'-tri-[(1-6C)alkyl]ureido, N-(1-6C)alkylsulphamoyl, N,N-di-[(1-6C)alkyl]sulphamoyl, (1-6C)alkanesulphonylamino, N-(1-6C)alkyl-(1-6C)alkanesulphonylamino or heterocyclyl-(1-6C)alkyl, and any heterocyclyl group within a $R^1$ substituent optionally bears 1 or 2 oxo substituents;

each $R^2$ group may be the same or different and is selected from halogeno, cyano, (1-8C)alkyl, (2-8C)alkenyl, (2-8C)alkynyl, (1-6C)alkoxy, (2-6C)alkenyloxy, (2-6C)alkynyloxy, fluoro-(1-6C)alkoxy, (1-6C)alkylthio, (1-6C)alkylsulphinyl, (1-6C)alkylsulphonyl, (1-6C)alkylamino, di-[(1-6C)alkyl]amino, (2-6C)alkanoyl, N-(1-6C)alkylcarbamoyl, N,N-di-[(1-6C)alkyl]carbamoyl, (1-6C)alkanoylamino, N-(1-6C)alkyl-(1-6C)alkanoylamino, (1-6C)alkoxy-(1-6C)alkyl, hydroxy-(1-6C)alkyl, (1-6C)alkoxy-(1-6C)alkoxy or hydroxy-(1-6C)alkoxy; and n is 0, 1 or 2 and, when n is 2, each $R^3$ group may be the same or different, and each $R^3$ group present is selected from hydrogen, halogeno, cyano, O$R^9$, trifluoromethyl, (1-8C)alkyl, (2-8C)alkenyl, (2-8C)alkynyl, (1-6C)alkoxy, halogeno-(1-6C)alkoxy, carbamoyl, N-(1-6C)alkylcarbamoyl, N,N-di-[(1-6C)alkyl]carbamoyl, (1-6C)alkanoylamino, (1-6C)alkylthio, (1-6C)alkylsulphinyl, (1-6C)alkylsulphonyl, hydroxy-(1-6C)alkyl, (1-6C)alkoxy-(1-6C)alkyl, (2-6C)alkanoyl, (1-6C)alkanesulphonylamino, (1-6C)alkoxy-(1-6C)alkoxy, hydroxy-(1-6C)alkoxy, amino-(1-6C)alkoxy, (1-6C)alkylamino-(1-6C)alkoxy and di-[(1-6C)alkyl]amino-(1-6C)alkoxy, wherein $R^9$ is fluoro-(1-6C)alkyl; or a pharmaceutically-acceptable salt thereof.

A further particular group of compounds of the invention are pyridine and pyrazine derivatives of Formula I above wherein:—

W is CH or N;
J is O or S;
each of $G_1$, $G_2$, $G_3$ and $G_4$ is selected from CH and N provided that not more than one of $G_1$, $G_2$, $G_3$ and $G_4$ represent N;
Ring A is selected from:
 (i) phenyl substituted by $R^1$ and optionally substituted by an $R^2$ group; or
 (ii) a 5- or 6-membered monocyclic heteroaryl ring with up to three ring nitrogen atoms, said ring being substituted by $R^1$ and optionally substituted by an $R^2$ group; or
 (iii) a 8-, 9- or 10-membered bicyclic ring system, wherein the ring of attachment to the central core pyridinyl ring is a phenyl or a monocyclic heteroaryl ring, and wherein said bicyclic ring system optionally contains up to two ring heteroatoms selected from oxygen and nitrogen and is optionally substituted by $R^1$ and optionally substituted by an $R^2$ group;

$R^1$ is a group of the formula:

$$R^4\text{—}X^1\text{—}$$

wherein $X^1$ is a direct bond or is selected from O, SO, SO$_2$, N($R^5$), CO, CON($R^5$), N($R^5$)CO, SO$_2$N($R^5$), N($R^5$)SO$_2$, C($R^5$)$_2$O, OC($R^5$)$_2$, C($R^5$)$_2$, C($R^5$)$_2$N($R^5$) and N($R^5$)C($R^5$)$_2$, wherein each $R^5$ is independently selected from hydrogen or (1-8C)alkyl, and when $X^1$ is a direct bond or is selected from C($R^5$)$_2$O, C($R^5$)$_2$ or C($R^5$)$_2$N($R^5$), wherein $R^5$ has any of the meanings defined hereinbefore, $R^4$ is hydroxy-(1-6C)alkyl, (1-6C)alkoxy-(1-6C)alkyl, $R^5$—S, $R^5$—S(O), $R^5$—SO$_2$, $R^5$—S-(1-6C)alkyl, $R^5$—S(O)-(1-6C)alkyl, $R^5$—SO$_2$-(1-6C)alkyl, N,N-di-($R^5$)sulphamoyl, N,N-di-($R^5$)sulphamoyl-(1-6C)alkyl, $R^5$—SO$_2$N($R^5$), $R^5$—SO$_2$N($R^5$)-(1-6C)alkyl, $R^5$—CON($R^5$), $R^5$—CON($R^5$)-(1-6C)alkyl, $R^5$—CO, $R^5$—CO-(1-6C)alkyl, $(R^5)_2$NCO, $(R^5)_2$NCO-(1-6C)alkyl, cyano, amino, $(R^6)$-amino, di-$(R^6)$-amino, amino-(1-6C)alkyl, $(R^6)$-amino-(1-6C)alkyl or di-$(R^6)$-amino-(1-6C)alkyl, wherein each $R^6$ present is (1-6C)alkyl;

and when $X^1$ is selected from O, SO, SO$_2$, N($R^5$), CO, CON($R^5$), N($R^5$)CO, SO$_2$N($R^5$), N($R^5$)SO$_2$, OC($R^5$)$_2$ and N($R^5$)C($R^5$)$_2$, wherein $R^5$ has any of the meanings defined hereinbefore, $R^4$ is hydroxy-(1-6C)alkyl, (1-6C)alkoxy-(1-6C)alkyl, $R^5$—S-(1-6C)alkyl, $R^5$—S(O)-(1-6C)alkyl, $R^5$—SO$_2$-(1-6C)alkyl, $R^5$—CON($R^5$)-(1-6C)alkyl, $R^5$—CO-(1-6C)alkyl, $(R^5)_2$NCO-(1-6C)alkyl, amino-(1-6C)alkyl, $(R^6)$-amino-(1-6C)alkyl or di-$(R^6)$-amino-(1-6C)alkyl, wherein each $R^6$ present is (1-6C)alkyl;

or $R^1$ is a group of the formula:

$$Q^1\text{-}X^2\text{—}$$

wherein $X^2$ is a direct bond or is selected from O, SO, $SO_2$, $N(R^7)$, $N[C(O)R^7]$, $N[C(O)N(R^7)_2]$, $N[C(O)OR^7]$, $N[SO_2$—$N(R^7)_2]$, CO, $CON(R^7)$, $N(R^7)CO$, $SO_2N(R^7)$, $N(R^7)SO_2$, O—$SO_2$, $SO_2$—O, $C(R^7)_2O$, $OC(R^7)_2$, $C(R^7)_2$, $C(R^7)_2N(R^7)$ and $N(R^7)C(R^7)_2$, wherein each $R^7$ is independently selected from hydrogen or (1-8C)alkyl;

and $Q^1$ is heterocyclyl, heterocyclyl-(1-6C)alkyl, heteroaryl or heteroaryl-(1-6C)alkyl, wherein any heterocyclyl or heteroaryl group within a $R^1$ substituent optionally bears 1, 2 or 3 substituents, wherein said substituents are independently selected from halogeno, trifluoromethyl, cyano, hydroxy, amino, carboxy, (1-8C)alkyl, (2-8C)alkenyl, (2-8C)alkynyl, (1-6C)alkoxy, halogeno-(1-6C)alkoxy, hydroxy-(1-6C)alkyl, (1-6C)alkoxy-(1-6C)alkyl, halogeno-(1-6C)alkyl, amino-(1-6C)alkyl, (1-6C)alkylamino-(1-6C)alkyl, di-[(1-6C)alkyl]amino-(1-6C)alkyl, (1-6C)alkylamino, di-[(1-6C)alkyl]amino, (1-6C)alkoxycarbonyl, N-(1-6C)alkylcarbamoyl, (1-6C)alkanoylamino or heterocyclyl-(1-6C)alkyl, and any heterocyclyl group within a $R^1$ substituent optionally bears 1 or 2 oxo substituents;

each $R^2$ group may be the same or different and is selected from halogeno, cyano, (1-8C)alkyl, (1-6C)alkoxy, (1-6C)alkylthio, (2-6C)alkanoyl, (1-6C)alkoxy-(1-6C)alkyl, hydroxy-(1-6C)alkyl, (1-6C)alkoxy-(1-6C)alkoxy or hydroxy-(1-6C)alkoxy;

n is 0, 1 or 2 and, when n is 2, each $R^3$ group may be the same or different, and each $R^3$ group present is selected from hydrogen, halogeno, cyano, $OR^9$, trifluoromethyl, (1-8C)alkyl, (1-6C)alkoxy, (1-6C)alkanoylamino, (1-6C)alkylthio, hydroxy-(1-6C)alkyl, (1-6C)alkoxy-(1-6C)alkyl, (2-6C)alkanoyl, (1-6C)alkoxy-(1-6C)alkoxy, hydroxy-(1-6C)alkoxy, wherein $R^9$ is fluoro-(1-6C)alkyl; or a pharmaceutically-acceptable salt thereof.

A further particular group of compounds of the invention are pyridine and pyrazine derivatives of Formula I above wherein:—

W is CH or N;
J is O or S;
each of $G_1$, $G_2$, $G_3$ and $G_4$ is selected from CH and N provided that not more than one of $G_1$, $G_2$, $G_3$ and $G_4$ represent N;
Ring A is selected from:
  (i) phenyl substituted by $R^1$ and optionally substituted by an $R^2$ group; or
  (ii) a 5- or 6-membered monocyclic heteroaryl ring with up to three ring nitrogen atoms, said ring being substituted by $R^1$ and optionally substituted by an $R^2$ group; or
  (iii) a 8-, 9- or 10-membered bicyclic ring system, wherein the ring of attachment to the central core pyridinyl ring is a phenyl or a monocyclic heteroaryl ring, and wherein said bicyclic ring system optionally contains up to two ring heteroatoms selected from oxygen and nitrogen and is optionally substituted by $R^1$ and optionally substituted by an $R^2$ group;
$R^1$ is a group of the formula:

$$R^4\text{—}X^1\text{—}$$

wherein $X^1$ is a direct bond or is selected from O, SO, $SO_2$, $N(R^5)$, CO, $CON(R^5)$, $N(R^5)CO$, $SO_2N(R^5)$, $N(R^5)SO_2$, $C(R^5)_2O$, $OC(R^5)_2$, $C(R^5)_2$, $C(R^5)_2N(R^5)$ and $N(R^5)C(R^5)_2$, wherein each $R^5$ is independently selected from hydrogen or (1-8C)alkyl, and when $X^1$ is a direct bond or is selected from $C(R^5)_2O$, $C(R^5)_2$ or $C(R^5)_2N(R^5)$, wherein $R^5$ has any of the meanings defined hereinbefore, $R^4$ is hydroxy-(1-6C)alkyl, (1-6C)alkoxy-(1-6C)alkyl, $R^5$—S, $R^5$—S(O), $R^5$—$SO_2$, $R^5$—$SO_2$—O, $R^5$—S-(1-6C)alkyl, $R^5$—S(O)-(1-6C)alkyl, $R^5$—$SO_2$-(1-6C)alkyl, N,N-di-($R^5$)sulphamoyl, N,N-di-($R^5$)sulphamoyl-(1-6C)alkyl, $R^5$—$SO_2N(R^5)$, $R^5$—$SO_2N(R^5)$-(1-6C)alkyl, $R^5$—$CON(R^5)$, $R^5$—$CON(R^5)$-(1-6C)alkyl, $R^5$—CO, $R^5$—CO-(1-6C)alkyl, $(R^5)_2NCO$, $(R^5)_2NCO$-(1-6C)alkyl, cyano, amino, $(R^6)$-amino, di-$(R^6)$-amino, amino-(1-6C)alkyl, $(R^6)$-amino-(1-6C)alkyl or di-$(R^6)$-amino-(1-6C)alkyl, wherein each $R^6$ present is (1-6C)alkyl;

and when $X^1$ is selected from O, SO, $SO_2$, $N(R^5)$, CO, $CON(R^5)$, $N(R^5)CO$, $SO_2N(R^5)$, $N(R^5)SO_2$, $OC(R^5)_2$ and $N(R^5)C(R^5)_2$, wherein $R^5$ has any of the meanings defined hereinbefore, $R^4$ is hydroxy-(1-6C)alkyl, (1-6C)alkoxy-(1-6C)alkyl, $R^5$—S-(1-6C)alkyl, $R^5$—S(O)-(1-6C)alkyl, $R^5$—$SO_2$-(1-6C)alkyl, $R^5$—$CON(R^5)$-(1-6C)alkyl, $R^5$—CO-(1-6C)alkyl, $(R^5)_2NCO$-(1-6C)alkyl, amino-(1-6C)alkyl, $(R^6)$-amino-(1-6C)alkyl or di-$(R^6)$-amino-(1-6C)alkyl, wherein each $R^6$ present is (1-6C)alkyl;

or $R^1$ is a group of the formula:

$$Q^1\text{-}X^2\text{—}$$

wherein $X^2$ is a direct bond or is selected from O, SO, $SO_2$, $N(R^7)$, $N[C(O)R^7]$, $N[C(O)N(R^7)_2]$, $N[C(O)OR^7]$, $N[SO_2$—$N(R^7)_2]$, CO, $CON(R^7)$, $N(R^7)CO$, $SO_2N(R^7)$, $N(R^7)SO_2$, O—$SO_2$, $SO_2$—O, $C(R^7)_2O$, $OC(R^7)_2$, $C(R^7)_2$, $C(R^7)_2N(R^7)$ and $N(R^7)C(R^7)_2$, wherein each $R^7$ is independently selected from hydrogen or (1-8C)alkyl;

and $Q^1$ is heterocyclyl, heterocyclyl-(1-6C)alkyl, heteroaryl or heteroaryl-(1-6C)alkyl, wherein any heterocyclyl or heteroaryl group within a $R^1$ substituent optionally bears 1, 2 or 3 substituents, wherein said substituents are independently selected from halogeno, trifluoromethyl, cyano, hydroxy, amino, carboxy, (1-8C)alkyl, (2-8C)alkenyl, (2-8C)alkynyl, (1-6C)alkoxy, halogeno-(1-6C)alkoxy, hydroxy-(1-6C)alkyl, (1-6C)alkoxy-(1-6C)alkyl, halogeno-(1-6C)alkyl, amino-(1-6C)alkyl, (1-6C)alkylamino-(1-6C)alkyl, di-[(1-6C)alkyl]amino-(1-6C)alkyl, (1-6C)alkylamino, di-[(1-6C)alkyl]amino, (1-6C)alkoxycarbonyl, N-(1-6C)alkylcarbamoyl, (1-6C)alkanoylamino or heterocyclyl-(1-6C)alkyl, and any heterocyclyl group within a $R^1$ substituent optionally bears 1 or 2 oxo substituents;

each $R^2$ group may be the same or different and is selected from halogeno, cyano, (1-8C)alkyl, (1-6C)alkoxy, (1-6C)alkylthio, (2-6C)alkanoyl, (1-6C)alkoxy-(1-6C)alkyl, hydroxy-(1-6C)alkyl, (1-6C)alkoxy-(1-6C)alkoxy or hydroxy-(1-6C)alkoxy;

n is 0, 1 or 2 and, when n is 2, each $R^3$ group may be the same or different, and each $R^3$ group present is selected from hydrogen, halogeno, cyano, $OR^9$, trifluoromethyl, (1-8C)alkyl, (1-6C)alkoxy, (1-6C)alkanoylamino, (1-6C)alkylthio, hydroxy-(1-6C)alkyl, (1-6C)alkoxy-(1-6C)alkyl, (2-6C)alkanoyl, (1-6C)alkoxy-(1-6C)alkoxy, hydroxy-(1-6C)alkoxy, wherein $R^9$ is fluoro-(1-6C)alkyl; or a pharmaceutically-acceptable salt thereof.

A further particular group of compounds of the invention are pyridine and pyrazine derivatives of Formula I above wherein:—

W is CH or N;
J is O;
each of $G_1$, $G_2$, $G_3$ and $G_4$ is selected from CH and N provided that not more than two of $G_1$, $G_2$, $G_3$ and $G_4$ represent N;
Ring A is selected from:
  (i) phenyl substituted by $R^1$ and optionally substituted by an $R^2$ group; or
  (ii) a 5- or 6-membered monocyclic heteroaryl ring with up to three ring nitrogen atoms, said ring being substituted by $R^1$ and optionally substituted by an $R^2$ group; or (iii) a 8-, 9- or 10-membered bicyclic ring system, wherein the ring of attachment to the central core pyridinyl ring is a phenyl or a monocyclic heteroaryl ring, and wherein said bicyclic ring system optionally contains up to two ring heteroatoms selected from oxygen and nitrogen and is optionally substituted by $R^1$ and optionally substituted by an $R^2$ group;

$R^1$ is a group of the formula:

$$R^4-X^1-$$

wherein $X^1$ is a direct bond or is selected from O, SO, $SO_2$, $N(R^5)$, CO, $CON(R^5)$, $N(R^5)CO$, $SO_2N(R^5)$, $N(R^5)SO_2$, $C(R^5)_2O$, $OC(R^5)_2$, $C(R^5)_2$, $C(R^5)_2N(R^5)$ and $N(R^5)C(R^5)_2$, wherein each $R^5$ is independently selected from hydrogen or (1-8C)alkyl, and when $X^1$ is a direct bond or is selected from $C(R^5)_2O$, $C(R^5)_2$ or $C(R^5)_2N(R^5)$, wherein $R^5$ has any of the meanings defined hereinbefore, $R^4$ is hydroxy-(1-3C)alkyl, (1-6C)alkoxy-(1-3C)alkyl, $R^5$—S, $R^5$—S(O), $R^5$—$SO_2$, $R^5$—$SO_2$—O, $R^5$—S-(1-3C)alkyl, $R^5$—S(O)-(1-3C)alkyl, $R^5$—$SO_2$-(1-3C)alkyl, N,N-di-($R^5$)sulphamoyl, N,N-di-($R^5$)sulphamoyl-(1-3C)alkyl, $R^5$—$SO_2N(R^5)$, $R^5$—$SO_2N(R^5)$-(1-3C)alkyl, $R^5$—$CON(R^5)$, $R^5$—$CON(R^5)$-(1-3C)alkyl, $R^5$—CO, $R^5$—CO-(1-3C)alkyl, $(R^5)_2NCO$, $(R^5)_2NCO$-(1-3C)alkyl, cyano, amino, $(R^6)$-amino, di-$(R^6)$-amino, amino-(1-3C)alkyl, $(R^6)$-amino-(1-3C)alkyl or di-$(R^6)$-amino-(1-3C)alkyl, wherein each $R^6$ present is (1-3C)alkyl;

and when $X^1$ is selected from O, SO, $SO_2$, $N(R^5)$, CO, $CON(R^5)$, $N(R^5)CO$, $SO_2N(R^5)$, $N(R^5)SO_2$, $OC(R^5)_2$ and $N(R^5)C(R^5)_2$, wherein $R^5$ has any of the meanings defined hereinbefore, $R^4$ is hydroxy-(1-3C)alkyl, (1-6C)alkoxy-(1-3C)alkyl, $R^5$—S-(1-3C)alkyl, $R^5$—S(O)-(1-3C)alkyl, $R^5$—$SO_2$-(1-3C)alkyl, $R^5$—$CON(R^5)$-(1-3C)alkyl, $R^5$—CO-(1-3C)alkyl, $(R^5)_2NCO$-(1-3C)alkyl, amino-(1-3C)alkyl, $(R^6)$-amino-(1-3C)alkyl or di-$(R^6)$-amino-(1-3C)alkyl, wherein each $R^6$ present is (1-3C)alkyl;

or $R^1$ is a group of the formula:

$$Q^1-X^2-$$

wherein $X^2$ is a direct bond or is selected from O, SO, $SO_2$, $N(R^7)$, $N[C(O)R^7]$, $N[C(O)N(R^7)_2]$, $N[C(O)OR^7]$, $N[SO_2-N(R^7)_2]$, CO, $CON(R^7)$, $N(R^7)CO$, $SO_2N(R^7)$, $N(R^7)SO_2$, O—$SO_2$, $SO_2$—O, $C(R^7)_2O$, $OC(R^7)_2$, $C(R^7)_2$, $C(R^7)_2N(R^7)$ and $N(R^7)C(R^7)_2$, wherein each $R^7$ is independently selected from hydrogen or (1-8C)alkyl;

and $Q^1$ is heterocyclyl, heterocyclyl-(1-3C)alkyl, heteroaryl or heteroaryl-(1-3C)alkyl, wherein said heterocyclyl or the heterocyclyl within the heterocyclyl-(1-3C)alkyl group is selected from piperidinyl, pyrrolidinyl, morpholinyl, piperazinyl, tetrahydro-2H-pyranyl, azetidinyl, 1,1-dioxotetrahydro-1,4-thiazinyl, imidazolinyl, azepanyl, 1H-imidazolyl, 1,4-diazepanyl, (1R,5S)-8-azabicyclo[3.2.1]octanyl, quinuclidinyl, (3R)-quinuclidinyl, 3,4,4a,5,6,7,8,8a-octahydro-2H-quinolinyl, 3,4,6,7,8,8a-hexahydro-1H-pyrrolo[2,1-c]pyrazinyl, 3,8-diazaspiro[5.5]undecanyl, 2,8-diazaspiro[4.5]decanyl, 4,9-diazaspiro[5.5]undecanyl, 2,3,3a,4,6,6a-hexahydro-1H-pyrrolo[3,4-c]pyrrolyl, 3,9-diazaspiro[5.5]undecanyl and (1S,4S)-3,6-diazabicyclo[2.2.1]heptanyl, and said heteroaryl or the heteroaryl within the heteroaryl-(1-3C)alkyl group is pyrazolyl, each of which optionally bears a halogeno, trifluoromethyl, cyano, hydroxy, amino, carboxy, (1-8C)alkyl, (2-8C)alkenyl, (2-8C)alkynyl, (1-6C)alkoxy, halogeno-(1-6C)alkoxy, hydroxy-(1-6C)alkyl, (1-6C)alkoxy-(1-6C)alkyl, cyano-(1-6C)alkyl, halogeno-(1-6C)alkyl, amino-(1-6C)alkyl, (1-6C)alkylamino-(1-6C)alkyl, di-[(1-6C)alkyl]amino-(1-6C)alkyl, (1-6C)alkylsulphonyl, (1-6C)alkylamino, di-[(1-6C)alkyl]amino, (1-6C)alkoxycarbonyl, N-(1-6C)alkylcarbamoyl, (1-6C)alkanoylamino, (2-6C)alkanoyl, hydroxy-(2-6C)alkanoyl, (1-6C)alkoxy-(2-6C)alkanoyl, carbamoyl-(1-6C)alkyl, N-(1-6C)alkylcarbamoyl-(1-6C)alkyl, N,N-di-[(1-6C)alkyl]carbamoyl-(1-6C)alkyl, (1-6C)alkoxy-(1-6C)alkoxycarbonyl, (1-6C)alkylamino-(2-6C)alkanoyl, di-[(1-6C)alkyl]amino-(2-6C)alkanoyl, (1-6C)alkanoylamino-(2-6C)alkanoyl, (1-6C)alkoxy-(1-6C)alkoxy-(2-6C)alkanoyl, heterocyclyl, heterocyclyl-(1-6C)alkyl, heteroaryl or heteroaryl-(1-6C)alkyl, and any heterocyclyl group within a $R^1$ substituent optionally bears 1 or 2 oxo substituents; wherein, any CH, $CH_2$, or $CH_3$ in any alkyl group present in the definition of $R^4$ that is connected to $X^1$ or present in the definition of $Q^1$ that is connected to $X^2$, can optionally be replaced by an O atom or a $SO_2$ group and adjacent carbon atoms in an alkyl chain can optionally be separated by the insertion into the chain of a C≡C group;

$R^2$ is selected from halogeno, cyano, (1-8C)alkyl, (1-6C)alkoxy, (1-6C)alkylthio, (2-6C)alkanoyl, (1-6C)alkylamino, carbamoyl, N-(1-6C)alkylcarbamoyl, N,N-di-[(1-6C)alkyl]carbamoyl, (1-6C)alkoxy-(1-6C)alkyl, hydroxy-(1-6C)alkyl, (1-6C)alkoxy-(1-6C)alkoxy, (1-6C)alkylamino-(1-6C)alkyl or hydroxy-(1-6C)alkoxy;

n is 0, 1 or 2 and, when n is 2, each $R^3$ group may be the same or different, and each $R^3$ group present is selected from hydrogen, fluoro, bromo, chloro, cyano, hydroxymethyl, methylcarbamoyl, $OR^9$, trifluoromethyl, methyl or propyl, wherein $R^9$ is methyl or trifluoromethyl; or a pharmaceutically-acceptable salt thereof.

A further particular group of compounds of the invention are pyridine and pyrazine derivatives of Formula I above wherein:—

W is CH or N;

J is O or S;

each of $G_1$, $G_2$, $G_3$ and $G_4$ is selected from CH and N provided that not more than one of $G_1$, $G_2$, $G_3$ and $G_4$ represent N;

Ring A is selected from:
(i) phenyl substituted by $R^1$ and optionally substituted by an $R^2$ group; or
(ii) pyrazolyl or pyridinyl, said ring being substituted by $R^1$ and optionally substituted by an $R^2$ group; or
(iii) naphthyl, quinolyl, 2,3-dihydro-1,4-benzodioxinyl, 1H-indazolyl, 1H-indolyl or 1,3-benzodioxolyl, wherein said bicyclic ring system is optionally substituted by $R^1$ and optionally substituted by an $R^2$ group;

$R^1$ is a group of the formula:

$$R^4-X^1-$$

wherein $X^1$ is a direct bond or is selected from O, SO, $SO_2$, $N(R^5)$, CO, $CON(R^5)$, $N(R^5)CO$, $SO_2N(R^5)$, $N(R^5)SO_2$, $C(R^5)_2O$, $OC(R^5)_2$, $C(R^5)_2$, $C(R^5)_2N(R^5)$ and $N(R^5)C(R^5)_2$, wherein each $R^5$ is independently selected from hydrogen or (1-8C)alkyl, and when $X^1$ is a direct bond or is selected from $C(R^5)_2O$, $C(R^5)_2$ or $C(R^5)_2N(R^5)$, wherein $R^5$ has any of the meanings defined hereinbefore, $R^4$ is hydroxy-(1-3C)alkyl, (1-6C)alkoxy-(1-3C)alkyl, $R^5$—S, $R^5$—S(O), $R^5$—$SO_2$, $R^5$—S-(1-3C)alkyl, $R^5$—S(O)-(1-3C)alkyl, $R^5$—$SO_2$-(1-3C)alkyl, N,N-di-($R^5$)sulphamoyl, N,N-di-($R^5$)sulphamoyl-(1-3C)alkyl, $R^5$—$SO_2N(R^5)$, $R^5$—$SO_2N(R^5)$-(1-3C)alkyl, $R^5$—$CON(R^5)$, $R^5$—$CON(R^5)$-(1-3C)alkyl, $R^5$—CO, $R^5$—CO-(1-3C)alkyl, $(R^5)_2NCO$, $(R^5)_2NCO$-(1-3C)alkyl, cyano, amino, $(R^6)$-amino, di-$(R^6)$— amino, amino-(1-3C)alkyl, $(R^6)$-amino-(1-3C)alkyl or di-$(R^6)$-amino-(1-3C)alkyl, wherein each $R^6$ present is (1-3C)alkyl;

and when $X^1$ is selected from O, SO, $SO_2$, $N(R^5)$, CO, $CON(R^5)$, $N(R^5)CO$, $SO_2N(R^5)$, $N(R^5)SO_2$, $OC(R^5)_2$ and $N(R^5)C$ $(R^5)_2$, wherein $R^5$ has any of the meanings defined hereinbefore, $R^4$ is hydroxy-(1-3C)alkyl, (1-6C)alkoxy-(1-3C)alkyl, $R^5$—S-(1-3C)alkyl, $R^5$—S(O)-(1-3C)alkyl, $R^5$—$SO_2$-(1-3C)alkyl, $R^5$—CON($R^5$)-(1-3C)alkyl, $R^5$—CO-(1-3C)alkyl, $(R^5)_2$NCO-(1-3C)alkyl, amino-(1-3C)alkyl, $(R^6)$-amino-(1-3C)alkyl or di-$(R^6)$-amino-(1-3C)alkyl, wherein each $R^6$ present is (1-3C)alkyl;

or $R^1$ is a group of the formula:

$$Q^1\text{-}X^2\text{—}$$

wherein $X^2$ is a direct bond or is selected from O, SO, $SO_2$, $N(R^7)$, $N[C(O)R^7]$, $N[C(O)N(R^7)_2]$, $N[C(O)OR^7]$, $N[SO_2$—$N(R^7)_2]$, CO, $CON(R^7)$, $N(R^7)CO$, $SO_2N(R^7)$, $N(R^7)SO_2$, O—$SO_2$, $SO_2$—O, $C(R^7)_2O$, $OC(R^7)_2$, $C(R^7)_2$, $C(R^7)_2N(R^7)$ and $N(R^7)C(R^7)_2$, wherein each $R^7$ is independently selected from hydrogen or (1-8C)alkyl;

and $Q^1$ is heterocyclyl or heterocyclyl-(1-3C)alkyl, wherein said heterocyclyl or the heterocyclyl within the heterocyclyl-(1-3C)alkyl group is selected from piperidinyl, pyrrolidinyl, morpholinyl and piperazinyl, each of which optionally bears a halogeno, trifluoromethyl, cyano, hydroxy, amino, carboxy, (1-8C)alkyl, (2-8C)alkenyl, (2-8C)alkynyl, (1-6C)alkoxy, halogeno-(1-6C)alkoxy, hydroxy-(1-6C)alkyl, (1-6C)alkoxy-(1-6C)alkyl, halogeno-(1-6C)alkyl, amino-(1-6C)alkyl, (1-6C)alkylamino-(1-6C)alkyl, di-[(1-6C)alkyl]amino-(1-6C)alkyl, (1-6C)alkylamino, di-[(1-6C)alkyl]amino, (1-6C)alkoxycarbonyl, N-(1-6C)alkylcarbamoyl, (1-6C)alkanoylamino or heterocyclyl-(1-6C)alkyl group, and any heterocyclyl group within a $R^1$ substituent optionally bears 1 or 2 oxo substituents;

each $R^2$ group is methoxy, ethoxy, propoxy, fluoro, bromo or chloro;

n is 0, 1 or 2 and, when n is 2, each $R^3$ group may be the same or different, and each $R^3$ group present is selected from hydrogen, fluoro, bromo, chloro, $OR^9$, trifluoromethyl, methyl or propyl, wherein $R^9$ is trifluoromethyl; or a pharmaceutically-acceptable salt thereof.

A further particular group of compounds of the invention are pyridine and pyrazine derivatives of Formula I above wherein:—

W is CH or N;
J is O or S;
each of $G_1$, $G_2$, $G_3$ and $G_4$ is selected from CH and N provided that not more than one of $G_1$, $G_2$, $G_3$ and $G_4$ represent N;
Ring A is selected from:
(i) phenyl substituted by $R^1$ and optionally substituted by an $R^2$ group; or
(ii) pyrazolyl, pyridinyl or thienyl, said ring being substituted by $R^1$ and optionally substituted by an $R^2$ group; or
(iii) naphthyl, quinolyl, 2,3-dihydro-1,4-benzodioxinyl, 1H-indazolyl, 1H-indolyl or 1,3-benzodioxolyl, wherein said bicyclic ring system is optionally substituted by $R^1$ and optionally substituted by an $R^2$ group;
$R^1$ is a group of the formula:

$$R^4\text{—}X^1\text{—}$$

wherein $X^1$ is a direct bond or is selected from O, SO, $SO_2$, $N(R^5)$, CO, $CON(R^5)$, $N(R^5)CO$, $SO_2N(R^5)$, $N(R^5)SO_2$, $C(R^5)_2O$, $OC(R^5)_2$, $C(R^5)_2$, $C(R^5)_2N(R^5)$ and $N(R^5)C(R^5)_2$, wherein each $R^5$ is independently selected from hydrogen or (1-8C)alkyl, and when $X^1$ is a direct bond or is selected from $C(R^5)_2O$, $C(R^5)_2$ or $C(R^5)_2N(R^5)$, wherein $R^5$ has any of the meanings defined hereinbefore, $R^4$ is hydroxy-(1-3C)alkyl, (1-6C)alkoxy-(1-3C)alkyl, $R^5$—S, $R^5$—S(O), $R^5$—$SO_2$, $R^5$—$SO_2$—O, $R^5$—S-(1-3C)alkyl, $R^5$—S(O)-(1-3C)alkyl, $R^5$—$SO_2$-(1-3C)alkyl, N,N-di-$(R^5)$sulphamoyl, N,N-di-$(R^5)$ sulphamoyl-(1-3C)alkyl, $R^5$—$SO_2N(R^5)$, $R^5$—$SO_2N(R^5)$-(1-3C)alkyl, $R^5$—$CON(R^5)$, $R^5$—$CON(R^5)$-(1-3C)alkyl, $R^5$—CO, $R^5$—CO-(1-3C)alkyl, $(R^5)_2$NCO, $(R^5)_2$NCO-(1-3C)alkyl, cyano, amino, $(R^6)$-amino, di-$(R^6)$— amino, amino-(1-3C)alkyl, $(R^6)$-amino-(1-3C)alkyl or di-$(R^6)$-amino-(1-3C)alkyl, wherein each $R^6$ present is (1-3C)alkyl;

and when $X^1$ is selected from O, SO, $SO_2$, $N(R^5)$, CO, $CON(R^5)$, $N(R^5)CO$, $SO_2N(R^5)$, $N(R^5)SO_2$, $OC(R^5)_2$ and $N(R^5)C(R^5)_2$, wherein $R^5$ has any of the meanings defined hereinbefore, $R^4$ is hydroxy-(1-3C)alkyl, (1-6C)alkoxy-(1-3C)alkyl, $R^5$—S-(1-3C)alkyl, $R^5$—S(O)-(1-3C)alkyl, $R^5$—$SO_2$-(1-3C)alkyl, $R^5$—CON($R^5$)-(1-3C)alkyl, $R^5$—CO-(1-3C)alkyl, $(R^5)_2$NCO-(1-3C)alkyl, amino-(1-3C)alkyl, $(R^6)$-amino-(1-3C)alkyl or di-$(R^6)$-amino-(1-3C)alkyl, wherein each $R^6$ present is (1-3C)alkyl;

or $R^1$ is a group of the formula:

$$Q^1\text{-}X^2\text{—}$$

wherein $X^2$ is a direct bond or is selected from O, SO, $SO_2$, $N(R^7)$, $N[C(O)R^7]$, $N[C(O)N(R^7)_2]$, $N[C(O)OR^7]$, $N[SO_2$—$N(R^7)_2]$, CO, $CON(R^7)$, $N(R^7)CO$, $SO_2N(R^7)$, $N(R^7)SO_2$, O—$SO_2$, $SO_2$—O, $C(R^7)_2O$, $OC(R^7)_2$, $C(R^7)_2$, $C(R^7)_2N(R^7)$ and $N(R^7)C(R^7)_2$, wherein each $R^7$ is independently selected from hydrogen or (1-8C)alkyl;

and $Q^1$ is heterocyclyl, heterocyclyl-(1-3C)alkyl, heteroaryl or heteroaryl-(1-3C)alkyl, wherein said heterocyclyl or the heterocyclyl within the heterocyclyl-(1-3C)alkyl group is selected from piperidinyl, pyrrolidinyl, morpholinyl and piperazinyl, and said heteroaryl or the heteroaryl within the heteroaryl-(1-3C)alkyl group is pyrazolyl, each of which optionally bears a halogeno, trifluoromethyl, cyano, hydroxy, amino, carboxy, (1-8C)alkyl, (2-8C)alkenyl, (2-8C)alkynyl, (1-6C)alkoxy, halogeno-(1-6C)alkoxy, hydroxy-(1-6C)alkyl, (1-6C)alkoxy-(1-6C)alkyl, halogeno-(1-6C)alkyl, amino-(1-6C)alkyl, (1-6C)alkylamino-(1-6C)alkyl, di-[(1-6C)alkyl]amino-(1-6C)alkyl, (1-6C)alkylamino, di-[(1-6C)alkyl]amino, (1-6C)alkoxycarbonyl, N-(1-6C)alkylcarbamoyl, (1-6C)alkanoylamino or heterocyclyl-(1-6C)alkyl group, and any heterocyclyl group within a $R^1$ substituent optionally bears 1 or 2 oxo substituents;

each $R^2$ group is methoxy, ethoxy, propoxy, fluoro, bromo or chloro;

n is 0, 1 or 2 and, when n is 2, each $R^3$ group may be the same or different, and each $R^3$ group present is selected from hydrogen, fluoro, bromo, chloro, $OR^9$, trifluoromethyl, methyl or propyl, wherein $R^9$ is trifluoromethyl; or a pharmaceutically-acceptable salt thereof.

A further particular group of compounds of the invention are pyridine and pyrazine derivatives of Formula I above wherein:—

W is suitably as defined in any one of paragraphs (a) to (b) above;
J is suitably as defined in any one of paragraphs (c) to (d) above;
$G_1$, $G_2$, $G_3$ and $G_4$ are suitably as defined in any one of paragraphs (e) to (j) above;
Ring A is suitably as defined in any one of paragraphs (k) to (u) above and is particularly as defined in any one of paragraphs (l) to (u) above;
$R^1$ is suitably as defined in any one of paragraphs (v) to (ee) above and is particularly as defined in any one of paragraphs (x) to (ee) above;
$R^2$ is suitably as defined in any one of paragraphs (ff) to (kk) above, and is particularly as defined in any one of paragraphs (gg) to (kk) above; and R³ is suitably as defined in any one of paragraphs (ll) to (qq) above, and is particularly as defined in any one of paragraphs (mm) to (qq) above.

A further particular group of compounds of the invention are pyridine and pyrazine derivatives of Formula I above wherein:—
W is suitably as defined in any one of paragraphs (a) to (b) above;
J is suitably as defined in any one of paragraphs (c) to (d) above;
$G_1$, $G_2$, $G_3$ and $G_4$ are suitably as defined in any one of paragraphs (e) to (j) above;
Ring A is suitably as defined in any one of paragraphs (k) to (u), (rr) and (ss) above and is particularly as defined in any one of paragraphs (l) to (u), (rr) and (ss) above;
R¹ is suitably as defined in any one of paragraphs (v) to (ee) and (tt) to (bbb) above and is particularly as defined in any one of paragraphs (x) to (ee) and (yy) to (bbb) above;
R² is suitably as defined in any one of paragraphs (ff) to (kk), (ccc) and (ddd) above, and is particularly as defined in any one of paragraphs (gg) to (kk), (ccc) and (ddd) above; and
R³ is suitably as defined in any one of paragraphs (ll) to (qq) above, and is particularly as defined in any one of paragraphs (mm) to (qq) above.

A yet further particular group of compounds of the invention are pyridine and pyrazine derivatives of Formula I above wherein:—
W is suitably as defined in any one of paragraphs (a) to (b) above;
J is suitably as defined in any one of paragraphs (c) to (d) above;
$G_1$, $G_2$, $G_3$ and $G_4$ are suitably as defined in any one of paragraphs (e) to (j) above;
Ring A is suitably as defined in any one of paragraphs (k) to (u), (rr), (ss), (eee) and (fff) above and is particularly as defined in any one of paragraphs (l) to (u), (rr), (ss), (eee) and (fff) above;
R¹ is suitably as defined in any one of paragraphs (v) to (ee), (tt) to (bbb) and (ggg) to (jjj) above and is particularly as defined in any one of paragraphs (x) to (ee), (yy) to (bbb) and (ggg) to (jjj) above;
R² is suitably as defined in any one of paragraphs (ff) to (kk), (ccc), (ddd), (kkk) and (lll) above, and is particularly as defined in any one of paragraphs (gg) to (kk), (ccc), (ddd), (kkk) and (lll) above; and
R³ is suitably as defined in any one of paragraphs (ll) to (qq) and (mmm) above, and is particularly as defined in any one of paragraphs (mm) to (qq) and (mmm) above.

A yet further particular group of compounds of the invention are pyridine and pyrazine derivatives of Formula I above wherein:—
W is suitably as defined in any one of paragraphs (a) to (b) above;
J is suitably as defined in any one of paragraphs (c) to (d) above;
$G_1$, $G_2$, $G_3$ and $G_4$ are suitably as defined in any one of paragraphs (e) to (j) and (nnn) above;
Ring A is suitably as defined in any one of paragraphs (k) to (u), (rr), (ss), (eee), (fff) and (ooo) to (ttt) above and is particularly as defined in any one of paragraphs (l) to (u), (rr), (ss), (eee), (fff) and (ooo) to (ttt) above;
R¹ is suitably as defined in any one of paragraphs (v) to (ee), (tt) to (bbb), (ggg) to (jjj) and (uuu) to (xxx) above and is particularly as defined in any one of paragraphs (x) to (ee), (yy) to (bbb), (ggg) to (jjj) and (uuu) to (xxx) above;
R² is suitably as defined in any one of paragraphs (ff) to (kk), (ccc), (ddd), (kkk), (lll) and (yyy) to (cccc) above, and is particularly as defined in any one of paragraphs (gg) to (kk), (ccc), (ddd), (kkk), (lll) and (yyy) to (cccc) above; and
R³ is suitably as defined in any one of paragraphs (ll) to (qq), (mmm), (dddd) and (eeee) above, and is particularly as defined in any one of paragraphs (mm) to (qq), (mmm), (dddd) and (eeee) above.

A further particular group of compounds of the invention are pyridine and pyrazine derivatives of Formula I above wherein:—
W is CH or N;
J is O or S;
each of $G_1$, $G_2$, $G_3$ and $G_4$ is selected from CH and N provided that not more than one of $G_1$, $G_2$, $G_3$ and $G_4$ represent N;
Ring A is phenyl, pyrazol-4-yl or pyridin-3-yl, wherein said ring is substituted by hydroxymethyl, 2-hydroxyethyl, 3-hydroxypropyl, methoxymethyl, ethoxymethyl, propoxymethyl, 2-methoxyethoxy, 2-ethoxyethoxy, methylsulphonyl, ethylsulphonyl, propylsulphonyl, methylsulphamoyl, ethylsulphamoyl, propylsulphamoyl, dimethylsulphamoyl, diethylsulphamoyl, cyclopropylsulphamoyl, methanesulphonamido, ethanesulphonamido, acetamido, carbamoyl, methylcarbamoyl, ethylcarbamoyl, 2-dimethylaminoethylcarbamoyl, dimethylaminomethylcarbamoyl, cyano, aminomethyl, 2-aminoethyl, 3-aminopropyl, dimethylaminomethyl, diethylaminomethyl, 2-dimethylaminoethyl, 2-diethylaminoethyl, 3-dimethylaminopropoxy, 2-dimethylaminoethoxy, dimethylaminomethoxy, pyrrolidin-1-yl, piperazin-1-yl, piperidin-4-yl, morpholino, pyrrolidin-1-ylmethyl, morpholinomethyl, piperazin-1-ylmethyl, piperidin-4-ylmethyl, 2-(pyrrolidin-1-yl)ethyl, 2-(morpholino)ethyl, 2-(piperazin-1-yl)ethyl, 2-(piperidin-4-yl)ethyl, 4-hydroxypiperidine-1-carbonyl, 1-methyl-4-piperidyl, 1-ethyl-4-piperidyl, 1-isopropyl-4-piperidyl, 1-tert-butoxycarbonyl-4-piperidyl or 1-methyl-1-oxido-piperidin-1-ium-4-yl, and optionally substituted with methoxy, ethoxy, propoxy, fluoro, bromo or chloro;
or Ring A is quinolyl, 2,3-dihydro-1,4-benzodioxin-6-yl, 1H-indazol-5-yl, 1H-indol-5-yl, 1H-indol-6-yl, 1,3-benzodioxol-5-yl or naphthyl, optionally substituted with hydroxymethyl, 2-hydroxyethyl, 3-hydroxypropyl, methoxymethyl, ethoxymethyl, propoxymethyl, 2-methoxyethoxy, 2-ethoxyethoxy, methylsulphonyl, ethylsulphonyl, propylsulphonyl, methylsulphamoyl, ethylsulphamoyl, propylsulphamoyl, dimethylsulphamoyl, diethylsulphamoyl, cyclopropylsulphamoyl, methanesulphonamido, ethanesulphonamido, acetamido, carbamoyl, methylcarbamoyl, ethylcarbamoyl, 2-dimethylaminoethylcarbamoyl, dimethylaminomethylcarbamoyl, cyano, aminomethyl, 2-aminoethyl, 3-aminopropyl, dimethylaminomethyl, diethylaminomethyl, 2-dimethylaminoethyl, 2-diethylaminoethyl, 3-dimethylaminopropoxy, 2-dimethylaminoethoxy, dimethylaminomethoxy, pyrrolidin-1-yl, piperazin-1-yl, piperidin-4-yl, morpholino, pyrrolidin-1-ylmethyl, morpholinomethyl, piperazin-1-ylmethyl, piperidin-4-ylmethyl, 2-(pyrrolidin-1-yl)ethyl, 2-(morpholino)ethyl, 2-(piperazin-1-yl)ethyl, 2-(piperidin-4-yl)ethyl, 4-hydroxypiperidine-1-carbonyl, 1-methyl-4-piperidyl, 1-ethyl-4-piperidyl, 1-isopropyl-4-piperidyl, 1-tert-butoxycarbonyl-4-piperidyl or 1-methyl-1-oxido-piperidin-1-ium-4-yl, and optionally substituted with methoxy, ethoxy, propoxy, fluoro, bromo, chloro, hydroxyl or amino;
n is 0, 1 or 2 and, when n is 2, each R³ group may be the same or different, and
each R³ group present is selected from hydrogen, halogeno, cyano, OR⁹, trifluoromethyl, (1-4C)alkyl, methoxy, ethoxy, propoxy, wherein R⁹ is trifluoromethyl or 2,2,2-trifluoroethyl; or a pharmaceutically-acceptable salt thereof.

A further particular group of compounds of the invention are pyridine and pyrazine derivatives of Formula I above wherein:—
W is CH or N;
J is O or S;
each of $G_1$, $G_2$, $G_3$ and $G_4$ is selected from CH and N provided that not more than one of $G_1$, $G_2$, $G_3$ and $G_4$ represent N;
Ring A is phenyl, pyrazol-4-yl or pyridin-3-yl, wherein said ring is substituted by hydroxymethyl, methoxymethyl, 2-methoxyethoxy, ethylsulphonyl, methylsulphamoyl, dimethylsulphamoyl, cyclopropylsulphamoyl, methanesulphonamido, acetamido, carbamoyl, methylcarbamoyl, 2-dimethylaminoethylcarbamoyl, cyano, aminomethyl, dimethylaminomethyl, pyrrolidin-1-yl, piperazin-1-yl, piperidin-4-yl, pyrrolidin-1-ylmethyl, morpholinomethyl, 4-hydroxypiperidine-1-carbonyl, 1-methyl-4-piperidyl, 1-ethyl-4-piperidyl, 1-isopropyl-4-piperidyl, 3-dimethylaminopropoxy, 1-tert-butoxycarbonyl-4-piperidyl or 1-methyl-1-oxido-piperidin-1-ium-4-yl, and optionally substituted with methoxy; or Ring A is quinolyl, 2,3-dihydro-1,4-benzodioxin-6-yl, 1H-indazol-5-yl, 1H-indol-5-yl, 1H-indol-6-yl, 1,3-benzodioxol-5-yl or naphthyl, optionally substituted with hydroxymethyl, methoxymethyl, 2-methoxyethoxy, ethylsulphonyl, methylsulphamoyl, dimethylsulphamoyl, cyclopropylsulphamoyl, methanesulphonamido, acetamido, carbamoyl, methylcarbamoyl, 2-dimethylaminoethylcarbamoyl, cyano, aminomethyl, dimethylaminomethyl, pyrrolidin-1-yl, piperazin-1-yl, piperidin-4-yl, pyrrolidin-1-ylmethyl, morpholinomethyl, 4-hydroxypiperidine-1-carbonyl, 1-methyl-4-piperidyl, 1-ethyl-4-piperidyl, 1-isopropyl-4-piperidyl, 3-dimethylaminopropoxy, 1-tert-butoxycarbonyl-4-piperidyl or 1-methyl-1-oxido-piperidin-1-ium-4-yl, and optionally substituted with methoxy;
n is 0, 1 or 2 and, when n is 2, each $R^3$ group may be the same or different, and each $R^3$ group present is selected from hydrogen, halogeno, $OR^9$, trifluoromethyl, (1-4C)alkyl, wherein $R^9$ is trifluoromethyl; or a pharmaceutically-acceptable salt thereof.

A further particular group of compounds of the invention are pyridine and pyrazine derivatives of Formula I above wherein:—
W is CH or N;
J is O or S;
each of $G_1$, $G_2$, $G_3$ and $G_4$ is selected from CH and N provided that not more than one of $G_1$, $G_2$, $G_3$ and $G_4$ represent N;
Ring A is phenyl, pyrazol-4-yl, pyridin-3-yl or thien-2-yl, wherein said ring is substituted by hydroxymethyl, methoxymethyl, 2-methoxyethoxy, ethylsulphonyl, methylsulphonyl, methylsulphonyloxy, methylsulphamoyl, cyclopropylsulphamoyl, dimethylsulphamoyl, 2-hydroxyethylsulphamoyl, cyclopropylsulphamoyl, methanesulphonamido, acetamido, carbamoyl, methylcarbamoyl, cyclopropylcarbamoyl, 2-hydroxyethylcarbamoyl, dimethylamino, 2-dimethylaminoethylcarbamoyl, 2-diethylaminoethylcarbamoyl, 3-diethylaminopropylcarbamoyl, cyano, cyanomethyl, aminomethyl, dimethylaminomethyl, pyrrolidin-1-yl, piperazin-1-yl, piperidin-4-yl, pyrazol-3-yl, pyrrolidin-1-ylmethyl, morpholino, morpholinomethyl, 2-morpholinoethylcarbamoyl, morpholine-4-carbonyl, morpholinosulphonyl, 4-hydroxypiperidine-1-carbonyl, 2-pyrrolidin-1-ylethylcarbamoyl, piperidin-1-yl, piperidin-4-yl, 1-methyl-4-piperidyl, 1-ethyl-4-piperidyl, 1-isopropyl-4-piperidyl, 1-piperidylmethyl, piperidine-4-carbonylamino, 4-methylpiperazine-1-carbonyl, 4-methylpiperazin-1-yl, 3-dimethylaminopropoxy, 1-tert-butoxycarbonyl-4-piperidyl or 1-methyl-1-oxido-piperidin-1-ium-4-yl, and optionally substituted with methoxy, methyl or fluoro;
or Ring A is quinolyl, 2,3-dihydro-1,4-benzodioxin-6-yl, 1H-indazol-5-yl, 1H-indol-5-yl, 1H-indol-6-yl, 1,3-benzodioxol-5-yl or naphthyl, optionally substituted with hydroxymethyl, methoxymethyl, 2-methoxyethoxy, ethylsulphonyl, methylsulphonyl, methylsulphonyloxy, methylsulphamoyl, cyclopropylsulphamoyl, dimethylsulphamoyl, 2-hydroxyethylsulphamoyl, cyclopropylsulphamoyl, methanesulphonamido, acetamido, carbamoyl, methylcarbamoyl, cyclopropylcarbamoyl, 2-hydroxyethylcarbamoyl, dimethylamino, 2-dimethylaminoethylcarbamoyl, 2-diethylaminoethylcarbamoyl, 3-diethylaminopropylcarbamoyl, cyano, cyanomethyl, aminomethyl, dimethylaminomethyl, pyrrolidin-1-yl, piperazin-1-yl, piperidin-4-yl, pyrazol-3-yl, pyrrolidin-1-ylmethyl, morpholino, morpholinomethyl, 2-morpholinoethylcarbamoyl, morpholine-4-carbonyl, morpholinosulphonyl, 4-hydroxypiperidine-1-carbonyl, 2-pyrrolidin-1-ylethylcarbamoyl, piperidin-1-yl, piperidin-4-yl, 1-methyl-4-piperidyl, 1-ethyl-4-piperidyl, 1-isopropyl-4-piperidyl, 1-piperidylmethyl, piperidine-4-carbonylamino, 4-methylpiperazine-1-carbonyl, 4-methylpiperazin-1-yl, 3-dimethylaminopropoxy, 1-tert-butoxycarbonyl-4-piperidyl or 1-methyl-1-oxido-piperidin-1-ium-4-yl, and optionally substituted with methoxy, methyl or fluoro;
n is 0, 1 or 2 and, when n is 2, each $R^3$ group may be the same or different, and
each $R^3$ group present is selected from hydrogen, halogeno, $OR^9$, trifluoromethyl, (1-4C)alkyl, wherein $R^9$ is trifluoromethyl; or a pharmaceutically-acceptable salt thereof.

A further particular group of compounds of the invention are pyridine and pyrazine derivatives of Formula I above wherein:—
when W is CH and J is O;
each of $G_1$, $G_2$, $G_3$ and $G_4$ is selected from CH and N provided that not more than one of $G_1$, $G_2$, $G_3$ and $G_4$ represent N;
Ring A is 4-(hydroxymethyl)phenyl, 3-(hydroxymethyl)phenyl, 4-(methoxymethyl)phenyl, 3-(methoxymethyl)phenyl, 2-(methoxymethyl)phenyl, 4-(2-methoxyethoxy)phenyl, 3-(ethylsulphonyl)phenyl, 4-(ethylsulphonyl)phenyl, 3-(methylsulphamoyl)phenyl, 4-(dimethylsulphamoyl)phenyl, 3-(dimethylsulphamoyl)phenyl, 4-(cyclopropylsulphamoyl)phenyl, 4-methanesulphonamidophenyl, 3-acetamidophenyl, 3-carbamoylphenyl, 3-(methylcarbamoyl)phenyl, 4-(2-dimethylaminoethylcarbamoyl)phenyl, 3-(2-dimethylaminoethylcarbamoyl)phenyl, 4-cyanophenyl, 3-cyanophenyl, 3-(aminomethyl)phenyl, 4-(aminomethyl)phenyl, 4-(dimethylaminomethyl)phenyl, 3-pyrrolidin-1-ylphenyl, 3-(piperazin-1-yl)phenyl, 4-piperazin-1-ylphenyl, 4-(4-piperidyl)phenyl, 3-(pyrrolidin-1-ylmethyl)phenyl, 4-(morpholinomethyl)phenyl, 3-(morpholinomethyl)phenyl, 4-(4-hydroxypiperidine-1-carbonyl)phenyl, 4-(piperazin-1-yl)-2-(methoxy)phenyl, 1-(4-piperidyl)pyrazol-4-yl, 6-piperazin-1-yl-3-pyridyl, 1-(1-methyl-4-piperidyl)pyrazol-4-yl, 1-(1-ethyl-4-piperidyl)pyrazol-4-yl, 1-(1-isopropyl-4-piperidyl)pyrazol-4-yl, 6-(3-dimethylaminopropoxy)pyridin-3-yl, 1-(1-tert-butoxycarbonyl-4-piperidyl)pyrazol-4-yl, 1-(1-methyl-1-oxido-piperidin-1-ium-4-yl)pyrazol-4-yl, quinol-8-yl, quinol-3-yl, quinol-4-yl, 2,3-dihydro-1,4-benzodioxin-6-yl, 1H-indazol-5-yl, 1H-indol-5-yl, 1H-indol-6-yl, 1,3-benzodioxol-5-yl or 1-naphthyl;
n is 0, 1 or 2 and, when n is 2, each $R^3$ group may be the same or different, and
each $R^3$ group present is selected from hydrogen, fluoro, bromo, chloro, $OR^9$, trifluoromethyl, methyl or propyl, wherein $R^9$ is trifluoromethyl;
and when W is CH and J is S;

each of $G_1$, $G_2$, $G_3$ and $G_4$ are CH;
Ring A is 1-(4-piperidyl)pyrazol-4-yl or 1-(1-tert-butoxycarbonyl-4-piperidyl)pyrazol-4-yl; and n is 0;
and when W is N and J is O;
each of $G_1$, $G_2$, $G_3$ and $G_4$ are CH;
Ring A is 1-(1-tert-butoxycarbonyl-4-piperidyl)pyrazol-4-yl; and n is 0;
and when W is N and J is S;
each of $G_1$, $G_2$, $G_3$ and $G_4$ are CH;
Ring A is 1-(1-tert-butoxycarbonyl-4-piperidyl)pyrazol-4-yl; and n is 0; or a pharmaceutically-acceptable salt thereof.

A further particular group of compounds of the invention are pyridine and pyrazine derivatives of Formula I above wherein:—
when W is CH and J is O;
each of $G_1$, $G_2$, $G_3$ and $G_4$ is selected from CH and N provided that not more than one of $G_1$, $G_2$, $G_3$ and $G_4$ represent N;
Ring A is 4-(dimethylaminomethyl)phenyl, 3-(aminomethyl)phenyl, 4-(aminomethyl)phenyl, 4-(ethylsulphonyl)phenyl, 3-(methylsulphonyl)phenyl, 3-(ethylsulphonyl)phenyl, 3-(methylsulphonyloxy)phenyl, 3-(2-dimethylaminoethylcarbamoyl)phenyl, 3-(2-diethylaminoethylcarbamoyl)phenyl, 4-(2-methoxyethoxy)phenyl, 3-dimethylaminophenyl, 3-(methoxymethyl)phenyl, 4-(hydroxymethyl)phenyl, 4-(2-hydroxyethylcarbamoyl)phenyl, 3-(methylcarbamoyl)phenyl, 3-(cyclopropylcarbamoyl)phenyl, 3-acetamidophenyl, 4-methanesulphonamidophenyl, 4-(dimethylsulphamoyl)phenyl, 4-(cyclopropylsulphamoyl)phenyl, 3-(cyclopropylsulphamoyl)phenyl, 3-(methylsulphamoyl)phenyl, 4-(2-hydroxyethylsulphamoyl)phenyl, 3-carbamoylphenyl, 4-carbamoylphenyl, 3-(hydroxymethyl)phenyl, 2-(methoxymethyl)phenyl, 4-(methoxymethyl)phenyl, 3-(dimethylsulphamoyl)phenyl, 3-cyanophenyl, 3-(cyanomethyl)phenyl, 4-(cyanomethyl)phenyl, 4-(2-dimethylaminoethylcarbamoyl)phenyl, 4-(3-dimethylaminopropylcarbamoyl)phenyl, 4-cyanophenyl, 3-(pyrrolidin-1-ylmethyl)phenyl, 3-(2-pyrrolidin-1-ylethylcarbamoyl)phenyl, 4-(morpholinomethyl)phenyl, 3-morpholinophenyl, 3-(2-morpholinoethylcarbamoyl)phenyl, 4-(morpholine-4-carbonyl)phenyl, 5-morpholinosulphonylphenyl, 3-piperazin-1-ylphenyl, 4-(4-hydroxypiperidine-1-carbonyl)phenyl, 4-piperazin-1-ylphenyl, 4-(piperazin-1-yl)-2-(fluoro)phenyl, 3-(4-methylpiperazine-1-carbonyl)phenyl, 3-(4-methylpiperazin-1-yl)phenyl, 3-(piperidine-4-carbonylamino)phenyl, 3-(pyrazol-3-yl)phenyl, 4-(4-piperidyl)phenyl, 3-(1-piperidyl)phenyl, 3-(1-piperidylmethyl)phenyl, 3-(morpholinomethyl)phenyl, 3-pyrrolidin-1-ylphenyl, 4-(piperazin-1-yl)-2-(methoxy)phenyl, 6-(3-dimethylaminopropoxy)pyridin-3-yl, 1-(4-piperidyl)pyrazol-4-yl, 1-(4-piperidyl)-3-(methyl)pyrazol-4-yl, 1-(1-tert-butoxycarbonyl-4-piperidyl)pyrazol-4-yl, 1-(1-methyl-4-piperidyl)pyrazol-4-yl, 1-(1-ethyl-4-piperidyl)pyrazol-4-yl, 1-(1-isopropyl-4-piperidyl)pyrazol-4-yl, 1-(1-methyl-1-oxido-piperidin-1-ium-4-yl)pyrazol-4-yl, 6-piperazin-1-yl-3-pyridyl, 6-(4-methylpiperazin-1-yl)-3-pyridyl, 5-(hydroxymethyl)thien-2-yl, quinol-8-yl, quinol-3-yl, quinol-4-yl, 2,3-dihydro-1,4-benzodioxin-6-yl, 1H-indazol-5-yl, 1H-indol-5-yl, 1H-indol-6-yl, 1,3-benzodioxol-5-yl or 1-naphthyl;
n is 0, 1 or 2 and, when n is 2, each $R^3$ group may be the same or different, and
each $R^3$ group present is selected from hydrogen, fluoro, bromo, chloro, $OR^9$, trifluoromethyl, methyl or propyl, wherein $R^9$ is trifluoromethyl;
and when W is CH and J is S;
each of $G_1$, $G_2$, $G_3$ and $G_4$ are CH;
Ring A is 1-(1-tert-butoxycarbonyl-4-piperidyl)pyrazol-4-yl, 1-(4-piperidyl)pyrazol-4-yl or 1-(1-methyl-4-piperidyl)pyrazol-4-yl;
and n is 0;
and when W is N and J is O;
each of $G_1$, $G_2$, $G_3$ and $G_4$ are CH;
Ring A is 1-(1-tert-butoxycarbonyl-4-piperidyl)pyrazol-4-yl, 1-(4-piperidyl)pyrazol-4-yl, 1-(1-methyl-4-piperidyl)pyrazol-4-yl, 3-(dimethylsulphamoyl)phenyl, 3-piperazin-1-ylphenyl, 6-piperazin-1-yl-3-pyridyl, 3-(1-piperidyl)phenyl, 3-pyrrolidin-1-ylphenyl, 4-(morpholinomethyl)phenyl, 6-(4-methylpiperazin-1-yl)-3-pyridyl, 3-morpholinophenyl, 3-methylsulphonylphenyl, 3-(morpholinomethyl)phenyl, 4-piperazin-1-ylphenyl, 4-(dimethylsulphamoyl)phenyl, 3-ethylsulphonylphenyl, 3-(4-methylpiperazin-1-yl)phenyl, 3-dimethylaminophenyl, 3-(cyanomethyl)phenyl, 3-(methoxymethyl)phenyl, 3-methylsulphonyloxyphenyl or 4-(cyanomethyl)phenyl;
and n is 0;
and when W is N and J is S;
each of $G_1$, $G_2$, $G_3$ and $G_4$ are CH;
Ring A is 1-(1-tert-butoxycarbonyl-4-piperidyl)pyrazol-4-yl or 1-(4-piperidyl)pyrazol-4-yl; and n is 0; or a pharmaceutically-acceptable salt thereof.

A further particular group of compounds of the invention are pyridine derivatives of Formula I above wherein:—
W is CH;
J is O;
each of $G_1$, $G_2$, $G_3$ and $G_4$ is selected from CH and N provided that not more than one of $G_1$, $G_2$, $G_3$ and $G_4$ represent N;
Ring A is 4-(dimethylaminomethyl)phenyl, 3-(aminomethyl)phenyl, 4-(aminomethyl)phenyl, 4-(ethylsulphonyl)phenyl, 3-(ethylsulphonyl)phenyl, 3-(2-dimethylaminoethylcarbamoyl)phenyl, 4-(2-methoxyethoxy)phenyl, 3-(methoxymethyl)phenyl, 4-(hydroxymethyl)phenyl, 3-(methylcarbamoyl)phenyl, 3-acetamidophenyl, 4-methanesulphonamidophenyl, 4-(dimethylsulphamoyl)phenyl, 4-(cyclopropylsulphamoyl)phenyl, 3-(methylsulphamoyl)phenyl, 3-carbamoylphenyl, 3-(hydroxymethyl)phenyl, 2-(methoxymethyl)phenyl, 4-(methoxymethyl)phenyl, 3-(dimethylsulphamoyl)phenyl, 3-cyanophenyl, 4-(2-dimethylaminoethylcarbamoyl)phenyl, 4-cyanophenyl, 3-(pyrrolidin-1-ylmethyl)phenyl, 4-(morpholinomethyl)phenyl, 3-piperazin-1-ylphenyl, 4-(4-hydroxypiperidine-1-carbonyl)phenyl, 4-piperazin-1-ylphenyl, 4-(4-piperidyl)phenyl, 3-(morpholinomethyl)phenyl, 3-pyrrolidin-1-ylphenyl, 4-(piperazin-1-yl)-2-(methoxy)phenyl, 6-(3-dimethylaminopropoxy)pyridin-3-yl, 1-(4-piperidyl)pyrazol-4-yl, 1-(1-tert-butoxycarbonyl-4-piperidyl)pyrazol-4-yl, 1-(1-methyl-4-piperidyl)pyrazol-4-yl, 1-(1-ethyl-4-piperidyl)pyrazol-4-yl, 1-(1-isopropyl-4-piperidyl)pyrazol-4-yl, 1-(1-methyl-1-oxido-piperidin-1-ium-4-yl)pyrazol-4-yl, 6-piperazin-1-yl-3-pyridyl, quinol-8-yl, quinol-3-yl, quinol-4-yl, 2,3-dihydro-1,4-benzodioxin-6-yl, 1H-indazol-5-yl, 1H-indol-5-yl, 1H-indol-6-yl, 1,3-benzodioxol-5-yl or 1-naphthyl;
n is 0, 1 or 2 and, when n is 2, each $R^3$ group may be the same or different, and
each $R^3$ group present is selected from hydrogen, fluoro, bromo, chloro, $OR^9$, trifluoromethyl, methyl or propyl, wherein $R^9$ is trifluoromethyl; or a pharmaceutically-acceptable salt thereof.

A further particular group of compounds of the invention are pyridine derivatives of Formula I above wherein:—
W is CH;
J is O;
each of $G_1$, $G_2$, $G_3$ and $G_4$ is selected from CH and N provided that not more than one of $G_1$, $G_2$, $G_3$ and $G_4$ represent N;

Ring A is 4-(dimethylaminomethyl)phenyl, 3-(aminomethyl)phenyl, 4-(aminomethyl)phenyl, 4-(ethylsulphonyl)phenyl, 3-(methylsulphonyl)phenyl, 3-(ethylsulphonyl)phenyl, 3-(methylsulphonyloxy)phenyl, 3-(2-dimethylaminoethylcarbamoyl)phenyl, 3-(2-diethylaminoethylcarbamoyl)phenyl, 3-dimethylaminophenyl, 4-(2-methoxyethoxy)phenyl, 3-(methoxymethyl)phenyl, 4-(hydroxymethyl)phenyl, 4-(2-hydroxyethylcarbamoyl)phenyl, 3-(methylcarbamoyl)phenyl, 3-(cyclopropylcarbamoyl)phenyl, 3-acetamidophenyl, 4-methanesulphonamidophenyl, 4-(dimethylsulphamoyl)phenyl, 4-(cyclopropylsulphamoyl)phenyl, 3-(cyclopropylsulphamoyl)phenyl, 3-(methylsulphamoyl)phenyl, 4-(2-hydroxyethylsulphamoyl)phenyl, 3-carbamoylphenyl, 4-carbamoylphenyl, 3-(hydroxymethyl)phenyl, 2-(methoxymethyl)phenyl, 4-(methoxymethyl)phenyl, 3-(dimethylsulphamoyl)phenyl, 3-cyanophenyl, 3-(cyanomethyl)phenyl, 4-(cyanomethyl)phenyl, 4-(2-dimethylaminoethylcarbamoyl)phenyl, 4-(3-dimethylaminopropylcarbamoyl)phenyl, 4-cyanophenyl, 3-(pyrrolidin-1-ylmethyl)phenyl, 3-(2-pyrrolidin-1-ylethylcarbamoyl)phenyl, 4-(morpholinomethyl)phenyl, 3-morpholinophenyl, 3-(2-morpholinoethylcarbamoyl)phenyl, 4-(morpholine-4-carbonyl)phenyl, 5-morpholinosulphonylphenyl, 3-piperazin-1-ylphenyl, 4-(4-hydroxypiperidine-1-carbonyl)phenyl, 4-piperazin-1-ylphenyl, 4-(piperazin-1-yl)-2-(fluoro)phenyl, 3-(4-methylpiperazine-1-carbonyl)phenyl, 3-(4-methylpiperazin-1-yl)phenyl, 3-(piperidine-4-carbonylamino)phenyl, 3-(pyrazol-3-yl)phenyl, 4-(4-piperidyl)phenyl, 3-(1-piperidyl)phenyl, 3-(1-piperidylmethyl)phenyl, 3-(morpholinomethyl)phenyl, 3-pyrrolidin-1-ylphenyl, 4-(piperazin-1-yl)-2-(methoxy)phenyl, 6-(3-dimethylaminopropoxy)pyridin-3-yl, 1-(4-piperidyl)pyrazol-4-yl, 1-(4-piperidyl)-3-(methyl)pyrazol-4-yl, 1-(1-tert-butoxycarbonyl-4-piperidyl)pyrazol-4-yl, 1-(1-methyl-4-piperidyl)pyrazol-4-yl, 1-(1-ethyl-4-piperidyl)pyrazol-4-yl, 1-(1-isopropyl-4-piperidyl)pyrazol-4-yl, 1-(1-methyl-1-oxido-piperidin-1-ium-4-yl)pyrazol-4-yl, 6-piperazin-1-yl-3-pyridyl, 6-(4-methylpiperazin-1-yl)-3-pyridyl, 5-(hydroxymethyl)thien-2-yl, quinol-8-yl, quinol-3-yl, quinol-4-yl, 2,3-dihydro-1,4-benzodioxin-6-yl, 1H-indazol-5-yl, 1H-indol-5-yl, 1H-indol-6-yl, 1,3-benzodioxol-5-yl or 1-naphthyl;

n is 0, 1 or 2 and, when n is 2, each R³ group may be the same or different, and each R³ group present is selected from hydrogen, fluoro, bromo, chloro, OR⁹, trifluoromethyl, methyl or propyl, wherein R⁹ is trifluoromethyl; or a pharmaceutically-acceptable salt thereof.

A further particular group of compounds of the invention are pyridine derivatives of Formula I above wherein:—
W is CH;
J is S;
each of $G_1$, $G_2$, $G_3$ and $G_4$ are CH;
Ring A is 1-(1-tert-butoxycarbonyl-4-piperidyl)pyrazol-4-yl or 1-(4-piperidyl)pyrazol-4-yl;
n is 0; or a pharmaceutically-acceptable salt thereof.

A further particular group of compounds of the invention are pyridine derivatives of Formula I above wherein:—
W is CH;
J is S;
each of $G_1$, $G_2$, $G_3$ and $G_4$ are CH;
Ring A is 1-(1-tert-butoxycarbonyl-4-piperidyl)pyrazol-4-yl, 1-(4-piperidyl)pyrazol-4-yl or 1-(1-methyl-4-piperidyl)pyrazol-4-yl;
n is 0; or a pharmaceutically-acceptable salt thereof.

A further particular group of compounds of the invention are pyrazine derivatives of Formula I above wherein:—
W is N;
J is O;
each of $G_1$, $G_2$, $G_3$ and $G_4$ are CH;
Ring A is 1-(1-tert-butoxycarbonyl-4-piperidyl)pyrazol-4-yl;
n is 0; or a pharmaceutically-acceptable salt thereof.

A further particular group of compounds of the invention are pyrazine derivatives of Formula I above wherein:—
W is N;
J is O;
each of $G_1$, $G_2$, $G_3$ and $G_4$ are CH;
Ring A is 1-(1-tert-butoxycarbonyl-4-piperidyl)pyrazol-4-yl, 1-(4-piperidyl)pyrazol-4-yl, 1-(1-methyl-4-piperidyl)pyrazol-4-yl, 3-(dimethylsulphamoyl)phenyl, 3-piperazin-1-ylphenyl, 6-piperazin-1-yl-3-pyridyl, 3-(1-piperidyl)phenyl, 3-pyrrolidin-1-ylphenyl, 4-(morpholinomethyl)phenyl, 6-(4-methylpiperazin-1-yl)-3-pyridyl, 3-morpholinophenyl, 3-methylsulphonylphenyl, 3-(morpholinomethyl)phenyl, 4-piperazin-1-ylphenyl, 4-(dimethylsulphamoyl)phenyl, 3-ethylsulphonylphenyl, 3-(4-methylpiperazin-1-yl)phenyl, 3-dimethylaminophenyl, 3-(cyanomethyl)phenyl, 3-(methoxymethyl)phenyl, 3-methylsulphonyloxyphenyl or 4-(cyanomethyl)phenyl;
n is 0; or a pharmaceutically-acceptable salt thereof.

A further particular group of compounds of the invention are pyrazine derivatives of Formula I above wherein:—
W is N;
J is S;
each of $G_1$, $G_2$, $G_3$ and $G_4$ are CH;
Ring A is 1-(4-piperidyl)pyrazol-4-yl;
n is 0; or a pharmaceutically-acceptable salt thereof.

A yet further particular group of compounds of the invention are pyridine and pyrazine derivatives of Formula I above wherein:—
W is CH;
J is O;
each of $G_1$, $G_2$, $G_3$ and $G_4$ is selected from CH and N provided that not more than one of $G_1$, $G_2$, $G_3$ and $G_4$ represent N;
Ring A is a phenyl, pyrazol-4-yl, pyridin-3-yl, thien-2-yl, thiazol-5-yl, 1H-1,2,3-triazol-4-yl or 3H-1,2,3-triazol-5-yl ring, wherein said ring is substituted by hydroxymethyl, 2-hydroxyethyl, 3-hydroxypropyl, methoxymethyl, cyanomethyl, acetyl, 2-methoxyacetyl, hydroxyacetyl, 2-hydroxypropionyl, 2-aminoethoxy, 2-methylaminoethoxy, 3-aminopropoxy, 3-methylaminopropoxy, 4-methylaminobutoxy, 2-methoxyethoxy, ethylsulphonyl, methylsulphonyl, methylsulphonyloxy, methylsulphamoyl, cyclopropylsulphamoyl, dimethylsulphamoyl, 2-hydroxyethylsulphamoyl, cyclopropylsulphamoyl, methanesulphonamido, acetamido, carbamoyl, methylcarbamoyl, cyclopropylcarbamoyl, 2-hydroxyethylcarbamoyl, dimethylamino, 2-dimethylaminoethylcarbamoyl, 3-dimethylaminopropylcarbamoyl, 2-diethylaminoethylcarbamoyl, 3-diethylaminopropylcarbamoyl, cyano, cyanomethyl, aminomethyl, dimethylaminomethyl, 2-(dimethylamino)ethoxy, 2-(diethylamino)ethoxy, 3-(dimethylamino)propoxy, 3-(diethylamino)propoxy, pyrrolidin-1-yl, pyrrolidin-3-yl, pyrrolidin-2-yl, piperazin-1-yl, piperidin-4-yl, piperidin-3-yl, pyrazol-3-yl, tetrahydropyran-2-yl, tetrahydropyran-4-yl, azetidinyl, 1,1-dioxotetrahydro-1,4-thiazinyl, imidazolinyl, azepanyl, 1H-imidazolyl, 1,4-diazepanyl, (1R,5S)-8-azabicyclo[3.2.1]octanyl, quinuclidinyl, (3R)-quinuclidinyl, 3,4,4a,5,6,7,8,8a-octahydro-2H-quinolinyl, 3,4,6,7,8,8a-hexahydro-1H-pyrrolo[2,1-c]pyrazinyl, pyrrolidin-1-ylmethyl, piperidin-4-ylmethyl, 1-methylpyrrolidin-3-yl, 1-methylpyrrolidin-3-ylmethyl, 1-methylpyrrolidin-3-ylmethoxy, 1-methylpyrrolidin-3-yloxy, 2-(1-methylpyrrolidin-3-yl)ethoxy, 2-pyrrolidin-1-ylethyl, 3-pyrrolidin-1-ylpropyl, 2-(1-methylpyrrolidin-2-yl)ethoxy, 2-(1-methylpyrrolidin-2-yl)ethylcarbamoyl, piperidin-3-ylmethyl, 1-methyl-piperidin-3-yl, 1-methyl-piperidin-3-ylmethoxy, 1-methyl-piperidin-3-yloxy, piperidin-3-ylmethoxy, 2-(1-methyl-piperidin-3-yl)ethoxy, 3-(1-methyl-piperidin-3-yl)propoxy, piperidin-4-yloxy, 1-methyl-piperidin-4-ylmethoxy, azetidin-3-ylmethyl, 2-azetidinylethyl, 3-azetidinylpropyl, 1-methyl-azetidin-3-yl, 1-methyl-azetidin-3-ylmethyl, 2-(3-hydroxy-pyrrolidin-1-yl)ethyl, 3-(3-hydroxy-pyrrolidin-1-yl)propyl, 3-(3-hydroxymethyl-pyrrolidin-1-yl)propyl, 2-(4-hydroxypiperidin-1-yl)ethyl, 3-(4-hydroxypiperidin-1-yl)propyl, 1-acetylpiperidin-4-yl, 1-methoxyacetylpiperidin-4-yl, 1-hydroxyacetylpiperidin-4-yl, 1-hydroxyacetylpiperidin-4-yl, 1-(2-hydroxypropionyl)piperidin-4-yl, 5-(methylcarbamoyl)-1-methyl-pyrrolidin-3-yl, 3-pyrrolidin-1-ylpropoxy, 2-pyrrolidin-1-ylethoxy, 2-(1-methylpiperidin-2-yl)ethoxy, 3-(1,1-dioxotetrahydro-1,4-thiazin-4-yl)propoxy, 2-(piperazin-1-yl)ethyl, 2-(1-methyl-piperazin-4-yl)ethoxy, 3-(1-methyl-piperazin-4-yl)propoxy, 2-(1-methyl-piperazin-4-yl)ethyl, 3-(1-methyl-piperazin-4-yl)propyl, 3-(1-sulphonyl-piperazin-4-yl)propoxy, 3-(1-methylsulphonylpiperazin-4-yl)-propoxy, 3-(1,1-dioxotetrahydro-1,4-thiazin-4-yl)propoxy, (1R,5S)-8-azabicyclo[3.2.1]octan-3-yloxy, [(2E)-4-(1,1-dioxidothiomorpholin-4-yl)but-2-en-1-yl]oxidanyl, (3R)-quinuclidin-8-ylcarbamoyl, morpholino, morpholinomethyl, 2-morpholinoethyl, 3-morpholinopropyl, 2-morpholinoethoxy, 3-morpholinopropoxy, 2-(2-morpholinoethoxy)ethoxy, 2-piperazin-4-ylethoxy, 2-(piperidin-4-yloxy)ethoxy, 2-(azetidin-3-yloxy)ethoxy, 3-(2,6-dimethylpiperazin-4-yl)propoxy, 1-methylpyrrolidin-3-yl-N-methylcarbamoyl, quinuclidinylcarbonyl, 2-imidazolin-1-ylethylcarbamoyl, 2-(piperidin-1-ylmethyl)piperidin-1-ylcarbonyl, 1-ethoxypiperidin-4-ylcarbamoyl, 2-pyrrolidin-1-ylcyclohex-1-yl-N-methylcarbamoyl, 2-(3-fluoropyrrolidin-1-yl)ethylcarbamoyl, 4-(2-dimethylaminoethyl)piperidin-1-ylcarbonyl, 2-(1-methylpiperidin-2-yl)-pyrrolidin-1-ylcarbonyl, 5-(morpholinylmethyl)pyrrolidin-1-ylcarbonyl, 5-(azepan-1-yl)pyrrolidin-1-ylcarbonyl, 2-(3,3-difluoropyrrolidin-1-yl)ethylcarbamyl, 2-(3-fluoropyrrolidin-1-yl)ethylcarbamyl, 3,4,4a,5,6,7,8,8a-octahydro-2H-quinolin-4-ylcarbamoyl, 1-dimethylaminocyclohex-1-ylmethylcarbamoyl, 2-morpholinoethylcarbamoyl, 2-1H-imidazolylethylcarbamoyl, 1-(pyridin-3-yl)piperazin-4-ylcarbonyl, 1-(pyridin-4-yl)piperazin-4-ylcarbonyl, 1,4-diazepanylcarbonyl, 1-(N-dimethylcarbamoylmethyl)piperazin-4-ylcarbonyl, 1-(carbamoylethyl)piperazin-4-ylcarbonyl, 4,6,7,8,8a-hexahydro-1H-pyrrolo[2,1-c]pyrazin-1-ylcarbonyl, morpholine-4-carbonyl, morpholinosulphonyl, 4-hydroxypiperidine-1-carbonyl, 2-pyrrolidin-1-ylethylcarbamoyl, piperidin-1-yl, piperidin-4-yl, 1-methyl-4-piperidyl, 1-methylpiperidin-4-ylmethyl, 1-(2-methoxyethyl)piperidin-4-ylcarbamoyl, 1-ethyl-4-piperidyl, 1-isopropyl-4-piperidyl, 1-piperidylmethyl, piperidine-4-carbonylamino, 4-methylpiperazine-1-carbonyl, 4-methylpiperazin-1-yl, 3-dimethylaminopropoxy, 1-tert-butoxycarbonyl-4-piperidyl or 1-methyl-1-oxido-piperidin-1-ium-4-yl, and optionally substituted with methyl, methoxy, ethoxy, fluoro or hydroxymethyl;

or Ring A is a quinolyl, 2,3-dihydro-1,4-benzodioxin-6-yl, 1H-indazol-5-yl, 1H-indol-5-yl, 1H-indol-6-yl, 1,3-benzodioxol-5-yl or naphthyl, optionally substituted by hydroxymethyl, 2-hydroxyethyl, 3-hydroxypropyl, methoxymethyl, cyanomethyl, acetyl, 2-methoxyacetyl, hydroxyacetyl, 2-hydroxypropionyl, 2-aminoethoxy, 2-methylaminoethoxy, 3-aminopropoxy, 3-methylaminopropoxy, 4-methylaminobutoxy, 2-methoxyethoxy, ethylsulphonyl, methylsulphonyl, methylsulphonyloxy, methylsulphamoyl, cyclopropylsulphamoyl, dimethylsulphamoyl, 2-hydroxyethylsulphamoyl, cyclopropylsulphamoyl, methanesulphonamido, acetamido, carbamoyl, methylcarbamoyl, cyclopropylcarbamoyl, 2-hydroxyethylcarbamoyl, dimethylamino, 2-dimethylaminoethylcarbamoyl, 3-dimethylaminopropylcarbamoyl, 2-diethylaminoethylcarbamoyl, 3-diethylaminopropylcarbamoyl, cyano, cyanomethyl, aminomethyl, dimethylaminomethyl, 2-(dimethylamino)ethoxy, 2-(diethylamino)ethoxy, 3-(dimethylamino)propoxy, 3-(diethylamino)propoxy, pyrrolidin-1-yl, pyrrolidin-3-yl, pyrrolidin-2-yl, piperazin-1-yl, piperidin-4-yl, piperidin-3-yl, pyrazol-3-yl, tetrahydropyran-2-yl, tetrahydropyran-4-yl, azetidinyl, 1,1-dioxotetrahydro-1,4-thiazinyl, imidazolinyl, azepanyl, 1H-imidazolyl, 1,4-diazepanyl, (1R,5S)-8-azabicyclo[3.2.1]octanyl, quinuclidinyl, (3R)-quinuclidinyl, 3,4,4a,5,6,7,8,8a-octahydro-2H-quinolinyl, 3,4,6,7,8,8a-hexahydro-1H-pyrrolo[2,1-c]pyrazinyl, pyrrolidin-1-ylmethyl, piperidin-4-ylmethyl, 1-methylpyrrolidin-3-yl, 1-methylpyrrolidin-3-ylmethyl, 1-methylpyrrolidin-3-ylmethoxy, 1-methylpyrrolidin-3-yloxy, 2-(1-methylpyrrolidin-3-yl)ethoxy, 2-pyrrolidin-1-ylethyl, 3-pyrrolidin-1-ylpropyl, 2-(1-methylpyrrolidin-2-yl)ethoxy, 2-(1-methylpyrrolidin-2-yl)ethylcarbamoyl, piperidin-3-ylmethyl, 1-methyl-piperidin-3-yl, 1-methyl-piperidin-3-ylmethoxy, 1-methyl-piperidin-3-yloxy, piperidin-3-ylmethoxy, 2-(1-methyl-piperidin-3-yl)ethoxy, 3-(1-methyl-piperidin-3-yl)propoxy, piperidin-4-yloxy, 1-methyl-piperidin-4-ylmethoxy, azetidin-3-ylmethyl, 2-azetidinylethyl, 3-azetidinylpropyl, 1-methyl-azetidin-3-yl, 1-methyl-azetidin-3-ylmethyl, 2-(3-hydroxy-pyrrolidin-1-yl)ethyl, 3-(3-hydroxy-pyrrolidin-1-yl)propyl, 3-(3-hydroxymethyl-pyrrolidin-1-yl)propyl, 2-(4-hydroxypiperidin-1-yl)ethyl, 3-(4-hydroxypiperidin-1-yl)propyl, 1-acetylpiperidin-4-yl, 1-methoxyacetylpiperidin-4-yl, 1-hydroxyacetylpiperidin-4-yl, 1-hydroxyacetylpiperidin-4-yl, 1-(2-hydroxypropionyl)piperidin-4-yl, 5-(methylcarbamoyl)-1-methyl-pyrrolidin-3-yl, 3-pyrrolidin-1-ylpropoxy, 2-pyrrolidin-1-ylethoxy, 2-(1-methylpiperidin-2-yl)ethoxy, 3-(1,1-dioxotetrahydro-1,4-thiazin-4-yl)propoxy, 2-(piperazin-1-yl)ethyl, 2-(1-methyl-piperazin-4-yl)ethoxy, 3-(1-methyl-piperazin-4-yl)propoxy, 2-(1-methyl-piperazin-4-yl)ethyl, 3-(1-methyl-piperazin-4-yl)propyl, 3-(1-sulphonyl-piperazin-4-yl)propoxy, 3-(1-methylsulphonylpiperazin-4-yl)-propoxy, 3-(1,1-dioxotetrahydro-1,4-thiazin-4-yl)propoxy, (1R,5S)-8-azabicyclo[3.2.1]octan-3-yloxy, [(2E)-4-(1,1-dioxidothiomorpholin-4-yl)but-2-en-1-yl]oxidanyl, (3R)-quinuclidin-8-ylcarbamoyl, morpholino, morpholinomethyl, 2-morpholinoethyl, 3-morpholinopropyl, 2-morpholinoethoxy, 3-morpholinopropoxy, 2-(2-morpholinoethoxy)ethoxy, 2-piperazin-4-ylethoxy, 2-(piperidin-4-yloxy)ethoxy, 2-(azetidin-3-yloxy)ethoxy, 3-(2,6-dimethylpiperazin-4-yl)propoxy, 1-methylpyrrolidin-3-yl-N-methylcarbamoyl, quinuclidinylcarbonyl, 2-imidazolin-1-ylethylcarbamoyl, 2-(piperidin-1-ylmethyl)piperidin-1-ylcarbonyl, 1-ethoxypiperidin-4-ylcarbamoyl, 2-pyrrolidin-1-ylcyclohex-1-yl-N-methylcarbamoyl, 2-(3-fluoropyrrolidin-1-yl)ethylcarbamoyl, 4-(2-dimethylaminoethyl)piperidin-1-ylcarbonyl, 2-(1-methylpiperidin-2-yl)-pyrrolidin-1-ylcarbonyl, 5-(morpholinylmethyl)pyrrolidin-1-ylcarbonyl, 5-(azepan-1-yl)pyrrolidin-1-ylcarbonyl, 2-(3,3-difluoropyrrolidin-1-yl)ethylcarbamyl, 2-(3-fluoropyrrolidin-1-yl)ethylcarbamyl, 3,4,4a,5,6,7,8,8a-octahydro-2H-quinolin-4-ylcarbamoyl, 1-dimethylaminocyclohex-1-ylmethylcarbamoyl, 2-morpholinoethylcarbamoyl, 2-1H-imidazolylethylcarbamoyl, 1-(pyridin-3-yl)piperazin-4-ylcarbonyl, 1-(pyridin-4-yl)piperazin-4-ylcarbonyl, 1,4-diazepanylcarbonyl, 1-(N-dimethylcarbamoylmethyl)piperazin-4-ylcarbonyl, 1-(carbamoylethyl)piperazin-4-ylcarbonyl, 4,6,7,8,8a-hexahydro-1H-pyrrolo[2,1-c]pyrazin-1-ylcarbonyl, morpholine-4-carbonyl, morpholinosulphonyl, 4-hydroxypiperidine-1-carbonyl, 2-pyrrolidin-1-ylethylcarbamoyl, piperidin-1-yl, piperidin-4-yl, 1-methyl-4-piperidyl, 1-methylpiperidin-4-ylmethyl, 1-(2-methoxyethyl)piperidin-4-ylcarbamoyl, 1-ethyl-4-piperidyl, 1-isopropyl-4-piperidyl, 1-piperidylmethyl, piperidine-4-carbonylamino, 4-methylpiperazine-1-carbonyl, 4-methylpiperazin-1-yl, 3-dimethylaminopropoxy, 1-tert-butoxycarbonyl-4-piperidyl or 1-methyl-1-oxido-piperidin-1-ium-4-yl, and optionally substituted with methyl, methoxy, ethoxy, fluoro or hydroxymethyl;

n is 0, 1 or 2 and, when n is 2, each $R^3$ group may be the same or different, and each $R^3$ group present is selected from hydrogen, fluoro, bromo, chloro, $OR^9$, trifluoromethyl, methyl or propyl, wherein $R^9$ is methyl or trifluoromethyl; or a pharmaceutically-acceptable salt thereof.

A yet further particular group of compounds of the invention are pyridine derivatives of Formula I above wherein:—
W is CH;
J is O;
each of $G_1$, $G_2$, $G_3$ and $G_4$ is selected from CH and N provided that not more than one of $G_1$, $G_2$, $G_3$ and $G_4$ represent N;
Ring A is a phenyl, pyrazol-4-yl, pyridin-3-yl, thien-2-yl, thiazol-5-yl, 1H-1,2,3-triazol-4-yl or 3H-1,2,3-triazol-5-yl ring, wherein said ring is substituted by hydroxymethyl, 2-hydroxyethyl, 3-hydroxypropyl, methoxymethyl, cyanomethyl, acetyl, 2-methoxyacetyl, 3-methoxypropionyl, 3-methoxy-2-methyl-propionyl, hydroxyacetyl, 2-hydroxypropionyl, 2-aminoethyl, 2-methylaminoethyl, 3-methylaminopropylcarbamoyl, 2-methylaminoethylcarbamoyl, 2-dimethylaminoethyl-N-methylcarbamoyl, 2-aminoethoxy, 2-methylaminoethoxy, 3-aminopropoxy, 3-methylaminopropoxy, 4-methylaminobutoxy, 2-methoxyethoxy, ethylsulphonyl, methylsulphonyl, methylsulphonyloxy, methylsulphamoyl, cyclopropylsulphamoyl, dimethylsulphamoyl, 2-hydroxyethylsulphamoyl, cyclopropylsulphamoyl, methanesulphonamido, acetamido, carbamoyl, methylcarbamoyl, cyclopropylcarbamoyl, 2-hydroxyethylcarbamoyl, dimethylamino, 2-dimethylaminoethylcarbamoyl, 3-dimethylaminopropylcarbamoyl, 2-diethylaminoethylcarbamoyl, 3-diethylaminopropylcarbamoyl, cyano, cyanomethyl, aminomethyl, dimethylaminomethyl, 2-(dimethylamino)ethoxy, 2-(diethylamino)ethoxy, 3-(dimethylamino)propoxy, 3-(diethylamino)propoxy, pyrrolidin-1-yl, pyrrolidin-3-yl, pyrrolidin-2-yl, piperazin-1-yl, piperidin-4-yl, piperidin-3-yl, pyrazol-3-yl, tetrahydropyran-2-yl, tetrahydropyran-4-yl, azetidinyl, 1,1-dioxotetrahydro-1,4-thiazinyl, imidazolinyl, azepanyl, 4-aminoazepan-1-ylcarbonyl, azepan-4-yloxy, 4-(4-piperidyl)piperidin-1-ylcarbonyl, 1H-imidazolyl, 1,4-diazepanyl, (1R,5S)-8-azabicyclo[3.2.1]octanyl, quinuclidinyl, (3R)-quinuclidinyl, 3,4,4a,5,6,7,8,8a-octahydro-2H-quinolinyl, 3,4,6,7,8,8a-hexahydro-1H-pyrrolo[2,1-c]pyrazinyl, 3,8-diazaspiro[5.5]undecan-3-ylcarbonyl, 2,8-diazaspiro[4.5]decan-8-ylcarbonyl, 3,9-diazaspiro[5.5]undecan-3-ylcarbonyl, (1S,4S)-3,6-diazabicyclo[2.2.1]heptan-6-ylcarbonyl, 3-aminoazetidin-1-ylcarbonyl, pyrrolidin-1-ylmethyl, (3S)-3-aminopiperidin-1-ylcarbonyl, (2S)-pyrrolidin-2-yl]methylcarbamoyl, 4,9-diazaspiro[5.5]undecan-4-ylcarbonyl, 2,3,3a,4,6,6a-hexahydro-1H-pyrrolo[3,4-c]pyrrol-5-ylcarbonyl, (3R)-3-(2-aminoethyl)-1-piperidylcarbonyl, piperidin-4-ylmethyl, 1-methylpyrrolidin-3-yl, 1-methylpyrrolidin-3-ylmethyl, 1-methylpyrrolidin-3-ylmethoxy, pyrrolidin-3-yloxy, pyrrolidin-2-yloxy, 1-methylpyrrolidin-3-yloxy, 2-(1-methylpyrrolidin-3-yl)ethoxy, 2-pyrrolidin-1-ylethyl, 3-pyrrolidin-1-ylpropyl, 2-(1-methylpyrrolidin-2-yl)ethoxy, 2-(1-methylpyrrolidin-2-yl)ethylcarbamoyl, piperidin-3-ylmethyl, 1-methyl-piperidin-3-yl, 1-methyl-piperidin-3-ylmethoxy, 1-methyl-piperidin-3-yloxy, piperidin-3-ylmethoxy, 2-(1-methyl-piperidin-3-yl)ethoxy, 3-(1-methyl-piperidin-3-yl)propoxy, piperidin-3-ylcarbamoyl, (3R)-piperidin-3-ylmethylcarbamoyl, piperidin-4-yloxy, 1-methyl-piperidin-4-ylmethoxy, azetidin-3-ylmethyl, 2-azetidinylethyl, 3-azetidinylpropyl, 1-methyl-azetidin-3-yl, 1-methyl-azetidin-3-ylmethyl, 2-(3-hydroxy-pyrrolidin-1-yl)ethyl, 3-(3-hydroxy-pyrrolidin-1-yl)propyl, 3-(3-hydroxymethyl-pyrrolidin-1-yl)propyl, 3-(2-hydroxymethyl-pyrrolidin-1-yl)propyl, 2-(2-hydroxymethyl-pyrrolidin-1-yl)ethyl, 2-(4-hydroxypiperidin-1-yl)ethyl, 3-(4-hydroxypiperidin-1-yl)propyl, 1-acetylpiperidin-4-yl, 1-methoxyacetylpiperidin-4-yl, 1-hydroxyacetylpiperidin-4-yl, 1-hydroxyacetylpiperidin-4-yl, 1-(2-hydroxypropionyl)piperidin-4-yl, 5-(methylcarbamoyl)-1-methyl-pyrrolidin-3-yl, 3-pyrrolidin-1-ylpropoxy, 2-pyrrolidin-1-ylethoxy, 2-(1-methylpiperidin-2-yl)ethoxy, 3-(1,1-dioxotetrahydro-1,4-thiazin-4-yl)propoxy, 2-(piperazin-1-yl)ethyl, 2-(1-methyl-piperazin-4-yl)ethoxy, 3-(1-methyl-piperazin-4-yl)propoxy, 2-(1-methyl-piperazin-4-yl)ethyl, 3-(1-methyl-piperazin-4-yl)propyl, (1-methyl-piperazin-4-yl)carbonyl, 3-(1-sulphonyl-piperazin-4-yl)propoxy, 3-(1-methylsulphonylpiperazin-4-yl)-propoxy, 1-(methylsulphonyl)piperidin-4-yl, 1-(cyclopropylsulphonyl)piperidin-4-yl, 1-(methoxycarbonyl)piperidin-4-yl, 1-(methoxymethylcarbonyl)piperidin-4-yl, 3-(1,1-dioxotetrahydro-1,4-thiazin-4-yl)propoxy, (1R,5S)-8-azabicyclo[3.2.1]octan-3-yloxy, [(2E)-4-(1,1-dioxidothiomorpholin-4-yl)but-2-en-1-yl]oxidanyl, (3R)-quinuclidin-8-ylcarbamoyl, morpholino, morpholinomethyl, 2-morpholinoethyl, 3-morpholinopropyl, 2-morpholinoethoxy, 3-morpholinopropoxy, 2-(2-morpholinoethoxy)ethoxy, 3-[(3R,5S)-3,5-dimethylpiperazin-1-yl]propoxy, (3S,5S)-5-(methoxymethyl)pyrrolidin-3-yloxy, (3S,4R)-3-methylaminotetrahydropyran-4-yloxy, 4-(2-pyridylmethyl)piperazin-1-ylcarbonyl, 2-piperazin-4-ylethoxy, 2-(piperidin-4-yloxy)ethoxy, 2-(azetidin-3-yloxy)ethoxy, 3-(2,6-dimethylpiperazin-4-yl)propoxy, 1-methylpyrrolidin-3-yl-N-methylcarbamoyl, quinuclidinylcarbonyl, 2-imidazolin-1-ylethylcarbamoyl, 2-(piperazin-1-ylmethyl)piperidin-1-ylcarbonyl, 1-ethoxypiperidin-4-ylcarbamoyl, 2-pyrrolidin-1-ylcyclohex-1-yl-N-methylcarbamoyl, 2-(3-fluoropyrrolidin-1-yl)ethylcarbamoyl, 4-(2-dimethylaminoethyl)piperidin-1-ylcarbonyl, 2-(1-methylpiperidin-2-yl)-pyrrolidin-1-ylcarbonyl, 5-(morpholinylmethyl)pyrrolidin-1-ylcarbonyl, 5-(azepan-1-yl)pyrrolidin-1-ylcarbonyl, 2-(3,3-difluoropyrrolidin-1-yl)ethylcarbamyl, 2-(3-fluoropyrrolidin-1-yl)ethylcarbamyl, 3,4,4a,5,6,7,8,8a-octahydro-2H-quinolin-4-ylcarbamoyl, 1-dimethylaminocyclohex-1-ylmethylcarbamoyl, 2-morpholinoethylcarbamoyl, 2-1H-imidazolylethylcarbamoyl, 1-(pyridin-3-yl)piperazin-4-ylcarbonyl, 1-(pyridin-4-yl)piperazin-4-ylcarbonyl, 1,4-diazepanylcarbonyl, 1-(N-dimethylcarbamoylmethyl)piperazin-4-ylcarbonyl, 1-(carbamoylethyl)piperazin-4-ylcarbonyl, 3,4,6,7,8,8a-hexahydro-1H-pyrrolo[2,1-c]pyrazin-1-ylcarbonyl, morpholine-4-carbonyl, morpholinosulphonyl, 4-hydroxypiperidine-1-carbonyl, 2-pyrrolidin-1-ylethylcarbamoyl, piperidin-1-yl, 4-(aminomethyl)piperidin-1-ylcarbonyl, 3-aminopyrrolidin-1-ylcarbonyl, 3-methylaminopyrrolidin-1-ylcarbonyl, piperidin-4-yl-N-methylcarbamoyl, 4-methylaminopiperidin-1-ylcarbonyl, 4-(piperazin-1-ylmethyl)piperidin-1-ylcarbonyl, 4-methylaminocyclohexylcarbonyl, pyrrolidin-3-ylcarbamoyl, 4-pyrrolidin-1-ylpiperidin-1-ylcarbonyl, (dimethylcarbamoylmethyl)piperazin-4-ylcarbonyl, 5-(N-methylcarbamoyl)pyrrolidin-3-yl, 1-(N,N-dimethylcarbamoylmethyl)

piperidin-4-yl, 1-(methylcarbamoylmethyl)piperidin-4-yl, 1-(carbamoylmethyl)piperidin-4-yl, 1-isopropylpiperidin-4-yl, 1-(2-hydroxyethyl)piperidin-4-yl, 1-(N,N-dimethylaminomethylcarbonyl)piperidin-4-yl, 1-methyl-4-piperidyl, 1-methylpiperidin-4-ylmethyl, 1-(2-methoxyethyl)piperidin-4-ylcarbamoyl, 1-ethyl-4-piperidyl, 1-isopropyl-4-piperidyl, 1-piperidylmethyl, piperidine-4-carbonylamino, 4-methylpiperazine-1-carbonyl, 4-methylpiperazin-1-yl, 1-(4-methylpiperazin-1-ylcarbonyl)piperidin-4-yl, 3-dimethylaminopropoxy, 1-tert-butoxycarbonyl-4-piperidyl or 1-methyl-1-oxido-piperidin-1-ium-4-yl, and optionally substituted with one or more methyl, methoxy, ethoxy, fluoro, hydroxymethyl, methoxymethyl, ethoxymethyl, cyano, 1-hydroxyethyl, dimethylcarbamoyl, dimethylamino, methylcarbamoyl, methylaminomethyl or carbamoyl groups; or Ring A is a quinolyl, 2,3-dihydro-1,4-benzodioxin-6-yl, 1H-indazol-5-yl, 1H-indol-5-yl, 1H-indol-6-yl, 1,3-benzodioxol-5-yl or naphthyl, optionally substituted by any of the substituents listed for substitution on the phenyl, pyrazol-4-yl, pyridin-3-yl, thien-2-yl, thiazol-5-yl, 1H-1,2,3-triazol-4-yl or 3H-1,2,3-triazol-5-yl rings above;

n is 0, 1 or 2 and the $(R^3)_n$ groups are selected from any one of the following 4-fluoro, 5-fluoro, 6-fluoro, 6-bromo, 6-propan-2-yl, 5-bromo, 4,6-difluoro, 6-chloro, 5-methyl, 6-methyl, 6-trifluoromethoxy, 5-trifluoromethyl, 6-methoxy, 7-methyl, 6,7-difluoro, 7-fluoro, 5-methoxy, 7-methoxy, 4-methoxy, 4-cyano, 7-cyano, 7-hydroxymethyl or 7-methylcarbamoyl; or a pharmaceutically-acceptable salt thereof.

A yet further particular group of compounds of the invention are pyridine derivatives of Formula I above wherein:—

W is CH;

J is O;

each of $G_1$, $G_2$, $G_3$ and $G_4$ is selected from CH and N provided that not more than one of $G_1$, $G_2$, $G_3$ and $G_4$ represent N;

Ring A is a phenyl, pyrazol-4-yl, pyridin-3-yl, thien-2-yl, thiazol-5-yl, 1H-1,2,3-triazol-4-yl or 3H-1,2,3-triazol-5-yl ring, wherein said ring is substituted by hydroxymethyl, 2-hydroxyethyl, 3-hydroxypropyl, methoxymethyl, cyanomethyl, acetyl, 2-methoxyacetyl, 3-methoxypropionyl, 3-methoxy-2-methyl-propionyl, hydroxyacetyl, 2-hydroxypropionyl, 2-aminoethyl, 2-methylaminoethyl, 3-methylaminopropylcarbamoyl, 2-methylaminoethylcarbamoyl, 2-dimethylaminoethyl-N-methylcarbamoyl, 2-aminoethoxy, 2-methylaminoethoxy, 3-aminopropoxy, 3-methylaminopropoxy, 4-methylaminobutoxy, 2-methoxyethoxy, ethylsulphonyl, methylsulphonyl, methylsulphonyloxy, methylsulphamoyl, cyclopropylsulphamoyl, dimethylsulphamoyl, 2-hydroxyethylsulphamoyl, cyclopropylsulphamoyl, methanesulphonamido, acetamido, carbamoyl, methylcarbamoyl, cyclopropylcarbamoyl, 2-hydroxyethylcarbamoyl, dimethylamino, 2-dimethylaminoethylcarbamoyl, 3-dimethylaminopropylcarbamoyl, 2-diethylaminoethylcarbamoyl, 3-diethylaminopropylcarbamoyl, cyano, cyanomethyl, aminomethyl, dimethylaminomethyl, 2-(dimethylamino)ethoxy, 2-(diethylamino)ethoxy, 3-(dimethylamino)propoxy, 3-(diethylamino)propoxy, pyrrolidin-1-yl, pyrrolidin-3-yl, pyrrolidin-2-yl, piperazin-1-yl, piperidin-4-yl, piperidin-3-yl, pyrazol-3-yl, tetrahydropyran-2-yl, tetrahydropyran-4-yl, azetidinyl, 1,1-dioxotetrahydro-1,4-thiazinyl, imidazolinyl, azepanyl, 4-aminoazepan-1-ylcarbonyl, azepan-4-yloxy, 4-(4-piperidyl)piperidin-1-ylcarbonyl, 1H-imidazolyl, 1,4-diazepanyl, (1R,5S)-8-azabicyclo[3.2.1]octanyl, quinuclidinyl, (3R)-quinuclidinyl, 3,4,4a,5,6,7,8,8a-octahydro-2H-quinolinyl, 3,4,6,7,8,8a-hexahydro-1H-pyrrolo[2,1-c]pyrazinyl, 3,8-diazaspiro[5.5]undecan-3-ylcarbonyl, 2,8-diazaspiro[4.5]decan-8-ylcarbonyl, 3,9-diazaspiro[5.5]undecan-3-yl carbonyl, (1S,4S)-3,6-diazabicyclo[2.2.1]heptan-6-ylcarbonyl, 3-aminoazetidin-1-ylcarbonyl, pyrrolidin-1-ylmethyl, (3S)-3-aminopiperidin-1-ylcarbonyl, (2S)-pyrrolidin-2-yl]methylcarbonyl, 4,9-diazaspiro[5.5]undecan-4-ylcarbonyl, 2,3,3a,4,6,6a-hexahydro-1H-pyrrolo[3,4-c]pyrrol-5-ylcarbonyl, (3R)-3-(2-aminoethyl)-1-piperidylcarbonyl, piperidin-4-ylmethyl, 1-methylpyrrolidin-3-yl, 1-methylpyrrolidin-3-ylmethyl, 1-methylpyrrolidin-3-ylmethoxy, pyrrolidin-3-yloxy, pyrrolidin-2-yloxy, 1-methylpyrrolidin-3-yloxy, 2-(1-methylpyrrolidin-3-yl)ethoxy, 2-pyrrolidin-1-ylethyl, 3-pyrrolidin-1-ylpropyl, 2-(1-methylpyrrolidin-2-yl)ethoxy, 2-(1-methylpyrrolidin-2-yl)ethylcarbamoyl, piperidin-3-ylmethyl, 1-methyl-piperidin-3-yl, 1-methyl-piperidin-3-ylmethoxy, 1-methyl-piperidin-3-yloxy, piperidin-3-ylmethoxy, 2-(1-methyl-piperidin-3-yl)ethoxy, 3-(1-methyl-piperidin-3-yl)propoxy, piperidin-3-ylcarbamoyl, (3R)-piperidin-3-ylmethylcarbamoyl, piperidin-4-yloxy, 1-methyl-piperidin-4-ylmethoxy, azetidin-3-ylmethyl, 2-azetidinylethyl, 3-azetidinylpropyl, 1-methyl-azetidin-3-yl, 1-methyl-azetidin-3-ylmethyl, 2-(3-hydroxy-pyrrolidin-1-yl)ethyl, 3-(3-hydroxy-pyrrolidin-1-yl)propyl, 3-(3-hydroxymethyl-pyrrolidin-1-yl)propyl, 3-(2-hydroxymethyl-pyrrolidin-1-yl)propyl, 2-(2-hydroxymethyl-pyrrolidin-1-yl)ethyl, 2-(4-hydroxypiperidin-1-yl)ethyl, 3-(4-hydroxypiperidin-1-yl)propyl, 1-acetylpiperidin-4-yl, 1-methoxyacetylpiperidin-4-yl, 1-hydroxyacetylpiperidin-4-yl, 1-hydroxyacetylpiperidin-4-yl, 1-(2-hydroxypropionyl)piperidin-4-yl, 5-(methylcarbamoyl)-1-methyl-pyrrolidin-3-yl, 3-pyrrolidin-1-ylpropoxy, 2-pyrrolidin-1-ylethoxy, 2-(1-methylpiperidin-2-yl)ethoxy, 3-(1,1-dioxotetrahydro-1,4-thiazin-4-yl)propoxy, 2-(piperazin-1-yl)ethyl, 2-(1-methyl-piperazin-4-yl)ethoxy, 3-(1-methyl-piperazin-4-yl)propoxy, 2-(1-methyl-piperazin-4-yl)ethyl, 3-(1-methyl-piperazin-4-yl)propyl, (1-methyl-piperazin-4-yl)carbonyl, 3-(1-sulphonyl-piperazin-4-yl)propoxy, 3-(1-methylsulphonylpiperazin-4-yl)-propoxy, 1-(methylsulphonyl)piperidin-4-yl, 1-(cyclopropylsulphonyl)piperidin-4-yl, 1-(methoxycarbonyl)piperidin-4-yl, 1-(methoxymethylcarbonyl)piperidin-4-yl, 3-(1,1-dioxotetrahydro-1,4-thiazin-4-yl)propoxy, (1R,5S)-8-azabicyclo[3.2.1]octan-3-yloxy, [(2E)-4-(1,1-dioxidothiomorpholin-4-yl)but-2-en-1-yl]oxidanyl, (3R)-quinuclidin-8-ylcarbamoyl, morpholino, morpholinomethyl, 2-morpholinoethyl, 3-morpholinopropyl, 2-morpholinoethoxy, 3-morpholinopropoxy, 2-(2-morpholinoethoxy)ethoxy, 3-[(3R,5S)-3,5-dimethylpiperazin-1-yl]propoxy, (3S,5S)-5-(methoxymethyl)pyrrolidin-3-yloxy, (3S,4R)-3-methylaminotetrahydropyran-4-yloxy, 4-(2-pyridylmethyl)piperazin-1-ylcarbonyl, 2-piperazin-4-ylethoxy, 2-(piperidin-4-yloxy)ethoxy, 2-(azetidin-3-yloxy)ethoxy, 3-(2,6-dimethylpiperazin-4-yl)propoxy, 1-methylpyrrolidin-3-yl-N-methylcarbamoyl, quinuclidinylcarbonyl, 2-imidazolin-1-ylethylcarbamoyl, 2-(piperidin-1-ylmethyl)piperidin-1-ylcarbonyl, 1-ethoxypiperidin-4-ylcarbamoyl, 2-pyrrolidin-1-ylcyclohex-1-yl-N-methylcarbamoyl, 2-(3-fluoropyrrolidin-1-yl)ethylcarbamoyl, 4-(2-dimethylaminoethyl)piperidin-1-ylcarbonyl, 2-(1-methylpiperidin-2-yl)-pyrrolidin-1-ylcarbonyl, 5-(morpholinylmethyl)pyrrolidin-1-ylcarbonyl, 5-(azepan-1-yl)pyrrolidin-1-ylcarbonyl, 2-(3,3-difluoropyrrolidin-1-yl)ethylcarbamyl, 2-(3-fluoropyrrolidin-1-yl)ethylcarbamyl, 3,4,4a,5,6,7,8,8a-octahydro-2H-quinolin-4-ylcarbamoyl, 1-dimethylaminocyclohex-1-ylmethylcarbamoyl, 2-morpholinoethylcarbamoyl, 2-1H-imidazolylethylcarbamoyl, 1-(pyridin-3-yl)piperazin-4-ylcarbonyl, 1-(pyridin-4-yl)piperazin-4-ylcarbonyl, 1,4-diazepanylcarbonyl, 1-(N-dimethylcarbamoylmethyl)piperazin-4-ylcarbonyl, 1-(carbamoylethyl)piperazin-4-ylcarbonyl, 3,4,6,7,8,8a-hexahydro-1H-pyrrolo[2,1-c]pyrazin-1-ylcarbonyl, morpholine-4-carbonyl, morpholinosulphonyl, 4-hydroxypiperidine-1-carbonyl, 2-pyrrolidin-1-ylethylcarbamoyl, piperidin-1-yl, 4-(aminomethyl)piperidin-1-ylcarbonyl, 3-aminopyrrolidin-1-ylcarbonyl, 3-methylaminopyrrolidin-1-ylcarbonyl, piperidin-4-yl-N-methylcarbamoyl, 4-methylaminopiperidin-1-ylcarbonyl, 4-(piperazin-1-ylmethyl)piperidin-1-ylcarbonyl, 4-methylaminocyclohexylcarbonyl, pyrrolidin-3-ylcarbamoyl, 4-pyrrolidin-1-ylpiperidin-1-ylcarbonyl, 1-(dimethylcarbamoylmethyl)piperazin-4-ylcarbonyl, 5-(N-methylcarbamoyl)pyrrolidin-3-yl, 1-(N,N-dimethylcarbamoylmethyl)piperidin-4-yl, 1-(methylcarbamoylmethyl)piperidin-4-yl, 1-(carbamoylmethyl)piperidin-4-yl, 1-isopropylpiperidin-4-yl, 1-(2-hydroxyethyl)piperidin-4-yl, 1-(N,N-dimethylaminomethylcarbonyl)piperidin-4-yl, 1-methyl-4-piperidyl, 1-methylpiperidin-4-ylmethyl, 1-(2-methoxyethyl)piperidin-4-ylcarbamoyl, 1-ethyl-4-piperidyl, 1-isopropyl-4-piperidyl, 1-piperidylmethyl, piperidine-4-carbonylamino, 4-methylpiperazine-1-carbonyl, 4-methylpiperazin-1-yl, 1-(4-methylpiperazin-1-ylcarbonyl)piperidin-4-yl, 3-dimethylaminopropoxy, 1-tert-butoxycarbonyl-4-piperidyl or 1-methyl-1-oxido-piperidin-1-ium-4-yl, and optionally substituted with one or more methyl, methoxy, ethoxy, fluoro, hydroxymethyl, methoxymethyl, ethoxymethyl, cyano, 1-hydroxyethyl, dimethylcarbamoyl, dimethylamino, methylcarbamoyl, methylaminomethyl or carbamoyl groups;

n is 0, 1 or 2 and the $(R^3)_n$ groups are selected from any one of the following 4-fluoro, 5-fluoro, 6-fluoro, 6-bromo, 6-propan-2-yl, 5-bromo, 4,6-difluoro, 6-chloro, 5-methyl, 6-methyl, 6-trifluoromethoxy, 5-trifluoromethyl, 6-methoxy, 7-methyl, 6,7-difluoro, 7-fluoro, 5-methoxy, 7-methoxy, 4-methoxy, 4-cyano, 7-cyano, 7-hydroxymethyl or 7-methylcarbamoyl; or a pharmaceutically-acceptable salt thereof.

A further particular group of compounds of the invention are pyrazine derivatives of Formula I above wherein:—
W is N;
J is O;
each of $G_1$, $G_2$, $G_3$ and $G_4$ are CH;
Ring A is 1-(1-tert-butoxycarbonyl-4-piperidyl)pyrazol-4-yl, 1-(4-piperidyl)pyrazol-4-yl, 1-(1-methyl-4-piperidyl)pyrazol-4-yl, 3-(dimethylsulphamoyl)phenyl, 3-piperazin-1-ylphenyl, 6-piperazin-1-yl-3-pyridyl, 3-(1-piperidyl)phenyl, 3-pyrrolidin-1-ylphenyl, 4-(morpholinomethyl)phenyl, 6-(4-methylpiperazin-1-yl)-3-pyridyl, 3-morpholinophenyl, 3-methylsulphonylphenyl, 3-(morpholinomethyl)phenyl, 4-piperazin-1-ylphenyl, 4-(dimethylsulphamoyl)phenyl, 3-ethylsulphonylphenyl, 3-(4-methylpiperazin-1-yl)phenyl, 3-dimethylaminophenyl, 3-(cyanomethyl)phenyl, 3-(methoxymethyl)phenyl, 3-methylsulphonyloxyphenyl, 4-(cyanomethyl)phenyl or 3-(carboxymethyl)phenyl;
n is 1 and $R^3$ is fluoro; or a pharmaceutically-acceptable salt thereof.

A further particular group of compounds of the invention are pyrazine derivatives of Formula I above wherein:—
W is N;
J is O;
each of $G_1$, $G_2$, $G_3$ and $G_4$ are CH;
Ring A is 1-(1-tert-butoxycarbonyl-4-piperidyl)pyrazol-4-yl, 1-(4-piperidyl)pyrazol-4-yl, 1-(1-methyl-4-piperidyl)pyrazol-4-yl, 3-(dimethylsulphamoyl)phenyl, 3-piperazin-1-ylphenyl, 6-piperazin-1-yl-3-pyridyl, 3-(1-piperidyl)phenyl, 3-pyrrolidin-1-ylphenyl, 4-(morpholinomethyl)phenyl, 6-(4-methylpiperazin-1-yl)-3-pyridyl, 3-morpholinophenyl, 3-methylsulphonylphenyl, 3-(morpholinomethyl)phenyl, 4-piperazin-1-ylphenyl, 4-(dimethylsulphamoyl)phenyl, 3-ethylsulphonylphenyl, 3-(4-methylpiperazin-1-yl)phenyl, 3-dimethylaminophenyl, 3-(cyanomethyl)phenyl, 3-(methoxymethyl)phenyl, 3-methylsulphonyloxyphenyl, 4-(cyanomethyl)phenyl, 3-methyl-1-piperidin-4-ylpyrazol-4-yl, 3-methyl-1-(1-methylpiperidin-4-yl)pyrazol-4-yl or 3-(carboxymethyl)phenyl;
n is 0 or n is 1 and the $R^3$ group, if present is fluoro; or a pharmaceutically-acceptable salt thereof.

A further particular group of compounds of the invention are pyrazine derivatives of Formula I above wherein:—
W is N;
J is S;
each of $G_1$, $G_2$, $G_3$ and $G_4$ are CH;
Ring A is 1-(4-piperidyl)pyrazol-4-yl or 3-(morpholino)phenyl;
n is 0; or a pharmaceutically-acceptable salt thereof.

A further particular group of compounds of the invention are pyridine derivatives of Formula I above wherein:—
W is CH;
J is O;
each of $G_1$, $G_2$, $G_3$ and $G_4$ is CH;
Ring A is a pyrazol-4-yl ring which is substituted at the 1-position by a $R^1$ group and is optionally substituted with one or two $R^2$ groups,
wherein the $R^1$ group is selected from 2-hydroxyethyl, 3-hydroxypropyl, 4-hydroxybutyl, 2-methoxyethyl, 3-methoxypropyl, 4-methoxybutyl, 2-methylaminoethyl, 3-methylaminopropyl, 4-methylaminobutyl, 2-dimethylaminoethyl, 3-dimethylaminopropyl, 4-dimethylaminobutyl, azetidin-3-yl, 1-methylazetidin-3-yl, 1-ethylazetidin-3-yl, pyrrolidin-3-yl, 1-methylpyrrolidin-3-yl, 1-ethylpyrrolidin-3-yl, 5-(N-methylcarbamoyl)pyrrolidin-3-yl, 1-methyl-5-(N-methylcarbamoyl)pyrrolidin-3-yl, piperidin-3-yl, 1-methylpiperidin-3-yl, 1-ethylpiperidin-3-yl, piperidin-4-yl, 1-methylpiperidin-4-yl, 1-ethylpiperidin-4-yl, 1-isopropylpiperidin-4-yl, 4-cyanomethylpiperidin-4-yl, 1-(carbamoylmethyl)piperidin-4-yl, 1-(N-methylcarbamoylmethyl)piperidin-4-yl, 1-(N,N-dimethylcarbamoylmethyl)piperidin-4-yl, 1-(N,N-dimethylaminomethylcarbonyl)piperidin-4-yl, 1-(2-hydroxyethyl)piperidin-4-yl, 8-methyl-8-azabicyclo[3.2.1]octan-3-yl, 1-(methoxycarbonyl)piperidin-4-yl, 1-(ethoxycarbonyl)piperidin-4-yl, 1-(tert-butoxycarbonyl)piperidin-4-yl, 1-acetylpiperidin-4-yl, 1-(2-hydroxyacetyl)piperidin-4-yl, 1-(2-hydroxypropionyl)piperidin-4-yl, 1-(2-methoxyacetyl)piperidin-4-yl, 1-(2-methoxypropionyl)piperidin-4-yl, 1-(3-methoxypropionyl)piperidin-4-yl, 1-[2-(2-methoxyethoxy)acetyl]piperidin-4-yl, 1-(2-methylaminoacetyl)piperidin-4-yl, 1-(3-methylaminopropionyl)piperidin-4-yl, 1-(2-dimethylaminoacetyl)piperidin-4-yl, 1-(3-dimethylaminpropionyl)piperidin-4-yl, 1-(2-acetamidoacetyl)piperidin-4-yl, 1-(3-acetamidopropionyl)piperidin-4-yl, tetrahydropyran-4-yl, azetidin-3-ylmethyl, 1-methylazetidin-3-ylmethyl, 1-ethylazetidin-3-ylmethyl, pyrrolidin-3-ylmethyl, 1-methylpyrrolidin-3-ylmethyl, 1-ethylpyrrolidin-3-ylmethyl, piperidin-3-ylmethyl, 1-methylpiperidin-3-ylmethyl, 1-ethylpiperidin-3-ylmethyl, piperidin-4-ylmethyl, 1-methylpiperidin-4-ylmethyl, 1-ethylpiperidin-4-ylmethyl, 2-azetidin-1-ylethyl, 3-azetidin-1-ylpropyl, 2-pyrrolidin-1-ylethyl, 3-pyrrolidin-1-ylpropyl, 2-(3-hydroxypyrrolidin-1-yl)ethyl, 3-(3-hydroxypyrrolidin-1-yl)propyl, 2-(2-hydroxymethylpyrrolidin-1-yl)ethyl, 3-(2-hydroxymethylpyrrolidin-1-yl)propyl, 2-morpholinoethyl, 3-morpholinopropyl, 2-piperidinoethyl, 3-piperidinopropyl, 2-(4-hydroxypiperidin-1-yl)ethyl, 3-(4-hydroxypiperidin-1-yl)propyl, 2-piperazin-1-ylethyl, 3-piperazin-1-ylpropyl, 2-(4-methylpiperazin-1-yl)ethyl and 3-(4-methylpiperazin-1-yl)propyl,
and wherein the optional $R^2$ groups are selected from 3-cyano, 3- or 5-methyl, 3- or 5-ethyl, 3,5-dimethyl, 3- or 5-hydroxymethyl, 3-(1-hydroxyethyl), 3- or 5-methoxymethyl, 3-methylaminomethyl, 3-dimethylaminomethyl, 3- or 5-methoxy, 3- or 5-ethoxy, 3-methylamino, 3-dimethylamino, 3-carbamoyl, 3-(N-methylcarbamoyl) and 3-(N,N-dimethylcarbamoyl);

n is 0 or n is 1 or 2 and the $(R^3)_n$ groups that are present are selected from 4-, 5-, 6- or 7-fluoro, 4,5-, 4,6-, 4,7-, 5,6-, 5,7- or 6,7-difluoro, 4-, 5-, 6- or 7-chloro, 4,6-dichloro, 4-, 5-, 6- or 7-bromo, 4-, 5-, 6- or 7-cyano, 4-, 5-, 6- or 7-methyl, 4-, 5-, 6- or 7-ethyl, 4-, 5-, 6- or 7-isopropyl, 7-hydroxymethyl, 5- or 6-trifluoromethyl, 4-, 5-, 6- or 7-methoxy and 5- or 6-trifluoromethoxy;

or each of $G_1$, $G_2$, $G_3$ and $G_4$ is selected from CH and N provided that only one of $G_1$, $G_2$, $G_3$ and $G_4$ is N, and wherein Ring A is a pyrazol-4-yl ring which is substituted at the 1-position by a $R^1$ group as defined immediately above and is optionally substituted with one or two $R^2$ groups as defined immediately above, and wherein n is 0 such that no $R^3$ group is present; or a pharmaceutically-acceptable salt thereof.

A further particular group of compounds of the invention are pyridine derivatives of Formula I above wherein:—

W is CH;
J is O;
each of $G_1$, $G_2$, $G_3$ and $G_4$ is CH;
Ring A is a pyrazol-4-yl ring which is substituted at the 1-position by a $R^1$ group and is optionally substituted with one or two $R^2$ groups,
wherein the $R^1$ group is selected from 2-hydroxyethyl, 3-hydroxypropyl, 2-dimethylaminoethyl, 3-dimethylaminopropyl, azetidin-3-yl, 1-methylazetidin-3-yl, pyrrolidin-3-yl, 1-methylpyrrolidin-3-yl, 5-(N-methylcarbamoyl)pyrrolidin-3-yl, 1-methyl-5-(N-methylcarbamoyl)pyrrolidin-3-yl, piperidin-3-yl, 1-methylpiperidin-3-yl, piperidin-4-yl, 1-methylpiperidin-4-yl, 1-ethylpiperidin-4-yl, 1-isopropylpiperidin-4-yl, 4-cyanomethylpiperidin-4-yl, 1-(carbamoylmethyl)piperidin-4-yl, 1-(N-methylcarbamoylmethyl)piperidin-4-yl, 1-(N,N-dimethylcarbamoylmethyl)piperidin-4-yl, 1-(2-hydroxyethyl)piperidin-4-yl, 1-(N,N-dimethylaminomethylcarbonyl)piperidin-4-yl, 8-methyl-8-azabicyclo[3.2.1]octan-3-yl, 1-(methoxycarbonyl)piperidin-4-yl, 1-(tert-butoxycarbonyl)piperidin-4-yl, 1-acetylpiperidin-4-yl, 1-(2-hydroxyacetyl)piperidin-4-yl, 1-(2-hydroxypropionyl)piperidin-4-yl, 1-(2-methoxyacetyl)piperidin-4-yl, 1-(2-methoxypropionyl)piperidin-4-yl, azetidin-3-ylmethyl, 1-methylazetidin-3-ylmethyl, pyrrolidin-3-ylmethyl, 1-methylpyrrolidin-3-ylmethyl, 1-methylpiperidin-3-ylmethyl, piperidin-4-ylmethyl, 1-methylpiperidin-4-ylmethyl, 2-azetidin-1-ylethyl, 3-azetidin-1-ylpropyl, 2-pyrrolidin-1-ylethyl, 3-pyrrolidin-1-ylpropyl, 2-(3-hydroxypyrrolidin-1-yl)ethyl, 3-(3-hydroxypyrrolidin-1-yl)propyl, 2-(2-hydroxymethylpyrrolidin-1-yl)ethyl, 3-(2-hydroxymethylpyrrolidin-1-yl)propyl, 2-morpholinoethyl, 3-morpholinopropyl, 2-piperidinoethyl, 3-piperidinopropyl, 2-(4-hydroxypiperidin-1-yl)ethyl, 3-(4-hydroxypiperidin-1-yl)propyl, 2-piperazin-1-ylethyl, 3-piperazin-1-ylpropyl, 2-(4-methylpiperazin-1-yl)ethyl and 3-(4-methylpiperazin-1-yl)propyl,
and wherein the optional $R^2$ groups are selected from 3-cyano, 3-methyl, 5-methyl, 3,5-dimethyl, 3-hydroxymethyl, 5-hydroxymethyl, 3-(1-hydroxyethyl), 3-methoxymethyl, 3-methylaminomethyl, 3-methoxy, 5-methoxy, 3-ethoxy, 5-ethoxy, 3-dimethylamino, 3-carbamoyl, 3-(N-methylcarbamoyl) and 3-(N,N-dimethylcarbamoyl);

n is 0 or n is 1 or 2 and the $(R^3)_n$ groups that are present are selected from 4-fluoro, 5-fluoro, 6-fluoro, 7-fluoro, 4,6-difluoro, 6,7-difluoro, 6-chloro, 5-bromo, 6-bromo, 4-cyano, 7-cyano, 5-methyl, 6-methyl, 7-methyl, 6-isopropyl, 7-hydroxymethyl, 5-trifluoromethyl, 4-, 5-, 6- or 7-methoxy and 6-trifluoromethoxy;

or each of $G_1$, $G_2$, $G_3$ and $G_4$ is selected from CH and N provided that only one of $G_1$, $G_2$, $G_3$ and $G_4$ is N, and wherein Ring A is a pyrazol-4-yl ring which is substituted at the 1-position by a $R^1$ group as defined immediately above and is optionally substituted with one or two $R^2$ groups as defined immediately above, and wherein n is 0 such that no $R^3$ group is present; or a pharmaceutically-acceptable salt thereof.

A further particular group of compounds of the invention are pyridine derivatives of Formula I above wherein:—

W is CH;
J is O;
each of $G_1$, $G_2$, $G_3$ and $G_4$ is CH;
Ring A is a pyrazol-4-yl ring which is substituted at the 1-position by a $R^1$ group and is optionally substituted with one $R^2$ group, wherein the $R^1$ group is selected from azetidin-3-yl, 1-methylazetidin-3-yl, pyrrolidin-3-yl, 1-methylpyrrolidin-3-yl, piperidin-3-yl, 1-methylpiperidin-3-yl, piperidin-4-yl, 1-methylpiperidin-4-yl, 1-ethylpiperidin-4-yl, 1-isopropylpiperidin-4-yl, 1-acetylpiperidin-4-yl, 1-(2-hydroxyacetyl)piperidin-4-yl, 1-(N,N-dimethylaminomethylcarbonyl)piperidin-4-yl, 1-(2-hydroxyethyl)piperidin-4-yl), 1-{(2S)-(2-hydroxypropionyl]piperidin-4-yl, 1-methylpyrrolidin-3-ylmethyl and 1-methylpiperidin-4-ylmethyl, and wherein the optional $R^2$ group is selected from 3-methyl, 5-methyl, 3-hydroxymethyl, 3-methoxymethyl, 3-methoxy, 5-methoxy, 3-ethoxy and 5-ethoxy;

n is 0 or n is 1 and the $R^3$ group, if present, is selected from 4-fluoro, 5-fluoro, 7-fluoro, 4-cyano, 7-methyl and 7-methoxy; or a pharmaceutically-acceptable salt thereof.

A further particular group of compounds of the invention are pyridine derivatives of Formula I above wherein:—

W is CH;
J is O;
each of $G_1$, $G_2$, $G_3$ and $G_4$ are CH;
Ring A is 1-(1-methylpiperidin-4-yl)pyrazol-4-yl, 3-methyl-1-piperidin-4-ylpyrazol-4-yl, 3-methyl-1-(1-methylpiperidin-4-yl)pyrazol-4-yl, 3-hydroxymethyl-1-(1-methylpiperidin-4-yl)pyrazol-4-yl, 3-methoxymethyl-1-(1-methylpiperidin-4-yl)pyrazol-4-yl, 3-methoxymethyl-1-piperidin-4-ylpyrazol-4-yl, 3-methoxymethyl-1-(1-(hydroxyacetyl)piperidin-4-yl)pyrazol-4-yl, 3-methoxymethyl-1-[1-[(2S)-2-hydroxypropanoyl]piperidin-4-yl]pyrazol-4-yl, 3-methoxymethyl-1-(1-(N-methylcarbamoylmethyl)piperidin-4-yl)pyrazol-4-yl, 3-hydroxymethyl-1-(1-(N,N-dimethylcarbamoylmethyl)piperidin-4-yl) pyrazol-4-yl, 3-methoxymethyl-1-(1-(N,N-dimethylaminomethylcarbonyl)piperidin-4-yl)pyrazol-4-yl, 3-methoxymethyl-1-(1-(2-hydroxyethyl)piperidin-4-yl) pyrazol-4-yl or 3-hydroxymethyl-1-[1-[(2S)-2-hydroxypropanoyl]piperidin-4-yl]pyrazol-4-yl;
n is 0 or 1 and when n is 1, $R^3$ is 4-fluoro, 4-cyano or 7-methoxy; or a pharmaceutically-acceptable salt thereof.

Particular compounds of the invention are, for example, the pyridine and pyrazine derivatives of the Formula I that are disclosed within the Examples that are set out hereinafter.

For example, a particular compound of the invention is a pyridine or pyrazine derivative of the Formula I selected from any one of the following:—

[3-[6-amino-5-(1,3-benzoxazol-2-yl)-3-pyridyl]phenyl] methanol;
[4-[6-amino-5-(1,3-benzoxazol-2-yl)-3-pyridyl]phenyl]-(4-hydroxy-1-piperidyl)methanone;
[4-[6-amino-5-(1,3-benzoxazol-2-yl)-3-pyridyl]phenyl] methanol;

3-(1,3-benzothiazol-2-yl)-5-[1-(4-piperidyl)pyrazol-4-yl]pyridin-2-amine;
3-(1,3-benzoxazol-2-yl)-5-(1H-indazol-5-yl)pyridin-2-amine;
3-(1,3-benzoxazol-2-yl)-5-(1H-indol-5-yl)pyridin-2-amine;
3-(1,3-benzoxazol-2-yl)-5-(1H-indol-6-yl)pyridin-2-amine;
3-(1,3-benzoxazol-2-yl)-5-(1-naphthyl)pyridin-2-amine;
3-(1,3-benzoxazol-2-yl)-5-(2,3-dihydro-1,4-benzodioxin-6-yl)pyridin-2-amine;
3-(1,3-benzoxazol-2-yl)-5-(2-methoxy-4-piperazin-1-ylphenyl)pyridin-2-amine;
3-(1,3-benzoxazol-2-yl)-5-(3-ethylsulphonylphenyl)pyridin-2-amine;
3-(1,3-benzoxazol-2-yl)-5-(3-piperazin-1-ylphenyl)pyridin-2-amine;
3-(1,3-benzoxazol-2-yl)-5-(3-pyrrolidin-1-ylphenyl)pyridin-2-amine;
3-(1,3-benzoxazol-2-yl)-5-(3-quinolyl)pyridin-2-amine;
3-(1,3-benzoxazol-2-yl)-5-(4-ethylsulphonylphenyl)pyridin-2-amine;
3-(1,3-benzoxazol-2-yl)-5-(4-piperazin-1-ylphenyl)pyridin-2-amine;
3-(1,3-benzoxazol-2-yl)-5-(4-quinolyl)pyridin-2-amine;
3-(1,3-benzoxazol-2-yl)-5-(6-piperazin-1-yl-3-pyridyl)pyridin-2-amine;
3-(1,3-benzoxazol-2-yl)-5-(8-quinolyl)pyridin-2-amine;
3-(1,3-benzoxazol-2-yl)-5-[1-(1-ethyl-4-piperidyl)pyrazol-4-yl]pyridin-2-amine;
3-(1,3-benzoxazol-2-yl)-5-[1-(1-isopropyl-4-piperidyl)pyrazol-4-yl]pyridin-2-amine;
3-(1,3-benzoxazol-2-yl)-5-[1-(1-methyl-1-oxido-piperidin-1-ium-4-yl)pyrazol-4-yl]pyridin-2-amine;
3-(1,3-benzoxazol-2-yl)-5-[1-(1-methyl-4-piperidyl)pyrazol-4-yl]pyridin-2-amine;
3-(1,3-benzoxazol-2-yl)-5-[1-(4-piperidyl)pyrazol-4-yl]pyridin-2-amine;
3-(1,3-benzoxazol-2-yl)-5-[2-(methoxymethyl)phenyl]pyridin-2-amine;
3-(1,3-benzoxazol-2-yl)-5-[3-(methoxymethyl)phenyl]pyridin-2-amine;
3-(1,3-benzoxazol-2-yl)-5-[3-(morpholinomethyl)phenyl]pyridin-2-amine;
3-(1,3-benzoxazol-2-yl)-5-[3-(pyrrolidin-1-ylmethyl)phenyl]pyridin-2-amine;
3-(1,3-benzoxazol-2-yl)-5-[4-(2-methoxyethoxy)phenyl]pyridin-2-amine;
3-(1,3-benzoxazol-2-yl)-5-[4-(4-piperidyl)phenyl]pyridin-2-amine;
3-(1,3-benzoxazol-2-yl)-5-[4-(dimethylaminomethyl)phenyl]pyridin-2-amine;
3-(1,3-benzoxazol-2-yl)-5-[4-(methoxymethyl)phenyl]pyridin-2-amine;
3-(1,3-benzoxazol-2-yl)-5-[4-(morpholinomethyl)phenyl]pyridin-2-amine;
3-(1,3-benzoxazol-2-yl)-5-[6-(3-dimethylaminopropoxy)-3-pyridyl]pyridin-2-amine;
3-(4,6-difluoro-1,3-benzoxazol-2-yl)-5-[1-(1-methyl-4-piperidyl)pyrazol-4-yl]pyridin-2-amine;
3-(4-fluoro-1,3-benzoxazol-2-yl)-5-[1-(1-methyl-4-piperidyl)pyrazol-4-yl]pyridin-2-amine;
3-(5-bromo-1,3-benzoxazol-2-yl)-5-[1-(1-methyl-4-piperidyl)pyrazol-4-yl]pyridin-2-amine;
3-(5-fluoro-1,3-benzoxazol-2-yl)-5-[1-(1-methyl-4-piperidyl)pyrazol-4-yl]pyridin-2-amine;
3-(5-methyl-1,3-benzoxazol-2-yl)-5-[1-(1-methyl-4-piperidyl)pyrazol-4-yl]pyridin-2-amine;
3-(6-bromo-1,3-benzoxazol-2-yl)-5-[1-(1-methyl-4-piperidyl)pyrazol-4-yl]pyridin-2-amine;
3-(6-chloro-1,3-benzoxazol-2-yl)-5-[1-(1-methyl-4-piperidyl)pyrazol-4-yl]pyridin-2-amine;
3-(6-fluoro-1,3-benzoxazol-2-yl)-5-[1-(1-methyl-4-piperidyl)pyrazol-4-yl]pyridin-2-amine;
3-(6-isopropyl-1,3-benzoxazol-2-yl)-5-[1-(1-methyl-4-piperidyl)pyrazol-4-yl]pyridin-2-amine;
3-(6-methyl-1,3-benzoxazol-2-yl)-5-[1-(1-methyl-4-piperidyl)pyrazol-4-yl]pyridin-2-amine;
3-[6-amino-5-(1,3-benzoxazol-2-yl)-3-pyridyl]benzamide;
3-[6-amino-5-(1,3-benzoxazol-2-yl)-3-pyridyl]benzonitrile;
3-[6-amino-5-(1,3-benzoxazol-2-yl)-3-pyridyl]-N-(2-dimethylaminoethyl)benzamide;
3-[6-amino-5-(1,3-benzoxazol-2-yl)-3-pyridyl]-N,N-dimethyl-benzenesulphonamide;
3-[6-amino-5-(1,3-benzoxazol-2-yl)-3-pyridyl]-N-methylbenzamide;
3-[6-amino-5-(1,3-benzoxazol-2-yl)-3-pyridyl]-N-methylbenzenesulphonamide;
3-oxazolo[4,5-b]pyridin-2-yl-5-[1-(4-piperidyl)pyrazol-4-yl]pyridin-2-amine;
3-oxazolo[4,5-c]pyridin-2-yl-5-[1-(4-piperidyl)pyrazol-4-yl]pyridin-2-amine;
3-oxazolo[5,4-b]pyridin-2-yl-5-[1-(4-piperidyl)pyrazol-4-yl]pyridin-2-amine;
3-oxazolo[5,4-c]pyridin-2-yl-5-[1-(4-piperidyl)pyrazol-4-yl]pyridin-2-amine;
4-[6-amino-5-(1,3-benzoxazol-2-yl)-3-pyridyl]benzonitrile;
4-[6-amino-5-(1,3-benzoxazol-2-yl)-3-pyridyl]-N-(2-dimethylaminoethyl)benzamide;
4-[6-amino-5-(1,3-benzoxazol-2-yl)-3-pyridyl]-N,N-dimethyl-benzenesulphonamide;
4-[6-amino-5-(1,3-benzoxazol-2-yl)-3-pyridyl]-N-cyclopropyl-benzenesulphonamide;
5-(1,3-benzodioxol-5-yl)-3-(1,3-benzoxazol-2-yl)pyridin-2-amine;
5-[1-(1-methyl-4-piperidyl)pyrazol-4-yl]-3-[5-(trifluoromethyl)-1,3-benzoxazol-2-yl]pyridin-2-amine;
5-[1-(1-methyl-4-piperidyl)pyrazol-4-yl]-3-[6-(trifluoromethoxy)-1,3-benzoxazol-2-yl]pyridin-2-amine;
5-[3-(aminomethyl)phenyl]-3-(1,3-benzoxazol-2-yl)pyridin-2-amine;
5-[4-(aminomethyl)phenyl]-3-(1,3-benzoxazol-2-yl)pyridin-2-amine;
N-[3-[6-amino-5-(1,3-benzoxazol-2-yl)-3-pyridyl]phenyl]acetamide;
N-[4-[6-amino-5-(1,3-benzoxazol-2-yl)-3-pyridyl]phenyl]methanesulphonamide;
tert-butyl 4-[4-[6-amino-5-(1,3-benzothiazol-2-yl)-3-pyridyl]pyrazol-1-yl]piperidine-1-carboxylate;
tert-butyl 4-[4-[6-amino-5-(1,3-benzoxazol-2-yl)-3-pyridyl]pyrazol-1-yl]piperidine-1-carboxylate; and
tert-butyl 4-[4-[5-amino-6-(1,3-benzoxazol-2-yl)pyrazin-2-yl]pyrazol-1-yl]piperidine-1-carboxylate; or a pharmaceutically-acceptable salt thereof.

A further particular compound of the invention is a pyridine or pyrazine derivative of the Formula I selected from any one of the following:—

3-(1,3-benzoxazol-2-yl)-5-(2-fluoro-4-piperazin-1-ylphenyl)pyridin-2-amine;
3-(1,3-benzoxazol-2-yl)-5-[3-(1-piperidyl)phenyl]pyridin-2-amine;
2-[3-[6-amino-5-(1,3-benzoxazol-2-yl)-3-pyridyl]phenyl]acetonitrile;
3-(1,3-benzoxazol-2-yl)-5-(3-methylsulphonylphenyl)pyridin-2-amine;

3-(1,3-benzoxazol-2-yl)-5-(3-morpholinophenyl)pyridin-2-amine;
3-(1,3-benzoxazol-2-yl)-5-(3-dimethylaminophenyl)pyridin-2-amine;
2-[4-[6-amino-5-(1,3-benzoxazol-2-yl)-3-pyridyl]phenyl]acetonitrile;
[3-[6-amino-5-(1,3-benzoxazol-2-yl)-3-pyridyl]phenyl]methanesulphonate;
3-(1,3-benzoxazol-2-yl)-5-[3-(4-methylpiperazin-1-yl)phenyl]pyridin-2-amine;
3-(1,3-benzoxazol-2-yl)-5-[6-(4-methylpiperazin-1-yl)-3-pyridyl]pyridin-2-amine;
3-oxazolo[4,5-c]pyridin-2-yl-5-[3-(pyrrolidin-1-ylmethyl)phenyl]pyridin-2-amine;
4-(6-amino-5-oxazolo[4,5-c]pyridin-2-yl-3-pyridyl)-N-(2-hydroxyethyl)benzenesulphonamide;
5-(3-methylsulphonylphenyl)-3-oxazolo[4,5-c]pyridin-2-yl-pyridin-2-amine;
5-(3-morpholinophenyl)-3-oxazolo[4,5-c]pyridin-2-yl-pyridin-2-amine;
[5-(6-amino-5-oxazolo[4,5-c]pyridin-2-yl-3-pyridyl)-2-thienyl]methanol;
3-(6-amino-5-oxazolo[4,5-c]pyridin-2-yl-3-pyridyl)-N-methyl-benzenesulphonamide;
3-(6-amino-5-oxazolo[4,5-c]pyridin-2-yl-3-pyridyl)-N-cyclopropyl-benzamide;
[4-(6-amino-5-oxazolo[4,5-c]pyridin-2-yl-3-pyridyl)phenyl]-(4-hydroxy-1-piperidyl)methanone;
4-(6-amino-5-oxazolo[4,5-c]pyridin-2-yl-3-pyridyl)benzamide;
5-(2-methyl-5-morpholinosulphonyl-phenyl)-3-oxazolo[4,5-c]pyridin-2-yl-pyridin-2-amine;
3-(6-amino-5-oxazolo[4,5-c]pyridin-2-yl-3-pyridyl)benzonitrile;
[4-(6-amino-5-oxazolo[4,5-c]pyridin-2-yl-3-pyridyl)phenyl]-morpholino-methanone;
5-(3-morpholinosulphonylphenyl)-3-oxazolo[4,5-c]pyridin-2-yl-pyridin-2-amine;
3-(6-amino-5-oxazolo[4,5-c]pyridin-2-yl-3-pyridyl)-N-(2-morpholinoethyl)benzamide;
3-(6-amino-5-oxazolo[4,5-c]pyridin-2-yl-3-pyridyl)-N-(2-diethylaminoethyl)benzamide;
2-[4-(6-amino-5-oxazolo[4,5-c]pyridin-2-yl-3-pyridyl)phenyl]acetonitrile;
4-(6-amino-5-oxazolo[4,5-c]pyridin-2-yl-3-pyridyl)-N-(3-dimethylaminopropyl)benzamide;
5-[4-(morpholinomethyl)phenyl]-3-oxazolo[4,5-c]pyridin-2-yl-pyridin-2-amine;
[3-(6-amino-5-oxazolo[4,5-c]pyridin-2-yl-3-pyridyl)phenyl]-(4-methylpiperazin-1-yl)methanone;
3-oxazolo[4,5-c]pyridin-2-yl-5-[3-(1-piperidylmethyl)phenyl]pyridin-2-amine;
3-oxazolo[4,5-c]pyridin-2-yl-5-[3-(1-piperidyl)phenyl]pyridin-2-amine;
3-(6-amino-5-oxazolo[4,5-c]pyridin-2-yl-3-pyridyl)-N-(2-pyrrolidin-1-ylethyl)benzamide;
5-[4-(aminomethyl)phenyl]-3-oxazolo[4,5-c]pyridin-2-yl-pyridin-2-amine;
3-(6-amino-5-oxazolo[4,5-c]pyridin-2-yl-3-pyridyl)-N-(2-dimethylaminoethyl)benzamide;
4-(6-amino-5-oxazolo[4,5-c]pyridin-2-yl-3-pyridyl)-N-(2-hydroxyethyl)benzamide;
N-[3-(6-amino-5-oxazolo[4,5-c]pyridin-2-yl-3-pyridyl)phenyl]piperidine-4-carboxamide;
5-[3-(aminomethyl)phenyl]-3-oxazolo[4,5-c]pyridin-2-yl-pyridin-2-amine;
3-oxazolo[4,5-c]pyridin-2-yl-5-[3-(2H-pyrazol-3-yl)phenyl]pyridin-2-amine;
3-(6-amino-5-oxazolo[5,4-b]pyridin-2-yl-3-pyridyl)benzonitrile;
4-(6-amino-5-oxazolo[5,4-b]pyridin-2-yl-3-pyridyl)-N-(2-hydroxyethyl)benzamide;
5-[3-(methoxymethyl)phenyl]-3-oxazolo[5,4-b]pyridin-2-yl-pyridin-2-amine;
3-(6-amino-5-oxazolo[5,4-b]pyridin-2-yl-3-pyridyl)-N-(2-dimethylaminoethyl)benzamide;
[4-(6-amino-5-oxazolo[5,4-b]pyridin-2-yl-3-pyridyl)phenyl]-(4-hydroxy-1-piperidyl)methanone;
3-(6-amino-5-oxazolo[5,4-b]pyridin-2-yl-3-pyridyl)-N-(2-diethylaminoethyl)benzamide;
3-oxazolo[5,4-b]pyridin-2-yl-5-[3-(pyrrolidin-1-ylmethyl)phenyl]pyridin-2-amine;
3-oxazolo[5,4-b]pyridin-2-yl-5-[3-(1-piperidylmethyl)phenyl]pyridin-2-amine;
3-(6-amino-5-oxazolo[5,4-b]pyridin-2-yl-3-pyridyl)-N-cyclopropyl-benzenesulphonamide;
4-(6-amino-5-oxazolo[5,4-b]pyridin-2-yl-3-pyridyl)-N-(3-dimethylaminopropyl)benzamide;
[4-(6-amino-5-oxazolo[5,4-b]pyridin-2-yl-3-pyridyl)phenyl]-morpholino-methanone;
5-[4-(aminomethyl)phenyl]-3-oxazolo[5,4-b]pyridin-2-yl-pyridin-2-amine;
4-(6-amino-5-oxazolo[5,4-b]pyridin-2-yl-3-pyridyl)-N-(2-hydroxyethyl)benzenesulphonamide;
3-oxazolo[5,4-b]pyridin-2-yl-5-[3-(2H-pyrazol-3-yl)phenyl]pyridin-2-amine;
2-[4-(6-amino-5-oxazolo[5,4-b]pyridin-2-yl-3-pyridyl)phenyl]acetonitrile;
3-(6-amino-5-oxazolo[5,4-b]pyridin-2-yl-3-pyridyl)-N-cyclopropyl-benzamide;
[3-(6-amino-5-oxazolo[5,4-b]pyridin-2-yl-3-pyridyl)phenyl]-(4-methylpiperazin-1-yl)methanone;
[5-(6-amino-5-oxazolo[5,4-b]pyridin-2-yl-3-pyridyl)-2-thienyl]methanol;
3-(6-amino-5-oxazolo[5,4-b]pyridin-2-yl-3-pyridyl)-N-(2-pyrrolidin-1-ylethyl)benzamide;
5-[4-(morpholinomethyl)phenyl]-3-oxazolo[5,4-b]pyridin-2-yl-pyridin-2-amine;
3-(6-amino-5-oxazolo[5,4-b]pyridin-2-yl-3-pyridyl)-N-(2-morpholinoethyl)benzamide;
5-(3-morpholinophenyl)-3-oxazolo[5,4-b]pyridin-2-yl-pyridin-2-amine;
5-(3-morpholinophenyl)-3-oxazolo[4,5-b]pyridin-2-yl-pyridin-2-amine;
3-(6-amino-5-oxazolo[4,5-b]pyridin-2-yl-3-pyridyl)-N-(2-morpholinoethyl)benzamide;
N-[3-(6-amino-5-oxazolo[4,5-b]pyridin-2-yl-3-pyridyl)phenyl]piperidine-4-carboxamide;
5-[4-(aminomethyl)phenyl]-3-oxazolo[4,5-b]pyridin-2-yl-pyridin-2-amine;
4-(6-amino-5-oxazolo[4,5-b]pyridin-2-yl-3-pyridyl)-N-(2-hydroxyethyl)benzamide;
3-(6-amino-5-oxazolo[4,5-b]pyridin-2-yl-3-pyridyl)-N-cyclopropyl-benzamide;
3-oxazolo[4,5-b]pyridin-2-yl-5-[3-(pyrrolidin-1-ylmethyl)phenyl]pyridin-2-amine;
[3-(6-amino-5-oxazolo[4,5-b]pyridin-2-yl-3-pyridyl)phenyl]-(4-methylpiperazin-1-yl)methanone;
3-(6-amino-5-oxazolo[4,5-b]pyridin-2-yl-3-pyridyl)-N-(2-pyrrolidin-1-ylethyl)benzamide;
3-(6-amino-5-oxazolo[4,5-b]pyridin-2-yl-3-pyridyl)-N-cyclopropyl-benzenesulphonamide;

3-oxazolo[4,5-b]pyridin-2-yl-5-[3-(1-piperidylmethyl)phenyl]pyridin-2-amine;
4-(6-amino-5-oxazolo[4,5-b]pyridin-2-yl-3-pyridyl)-N-(3-dimethylaminopropyl)benzamide;
[4-(6-amino-5-oxazolo[4,5-b]pyridin-2-yl-3-pyridyl)phenyl]-(4-hydroxy-1-piperidyl)methanone;
[4-(6-amino-5-oxazolo[4,5-b]pyridin-2-yl-3-pyridyl)phenyl]-morpholino-methanone;
5-[4-(morpholinomethyl)phenyl]-3-oxazolo[5,4-c]pyridin-2-yl-pyridin-2-amine;
[4-(6-amino-5-oxazolo[5,4-c]pyridin-2-yl-3-pyridyl)phenyl]-(4-hydroxy-1-piperidyl)methanone;
5-[4-(aminomethyl)phenyl]-3-oxazolo[5,4-c]pyridin-2-yl-pyridin-2-amine;
3-oxazolo[5,4-c]pyridin-2-yl-5-[3-(pyrrolidin-1-ylmethyl)phenyl]pyridin-2-amine;
3-oxazolo[5,4-c]pyridin-2-yl-5-[3-(1-piperidyl)phenyl]pyridin-2-amine;
3-(6-amino-5-oxazolo[5,4-c]pyridin-2-yl-3-pyridyl)-N-cyclopropyl-benzamide;
3-(6-amino-5-oxazolo[5,4-c]pyridin-2-yl-3-pyridyl)-N-methyl-benzenesulphonamide;
3-(6-amino-5-oxazolo[5,4-c]pyridin-2-yl-3-pyridyl)-N-(2-morpholinoethyl)benzamide;
[3-(6-amino-5-oxazolo[5,4-c]pyridin-2-yl-3-pyridyl)phenyl]-(4-methylpiperazin-1-yl)methanone;
5-(3-morpholinophenyl)-3-oxazolo[5,4-c]pyridin-2-yl-pyridin-2-amine;
3-(1,3-benzothiazol-2-yl)-5-[1-(1-methyl-4-piperidyl)pyrazol-4-yl]pyridin-2-amine;
3-(1,3-benzoxazol-2-yl)-5-[1-(4-piperidyl)pyrazol-4-yl]pyrazin-2-amine;
3-(1,3-benzoxazol-2-yl)-5-[1-(1-methyl-4-piperidyl)pyrazol-4-yl]pyrazin-2-amine;
3-(1,3-benzothiazol-2-yl)-5-[1-(4-piperidyl)pyrazol-4-yl]pyrazin-2-amine;
3-[5-amino-6-(1,3-benzoxazol-2-yl)pyrazin-2-yl]-N,N-dimethyl-benzenesulphonamide;
3-(1,3-benzoxazol-2-yl)-5-(3-piperazin-1-ylphenyl)pyrazin-2-amine;
3-(1,3-benzoxazol-2-yl)-5-(6-piperazin-1-yl-3-pyridyl)pyrazin-2-amine;
3-(1,3-benzoxazol-2-yl)-5-[3-(1-piperidyl)phenyl]pyrazin-2-amine;
3-(1,3-benzoxazol-2-yl)-5-(3-pyrrolidin-1-ylphenyl)pyrazin-2-amine;
3-(1,3-benzoxazol-2-yl)-5-[4-(morpholinomethyl)phenyl]pyrazin-2-amine;
3-(1,3-benzoxazol-2-yl)-5-[6-(4-methylpiperazin-1-yl)-3-pyridyl]pyrazin-2-amine;
3-(1,3-benzoxazol-2-yl)-5-(3-morpholinophenyl)pyrazin-2-amine;
3-(1,3-benzoxazol-2-yl)-5-(3-methylsulphonylphenyl)pyrazin-2-amine;
3-(1,3-benzoxazol-2-yl)-5-[3-(morpholinomethyl)phenyl]pyrazin-2-amine;
3-(1,3-benzoxazol-2-yl)-5-(4-piperazin-1-ylphenyl)pyrazin-2-amine;
4-[5-amino-6-(1,3-benzoxazol-2-yl)pyrazin-2-yl]-N,N-dimethyl-benzenesulphonamide;
3-(1,3-benzoxazol-2-yl)-5-(3-ethylsulphonylphenyl)pyrazin-2-amine;
3-(1,3-benzoxazol-2-yl)-5-[3-(4-methylpiperazin-1-yl)phenyl]pyrazin-2-amine;
3-(1,3-benzoxazol-2-yl)-5-(3-dimethylaminophenyl)pyrazin-2-amine;
2-[3-[5-amino-6-(1,3-benzoxazol-2-yl)pyrazin-2-yl]phenyl]acetonitrile;
3-(1,3-benzoxazol-2-yl)-5-[3-(methoxymethyl)phenyl]pyrazin-2-amine;
[3-[5-amino-6-(1,3-benzoxazol-2-yl)pyrazin-2-yl]phenyl] methanesulphonate; and
2-[4-[5-amino-6-(1,3-benzoxazol-2-yl)pyrazin-2-yl]phenyl] acetonitrile; or a pharmaceutically-acceptable salt thereof.

A yet further particular compound of the invention is a pyridine or pyrazine derivative of the Formula I selected from any one of the following:—
3-(1,3-benzoxazol-2-yl)-5-[3-(methoxymethyl)-1-(4-piperidyl)pyrazol-4-yl]pyridin-2-amine;
[4-[6-amino-5-(1,3-benzoxazol-2-yl)-3-pyridyl]-1-(1-methyl-4-piperidyl)pyrazol-3-yl]methanol;
3-(4-fluoro-1,3-benzoxazol-2-yl)-5-[1-(1-methyl-4-piperidyl)pyrazol-4-yl]pyridin-2-amine;
3-(1,3-benzoxazol-2-yl)-5-[3-methyl-1-(1-methyl-4-piperidyl)pyrazol-4-yl]pyridin-2-amine;
[4-[6-amino-5-(1,3-benzoxazol-2-yl)-3-pyridyl]-1-(4-piperidyl)pyrazol-3-yl]methanol;
3-(1,3-benzoxazol-2-yl)-5-[1-(4-piperidyl)pyrazol-4-yl]pyridin-2-amine;
3-(1,3-benzoxazol-2-yl)-5-[3-methyl-1-(4-piperidyl)pyrazol-4-yl]pyridin-2-amine;
3-(1,3-benzoxazol-2-yl)-5-[3-ethoxy-1-(1-methyl-4-piperidyl)pyrazol-4-yl]pyridin-2-amine;
1-[4-[4-[6-amino-5-(1,3-benzoxazol-2-yl)-3-pyridyl]pyrazol-1-yl]-1-piperidyl]-2-hydroxy-ethanone;
3-(1,3-benzoxazol-2-yl)-5-[1-(3-pyrrolidin-1-ylpropyl)pyrazol-4-yl]pyridin-2-amine;
3-(1,3-benzoxazol-2-yl)-5-[1-(1-methyl-4-piperidyl)pyrazol-4-yl]pyridin-2-amine;
3-(1,3-benzoxazol-2-yl)-5-(1-pyrrolidin-3-ylpyrazol-4-yl)pyridin-2-amine;
3-(1,3-benzoxazol-2-yl)-5-(2-methoxy-4-piperazin-1-ylphenyl)pyridin-2-amine;
3-oxazolo[5,4-b]pyridin-2-yl-5-[1-(4-piperidyl)pyrazol-4-yl]pyridin-2-amine; and
3-(1,3-benzoxazol-2-yl)-5-[1-(1-methyl-4-piperidyl)pyrazol-4-yl]pyrazin-2-amine; or a pharmaceutically-acceptable salt thereof.

A yet further particular compound of the invention is a pyridine derivative of the Formula I selected from any one of the following:—
3-(1,3-benzoxazol-2-yl)-5-[1-(1-methylpiperidin-4-yl)-1H-pyrazol-4-yl]pyridin-2-amine;
3-(4-fluoro-1,3-benzoxazol-2-yl)-5-[1-(1-methylpiperidin-4-yl)-1H-pyrazol-4-yl]pyridin-2-amine;
3-(1,3-benzoxazol-2-yl)-5-(3-methyl-1-piperidin-4-yl-1H-pyrazol-4-yl)pyridin-2-amine;
3-(1,3-benzoxazol-2-yl)-5-[3-methyl-1-(1-methylpiperidin-4-yl)-1H-pyrazol-4-yl]pyridin-2-amine;
{4-[6-amino-5-(1,3-benzoxazol-2-yl)pyridin-3-yl]-1-(1-methylpiperidin-4-yl)-1H-pyrazol-3-yl}methanol;
3-(1,3-benzoxazol-2-yl)-5-[3-(methoxymethyl)-1-(1-methylpiperidin-4-yl)-1H-pyrazol-4-yl]pyridin-2-amine;
3-(4-fluoro-1,3-benzoxazol-2-yl)-5-[3-(methoxymethyl)-1-piperidin-4-yl-1H-pyrazol-4-yl]pyridin-2-amine;
{4-[6-amino-5-(4-fluoro-1,3-benzoxazol-2-yl)pyridin-3-yl]-1-(1-methylpiperidin-4-yl)-1H-pyrazol-3-yl}methanol;
3-(4-fluoro-1,3-benzoxazol-2-yl)-5-[3-(methoxymethyl)-1-(1-methylpiperidin-4-yl)-1H-pyrazol-4-yl]pyridin-2-amine;
2-(4-{4-[6-amino-5-(1,3-benzoxazol-2-yl)pyridin-3-yl]-3-(methoxymethyl)-1H-pyrazol-1-yl}piperidin-1-yl)-2-oxoethanol;

(2S)-1-(4-{4-[6-amino-5-(1,3-benzoxazol-2-yl)pyridin-3-yl]-3-(methoxymethyl)-1H-pyrazol-1-yl}piperidin-1-yl)-1-oxopropan-2-ol;
2-(4-{4-[6-amino-5-(1,3-benzoxazol-2-yl)pyridin-3-yl]-3-(methoxymethyl)-1H-pyrazol-1-yl}piperidin-1-yl)-N-methylacetamide;
2-(4-{4-[6-amino-5-(1,3-benzoxazol-2-yl)pyridin-3-yl]-3-(hydroxymethyl)-1H-pyrazol-1-yl}piperidin-1-yl)-N,N-dimethylacetamide;
(2S)-1-(4-{4-[6-amino-5-(1,3-benzoxazol-2-yl)pyridin-3-yl]-3-(hydroxymethyl)-1H-pyrazol-1-yl}piperidin-1-yl)-1-oxopropan-2-ol;
2-[2-amino-5-[3-(methoxymethyl)-1-(1-methyl-4-piperidyl)pyrazol-4-yl]-3-pyridyl]-1,3-benzoxazole-4-carbonitrile;
2-[2-amino-5-[3-methyl-1-(1-methyl-4-piperidyl)pyrazol-4-yl]-3-pyridyl]-1,3-benzoxazole-4-carbonitrile;
[4-[6-amino-5-(7-methoxy-1,3-benzoxazol-2-yl)-3-pyridyl]-1-(1-methyl-4-piperidyl)pyrazol-3-yl]methanol;
3-(7-methoxy-1,3-benzoxazol-2-yl)-5-[3-(methoxymethyl)-1-(1-methyl-4-piperidyl)pyrazol-4-yl]pyridin-2-amine;
1-[4-[4-[6-amino-5-(1,3-benzoxazol-2-yl)-3-pyridyl]-3-(methoxymethyl)pyrazol-1-yl]-1-piperidyl]-2-dimethylaminoethanone; and
2-[4-[4-[6-amino-5-(1,3-benzoxazol-2-yl)-3-pyridyl]-3-(methoxymethyl)pyrazol-1-yl]-1-piperidyl]ethanol; or a pharmaceutically-acceptable salt thereof.

Another aspect of the present invention provides a process for preparing a compound of the Formula I, or a pharmaceutically-acceptable salt thereof. A suitable process is illustrated by the following representative process variants in which, unless otherwise stated, $G_1$, $G_2$, $G_3$, $G_4$, Ring A, J, W, n, and $R^3$ have any of the meanings defined hereinbefore. Necessary starting materials may be obtained by standard procedures of organic chemistry. The preparation of such starting materials is described in conjunction with the following representative process variants and within the accompanying Examples. Alternatively necessary starting materials are obtainable by analogous procedures to those illustrated which are within the ordinary skill of an organic chemist.

Suitable process variants include, for example, the following:—

(a) The reaction of a carboxylic acid of the Formula II

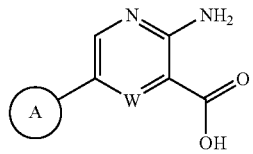

II or a reactive derivative thereof, wherein W and Ring A have any of the meanings defined hereinbefore except that any functional group present on Ring A is protected if necessary, with a compound of the Formula III

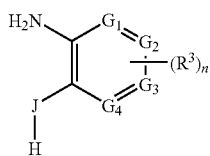

III wherein $G_1$, $G_2$, $G_3$, $G_4$, J, n and $R^3$ have any of the meanings defined hereinbefore except that any functional group is protected if necessary, in the presence of a suitable acid, to form a compound of the Formula I, whereafter any protecting group that is present is removed.

A suitable reactive derivative of a carboxylic acid of the Formula II is, for example an acyl halide, for example an acyl chloride formed by the reaction of the acid with an inorganic acid chloride, for example thionyl chloride; a mixed anhydride, for example an anhydride formed by the reaction of the acid with a chloroformate such as isobutyl chloroformate; an active ester, for example an ester formed by the reaction of the acid with a phenol such as pentafluorophenol, with an ester such as pentafluorophenyl trifluoroacetate or with an alcohol such as methanol, ethanol, isopropanol, butanol or N-hydroxybenzotriazole; an acyl azide, for example an azide formed by the reaction of the acid with an azide such as diphenylphosphoryl azide; an acyl cyanide, for example a cyanide formed by the reaction of an acid with a cyanide such as diethylphosphoryl cyanide; or the product of the reaction of the acid with a carbodiimide such as dicyclohexylcarbodiimide or with a uronium compound such as 2-(7-azabenzotriazol-1-yl)-1,1,3,3-tetramethyluronium hexafluorophosphate(V) or with 1-hydroxybenzotriazole.

A suitable acid for the reaction is, for example, an inorganic acid such as, for example, hydrochloric acid, hydrobromic acid or polyphosphoric acid or, for example, an organic acid such as, for example, acetic acid or trifluoroacetic acid. Conveniently, the acid used in the reaction is polyphosphoric acid and the reaction is conveniently carried out at a temperature in the range, for example, 50 to 250° C., conveniently at or near 200° C.

Carboxylic acid compounds of the Formula II, including reactive derivatives thereof such as an ester thereof, may, for example, be prepared by the cross coupling reaction, conveniently in the presence of a suitable catalyst, of a compound of the Formula IV

IV wherein Ring A has any of the meanings defined hereinbefore except that any functional group present on Ring A is protected if necessary and Y is $Sn(L^0)_3$, ZnI or $B(L^1)(L^2)$, wherein $L^0$ is a suitable ligand for the tin atom and wherein each of $L^1$ and $L^2$, which may be the same or different, is a suitable ligand for the boron atom, with a pyridine or pyrazine compound of the Formula V

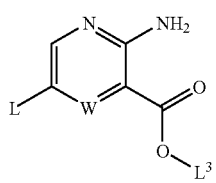

V wherein L is a displaceable group, $L^3$ is hydrogen or a protecting group such as methyl and W has any of the meanings defined hereinbefore, whereafter any protecting group that is present is removed.

A suitable value for the ligand $L^0$ which is present on the Sn atom of the tin reagent includes, for example (1-6C)alkyl, such as for example n-butyl.

A suitable value for the ligands $L^1$ and $L^2$ which are present on the boron atom of the organoboron reagent include, for example, a hydroxyl or a (1-4C)alkoxy, for example a methoxy, ethoxy, propoxy, isopropoxy or butoxy ligand. Alternatively the ligands $L^1$ and $L^2$ may be linked such that, together with the boron atom to which they are attached, they form a ring. For example, $L^1$ and $L^2$ together may define an oxy-(2-4C)alkylene-oxy group, for example an oxyethyleneoxy, oxytrimethyleneoxy group or —O—C(CH$_3$)$_2$C(CH$_3$)$_2$—O— group such that, together with the boron atom to which they are attached, they form a cyclic boronic acid ester group. Particularly suitable organoboron reagents include, for example, compounds wherein each of $L^1$ and $L^2$ is a hydroxy, a isopropoxy or an ethyl group or $L^1$ and $L^2$ together define a group of formula —O—C(CH$_3$)$_2$C(CH$_3$)$_2$—O—.

A suitable displaceable group L is, for example, a halogeno group such as a chloro, bromo, iodo group or a trifluoromethanesulphonyl group.

A suitable catalyst for the cross coupling reaction includes, for example, a metallic catalyst such as a palladium(0), palladium(II), nickel(0) or nickel(II) catalyst, for example tetrakis(triphenylphosphine)palladium(0), palladium(II) chloride, palladium(II) bromide, bis(triphenylphosphine) palladium(II) chloride, tetrakis(triphenylphosphine)nickel (0), nickel(II) chloride, nickel(II) bromide, bis (triphenylphosphine)nickel(II) chloride, [1,1'-bis (diphenylphosphino)ferrocene]dichloropalladium(II) or tris (dibenzilideneacetone)dipalladium. Optionally, the catalyst can be formed in-situ by the reaction of one or more of the above catalysts with a trialkylphosphine, such as, for example, tri-N-butylphosphine or tricyclohexylphosphine.

Conveniently, the reaction is conducted in the presence of a suitable base such as an alkali or alkaline earth metal carbonate or hydroxide, for example sodium carbonate, caesium carbonate or potassium carbonate, caesium fluoride, or an organic base such as pyridine, 4-dimethylaminopyridine, triethylamine or N-methylmorpholine.

The reaction is conveniently carried out in the presence of a suitable solvent or diluent, for example N,N-dimethylformamide, water, tetrahydrofuran, 1,4-dioxane, 1,2-dimethoxyethane, benzene, toluene, xylene, methanol or ethanol and at a temperature in the range, for example 10 to 250° C., preferably in the range 60 to 180° C.

The cross-coupling reaction can also be conducted where the Y group of compound IV is hydrogen. Such a reaction is conveniently carried out in the presence of a suitable catalyst as defined herein-before. Conveniently, a suitable base is also present for such a reaction such as an alkali or alkaline earth metal carbonate or hydroxide, for example sodium carbonate, caesium carbonate or potassium carbonate, caesium fluoride, or an organic base such as pyridine, 4-dimethylaminopyridine, triethylamine or N-methylmorpholine.

The reaction is conveniently carried out in the presence of a suitable solvent or diluent, for example N,N-dimethylformamide, N,N-dimethylacetamide or dimethyl sulphoxide and at a temperature in the range, for example 10 to 250° C., preferably in the range 100 to 180° C. Typical conditions for such a reaction are described in *Organic Letters*, 2003, 5, 4835.

Carboxylic acids of the Formula II can also be prepared using an inverse coupling process to that described above, wherein the compound of Formula IV would have an L group (which is a displacable group as defined hereinbefore) in place of the Y group and the compound of Formula V would have a Y group (being Sn($L^0$)$_3$, ZnI or B($L^1$)($L^2$) as defined hereinbefore) present in place of the L group. Suitable conditions for the reaction would be those described above.

Compounds of the Formulae III, IV and V may be obtained by conventional procedures or are commercially available, known in the literature, or they can be prepared by standard processes known in the art.

(b) The cross coupling reaction, conveniently in the presence of a suitable catalyst as defined hereinbefore, of a pyridine or pyrazine compound of the Formula VI

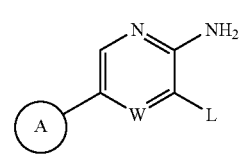

VI wherein L is a displaceable group as defined hereinbefore and W and Ring A have any of the meanings defined hereinbefore except that any functional group present on Ring A is protected if necessary, with a compound of the Formula VII

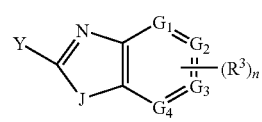

VII wherein Y is Sn($L^0$)$_3$, ZnI or B($L^1$)($L^2$), wherein $L^0$ is a suitable ligand for the tin atom and wherein each of $L^1$ and $L^2$, which may be the same or different, is a suitable ligand for the boron atom as defined hereinbefore, and $G_1$, $G_2$, $G_3$, $G_4$, J, n and $R^3$ have any of the meanings defined hereinbefore except that any functional group is protected if necessary, whereafter any protecting group that is present is removed.

Conveniently, the reaction is conducted in the presence of a suitable base such as an alkali or alkaline earth metal carbonate or hydroxide, for example sodium carbonate, caesium carbonate or potassium carbonate, caesium fluoride, or an organic base such as pyridine, 4-dimethylaminopyridine, triethylamine or morpholine.

The reaction is conveniently carried out in the presence of a suitable inert solvent or diluent, for example N,N-dimethylformamide, water, tetrahydrofuran, 1,4-dioxane, 1,2-dimethoxyethane, benzene, toluene, xylene, methanol or ethanol and at a temperature in the range, for example 10 to 250° C., preferably in the range 60 to 180° C.

The cross-coupling reaction can also be conducted where the Y group of compound IV is hydrogen. Suitable conditions for the procedure are as described for the preparation of compounds of the Formula II in process variant (a).

Compounds of the Formula VI may be prepared, for example, by the cross coupling reaction, conveniently in the presence of a suitable catalyst as defined hereinbefore, of a pyridine or pyrazine compound of the Formula VIII

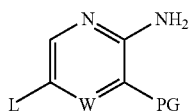

wherein L is a displaceable group as defined hereinbefore and PG is a protecting group and W has any of the meanings defined hereinbefore, with a compound of the Formula IV

wherein Y is $Sn(L^0)_3$, ZnI or $B(L^1)(L^2)$, wherein $L^0$ is a suitable ligand for the tin atom and wherein each of $L^1$ and $L^2$, which may be the same or different, is a suitable ligand for the boron atom as defined hereinbefore and Ring A has any of the meanings defined hereinbefore except that any functional group present on Ring A is protected if necessary, whereafter the protecting group PG is converted by way of a functional group interconversion into a displaceable group L.

A suitable protecting group PG is, for example, a hydrogen group that may be converted to a bromo group by brominating conditions such as phosphorous tribromide or N-bromosuccinimide, conveniently in the presence of a suitable base such as pyridine or triethylamine, in a suitable solvent such as methylene chloride and at a suitable temperature such as −30 to 100° C., conveniently at or near 30° C.

Conveniently, the protecting group PG is a displaceable group L as defined hereinbefore, in which case, provided that the compound of Formula IV reacts selectively with the displaceable group that is located at the 4-position (relative to the amino group) in the pyridine or pyrazine compound of the Formula VIII, no conversion of the protecting group is necessary.

The cross-coupling reaction can also be conducted where the Y group of compound IV is hydrogen. Suitable conditions for the procedure are as described for the preparation of compounds of the Formula II in process variant (a).

Compounds of the Formula VIII are commercially available, known in the literature or can be prepared by standard processes known in the art.

Compounds of the Formula VII may be prepared by the reaction of a compound of the Formula IX

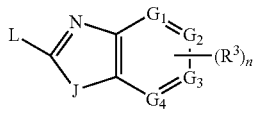

wherein L is a displaceable group as defined hereinbefore and $G_1$, $G_2$, $G_3$, $G_4$, J, n and $R^3$ have any of the meanings defined hereinbefore except that any functional group is protected if necessary, with a boron, tin or zinc reagent, whereafter any protecting group that is present is removed.

Conveniently, L is a halogeno group such as a bromo or iodo group.

Synthetic procedures for forming heteroarylboron reagents from heteroaryl halides are well known in the art, for example, a 2-halogeno-substituted benzoxazole compound of the Formula IX may be reacted with a boron reagent such as bis(pinacolato)diboron or diborane, conveniently in the presence of a suitable base such as pyridine or triethylamine, in a solvent such as tetrahydrofuran and at a temperature in the range −10 to 75° C., conveniently in the range 0 to 30° C.

Synthetic procedures for forming heteroarylzinc or tin reagents from heteroaryl halides are also well known in the art, for example, a 2-halogeno-substituted benzoxazole compound of the Formula IX may be reacted with an alkyl lithium in a solvent such as tetrahydrofuran at a temperature in the range −100° C. to 25° C., and then transmetallated with zinc iodide or a trialkyltin halide to form the heteroarylzinc or tin reagent.

Compounds of the Formula IX are commercially available, known in the literature, or can be prepared by standard processes known in the art.

(c) The cross coupling reaction, conveniently in the presence of a suitable catalyst as defined hereinbefore, of a compound of the Formula X

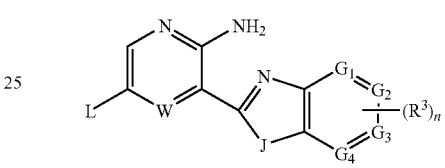

wherein L is a displaceable group as defined hereinbefore and $G_1$, $G_2$, $G_3$, $G_4$, J, W, n and $R^3$ have any of the meanings defined hereinbefore except that any functional group is protected if necessary, with a compound of the Formula IV

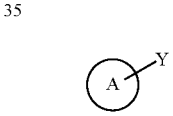

wherein Y is $Sn(L^0)_3$, ZnI or $B(L^1)(L^2)$, wherein $L^0$ is a suitable ligand for the tin atom and wherein each of $L^1$ and $L^2$, which may be the same or different, is a suitable ligand for the boron atom as defined hereinbefore and Ring A has any of the meanings defined hereinbefore except that any functional group present on Ring A is protected if necessary, whereafter any protecting group that is present is removed.

Conveniently, the reaction is conducted in the presence of a suitable base such as an alkali or alkaline earth metal carbonate, hydroxide or phosphate, for example sodium carbonate, caesium carbonate or potassium carbonate, caesium fluoride, sodium phosphate, potassium phosphate, or an organic base such as pyridine, 4-dimethylaminopyridine, triethylamine or N-methyl morpholine.

The reaction is conveniently carried out in the presence of a suitable solvent or diluent, for example N,N-dimethylformamide, water, tetrahydrofuran, 1,4-dioxan, 1,2-dimethoxyethane, benzene, toluene, xylene, methanol or ethanol and at a temperature in the range, for example 10 to 250° C., preferably in the range 60 to 180° C.

The cross-coupling reaction can also be conducted where the Y group of compound IV is hydrogen. Suitable conditions for the procedure are as described for the preparation of compounds of the Formula II in process variant (a).

Compound of the Formula I can also be prepared using an inverse coupling process to that described above, wherein the compound of Formula IV would have an L group (which is a displacable group as defined hereinbefore) in place of the Y group and the compound of Formula X would have a Y group (being Sn(L⁰)₃, ZnI or B(L¹)(L²) as defined hereinbefore) present in place of the L group. Suitable conditions for the reaction would be those described immediately above. The compound of the Formula X can have a protecting group on the NH₂ group of the pyridine or pyrazine ring. Suitable examples of such a protected NH₂ group include, for example, a di-(tert-butoxycarbonyl)amino group or a 2,5-dimethylpyrrol-1-yl group.

Compounds of the Formula X may be produced using analogous procedures to those described in process variant (a) hereinbefore. For example, a carboxylic acid, or a reactive derivative thereof as defined hereinbefore, of the Formula XI

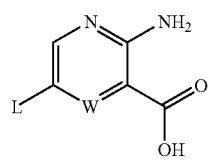

XI wherein L is a displaceable group as defined hereinbefore and W has any of the meanings defined hereinbefore, may be reacted with a compound of the Formula III

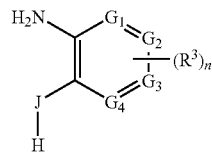

III wherein $G_1$, $G_2$, $G_3$, $G_4$, J, n and $R^3$ have any of the meanings defined hereinbefore except that any functional group is protected if necessary, to form a compound of the Formula I, whereafter any protecting group that is present is removed.

A suitable reactive derivative of a carboxylic acid of the Formula XI is, for example, an acyl halide, for example an acyl chloride formed by the reaction of the acid with an inorganic acid chloride, for example thionyl chloride; a mixed anhydride, for example an anhydride formed by the reaction of the acid with a chloroformate such as isobutyl chloroformate; an active ester, for example an ester formed by the reaction of the acid with a phenol such as pentafluorophenol, with an ester such as pentafluorophenyl trifluoroacetate or with an alcohol such as methanol, ethanol, isopropanol, butanol or N-hydroxybenzotriazole; an acyl azide, for example an azide formed by the reaction of the acid with an azide such as diphenylphosphoryl azide; an acyl cyanide, for example a cyanide formed by the reaction of an acid with a cyanide such as diethylphosphoryl cyanide; or the product of the reaction of the acid with a carbodiimide such as dicyclohexylcarbodiimide or with a uronium compound such as 2-(7-azabenzotriazol-1-yl)-1,1,3,3-tetramethyluronium hexafluorophosphate(V) or with 1-hydroxybenzotriazole.

A suitable acid for the reaction is, for example, an inorganic acid such as, for example, hydrochloric acid, hydrobromic acid or polyphosphoric acid or, for example, an organic acid such as, for example, acetic acid or trifluoroacetic acid. Conveniently, the acid used in the reaction is polyphosphoric acid and the reaction is conveniently carried out at a temperature in the range, for example, 50 to 250° C., conveniently at or near 200° C.

Alternatively, compounds of the Formula X may be produced by reacting a carboxylic acid, or a reactive derivative thereof as defined hereinbefore, of the Formula XIa

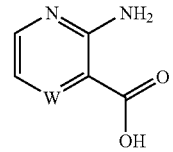

XIa wherein W has any of the meanings defined hereinbefore, with a compound of the Formula III

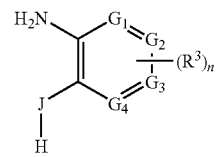

III wherein $G_1$, $G_2$, $G_3$, $G_4$, J, n and $R^3$ have any of the meanings defined hereinbefore except that any functional group is protected if necessary, to form a compound of the Formula Xa

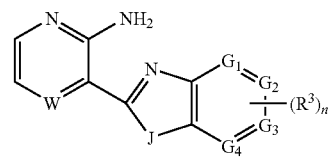

Xa which is halogenated by reacting with a halogenating agent, for example a brominating agent, such as for example bromine or 1-bromopyrrolidine-2,5-dione to form a compound of the Formula X, whereafter any protecting group that is present is removed.

A suitable reactive derivative of a carboxylic acid of the Formula XIa is, for example, an acyl halide, for example an acyl chloride formed by the reaction of the acid with an inorganic acid chloride, for example thionyl chloride or by the reaction of the acid with triphenylphosphine and 2,2,2-trichloroacetonitrile; a mixed anhydride, for example an anhydride formed by the reaction of the acid with a chloroformate such as isobutyl chloroformate; an active ester, for example an ester formed by the reaction of the acid with a phenol such as pentafluorophenol, with an ester such as pentafluorophenyl trifluoroacetate or with an alcohol such as methanol, ethanol, isopropanol, butanol or N-hydroxybenzotriazole; an acyl azide, for example an azide formed by the reaction of the acid with an azide such as diphenylphosphoryl azide; an acyl cyanide, for example a cyanide formed by the reaction of an acid with a cyanide such as diethylphosphoryl cyanide; or the product of the reaction of the acid with a carbodiimide such as dicyclohexylcarbodiimide or with a uronium compound such as 2-(7-azabenzotriazol-1-yl)-1,1,3,3-tetramethyluronium hexafluorophosphate(V) or with 1-hydroxybenzotriazole.

A suitable acid for the coupling reaction is, for example, an inorganic acid such as, for example, hydrochloric acid, hydrobromic acid or polyphosphoric acid or, for example, an organic acid such as, for example, acetic acid or trifluoroacetic acid. Conveniently, the acid used in the reaction is polyphosphoric acid and the reaction is conveniently carried out at a temperature in the range, for example, 50 to 250° C., conveniently at or near 150° C.

The halogenation of compound Xa is suitably carried out in the presence of a solvent or diluent such as for example, N,N-dimethylformamide, tetrahydrofuran, 1,4-dioxane, 1,2-dimethoxyethane, benzene, halogenated solvents such as dichloromethane, chloroform or carbon tetrachloride and at a temperature in the range, for example −50° C. to 100° C., preferably in the range 0° C. to 30° C.

Compounds of the Formula XI and XIa may be obtained by conventional procedures such as those disclosed in the Examples that are set out hereinafter or they are commercially available, known in the literature, or they can be prepared by standard processes known in the art.

(d) For the production of those compounds of the Formula I wherein $R^1$ is a group of the formula $R^4$—$X^1$— wherein $X^1$ is $N(R^5)CO$, the acylation, conveniently in the presence of a suitable base, of an amine of the Formula XII $$R^4\text{—}NH(R^5) \qquad \text{XII}$$

wherein $R^4$ and $R^5$ have any of the meanings defined hereinbefore except that any functional group is protected if necessary, with a carboxylic acid of the Formula XIII

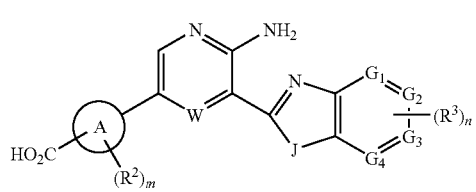

XIII or a reactive derivative thereof as defined hereinbefore, wherein m is 0, 1, 2 or 3 and $R^2$, $G_1$, $G_2$, $G_3$, $G_4$, J, W, n and $R^3$ have any of the meanings defined hereinbefore except that any functional group is protected if necessary, whereafter any protecting group that is present is removed.

A suitable base is, for example, an organic amine base such as, for example, pyridine, 2,6-lutidine, collidine, 4-dimethylaminopyridine, triethylamine, N-methylmorpholine or diazabicyclo[5.4.0]undec-7-ene, or, for example, an alkali or alkaline earth metal carbonate or hydroxide, for example sodium carbonate, potassium carbonate, calcium carbonate, sodium hydroxide or potassium hydroxide.

The reaction is conveniently carried out in the presence of a suitable inert solvent or diluent, for example an ester such as ethyl acetate, a halogenated solvent such as methylene chloride, chloroform or carbon tetrachloride, an ether such as tetrahydrofuran or 1,4-dioxane, an aromatic solvent such as toluene. Conveniently, the reaction is carried out in the presence of a dipolar aprotic solvent such as N,N-dimethylformamide, N,N-dimethylacetamide, N-methylpyrrolidin-2-one or dimethyl sulphoxide. The reaction is conveniently carried out at a temperature in the range, for example, 0 to 120° C., preferably at or near ambient temperature.

Carboxylic acid starting materials of the Formula XIII may be obtained by conventional procedures such as those disclosed in the Examples that are set out hereinafter. For example, using an analogous procedure to that described in process variant (c), a compound of the Formula X

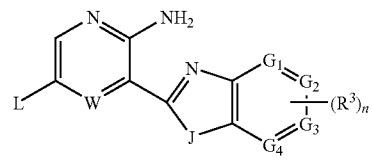

X wherein L is a displaceable group as defined hereinbefore and $G_1$, $G_2$, $G_3$, $G_4$, J, W, n and $R^3$ have any of the meanings defined hereinbefore except that any functional group is protected if necessary, may be reacted, conveniently in the presence of a suitable catalyst as defined hereinbefore, with a compound of the Formula XIV

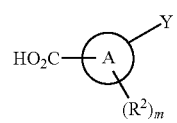

XIV wherein Y is $Sn(L^0)_3$, ZnI or $B(L^1)(L^2)$, wherein $L^0$ is a suitable ligand for the tin atom and wherein each of $L^1$ and $L^2$, which may be the same or different, is a suitable ligand for the boron atom as defined hereinbefore and m is 0, 1, 2 or 3 and Ring A and $R^2$ have any of the meanings defined hereinbefore except that any functional group is protected if necessary, whereafter any protecting group that is present is removed.

Conveniently, the reaction is conducted in the presence of a suitable base such as an alkali or alkaline earth metal carbonate or hydroxide, for example sodium carbonate, caesium carbonate or potassium carbonate, caesium carbonate, or an organic base such as pyridine, 4-dimethylaminopyridine, triethylamine or N-methylmorpholine.

The reaction is conveniently carried out in the presence of a suitable inert solvent or diluent, for example N,N-dimethylformamide, tetrahydrofuran, 1,4-dioxane, 1,2-dimethoxyethane, benzene, toluene, xylene, methanol or ethanol and at a temperature in the range, for example 10 to 250° C., preferably in the range 60 to 180° C.

The cross-coupling reaction can also be conducted where the Y group of compound IV is hydrogen. Suitable conditions for the procedure are as described for the preparation of compounds of the Formula II in process variant (a).

Compounds of the Formula XII and of the Formula XIV may be obtained by conventional procedures such as those disclosed in the Examples that are set out hereinafter or they are commercially available, known in the literature, or they can be prepared by standard processes known in the art.

(e) For the production of those compounds of the Formula I wherein $R^1$ is a group of the formula $Q^1$-$X^2$— wherein $X^2$ is $N(R^7)CO$, the acylation, conveniently in the presence of a suitable base as defined hereinbefore, of an amine of the Formula XV $$Q^1\text{-}NH(R^7) \qquad \text{XV}$$

wherein $Q^1$ and $R^7$ have any of the meanings defined hereinbefore except that any functional group is protected if necessary, with a carboxylic acid of the Formula XIII

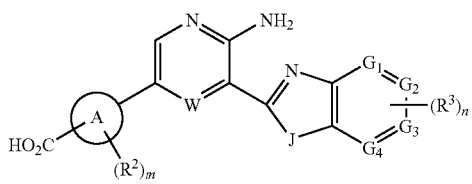

or a reactive derivative thereof as defined hereinbefore, wherein m is 0, 1, 2 or 3 and $R^2$, $G_1$, $G_2$, $G_3$, $G_4$, J, W, n and $R^3$ have any of the meanings defined hereinbefore except that any functional group is protected if necessary, whereafter any protecting group that is present is removed.

The reaction is conveniently carried out in the presence of a suitable inert solvent or diluent, such as those defined hereinbefore for process variant (d). The reaction is conveniently carried out at a temperature in the range, for example, 0 to 120° C., preferably at or near ambient temperature.

Compounds of the Formula XV may be obtained by conventional procedures such as those disclosed in the Examples that are set out hereinafter or they are commercially available, known in the literature, or they can be prepared by standard processes known in the art.

(f) For the production of those compounds of the Formula I wherein $R^1$ is a group of the formula $R^4$—$X^1$— wherein $X^1$ is O, the reaction of a phenol of the Formula XVI

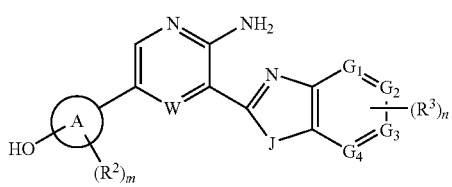

wherein m is 0, 1, 2 or 3 and $R^2$, $G_1$, $G_2$, $G_3$, $G_4$, J, W, n and $R^3$ have any of the meanings defined hereinbefore except that any functional group is protected if necessary, with an alkylating agent of the Formula XVII $R^4$-L    XVII wherein L is a displaceable group as defined hereinbefore and $R^4$ has any of the meanings defined hereinbefore except that any functional group is protected if necessary, whereafter any protecting group that is present is removed.

The alkylation reaction is conveniently carried out in the presence of a suitable base as defined hereinbefore. For example, a suitable base is, for example, an organic amine base such as, for example, pyridine, 2,6-lutidine, collidine, 4-dimethylaminopyridine, triethylamine, N-methylmorpholine or diazabicyclo[5.4.0]undec-7-ene, or, for example, an alkali or alkaline earth metal carbonate or hydroxide, for example sodium carbonate, potassium carbonate, calcium carbonate, sodium hydroxide or potassium hydroxide.

The reaction is conveniently carried out in the presence of a suitable inert solvent or diluent, for example an ester such as ethyl acetate, a halogenated solvent such as methylene chloride, an ether such as tetrahydrofuran or 1,4-dioxane or an aromatic solvent such as toluene. Conveniently, the reaction is carried out in the presence of a dipolar aprotic solvent such as N,N-dimethylformamide, N,N-dimethylacetamide, N-methylpyrrolidin-2-one or dimethyl sulphoxide. The reaction is conveniently carried out at a temperature in the range, for example, 0 to 150° C., conveniently in the range, for example, 50 to 120° C.

Alternatively, the displaceable group L may be a hydroxy group, in which case the reaction is carried out in the presence of a mixture of an azo compound such as diethyl or di-tert-butyl azodicarboxylate and a phosphine such as triphenylphosphine. The reaction is conveniently carried out in the presence of a suitable inert solvent or diluent, for example a halogenated solvent such as methylene chloride or an ether such as tetrahydrofuran at a temperature in the range, for example, 10 to 150° C., preferably at or near ambient temperature.

Compounds of the Formula XVI may be prepared using analogous procedures to those described in process variant (a) hereinbefore. For example, a carboxylic acid of the Formula XVIII

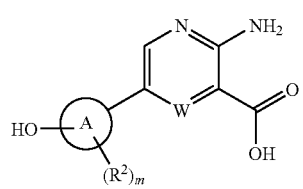

or a reactive derivative thereof as defined hereinbefore, wherein m is 0, 1, 2 or 3 and Ring A, W and $R^2$ have any of the meanings defined hereinbefore except that any functional group is protected if necessary, may be reacted with a compound of the Formula III

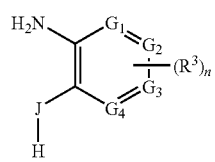

wherein $G_1$, $G_2$, $G_3$, $G_4$, J, n and $R^3$ have any of the meanings defined hereinbefore except that any functional group is protected if necessary, in the presence of a suitable acid, to form a compound of the Formula I, whereafter any protecting group that is present is removed.

A suitable reactive derivative of a carboxylic acid of the Formula XVIII is, for example an acyl halide, for example an acyl chloride formed by the reaction of the acid with an inorganic acid chloride, for example thionyl chloride; a mixed anhydride, for example an anhydride formed by the reaction of the acid with a chloroformate such as isobutyl chloroformate; an active ester, for example an ester formed by the reaction of the acid with a phenol such as pentafluorophenol, with an ester such as pentafluorophenyl trifluoroacetate or with an alcohol such as methanol, ethanol, isopropanol, butanol or N-hydroxybenzotriazole; an acyl azide, for example an azide formed by the reaction of the acid with an azide such as diphenylphosphoryl azide; an acyl cyanide, for example a cyanide formed by the reaction of an acid with a cyanide such as diethylphosphoryl cyanide; or the product of the reaction of the acid with a carbodiimide such as dicyclohexylcarbodiimide or with a uronium compound such as 2-(7-azabenzotriazol-1-yl)-1,1,3,3-tetramethyluronium hexafluorophosphate(V) or with 1-hydroxybenzotriazole.

A suitable acid for the reaction is, for example, an inorganic acid such as, for example, hydrogen chloride, hydrogen bromide or polyphosphoric acid or, for example, an organic acid such as, for example, acetic acid or trifluoroacetic acid. Conveniently, the acid used in the reaction is polyphosphoric acid and the reaction is conveniently carried out at a temperature in the range, for example, 50 to 250° C., conveniently at or near 200° C.

Compounds of the Formula XVIII may be obtained by analogous procedures to those described in the starting material portion of process variant (a) hereinbefore. For example, pyridine or pyrazine carboxylic acids of the Formula XVIII, including reactive derivatives thereof such as an ester thereof, may be prepared by the cross coupling reaction, conveniently in the presence of a suitable catalyst as defined hereinbefore, of a compound of the Formula XIX

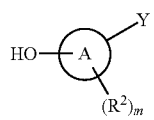

XIX wherein Y is $Sn(L^0)_3$, ZnI or $B(L^1)(L^2)$, wherein $L^0$ is a suitable ligand for the tin atom and wherein each of $L^1$ and $L^2$, which may be the same or different, is a suitable ligand for the boron atom as defined hereinbefore and m is 0, 1, 2 or 3 and Ring A and $R^2$ have any of the meanings defined hereinbefore except that any functional group is protected if necessary, with a pyrazine of the Formula V

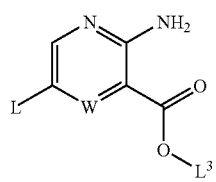

V or a reactive derivative thereof as defined hereinbefore, wherein L is a displaceable group as defined hereinbefore and $L^3$ is hydrogen or a protecting group such as methyl and W has any of the meanings defined hereinbefore, whereafter any protecting group that is present may be removed.

Compounds of the Formulae XVII and XIX may be obtained by conventional procedures such as those disclosed in the Examples that are set out hereinafter or they are commercially available, known in the literature, or they can be prepared by standard processes known in the art.

(g) For the production of those compounds of the Formula I wherein $R^1$ is a group of the formula $Q^1$-$X^2$— wherein $Q^1$ is a heterocyclyl, heterocyclyl-(1-6C)alkyl, heteroaryl, heteroaryl-(1-6C)alkyl, aryl, aryl-(1-6C)alkyl, cycloalkyl or cycloalkyl-(1-6C)alkyl group and $X^2$ is O, the reaction of a phenol of the Formula XVI

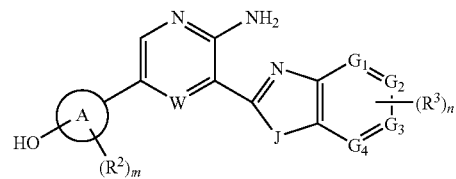

XVI wherein m is 0, 1, 2 or 3 and Ring A, $R^2$, $G_1$, $G_2$, $G_3$, $G_4$, J, W, n and $R^3$ have any of the meanings defined hereinbefore except that any functional group is protected if necessary, with an alkylating agent of the Formula XX $Q^1$-L    XX wherein L is a displaceable group as defined hereinbefore and $Q^1$ has any of the meanings defined immediately above except that any functional group is protected if necessary, whereafter any protecting group that is present is removed.

The alkylation reaction is conveniently carried out in the presence of a suitable base as defined hereinbefore, in the presence of a suitable inert solvent or diluent as defined hereinbefore and at a temperature in the range, for example, 0 to 150° C., conveniently in the range, for example, 50 to 120° C.

Alternatively, the displaceable group L may be a hydroxy group, in which case the reaction is carried out in the presence of a suitable dehydrating agent as defined hereinbefore.

Compounds of the Formula XX may be obtained by conventional procedures such as those disclosed in the Examples that are set out hereinafter or they are commercially available, known in the literature, or they can be prepared by standard processes known in the art.

(h) The reaction of a compound of the Formula XXI

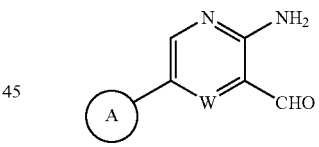

XXI wherein W and Ring A have any of the meanings defined hereinbefore except that any functional group present on Ring A is protected if necessary, with a compound of the Formula III

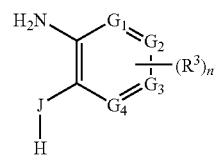

III wherein J, $G_1$, $G_2$, $G_3$, $G_4$, n and $R^3$ have any of the meanings defined hereinbefore except that any functional group is protected if necessary, to provide an intermediate compound or compounds of the Formulae XXII

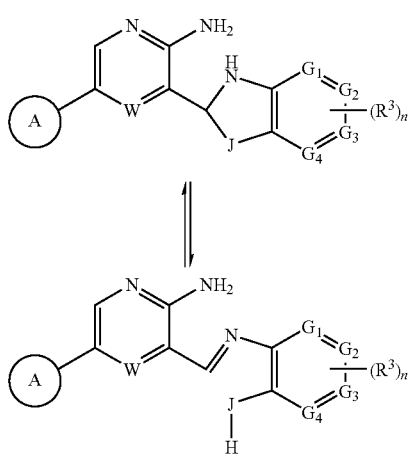

XXII which is oxidised by a suitable oxidising agent, to form a compound of the Formula I, whereafter any protecting group that is present is removed.

The first step in the reaction is conveniently carried out in the presence of a suitable a suitable inert solvent or diluent, for example an alcohol or ester such as methanol, ethanol, isopropanol or ethyl acetate, a halogenated solvent such as methylene chloride, chloroform or carbon tetrachloride, an ether such as tetrahydrofuran or 1,4-dioxane, an aromatic solvent such as toluene, a dipolar aprotic solvent such as N,N-dimethylformamide, N,N-dimethylacetamide, N-methylpyrrolidin-2-one or dimethyl sulphoxide. Conveniently, the reaction is carried out in the presence of methanol. The reaction is conveniently carried out at a temperature in the range, for example, 0 to 120° C., conveniently at or near 50° C.

A suitable agent for the oxidation reaction is, for example, an oxidising agent such as, for example, manganese(IV) oxide, 1,1,1-tris(acetyloxy)-1,1-dihydro-1,2-benziodoxol-3-(1H)-one (Dess-Martin periodinane), potassium permanganate, oxone, m-chloroperbenzoic acid, pyridinium chlorochromate, ammonium cerium (IV) nitrate. Conveniently, the oxidising agent is manganese(IV) oxide. The reaction is conveniently carried out in the presence of a suitable solvent or diluent, such as for example dichloromethane. The reaction is conveniently carried out at a temperature in the range, for example, 0 to 50° C., conveniently at or near 25° C.

Alternatively, the oxidation reaction can be carried out by way of exposure to atmospheric oxygen.

Compounds of the Formula XXI, including reactive derivatives thereof, may, for example, be prepared by reacting a compound of the Formula XXIII

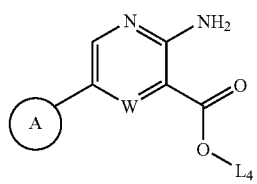

XXIII or a reactive derivative thereof, wherein $L_4$ is methyl or hydrogen and W and Ring A have any of the meanings defined hereinbefore except that any functional group present on Ring A is protected if necessary, with a reducing agent to either (i) when $L_4$ is methyl form a compound of the Formula XXI or alternatively; (ii) when $L_4$ is hydrogen, form a pyridylmethanol or pyrazinylmethanol compound, which is subsequently oxidised to form a compound of the Formula XXI; whereafter any protecting group that is present is removed.

A suitable reactive derivative of a carboxylic acid of the Formula XXIII is, for example an acyl halide, for example an acyl chloride formed by the reaction of the acid with an inorganic acid chloride, for example thionyl chloride; a mixed anhydride, for example an anhydride formed by the reaction of the acid with a chloroformate such as isobutyl chloroformate; an active ester, for example an ester formed by the reaction of the acid with a phenol such as pentafluorophenol, with an ester such as pentafluorophenyl trifluoroacetate or with an alcohol such as methanol, ethanol, isopropanol, butanol or N-hydroxybenzotriazole; an acyl azide, for example an azide formed by the reaction of the acid with an azide such as diphenylphosphoryl azide; an acyl cyanide, for example a cyanide formed by the reaction of an acid with a cyanide such as diethylphosphoryl cyanide; or the product of the reaction of the acid with a carbodiimide such as dicyclohexylcarbodiimide or with a uronium compound such as 2-(7-azabenzotriazol-1-yl)-1,1,3,3-tetramethyluronium hexafluorophosphate(V) or with 1-hydroxybenzotriazole.

For reactions where the compound of Formula XXIII in which $L_4$ is methyl, is converted directly into a compound of the Formula XXI, a suitable reducing agent is an aluminium hydride such as for example dibutyl aluminium hydride. The reaction is conveniently carried out in the presence of a suitable solvent or diluent, such as for example tetrahydrofuran or diethyl ether The reaction is conveniently carried out at a temperature in the range, for example, −100 to 0° C., conveniently at or near −78° C.

For reactions where the compound of Formula XXIII in which $L_4$ is hydrogen, is initially reduced to form a pyridylmethanol or pyrazinylmethanol compound, a suitable reducing agent is, for example, an aluminium or boron derived hydride, such as for example lithium aluminium hydride. The reaction is conveniently carried out in the presence of a suitable solvent or diluent, such as for example tetrahydrofuran or diethyl ether. The reaction is conveniently carried out at a temperature in the range, for example, −50 to 0° C. A suitable agent for the subsequent oxidation reaction is, for example, an oxidising agent such as, for example, manganese(IV) oxide, dess-Martin periodinane, potassium permanganate, oxone, m-chloroperbenzoic acid, pyridinium chlorochromate, ammonium cerium (IV) nitrate. Conveniently, the oxidising agent is manganese(IV) oxide. The reaction is conveniently carried out in the presence of a suitable solvent or diluent, such as for example dichloromethane. The reaction is conveniently carried out at a temperature in the range, for example, 0 to 50° C., conveniently at or near 25° C.

Compounds of the Formula XXIII may be obtained by analogous procedures to those used for preparation of compounds of Formula II as described in variant (a).

(i) The reaction of a compound of the Formula XXIII

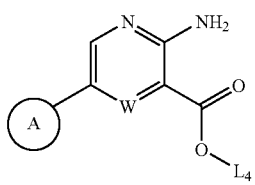

XXIII wherein $L_4$ is a reactive derivative as defined hereinbefore or methyl or hydrogen and W and Ring A have any of the meanings defined hereinbefore except that any functional group present on Ring A is protected if necessary, with a compound of the Formula XXIV

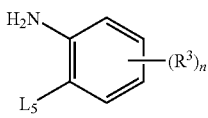

XXIV wherein $L_5$ is iodo or bromo and n and $R^3$ have any of the meanings defined hereinbefore except that any functional group is protected if necessary, to provide an amide of the Formula XXV

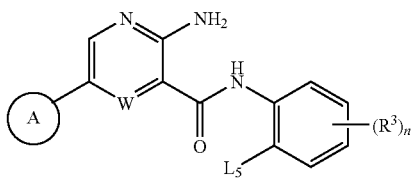

XXV which is cyclised, conveniently in the presence of a suitable catalyst, a suitable base and a copper binding ligand, to form a compound of the Formula I in which J is O, whereafter any protecting group that is present is removed.

When the $L_4$ group of the compound of Formula XXIII is, for example, methyl, the amide formation reaction is conveniently carried out in the presence of a suitable coupling reagent, for example, a trialkylaluminium such as, for example, trimethylaluminium. The reaction is conveniently carried out in the presence of a suitable inert solvent or diluent such as toluene. The reaction is conveniently carried out at a temperature in the range, for example, 0 to 160° C., conveniently at or near 120° C.

When the $L_4$ group of the compound of Formula XXIII is, for example, hydrogen, the amide formation reaction is conveniently carried out in the presence of a suitable base, for example, an organic amine base such as, for example, pyridine, 2,6-lutidine, collidine, 4-dimethylaminopyridine, triethylamine, morpholine, N-methylmorpholine or diazabicyclo[5.4.0]undec-7-ene, or, for example, an alkali or alkaline earth metal carbonate or hydroxide, for example sodium carbonate, potassium carbonate, calcium carbonate, sodium hydroxide or potassium hydroxide. The reaction is conveniently carried out in the presence of a suitable inert solvent or diluent, for example an alcohol or ester such as methanol, ethanol, isopropanol or ethyl acetate, a halogenated solvent such as methylene chloride, chloroform or carbon tetrachloride, an ether such as tetrahydrofuran or 1,4-dioxane, an aromatic solvent such as toluene. Conveniently, the reaction is carried out in the presence of a dipolar aprotic solvent such as N,N-dimethylformamide, N,N-dimethylacetamide, N-methylpyrrolidin-2-one or dimethyl sulphoxide. The reaction is conveniently carried out at a temperature in the range, for example, 0 to 120° C., conveniently at or near ambient temperature.

A suitable catalyst for the cyclisation reaction is, for example, copper (I) iodide.

A suitable base for the cyclisation reaction is, for example, caesium carbonate or potassium carbonate and a suitable copper binding ligand for the cyclisation reaction is 1,10-phenanthroline. The reaction is conveniently carried out in the presence of a suitable solvent or diluent, for example N,N-dimethylacetamide or 1,2-dimethoxyethane. The reaction is conveniently carried out at a temperature in the range, for example, 0 to 160° C., conveniently at or near 120° C.

Compounds of the Formula XXIV may be obtained by conventional procedures such as those disclosed in the Examples that are set out hereinafter or they are commercially available, known in the literature, or they can be prepared by standard processes known in the art.

(j) For the production of those compounds of the Formula I wherein J is S, the reaction of a compound of the Formula XXIII

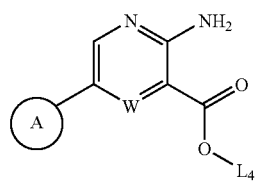

XXIII wherein $L_4$ is a reactive derivative as defined herein-before or methyl or hydrogen and W and Ring A have any of the meanings defined hereinbefore except that any functional group present on Ring A is protected if necessary, with a compound of the Formula XXIV

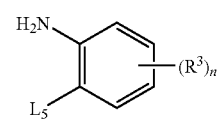

XXIV

wherein $L_5$ is bromo or iodo and n and $R^3$ have any of the meanings defined hereinbefore except that any functional group is protected if necessary, to provide an amide of the Formula XXV

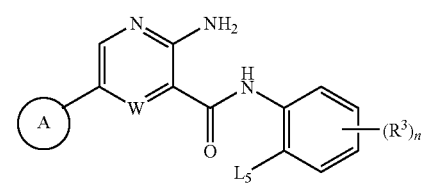

XXV which is subsequently reacted with phosphorus pentasulphide or 2,4-bis(4-methoxyphenyl)-1,3-dithia-2,4-diphosphetane-2,4-disulphide (Lawesson's reagent) to provide a compound of Formula XXVI

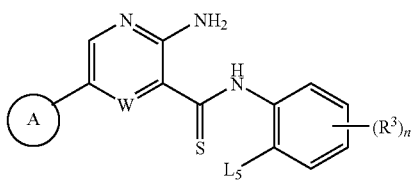

XXVI which is then cyclised, conveniently in the presence of a suitable catalyst, a suitable base and a copper binding ligand as defined hereinbefore, to form a compound of the Formula I in which J is S, whereafter any protecting group that is present is removed.

The amide formation and cyclisation reactions are carried out as described hereinbefore in process variant (i).

The reaction for converting a compound of Formula XXV into a compound of Formula XXVI is conveniently carried out in the presence of a suitable solvent or diluent, for example an ester such as ethyl acetate, a halogenated solvent such as methylene chloride, chloroform or carbon tetrachloride, an ether such as tetrahydrofuran or 1,4-dioxane, an aromatic solvent such as toluene. Conveniently, the reaction is carried out in the presence of toluene at a temperature in the range, for example 10 to 150° C., preferably at or near 110° C.

(k) For the production of those compounds of the Formula I wherein J is S, the reaction of a compound of the Formula XXIII

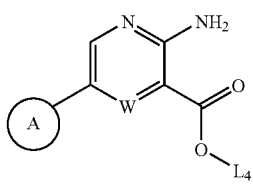

XXIII wherein $L_4$ is a reactive derivative as defined herein-before or methyl or hydrogen and W and Ring A have any of the meanings defined hereinbefore except that any functional group present on Ring A is protected if necessary, with a compound of the Formula XXVII

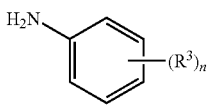

XXVII wherein n and $R^3$ have any of the meanings defined hereinbefore except that any functional group is protected if necessary, to provide an amide of the Formula XXVIII

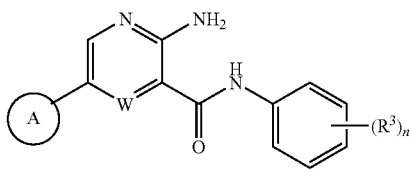

XXVIII which is subsequently reacted with phosphorus pentasulphide or 2,4-bis(4-methoxyphenyl)-1,3-dithia-2,4-diphosphetane-2,4-disulphide (Lawesson's reagent) to provide a compound of Formula XXX

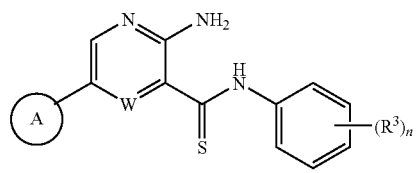

XXIX which is subsequently oxidised, conveniently in the presence of a suitable oxidising agent, to form a compound of the Formula I in which J is S, whereafter any protecting group that is present is removed.

The amide formation reaction is carried out as described hereinbefore in process variant (i).

The reaction for converting a compound of Formula XXVIII into a compound of Formula XXIX is conveniently carried out in the presence of a suitable solvent or diluent, for example an ester such as ethyl acetate, a halogenated solvent such as methylene chloride, chloroform or carbon tetrachloride, an ether such as tetrahydrofuran or 1,4-dioxane, an aromatic solvent such as toluene. Conveniently, the reaction is carried out in the presence of toluene at a temperature in the range, for example 10 to 150° C., preferably at or near 110° C.

A suitable agent for the ring-closing reaction is, for example, an oxidising agent such as, for example, 2,3-dichloro-5,6-dicyano-1,4-benzoquinone (DDQ), ammonium cerium (IV) nitrate, potassium ferricyanide or Dess-Martin periodinane. Conveniently, the oxidising agent is Dess-Martin periodinane. The reaction is conveniently carried out in the presence of a suitable solvent or diluent, such as for example an ester such as ethyl acetate, a halogenated solvent such as dichloromethane, chloroform or carbon tetrachloride, an ether such as tetrahydrofuran or 1,4-dioxane, an aromatic solvent such as toluene. Conveniently, the reaction is carried out in the presence of a halogenated solvent such as dichloromethane. The reaction is conveniently carried out at a temperature in the range, for example, 0 to 50° C., conveniently at or near 25° C.;

(l) The reaction of a compound of the Formula XXV

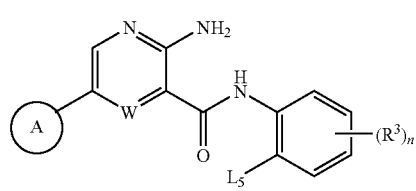

XXV or a reactive derivative thereof, wherein $L_5$, W, Ring A, $R^3$ and n have any of the meanings defined hereinbefore except that any functional group present are protected if necessary, with a thiol introducing agent, to provide a compound of the Formula XXX

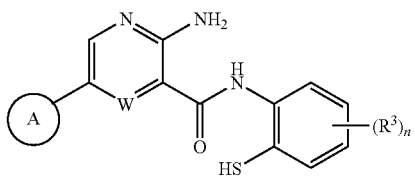

XXX which is subsequently cyclised, optionally in the presence of a dehydrating agent such as a carbodiimide reagent such as for example dicyclohexylcarbodiimide or 1-(3-dimethylaminopropyl)-3-ethylcarbodiimide, to form a compound of the Formula I, whereafter any protecting group that is present is removed.

The skilled person would appreciate that various procedures for converting the $L_5$ group on compound of Formula XXV to an SH group are known in the art. One example is where the thiol converting agent is 2-ethylhexyl 3-mercaptopropionate and a suitable base such as for example sodium ethoxide is used for deprotection of the protecting group on the SH (as described in *Organic Letters*, 2007, 3687).

The cyclisation reaction is conveniently carried out in the presence of a suitable solvent or diluent, for example an ester such as ethyl acetate, a halogenated solvent such as methylene chloride, chloroform or carbon tetrachloride, an ether such as tetrahydrofuran or 1,4-dioxane, an aromatic solvent such as toluene, a dipolar aprotic solvent such as N,N-dimethylformamide, N,N-dimethylacetamide, N-methylpyrrolidin-2-one or dimethyl sulphoxide. The reaction is conveniently carried out at a temperature in the range, for example, 25 to 200° C., conveniently at in the range of 50 to 150° C.; and (m) The reaction of a carboxylic acid of the Formula II

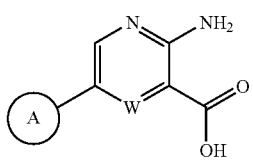

II or a reactive derivative thereof, wherein W and Ring A have any of the meanings defined hereinbefore except that any functional group present on Ring A is protected if necessary, with a compound of the Formula XXXI:

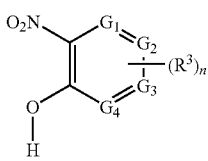

XXXI wherein $G_1$, $G_2$, $G_3$, $G_4$, J, n and $R^3$ have any of the meanings defined hereinbefore except that any functional group is protected if necessary, to form a compound of the Formula XXXII:

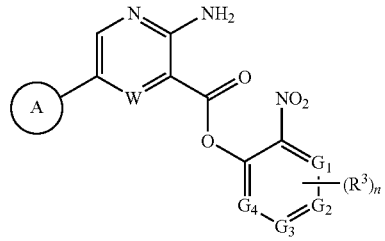

XXXII which is cyclized in the presence of a suitable reducing agent to form a compound of the Formula I, whereafter any protecting group that is present is removed.

This type of reaction is described in *J. Chem. Soc.* (section D), 1969, 12, 680 or *Pakistan J. of Scientific and Industrial Research* 1980, 23, 166

The ester formation reaction is conveniently carried out in the presence of a suitable base, such as for example, an organic amine base such as, for example, pyridine, 2,6-lutidine, collidine, 4-dimethylaminopyridine, triethylamine, morpholine, N-methylmorpholine or diazabicyclo[5.4.0]undec-7-ene or, for example, an alkali or alkaline earth metal carbonate or hydroxide, for example sodium carbonate, potassium carbonate, calcium carbonate, sodium hydroxide or potassium hydroxide. The reaction is conveniently carried out in the presence of a suitable inert solvent or diluent, for example an ester such as ethyl acetate, a halogenated solvent such as methylene chloride, chloroform or carbon tetrachloride, an ether such as tetrahydrofuran or 1,4-dioxane, an aromatic solvent such as toluene. Conveniently, the reaction is carried out in the presence of a dipolar aprotic solvent such as N,N-dimethylformamide, N,N-dimethylacetamide, N-methylpyrrolidin-2-one or dimethyl sulphoxide. The reaction is conveniently carried out at a temperature in the range, for example, 0 to 120° C., conveniently at or near ambient temperature.

A suitable reducing agent for the reaction is, for example, iron, tin or zinc in a suitable inorganic or organic acid such as acetic acid and at a temperature in the range, for example, 20 to 110° C. A suitable reducing agent for the reaction is also, for example, hydrogenation in the presence of a suitable metallic catalyst such as palladium on charcoal. Conveniently, the reaction is carried out in a suitable inert solvent or diluent, for example, ethanol under hydrogen pressure. An alternative suitable reducing agent for the reaction is also, for example, triethylphosphite. Conveniently, the reaction is carried out in a suitable inert solvent or diluent, for example, tert-butylbenzene at a temperature in the range, for example 100 to 200° C.

It is to be understood that any compound of Formula I obtained by any of the processes described hereinbefore can be converted into another compound of the Formula I if required. For example, a reductive amination reaction can be carried out to couple a compound of Formula I obtained by any of the processes described hereinbefore having a nitrogen containing heterocyclyl ring such as, for example, piperidin-4-yl as an $R^1$ group with a suitable aldehyde or ketone to obtain another compound of the Formula I, for example, if formaldehyde, or a equivalent thereof, is used, a compound of Formula I having a 1-methylpiperidin-4-yl $R^1$ group may be obtained. A suitable reducing agent for such a reductive amination reaction is, for example, a hydride reducing agent, for example an alkali metal aluminium hydride such as lithium aluminium hydride or, preferably, an alkali metal borohydride such as sodium borohydride, sodium cyanoborohydride, sodium triethylborohydride, sodium trimethoxyborohydride and sodium triacetoxyborohydride. The reaction is conveniently performed in a suitable inert solvent or diluent, for example tetrahydrofuran and diethyl ether for the more powerful reducing agents such as lithium aluminium hydride, and, for example, methylene chloride or a protic solvent such as methanol and ethanol for the less powerful reducing agents such as sodium triacetoxyborohydride and sodium cyanoborohydride. The reaction is performed at a temperature in the range, for example, 10 to 80° C., conveniently at or near ambient temperature.

A further conversion reaction is where a compound of Formula I obtained by any of the processes described hereinbefore bearing a hydroxyalkyl substitutent on Ring A is activated and then reacted with an appropriate optionally substituted nitrogen containing heterocyclyl ring such as for example 1-methylpiperazine or azetidine, to obtain another compound of the Formula I. For example, if, a compound of Formula I having a 2-hydroxyethyl substituent on Ring A is activated and reacted with 1-methylpiperazine, a compound with a 2-(1-methylpiperazin-4-yl)ethyl $R^1$ group may be obtained. A suitable activating agent for such a reaction is, for example, methanesulphonyl chloride. The reaction is conveniently performed in a suitable inert solvent or diluent, for example tetrahydrofuran, dimethyformide or N-methyl-pyrrolidin-2-one. The reaction is performed at a temperature in the range, for example, 10 to 150° C.

When a pharmaceutically-acceptable salt of a pyridine or pyrazine derivative of the Formula I is required, for example an acid-addition salt, it may be obtained by, for example, reaction of said pyridine or pyrazine derivative with a suitable acid.

When a pharmaceutically-acceptable pro-drug of a pyridine or pyrazine derivative of the Formula I is required, it may be obtained using a conventional procedure. For example, an in vivo cleavable ester of a pyridine or pyrazine derivative of the Formula I may be obtained by, for example, reaction of a compound of the Formula I containing a carboxy group with a pharmaceutically-acceptable alcohol or by reaction of a compound of the Formula I containing a hydroxy group with a pharmaceutically-acceptable carboxylic acid. For example, an in vivo cleavable amide of a pyridine or pyrazine derivative of the Formula I may be obtained by, for example, reaction of a compound of the Formula I containing a carboxy group with a pharmaceutically-acceptable amine or by reaction of a compound of the Formula I containing an amino group with a pharmaceutically-acceptable carboxylic acid.

It will also be appreciated by the person skilled in the organic synthetic arts that certain of the ring substituents in the compounds of the present invention may be introduced by standard aromatic substitution reactions or generated by conventional functional group modifications either prior to or immediately following the processes mentioned above, and as such are included in the process aspect of the invention. Such reactions and modifications include, for example, introduction of a substituent by means of an aromatic substitution reaction, reduction of substituents, alkylation of substituents, acylation of substituents, amidation of substituents and oxidation of substituents. The reagents and reaction conditions for such procedures are well known in the chemical art. Particular examples of aromatic substitution reactions include the introduction of a nitro group using concentrated nitric acid, the introduction of an acyl group using, for example, an acyl halide and Lewis acid (such as aluminium trichloride) under Friedel Crafts conditions; the introduction of an alkyl group using an alkyl halide and Lewis acid (such as aluminium trichloride) under Friedel Crafts conditions; and the introduction of a halogeno group. Particular examples of modifications include the reduction of a nitro group to an amino group by for example, catalytic hydrogenation with a nickel catalyst or treatment with iron in the presence of hydrochloric acid with heating; oxidation of alkylthio to alkylsulphinyl or alkylsulphonyl.

It will also be appreciated that, in some of the reactions mentioned hereinbefore, it may be necessary or desirable to protect any sensitive groups in the compounds. The instances where protection is necessary or desirable and suitable methods for protection are known to those skilled in the art. Conventional protecting groups may be used in accordance with standard practice (for illustration see T. W. Green, Protective Groups in Organic Synthesis, John Wiley and Sons, 1991). Thus, if reactants include groups such as amino, carboxy or hydroxy, it may be desirable to protect the group in some of the reactions mentioned herein.

A suitable protecting group for an amino or alkylamino group is, for example, an acyl group, for example an alkanoyl group such as acetyl, an alkoxycarbonyl group, for example a methoxycarbonyl, ethoxycarbonyl or t-butoxycarbonyl group, an arylmethoxycarbonyl group, for example benzyloxycarbonyl, or an aroyl group, for example benzoyl. The deprotection conditions for the above protecting groups necessarily vary with the choice of protecting group. Thus, for example, an acyl group such as an alkanoyl or alkoxycarbonyl group or an aroyl group may be removed for example, by hydrolysis with a suitable base such as an alkali metal hydroxide, for example lithium or sodium hydroxide. Alternatively an acyl group such as a t-butoxycarbonyl group may be removed, for example, by treatment with a suitable acid as hydrochloric, sulphuric or phosphoric acid or trifluoroacetic acid and an arylmethoxycarbonyl group such as a benzyloxycarbonyl group may be removed, for example, by hydrogenation over a catalyst such as palladium-on-carbon, or by treatment with a Lewis acid for example boron tris(trifluoroacetate). A suitable alternative protecting group for a primary amino group is, for example, a phthaloyl group which may be removed by treatment with an alkylamine, for example dimethylaminopropylamine, or with hydrazine.

A suitable protecting group for a hydroxy group is, for example, an acyl group, for example an alkanoyl group such as acetyl, an aroyl group, for example benzoyl, or an arylmethyl group, for example benzyl. The deprotection conditions for the above protecting groups will necessarily vary with the choice of protecting group. Thus, for example, an acyl group such as an alkanoyl or an aroyl group may be removed, for example, by hydrolysis with a suitable base such as an alkali metal hydroxide, for example lithium or sodium hydroxide. Alternatively an arylmethyl group such as a benzyl group may be removed, for example, by hydrogenation over a catalyst such as palladium-on-carbon.

A suitable protecting group for a carboxy group is, for example, an esterifying group, for example a methyl or an ethyl group which may be removed, for example, by hydrolysis with a base such as sodium hydroxide, or for example a t-butyl group which may be removed, for example, by treatment with an acid, for example an organic acid such as trifluoroacetic acid, or for example a benzyl group which may be removed, for example, by hydrogenation over a catalyst such as palladium-on-carbon.

The protecting groups may be removed at any convenient stage in the synthesis using conventional techniques well known in the chemical art.

Certain of the intermediates defined herein are novel and these are provided as a further feature of the invention. For example, many compounds of the Formulae XI, IV, XXI and XXIII are novel compounds. Many compounds of the Formulae X, XIII, XVI, XVIII, XXII, XXVI, XXIX, XXX and XXXII are also novel compounds. Many compounds of the Formulae II, XXI, XXIII, XXV are also novel compounds.
Biological Assays The following assays can be used to measure the effects of the compounds of the present invention as inhibitors of Axl and cMet tyrosine kinase enzymes, as inhibitors in vitro of the phosphorylation of Axl expressed on NCI H1299 lung large cell carcinoma cells and as inhibitors in vitro of the phosphorylation of cMet expressed on MKN45 cells.

(a) In Vitro Axl Kinase Assay

The assay used AlphaScreen technology (Gray et al., *Analytical Biochemistry,* 2003, 313: 234-245) to determine the ability of test compounds to inhibit phosphorylation by recombinant Axl tyrosine kinase.

N-terminal GST-Axl kinase domain encompassing amino acids 473 to 894 of Axl (GenBank Accession No NM_021913) was expressed in SF126 insect cells and purified using the GST epitope tag, using standard purification techniques.

Test compounds were prepared as 10 mM stock solutions in dimethylsulphoxide (DMSO) and diluted in DMSO as required. Aliquots (120 nl) of compound dilutions were filled into the wells of a Greiner 384-well low volume (LV) white polystyrene plate (Greiner Bio-one) using acoustic dispensing (Labcyte Echo 550). A 10 µl mixture of recombinant purified Axl enzyme, biotinylated peptide substrate (Biotin poly-GAT; CisBio, Catalogue No. 61GATBLB), 0.2 µM adenosine triphosphate (ATP) and a buffer solution [comprising 20 mM Tris-HCl pH 7.5 buffer, 0.01% v/v Tween, 5 mM dithiothreitol (DTT) and 10 mM manganese chloride] was incubated with the compounds at room temperature for 20 minutes.

Control wells that produced a maximum signal corresponding to maximum enzyme activity were created by using 100% DMSO instead of test compound. Control wells that produced a minimum signal corresponding to 100% inhibited enzyme were created by adding 10 µM of Staurosporine.

Each reaction was stopped by the addition of 5 µl of a mixture of 500 mM EDTA, 3 mg/ml bovine serum albumin (BSA) and 20 mM Tris-HCl pH 7.4 buffer containing 40 ng/µl AlphaScreen Streptavidin donor and anti-p-Tyr-100 acceptor beads (Perkin Elmer, Catalogue No. 6760620M). The resultant signals arising from laser light excitation at 680 nM were read using a Packard Envision instrument. The mean data values for each test compound concentration, 100% DMSO control wells and 100% inhibition control wells were used to generate a dose response curve from which the test compound's $IC_{50}$ value and percentage kinase inhibition value at 1 µM concentration were calculated. The $IC_{50}$ value is the concentration of test compound that inhibited 50% of kinase activity. The percentage kinase inhibition value is the percentage of Axl tyrosine kinase activity inhibited by the test compound at a concentration of 1 µM.

(b) Cellular Phospho-Axl ELISA Assay

This assay uses a conventional ELISA method to determine the ability of test compounds to inhibit phosphorylation of tyrosine residues in Axl.

An NCI H1299 lung large cell carcinoma cell line [American Type Culture Collection (ATCC) CRL 5803] was routinely maintained at 37° C. with 5% $CO_2$ in RPMI containing 10% foetal calf serum (FCS) and 2 mM L-glutamine. For the assay, the cells were detached from the culture flask with 'Accutase' (Innovative Cell Technologies Inc., San Diego, Calif., USA; Catalogue No. AT104) using standard tissue culture methods and re-suspended in media to give $0.9 \times 10^5$ cells per ml. 100 µl Aliquots were seeded into each of the wells of a clear 96 well tissue culture plate and the plates were incubated overnight at 37° C. with 5% $CO_2$ to allow the cells to adhere to the wells.

Test compounds were prepared as 10 mM stock solutions in DMSO and serially diluted as required in DMSO to give a range of concentrations. Aliquots of each compound concentration were added to the cells in each well using the Echo 550 (Labcyte Inc., Sunnyvale, Calif., US). Control cells received DMSO only. The cells were incubated for 2 hours at 37° C. with 5% $CO_2$.

The resultant cells were stimulated with 100 ng/ml recombinant mouse GAS6 (R&D Systems Europe Ltd, Abingdon, Oxfordshire, UK; Catalogue No. 986-GS) for 10 minutes at 37° C. with 5% $CO_2$. Cells were lysed by the addition of 50 µl/well of lysis buffer comprising 20 mM Tris-HCl pH 8.0, 137 mM sodium chloride, 2 mM EDTA, 10% v/v glycerol, 1% v/v Igepal CA-630 (Sigma-Aldrich Company Ltd, Gillingham, Dorset, UK; Catalogue No. I3021), 0.5 mM sodium orthovanadate, 1 mM sodium pyrophosphate, 10 mM sodium pyrophosphate, 10 mM glycerophosphate and 1× protease inhibitor tablets (Roche; catalogue number 11836153001). The resultant tissue culture plates were incubated on ice for 30 minutes to ensure full lysis.

High-binding ELISA plates (Corning B.V. Life Sciences, Schiphol-Rijk, The Netherlands; Catalogue No. #3925) were coated with an anti-Axl antibody (R&D Systems; Catalogue No. AF154) at room temperature for 16 hours. The wells were washed 3 times with 250 µl per well of PBS containing 0.05% v/v Tween (PBS/T). The wells were treated with 3% w/v BSA in PBS at ambient temperature for 2 hours and subsequently washed 3 times with 250 µl per well of PBS/T.

50 µl Aliquots of the NCI H1299 cell lysates were added to the ELISA plates. The ELISA plates were incubated for 16 hours at 4° C. and then washed 3 times with 250 µl per well of PBS/T. The cells were incubated for 1 hour at room temperature with a mouse anti-Phospho tyrosine antibody (Upstate, Catalogue No 05-321) diluted in 1% w/v BSA in PBS. Plates were washed three times with 250 µl per well of PBS/T. Subsequently, plates were incubated for 1 hour at room temperature with an anti-mouse horseradish peroxidase conjugated secondary antibody diluted in 1% w/v BSA in PBS.

The plates were washed 3 times with 250 µl per well of PBS/T. Fluorogenic substrate was made up according to manufacturers instructions (Pierce Biotechnology Inc., Rockford Ill., USA; Catalogue No. 15169). 100 µl Aliquots of substrate solution were added to each of the wells and fluorescence was read on a Tecan Ultra plate reader (Tecan UK Ltd., Reading, Berkshire, UK). Fluorescence dose response data obtained with each compound were analysed and the degree of inhibition of phospho-Axl was calculated and expressed as an $IC_{50}$ value and/or a percentage kinase inhibition value at 1 µM concentration. The $IC_{50}$ value is the concentration of test compound that inhibited 50% of kinase activity. The percentage kinase inhibition value is the percentage of kinase activity inhibited by the test compound at a concentration of 1 µM.

(c) In Vitro c-Met Kinase Assay

The assay used AlphaScreen technology (Gray et al., *Analytical Biochemistry,* 2003, 313: 234-245) to determine the ability of test compounds to prevent the activation of c-Met, in which wild type activated c-Met phosphorylates a mutant form of c-Met lacking catalytic activity but retaining the ability to be phosphorylated on the activating residues.

Kinase activity assays were performed in 384-well low-volume white plates (Greiner, 784075) with a total volume of 12 µL in each well. Each kinase reaction contained 40 pg (100 pM) $pY^{1234}pY^{1235}$c-Met(1074-1366) kinase domain, 44 ng (100 nM) cMyc-[D1204N,R1208Q]c-Met(1069-1366)-biotin, 25 mM HEPES (pH7.4), 0.1 mM sodium orthovanadate, 1 mM DTT, 0.01% (v/v) Tween-20, 10 mM magnesium chloride, 0.1% BSA, 50 µM ATP.

Various concentrations of test compounds were each added in 6% (v/v) DMSO to yield a final assay DMSO concentration of 1% (v/v). The kinase reactions were incubated at room temperature for 60 minutes and stopped by adding 5 µL containing 0.5 ng anti-$pYpY^{1234/1235}$c-Met rabbit polyclonal antibody (generated as described below) with 200 ng rabbit IgG Protein A Alphascreen acceptor beads (Perkin Elmer 6760617R) & 200 ng streptavidin donor beads (Perkin Elmer 6760617R) in 25 mM HEPES (pH 7.4), 84.5 mM EDTA, 0.3% BSA under low-level light conditions. Plates were sealed under low-level light conditions & incubated in the dark for 20 hours. Plates were read using an Envision (Perkin Elmer) with excitation at 680 nM, emission 520-620 nM. The mean data values for each test compound concentration, untreated control wells and 100% inhibition control wells were used to determine the test compound's $IC_{50}$ value. The $IC_{50}$ value is the concentration of test compound that inhibits 50% of c-Met kinase activity.

The anti-$pYpY^{1234/1235}$c-Met rabbit polyclonal antibody used in the above assay, was generated by the immunisation of rabbits. Rabbits were immunised 4 times over a 3 month period with Ac-RDMYDKEY(p)Y(p)SVHN(Ahx)C-amide peptide conjugated to BSA (Harlan Sera Labs). Serum was taken at a terminal bleed and this was purified by an ammonium sulphate precipitation followed by affinity purification on dual phosphorylated peptide and non-phosphorylated peptide affinity columns.

(d) Cellular c-Met Inhibition Assay

These and other assays can be used to indicate the ability of a test compound to inhibit c-Met mediated cellular signalling in mammalian cell lines, for example the human tumour cell line MKN45. This is achieved by measuring the amount of phosphorylated c-Met within a cell following compound treatment.

MKN45 cells were routinely passaged in DMEM (Gibco BRL, product number 41966-029) plus 10% foetal calf serum (FCS), 1% L-glutamine (Gibco BRL, product number 25030024), to a confluence not greater than 85%. To undertake the assay, MKN45 cells were seeded at $2\times10^4$ cells/well in DMEM plus 0.5% foetal calf serum, 1% L-glutamine in 96 well plates (Costar, product number 3904) and incubated at 37° C. (+5% $CO_2$) in a humidified incubator. Once the cells had fully adhered (typically following overnight incubation) plates were dosed with 25 µl compound (diluted from 10 mM stock in DMSO using serum free DMEM) and the plates were returned to a humidified 37° C. (+5% $CO_2$) incubator for one hour. Following incubation the cells were fixed by adding formaldehyde (4% final concentration) and incubating at room temperature for 20 minutes. The fixative solution was removed and the wells were washed three times with 100 µl phosphate buffered saline (PBS) before permeabilising the cells by the addition of 50 µl/well 0.1% triton/PBS for 20 minutes at room temperature. The permeabilisation solution was removed and the cells were washed twice more with 100 µl/well PBS before the addition of 40 µl/well anti-phospho $pYpY^{1230/4/5}$ c-Met (Biosource, product number 44-888G-CS2), diluted 1/500 with PBS plus 10% FCS. Following incubation at room temperature for 1 hour, the antibody solution was removed and the wells were washed twice with 100 µl/well PBS. 50 µl/well 1/400 goat anti-rabbit Alexa Fluor 594 secondary antibody (Molecular Probes, product number A11012) and 1/10000 Hoescht (Molecular Probes, product number H-3570) diluted with PBS plus 10% FCS was added and the plate incubated in the dark at room temperature for one hour. Finally, the plates were washed three times with 100 µl/well PBS, leaving the final wash in the wells before sealing the plates. The plates were read using an Arrayscan II (Cellomics). The mean average intensity fluorescence values for each test compound concentration, untreated control wells and 100% inhibition control wells were used to determine the test compound's $IC_{50}$ value. The $IC_{50}$ value is the concentration of test compound that inhibits 50% of c-Met phosphorylation.

Although the pharmacological properties of the compounds of the Formula I vary with structural change as expected, in general activity possessed by compounds of the Formula I may be demonstrated at the following concentrations or doses in one or more of the above tests (a), (b), (c) and (d):—

| | |
|---|---|
| Test (a):- | $IC_{50}$ versus Axl tyrosine kinase in the range, for example, 1 nM-25 µM; |
| Test (b):- | $IC_{50}$ versus cellular phospho-Axl in the range, for example, 1 nM-25 µM; |
| Test (c):- | $IC_{50}$ versus c-Met tyrosine kinase, in the range for example, 0.1-20 µM; |
| Test (d):- | $IC_{50}$ versus cellular phospho-c-Met ($pYpYpY^{1230/4/5}$) in the range, for example, 0.01-20 µM; |

Preferred compounds of the invention possess activity at the following concentrations or doses in one or more of the above tests (a), (b), (c) and (d):—

Test (a):—$IC_{50}$ versus Axl tyrosine kinase in the range, for example, 1 nM-10 µM;

Test (b):—$IC_{50}$ versus cellular phospho-Axl in the range, for example, 1 nM-10 µM;

Test (c):—$IC_{50}$ versus c-Met tyrosine kinase in the range, for example, 0.1-10 µM;

Test (d):—$IC_{50}$ versus cellular phospho-c-Met ($pYpYpY^{1230/4/5}$) in the range, for example, 0.01-10 µM;

For example, the pyridine compound disclosed as the second Compound listed in Table III within Example 7 possesses activity in Test (a) with an $IC_{50}$ versus Axl tyrosine kinase of approximately 24 nM; and activity in Test (b) with an $IC_{50}$ versus cellular phospho-Axl of approximately 39 nM (this mean $IC_{50}$ value was later recalculated from a larger number of replicates and found to be 111 nM); and activity in Test (c) with an $IC_{50}$ versus c-Met tyrosine kinase of approximately 1.95 µM; and activity in Test (d) with an $IC_{50}$ versus cellular phospho-c-Met ($pYpYpY^{1230/4/5}$) of approximately 0.59 µM (this mean $IC_{50}$ value was later recalculated from a larger number of replicates and found to be 0.95 µM).

For example, the pyridine compound disclosed as Example 23 possesses activity in Test (a) with an $IC_{50}$ versus Axl tyrosine kinase of approximately 0.8 nM; and activity in Test (b) with an $IC_{50}$ versus cellular phospho-Axl of approximately 18 nM.

For example, the pyridine compound disclosed as the nineteenth compound listed in Table XV within Example 41 possesses activity in Test (a) with an $IC_{50}$ versus Axl tyrosine kinase of approximately 0.8 nM; and activity in Test (b) with an $IC_{50}$ versus cellular phospho-Axl of approximately 7 nM.

For example, the pyridine compound disclosed as the twenty sixth compound listed in Table XV within Example 41 possesses activity in Test (a) with an $IC_{50}$ versus Axl tyrosine kinase of approximately 0.3 nM; and activity in Test (b) with an $IC_{50}$ versus cellular phospho-Axl of approximately 3 nM.

For example, the pyridine compound disclosed as the first compound listed in Table XXVI within Example 67 possesses activity in Test (a) with an $IC_{50}$ versus Axl tyrosine kinase of approximately 0.7 nM.

For example, the pyridine compound disclosed in Example 66 possesses activity in Test (a) with an $IC_{50}$ versus Axl tyrosine kinase of approximately 0.6 nM.

For example, the pyridine compound disclosed as the forty second compound listed in Table XV within Example 41 possesses activity in Test (a) with an $IC_{50}$ versus Axl tyrosine kinase of approximately 0.2 nM.

For example, the pyridine compound disclosed as the fourteenth compound listed in Table XXV within Example 62 possesses activity in Test (a) with an $IC_{50}$ versus Axl tyrosine kinase of approximately 0.1 nM.

For example, the pyridine compound disclosed as Example 22 possesses activity in Test (a) with an $IC_{50}$ versus Axl tyrosine kinase of approximately 0.4 nM; and activity in Test (b) with an $IC_{50}$ versus cellular phospho-Axl of approximately 16 nM.

For example, the pyridine and pyrazine compounds disclosed within the Examples possess activity in Test (a) at the levels illustrated in Table A.

TABLE A

| Example number | % Axl tyrosine kinase inhibition at 1 µM concentration |
| --- | --- |
| 1 | 99.8 |
| 2.1 | 93.7 |
| 2.2 | 99.5 |
| 2.3 | 98.6 |
| 2.4 | 99.1 |
| 2.5 | 73.5 |
| 2.6 | 99.0 |
| 2.7 | 99.1 |
| 2.8 | 96.5 |
| 2.9 | 40.3 |
| 2.10 | 99.5 |
| 2.11 | 98.9 |
| 2.12 | 48.7 |
| 2.13 | 99.7 |
| 2.14 | 99.9 |
| 2.15 | 80.2 |
| 2.16 | 94.0 |
| 2.17 | 68.9 |
| 2.18 | #99.8 |
| 2.19 | 99.8 |
| 2.20 | 97.6 |
| 2.21 | 45.4 |
| 2.22 | 97.9 |
| 2.23 | 87.2 |
| 2.24 | 88.9 |
| 2.25 | 60.3 |
| 2.26 | 99.5 |
| 2.27 | 98.0 |
| 2.28 | 85.1 |
| 2.29 | 31.3 |
| 2.30 | 96.1 |
| 2.31 | 45.1 |
| 2.32 | 22.4 |
| 2.33 | 92.5 |
| 2.34 | 67.3 |
| 2.35 | 93.3 |
| 2.36 | 98.5 |
| 2.37 | 91.9 |
| 2.38 | 99.0 |
| 2.39 | 17.1* |
| 2.40 | 40.7 |
| 2.41 | 99.9 |
| 2.42 | 15.8** |
| 2.43 | 9.8*** |
| 2.44 | 25.0 |
| 2.45 | 99.9 |
| 2.46 | 46.4 |
| 2.47 | 98.0 |
| 2.48 | 97.1 |
| 2.49 | 93.6, 94.5† |
| 2.50 | 90.0 |
| 2.51 | 93.1 |
| 2.52 | 81.0 |
| 2.53 | 4.2**** |
| 2.54 | 99.8 |
| 2.55 | 99.2 |
| 3 | 100.0, 99.8† |
| 4.1 | 100.0 |
| 5 | 100.0 |
| 6 | 99.9 |
| 7.1 | 99.9 |
| 7.2 | 96.6 |
| 7.3 | 99.3 |
| 7.4 | 99.6 |
| 7.5 | 99.1 |
| 7.6 | 99.9 |
| 7.7 | 99.0 |
| 7.8 | 98.9 |
| 7.9 | 99.7 |
| 7.10 | 95.7 |
| 7.11 | 98.1 |
| 8 | 99.2 |
| 8A.1 | 95.6 |
| 8A.2 | 99.2 |
| 8A.3 | ### |
| 8A.4 | 89.8, 86.6† |
| 8A.5 | 96.8 |
| 8A.6 | 97.7 |
| 8A.7 | 87.8 |
| 8A.8 | 97.1 |
| 8A.9 | 98.7 |
| 8A.10 | 13.1***** |
| 8A.11 | 89.6 |
| 8A.12 | 97.8 |
| 8A.13 | 71.3 |
| 8A.14 | 86.5 |
| 8A.15 | 97.7 |
| 8A.16 | 99.4 |
| 8A.17 | 99.8 |
| 8A.18 | 98.9, 99.0† |
| 8A.19 | 94.3 |
| 8A.20 | 95.2 |
| 8A.21 | 85.8 |
| 8A.22 | 95.3 |
| 8A.23 | 99.1 |
| 8A.24 | 95.6 |
| 8A.25 | 98.7 |
| 8A.26 | 97.9 |
| 8A.27 | 98.6 |
| 8A.28 | 97.5 |
| 9 | 98.8 |
| 9A.1 | 89.8 |
| 9A.2 | 97.0 |
| 9A.3 | 73.4 |
| 9A.4 | 93.5 |
| 9A.5 | 75.2 |
| 9A.6 | 95.6 |
| 9A.7 | 91.7 |
| 9A.8 | 96.5 |
| 9A.9 | 95.3 |
| 9A.10 | 93.8 |
| 9A.11 | 98.8 |
| 9A.12 | 97.4 |
| 9A.13 | 98.3 |
| 9A.14 | 97.0 |
| 9A.15 | 83.7 |
| 9A.16 | 97.7 |
| 9A.17 | 73.2 |
| 9A.18 | 80.8 |
| 9A.19 | 95.6 |
| 9A.20 | 94.8 |
| 9A.21 | 95.6 |

TABLE A-continued

| Example number | % Axl tyrosine kinase inhibition at 1 μM concentration |
|---|---|
| 9A.22 | 81.9 |
| 9A.23 | 75.3 |
| 10 | 98.8 |
| 10A.1 | 55.3, 52.6† |
| 10A.2 | 63.9 |
| 10A.3 | 87.2 |
| 10A.4 | 99.0 |
| 10A.5 | 91.4 |
| 10A.6 | 37.8 |
| 10A.7 | 95.9 |
| 10A.8 | 57.4 |
| 10A.9 | 82.5 |
| 10A.10 | 90.0 |
| 10A.11 | 88.4 |
| 10A.12 | 99.0 |
| 10A.13 | 91.1 |
| 10A.14 | 92.7 |
| 10A.15 | 98.4 |
| 10A.16 | 99.9 |
| 10A.17 | 40.3 |
| 10A.18 | 84.7 |
| 10A.19 | 90.1 |
| 11 | 99.0 |
| 11A.1 | 99.6, 99.4† |
| 11A.2 | 97.5 |
| 11A.3 | 87.7 |
| 11A.4 | 98.8 |
| 11A.5 | 97.4 |
| 11A.6 | 90.0 |
| 11A.7 | 80.3 |
| 11A.8 | 39.6 |
| 11A.9 | 99.3 |
| 11A.10 | 81.5 |
| 11A.11 | 86.5 |
| 11A.12 | 93.7 |
| 12 | 90.6 |
| 13 | 95.4, 99.0† |
| 14 | 99.9## |
| 15 | 93.1, 99.4† |
| 16 | 99.8 |
| 17 | 99.6 |
| 17A.1 | 98.5 |
| 18 | 99.3 |
| 19 | 99.6 |
| 20.1 | 91.8 |
| 20.2 | 99.6, 99.3† |
| 20.3 | 99.3, 98.7† |
| 20.4 | 89.2 |
| 20.5 | 85.6 |
| 20.6 | 99.1, 99.2† |
| 20.7 | 99.6 |
| 20.8 | 98.9 |
| 20.9 | 92.1 |
| 20.10 | 99.1 |
| 20.11 | 100.0 |
| 20.12 | 92.7 |
| 20.13 | 97.2 |
| 20.14 | 99.2 |
| 20.15 | 96.9 |
| 20.16 | 99.6 |
| 20.17 | 98.8 |
| 20.18 | 98.1 |
| 20.19 | 98.3 |
| 20.20 | 99.9 |
| 21 | 9.7†† |
| 22 | 100.0 |
| 23 | 100.0 |
| 24 | 100.0 |
| 25.1 | 95.0 |
| 25.2 | 100.0 |
| 25.3 | 100.0 |
| 25.4 | 100.0 |
| 25.5 | 82.9 |
| 25.6 | 99.5 |
| 25.7 | 99.1 |
| 25.8 | 99.8 |
| 25.9 | 99.3 |
| 25.10 | 97.7 |
| 25.11 | 99.6 |
| 25.12 | 38.2 |
| 25.13 | 100.0 |
| 25.14 | 100.0 |
| 25.15 | 99.9 |
| 25.16 | 99.9 |
| 25A | 100.0 |
| 26 | 99.3 |
| 27.1 | 100.0 |
| 27.2 | 99.9 |
| 27.3 | 96.4 |
| 27.4 | 99.2 |
| 27.5 | 98.4 |
| 27.6 | 99.9 |
| 27.7 | 99.8 |
| 28 | 99.3 |
| 29.1 | 99.7 |
| 29.2 | 99.8 |
| 29.3 | 99.9 |
| 29.4 | 99.1 |
| 29.5 | 99.9 |
| 29.6 | 99.9 |
| 29.7 | 99.8 |
| 29.8 | 88.7 |
| 30 | 99.8 |
| 31.1 | 100.0 |
| 31.2 | 99.9 |
| 31.3 | 100.0 |
| 31.4 | 99.9 |
| 31.5 | 100.0 |
| 31.6 | 99.7 |
| 31.7 | 99.7 |
| 31.8 | 99.7 |
| 31.9 | 99.8 |
| 31.10 | 94.3 |
| 32 | 99.9 |
| 33 | 99.9 |
| 34.1 | 99.8 |
| 34.2 | 100.0 |
| 34.3 | 99.7 |
| 35 | 99.6 |
| 35A | 100 |
| 36 | 100.0 |
| 37 | 98.4 |
| 38.1 | 99.5 |
| 38.2 | 100.0 |
| 38.3 | 100.0 |
| 38.4 | 97.3 |
| 38.5 | 100.0 |
| 38A.1 | 97.8 |
| 38A.2 | 100.0 |
| 38A.3 | 99.9 |
| 39 | 99.9 |
| 40 | 100.0 |
| 41.1 | 99.8 |
| 41.2 | 99.3 |
| 41.3 | 99.4 |
| 41.4 | 99.8 |
| 41.5 | 99.8 |
| 41.6 | 99.9 |
| 41.7 | #### |
| 41.8 | 99.7 |
| 41.9 | 100.0 |
| 41.10 | 99.7 |
| 41.11 | 74.7 |
| 41.12 | 94.0 |
| 41.13 | 100.0 |
| 41.14 | 100.0 |
| 41.15 | 98.4 |
| 41.16 | 98.3 |
| 41.17 | 84.8 |
| 41.18 | 100.0 |
| 41.19 | 100.0 |
| 41.20 | 99.7 |

TABLE A-continued

| Example number | % Axl tyrosine kinase inhibition at 1 μM concentration |
|---|---|
| 41.21 | 100.0 |
| 41.22 | 100.0 |
| 41.23 | 100.0 |
| 41.24 | 92.1 |
| 41.25 | 99.8 |
| 41.26 | 100.0 |
| 41.27 | 100.0 |
| 41.28 | 100.0 |
| 41.29 | 99.9 |
| 41.30 | 99.5 |
| 41.31 | 99.9 |
| 41.32 | 100.0 |
| 41.33 | 99.6 |
| 41.34 | 100.0 |
| 41.35 | 99.8 |
| 41.36 | 100.0 |
| 41.37 | 99.5 |
| 41.39 | 100.0 |
| 41.40 | 99.2 |
| 41.41 | 99.7 |
| 41.42 | 100.0 |
| 41.43 | 100.0 |
| 42 | 99.7 |
| 43A.1 | 98.9 |
| 43A.2 | 97.2 |
| 43A.3 | 98.7 |
| 43B.1 | 99.8 |
| 43B.2 | 96.9 |
| 43B.3 | 99.6 |
| 43B.4 | 99.3 |
| 43B.5 | 99.4 |
| 43B.6 | 96.4 |
| 43B.7 | 98.1 |
| 43B.8 | 19.0††† |
| 43B.9 | 98.2 |
| 43B.10 | 98.4 |
| 43B.11 | 98.1 |
| 43B.12 | 98.8 |
| 43B.13 | 96.8 |
| 43B.14 | 95.1 |
| 43B.15 | 86.0 |
| 43B.16 | 95.3 |
| 43B.17 | 99.5 |
| 43B.18 | 99.9 |
| 43B.19 | 95.8 |
| 43B.20 | 98.9 |
| 43B.21 | 99.6 |
| 43B.22 | 97.7 |
| 43B.23 | 95.3 |
| 43B.24 | 98.2 |
| 43B.25 | 97.5 |
| 43B.26 | 97.7 |
| 43B.27 | 98.2 |
| 43B.28 | 98.7 |
| 43B.29 | 93.6 |
| 43B.30 | 98.9 |
| 43B.31 | 97.1 |
| 43B.32 | 98.6 |
| 43B.33 | 98.1 |
| 43B.34 | 95.7 |
| 43B.35 | 95.9 |
| 43B.36 | 98.3 |
| 43B.37 | 97.6 |
| 43B.38 | 8.1†††† |
| 43B.39 | 98.2 |
| 43B.40 | 97.7 |
| 43B.41 | 99.0 |
| 43B.42 | 96.6 |
| 43B.43 | 92.3 |
| 43C.1 | 99.4 |
| 43C.2 | 97.1 |
| 43C.3 | 99.4 |
| 43C.4 | 99.8 |
| 43C.5 | 99.7 |
| 43C.6 | 99.8 |
| 43C.7 | 99.1 |
| 43C.8 | 99.9 |
| 43C.9 | 99.9 |
| 43C.10 | 98.9 |
| 43C.11 | 98.9 |
| 43C.12 | 99.6 |
| 43C.13 | 99.9 |
| 43C.14 | 99.3 |
| 43C.15 | 97.2 |
| 43C.16 | 98.1 |
| 43C.17 | 93.5 |
| 43C.18 | 99.8 |
| 43C.19 | 99.7 |
| 43C.20 | 98.1 |
| 43C.21 | 99.3 |
| 43C.22 | 98.2 |
| 43C.23 | 99.3 |
| 43C.24 | 99.6 |
| 43C.25 | 99.5 |
| 43C.26 | 99.6 |
| 43C.27 | 99.4 |
| 43C.28 | 51.0 |
| 43C.29 | 99.9 |
| 43C.30 | 99.0 |
| 43C.31 | 99.3 |
| 43C.32 | 99.8 |
| 43C.33 | 99.8 |
| 43C.34 | 99.1 |
| 43C.35 | 99.2 |
| 43C.36 | 99.8 |
| 43C.37 | 99.4 |
| 43C.38 | 99.8 |
| 44 | 99.6 |
| 45A.1 | 92.9 |
| 45A.2 | 96.6 |
| 45A.3 | 98.0 |
| 45A.4 | 98.5 |
| 45A.5 | 98.8 |
| 45A.6 | 97.4 |
| 45A.7 | 97.7 |
| 45A.8 | 99.8 |
| 45A.9 | 99.0 |
| 45A.10 | 97.5 |
| 45A.11 | 96.7 |
| 45A.12 | 96.3 |
| 45A.13 | 98.2 |
| 45A.14 | 89.9 |
| 45A.15 | 99.7 |
| 45A.16 | 94.2 |
| 45A.17 | 99.6 |
| 45A.18 | 99.7 |
| 45A.19 | 98.7 |
| 45A.20 | 98.9 |
| 45A.21 | 96.4 |
| 45A.22 | 97.1 |
| 45A.23 | 99.8 |
| 45A.24 | 95.8 |
| 45A.25 | 97.8 |
| 45A.26 | 99.6 |
| 45A.27 | 97.9 |
| 45A.28 | 97.5 |
| 45A.29 | 98.8 |
| 45A.30 | 97.4 |
| 45A.31 | 95.9 |
| 45A.32 | 99.6 |
| 45A.33 | 97.7 |
| 45A.34 | 99.7 |
| 45A.35 | 98.4 |
| 45A.36 | 99.3 |
| 45A.37 | 92.2 |
| 45A.38 | 98.4 |
| 45A.39 | 98.4 |
| 45A.40 | 98.3 |
| 45A.41 | 99.0 |
| 45A.42 | 99.3 |
| 45A.43 | 99.9 |
| 45A.44 | 99.3 |

TABLE A-continued

| Example number | % Axl tyrosine kinase inhibition at 1 μM concentration |
|---|---|
| 45A.45 | 93.8 |
| 45A.46 | 99.1 |
| 45A.47 | 96.1 |
| 45A.48 | 98.3 |
| 45A.49 | 96.1 |
| 45A.50 | 93.7 |
| 45A.51 | 98.5 |
| 45A.52 | 94.3 |
| 45A.53 | 98.8 |
| 45A.54 | 97.8 |
| 45A.55 | 98.9 |
| 45A.56 | 98.9 |
| 45A.57 | 96.9 |
| 45A.58 | 97.0 |
| 45A.59 | 88.8 |
| 45A.60 | 98.1 |
| 45A.61 | 95.1 |
| 45A.62 | 97.3 |
| 45A.63 | 99.1 |
| 45A.64 | 98.6 |
| 45A.65 | 98.3 |
| 45A.66 | 99.9 |
| 45A.67 | 96.8 |
| 45A.68 | 91.3 |
| 45A.69 | 96.7 |
| 45A.70 | 98.8 |
| 45A.71 | 93.7 |
| 45A.72 | 99.6 |
| 45A.73 | 96.0 |
| 45A.74 | 99.9 |
| 45A.75 | 91.6 |
| 45A.76 | 96.7 |
| 45A.77 | 96.1 |
| 45A.78 | 97.7 |
| 45A.79 | 99.0 |
| 45A.80 | 99.7 |
| 45A.81 | 99.6 |
| 45A.82 | 98.4 |
| 45A.83 | 98.9 |
| 45A.84 | 99.1 |
| 45A.85 | 99.8 |
| 45A.86 | 95.8 |
| 45A.87 | 77.4 |
| 45A.88 | 99.8 |
| 45A.89 | 91.7 |
| 45A.90 | 98.9 |
| 45A.91 | 96.3 |
| 45A.92 | 99.7 |
| 45A.93 | 99.3 |
| 45A.94 | 98.9 |
| 45A.95 | 99.5 |
| 45A.96 | 99.1 |
| 45A.97 | 968 |
| 45A.98 | 97.6 |
| 45A.99 | 95.9 |
| 45A.100 | 95.3 |
| 45A.101 | 99.1 |
| 45A.102 | 99.2 |
| 45A.103 | 97.3 |
| 45A.104 | 99.8 |
| 45A.105 | 98.4 |
| 45A.106 | 98.4 |
| 45A.107 | 95.0 |
| 45B.1 | 98.1 |
| 45B.2 | 96.1 |
| 45B.3 | 97.7 |
| 45B.4 | 99.6 |
| 45B.5 | 99.9 |
| 45B.6 | 95.9 |
| 46 | 95.9 |
| 47 | ##### |
| 48 | 93.5 |
| 49 | 73.4 |
| 50 | 47.6 |
| 51 | 99.9 |
| 52 | 99.8 |
| 53.1 | 99.7 |
| 53.2 | 97.8 |
| 53.3 | 98.8 |
| 53.4 | 99.2 |
| 53.5 | 100.0 |
| 53.6 | 100.0 |
| 53.7 | 99.4 |
| 53.8 | 99.9 |
| 54 | 99.5 |
| 55.1 | 99.0 |
| 55.2 | 98.8 |
| 55.3 | 99.5 |
| 56 | 99.3 |
| 57.1 | 98.5 |
| 57.2 | 99.4 |
| 57.3 | 98.7 |
| 57.4 | 99.3 |
| 57.5 | 99.8 |
| 57.6 | 99.8 |
| 57.7 | 99.6 |
| 58 | 99.5 |
| 59.1 | 99.3 |
| 59.2 | 98.1 |
| 59.3 | 98.9 |
| 59.4 | 98.9 |
| 59.5 | 99.7 |
| 59.6 | 99.9 |
| 59.7 | 99.6 |
| 59.8 | 98.2 |
| 59.9 | 99.1 |
| 59.10 | 99.1 |
| 59.11 | 99.0 |
| 59.12 | 99.6 |
| 59.13 | 99.7 |
| 60 | 99.8 |
| 61 | 99.9 |
| 62.1 | 100.0 |
| 62.2 | 98.8 |
| 62.3 | 99.9 |
| 62.4 | 99.8 |
| 62.5 | 99.5 |
| 62.6 | 100.0 |
| 62.7 | 100.0 |
| 62.9 | 99.4 |
| 62.10 | 100.0 |
| 62.11 | 99.8 |
| 62.13 | 100.0 |
| 62.14 | 100.0 |
| 62.15 | 100.0 |
| 63 | 98.4 |
| 64 | 99.1 |
| 65 | 100.0 |
| 66 | 100.0 |
| 67.1 | 100.0 |
| 67.2 | 100.0 |
| 68 | 100.0 |
| 69 | 100.0 |
| 70 | 99.9 |

TABLE A-continued

| Example number | % Axl tyrosine kinase inhibition at 1 μM concentration |
|---|---|
| 71 | 100.0 |
| 72 | 100.0 | the compound disclosed in Example 2.18 had an activity in Test (b) with an $IC_{50}$ versus cellular phospho-Axl of approximately 0.07 μM.
*the compound disclosed in Example 2.39 inhibited 58.6% of Axl tyrosine kinase activity at a concentration of 30 μM.
**the compound disclosed in Example 2.42 inhibited 53.6% of Axl tyrosine kinase activity at a concentration of 30 μM.
***the compound disclosed in Example 2.43 inhibited 57% of Axl tyrosine kinase activity at a concentration of 30 μM.
****the compound disclosed in Example 2.53 inhibited 82% of Axl tyrosine kinase activity at a concentration of 30 μM.
*****the compound disclosed in Example 8A.10 inhibited 79.5% of Axl tyrosine kinase activity at a concentration of 30 μM.
the compound disclosed in Example 14 had an activity in Test (b) with an $IC_{50}$ versus cellular phospho-Axl of approximately 0.101 μM.
the compound disclosed in Example 8A.3 inhibited 100% of Axl tyrosine kinase activity at a concentration of 30 μM.
the compound disclosed in Example 41.7 had an activity in Test (b) with an $IC_{50}$ versus cellular phospho-Axl of approximately 0.234 μM.
the compound disclosed in Example 47 inhibited 99.5% of Axl tyrosine kinase activity at a concentration of 30 μM.
†this is a mean $IC_{50}$ value calculated from a larger number of replicates than were used to calculate the first value quoted for the given Example.
††the compound disclosed in Example 21 inhibited 76.4% of Axl tyrosine kinase activity at a concentration of 30 μM.
†††the compound disclosed in Example 43B.8 inhibited 98% of Axl tyrosine kinase activity at a concentration of 30 μM.
††††the compound disclosed in Example 43B.38 inhibited 95.3% of Axl tyrosine kinase activity at a concentration of 30 μM.

According to a further aspect of the invention there is provided a pharmaceutical composition, which comprises a pyridine or pyrazine derivative of the Formula I, or a pharmaceutically-acceptable salt thereof, as defined hereinbefore in association with a pharmaceutically-acceptable diluent or carrier.

The compositions of the invention may be in a form suitable for oral use (for example as tablets, lozenges, hard or soft capsules, aqueous or oily suspensions, emulsions, dispersible powders or granules, syrups or elixirs), for topical use (for example as creams, ointments, gels, or aqueous or oily solutions or suspensions), for administration by inhalation (for example as a finely divided powder or a liquid aerosol), for administration by insufflation (for example as a finely divided powder) or for parenteral administration (for example as a sterile aqueous or oily solution for intravenous, subcutaneous, intraperitoneal or intramuscular dosing) or as a suppository for rectal dosing.

The compositions of the invention may be obtained by conventional procedures using conventional pharmaceutical excipients, well known in the art. Thus, compositions intended for oral use may contain, for example, one or more colouring, sweetening, flavouring and/or preservative agents.

The amount of active ingredient that is combined with one or more excipients to produce a single dosage form will necessarily vary depending upon the host treated and the particular route of administration. For example, a formulation intended for oral administration to humans will generally contain, for example, from 1 mg to 1 g of active agent (more suitably from 1 to 250 mg, for example from 1 to 100 mg) compounded with an appropriate and convenient amount of excipients which may vary from about 5 to about 98 percent by weight of the total composition.

The size of the dose for therapeutic or prophylactic purposes of a compound of the Formula I will naturally vary according to the nature and severity of the disease state, the age and sex of the animal or patient and the route of administration, according to well known principles of medicine.

In using a compound of the Formula I for therapeutic or prophylactic purposes it will generally be administered so that a daily dose in the range, for example, 1 mg/kg to 100 mg/kg body weight is received, given if required in divided doses. In general, lower doses will be administered when a parenteral route is employed. Thus, for example, for intravenous administration, a dose in the range, for example, 1 mg/kg to 25 mg/kg body weight will generally be used. Similarly, for administration by inhalation, a dose in the range, for example, 1 mg/kg to 25 mg/kg body weight will be used. Oral administration is however preferred, particularly in tablet form. Typically, unit dosage forms will contain about 10 mg to 0.5 g of a compound of this invention.

As stated above, antagonism of the activity of Axl and/or c-Met receptor kinases, is expected to be beneficial in the treatment of a number of cell proliferative disorders such as cancer.

We have now found that the novel pyridine or pyrazine derivatives described herein possess potent activity against cell proliferative disorders. It is believed that the compounds provide a useful treatment of cell proliferative disorders, for example to provide an anti-tumour effect, by way of a contribution from inhibition of Axl and/or c-Met receptor tyrosine kinases. In addition, as stated hereinbefore, Axl and c-Met are involved in angiogenesis, the process of forming new blood vessels that is critical for continuing tumour growth. It is therefore believed that the compounds of the present invention are expected to be beneficial in the treatment of a number of disease states that are associated with angiogenesis and/or increased vascular permeability such as cancer, especially in inhibiting the development of tumours.

Particular compounds of the invention possess better potency against Axl receptor tyrosine kinases than against c-Met receptor kinases.

According to this further aspect of the invention there is provided a pyridine or pyrazine derivative of the Formula I, or a pharmaceutically-acceptable salt thereof, as defined hereinbefore for use as a medicament in a warm-blooded animal such as man.

According to a further aspect of the invention, there is provided a pyridine or pyrazine derivative of the Formula I, or a pharmaceutically-acceptable salt thereof, as defined hereinbefore for use in the treatment (or prophylaxis) of cell proliferative disorders or in the treatment (or prophylaxis) of disease states associated with angiogenesis and/or vascular permeability.

According to a further aspect of the invention, there is provided the use of a pyridine or pyrazine derivative of the Formula I, or a pharmaceutically-acceptable salt thereof, as defined hereinbefore in the manufacture of a medicament for use in the treatment (or prophylaxis) of cell proliferative disorders or in the treatment (or prophylaxis) of disease states associated with angiogenesis and/or vascular permeability.

According to this aspect of the invention there is also provided a method for the treatment (or prophylaxis) of cell proliferative disorders in a warm-blooded animal in need of such treatment (or prophylaxis) or for the treatment (or prophylaxis) of disease states associated with angiogenesis and/or vascular permeability in a warm-blooded animal in need of such treatment (or prophylaxis) which comprises administering to said animal an effective amount of a pyridine or pyrazine derivative of the Formula I, or a pharmaceutically-acceptable salt thereof, as defined hereinbefore.

Suitable cell proliferative disorders include neoplastic disorders, for example, cancers of the lung (non-small cell lung cancer, small cell lung cancer and bronchioalveolar cancer), gastrointestine (such as colon, rectal and stomach tumours), prostate, breast, kidney, liver, brain (such as glioblastoma), bile duct, bone, bladder, head and neck, oesophagus, ovary, pancreas, testes, thyroid, cervix and vulva and skin (such as dermatofibrosarcoma protruberans) and in leukaemias and lymphomas such as chronic myelogenous leukaemia (CML), chronic myelomonocytic leukaemia (CMML), acute lymphocytic leukaemia (ALL), chronic neutrophilic leukaemia (CNL), acute myelogenous leukaemia (AML) and multiple myeloma.

According to this aspect of the invention there is also provided a method for treating cell proliferative disorders (such as solid tumour disease) in a warm-blooded animal in need of such treatment which comprises administering to said animal an effective amount of a pyridine or pyrazine derivative of the Formula I, or a pharmaceutically-acceptable salt thereof, as defined hereinbefore.

Other suitable cell proliferative disorders include non-malignant disorders such as blood vessel disease (for example atherosclerosis and restenosis, for example in the process of restenosis subsequent to balloon angioplasty and heart arterial by-pass surgery), fibrotic diseases (for example kidney fibrosis, hepatic cirrhosis, lung fibrosis and multicystic renal dysplasia), glomerulonephritis, benign prostatic hypertrophy, inflammatory diseases (for example rheumatoid arthritis and inflammatory bowel disease), multiple sclerosis, psoriasis, hypersensitivity reactions of the skin, allergic asthma, insulin-dependent diabetes, diabetic retinopathy and diabetic nephropathy.

Suitable disease states associated with angiogenesis and/or vascular permeability include, for example, the undesirable or pathological angiogenesis seen in diabetic retinopathy, psoriasis, cancer, rheumatoid arthritis, atheroma, Kaposi's sarcoma and haemangioma.

According to a further aspect of the invention there is provided a pyridine or pyrazine derivative of the Formula I, or a pharmaceutically-acceptable salt thereof, as defined hereinbefore for use in the treatment (or prevention) of those tumours which are sensitive to inhibition of Axl and/or c-Met that are involved in the signal transduction steps which lead to the proliferation, survival, invasiveness and migratory ability of tumour cells.

According to a further feature of this aspect of the invention there is provided the use of a pyridine or pyrazine derivative of the Formula I, or a pharmaceutically-acceptable salt thereof, as defined hereinbefore in the manufacture of a medicament for use in the treatment (or prevention) of those tumours which are sensitive to inhibition of Axl and/or c-Met receptor enzymes that are involved in the signal transduction steps which lead to the proliferation, survival, invasiveness and migratory ability of tumour cells.

According to a further feature of this aspect of the invention there is provided a method for the treatment (or prevention) of a warm-blooded animal having tumours which are sensitive to inhibition of Axl or c-Met receptor enzymes that are involved in the signal transduction steps which lead to the proliferation, survival, invasiveness and migratory ability of tumour cells which comprises administering to said animal an effective amount of a pyridine or pyrazine derivative of the Formula I, or a pharmaceutically-acceptable salt thereof, as defined hereinbefore.

According to a further aspect of the invention there is provided a pyridine or pyrazine derivative of the Formula I, or a pharmaceutically-acceptable salt thereof, as defined hereinbefore for use in providing an Axl and/or c-Met receptor enzyme inhibitory effect.

According to a further feature of this aspect of the invention there is provided the use of a pyridine or pyrazine derivative of the Formula I, or a pharmaceutically-acceptable salt thereof, as defined hereinbefore in the manufacture of a medicament for use in providing a Axl and/or c-Met receptor enzyme inhibitory effect.

According to a further aspect of the invention there is also provided a method for inhibiting an Axl and/or c-Met receptor enzyme which comprises administering an effective amount of a pyridine or pyrazine derivative of the Formula I, or a pharmaceutically-acceptable salt thereof, as defined hereinbefore.

The anti-cancer treatment defined hereinbefore may be applied as a sole therapy or may involve, in addition to the compound of the invention, conventional surgery or radiotherapy or chemotherapy. Such chemotherapy may include one or more of the following categories of anti-tumour agents:—

(i) other antiproliferative/antineoplastic drugs and combinations thereof, as used in medical oncology, such as alkylating agents (for example cis-platin, oxaliplatin, carboplatin, cyclophosphamide, nitrogen mustard, melphalan, chlorambucil, busulphan, temozolamide and nitrosoureas); antimetabolites (for example gemcitabine and antifolates such as fluoropyrimidines like 5-fluorouracil and tegafur, raltitrexed, methotrexate, cytosine arabinoside, and hydroxyurea); anti-tumour antibiotics (for example anthracyclines like adriamycin, bleomycin, doxorubicin, daunomycin, epirubicin, idarubicin, mitomycin-C, dactinomycin and mithramycin); antimitotic agents (for example vinca alkaloids like vincristine, vinblastine, vindesine and vinorelbine and taxoids like taxol and taxotere and polokinase inhibitors); and topoisomerase inhibitors (for example epipodophyllotoxins like etoposide and teniposide, amsacrine, topotecan and camptothecin);

(ii) cytostatic agents such as antioestrogens (for example tamoxifen, fulvestrant, toremifene, raloxifene, droloxifene and iodoxyfene), antiandrogens (for example bicalutamide, flutamide, nilutamide and cyproterone acetate), LHRH antagonists or LHRH agonists (for example goserelin, leuprorelin and buserelin), progestogens (for example megestrol acetate), aromatase inhibitors (for example as anastrozole, letrozole, vorazole and exemestane) and inhibitors of 5α-reductase such as finasteride;

(iii) anti-invasion agents [for example c-Src kinase family inhibitors like 4-(6-chloro-2,3-methylenedioxyanilino)-7-[2-(4-methylpiperazin-1-yl)ethoxy]-5-tetrahydropyran-4-yloxyquinazoline (AZD0530; International Patent Application WO 01/94341), N-(2-chloro-6-methylphenyl)-2-{6-[4-(2-hydroxyethyl)piperazin-1-yl]-2-methylpyrimidin-4-ylamino}thiazole-5-carboxamide (dasatinib, BMS-354825; *J. Med. Chem.*, 2004, 47, 6658-6661) and bosutinib (SKI-606), and metalloproteinase inhibitors like marimastat, inhibitors of urokinase plasminogen activator receptor function or antibodies to Heparanase];

(iv) inhibitors of growth factor function: for example such inhibitors include growth factor antibodies and growth factor receptor antibodies (for example the anti-erbB2 antibody trastuzumab [Herceptin™], the anti-EGFR antibody panitumumab, the anti-erbB1 antibody cetuximab [Erbitux, C225] and any growth factor or growth factor receptor antibodies disclosed by Stern et al. Critical reviews in oncology/haematology, 2005, Vol. 54, pp 11-29); such inhibitors also include tyrosine kinase inhibitors, for example inhibitors of the epidermal growth factor family (for example EGFR family tyrosine kinase inhibitors such as N-(3-chloro-4-fluorophenyl)-7-methoxy-6-(3-morpholinopropoxy)quinazolin-4-amine (gefitinib, ZD 1839), N-(3-ethynylphenyl)-6,7-bis(2-methoxyethoxy)quinazolin-4-amine (erlotinib, OSI-774) and 6-acrylamido-N-(3-chloro-4-fluorophenyl)-7-(3-morpholinopropoxy)-quinazolin-4-amine (CI 1033), erbB2 tyrosine kinase inhibitors such as lapatinib); inhibitors of the hepatocyte growth factor family; inhibitors of the insulin growth factor family; inhibitors of the platelet-derived growth factor family such as imatinib and/or nilotinib (AMN107); inhibitors of serine/threonine kinases (for example Ras/Raf signalling inhibitors such as farnesyl transferase inhibitors, for example sorafenib (BAY 43-9006), tipifarnib (R115777) and lonafarnib (SCH66336)), inhibitors of cell signalling through MEK and/or AKT kinases, c-kit inhibitors, abl kinase inhibitors, PI3 kinase inhibitors, Plt3 kinase inhibitors, CSF-1R kinase inhibitors, IGF receptor (insulin-like growth factor) kinase inhibitors; aurora kinase inhibitors (for example AZD1152, PH739358, VX-680, MLN8054, R763, MP235, MP529, VX-528 AND AX39459) and cyclin dependent kinase inhibitors such as CDK2 and/or CDK4 inhibitors;

(v) antiangiogenic agents such as those which inhibit the effects of vascular endothelial growth factor, [for example the anti-vascular endothelial cell growth factor antibody bevacizumab (Avastin™) and for example, a VEGF receptor tyrosine kinase inhibitor such as vandetanib (ZD6474), vatalanib (PTK787), sunitinib (SU11248), axitinib (AG-013736), pazopanib (GW 786034) and 4-(4-fluoro-2-methylindol-5-yloxy)-6-methoxy-7-(3-pyrrolidin-1-ylpropoxy)quinazoline (AZD2171; Example 240 within WO 00/47212), compounds such as those disclosed in International Patent Applications WO97/22596, WO 97/30035, WO 97/32856 and WO 98/13354 and compounds that work by other mechanisms (for example linomide, inhibitors of integrin $\alpha v \beta 3$ function and angiostatin)];

(vi) vascular damaging agents such as Combretastatin A4 and compounds disclosed in International Patent Applications WO 99/02166, WO 00/40529, WO 00/41669, WO 01/92224, WO 02/04434 and WO 02/08213;

(vii) an endothelin receptor antagonist, for example zibotentan (ZD4054) or atrasentan;

(viii) antisense therapies, for example those which are directed to the targets listed above, such as ISIS 2503, an anti-ras antisense;

(ix) gene therapy approaches, including for example approaches to replace aberrant genes such as aberrant p53 or aberrant BRCA1 or BRCA2, GDEPT (gene-directed enzyme pro-drug therapy) approaches such as those using cytosine deaminase, thymidine kinase or a bacterial nitroreductase enzyme and approaches to increase patient tolerance to chemotherapy or radiotherapy such as multi-drug resistance gene therapy; and (x) immunotherapy approaches, including for example ex-vivo and in-vivo approaches to increase the immunogenicity of patient tumour cells, such as transfection with cytokines such as interleukin 2, interleukin 4 or granulocyte-macrophage colony stimulating factor, approaches to decrease T-cell anergy, approaches using transfected immune cells such as cytokine-transfected dendritic cells, approaches using cytokine-transfected tumour cell lines and approaches using anti-idiotypic antibodies.

According to this aspect of the invention there is provided a combination suitable for use in the treatment of cancer comprising a compound of formula I as defined hereinbefore or a pharmaceutically acceptable salt thereof and any one of the anti tumour agents listed under (i)-(ix) above.

Therefore in a further aspect of the invention there is provided a compound of formula (I) or a pharmaceutically acceptable salt thereof in combination with an anti-tumour agent selected from one listed under (i)-(ix) herein above.

Herein, where the term "combination" is used it is to be understood that this refers to simultaneous, separate or sequential administration. In one aspect of the invention "combination" refers to simultaneous administration. In another aspect of the invention "combination" refers to separate administration. In a further aspect of the invention "combination" refers to sequential administration. Where the administration is sequential or separate, the delay in administering the second component should not be such as to lose the beneficial effect of the combination.

According to a further aspect of the invention there is provided a pharmaceutical composition which comprises a compound of formula (I) or a pharmaceutically acceptable salt thereof in combination with an anti-tumour agent selected from one listed under (i)-(ix) herein above, in association with a pharmaceutically acceptable diluent or carrier.

According to a further aspect of the invention there is provided a pharmaceutical composition which comprises a compound of formula (I) or a pharmaceutically acceptable salt thereof in combination with an anti-tumour agent selected from one listed under (i)-(ix) herein above, in association with a pharmaceutically acceptable diluent or carrier for use in treating cancer.

According to another feature of the invention there is provided the use of a compound of the formula (I) or a pharmaceutically acceptable salt thereof in combination with an anti-tumour agent selected from one listed under (i)-(ix) herein above, in the manufacture of a medicament for use in cancer in a warm-blooded animal, such as man.

Therefore in an additional feature of the invention, there is provided a method of treating cancer in a warm-blooded animal, such as man, in need of such treatment which comprises administering to said animal an effective amount of a compound of formula (I) or a pharmaceutically acceptable salt thereof in combination with an anti-tumour agent selected from one listed under (i)-(ix) herein above.

According to a further aspect of the present invention there is provided a kit comprising a compound of formula (I) or a pharmaceutically acceptable salt thereof in combination with an anti-tumour agent selected from one listed under (i)-(ix) herein above.

According to a further aspect of the present invention there is provided a kit comprising:
a) a compound of formula (I) or a pharmaceutically acceptable salt thereof in a first unit dosage form;
b) an anti-tumour agent selected from one listed under (i)-(ix) herein above; in a second unit dosage form; and
c) container means for containing said first and second dosage forms.

Although the compounds of the Formula I are primarily of value as therapeutic agents for use in warm-blooded animals (including man), they are also useful whenever it is required to inhibit the effects of Axl or c-Met receptor tyrosine kinase enzymes. Thus, they are useful as pharmacological standards for use in the development of new biological tests and in the search for new pharmacological agents.

The invention will now be illustrated in the following Examples in which, generally:
  (i) operations were carried out at ambient temperature, i.e. in the range 17 to 25° C. and under an atmosphere of an inert gas such as nitrogen unless otherwise stated;
  (ii) evaporations were carried out by rotary evaporation or utilising Genevac equipment in vacuo and work-up procedures were carried out after removal of residual solids by filtration;
  (iii) column chromatography (by the flash procedure) was performed on Merck Kieselgel silica (Art. 9385) obtained from E. Merck, Darmstadt, Germany or using proprietary pre-packed normal phase silica cartridges, for example SiliCycle™ disposable chromatography cartridges, or high pressure liquid chromatography (HPLC) was performed on C18 reverse phase silica, for example on a X Bridge 5 μm C-18 60 Å preparative reversed-phase column;
(iv) ion exchange chromatography was performed using pre-packed IST Isolute® SCX-2 columns;
(v) preparative chromatography was performed on a Gilson instrument with an X Bridge 5 μm C18 column (19×100 mm), with a flow rate of 25 ml/min and solvent system of 1% aqueous ammonia: acetonitrile with a gradient in the range of 25-95% (this is described hereinafter as 'X Bridge preparative chromatography');
(vi) yields, where present, are not necessarily the maximum attainable;
(vii) in general, the structures of end-products of the Formula I were confirmed by nuclear magnetic resonance (NMR) spectroscopy; NMR chemical shift values were measured on the delta scale [proton magnetic resonance spectra were determined using a Bruker DPX 400 (400 MHz) or a Bruker DRX 500 (500 MHz) instrument]; measurements were taken at ambient temperature unless otherwise specified; the following abbreviations have been used: s, singlet; d, doublet; t, triplet; q, quartet; m, multiplet; dd, doublet of doublets; ddd, doublet of doublet of doublet; dt, doublet of triplets; bs, broad signal;
(viii) in general, end-products of the Formula I were also characterised by mass spectroscopy following liquid chromatography (LCMS); LCMS was carried out using an Agilent 1100 or Waters Alliance HT (2790 & 2795) fitted with a Waters ZQ ESCi mass spectrometer and an X Bridge 5 μm C-18 column (2.1×50 mm) at a flow rate of 1.1 ml/min, using a solvent system of 95% A+5% C to 95% B+5% C over 4 minutes, where A=water, B=acetonitrile, C=1:1 acetonitrile:water 1% ammonia; in general, the retention time (RT) of each product under these chromatographic conditions was noted;
(ix) intermediates were not generally fully characterised and purity was assessed by thin layer chromatographic, mass spectral, HPLC and/or NMR analysis;
(x) Where HPLC retention times are quoted for Examples 40 to 72, the following conditions were used unless otherwise stated. Analytical LC-MS was carried out using a Waters Alliance HT (2695) fitted with a Waters ZQ or ZMD ESCi mass spectrometer and a Sunfire 3.5 μm C-18 column (4.6×50 mm) at a flow rate of 2.5 ml/min, using a solvent system of 95% A+5% C to 95% B+5% C over 4 minutes, where A=water, B=acetonitrile, C=5% HCOOH in Methanol; retention time of each product is quoted in minutes;
(xi) Conventional TFA deprotection can be carried out as follows. Trifluoroacetic acid is added to a solution of the Boc protected compound in dichloromethane at room temperature. After 2 hours, the mixture is concentrated and purified. Conventional hydrogen chloride deprotection can be carried out as follows. A 4N solution of hydrogen chloride is added to the Boc protected compound at room temperature. After 2 hours of stirring, the reaction mixture is concentrated and purified;
(xii) the following abbreviations have been used:—
DMF N,N-dimethylformamide
DMSO dimethyl sulphoxide
$CDCl_3$ deutero-chloroform
HATU O-(7-azabenzotriazol-1-yl)-N,N,N'N'-tetramethyluronium hexafluorophosphate
HOBT N-hydroxybenzotriazole
NMP 1-methylpyrrolidin-2-one
DME 1,2-dimethoxyethane
DCM dichloromethane
$PdCl_2(dppf)$ 1,1'-bis(diphenylphosphino)ferrocene-dichloropalladium(II) in complex with dichloromethane
PPA polyphosphoric acid
DMA dimethylacetamide
DMAP 4-dimethylaminopyridine
THF tetrahydrofuran
TFA trifluoroacetic acid

EXAMPLE 1

3-Benzoxazol-2-yl-5-[4-(dimethylaminomethyl)phenyl]pyridin-2-amine

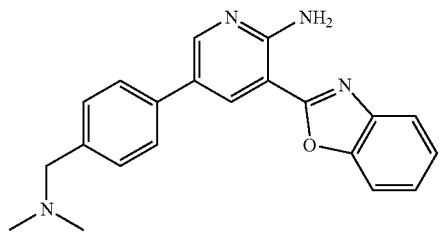

2M Sodium carbonate solution (0.4 ml) was added to a solution of 3-(benzoxazol-2-yl)-5-bromo-pyridin-2-amine (0.10 g), [4-(dimethylaminomethyl)phenyl]boronic acid (0.075 g) and dichlorobis(triphenylphosphine)palladium (II) (0.003 g) in a mixture of 2:7:3:2 DMF:DME:water:ethanol (3 ml). The reaction mixture was heated at 160° C. for 7 mins in a 100 W microwave oven. The solvent was evaporated in a Genevac and NMP (1.8 ml) was added. The mixture was filtered and purified by X bridge preparative HPLC. There was thus obtained the title compound (0.021 g); Mass Spectrum: M+H⁺ 344, RT 2.82 min.

The 3-(benzoxazol-2-yl)-5-bromo-pyridin-2-amine used as a starting material was prepared as follows:—

2-Aminophenol (4.02 g) was added in one portion to 2-amino-5-bromo-pyridine-3-carboxylic acid (8.0 g) in polyphosphoric acid (20 ml). The resulting mixture was stirred at 200° C. for 7 hours. The mixture was allowed to cool to 150° C. and poured into water (3 L) with rapid stirring. The resulting suspension was adjusted to pH 12 by addition of sodium hydroxide solution and the resulting precipitate was collected by filtration. The solid was then washed with methanol (200 ml) and dried under vacuum. There was thus obtained 3-(1,3-benzoxazol-2-yl)-5-bromo-pyridin-2-amine (4.90 g); NMR Spectrum: (DMSOd⁶) 7.47 (m, 2H), 7.83 (m, 4H), 8.32 (d, 1H), 8.38 (d, 1H); Mass Spectrum: M+H⁺ 292.08, RT 2.78 min.

EXAMPLE 2

Using an analogous procedure to that described in Example 1, the appropriate bromopyridine was reacted with the appropriate boronic acid or, where stated, an appropriate boronate ester, to give the compounds described in Table I. Unless otherwise stated, the boronic acids and boronate esters that were used were commercially available.

TABLE I

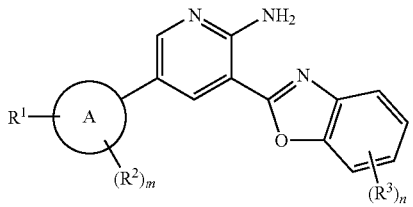

| No. & Note | R¹-A | m | R² | n | R³ |
|---|---|---|---|---|---|
| [1] | 4-ethylsulphonylphenyl | 0 | | 0 | |
| [2] | 1-(1-tert-butoxycarbonyl-4-piperidyl)pyrazol-4-yl | 0 | | 0 | |
| [3] | 1-(4-piperidyl)pyrazol-4-yl | 0 | | 0 | |
| [4] | 3-(aminomethyl)phenyl | 0 | | 0 | |
| [5] | 3-ethylsulphonylphenyl | 0 | | 0 | |
| [6] | 3-(pyrrolidin-1-ylmethyl)phenyl | 0 | | 0 | |
| [7] | 4-(morpholinomethyl)phenyl | 0 | | 0 | |
| [8] | 3-(2-dimethylaminoethylcarbamoyl)phenyl | 0 | | 0 | |
| [9] | 4-(2-methoxyethoxy)phenyl | 0 | | 0 | |
| [10] | 3-piperazin-1-ylphenyl | 0 | | 0 | |
| [11] | 4-(4-hydroxypiperidine-1-carbonyl)phenyl | 0 | | 0 | |
| [12] | 8-quinolyl | 0 | | 0 | |
| [13] | 4-(aminomethyl)phenyl | 0 | | 0 | |
| [14] | 4-piperazin-1-ylphenyl | 0 | | 0 | |
| [15] | 3-(methoxymethyl)phenyl | 0 | | 0 | |
| [16] | 4-(hydroxymethyl)phenyl | 0 | | 0 | |
| [17] | 3-(methylcarbamoyl)phenyl | 0 | | 0 | |
| [18] | 4-(4-piperidyl)phenyl | 0 | | 0 | |
| [19] | 6-piperazin-1-yl-3-pyridyl | 0 | | 0 | |
| [20] | 3-acetamidophenyl | 0 | | 0 | |
| [21] | 2,3-dihydro-1,4-benzodioxin-6-yl | 0 | | 0 | |
| [22] | 3-(morpholinomethyl)phenyl | 0 | | 0 | |
| [23] | 1H-indazol-5-yl | 0 | | 0 | |
| [24] | 3-quinolyl | 0 | | 0 | |
| [25] | 4-quinolyl | 0 | | 0 | |
| [26] | 6-(3-dimethylaminopropoxy)-3-pyridyl | 0 | | 0 | |
| [27] | 4-methanesulphonamidophenyl | 0 | | 0 | |
| [28] | 4-(dimethylsulphamoyl)phenyl | 0 | | 0 | |
| [29] | 1H-indol-5-yl | 0 | | 0 | |
| [30] | 4-(cyclopropylsulphamoyl)phenyl | 0 | | 0 | |
| [31] | 1H-indol-6-yl | 0 | | 0 | |
| [32] | 3-pyrrolidin-1-ylphenyl | 0 | | 0 | |
| [33] | 3-(methylsulphamoyl)phenyl | 0 | | 0 | |
| [34] | 3-carbamoylphenyl | 0 | | 0 | |
| [35] | 3-(hydroxymethyl)phenyl | 0 | | 0 | |
| [36] | 2-(methoxymethyl)phenyl | 0 | | 0 | |
| [37] | 4-(methoxymethyl)phenyl | 0 | | 0 | |
| [38] | 4-piperazin-1-yl-phenyl | 1 | 2-methoxy | 0 | |
| [39] | 3-(dimethylsulphamoyl)phenyl | 0 | | 0 | |
| [40] | 3-cyanophenyl | 0 | | 0 | |
| [41] | 4-(2-dimethylaminoethylcarbamoyl)phenyl | 0 | | 0 | |
| [42] | 1,3-benzodioxol-5-yl | 0 | | 0 | |
| [43] | 1-naphthyl | 0 | | 0 | |
| [44] | 4-cyanophenyl | 0 | | 0 | |
| [45] | 4-piperazin-1-yl-phenyl | 1 | 2-fluoro | 0 | |
| [46] | 3-(1-piperidyl)phenyl | 0 | | 0 | |
| [47] | 3-(cyanomethyl)phenyl | 0 | | 0 | |
| [48] | 3-methylsulphonylphenyl | 0 | | 0 | |
| [49] | 3-morpholinophenyl | 0 | | 0 | |
| [50] | 3-dimethylaminophenyl | 0 | | 0 | |
| [51] | 4-(cyanomethyl)phenyl | 0 | | 0 | |
| [52] | 3-methylsulphonyloxyphenyl | 0 | | 0 | |
| [53] | 3-(4-methylpiperazin-1-yl)phenyl | 0 | | 0 | |
| [54] | 6-(4-methylpiperazin-1-yl)-3-pyridyl | 0 | | 0 | |
| [55] | 1-(tetrahydropyran-2-yl)pyrazol-4-yl | 0 | | 0 | |

Notes The products gave the characterising data shown below.

[1] Mass Spectrum: M+H⁺ 380.22; RT 2.65 min.

[2] Mass Spectrum: M+H⁺ 461.1; RT 3.87 min; NMR Spectrum: (DMSOd⁶) 8.53 (d, 1H), 8.44 (d, 1H), 8.36 (s, 1H), 7.93 (s, 1H), 7.84 (d, 1H), 7.79 (d, 1H), 7.65 (bs, 2H), 7.40-7.50 (m, 2H), 4.32-4.42 (m, 1H), 3.99-4.14 (m, 2H), 2.94 (bs, 2H), 2.01-2.12 (m, 2H), 1.76-1.89 (m, 2H), 1.43 (s, 9H).

The tert-butyl 4-[4-(4,4,5,5-tetramethyl-1,3,2-dioxaborolan-2-yl)pyrazol-1-yl]piperidine-1-carboxylate used as a reagent was prepared as described in Cui et al US Pat Appl US 2006046991.

[3] This compound was prepared from tert-butyl 4-[4-[6-amino-5-(1,3-benzoxazol-2-yl)-3-pyridyl]pyrazol-1-yl]piperidine-1-carboxylate [Example 2(2)] by removal of the Boc group using trifluoroacetic acid in DCM. The resultant product gave the following characterising data: Mass Spectrum: M+H⁺ 361.31; RT 1.12 min; NMR Spectrum: (DMSOd⁶) 8.53 (d, 1H), 8.44 (d, 1H), 8.29 (s, 1H), 7.91 (s, 1H), 7.78-7.86 (m, 2H), 7.62 (s, 2H), 7.41-7.49 (m, 2H), 4.20 (tt, 1H), 3.06 (d, 2H), 2.61 (td, 2H), 2.33 (quintet, 1H), 2.00 (d, 2H), 1.82 (qd, 2H). Tert-butyl 4-(4-(4,4,5,5-tetramethyl-1,3,2-dioxaborolan-2-yl)-1H-pyrazol-1-yl)piperidine-1-carboxylate was used as a starting material to prepare compound [3].

[4] Mass Spectrum: M+H⁺ 316; RT 2.35 min.

[5] Mass Spectrum: M+H⁺ 380.22; RT 2.64 min.

[6] Mass Spectrum: M+H⁺ 370; RT 3.12 min.

[7] Mass Spectrum: M+H⁺ 387; RT 2.66 min. 4-[[4-(4,4,5,5-tetramethyl-1,3,2-dioxaborolan-2-yl)phenyl]methyl]morpholine was used as a starting material to prepare compound [7].

[8] Mass Spectrum: M+H⁺ 402.47; RT 2.06 min.

[9] Mass Spectrum: M+H⁺ 362.25; RT 2.91 min.

[10] Tert-butyl 4-[3-(4,4,5,5-tetramethyl-1,3,2-dioxaborolan-2-yl)phenyl]piperazine-1-carboxylate was used as a reagent and after coupling, the Boc group was removed with trifluoroacetic acid in DCM. The resultant product gave the following characterising data: Mass Spectrum: M+H⁺ 372.11; RT 2.41 min; NMR Spectrum: (DMSOd⁶) 8.56 (1H, d), 8.47 (1H, d), 7.79-7.88 (2H, m), 7.76 (2H, s), 7.41-7.50 (2H, m), 7.31 (1H, t), 7.18 (1H, s), 7.07 (1H, d), 6.92 (1H, dd), 3.15 (4H, t), 2.87 (4H, t).

The tert-butyl 4-[3-(4,4,5,5-tetramethyl-1,3,2-dioxaborolan-2-yl)phenyl]piperazine-1-carboxylate used as a reagent was prepared as follows:

Di-tert-butyl dicarbonate (4.93 g) was added slowly to a mixture of 1-(3-bromophenyl)piperazine (4.95 g), triethylamine (4.2 g) and DMAP (0.25 g) in a solution of acetonitrile (50 ml) and resulting solution was stirred for 1 hour. The reaction mixture was then evaporated and diluted with DCM (200 ml), and then washed with water (100 ml). The organic layer was dried over magnesium sulfate, filtered through a silica pad and evaporated under reduced pressure. There was thus obtained tert-butyl 4-(3-bromophenyl)piperazine-1-carboxylate (7.44 g); Mass Spectrum: M+H⁺ 341; RT 3.01 min; NMR Spectrum: (DMSOd⁶) 7.11 (1H, t), 7.03 (1H, t), 6.98 (1H, ddd), 6.82 (1H, ddd), 3.56 (4H, t), 3.13 (4H, t), 1.48 (9H, s).

Dichlorobis(triphenylphosphine)palladium (TI) (0.172 g), tert-butyl 4-(3-bromophenyl)piperazine-1-carboxylate (3.59 g), bis(pinacolato)diboron (3.21 g) and potassium acetate (2.06 g) were combined in a flask which was then dried in a dessicator containing phosphorus pentoxide. The flask was then flushed with nitrogen and 1,4-dioxane (100 ml) was added. The resulting suspension was stirred at 80° C. for 20 hours. The mixture was allowed to cool and then the solvent was evaporated under reduced pressure. The residue was redissolved in ethyl acetate (100 ml) and washed with water (100 ml), then dried over magnesium sulfate, filtered through a silica pad and evaporated. The resultant product was purified by flash silica chromatography (elution solvent 25% ethyl acetate in isohexane). There was thus obtained tert-butyl 4-[3-(4,4,5,5-tetramethyl-1,3,2-dioxaborolan-2-yl)phenyl]piperazine-1-carboxylate (3.34 g); Mass Spectrum: M+H=389; RT 3.23 min; NMR Spectrum: (DMSOd$_6$) 7.32 (3H, m), 7.02 (1H, ddd), 3.57 (4H, t), 3.15 (4H, t), 1.48 (9H, s), 1.33 (12H, s).

[11] Mass Spectrum: M+H$^+$ 414; RT 2.03 min.

The (4-hydroxypiperidin-1-yl)-[4-(4,4,5,5-tetramethyl-1,3,2-dioxaborolan-2-yl)phenyl]methanone used as a reagent was prepared as follows:

1-Ethyl-3-(3-dimethylaminopropyl)carbodiimide hydrochloride (1.15 g) was added to a solution of 4-(4,4,5,5-tetramethyl-1,3,2-dioxaborolan-2-yl)benzoic acid (1.25 g) and HOBT (0.82 g) in DMF (12 ml) under an atmosphere of argon. The mixture was stirred for four hours. The mixture was then added slowly to a solution of piperidin-4-ol (0.61 g) in DMF (6 ml). The mixture was stirred overnight, then concentrated under reduced pressure and dichloromethane (50 ml) was added. The resultant mixture was washed with water (20 ml), saturated sodium hydrogen carbonate solution twice (2×20 ml) and water (50 ml). The solution was the dried over magnesium sulfate and evaporated to give an oil. Diethyl ether (20 ml) was added to this oil and the mixture was stirred for 30 min. The resultant mixture was filtered and concentrated under reduced pressure. There was thus obtained (4-hydroxypiperidin-1-yl)-[4-(4,4,5,5-tetramethyl-1,3,2-dioxaborolan-2-yl)phenyl]methanone (2.10 g); Mass Spectrum: M+H$^+$ 332; NMR Spectrum: (DMSOd$^6$ at 100° C.) 7.70 (d, 2H), 7.33 (2, 2H), 4.42 (d, 1H), 3.80-3.68 (m, 2H), 3.22-3.10 (m, 2H), 1.80-1.67 (m, 2H), 1.5-1.3 (m, 2H), 1.30 (s, 12H).

[12] Mass Spectrum: M+H$^+$ 339.22; RT 2.76 min.

[13] Mass Spectrum: M+H$^+$ 316; RT 2.31 min.

[14] Tert-butyl 4-(4-(4,4,5,5-tetramethyl-1,3,2-dioxaborolan-2-yl)phenyl)piperazine-1-carboxylate was used as a reagent and after coupling, the Boc group was removed with trifluoroacetic acid in DCM. The resultant product gave the following characterising data: Mass Spectrum: M+H$^+$ 372.11; RT 2.36 min; NMR Spectrum: (DMSOd$^6$) 8.53 (1H, d), 8.43 (1H, d), 7.79-7.87 (2H, m), 7.66 (2H, s), 7.56 (2H, d), 7.41-7.49 (2H, m), 7.02 (2H, d), 3.10 (4H, t), 2.86 (4H, t).

[15] Mass Spectrum: M+H$^+$ 332.23; RT 2.96 min.

[16] Mass Spectrum: M+H$^+$ 318.45; RT 2.1 min.

[17] Mass Spectrum: M+H$^+$ 345.24; RT 2.34 min.

[18] Tert-butyl 4-(4-(4,4,5,5-tetramethyl-1,3,2-dioxaborolan-2-yl)phenyl)piperidine-1-carboxylate was used as a reagent and after coupling, the Boc group was removed with trifluoroacetic acid in DCM. The resultant product gave the following characterising data: Mass Spectrum: M+H$^+$ 371.33; RT 1.89 min; NMR Spectrum: (DMSOd$^6$) 8.57 (1H, d), 8.48 (1H, d), 7.79 (2H, s), 7.79-7.88 (2H, m), 7.63 (2H, d), 7.40-7.49 (2H, m), 7.32 (2H, d), 3.04 (2H, d), 2.55-2.66 (3H, m), 1.71 (2H, d), 1.54 (2H, qd).

The tert-butyl 4-(4-(4,4,5,5-tetramethyl-1,3,2-dioxaborolan-2-yl)phenyl)piperidine-1-carboxylate used as a reagent was prepared as follows:

Di-tert-butyl dicarbonate (0.914 ml) was added in one portion to 4-(4-bromophenyl)piperidine hydrochloride (1.0 g) and triethylamine (1.260 ml) in DCM (34 ml). The resulting solution was stirred for 70 minutes. The reaction mixture was evaporated and washed with isohexane. The filtrate was evaporated and there was thus obtained tert-butyl 4-(4-bromophenyl)piperidine-1-carboxylate (1.191 g); Mass Spectrum: M−tBu$^+$=281.28; RT 2.33 min; NMR Spectrum: (DMSOd$^6$) 7.53 (2H, d), 7.27 (2H, d), 4.12 (2H, d), 2.75-2.96 (2H, m), 2.68-2.79 (1H, m), 1.79 (2H, d), 1.47 (9H, s), 1.44-1.58 (2H, m).

Dichlorobis(triphenylphosphine)palladium (II) (0.043 g) was added in one portion to tert-butyl 4-(4-bromophenyl)piperidine-1-carboxylate (0.400 g), bis(pinacolato)diboron (0.358 g) and potassium acetate (0.392 g) in DMSO (4 ml). The resulting suspension was stirred at 80° C. for 20 hours. The mixture was allowed to cool and then partitioned between ethyl acetate and water (20 ml). The organic layer was collected, and the aqueous layer extracted with ethyl acetate (20 ml). The organic layers were combined and washed with saturated brine (20 ml), dried over magnesium sulfate, filtered and evaporated. The resultant product was purified by flash silica chromatography (elution gradient 0 to 20% ethyl acetate in isohexane). There was thus obtained tert-butyl 4-(4-(4,4,5,5-tetramethyl-1,3,2-dioxaborolan-2-yl)phenyl)piperidine-1-carboxylate (0.378 g); Mass Spectrum: M−tBu$^+$=288.44; RT 2.64 min; NMR Spectrum: (DMSOd$^6$) 7.61 (2H, d), 7.26 (2H, d), 4.07 (2H, d), 2.71-2.91 (2H, m), 2.65-2.77 (1H, m), 1.74 (2H, d), 1.42 (9H, s), 1.42-1.55 (2H, m), 1.29 (12H, s).

[19] tert-butyl 4-(5-(4,4,5,5-tetramethyl-1,3,2-dioxaborolan-2-yl)pyridin-2-yl)piperazine-1-carboxylate was used as a reagent and after coupling, the Boc group was removed with trifluoroacetic acid in DCM. The resultant product gave the following characterising data: Mass Spectrum: M+H$^+$ 373.09; RT 2.19 min; NMR Spectrum: (DMSOd$^6$) 8.53 (1H, d), 8.47 (1H, d), 8.44 (1H, d), 7.79-7.91 (3H, m), 7.70 (2H, s), 7.41-7.49 (2H, m), 6.90 (1H, d), 3.47 (4H, t), 2.82 (4H, t)).

[20] Mass Spectrum: M+H$^+$ 345.46; RT 2.11 min.

[21] Mass Spectrum: M+H$^+$ 346.22; RT 2.97 min.

[22] Mass Spectrum: M+H$^+$ 386; RT 2.66 min.

[23] Mass Spectrum: M+H$^+$ 328.24; RT 2.46 min.

[24] Mass Spectrum: M+H$^+$ 339.22; RT 2.63 min.

[25] Mass Spectrum: M+H$^+$ 339.22; RT 2.71 min.

[26] N,N-dimethyl-3-[[5-(4,4,5,5-tetramethyl-1,3,2-dioxaborolan-2-yl)-2-pyridyl]oxy]propan-1-amine was used as a starting material to prepare compound [26]. The resultant product gave the following characterising data: Mass Spectrum: M+H$^+$ 389; RT 2.78 min.

[27] Mass Spectrum: M+H$^+$ 381.16; RT 1.88 min.

[28] Mass Spectrum: M+H$^+$ 392.22; RT 2.82 min.

[29] Mass Spectrum: M+H$^+$ 327.45; RT 2.54 min.

[30] Mass Spectrum: M+H$^+$ 406; RT 2.63 min.

[31] Mass Spectrum: M+H$^+$ 327.39; RT 2.62 min.

[32] Mass Spectrum: M+H$^+$ 357.28; RT 3.55 min.

[33] Mass Spectrum: M+H$^+$ 381.21; RT 2.55 min.

[34] Mass Spectrum: M+H$^+$ 330; RT 2.10 min.

[35] Mass Spectrum: M+H$^+$ 318.44; RT 2.13 min.

[36] Mass Spectrum: M+H$^+$ 332.28; RT 2.97 min.

[37] Mass Spectrum: M+H$^+$ 332.23; RT 2.95 min.

[38] Tert-butyl 4-[3-methoxy-4-[4,4,5,5-tetra(methyl)-1,3,2-dioxaborolan-2-yl]phenyl]piperazine-1-carboxylate was used as a reagent and after coupling, the Boc group was cleaved in the course of the concentration of the reaction medium with residual formic acid. The resultant product gave the following characterising data: Mass Spectrum: M+H⁺ 402; RT 2.36 min.

The tert-butyl 4-[3-methoxy-4-[4,4,5,5-tetra(methyl)-1,3,2-dioxaborolan-2-yl]phenyl]piperazine-1-carboxylate used as a reagent was prepared as follows:

Di-tert-butyl dicarbonate (8.77 ml) was added slowly to 1-(3-methoxyphenyl)piperazine (6.6 g) and triethylamine (9.57 ml) in DCM (50 ml). The resulting solution was stirred for 1 hour. The reaction mixture was then evaporated and diluted with ethyl acetate (200 ml), and washed sequentially with water (100 ml) and saturated brine (50 ml). The organic layer was dried over magnesium sulfate, filtered and evaporated to afford an oil which crystallised on standing to give tert-butyl 4-(3-methoxyphenyl)piperazine-1-carboxylate (9.30 g), Mass Spectrum: M−tBu⁺ 237; RT 2.52 min; NMR Spectrum: (DMSOd$_6$) 7.12 (t, 1H), 6.54 (dd, 1H), 6.48 (t, 1H), 6.40 (dd, 1H), 3.73 (s, 3H), 3.47 (m, 4H), 3.09 (m, 4H), 1.44 (s, 9H).

Bromine (0.85 ml) was added to tert-butyl 4-(3-methoxyphenyl)piperazine-1-carboxylate (4.0 g) in acetic acid (30 ml). The resulting solution was stirred at 0° C. for 1 hour. The reaction mixture was then evaporated to dryness, redissolved in ethyl acetate and washed with saturated sodium hydrogen carbonate. The organic layer was dried over magnesium sulfate, filtered and evaporated to afford crude product. This material was purified by flash silica chromatography (elution gradient 0 to 10% ethyl acetate in DCM). There was thus obtained tert-butyl 4-(4-bromo-3-methoxyphenyl)piperazine-1-carboxylate (3.89 g); Mass Spectrum: M−tBu+ 315; RT 2.77 min; NMR Spectrum: (DMSOd$_6$) 7.36 (d, 1H), 6.66 (d, 1H), 6.47 (dd, 1H), 3.84 (s, 3H), 3.47 (m, 4H), 3.16 (m, 4H), 1.44 (s, 9H).

1,1'-Bis(diphenylphosphino)ferrocenedichloropalladium (II) (0.097 g) was added to bis(pinacolato)diboron (0.41 g), tert-butyl 4-(4-bromo-3-methoxyphenyl)piperazine-1-carboxylate (0.50 g) and potassium acetate (0.46 g) in DMSO (10 ml). The resulting solution was stirred at 140° C. for 1 hour. The reaction mixture was then diluted with ethyl acetate (100 ml), and washed sequentially with water (100 ml) and saturated brine (10 ml). The organic layer was dried over magnesium sulfate, filtered and evaporated to afford crude product. This material was purified by flash silica chromatography (elution gradient 10 to 50% ethyl acetate in isohexane). There was thus obtained tert-butyl 4-[3-methoxy-4-(4,4,5,5-tetramethyl-1,3,2-dioxaborolan-2-yl)phenyl]piperazine-1-carboxylate (0.50 g); Mass Spectrum: M+H⁺ 419.39; RT 2.75 min.

[39] Mass Spectrum: M+H⁺ 395.21; RT 2.8 min.
[40] Mass Spectrum: M+H⁺ 313.23; RT 2.73 min.
[41] Mass Spectrum: M+H⁺ 402.32; RT 2.37 min. N-(2-(dimethylamino)ethyl)-4-(4,4,5,5-tetramethyl-1,3,2-dioxaborolan-2-yl)benzamide was used as a starting material to prepare compound [41].
[42] Mass Spectrum: M+H⁺ 332.23; RT 2.83 min.
[43] Mass Spectrum: M+H⁺ 338.24; RT 3.25 min.
[44] Mass Spectrum: M+H⁺ 313.23; RT 2.73 min.
[45] Tert-butyl 4-[3-fluoro-4-(4,4,5,5-tetramethyl-1,3,2-dioxaborolan-2-yl)phenyl]piperazine-1-carboxylate was used as a reagent and after coupling, the Boc group was removed with trifluoroacetic acid in DCM. The resultant product gave the following characterising data: Mass Spectrum: M+H⁺ 390.32; RT 2.54 min; NMR Spectrum: (DMSOd⁶) 8.89 (brs, 1H), 8.42 (d, 1H), 7.85 (m, 2H), 7.55 (t, 1H), 7.47 (m, 1H), 7.27 (s, 1H), 7.15 (s, 1H), 7.02 (s, 1H), 6.96 (m, 1H), 3.47 (m, 4H), 3.28 (m, 4H).

The tert-butyl 4-[3-fluoro-4-(4,4,5,5-tetramethyl-1,3,2-dioxaborolan-2-yl)phenyl]piperazine-1-carboxylate used as a reagent was prepared as follows:

Di-tert-butyl dicarbonate (6.58 ml) was added slowly to 1-(3-fluorophenyl)piperazine (4.64 g) and triethylamine (7.18 ml) in DCM (50 ml) and the resulting solution was stirred for 1 hour. The reaction mixture was then evaporated and diluted with ethyl acetate (200 ml), and washed sequentially with water (100 ml) and saturated brine (50 ml). The organic layer was dried over magnesium sulfate, filtered and evaporated to afford an oil which crystallised on standing to give tert-butyl 4-(3-fluorophenyl)piperazine-1-carboxylate (7.20 g); Mass Spectrum: M−tBu⁺ 225; RT 2.81 min; NMR Spectrum: (DMSOd$_6$) 7.23 (m, 1H), 6.77 (m, 2H), 6.57 (m, 1H), 3.47 (m, 4H), 3.16 (m, 4H), 1.42 (s, 9H).

Bromine (0.809 ml) was added to tert-butyl 4-(3-fluorophenyl)piperazine-1-carboxylate (4.0 g) in acetic acid (30 ml). The resulting solution was stirred for 1 hour. The reaction mixture was then evaporated to dryness, redissolved in ethyl acetate and washed with saturated sodium hydrogen carbonate. The organic layer was dried over magnesium sulfate, filtered and evaporated to dryness. The resulting solid was purified by flash silica chromatography (elution gradient 0 to 10% ethyl acetate in DCM). There was thus obtained tert-butyl 4-(4-bromo-3-fluorophenyl)piperazine-1-carboxylate (1.95 g); Mass Spectrum: M−tBu⁺ 303; RT 3.09 min; NMR Spectrum: (DMSOd$_6$) 7.47 (t, 1H), 6.96 (dd, 1H), 6.75 (dd, 1H), 3.47 (m, 4H), 3.16 (m, 4H), 1.42 (s, 9H).

1,1'-Bis(diphenylphosphino)ferrocenedichloropalladium (II) (0.14 g) was added to bis(pinacolato)diboron (0.59 g), tert-butyl 4-(4-bromo-3-fluorophenyl)piperazine-1-carboxylate (0.70 g) and potassium acetate (0.67 g) in DMSO (10 ml) and the resulting solution was stirred at 120° C. for 1 hour. The reaction mixture was then diluted with ethyl acetate (100 ml), and washed sequentially with water (50 ml) three times. The organic layer was dried over magnesium sulfate, filtered and evaporated to dryness. The resultant solid was purified by flash silica chromatography (elution gradient 20 to 70% ethyl acetate in isohexane). There was thus obtained tert-butyl 4-[3-fluoro-4-(4,4,5,5-tetramethyl-1,3,2-dioxaborolan-2-yl)phenyl]piperazine-1-carboxylate (0.26 g); Mass Spectrum: M+H⁺ 351; RT 3.16 min.

[46] Mass Spectrum: M+H⁺ 371.6; RT 3.49 min; NMR Spectrum: (CDCl$_3$) 8.52 (1H, d), 8.48 (1H, d), 7.75 (1H, ddd), 7.60 (1H, ddd), 7.32-7.38 (3H, m), 7.13 (1H, dd), 7.05 (1H, d), 6.95 (2H, br s), 6.95 (1H, dd), 3.25 (4H, m), 1.76 (4H, m), 1.62 (2H, m).

[47] Mass Spectrum: M+H⁺ 327.5; RT 2.66 min; NMR Spectrum: (CDCl$_3$) 8.53 (1H, d), 8.48 (1H, d), 7.76 (1H, ddd), 7.61 (1H, ddd), 7.58 (1H, d), 7.55 (1H, br.s), 7.49 (1H, dd), 7.37-7.39 (2H, m), 7.34 (1H, dd), 7.02 (2H, br s), 3.85 (2H, s).

[48] Mass Spectrum: M+H⁺ 366.4; RT 2.38 min.

[49] 4-(3-(4,4,5,5-tetramethyl-1,3,2-dioxaborolan-2-yl)phenyl)morpholine was used as a starting material to prepare compound [49]. The resultant product gave the following characterising data: Mass Spectrum: M+H⁺ 373.5; RT 2.77 min.

[50] Mass Spectrum: M+H⁺ 331.5; RT 3.09 min; NMR Spectrum: (CDCl₃) 8.53 (1H, d), 8.50 (1H, d), 7.75 (1H, ddd), 7.60 (1H, ddd), 7.37 (2H, m), 7.33 (1H, d), 6.95 (1H, ddd), 6.91 (1H, dd), 6.9 (2H, br s), 6.76 (1H, ddd), 3.04 (6H, s).

[51] Mass Spectrum: M+H⁺ 327.4; RT 2.65 min.

[52] Mass Spectrum: M+H⁺ 382.5; RT 2.66 min.

[53] This product was obtained by reacting 3-(1,3-Benzoxazol-2-yl)-5-(3-piperazin-1-ylphenyl)pyridin-2-amine [Example 2(10)] in a methylation procedure analagous to that described in Example 3 hereinafter. The resultant product gave the following characterising data: Mass Spectrum: M+H⁺ 386.5; RT 2.66 min. tert-butyl 4-[3-(4,4,5,5-tetramethyl-1,3,2-dioxaborolan-2-yl)phenyl]piperazine-1-carboxylate was used as a reagent and after coupling, the Boc group was removed with trifluoroacetic acid in DCM.

[54] This product was obtained by reacting 3-(1,3-Benzoxazol-2-yl)-5-[6-(piperazin-1-yl)-3-pyridyl]pyridin-2-amine [Example 2(19)] in a methylation procedure analagous to that described in Example 3 hereinafter. The resultant product gave the following characterising data: Mass Spectrum: M+H⁺ 387.5; RT 2.40 min. tert-butyl 4-[5-(4,4,5,5-tetramethyl-1,3,2-dioxaborolan-2-yl)-2-pyridyl]piperazine-1-carboxylate was used as a reagent and after coupling, the Boc group was removed with trifluoroacetic acid in DCM.

[55] The following conditions were used to prepare Example 2(55). Bis(triphenylphosphine) Palladium (II) Chloride (60.5 mg) was added to a stirred degassed suspension of 1-tetrahydropyran-2-yl-4-(4,4,5,5-tetramethyl-1,3,2-dioxaborolan-2-yl)pyrazole (779 mg), 3-(1,3-benzoxazol-2-yl)-5-bromo-pyridin-2-amine (500 mg) and caesium fluoride (524 mg) dissolved in methanol (15 ml) under Argon atmosphere. The resulting mixture was heated in the microwave at 120° C. for 20 minutes. The mixture was concentrated under reduce pressure and adsorbed on silica gel. The crude product was purified by flash chromatography on silica gel eluting with 10 to 80% ethyl acetate in petroleum ether. The solvent was evaporated to dryness to afford 3-(1,3-benzoxazol-2-yl)-5-(1-tetrahydropyran-2-ylpyrazol-4-yl)pyridin-2-amine (444 mg). NMR Spectrum: (CDCl3) 1.60-1.82 (m, 3H), 2.04-2.23 (m, 3H), 3.71-3.79 (m, 1H), 4.08-4.15 (m, 1H), 5.44 (dd, 1H), 6.91 (bs, 2H), 7.34-7.41 (m, 2H), 7.60 (dd, 1H), 7.75 (dd, 1H), 7.84 (s, 1H), 7.89 (s, 1H), 8.39 (d, 1H), 8.41 (d, 1H); Mass spectrum: M+H⁺ 362

The 1-tetrahydropyran-2-yl-4-(4,4,5,5-tetramethyl-1,3,2-dioxaborolan-2-yl)pyrazole used as starting material was prepared as follows:

A solution of butyllithium (18.17 ml, 2.5M in hexanes) was added to 4-bromo-1-tetrahydropyran-2-yl-pyrazole, in solution in THF (400 ml) between −100° C. and −80° C. under nitrogen atmosphere. The mixture was stirred for 1 hour at −90° C. Trimethoxyborane (5.07 ml) was added at −70° C. and the mixture was stirred for a further 30 minutes. The mixture was quenched with a 15% solution of ammonium chloride (5 ml); the mixture was allowed to warm to room temperature and was stirred for 30 minutes. The organic layer was separated and the aqueous layer was extracted with 20 ml of THF. The combined organic portions were dried over magnesium sulphate and the solvent was evaporated under reduce pressure to afford the crude boronic acid. 2,3-dimethylbutane-2,3-diol (5.11 g) was added to the boronic acid in solution in THF with 4 A molecular sieves (100 mg). The mixture was stirred at room temperature for 15 hours. The mixture was evaporated under reduce pressure. Water (5 ml) was added and the mixture was extracted with heptane (3×10 ml), dried over magnesium sulphate, filtered and evaporated under reduce pressure to afford 1-tetrahydropyran-2-yl-4-(4,4,5,5-tetramethyl-1,3,2-dioxaborolan-2-yl)pyrazole (8.80 g). NMR Spectrum: (CDCl3) 1.31 (s, 1H), 1.54-1.76 (m, 4H), 1.95-2.17 (m, 2H), 3.66-3.73 (m, 1H), 4.01-4.07 (m, 1H), 5.41 (dd, 1H), 7.82 (s, 1H), 7.94 (s, 1H)

4-Bromo-1-tetrahydropyran-2-yl-pyrazole was synthesized according to Tolf et al., *Acta Chemica Scandinavica, Series B: Organic Chemistry and Biochemistry* (1982), B36 (2), 101-7.

EXAMPLE 3

3-(1,3-Benzoxazol-2-yl)-5-[1-(1-methyl-4-piperidyl)pyrazol-4-yl]pyridin-2-amine

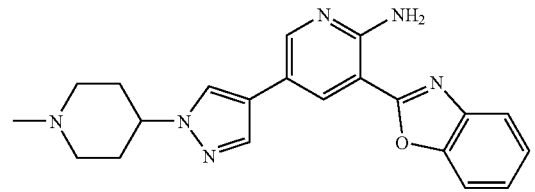

3-(1,3-Benzoxazol-2-yl)-5-[1-(4-piperidyl)pyrazol-4-yl]pyridin-2-amine (1.8 g) was added to a mixture of acetic acid (2.86 µL) and 37% aqueous formaldehyde (0.583 ml) dissolved in methanol (40 ml) and the resulting solution was stirred for 15 minutes. Sodium cyanoborohydride (0.377 g) was then added and the mixture was stirred for a further 3 hours. The reaction mixture was concentrated to dryness and diluted with DCM and purified by flash chromatography on silica gel (eluting with a gradient of 5 to 10% 7N methanolic ammonia in dichloromethane). The solvent was evaporated to dryness and there was thus obtained 3-(1,3-benzoxazol-2-yl)-5-[1-(1-methyl-4-piperidyl)pyrazol-4-yl]pyridin-2-amine (1.180 g); Mass Spectrum: M+H⁺ 375.1; RT 1.73 min; NMR Spectrum: (DMSOd⁶) 8.53 (d, 1H), 8.44 (d, 1H), 8.32 (d, 1H), 7.92 (d, 1H), 7.85 (m, 1H), 7.80 (m, 1H), 7.64 (br s, 2H), 7.46 (m, 2H), 4.13 (m, 1H), 2.88 (br m, 2H), 2.23 (s, 3H), 2.04 (m, 6H).

EXAMPLE 4

Using an analogous procedure to that described in Example 3, the appropriate aldehyde or ketone was reacted with the appropriate amine give the compounds described in Table II.

TABLE II

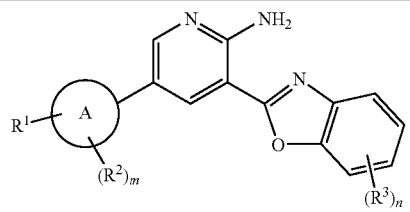

| No. & Note | R¹-A | m | R² | n | R³ |
|---|---|---|---|---|---|
| [1] | 1-(1-ethyl-4-piperidyl)pyrazol-4-yl | 0 | | 0 | |

[1] Acetaldehyde was used to prepare compound [1]. The product gave the following characterizing data: Mass Spectrum: M+H⁺ 389.30; RT 1.52 min; NMR Spectrum: (DMSOd⁶) 8.53 (1H, d), 8.44 (1H, d), 8.32 (1H, s), 7.91 (1H, s), 7.82-7.87 (1H, m), 7.77-7.82 (1H, m), 7.62 (2H, s), 7.41-7.50 (2H, m), 4.09-4.20 (1H, m), 2.99 (2H, d), 2.40 (2H, q), 1.92-2.14 (6H, m), 1.04 (3H, t).

EXAMPLE 5

3-(1,3-Benzoxazol-2-yl)-5-[1-(1-isopropyl-4-piperidyl)pyrazol-4-yl]pyridin-2-amine

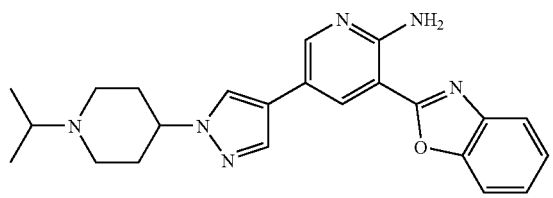

2-Iodopropane (0.029 ml) was added in one portion to 3-(1,3-benzoxazol-2-yl)-5-[1-(4-piperidyl)pyrazol-4-yl]pyridin-2-amine (0.100 g) and triethylamine (0.05 8 ml) in DMA (3 ml) and the resulting solution was stirred for 30 minutes. A further portion of 2-iodopropane (0.029 ml) was added, the temperature was increased to 50° C. and the reaction mixture was stirred for a further 90 minutes. A third portion of 2-iodopropane (0.029 ml) was added, and then triethylamine (0.058 ml) was added and the reaction heated at 50° C. for a further hour. The reaction mixture was then evaporated to dryness and redissolved in DMSO (3.6 ml) and the crude product was purified by preparative X bridge HPLC (C18 OBD column, 5μ silica, 21 mm diameter, 100 mm length using decreasingly polar mixtures of water containing 1% ammonia and MeCN as eluents). There was thus obtained 3-(1,3-benzoxazol-2-yl)-5-[1-(1-isopropyl-4-piperidyl) pyrazol-4-yl]pyridin-2-amine (0.065 g); Mass Spectrum: M+H+ 403.17; RT 2.49 min; NMR Spectrum: (DMSOd6) 8.53 (1H, d), 8.44 (1H, d), 8.32 (1H, s), 7.90 (1H, s), 7.82-7.86 (1H, m), 7.77-7.81 (1H, m), 7.62 (2H, s), 7.41-7.49 (2H, m), 4.05-4.16 (1H, m), 2.91 (2H, d), 2.77 (1H, quintet), 2.29 (2H, t), 2.02-2.11 (2H, m), 1.94 (2H, qd), 1.01 (6H, d).

EXAMPLE 6

3-(4-Fluoro-1,3-benzoxazol-2-yl)-5-[1-(1-methyl-4-piperidyl)pyrazol-4-yl]pyridin-2-amine

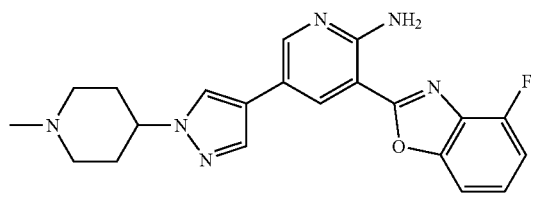

2M Trimethylaluminium in toluene (0.75 ml) was added to a solution of 2-bromo-6-fluoro-aniline (0.229 g) in toluene (30 ml). The mixture was stirred for 30 minutes, then methyl 2-amino-5-[1-(1-methyl-4-piperidyl)pyrazol-4-yl]pyridine-3-carboxylate (0.19 g) was added. The mixture was heated to 120° C. for 18 hours, allowed to cool and then quenched with 10% aqueous Rochelle's salt solution. The organic fraction was purified by SCX ion-exchange chromatography to give crude 2-amino-N-(2-bromo-6-fluorophenyl)-5-[1-(1-methylpiperidin-4-yl)pyrazol-4-yl]pyridine-3-carboxamide; Mass Spectrum: M+H+ 472.1; RT 0.87 min.

2-Amino-N-(2-bromo-6-fluorophenyl)-5-[1-(1-methylpiperidin-4-yl)pyrazol-4-yl]pyridine-3-carboxamide was dissolved in DME (10 ml) and added to a mixture of copper iodide (0.03 g), 1,10-phenanthroline (0.058 g) and caesium carbonate (0.156 g). The mixture was heated to 120° C. for in a 100 W microwave reactor for 1 hour, then allowed to cool and diluted with methanol (10 ml). The mixture was purified by SCX ion-exchange chromatography (elution with 7M methanolic ammonia) and then concentrated to dryness. The crude product was then purified by preparative HPLC. There was thus obtained 3-(4-fluoro-1,3-benzoxazol-2-yl)-5-[1-(1-methyl-4-piperidyl)pyrazol-4-yl]pyridin-2-amine (0.021 g); Mass Spectrum: M+H+ 392.18; RT 1.23 min.

The methyl 2-amino-5-[1-(1-methyl-4-piperidyl)pyrazol-4-yl]pyridine-3-carboxylate used as a reagent was prepared as follows:

Tetrakis(triphenylphosphine)palladium(0) (0.915 g) was added to a solution of methyl 2-amino-5-bromo-pyridine-3-carboxylate (3.66 g), tert-butyl 4-(4-(4,4,5,5-tetramethyl-1,3,2-dioxaborolan-2-yl)-1H-pyrazol-1-yl)piperidine-1-carboxylate (6.57 g) and caesium carbonate (4.31 ml) in dioxane (150 ml) and water (38 ml) under an atmosphere of nitrogen. The resulting mixture was stirred at 80° C. for 2 hours, then evaporated to dryness and redissolved in ethyl acetate (200 ml). This mixture was washed with water (200 ml) and then saturated with brine (200 ml). The organic layer was dried over magnesium sulfate, filtered and then evaporated under reduced pressure. The residue was purified by flash silica chromatography (elution gradient 0 to 5% 7M methanolic ammonia in DCM). There was thus obtained methyl 2-amino-5-[1-(1-tert-butoxycarbonyl-4-piperidyl)pyrazol-4-yl]pyridine-3-carboxylate (2.99 g); Mass Spectrum: M+H+ 402.24; RT 1.78 min.

Thionyl chloride (0.598 ml) was added dropwise to a solution of methyl 2-amino-5-[1-(1-tert-butoxycarbonyl-4-piperidyl)pyrazol-4-yl]pyridine-3-carboxylate (2.99 g) in methanol (100 ml). The resulting solution was stirred at 80° C. for 3 hours, then concentrated under reduced pressure. The reside was purified by SCX ion exchange chromatography (elution with 7M methanolic ammonia). There was thus obtained methyl 2-amino-5-[1-(4-piperidyl)pyrazol-4-yl]pyridine-3-carboxylate (2.69 g); Mass Spectrum: M+H+ 302.2; RT 0.63 min.

Acetic acid (4.26 μL) was added to a solution of methyl 2-amino-5-[1-(4-piperidyl)pyrazol-4-yl]pyridine-3-carboxylate (2.245 g) and 37% aqueous formaldehyde (0.666 ml) in methanol (100 ml). The resulting mixture was stirred for 5 minutes. Sodium cyanoborohydride (0.562 g) was then added and the mixture was stirred for a further 30 minutes, then concentrated under reduced pressure. The residue was purified by SCX ion exchange chromatography (elution with 7M methanolic ammonia) and pure fractions were evaporated to dryness. The crude product was purified by flash silica chromatography (elution gradient 0 to 10% 7M methanolic ammonia in DCM). There was thus obtained methyl 2-amino-5-[1-(1-methyl-4-piperidyl)pyrazol-4-yl]pyridine-3-carboxylate (1.990 g); Mass Spectrum: M+H+ 316.2; RT 0.64 min; NMR Spectrum: (DMSOd6) 8.43 (d, 1H), 8.14 (d, 1H), 8.12 (d, 1H), 7.75 (d, 1H), 7.03 (br s, 2H), 4.02 (m, 1H), 3.78 (s, 3H), 2.79 (br m, 2H), 2.14 (s, 3H), 1.93 (m, 6H).

The title compound can also be prepared by the following process:

37% aqueous formaldehyde (0.015 ml) at 0° C., was added to a stirred solution of 3-(4-fluoro-1,3-benzoxazol-2-yl)-5-[1-(4-piperidyl)pyrazol-4-yl]pyridin-2-amine dissolved in dichloromethane (6 ml) and methanol (6 ml) over a period of 5 minutes. The resulting mixture was stirred at 0° C. for 10 minutes. Sodium triacetoxyhydroborate (233 mg) was added at 0° C. to the mixture and stirred at 0° C. for 1 hour. A solution of 7N ammonia in methanol (20 ml) was added to the mixture and adsorbed on silica gel. The crude product was purified by flash chromatography on silica gel eluting with 2 to 6% methanolic ammonia (7 N) in dichloromethane. The solvent was evaporated to dryness and tritured in hot acetonitrile, filtered and dried under reduce pressure to afford 3-(4-fluoro-1,3-benzoxazol-2-yl)-5-[1-(1-methyl-4-piperidyl)pyrazol-4-yl]pyridin-2-amine (268 mg) as a solid.

EXAMPLE 7

Using analogous procedures to those described in Example 6, the appropriate 2-bromoaniline was reacted with the appropriate pyridine-3-carboxylate to give the compounds described in Table III. Unless otherwise stated, the required 2-bromoanilines that were used were commercially available.

TABLE III

| No. & Note | R[1]-A | m | R[2] | n | R[3] |
|---|---|---|---|---|---|
| [1] | 1-(1-methyl-4-piperidyl)pyrazol-4-yl | 0 | | 1 | 5-fluoro |
| [2] | 1-(1-methyl-4-piperidyl)pyrazol-4-yl | 0 | | 1 | 6-fluoro |
| [3] | 1-(1-methyl-4-piperidyl)pyrazol-4-yl | 0 | | 1 | 6-bromo |
| [4] | 1-(1-methyl-4-piperidyl)pyrazol-4-yl | 0 | | 1 | 6-propan-2-yl |
| [5] | 1-(1-methyl-4-piperidyl)pyrazol-4-yl | 0 | | 1 | 5-bromo |
| [6] | 1-(1-methyl-4-piperidyl)pyrazol-4-yl | 0 | | 2 | 4,6-difluoro |
| [7] | 1-(1-methyl-4-piperidyl)pyrazol-4-yl | 0 | | 1 | 6-chloro |
| [8] | 1-(1-methyl-4-piperidyl)pyrazol-4-yl | 0 | | 1 | 5-methyl |
| [9] | 1-(1-methyl-4-piperidyl)pyrazol-4-yl | 0 | | 1 | 6-methyl |
| [10] | 1-(1-methyl-4-piperidyl)pyrazol-4-yl | 0 | | 1 | 6-trifluoromethoxy |
| [11] | 1-(1-methyl-4-piperidyl)pyrazol-4-yl | 0 | | 1 | 5-trifluoromethyl |

[1] Mass Spectrum: M+H⁺ 393.18; RT 1.15 min; NMR Spectrum: (DMSOd⁶) 8.55 (d, 1H), 8.42 (d, 1H), 8.32 (d, 1H), 7.91 (d, 1H), 7.82 (dd, 1H), 7.72 (dd, 1H), 7.62 (br s, 2H), 7.31 (ddd, 1H), 4.13 (m, 1H), 2.89 (br m, 2H), 2.24 (s, 3H), 2.04 (m, 6H).

[2] Mass Spectrum: M+H⁺ 393.25; RT 1.18 min; NMR Spectrum: (DMSOd⁶) 8.46 (d, 1H), 8.32 (d, 1H), 8.24 (d, 1H), 7.84 (d, 1H), 7.80 (dd, 1H), 7.70 (dd, 1H), 7.52 (br s, 2H), 7.25 (ddd, 1H), 4.06 (m, 1H), 2.82 (br m, 2H), 2.17 (s, 3H), 1.97 (m, 6H).

[3] Mass Spectrum: M+H⁺ 452.1; RT 1.39 min.
[4] Mass Spectrum: M+H⁺ 416.23; RT 1.47 min.
[5] Mass Spectrum: M−H⁺ 452.1; RT 1.42 min.

[6] Mass Spectrum: M+H⁺ 411.3; RT 1.23 min.
[7] Mass Spectrum: M+H⁺ 408.15; RT 1.34 min.
[8] Mass Spectrum: M+H⁺ 388.2; RT 2.13 min.
[9] Mass Spectrum: M+H⁺ 388.2; RT 1.40 min.
[10] Mass Spectrum: M+H⁺ 458.17; RT 1.53 min.
[11] Mass Spectrum: M+H⁺ 442.17; RT 1.52 min.

EXAMPLE 8

3-Oxazolo[4,5-c]pyridin-2-yl-5-[1-(4-piperidyl)pyrazol-4-yl]pyridin-2-amine

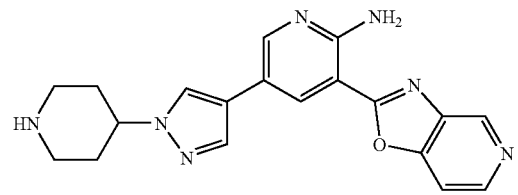

2M Sodium carbonate solution (0.206 ml) was added in one portion to a stirred suspension of 5-bromo-3-oxazolo[4,5-c]pyridin-2-yl-pyridin-2-amine (0.100 g), tert-butyl 4-(4-(4,4,5,5-tetramethyl-1,3,2-dioxaborolan-2-yl)-1H-pyrazol-1-yl)piperidine-1-carboxylate (0.143 g) and bis (triphenylphosphine)palladium(II) chloride (0.012 g) in a mixture of 2:7:3:2 DMF:DME:water:ethanol (3 ml). The reaction was heated to 140° C. for 20 minutes in a 100 W microwave reactor. The mixture was concentrated to dryness and redissolved in DCM (3 ml). Trifluoroacetic acid (3 ml) was then added dropwise over a period of 1 minute. The resulting solution was stirred for 10 minutes and then evaporated to dryness. The resultant solid was purified by SCX ion exchange chromatography (elution with 7M methanolic ammonia). The solution was then evaporated to dryness and purified by preparative HPLC (Waters XBridge Prep C18 OBD column, 5µ silica, 21 mm diameter, 150 mm length), using decreasingly polar mixtures of water (containing 1% formic acid) and acetonitrile as eluents. Fractions containing the desired compound were purified again by SCX ion-exchange chromatography, eluted from the column using 7N methanolic ammonia followed by DCM, then evaporated to dryness. There was thus obtained 3-oxazolo[4,5-c]pyridin-2-yl-5-[1-(4-piperidyl)pyrazol-4-yl]pyridin-2-amine (0.024 g); Mass Spectrum: M+H⁺ 362.40; RT 0.94 min; NMR Spectrum: (DMSOd⁶) 9.14 (1H, s), 8.62 (1H, d), 8.58 (1H, d), 8.45 (1H, d), 8.30 (1H, s), 7.92 (1H, s), 7.89 (1H, dd), 7.64 (2H, s), 4.17-4.28 (1H, m), 3.09 (2H, d), 2.65 (2H, t), 2.02 (2H, d), 1.84 (2H, qd).

The 5-bromo-3-oxazolo[4,5-c]pyridin-2-yl-pyridin-2-amine used as a reagent was prepared as follows:

3-Aminopyridin-4-ol (2.90 g) and 2-amino-5-bromo-pyridine-3-carboxylic acid (5.72 g) were added to polyphosphoric acid (100 ml) and stirred at 200° C. for 5 hours. The reaction mixture was quenched with water (100 ml) and the mixture was basified with 10N sodium hydroxide until pH was 12.5. The resulting precipitate was collected by filtration, washed with water then methanol and dried under vacuum. There was thus obtained 5-bromo-3-(oxazolo[4,5-c]pyridin-2-yl)pyridin-2-amine (6.06 g);

EXAMPLE 8A

Using an analogous procedure to that described in Example 8, the appropriate bromopyridine was reacted with the appropriate boronic acid or, where stated, an appropriate boronate ester, to give the compounds described in Table IV. Unless otherwise stated, Boc protected reagents were not used in the procedure for these compounds.

TABLE IV

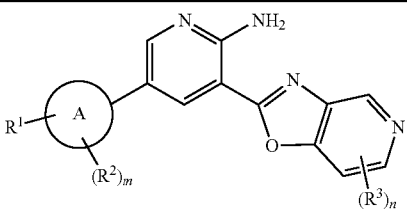

| No. & Note | R$^1$-A | m | R$^2$ | n | R$^3$ |
|---|---|---|---|---|---|
| [1] | 3-(pyrrolidin-1-ylmethyl)phenyl | 0 | | 0 | |
| [2] | 4-(2-hydroxyethylsulphamoyl)phenyl | 0 | | 0 | |
| [3] | 3-methylsulphonylphenyl | 0 | | 0 | |
| [4] | 3-morpholinophenyl | 0 | | 0 | |
| [5] | 5-(hydroxymethyl)-2-thienyl | 0 | | 0 | |
| [6] | 3-(methylsulphamoyl)phenyl | 0 | | 0 | |
| [7] | 3-(cyclopropylcarbamoyl)phenyl | 0 | | 0 | |
| [8] | 4-(4-hydroxypiperidine-1-carbonyl)phenyl | 0 | | 0 | |
| [9] | 4-carbamoylphenyl | 0 | | 0 | |
| [10] | 5-morpholinosulphonyl-phenyl | 1 | 2-methyl | 0 | |
| [11] | 3-cyanophenyl | 0 | | 0 | |
| [12] | 4-(morpholine-4-carbonyl)phenyl | 0 | | 0 | |
| [13] | 3-morpholinosulphonylphenyl | 0 | | 0 | |
| [14] | 3-(2-morpholinoethylcarbamoyl)phenyl | 0 | | 0 | |
| [15] | 3-(2-diethylaminoethylcarbamoyl)phenyl | 0 | | 0 | |
| [16] | 4-(cyanomethyl)phenyl | 0 | | 0 | |
| [17] | 4-(3-dimethylaminopropylcarbamoyl)phenyl | 0 | | 0 | |
| [18] | 4-(morpholinomethyl)phenyl | 0 | | 0 | |
| [19] | 3-(4-methylpiperazine-1-carbonyl)phenyl | 0 | | 0 | |
| [20] | 3-(1-piperidylmethyl)phenyl | 0 | | 0 | |
| [21] | 3-(1-piperidyl)phenyl | 0 | | 0 | |
| [22] | 3-(2-pyrrolidin-1-ylethylcarbamoyl)phenyl | 0 | | 0 | |
| [23] | 4-(aminomethyl)phenyl | 0 | | 0 | |
| [24] | 3-(dimethylaminoethylcarbamoyl)phenyl | 0 | | 0 | |
| [25] | 4-(2-hydroxyethylcarbamoyl)phenyl | 0 | | 0 | |
| [26] | 3-(piperidine-4-carbonylamino)phenyl | 0 | | 0 | |
| [27] | 3-(aminomethyl)phenyl | 0 | | 0 | |
| [28] | 3-(2H-pyrazol-3-yl)phenyl | 0 | | 0 | |

Notes The products gave the characterising data shown below.

[1] Mass Spectrum: M+H$^+$ 291.24; RT 1.90 min; NMR Spectrum: (DMSOd$^6$) 9.14 (1H, s), 8.62 (1H, d), 8.39 (1H, d), 8.35 (1H, d), 7.89 (1H, d), 7.87 (2H, s).

[2] Mass Spectrum: M+H$^+$ 412.28; RT 1.17 min.

[3] Mass Spectrum: M+H$^+$ 367.32; RT 1.30 min.

[4] Mass Spectrum: M+H$^+$ 374.39; RT 1.50 min.

[5] Mass Spectrum: M+H$^+$ 325.32; RT 1.19 min.

[6] Mass Spectrum: M+H$^+$ 382.32; RT 1.36 min.

[7] Mass Spectrum: M+H$^+$ 372.40; RT 1.55 min; NMR Spectrum: (DMSOd$^6$) 9.16 (1H, d), 8.71 (1H, d), 8.63 (1H, d), 8.60 (1H, d), 8.59 (1H, s), 8.12 (1H, t), 7.95 (1H, dd), 7.89 (2H, s), 7.87 (1H, t), 7.81 (1H, d), 7.56 (1H, t), 2.88 (1H, dsextet), 0.70-0.77 (2H, m), 0.58-0.64 (2H, m). N-cyclopropyl-3-(4,4,5,5-tetramethyl-1,3,2-dioxaborolan-2-yl)benzamide was used as a starting material to prepare compound [7]

[8] Mass Spectrum: M+H$^+$ 416.35; RT 1.10 min. (4-hydroxy-1-piperidyl)-[4-(4,4,5,5-tetramethyl-1,3,2-dioxaborolan-2-yl)phenyl]methanone was used as a starting material to prepare compound [8]

[9] Mass Spectrum: M+H$^+$ 332.35; RT 1.04 min; NMR Spectrum: (DMSOd$^6$) 9.16 (1H, d), 8.73 (1H, d), 8.63 (1H, d), 8.61 (1H, d), 8.05 (1H, s), 7.99 (2H, d), 7.94 (1H, dd), 7.92 (2H, s), 7.83 (2H, d), 7.40 (1H, s).

[10] Mass Spectrum: M+H$^+$ 450.43; RT 1.87 min.

[11] Mass Spectrum: M+H$^+$ 314.4; RT 1.86 min.

[12] Mass Spectrum: M+H$^+$ 402.45; RT 1.43 min. morpholino-[4-(4,4,5,5-tetramethyl-1,3,2-dioxaborolan-2-yl)phenyl]methanone was used as a starting material to prepare compound [12].

[13] Mass Spectrum: M+H$^+$ 436.43; RT 1.79 min.

[14] Mass Spectrum: M+H$^+$ 445.47; RT 1.41 min.

[15] Mass Spectrum: M+H$^+$ 431.3; RT 2.02 min.

[16] Mass Spectrum: M+H$^+$ 328.43; RT 1.78 min.

[17] Mass Spectrum: M+H$^+$ 417.29; RT 1.97 min. N-[3-(dimethylamino)propyl]-4-(4,4,5,5-tetramethyl-1,3,2-dioxaborolan-2-yl)benzamide was used as a starting material to prepare compound [17].

[18] Mass Spectrum: M+H$^+$ 388.31; RT 1.94 min. 4-[[4-(4,4,5,5-tetramethyl-1,3,2-dioxaborolan-2-yl)phenyl]methyl]morpholine was used as a starting material to prepare compound [18].

[19] Mass Spectrum: M+H$^+$ 415.27; RT 1.63 min.

[20] Mass Spectrum: M+H$^+$ 386.49; RT 2.37 min.

[21] Mass Spectrum: M+H$^+$ 372.49; RT 2.52 min.

[22] Mass Spectrum: M+H$^+$ 429.47; RT 1.70 min.

[23] Mass Spectrum: M+H$^+$ 316.44; RT 1.44 min.

[24] Mass Spectrum: M+H$^+$ 403.48; RT 1.47 min.

[25] Mass Spectrum: M+H$^+$ 374.44; RT 1.22 min.

[26] 3-[(1-Tert-butoxycarbonylpiperidine-4-carbonyl)amino]phenylboronic acid was used as a reagent and after coupling, the Boc group was removed with 2M HCL. The resultant product gave the following characterising data: Mass Spectrum: M+H$^+$ 415.27; RT 2.21 min.

The [3-[(1-tert-butoxycarbonylpiperidine-4-carbonyl)amino]phenyl]boronic acid used as a reagent was synthesised as follows:

Diisopropylethylamine (14.93 ml) was added to a solution of 1-tert-butoxycarbonyl piperidine-4-carboxylic acid (15.69 g) and HATU (20.06 g) in DMA (400 ml) and the solution was stirred for 20 minutes. 3-Aminophenylboronic acid (7.97 g) was then added and the solution stirred for a further 30 minutes. The mixture was concentrated under reduced pressure, and the reside was dissolved in acetonitrile (300 ml). 7M Ammonia in methanol (60 ml) was added and the resulting mixture was filtered. The filtrate was concentrated under reduced pressure and then purified by silica gel chromatography (eluting with 2 to 8% methanol in DCM). There was thus obtained [3-[(1-tert-butoxycarbonylpiperidine-4-carbonyl)amino]phenyl]boronic acid (16.0 g); Mass Spectrum: M+H$^+$ 347.49; RT 1.74 min; NMR Spectrum: (DMSOd$^6$) 9.85 (1H, s), 8.00 (2H, s), 7.86 (1H, s), 7.71 (1H, d), 7.47 (1H, d), 7.25 (1H, t), 4.00 (2H, d), 3.61 (2H, m), 3.14 (2H, m), 1.76 (2H, m), 1.49 (2H, m), 1.41 (9H, s).

[27] 3-[(Tert-butoxycarbonylamino)methyl]phenylboronic acid was used as a reagent and after coupling, the Boc group was removed with 2M HCL. The resultant product gave the following characterising data: Mass Spectrum: M+H$^+$ 318.3; RT 1.75 min.

[28] Mass Spectrum: M+H$^+$ 355.44; RT 1.72 min.

EXAMPLE 9

3-Oxazolo[5,4-b]pyridin-2-yl-5-[1-(4-piperidyl)pyrazol-4-yl]pyridin-2-amine

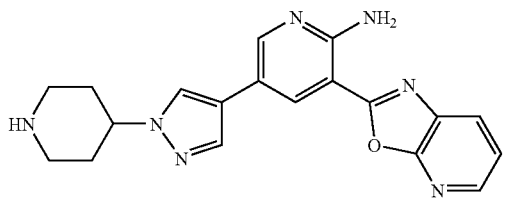

2M Sodium carbonate solution (0.206 ml) was added in one portion to a stirred suspension of 5-bromo-3-oxazolo[5,4-b]pyridin-2-yl-pyridin-2-amine (0.100 g), tert-butyl 4-[4-(4,4,5,5-tetramethyl-1,3,2-dioxaborolan-2-yl)pyrazol-1-yl]piperidine-1-carboxylate (0.143 g) and bis(triphenylphosphine)palladium(II) chloride (0.012 g) in a mixture of 2:7:3:2 DMF:DME:water:ethanol (3 ml). The reaction was heated to 160° C. for 20 minutes in a 100 W microwave reactor. The mixture was concentrated to dryness and redissolved in DCM (3 ml). Trifluoroacetic acid (3 ml) was then added dropwise over a period of 1 minute. The resulting solution was stirred for 10 minutes and then evaporated to dryness. The resultant solid was purified by SCX ion exchange chromatography (elution with 7M methanolic ammonia). The solution was then evaporated to dryness and the residue was purified by preparative HPLC (Waters XBridge Prep C18 OBD column, 5μ silica, 21 mm diameter, 150 mm length), using decreasingly polar mixtures of water (containing 1% formic acid) and acetonitrile as eluents. Fractions containing the desired compound were purified again by SCX, eluted from the column using 7N methanolic ammonia followed by DCM, then evaporated to dryness. There was thus obtained 3-oxazolo[5,4-b]pyridin-2-yl-5-[1-(4-piperidyl)pyrazol-4-yl]pyridin-2-amine (0.052 g); Mass Spectrum: M+H$^+$ 362.34; RT 1.28 min; NMR Spectrum: (DMSOd$^6$) 8.57 (1H, d), 8.46 (1H, d), 8.40 (1H, dd), 8.34 (1H, s), 8.24-8.30 (1H, m), 7.94 (1H, s), 7.65 (2H, s), 7.48-7.56 (1H, m), 4.15-4.27 (1H, m), 3.08 (2H, d), 2.63 (2H, t), 2.01 (2H, d), 1.84 (2H, qd).

The 5-bromo-3-oxazolo[5,4-b]pyridin-2-yl-pyridin-2-amine used as a reagent was prepared as follows:

3-Aminopyridin-2-ol (0.20 g) and 2-amino-5-bromo-pyridine-3-carboxylic acid (0.394 g) were stirred in polyphosphoric acid (10 ml) at 200° C. for 5 hours. The reaction mixture was quenched with water (10 ml) and the mixture was basified to pH 11.6 by addition of 10N sodium hydroxide solution. The resulting precipitate was collected by filtration, washed with water (10 ml) then methanol (10 ml) and dried under vacuum. There was thus obtained 5-bromo-3-oxazolo[5,4-b]pyridin-2-yl-pyridin-2-amine (0.253 g); Mass Spectrum: M+H$^+$ 291.15; RT 2.10 min; NMR Spectrum: (DMSOd$^6$) 8.41 (1H, dd), 8.38 (1H, d), 8.34 (1H, d), 8.29 (1H, dd), 7.85 (2H, s), 7.53 (1H, dd).

EXAMPLE 9A

Using an analogous procedure to that described in Example 9, the appropriate bromopyridine was reacted with the appropriate boronic acid or, where stated, an appropriate boronate ester, to give the compounds described in Table V. Unless otherwise stated, Boc protected reagents were not used in the procedure for these compounds.

TABLE V

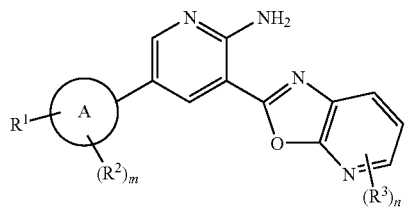

| No. & Note | R$^1$-A | m | R$^2$ | n | R$^3$ |
|---|---|---|---|---|---|
| [1] | 3-cyanophenyl | 0 | | 0 | |
| [2] | 4-(2-hydroxyethylcarbamoyl)phenyl | 0 | | 0 | |
| [3] | 3-[(1-tert-butoxycarbonylpiperidine-4-carbonyl)amino]phenyl | 0 | | 0 | |
| [4] | 3-(methoxymethyl)phenyl | 0 | | 0 | |
| [5] | 3-(2-dimethylaminoethylcarbamoyl)phenyl | 0 | | 0 | |
| [6] | 4-(4-hydroxypiperidine-1-carbonyl)phenyl | 0 | | 0 | |
| [7] | 3-(2-diethylaminoethylcarbamoyl)phenyl | 0 | | 0 | |
| [8] | 3-(pyrrolidin-1-ylmethyl)phenyl | 0 | | 0 | |
| [9] | 3-(1-piperidylmethyl)phenyl | 0 | | 0 | |
| [10] | 3-(cyclopropylsulphamoyl)phenyl | 0 | | 0 | |
| [11] | 4-(3-dimethylaminopropylcarbamoyl)phenyl | 0 | | 0 | |
| [12] | 4-(morpholine-4-carbonyl)phenyl | 0 | | 0 | |
| [13] | 4-(aminomethyl)phenyl | 0 | | 0 | |
| [14] | 4-(2-hydroxyethylsulphamoyl)phenyl | 0 | | 0 | |
| [15] | 3-(2H-pyrazol-3-yl)phenyl | 0 | | 0 | |
| [16] | 4-(cyanomethyl)phenyl | 0 | | 0 | |
| [17] | 3-(cyclopropylcarbamoyl)phenyl | 0 | | 0 | |
| [18] | 3-(4-methylpiperazine-1-carbonyl)phenyl | 0 | | 0 | |
| [19] | 5-(hydroxymethyl)-2-thienyl | 0 | | 0 | |
| [20] | 3-(2-pyrrolidin-1-ylethylcarbamoyl)phenyl | 0 | | 0 | |
| [21] | 4-(morpholinomethyl)phenyl | 0 | | 0 | |
| [22] | 3-(2-morpholinoethylcarbamoyl)phenyl | 0 | | 0 | |
| [23] | 3-morpholinophenyl | 0 | | 0 | |

Notes The products gave the characterising data shown below.

[1] Mass Spectrum: M+H$^+$ 314.36; RT 2.08 min.

[2] Mass Spectrum: M+H$^+$ 376.43; RT 1.42 min.

[3] [3-[(1-tert-butoxycarbonylpiperidine-4-carbonyl)amino]phenyl]boronic acid was used as a reagent. The product gave the following characterising data: Mass Spectrum: M+H$^+$ 415.46; RT 2.40 min. This mass ion corresponds to the Boc de-protected compound.

[4] Mass Spectrum: M+H$^+$ 333.41; RT 2.15 min.

[5] Mass Spectrum: M+H$^+$ 403.47; RT 1.67 min.

[6] (4-hydroxy-1-piperidyl)-[4-(4,4,5,5-tetramethyl-1,3,2-dioxaborolan-2-yl)phenyl]methanone was used as a starting material to prepare compound [6]. The product gave the following characterising data: Mass Spectrum: M+H$^+$ 416.42; RT 1.48 min.

[7] Mass Spectrum: M+H$^+$ 431.47; RT 1.93 min.

[8] Mass Spectrum: M+H$^+$ 372.48; RT 2.34 min.

[9] Mass Spectrum: M+H$^+$ 386.39; RT 2.60 min.

[10] Mass Spectrum: M+H$^+$ 408.39; RT 1.98 min.

[11] N-[3-(dimethylamino)propyl]-4-(4,4,5,5-tetramethyl-1,3,2-dioxaborolan-2-yl)benzamide was used as a starting material to prepare compound [11]. The product gave the following characterising data: Mass Spectrum: M+H$^+$ 417.47; RT 1.71 min.

[12] morpholino-[4-(4,4,5,5-tetramethyl-1,3,2-dioxaborolan-2-yl)phenyl]methanone was used as a starting material to prepare compound [12]. The product gave the following characterising data: Mass Spectrum: M+H$^+$ 402.43; RT 1.64 min.

[13] Mass Spectrum: M+H⁺ 319.44; RT 1.67 min.
[14] Mass Spectrum: M+H⁺ 412.38; RT 1.54 min.
[15] Mass Spectrum: M+H⁺ 355.46; RT 1.92 min.
[16] Mass Spectrum: M+H⁺ 328.40; RT 2.01 min.
[17] N-cyclopropyl-3-(4,4,5,5-tetramethyl-1,3,2-dioxaborolan-2-yl)benzamide was used as a starting material to prepare compound [17]. The product gave the following characterising data: Mass Spectrum: M+H⁺ 372.44; RT 1.78 min.
[18] Mass Spectrum: M+H⁺ 415.42; RT 1.56 min.
[19] Mass Spectrum: M+H⁺ 325.36; RT 1.65 min.
[20] Mass Spectrum: M+H⁺ 429.47; RT 1.84 min.
[21] 4-[[4-(4,4,5,5-tetramethyl-1,3,2-dioxaborolan-2-yl)phenyl]methyl]morpholine was used as a starting material to prepare compound [21]. The product gave the following characterising data: Mass Spectrum: M+H⁺ 388.47; RT 1.93 min.
[22] Mass Spectrum: M+H⁺ 445.41; RT 1.60 min.
[23] Mass Spectrum: M+H⁺ 374.27; RT 2.28 min.

EXAMPLE 10

3-Oxazolo[4,5-b]pyridin-2-yl-5-[1-(4-piperidyl)pyrazol-4-yl]pyridin-2-amine

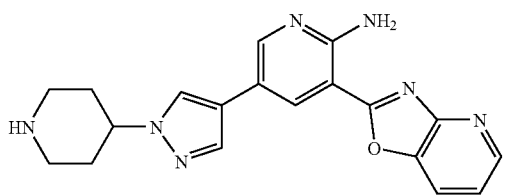

2M Sodium carbonate solution (0.206 ml) was added in one portion to a stirred suspension of 5-bromo-3-oxazolo[4,5-b]pyridin-2-yl-pyridin-2-amine (0.100 g), tert-butyl 4-[4-(4,4,5,5-tetramethyl-1,3,2-dioxaborolan-2-yl)pyrazol-1-yl]piperidine-1-carboxylate (0.143 g) and bis(triphenylphosphine)palladium(II) chloride (0.012 g) in a mixture of 2:7:3:2 DMF:DME:water:ethanol (3 ml). The reaction was heated to 160° C. for 20 minutes in a 100 W microwave reactor. The mixture was then concentrated to dryness and redissolved in DCM (3 ml). Trifluoroacetic acid (3 ml) was added dropwise over a period of 1 minute. The resulting solution was stirred for 10 minutes and then evaporated to dryness. The crude product was purified by SCX ion exchange chromatography. The desired product was eluted from the column using 7M ammonia in methanol and fractions containing product were evaporated to dryness. The crude material was purified by preparative HPLC (Waters XBridge Prep C18 OBD column, 5μ silica, 21 mm diameter, 150 mm length), using decreasingly polar mixtures of water (containing 1% formic acid) and acetonitrile as eluents. Fractions containing the desired compound were purified by SCX chromatography, eluted from the column using 7M ammonia in methanol then DCM. There was thus obtained 3-oxazolo[4,5-b]pyridin-2-yl-5-[1-(4-piperidyl)pyrazol-4-yl]pyridin-2-amine (0.028 g); Mass Spectrum: M+H⁺ 362.33; RT 1.13 min.; NMR Spectrum: (DMSOd⁶) 8.59 (1H, d), 8.56 (1H, dd), 8.46 (1H, d), 8.30 (1H, s), 8.22 (1H, dd), 7.91 (1H, s), 7.65 (2H, s), 7.49 (1H, dd), 4.15-4.25 (1H, m), 3.07 (2H, d), 2.62 (2H, t), 2.01 (2H, d), 1.82 (2H, qd).

The 5-bromo-3-oxazolo[4,5-b]pyridin-2-yl-pyridin-2-amine used as a reagent was prepared as follows:

2-Aminopyridin-3-ol (0.20 g) and 2-amino-5-bromo-pyridine-3-carboxylic acid (0.394 g) were stirred in polyphosphoric acid (10 ml) at 200° C. for 5 hours. The reaction mixture was quenched with water (10 ml) and the mixture was basified to pH 11.6 by addition of 10N sodium hydroxide solution. The precipitate was collected by filtration, washed with water (10 ml) then methanol (10 ml) and dried under vacuum. There was thus obtained 5-bromo-3-oxazolo[4,5-b]pyridin-2-yl-pyridin-2-amine (0.250 g); Mass Spectrum: M+H⁺ 291.14; RT 1.91 min; NMR Spectrum: (DMSOd⁶) 8.56 (1H, dd), 8.40 (1H, d), 8.36 (1H, d), 8.23 (1H, dd), 7.84 (2H, s), 7.50 (1H, dd).

EXAMPLE 10A

Using an analogous procedure to that described in Example 10, the appropriate bromopyridine was reacted with the appropriate boronic acid or, where stated, an appropriate boronate ester, to give the compounds described in Table VI. Unless otherwise stated, Boc protected reagents were not used in the procedure for these compounds.

TABLE VI

| No. & Note | R¹-A | m | R² | n | R³ |
|---|---|---|---|---|---|
| [1] | 3-morpholinophenyl | 0 | | 0 | |
| [2] | 3-(2-morpholinoethylcarbamoyl)phenyl | 0 | | 0 | |
| [3] | 3-[(1-tert-butoxycarbonylpiperidine-4-carbonyl)amino]phenyl | 0 | | 0 | |
| [4] | 4-(aminomethyl)phenyl | 0 | | 0 | |
| [5] | 4-(2-hydroxyethylcarbamoyl)phenyl | 0 | | 0 | |
| [6] | 3-(cyclopropylcarbamoyl)phenyl | 0 | | 0 | |
| [7] | 3-(pyrrolidin-1-ylmethyl)phenyl | 0 | | 0 | |
| [8] | 3-(4-methylpiperazine-1-carbonyl)phenyl | 0 | | 0 | |
| [9] | 3-(2-pyrrolidin-1-ylethylcarbamoyl)phenyl | 0 | | 0 | |
| [10] | 3-(cyclopropylsulphamoyl)phenyl | 0 | | 0 | |
| [11] | 3-(1-piperidylmethyl)phenyl | 0 | | 0 | |
| [12] | 4-(3-dimethylaminopropylcarbamoyl)phenyl | 0 | | 0 | |
| [13] | 4-(4-hydroxypiperidine-1-carbonyl)phenyl | 0 | | 0 | |
| [14] | 4-(morpholine-4-carbonyl)phenyl | 0 | | 0 | |
| [15] | 4-(2-dimethylaminoethylcarbamoyl)phenyl | 0 | | 0 | |
| [16] | 3-(methoxymethyl)phenyl | 0 | | 0 | |
| [17] | 3-(piperidin-1-yl)phenyl | 0 | | 0 | |
| [18] | 3-(2-dimethylaminoethylcarbamoyl)phenyl | 0 | | 0 | |
| [19] | 5-(hydroxymethyl)thien-2-yl | 0 | | 0 | |

Notes The products gave the characterising data shown below.

[1] Mass Spectrum: M+H⁺ 374.45; RT 1.58 min.
[2] Mass Spectrum: M+H⁺ 445.44; RT 1.05 min.
[3] [3-[(1-tert-butoxycarbonylpiperidine-4-carbonyl)amino]phenyl]boronic acid was used as a reagent. The resultant product gave the following characterising data:—Mass Spectrum: M+H⁺ 515.49; RT 2.05 min. This mass ion corresponds to the Boc de-protected compound.
[4] Mass Spectrum: M+H⁺ 301.39; RT 0.85 min.
[5] Mass Spectrum: M+H⁺ 376.42; RT 1.05 min.
[6] N-cyclopropyl-3-(4,4,5,5-tetramethyl-1,3,2-dioxaborolan-2-yl)benzamide was used as a starting material to prepare compound [6]. The resultant product gave the following characterising data: Mass Spectrum: M+H⁺ 372.43; RT 1.38 min.
[7] Mass Spectrum: M+H⁺ 372.47; RT 1.09 min.

[8] Mass Spectrum: M+H⁺ 415.44; RT 0.93 min.
[9] Mass Spectrum: M+H⁺ 429.46; RT 1.08 min.
[10] Mass Spectrum: M+H⁺ 408.35; RT 1.68 min.
[11] Mass Spectrum: M+H⁺ 386.47; RT 1.11 min.
[12] N-[3-(dimethylamino)propyl]-4-(4,4,5,5-tetramethyl-1,3,2-dioxaborolan-2-yl)benzamide was used as a starting material to prepare compound [12]. The resultant product gave the following characterising data: Mass Spectrum: M+H⁺ 417.46; RT 1.01 min.
[13] (4-hydroxy-1-piperidyl)-[4-(4,4,5,5-tetramethyl-1,3,2-dioxaborolan-2-yl)phenyl]methanone was used as a starting material to prepare compound [13]. The resultant product gave the following characterising data: Mass Spectrum: M+H⁺ 416.41; RT 1.12 min.
[14] morpholino-[4-(4,4,5,5-tetramethyl-1,3,2-dioxaborolan-2-yl)phenyl]methanone was used as a starting material to prepare compound [14]. The resultant product gave the following characterising data: Mass Spectrum: M+H⁺ 402.41; RT 1.26 min.
[15] The following conditions were used. Tris(dibenzilideneacetone)dipalladium (47.2 mg), tricyclohexylphosphine (28.9 mg) and potassium phosphate (656 mg) were added to a degassed solution of 5-bromo-3-oxazolo[4,5-b]pyridin-2-yl-pyridin-2-amine (300 mg, 1.03 mmol), N-(2-dimethylaminoethyl)-4-(4,4,5,5-tetramethyl-1,3,2-dioxaborolan-2-yl)benzamide (361 mg, 1.13 mmol) in 1,4-dioxane (2 ml) and water (0.400 ml) under nitrogen atmosphere. The suspension was stirred at 90° C. for 4 hours. The mixture was filtered and the solvent was removed. The mixture was adsorbed on silica gel, the crude product was purified by flash chromatography on silica gel eluting with 10% methanol in dichloromethane follow by 10% methanolic ammonia (7 N) in dichloromethane. The solvent was evaporated to dryness to afford 4-(6-amino-5-oxazolo[4,5-b]pyridin-2-yl-3-pyridyl)-N-(2-dimethylaminoethyl)benzamide after stirring overnight in acetonitrile. NMR Spectrum: (DMSO-d6) 2.19 (s, 6H), 2.42 (t, 2H), 3.35-3.42 (m, 2H), 7.50 (dd, 1H), 7.84 (d, 2H), 7.91 (bs, 2H), 7.95 (d, 2H), 8.26 (dd, 1H), 8.45 (t, 1H), 8.56 (dd, 1H), 8.61 (d, 1H), 8.73 (d, 1H); Mass spectrum: M+H⁺ 403
[16] Mass Spectrum: M+H⁺ 333.41; RT 1.66 min.
[17] Mass Spectrum: M+H⁺ 372.46; RT 1.20 min.
[18] Mass Spectrum: M+H⁺ 403.45; RT 1.02 min.
[19] Mass Spectrum: M+H⁺ 325.36; RT 1.28 min.

EXAMPLE 11

3-Oxazolo[5,4-c]pyridin-2-yl-5-[1-(4-piperidyl)pyrazol-4-yl]pyridin-2-amine

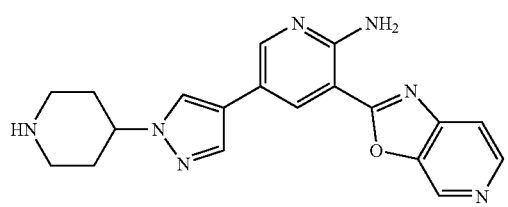

2M Sodium carbonate solution (0.249 ml) was added in one portion to a stirred suspension of 5-bromo-3-oxazolo[5,4-c]pyridin-2-yl-pyridin-2-amine (0.121 g), tert-butyl 4-[4-(4,4,5,5-tetramethyl-1,3,2-dioxaborolan-2-yl)pyrazol-1-yl]piperidine-1-carboxylate (0.188 g) and bis(triphenylphosphine)palladium(II) chloride (0.015 g) in a mixture of 2:7:3:2 DMF:DME:water:ethanol (4 ml). The reaction was heated to 160° C. for 20 minutes in a 100 W microwave reactor. The mixture was then concentrated to dryness and redissolved in DCM (3 ml). Trifluoroacetic acid (3 ml) was added dropwise over a period of 1 minute. The resulting solution was stirred for 15 minutes and then evaporated to dryness. The crude product was purified by SCX ion exchange chromatography. The desired product was eluted from the column using 7M methanolic ammonia. The crude material was purified by preparative HPLC (Waters XBridge Prep C18 OBD column, 5µ silica, 21 mm diameter, 100 mm length), using decreasingly polar mixtures of water (containing 1% formic acid) and acetonitrile as eluents. Fractions containing the desired compound were purified by SCX chromatography, eluted from the column using 7M methanolic ammonia then DCM, and evaporated to dryness. There was thus obtained 3-oxazolo[5,4-c]pyridin-2-yl-5-[1-(4-piperidyl)pyrazol-4-yl]pyridin-2-amine (0.032 g); Mass Spectrum: M+H⁺ 362.11; RT 1.56 min.; NMR Spectrum: (DMSOd⁶) 9.14 (1H, s), 8.62 (1H, d), 8.57 (1H, d), 8.45 (1H, d), 8.30 (1H, s), 7.91 (1H, s), 7.89 (1H, dd), 7.64 (2H, s), 4.14-4.25 (1H, m), 3.06 (2H, d), 2.61 (2H, td), 2.24 (1H, s), 1.96-2.04 (2H, m), 1.82 (2H, qd).

The 5-bromo-3-oxazolo[5,4-c]pyridin-2-yl-pyridin-2-amine used as a reagent was prepared as follows:

4-Aminopyridin-3-ol (0.074 g) and 2-amino-5-bromo-pyridine-3-carboxylic acid (0.146 g) were stirred in polyphosphoric acid (5 ml) at 200° C. for 4 hours. The reaction mixture was quenched with water (5 ml) and the mixture was basified to pH 13.4 by addition of 10N sodium hydroxide solution. The precipitate was collected by filtration, washed with water (5 ml) and dried under vacuum. There was thus obtained 5-bromo-3-oxazolo[5,4-c]pyridin-2-yl-pyridin-2-amine (0.121 g); Mass Spectrum: M+H⁺ 291.17; RT 1.88 min; NMR Spectrum: (DMSOd⁶) 9.14 (1H, s), 8.62 (1H, d), 8.38 (1H, s), 8.35 (1H, s), 7.88 (1H, d), 7.83 (2H, s).

EXAMPLE 11A

Using an analogous procedure to that described in Example 11, the appropriate bromopyridine was reacted with the appropriate boronic acid or, where stated, an appropriate boronate ester, to give the compounds described in Table VII. Unless otherwise stated, Boc protected reagents were not used in the procedure for these compounds.

TABLE VII

| No. & Note | R¹-A | m | R² | n | R³ |
|---|---|---|---|---|---|
| [1] | 4-(morpholinomethyl)phenyl | 0 | | 0 | |
| [2] | 4-(4-hydroxypiperidine-1-carbonyl)phenyl | 0 | | 0 | |
| [3] | 3-[(1-tert-butoxycarbonylpiperidine-4-carbonyl)amino]phenyl | 0 | | 0 | |
| [4] | 4-(aminomethyl)phenyl | 0 | | 0 | |
| [5] | 3-(pyrrolidin-1-ylmethyl)phenyl | 0 | | 0 | |
| [6] | 3-(1-piperidyl)phenyl | 0 | | 0 | |
| [7] | 3-(cyclopropylcarbamoyl)phenyl | 0 | | 0 | |
| [8] | 3-(methylsulphamoyl)phenyl | 0 | | 0 | |

TABLE VII-continued

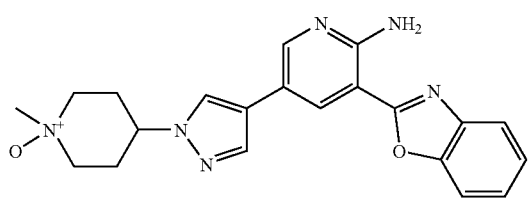

| No. & Note | R¹-A | m | R² | n | R³ |
|---|---|---|---|---|---|
| [9] | 3-[(Tert-butoxycarbonylamino)methyl]phenyl | 0 | | 0 | |
| [10] | 3-(2-morpholinoethylcarbamoyl)phenyl | 0 | | 0 | |
| [11] | 3-(4-methylpiperazine-1-carbonyl)phenyl | 0 | | 0 | |
| [12] | 3-morpholinophenyl | 0 | | 0 | |

Notes The products gave the characterising data shown below.

[1] 4-[[4-(4,4,5,5-tetramethyl-1,3,2-dioxaborolan-2-yl)phenyl]methyl]morpholine was used as a starting material to prepare compound [1]. The resultant product gave the following characterising data: Mass Spectrum: M+H⁺ 388.29; RT 1.94 min.

[2] (4-hydroxy-1-piperidyl)-[4-(4,4,5,5-tetramethyl-1,3,2-dioxaborolan-2-yl)phenyl]methanone was used as a starting material to prepare compound [2]. The resultant product gave the following characterising data: Mass Spectrum: M+H⁺ 416.25; RT 1.50 min.

[3] [3-[(1-tert-butoxycarbonylpiperidine-4-carbonyl)amino]phenyl]boronic acid was used as a reagent. The resultant product gave the following characterising data: Mass Spectrum: M+H⁺ 415; RT 2.41 min. This mass ion corresponds to the Boc de-protected compound.

[4] Mass Spectrum: M+H⁺ 318; RT 1.70 min.

[5] Mass Spectrum: M+H⁺ 372; RT 3.72 min.

[6] Mass Spectrum: M+H⁺ 372; RT 2.70 min.

[7] N-cyclopropyl-3-(4,4,5,5-tetramethyl-1,3,2-dioxaborolan-2-yl)benzamide was used as a starting material to prepare compound [7]. The resultant product gave the following characterising data: Mass Spectrum: M+H⁺ 372; RT 1.79 min.

[8] Mass Spectrum: M+H⁺ 382; RT 1.75 min.

[9] [3-[(Tert-butoxycarbonylamino)methyl]phenyl]boronic acid was used as a reagent. The resultant product gave the following characterising data: Mass Spectrum: M+H⁺ 318; RT 2.37 min. This mass ion corresponds to the Boc de-protected compound.

[10] Mass Spectrum: M+H⁺ 445; RT 1.64 min.

[11] Mass Spectrum: M+H⁺ 415; RT 1.64 min.

[12] Mass Spectrum: M+H⁺ 374.32; RT 2.06 min; NMR Spectrum: (DMSOd₆) 9.16 (s, 1H), 8.62 (s, 2H), 8.52 (s, 1H), 7.91 (d, 1H), 7.83 (s, 2H), 7.33 (t, 1H), 7.24 (s, 1H), 7.14 (d, 1H), 6.96 (d, 1H), 3.81 (m, 4H), 3.22 (m, 4H).

EXAMPLE 12

3-(1,3-Benzoxazol-2-yl)-5-[1-(1-methyl-1-oxido-piperidin-1-ium-4-yl)pyrazol-4-yl]pyridin-2-amine 3-Chlorobenzenecarboperoxoic acid (0.046 g) was added to 3-(1,3-benzoxazol-2-yl)-5-[1-(1-methyl-4-piperidyl)pyrazol-4-yl]pyridin-2-amine (0.100 g) in DCM (10 ml). The resulting solution was stirred for 5 minutes. The resultant precipitate was collected by filtration, washed with DCM (2 ml) and dried under vacuum. The residue was purified by SCX ion exchange chromatography (elution with 7M methanolic ammonia) and there was thus obtained 3-(1,3-benzoxazol-2-yl)-5-[1-(1-methyl-1-oxido-piperidin-1-ium-4-yl)pyrazol-4-yl]pyridin-2-amine (0.026 g); Mass Spectrum: M+H⁺ 391.29; RT 1.18 min; NMR Spectrum: (DMSOd⁶) 8.49 (d, 1H), 8.41 (d, 1H), 8.32 (s, 1H), 7.88 (s, 1H), 7.78 (dd, 1H), 7.73 (dd, 1H), 7.57 (br s, 2H), 7.38 (m, 2H), 4.26 (tt, 1H), 3.46 (m, 2H), 3.11 (s, 3H), 3.06 (m, 2H), 2.68 (m, 2H), 1.90 (br m, 2H).

EXAMPLE 13 tert-butyl 4-[4-[6-Amino-5-(1,3-benzothiazol-2-yl)-3-pyridyl]pyrazol-1-yl]piperidine-1-carboxylate 3-(1,3-Benzothiazol-2-yl)-5-bromo-pyridin-2-amine (0.962 g), tert-butyl 4-(4-(4,4,5,5-tetramethyl-1,3,2-dioxaborolan-2-yl)-1H-pyrazol-1-yl)piperidine-1-carboxylate (1.304 g), bis(triphenylphosphine) palladium(II) chloride (0.110 g) and sodium carbonate (0.400 g) in DMF/DME/ethanol (34 ml, 2:7:2 ratio) and water (3.5 ml) were stirred at 100° C. for 6 hours. The reaction mixture was concentrated. The residue was dissolved in DCM (30 ml) and filtered through a pad of silica (elution: ethyl acetate) and the filtrate was concentrated. The crude product was purified by flash chromatography on silica gel (eluting with 70 to 100% ethyl acetate in petroleum ether). There was thus obtained tert-butyl 4-(4-(6-amino-5-(benzo[d]thiazol-2-yl)pyridin-3-yl)-1H-pyrazol-1-yl)piperidine-1-carboxylate (0.870 g); Mass Spectrum: M+H⁺ 477; NMR Spectrum: (CDCl₃) 8.32 (d, 1H), 8.02 (d, 1H), 8.00 (s, 1H), 7.91 (d, 1H), 7.76 (s, 1H), 7.66 (s, 1H), 7.50 (dd, 1H), 7.41 (dd, 1H), 7.13 (bs, 2H), 4.29-4.37

(m, 1H), 4.28 (bs, 2H), 2.92 (bs, 2H), 2.16-2.23 (m, 2H), 2.01 (dd, 1H), 1.96 (dd, 1H), 1.49 (s, 9H).

The 3-(1,3-benzothiazol-2-yl)-5-bromo-pyridin-2-amine used as starting material was made as follows:

2-Amino-5-bromo-pyridine-3-carboxylic acid (1.52 g) and 2-aminobenzenethiol (0.749 ml) were added to polyphosphoric acid (5.26 ml) at 200° C. under nitrogen. The resulting suspension was stirred at 200° C. for 20 hours. After cooling, iced water was added (150 ml) and the mixture was stirred for 30 minutes. The mixture was basified to pH 11 with concentrated sodium hydroxyde solution. The solid was filtered and washed with water (30 ml) and methanol (15 ml). The material was then dried under vacuum over $P_2O_5$. There was thus obtained 3-(1,3-benzothiazol-2-yl)-5-bromo-pyridin-2-amine (1.6 g); Mass Spectrum: M+H$^+$ 308 and 306; NMR Spectrum: (DMSOd$_6$) 8.25 (d, 1H), 8.16 (d, 1H), 8.15 (d, 1H), 8.11 (d, 1H), 8.09 (bs, 2H), 7.57 (dd, 1H), 7.49 (dd, 1H).

EXAMPLE 14

3-(1,3-Benzothiazol-2-yl)-5-[1-(4-piperidyl)pyrazol-4-yl]pyridin-2-amine

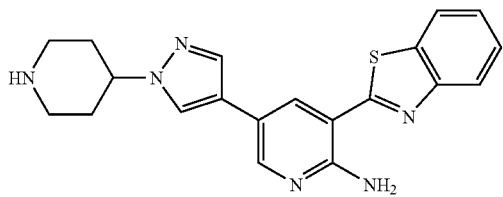

Trifluoroacetic acid (3 ml) was added to a stirred solution of tert-butyl-4-[4-[6-amino-5-(1,3-benzothiazol-2-yl)-3-pyridyl]pyrazol-1-yl]piperidine-1-carboxylate (0.300 g) in dichloromethane (4 ml). The mixture was stirred for 1 hour, then concentrated under reduced pressure. The residue was dissolved in DCM (60 ml) and the solution was washed with a 0.5M solution of aqueous sodium hydroxide (30 ml). The organic phases were washed with water (15 ml) and brine (15 ml). The aqueous phase was extracted with DCM (3×30 ml), and then the organic layers were combined and concentrated under reduced pressure. The residue was stirred in acetonitrile (10 ml) for 18 hours. The solid was filtered and dried under vacuum. There was thus obtained 3-(1,3-benzothiazol-2-yl)-5-[1-(4-piperidyl)pyrazol-4-yl]pyridin-2-amine (0.109 g); Mass Spectrum: M+H$^+$ 377; NMR Spectrum: (DMSOd$_6$ and CF$_3$CO$_2$D) 8.73 (d, 1H), 8.56 (d, 1H), 8.53 (s, 1H), 8.26 (d, 1H), 8.21 (d, 1H), 8.16 (s, 1H), 7.66 (dd, 1H), 7.59 (dd, 1H), 4.52-4.62 (m, 1H), 3.41-3.52 (m, 2H), 3.09-3.21 (m, 2H), 2.24-2.33 (m, 2H), 2.10-2.23 (m, 2H).

EXAMPLE 15

Tert-butyl 4-[4-[5-amino-6-(1,3-benzoxazol-2-yl)pyrazin-2-yl]pyrazol-1-yl]piperidine-1-carboxylate

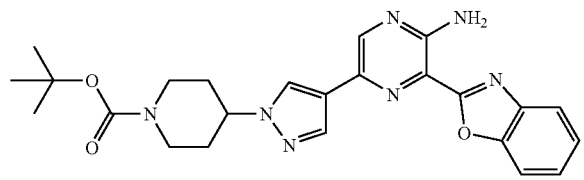

2-Aminophenol (0.059 ml) was added to a solution of tert-butyl 4-[4-(5-amino-6-formyl-pyrazin-2-yl)pyrazol-1-yl]piperidine-1-carboxylate (0.200 g) in methanol (4 ml) over a period of 2 minutes under an atmosphere of argon. The resulting solution was stirred at 50° C. for 6 hours. The mixture was filtered and the filtrate was concentrated under reduced pressure. The resulting product was purified by flash chromatography on silica gel (eluting with 50 to 60% ethyl acetate in petroleum ether). The solvent was evaporated to dryness, Manganese(IV) oxide (0.046 g) was added to the solid dissolved in dichloromethane (4 ml) and the mixture was stirred 3 hours. The mixture was filtered through celite, then purified by flash chromatography on silica gel (eluting with 30 to 70% ethyl acetate in petroleum ether). There was thus obtained tert-butyl 4-[4-[5-amino-6-(1,3-benzoxazol-2-yl)pyrazin-2-yl]pyrazol-1-yl]piperidine-1-carboxylate (0.008 g); Mass Spectrum: M+H$^+$ 362; NMR Spectrum: (CDCl$_3$) 8.43 (s, 1H), 8.04 (s, 1H), 7.98 (s, 1H), 7.80 (d, 1H), 7.71 (d, 1H), 7.38-7.48 (m, 2H), 7.01 (bs, 2H), 4.22-4.50 (m, 3H), 2.93 (bs, 2H), 2.16-2.26 (m, 2H), 1.93-2.07 (m, 2H), 1.49 (s, 9H).

The tert-butyl 4-[4-(5-amino-6-formyl-pyrazin-2-yl)pyrazol-1-yl]piperidine-1-carboxylate used as starting material was made as follows:

1,1'-Bis(diphenylphosphino)ferrocenedichloropalladium (II) (2.245 g) was added to a mixture of caesium fluoride (18.85 g), methyl 3-amino-6-bromopyrazine-2-carboxylate (14.4 g) and tert-butyl 4-(4-(4,4,5,5-tetramethyl-1,3,2-dioxaborolan-2-yl)-1H-pyrazol-1-yl)piperidine-1-carboxylate (30.4 g) in methanol (450 ml). The resulting mixture was stirred at 60° C. for 1 hour at which time a further portion of tert-butyl 4-(4-(4,4,5,5-tetramethyl-1,3,2-dioxaborolan-2-yl)-1H-pyrazol-1-yl)piperidine-1-carboxylate (15.0 g) was added. The resultant mixture was stirred for a further 3 hours at 60° C. The reaction mixture was concentrated under reduced pressure and redissolved in ethyl acetate (500 ml), then washed twice with water (2×250 ml). The organic extract was dried with magnesium sulfate, filtered and concentrated under reduced pressure. The material so obtained was purified by flash silica chromatography on Flash 75 equipment, elution gradient 0 to 4% methanol in dichloromethane. There was thus obtained methyl 3-amino-6-(1-(1-(tert-butoxycarbonyl)piperidin-4-yl)-1H-pyrazol-4-yl)pyrazine-2-carboxylate (24.98 g); Mass Spectrum: M−H$^+$ 401; RT 2.09 min; NMR Spectrum: (DMSOd$_6$) 8.44 (s, 1H), 7.95 (s, 1H), 7.92 (s, 1H), 6.37 (brs, 2H), 4.30 (m, 1H), 3.98 (s, 3H), 2.93 (t, 2H), 2.18 (d, 2H), 1.98 (m, 2H), 1.66 (s, 2H), 1.50 (s, 9H).

A solution of lithium aluminium hydride (1.24 ml, 1M in THF) was added dropwise to a solution of methyl 3-amino-6-(1-(1-(tert-butoxycarbonyl)piperidin-4-yl)-1H-pyrazol-4-yl)pyrazine-2-carboxylate (0.50 g) in THF (15 ml) at −30° C. over a period of 5 minutes. The resulting solution was stirred at −30° C. to 0° C. for 5 hours. Solid sodium sulfate decahydrate was added and the mixture was stirred for 30 minutes. The suspension was filtered and the filtrate was evaporated under reduced pressure. The crude product was purified by flash chromatography on silica gel (eluting with 2 to 5% methanol in DCM). There was thus obtained tert-butyl 4-(4-(5-amino-6-(hydroxymethyl)pyrazin-2-yl)-1H-pyrazol-1-yl)piperidine-1-carboxylate (0.326 g); Mass spectrum: M+H$^+$ 373.

Manganese(IV) oxide (0.743 g) was added to a solution of tert-butyl 4-(4-(5-amino-6-(hydroxymethyl)pyrazin-2-yl)-1H-pyrazol-1-yl)piperidine-1-carboxylate (0.320 g) in DCM (10 ml) over a period of 5 minutes. The resulting solution was stirred for 2 hours, then the mixture was filtered. The crude product was purified by flash chromatography on silica gel (eluting with 50 to 70% ethyl acetate in petroleum ether). There was thus obtained tert-butyl 4-(4-(5-amino-6-formylpyrazin-2-yl)-1H-pyrazol-1-yl)piperidine-1-carboxylate (0.224 g); NMR Spectrum: (CDCl$_3$) 10.07 (s, 1H), 8.47 (s, 1H), 7.95 (s, 1H), 7.94 (s, 1H), 6.39 (m, 2H), 4.18-4.38 (m, 3H), 2.90 (m, 2H), 2.11-2.23 (m, 2H), 1.89-2.02 (m, 2H), 1.48 (s, 9H).

EXAMPLE 16

3-(1,3-Benzothiazol-2-yl)-5-[1-(1-methyl-4-piperidyl)pyrazol-4-yl]pyridin-2-amine

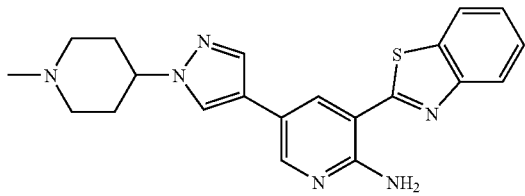

37% Aqueous formaldehyde (0.060 ml) was added to a stirred solution of 3-(1,3-benzothiazol-2-yl)-5-[1-(4-piperidyl)pyrazol-4-yl]pyridin-2-amine (0.250 g) dissolved in methanol (2.5 ml) and DCM (2.5 ml). Sodium triacetoxyhydroborate (0.141 g) was added and the resulting solution was for 30 minutes. The mixture was concentrated. DCM and 7N methanol/ammonia were added. The mixture was concentrated on silica gel and the residue was purified by flash chromatography on silica gel eluting with 2 to 10% methanolic ammonia (7 N) in DCM. The solvent was evaporated to dryness to afford a solid. Acetonitrile (4 ml) was added and the solution was stirred overnight. The solid was filtered, and dried under vacuum. There was thus obtained 3-(1,3-benzothiazol-2-yl)-5-[1-(1-methyl-4-piperidyl)pyrazol-4-yl]pyridin-2-amine (0.198 g); Mass Spectrum: M+H$^+$ 391; NMR Spectrum (DMSOd6): 8.48 (d, 1H), 8.33 (s, 1H), 8.16 (d, 1H), 8.15 (d, 1H), 8.10 (d, 1H), 7.93 (s, 1H), 7.88 (bs, 2H), 7.57 (dd, 1H), 7.49 (dd, 1H), 4.08-4.18 (m, 1H), 2.84-2.92 (m, 2H), 2.22 (s, 3H), 1.94-2.12 (m, 6H).

EXAMPLE 17

3-(1,3-Benzoxazol-2-yl)-5-[1-(4-piperidyl)pyrazol-4-yl]pyrazin-2-amine

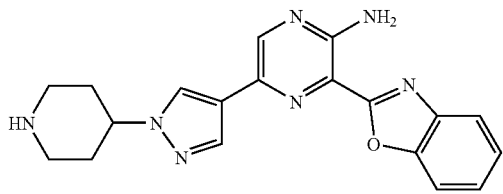

TFA (3 ml) was added in one portion to a stirred suspension of tert-butyl 4-[4-[5-amino-6-(1,3-benzoxazol-2-yl)pyrazin-2-yl]pyrazol-1-yl]piperidine-1-carboxylate (0.2 g). The resulting solution was stirred at for 2 hours under an atmosphere of argon. The mixture was evaporated, and a 7N solution of ammonia in methanol (2 ml) was added at 0° C. The resulting solution was evaporated, redissolved in dimethylformamide (2 ml) and filtered on a Millipore filter. The reaction mixture was purified by preparative HPLC using a Waters X-Terra reverse-phase column (C-18, 5 microns silica, 19 mm diameter, 100 mm length, flow rate of 40 ml/minute) and decreasingly polar mixtures of water (containing 0.2% ammonium carbonate) and acetonitrile as eluent. The fractions containing the desired compound were evaporated to dryness. There was thus obtained 3-(1,3-benzoxazol-2-yl)-5-[1-(4-piperidyl)pyrazol-4-yl]pyrazin-2-amine (0.078 g); Mass Spectrum: M+H$^+$ 362; NMR Spectrum (DMSO-d6): 8.67 (s, 1H), 8.33 (s, 1H), 8.02 (s, 1H), 7.90 (d, 1H), 7.89 (d, 1H), 7.84 (bs, 2H), 7.51 (dd, 1H), 7.47 (dd, 1H), 4.21-4.32 (m, 1H), 3.01-3.10 (m, 2H), 2.56-2.65 (m, 2H), 1.96-2.04 (m, 2H), 1.77-1.89 (m, 2H).

The tert-butyl 4-[4-[5-amino-6-(1,3-benzoxazol-2-yl)pyrazin-2-yl]pyrazol-1-yl]piperidine-1-carboxylate used as starting material was made as follows:

Solid bis(triphenylphosphine palladium (II) chloride (0.051 g) was added in one portion to a stirred suspension of 3-(1,3-benzoxazol-2-yl)-5-bromo-pyrazin-2-amine (0.42 g), caesium fluoride (0.160 ml) and tert-butyl 4-[4-(4,4,5,5-tetramethyl-1,3,2-dioxaborolan-2-yl)pyrazol-1-yl]piperidine-1-carboxylate (0.544 g) dissolved in degassed methanol (7 ml) and DCM (3 ml). The resulting solution was stirred at 50° C. for 16 hours under an atmosphere of argon. The mixture was then evaporated and water (20 ml) was added. The mixture was extracted with DCM (2×50 ml), dried over mafnesium sulfate, filtered and evaporated under reduce pressure. The crude product was adsorbed on silica gel and was purified by flash chromatography (eluting with 70 to 100% diethyl ether in petroleum ether then with 50% to 60% ethyl acetate in petroleum ether). The solvent was evaporated to dryness. There was thus obtained Tert-butyl 4-[4-[5-amino-6-(1,3-benzoxazol-2-yl)pyrazin-2-yl]pyrazol-1-yl]piperidine-1-carboxylate (0.505 g); Mass Spectrum: M+H$^+$ 506; NMR Spectrum (CDCl$_3$): 8.43 (s, 1H), 8.04 (s, 1H), 7.98 (s, 1H), 7.80 (d, 1H), 7.71 (d, 1H), 7.38-7.48 (m, 2H), 4.21-4.40 (m, 3H), 2.92 (bs, 2H), 2.16-2.24 (m, 2H), 2.94-2.05 (m, 2H), 1.49 (s, 9H).

The 3-(1,3-benzoxazol-2-yl)-5-bromo-pyrazin-2-amine used as starting material was made as follows:

In 6 separated batches, 3-aminopyrazine-2-carboxylic acid (0.5 g), 2-aminophenol (0.392 ml) and polymer bound triphenylphosphine (3 mmol/g) (3.59 g) and 2,2,2-trichloroacetonitrile (0.721 ml) were suspended in acetonitrile (10 ml) and sealed into a microwave tube. The reaction was heated at 150° C. over a period of 20 minutes in a microwave. The reaction mixture was diluted with methanol, filtered, absorbed on silica gel and purified by flash chromatography on silica gel (eluting with 1 to 3% methanol in DCM). The solvent was evaporated to dryness. There was thus obtained 3-(1,3-benzoxazol-2-yl)pyrazin-2-amine (0.384 g); Mass Spectrum: M+H$^+$ 213; NMR Spectrum (DMSOd6): 8.28 (d, 1H), 8.05 (d, 1H), 7.90 (dd, 1H), 7.89 (bs, 2H), 7.85 (dd, 1H), 7.51 (ddd, 1H), 7.47 (ddd, 1H).

Solid 1-bromopyrrolidine-2,5-dione (0.461 g) was added to a stirred suspension of 3-(1,3-benzoxazol-2-yl)pyrazin-2-amine (0.5 g) dissolved in N,N-dimethylformamide (15 ml). The resulting solution was stirred for 16 hours. The mixture was evaporated under reduce pressure and water (25 ml) was added, then the solid was filtered and dried. The solid was dissolved in DCM and adsorbed on silica gel. The crude product was purified by flash chromatography (eluting with 30 to 60% ethyl acetate in petroleum ether). The solvent was evaporated to dryness. There was thus obtained 3-(1,3-benzoxazol-2-yl)-5-bromo-pyrazin-2-amine (0.425 g); Mass Spectrum: M+H+ 291; NMR Spectrum (DMSOd6): 8.43 (s, 1H), 8.08 (bs, 2H), 7.91 (d, 1H), 7.89 (d, 1H), 7.52 (ddd, 1H), 7.48 (ddd, 1H).

EXAMPLE 17-A1

3-(6-fluoro-1,3-benzoxazol-2-yl)-5-[1-(4-piperidyl) pyrazol-4-yl]pyrazin-2-amine

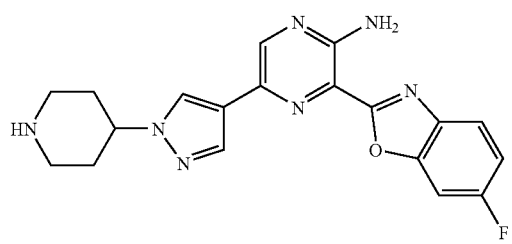

Using analogous procedures to those described in Example 17, tert-butyl 4-[4-[5-amino-6-(6-fluoro-1,3-benzoxazol-2-yl)pyrazin-2-yl]pyrazol-1-yl]piperidine-1-carboxylate (100 mg) was reacted with TFA to give 3-(6-fluoro-1,3-benzoxazol-2-yl)-5-[1-(4-piperidyl)pyrazol-4-yl]pyrazin-2-amine (46 mg). NMR Spectrum: (400 MHz, MeOD) 8.60 (s, 1H), 8.35 (s, 1H), 8.20 (s, 1H), 7.90 (dd, 1H), 7.60 (dd, 1H), 7.30 (dd, 1H), 4.20 (m, 1H), 3.70 (m, 1H), 3.30 (m, 2H), 2.50 (m, 4H); Mass spectrum: M+H+ 380

The tert-butyl 4-[4-[5-amino-6-(6-fluoro-1,3-benzoxazol-2-yl)pyrazin-2-yl]pyrazol-1-yl]piperidine-1-carboxylate used as starting material was prepared as follows: 3-aminopyrazine-2-carboxylic acid (5 g) and 2-amino-5-fluoro-phenol (5.94 g) were dissolved in DMF (30 ml). Triethylamine (5.81 g) and HATU (19.13 g) were added to the solution. The resulting mixture was stirred at room temperature for 24 hours, diluted with ethyl acetate (100 ml) and washed with brine (3×20 ml). The organic layer was dried over sodium sulfate. The precipitate was collected, recrystallized in ethanol and further purified by chromatography on silica gel (hexane/ethyl acetate/Methanol) to give 3-amino-N-(4-fluoro-2-hydroxy-phenyl)pyrazine-2-carboxamide (6 g). NMR Spectrum: (400 MHz, DMSOd6) 10.8 (s, 1H), 10.2 (s, 1H), 8.30 (m, 2H), 7.80 (s, 1H), 7.50 (br, 2H), 6.60 (m, 2H). Mass spectrum: M+H+ 249.

3-amino-N-(4-fluoro-2-hydroxy-phenyl)pyrazine-2-carboxamide (1.6 g) and triphenylphosphine (5.07 g) were dissolved into pyridine (20 ml). The mixture was cooled to −10° C. in a ice-salt bath. Then, 2,2,2-trichloroacetonitrile (2.79 g) was added slowly. The resulting mixture was heated to reflux for 12 hours. The resulting mixture was diluted with ethyl acetate/methanol (4/1, 100 ml). The mixture was filtered by celite (diatomaceous earth), and the mixture was washed with 1M HCl. The organic layer was concentrated and the residue was purified by chromatography on silica gel (hexane/ethyl acetate/Methanol) to yield 3-(6-fluoro-1,3-benzoxazol-2-yl) pyrazin-2-amine (0.3 g). NMR Spectrum: (400 MHz, DMSOd6) 8.23 (s, 1H), 8.00 (s, 1H), 7.85 (m, 1H), 7.80 (m, 4H), 7.30 (m, 1H); Mass spectrum: M+H+ 231.

3-(6-fluoro-1,3-benzoxazol-2-yl)pyrazin-2-amine (300 mg) was reacted with 1-bromopyrrolidine-2,5-dione using analogous procedures to those described in the starting material portion of Example 17 to give 5-bromo-3-(6-fluoro-1,3-benzoxazol-2-yl)pyrazin-2-amine (150 mg), which was reacted with tert-butyl 4-[4-(4,4,5,5-tetramethyl-1,3,2-dioxaborolan-2-yl)pyrazol-1-yl]piperidine-1-carboxylate (183 mg) to give tert-butyl 4-[4-[5-amino-6-(6-fluoro-1,3-benzoxazol-2-yl)pyrazin-2-yl]pyrazol-1-yl]piperidine-1-carboxylate (150 mg) according to the starting material portion of the procedure described in Example 17, except that 1,1'-bis(diphenylphosphino)ferrocenedichloropalladium(II) was used as the catalyst, 2M sodium carbonate as the base and dioxane:toluene (1:1) as the solvent. NMR Spectrum: (400 MHz, DMSOd6) 8.50 (s, 1H), 8.25 (s, 1H), 8.05 (s, 1H), 7.80 (dd, 1H), 7.50 (dd, 1H), 7.20 (dd, 1H), 4.40 (m, 1H), 4.20 (m, 1H), 3.00 (m, 2H), 2.10 (m, 1H), 1.90 (m, 3H), 1.50 (s, 9H) Mass spectrum: M+H+ 480.

EXAMPLE 18

3-(1,3-benzoxazol-2-yl)-5-[1-(1-methyl-4-piperidyl) pyrazol-4-yl]pyrazin-2-amine

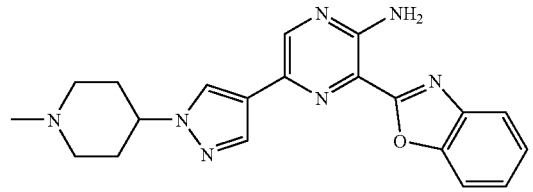

37% Aqueous formaldehyde (0.049 ml) was added to a stirred solution 3-(1,3-benzoxazol-2-yl)-5-[1-(4-piperidyl) pyrazol-4-yl]pyrazin-2-amine (200 mg, 0.55 mmol) dissolved in methanol (2 ml) and DCM (2 ml) over a period of 5 minutes at 0° C. under an atmosphere of argon. The resulting solution was stirred at 0° C. for 5 minutes. Sodium triacetoxyborohydride (0.141 g) was added and the mixture was stirred for 5 minutes at ambient temperature. A solution of ammonia in methanol 7N (1 ml) was added and the mixture was adsorbed on silica gel. The crude product was purified by flash chromatography on silica gel (eluting with 1 to 5% methanolic ammonia (7 N) in dichloromethane). The solvent was evaporated to dryness and there was thus obtained 3-(1, 3-benzoxazol-2-yl)-5-[1-(1-methyl-4-piperidyl)pyrazol-4-yl]pyrazin-2-amine (0.165 g); Mass Spectrum: M+H+ 376; NMR Spectrum (DMSOd6): 8.67 (s, 1H), 8.36 (s, 1H), 8.03 (s, 1H), 7.90 (d, 1H), 7.88 (d, 1H), 7.84 (bs, 2H), 7.51 (dd, 1H), 7.47 (dd, 1H), 4.13-4.24 (m, 1H), 2.82-2.94 (m, 2H), 2.21 (s, 3H), 1.95-2.12 (m, 6H).

EXAMPLE 19

3-(1,3-Benzothiazol-2-yl)-5-[1-(4-piperidyl)pyrazol-4-yl]pyrazin-2-amine

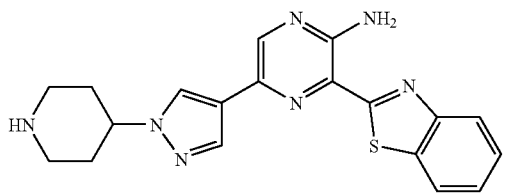

Chlorotrimethylsilane (0.332 ml) was added portionwise to a stirred solution of tert-butyl 4-[4-(5-amino-6-formyl-pyrazin-2-yl)pyrazol-1-yl]piperidine-1-carboxylate (0.4 g) and 2-aminobenzenethiol (0.115 ml) dissolved in DMF (3.2 ml). The reaction was sealed and the resulting solution was stirred at 100° C. for 2 hours. Water was added (0.5 ml) and the mixture was sonicated for 30 minutes. The reaction mixture was purified by preparative HPLC using a Waters X-Terra reverse-phase column (5 microns silica, 30 mm diameter, 150 mm length) and decreasingly polar mixtures of water (containing 0.2% ammonium carbonate) and acetonitrile as eluent. The fractions were evaporated to dryness. The solid was stirred in acetonitrile (5 ml) overnight then concentrated. There was thus obtained 3-(1,3-benzothiazol-2-yl)-5-[1-(4-piperidyl)pyrazol-4-yl]pyrazin-2-amine (0.105 g); Mass Spectrum: M+H$^+$ 378; NMR Spectrum (DMSOd6): 8.63 (s, 1H), 8.32 (s, 1H), 8.16 (s, 1H), 8.13 (d, 1H), 8.0 (d, 1H), 7.95 (bs, 2H), 7.57 (dd, 1H), 7.5 (dd, 1H), 4.21-4.32 (m, 1H), 3.02-3.10 (m, 2H), 2.55-2.67 (m, 2H), 1.96-2.04 (m, 2H), 1.76-1.88 (m, 2H).

The tert-butyl 4-(4-(5-amino-6-formylpyrazin-2-yl)-1H-pyrazol-1-yl)piperidine-1-carboxylate used as starting material was made as follows:

A solution of aluminium(III) lithium hydride (9.69 ml, 1.0 M in THF) was added dropwise to methyl 3-amino-6-[1-(1-tert-butoxycarbonyl-4-piperidyl)pyrazol-4-yl]pyrazine-2-carboxylate (3.0 g) dissolved in THF (80 ml) over a period of 5 minutes. The resulting solution was stirred at −20° C. to 0° C. for 5 hours. Solid sodium sulfate decahydrate was added, the mixture was stirred 30 minutes. The suspension was filtered and the filtrate was evaporated under reduced pressure. The crude product was purified by flash chromatography on silica gel (eluting with 2 to 5% methanol in dichloromethane). The solvent was evaporated to dryness. There was thus obtained tert-butyl 4-[4-[5-amino-6-(hydroxymethyl) pyrazin-2-yl]pyrazol-1-yl]piperidine-1-carboxylate (1.84 g); Mass Spectrum: M+H$^+$ 375; NMR Spectrum (CDCl$_3$): 8.18 (s, 1H), 7.90 (s, 1H), 7.86 (s, 1H), 4.71 (bs, 2H), 4.70 (d, 2H), 4.17-4.38 (m, 3H), 3.46 (t, 1H), 2.91 (bs, 2H), 2.12-2.22 (m, 2H), 1.90-2.02 (m, 2H), 1.48 (s, 9H).

A mixture of manganese(IV) oxide (0.743 g) was added to tert-butyl 4-[4-[5-amino-6-(hydroxymethyl)pyrazin-2-yl] pyrazol-1-yl]piperidine-1-carboxylate (0.32 g) dissolved in DCM (10 ml) over a period of 5 minutes. The resulting solution was stirred for 2 hours, then filtered. The filtrate was purified by flash chromatography on silica gel (eluting with 50 to 70% ethyl acetate in petroleum ether). The solvent was evaporated to dryness and there was thus obtained tert-butyl 4-[4-(5-amino-6-formyl-pyrazin-2-yl)pyrazol-1-yl]piperidine-1-carboxylate (0.224 g); Mass Spectrum: M+H$^+$ 373; NMR Spectrum (CDCl$_3$): 10.07 (s, 1H), 8.47 (s, 1H), 7.95 (s, 1H), 7.94 (s, 1H), 4.19-4.37 (m, 3H), 2.91 (bs, 2H), 2.15-2.22 (m, 2H), 1.93-2.01 (m, 2H), 1.59 (s, 9H).

EXAMPLE 20

Using an analogous procedure to that described in Example 1, the appropriate bromopyrazine was reacted with the appropriate boronic acid or, where stated, an appropriate boronate ester, to give the compounds described in Table VIII.

TABLE VIII

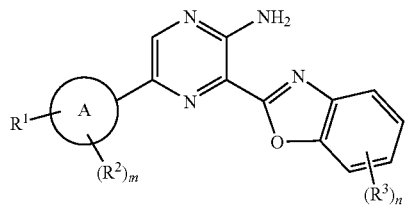

| No. & Note | R$^1$-A | m | R$^2$ | n | R$^3$ |
|---|---|---|---|---|---|
| [1] | 3-(dimethylsulphamoyl)phenyl | 0 | | 0 | |
| [2] | 3-piperazin-1-ylphenyl | 0 | | 0 | |
| [3] | 6-piperazin-1-yl-3-pyridyl | 0 | | 0 | |
| [4] | 3-(1-piperidyl)phenyl | 0 | | 0 | |
| [5] | 3-pyrrolidin-1-ylphenyl | 0 | | 0 | |
| [6] | 4-(morpholinomethyl)phenyl | 0 | | 0 | |
| [7] | 6-(4-methylpiperazin-1-yl)-3-pyridyl | 0 | | 0 | |
| [8] | 3-morpholinophenyl | 0 | | 0 | |
| [9] | 3-methylsulphonylphenyl | 0 | | 0 | |
| [10] | 3-(morpholinomethyl)phenyl | 0 | | 0 | |
| [11] | 4-piperazin-1-ylphenyl | 0 | | 0 | |
| [12] | 4-(dimethylsulphamoyl)phenyl | 0 | | 0 | |
| [13] | 3-ethylsulphonylphenyl | 0 | | 0 | |
| [14] | 3-(4-methylpiperazin-1-yl)phenyl | 0 | | 0 | |
| [15] | 3-dimethylaminophenyl | 0 | | 0 | |
| [16] | 3-(cyanomethyl)phenyl | 0 | | 0 | |
| [17] | 3-(methoxymethyl)phenyl | 0 | | 0 | |
| [18] | 3-methylsulphonyloxyphenyl | 0 | | 0 | |
| [19] | 4-(cyanomethyl)phenyl | 0 | | 0 | |
| [20] | 1-(piperidin-4-yl)pyrazol-4-yl | 1 | 3-methyl | 0 | |

Notes The products gave the characterising data shown below.

[1] Mass Spectrum: M+H$^+$ 396.4; RT 2.45 min.

[2] Tert-butyl 4-[3-(4,4,5,5-tetramethyl-1,3,2-dioxaborolan-2-yl)phenyl]piperazine-1-carboxylate was used as a reagent and after coupling, the Boc group was removed with trifluoroacetic acid in DCM. The resultant product gave the following characterising data: Mass Spectrum: M+H$^+$ 373.36; RT 2.39 min.

[3] Tert-butyl 4-[5-(4,4,5,5-tetramethyl-1,3,2-dioxaborolan-2-yl)-2-pyridyl]piperazine-1-carboxylate was used as a reagent and after coupling, the Boc group was removed with trifluoroacetic acid in DCM. The resultant product gave the following characterising data: Mass Spectrum: M+H$^+$ 374.35; RT 2.24 min.

[4] Mass Spectrum: M+H$^+$ 372.47; RT 3.12 min.

[5] Mass Spectrum: M+H$^+$ 358.45; RT 3.10 min.

[6] 4-[[4-(4,4,5,5-tetramethyl-1,3,2-dioxaborolan-2-yl) phenyl]methyl]morpholine was used as a starting material to prepare compound [6]. The resultant product gave the following characterising data: Mass Spectrum: M+H$^+$ 388.46; RT 2.35 min.

[7] The product was obtained by reacting 3-(1,3-Benzoxazol-2-yl)-5-(6-piperazin-1-yl-3-pyridyl)pyrazin-2-amine in a methylation procedure analogous to that described in Example 3. The resultant product gave the following characterising data: Mass Spectrum: M+H+ 388.41; RT 2.38 min; NMR Spectrum: (DMSOd$_6$) 8.85 (d, 2H), 8.18 (d, 1H), 7.92 (m, 4H), 7.52 (m, 2H), 6.99 (d, 1H), 3.60 (m, 4H), 2.42 (m, 4H), 2.22 (s, 3H). Tert-butyl 4-(5-(4,4,5,5-tetramethyl-1,3,2-dioxaborolan-2-yl)pyridin-2-yl)piperazine-1-carboxylate was used as a reagent and after coupling, the Boc group was removed with trifluoroacetic acid in DCM.

[8] Mass Spectrum: M+H+ 374.45; RT 2.46 min.
[9] Mass Spectrum: M+H+ 367.37; RT 2.16 min.
[10] Mass Spectrum: M+H+ 388.46; RT 2.36 min.
[11] The product was obtained by reacting 3-(1,3-Benzoxazol-2-yl)-5-(4-piperazin-1-ylphenyl)pyrazin-2-amine in a methylation procedure analogous to that described in Example 3. The resultant product gave the following characterising data: Mass Spectrum: M+H+ 373.34; RT 2.52 min. Tert-butyl 4-[4-(4,4,5,5-tetramethyl-1,3,2-dioxaborolan-2-yl)phenyl]piperazine-1-carboxylate was used as a reagent and after coupling, the Boc group was removed with trifluoroacetic acid in DCM.
[12] Mass Spectrum: M+H+ 396.4; RT 2.46 min.
[13] Mass Spectrum: M+H+ 381.38; RT 2.29 min.
[14] The product was obtained by reacting 3-(1,3-benzoxazol-2-yl)-5-(3-piperazin-1-ylphenyl)pyrazin-2-amine in a methylation procedure analagous to that described in Example 3. The resultant product gave the following characterising data: Mass Spectrum: M+H+ 387.38; RT 2.54 min; NMR Spectrum: (DMSOd$_6$) 8.93 (s, 1H), 8.02 (s, 2H), 7.94 (m, 2H), 7.59 (s, 1H), 7.52 (m, 3H), 7.38 (t, 1H), 7.01 (d, 1H), 3.30 (m, 4H), 2.50 (4H), 2.27 (s, 3H). tert-butyl 4-(3-(4,4,5,5-tetramethyl-1,3,2-dioxaborolan-2-yl)-phenyl)piperazine-1-carboxylate was used as a reagent and after coupling, the Boc group was removed with trifluoroacetic acid in DCM.
[15] Mass Spectrum: M+H+ 332.44; RT 2.75 min.
[16] Mass Spectrum: M+H+ 328.4; RT 2.39 min.
[17] Mass Spectrum: M+H+ 333.41; RT 2.54 min.
[18] Mass Spectrum: M+H+ 383.37; RT 2.40 min.
[19] Mass Spectrum: M+H+ 328.32; RT 2.59 min; NMR Spectrum: (DMSOd$^6$) 8.96 (s, 1H), 8.15 (d, 2H), 8.06 (s, 2H), 7.96 (dd, 2H), 7.50 (m, 4H), 4.14 (s, 2H).
[20] Compound [20] was prepared using the following method. 3-(1,3-benzoxazol-2-yl)-5-bromo-pyrazin-2-amine (69 mg), tert-butyl 4-[3-methyl-4-(4,4,5,5-tetramethyl-1,3,2-dioxaborolan-2-yl)pyrazol-1-yl]piperidine-1-carboxylate (93 mg) and bis(triphenylphosphine) palladium chloride (16.64 mg) and caesium fluoride (108 mg) in methanol (1.5 ml) were degassed under vacuum and argon, stirred at 130° C. for 20 nm. The mixture was concentrated, dissolved in dichloromethane and filtered. The filtrate was purified by flash chromatography on silica gel eluting with 50 to 100% ethyl acetate in petroleum ether. The solvent was evaporated to dryness to afford tert-butyl 4-[4-[5-amino-6-(1,3-benzoxazol-2-yl)pyrazin-2-yl]-3-methyl-pyrazol-1-yl]piperidine-1-carboxylate (71.0 mg). The N-tert-butoxycarbonyl group on the resultant product was removed by treatment with trifluoroacetic acid to afford 3-(1,3-benzoxazol-2-yl)-5-[3-methyl-1-(4-piperidyl)pyrazol-4-yl]pyrazin-2-amine (62.0 mg) as a solid. NMR Spectrum(DMSO-d$_6$): 1.75-1.85 (m, 1.5H), 1.94-2.01 (m, 2H), 2.05 (bs, 0.5H), 2.09-2.16 (m, 0.5H), 2.53 (s, 2.25H), 2.54 (s, 0.75H), 2.55-2.63 (m, 1.5H), 3.03-3.09 (m, 1.5H), 3.10-3.16 (m, 0.5H), 4.10-4.19 (m, 1H), 7.44-7.53 (m, 2H), 7.78 (bs, 2H), 7.86 (dd, 1H), 7.90 (dd, 1H), 8.25 (s, 0.75H), 8.31 (s, 0.25H), 8.56 (s, 0.75H), 8.57 (s, 0.25H); Mass Spectrum: M+H+: 376.

The tert-butyl 4-[3-methyl-4-(4,4,5,5-tetramethyl-1,3,2-dioxaborolan-2-yl)pyrazol-1-yl]piperidine-1-carboxylate used as starting material was prepared as follows: tert-butyl 4-(4-bromo-3-methyl-pyrazol-1-yl)piperidine-1-carboxylate (500 mg), 4,4,5,5-tetramethyl-2-(4,4,5,5-tetramethyl-1,3,2-dioxaborolan-2-yl)-1,3,2-dioxaborolane (738 mg), PdCl$_2$(dppf) (117 mg) and potassium acetate (0.428 mL, 4.36 mmol) in degassed DMSO (7.5 mL) were stirred at 80° C. for 4 hours under argon. The reaction mixture was allowed to cool to room temperature under stirring over a period of 1 hour, quenched with water (25 ml) and extracted with ethyl acetate (3×40 ml). The combined organic phases were washed with water (3×30 ml), a saturated aqueous solution of brine (1×20 ml), dried over magnesium sulfate and concentrated to afford the crude product. The crude product was purified by flash chromatography on silica gel eluting with 10 to 30% ethyl acetate in petroleum ether. The solvent was evaporated to dryness to afford tert-butyl 4-[3-methyl-4-(4,4,5,5-tetramethyl-1,3,2-dioxaborolan-2-yl)pyrazol-1-yl]piperidine-1-carboxylate (189 mg) as a solid. NMR Spectrum: (DMSOd6) 1.24 (s, 12H), 1.41 (s, 9H), 1.71 (dd, 1H), 1.76 (dd, 1H), 1.89-1.97 (m, 2H), 2.22 (s, 3H), 2.86 (bs, 2H), 4.01 (bs, 2H), 4.19-4.29 (m, 1H), 7.82 (s, 1H)

EXAMPLE 21

Tert-butyl 4-[4-[6-amino-5-(1,3-benzoxazol-2-yl)-3-pyridyl]-3-methyl-pyrazol-1-yl]piperidine-1-carboxylate

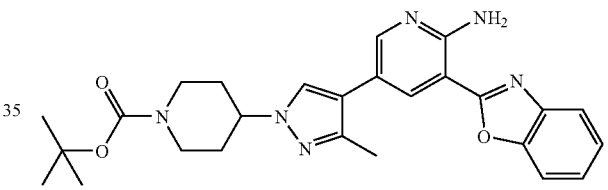

A mixture of 3-(1,3-benzoxazol-2-yl)-5-(4,4,5,5-tetramethyl-1,3,2-dioxaborolan-2-yl)pyridin-2-amine (600 mg), tert-butyl 4-(4-bromo-3-methyl-pyrazol-1-yl)piperidine-1-carboxylate (557 mg), tris(dibenzylideneacetone)dipalladium (74.1 mg), tricyclohexylphosphine (45.4 mg) and potassium phosphate (584 mg) in 1,4-dioxane (3.4 mL) and water (0.4 mL) was degassed with argon, then stirred at 100° C. for 3 h under argon. Solvents were removed. The crude product was adsorbed on silica gel and purified by flash chromatography on silica gel eluting with 5 to 10% methanol in dichloromethane. The solvent was evaporated to dryness to afford tert-butyl 4-[4-[6-amino-5-(1,3-benzoxazol-2-yl)-3-pyridyl]-3-methyl-pyrazol-1-yl]piperidine-1-carboxylate (500 mg); NMR Spectrum: (DMSOd6) 1.43 (s, 9H), 1.78 (dd, 1H), 1.83 (dd, 1H), 1.99-2.07 (m, 2H), 2.33 (s, 3H), 2.91 (bs, 2H), 4.01-4.11 (m, 2H), 4.24-4.32 (m, 1H), 7.42-7.50 (m, 2H), 7.65 (bs, 2H), 7.77-7.83 (m, 2H), 8.10 (s, 1H), 8.29 (d, 1H), 8.35 (d, 1H); Mass spectrum: M+H+: 475

The 3-(1,3-benzoxazol-2-yl)-5-(4,4,5,5-tetramethyl-1,3,2-dioxaborolan-2-yl)pyridin-2-amine used as a reagent was prepared as follows:

3-(1,3-Benzoxazol-2-yl)-5-bromo-pyridin-2-amine (1.83 g), potassium acetate (1.92 g), 1,1'-bis(diphenylphosphino)ferrocenedichloropalladium(II)-dichloromethane adduct (0.255 g) and 4,4,4',4',5,5,5',5'-octamethyl-2,2'-bi(1,3,2-dioxaborolane) (3.20 g) were mixed in dioxane (20 ml). The resulting suspension was degassed with argon and stirred at 80° C. overnight. LCMS monitoring showed complete conversion. The reaction mixture was diluted with chloroform (60 ml). The insolubles were removed by filtration and washed with chloroform (60 ml). The filtrate was concentrated to give a solid, which was taken up into ethyl acetate (20 ml). A solid was obtained after concentration of the chloroform solution. The solid was collected by filtration, washed with ethyl acetate (20 ml) to give 3-(1,3-benzoxazol-2-yl)-5-(4,4,5,5-tetramethyl-1,3,2-dioxaborolan-2-yl)pyridin-2-amine (1.37 g); NMR Spectrum: (CDCl3) 1.37 (s, 12H), 7.32-7.39 (m, 2H), 7.44 (bs, 2H), 7.57 (dd, 1H), 7.72 (dd, 1H), 8.58 (d, 1H), 8.70 (d, 1H); Mass spectrum: M+H$^+$: 338

The tert-butyl 4-(4-bromo-3-methyl-pyrazol-1-yl)piperidine-1-carboxylate used as a reagent was prepared as follows:

Sodium hydride (60% dispersion in mineral oil, 11.53 g) was added portionwise to a stirred solution of 4-bromo-3-methyl-1H-pyrazole (42.2 g) dissolved in DMF (600 ml) over a period of 15 minutes at 0° C. under nitrogen. The resulting slurry was stirred at 0° C. for 1 hour. Then tert-butyl 4-methylsulphonyloxypiperidine-1-carboxylate (73.2 g) was added and the mixture was stirred 1 hour at room temperature then heated to 90° C. overnight. The reaction mixture was then allowed to stir at room temperature over a period of 2 days, quenched with water (2 ml), concentrated to dryness, diluted with ethyl acetate (1500 ml), washed with water (2×1000 ml), brine (1000 ml), dried over magnesium sulfate and concentrated to afford the crude product. A purification by flash chromatography on silica gel eluting with 20% ethyl acetate in petroleum ether afforded tert-butyl 4-(4-bromo-5-methyl-pyrazol-1-yl)piperidine-1-carboxylate (22.5 g) (NMR Spectrum: (DMSOd6) 1.42 (s, 9H), 1.72-1.86 (m, 4H), 2.28 (s, 3H), 2.91 (bs, 2H), 3.96-4.13 (m, 2H), 4.34-4.43 (m, 1H), 7.50 (s, 1H); Mass spectrum: M−tBu: 288,290), and tert-butyl 4-(4-bromo-3-methyl-pyrazol-1-yl)piperidine-1-carboxylate (28.7 g) (NMR Spectrum (DMSOd6): 1.44 (s, 9H), 1.70 (dd, 1H), 1.75 (dd, 1H), 1.91-1.99 (m, 2H), 2.11 (s, 3H), 2.87 (bs, 2H), 4.95-4.10 (m, 2H), 4.21-4.30 (m, 1H), 7.95 (s, 1H); Mass spectrum: M−tBu: 288,290).

EXAMPLE 22

3-(1,3-benzoxazol-2-yl)-5-[3-methyl-1-(4-piperidyl)pyrazol-4-yl]pyridin-2-amine

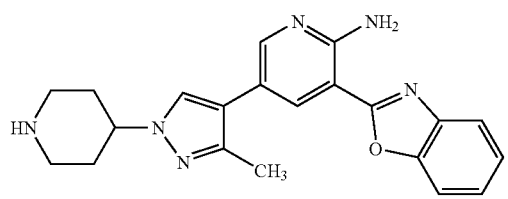

To a solution of tert-butyl 4-[4-[6-amino-5-(1,3-benzoxazol-2-yl)-3-pyridyl]-3-methyl-pyrazol-1-yl]piperidine-1-carboxylate (500 mg) in dichloromethane (3 ml) was added TFA (1 ml). The solution was stirred at 25° C. for 2 hours. The mixture was evaporated to dryness, then the residue was diluted in dichloromethane and ammonia in methanol 7N was added. After removal of solvents, the crude product was purified by flash chromatography on silica gel eluting with 10% methanol in dichloromethane followed by 10 to 25% methanolic ammonia (7 N) in dichloromethane. The solvent was evaporated to dryness to afford a solid which was stirred in acetonitrile overnight, filtered and dried to afford 3-(1,3-benzoxazol-2-yl)-5-[3-methyl-1-(4-piperidyl)pyrazol-4-yl]pyridin-2-amine (290 mg) as a solid; NMR Spectrum: (DMSOd6) 1.77 (dd, 1H), 1.82 (dd, 1H), 1.93-1.99 (m, 2H), 2.12 (bs, 1H), 2.32 (s, 3H), 2.58 (ddd, 1H), 3.01-3.07 (m, 2H), 4.06-4.25 (m, 1H), 7.41-7.48 (m, 2H), 7.64 (bs, 2H), 7.80 (dd, 1H), 7.84 (dd, 1H), 8.04 (s, 1H), 8.28 (d, 1H), 8.35 (d, 1H); Mass spectrum: M+H$^+$: 375

EXAMPLE 23

3-(1,3-benzoxazol-2-yl)-5-[3-methyl-1-(1-methyl-4-piperidyl)pyrazol-4-yl]pyridin-2-amine

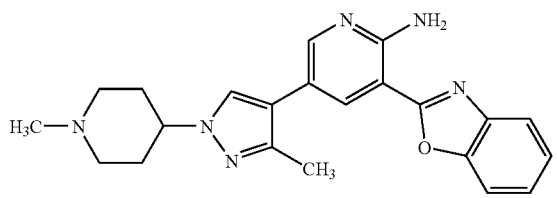

37% Aqueous formaldehyde (0.042 ml) at 0° C. was added to a stirred solution of 3-(1,3-benzoxazol-2-yl)-5-[3-methyl-1-(4-piperidyl)pyrazol-4-yl]pyridin-2-amine (178 mg) dissolved in methanol (2 ml) and dichloromethane (2 ml) over a period of 5 minutes under argon. The resulting solution was stirred at 0° C. for 5 minutes. Then sodium triacetoxyhydroborate (121 mg) was added and the mixture was stirred for 5 minutes at 25° C. A solution of ammonia in methanol 7N (2 ml) was added and the mixture was adsorbed on silica gel. The crude product was purified by flash chromatography on silica gel eluting with 5% methanolic ammonia (7 N) in dichloromethane. The solvent was evaporated to dryness, then the resulting solid was stirred in acetonitrile overnight, filtered and dried to afford 3-(1,3-benzoxazol-2-yl)-5-[3-methyl-1-(1-methyl-4-piperidyl)pyrazol-4-yl]pyridin-2-amine (125 mg) as a solid; NMR Spectrum: (DMSOd6) 1.88-2.11 (m, 6H), 2.21 (s, 3H), 2.33 (s, 3H), 2.81-2.93 (m, 2H), 3.97-4.11 (m, 1H), 7.38-7.50 (m, 2H), 7.65 (bs, 2H), 7.79 (d, 1H), 7.84 (d, 1H), 8.07 (s, 1H), 8.28 (s, 1H), 8.35 (s, 1H); Mass spectrum: M+H$^+$: 389

EXAMPLE 24

3-(1,3-benzoxazol-2-yl)-5-[5-methyl-1-(4-piperidyl)pyrazol-4-yl]pyridin-2-amine

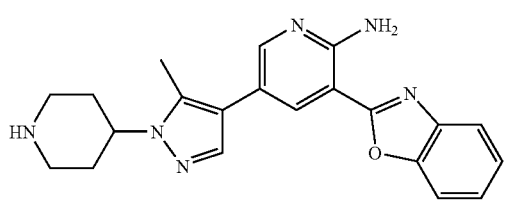

3-(1,3-benzoxazol-2-yl)-5-(4,4,5,5-tetramethyl-1,3,2-dioxaborolan-2-yl)pyridin-2-amine (400 mg), tert-butyl 4-(4-bromo-5-methyl-pyrazol-1-yl)piperidine-1-carboxylate (371 mg), tris(dibenzylideneacetone)dipalladium (49 mg), tricyclohexylphosphine (30 mg) and potassium phosphate (389 mg, 1.83 mmol) in dioxane (2.4 ml) and water (0.4 ml) were stirred at 100° C. for 3 h under argon. The reaction mixture was filtered and purified by preparative HPLC using a Waters X-Terra reverse-phase column (C-18, 5 micron silica, 19 mm diameter, 100 mm length, flow rate of 40 ml/min) and decreasingly polar mixtures of water (containing 0.2% ammonium carbonate) and acetonitrile as eluent. The fractions containing the desired compound were evaporated to dryness to afford tert-butyl 4-[4-[6-amino-5-(1,3-benzoxazol-2-yl)-3-pyridyl]-5-methyl-pyrazol-1-yl]piperidine-1-carboxylate (214 mg). NMR Spectrum: (DMSOd6) 1.43 (s, 9H), 1.83-1.92 (m, 4H), 2.42 (s, 3H), 2.95 (bs, 2H), 4.02-4.14 (m, 2H), 4.39-4.48 (m, 1H), 7.42-7.49 (m, 2H), 7.66 (s, 1H), 7.67 (bs, 2H), 7.79 (d, 1H), 7.84 (d, 1H), 8.22 (d, 1H), 8.29 (d, 1H); Mass spectrum: M+H⁺ 475 TFA (1 ml) was added to a solution of tert-butyl 4-[4-[6-amino-5-(1,3-benzoxazol-2-yl)-3-pyridyl]-5-methyl-pyrazol-1-yl]piperidine-1-carboxylate (126 mg) in dichloromethane (1 ml). The solution was stirred at 25° C. for 1 hour. After evaporation of the solvents, the crude mixture was diluted in dichloromethane and 7N methanolic ammonia was added. After evaporation of the solvents, the residue was purified by flash chromatography on silica gel eluting with 10% methanol in dichloromethane and 10 to 25% methanolic ammonia (7N) in dichloromethane. The solvent was evaporated to dryness and triturated in acetonitrile to afford 3-(1,3-benzoxazol-2-yl)-5-[5-methyl-1-(4-piperidyl)pyrazol-4-yl]pyridin-2-amine (66 mg). NMR Spectrum: (DMSOd6) 1.79-1.87 (m, 2H), 1.90-2.01 (m, 2H), 2.40 (s, 3H), 2.65-2.75 (m, 2H), 3.07-3.15 (m, 2H), 4.23-4.33 (m, 1H), 7.40-7.49 (m, 2H), 7.65 (s, 1H), 7.67 (bs, 2H), 7.79 (dd, 1H), 7.84 (dd, 1H), 8.21 (d, 1H), 8.29 (d, 1H); Mass spectrum: M+H⁺ 375.

EXAMPLE 25

Using analogous procedure to those described in Example 24, the corresponding pyridine boronate ester was reacted with the appropriate bromo-aryl/heteroaryl to give the compounds described in Table IX.

TABLE IX

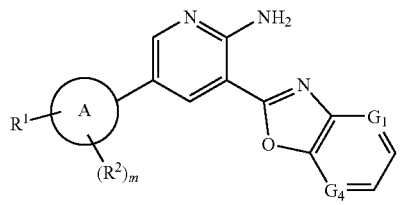

| No. & Note | R¹-A | m | R² | G₁ | G₄ |
|---|---|---|---|---|---|
| [1] | 1-[4-(cyanomethyl)-4-piperidyl]pyrazol-4-yl | 0 | | CH | CH |
| [2] | 1-(piperidin-4-yl)pyrazol-4-yl | 1 | 3-methoxy | CH | CH |
| [3] | 1-(piperidin-4-yl)pyrazol-4-yl | 1 | 3-ethoxy | CH | CH |
| [4] | 1-(piperidin-4-yl)pyrazol-4-yl | 1 | 5-ethoxy | CH | CH |
| [5] | 2-(4-methylpiperazin-1-yl)thiazol-5-yl | 0 | | CH | CH |
| [6] | 4-(4-methylpiperazin-1-yl)phenyl | 1 | 3-methoxy | N | CH |
| [7] | 4-(4-methylpiperazin-1-yl)phenyl | 0 | | N | CH |
| [8] | 4-piperazin-1-ylphenyl | 1 | 3-methoxy | N | CH |
| [9] | 4-piperazin-1-ylphenyl | 0 | | N | CH |
| [10] | 4-(4-methylpiperazin-1-yl)phenyl | 0 | | CH | N |
| [11] | 4-piperazin-1-ylphenyl | 0 | | CH | N |
| [12] | 2-(4-methylpiperazin-1-yl)thiazol-5-yl | 0 | | CH | N |
| [13] | 1-(piperidin-4-yl)pyrazol-4-yl | 1 | 3-hydroxymethyl | CH | CH |
| [14] | 1-(piperidin-4-yl)pyrazol-4-yl | 1 | 3-methoxymethyl | CH | CH |
| [15] | 1-(piperidin-4-yl)pyrazol-4-yl | 1 | 3-methyl | CH | N |
| [16] | 1-(piperidin-4-yl)pyrazol-4-yl | 1 | 3-methyl | N | CH |

[1] Compound [1] was prepared according to the procedure described in Example 24 except that the reaction was carried out in the presence of 1,1'-bis(diphenylphosphino)ferrocenedichloropalladium(II) and caesium carbonate was used as a base. The N-tert-butoxycarbonyl group on the resultant product was removed by conventional treatment with trifluoroacetic acid as described in Example 24. The derived product so obtained (95 mg) gave the following characterising data. NMR Spectrum: (DMSOd6) 1.85-1.96 (m, 2H), 2.11 (bs, 1H), 2.41-2.48 (m, 2H), 2.53-2.62 (m, 2H), 2.76-2.86 (m, 2H), 3.10 (s, 2H), 7.41-7.50 (m, 2H), 7.69 (bs, 2H), 7.79-7.82 (m, 1H), 7.83-7.87 (m, 1H), 8.06 (s, 1H), 8.52 (d, 1H), 8.55 (s, 1H), 8.60 (d, 1H); Mass spectrum: M+H⁺ 400.

The tert-butyl 4-(4-bromopyrazol-1-yl)-4-(cyanomethyl) piperidine-1-carboxylate used as starting material was prepared as follows:

4-bromo-1H-pyrazole (362 mg), 1,8-diazabicyclo[5.4.0] undec-7-ene (0.368 ml) and tert-butyl 4-(cyanomethylene) piperidine-1-carboxylate (547 mg) in acetonitrile (10 ml) were stirred at 45° C. for 6 hours. The crude reaction was concentrated on dicalite (diatomaceous earth) and was purified by flash chromatography on silica gel eluting with 0 to 20% ethyl acetate in petroleum ether. The solvent was evaporated to dryness to afford tert-butyl 4-(4-bromopyrazol-1-yl)-4-(cyanomethyl)piperidine-1-carboxylate (570 mg) as a white foam. NMR Spectrum: (DMSO-d6) 1.45 (s, 9H), 1.94-2.04 (m, 2H), 2.54-2.62 (m, 2H), 2.80 (s, 2H), 2.93-3.04 (m, 2H), 3.88 (bs, 2H), 7.57 (s, 1H), 7.73 (s, 1H)

Tert-butyl 4-(cyanomethylene)piperidine-1-carboxylate used as starting material was synthesized according to Rodgers et al., US patent application US2007135461.

[2] Compound [2] was prepared according to the procedure described in Example 24 except that the reaction was carried out at 120° C. The N-tert-butoxycarbonyl group on the resultant product was removed by conventional treatment with 4N hydrogen chloride in dioxane. The product so obtained (91 mg) gave the following characterising data. NMR Spectrum: (CDCl3) 1.83-1.95 (m, 2H), 2.13-2.24 (m, 2H), 2.71-2.83 (m, 2H), 3.21-3.31 (m, 2H), 4.03 (s, 3H), 4.03-4.11 (m, 1H), 6.82 (bs, 2H), 7.33-7.40 (m, 2H), 7.53 (s, 1H), 7.58-7.63 (m, 1H), 7.71-7.77 (m, 1H), 8.49 (d, 1H), 8.51 (d, 1H); Mass spectrum: M+H⁺ 391.

The tert-butyl 4-(4-bromo-3-methoxy-pyrazol-1-yl)piperidine-1-carboxylate used as starting material was made as follows:

Dimethyl sulfate (1.24 ml) was added to 1-acetyl-2H-pyrazol-3-one (1.5 g) (Boulla et al. PCT Fr. Appl. FR2862647) and potassium carbonate (1.64 g) dissolved in butan-2-one (35 ml). The resulting suspension was stirred at reflux for 90 minutes. The reaction mixture was allowed to cool to room temperature. The insolubles were removed by filtration and the filtrate was concentrated to give a black oil. An aqueous solution of NaOH (0.595 ml, 10N) was added to this black oil dissolved in THF (20 ml) and methanol (20 ml). The resulting solution was stirred at room temperature for 30 minutes. The reaction mixture was concentrated to dryness, taken up into ethyl acetate, washed with brine and dried over magnesium sulphate. The organic phase was concentrated to give the desired 3-methoxypyrazole (0.775 g). NMR Spectrum: (CDCl3) 3.92 (s, 3H), 5.74 (s, 1H), 7.37 (s, 1H), 9.07 (bs, 1H)

A solution of bromine (0.405 ml) in dichloromethane (8 ml) at 0-5° C. was added dropwise to a mixture of 3-methoxypyrazole (775 mg) and sodium carbonate (1.67 mg) in dichloromethane (16 ml) under argon over a period of 10 minutes. The resulting suspension was stirred at 0-5° C. for 30 minutes. Aqueous sodium thiosulfate (2.37 ml, 0.1N) at 0-5° C. was added to the stirred suspension and the resulting mixture was stirred at 0-5° C. for 1 hour. The reaction mixture was allowed to warm to room temperature and quenched with water. The phases were separated. The aqueous phase was extracted with dichloromethane. The combined organic phases were washed with water, dried over magnesium sulfate and concentrated to afford a brown oil. Hydrogen chloride (4N in dioxane) (1.975 ml) was added to this brown oil. The mixture was diluted in dioxane and triturated. The resulting precipitate was collected by filtration, washed with dioxane and diethyl ether and dried to a constant weight to afford 4-bromo-3-methoxy-1H-pyrazole, hydrochloride salt (1 g) as a solid, which was used without further purification. NMR Spectrum: (DMSOd6) 3.82 (s, 3H), 7.78 (s, 1H), 7.99 (bs, 2H)

Sodium hydride (354 mg, 60% dispersion in oil) was added portionwise to a solution of 4-bromo-3-methoxy-2H-pyrazole, hydrochloride salt (755 mg) in degassed DMF (12 ml) under argon at room temperature. The resulting suspension was stirred at room temperature for 10 minutes. tert-butyl 4-methylsulphonyloxypiperidine-1-carboxylate (1.087 g) was added to the stirred suspension. The resulting mixture was stirred at 90° C. for 20 hours. The reaction mixture was allowed to cool to room temperature, quenched with water, diluted with ethyl acetate then water and extracted with ethyl acetate. The combined organic phases were washed with brine, dried over magnesium sulfate and concentrated. The residue was purified by flash chromatography on silica gel eluting with 0 to 20% ethyl acetate in petroleum ether. The solvent was evaporated to dryness to afford tert-butyl 4-(4-bromo-3-methoxy-pyrazol-1-yl)piperidine-1-carboxylate (670 mg). NMR Spectrum: (CDCl3) 1.47 (s, 9H), 1.78 (dd, 1H), 1.83 (dd, 1H), 2.03-2.10 (m, 2H), 2.78-2.93 (m, 2H), 3.93 (s, 3H), 3.99-4.07 (m, 1H), 4.13-4.31 (m, 2H), 7.24 (s, 1H)

[3] Compound [3] was prepared according to the first portion of the procedure described in Example 24 except that the reaction was carried out at 120° C. using a 4:1 mixture of tert-butyl 4-(4-bromo-3-ethoxy-pyrazol-1-yl)piperidine-1-carboxylate and tert-butyl 4-(4-bromo-5-ethoxy-pyrazol-1-yl)piperidine-1-carboxylate (470 mg). Before the N-tert-butoxycarbonyl deprotection step, the mixture was purified by flash chromatography on silica gel eluting with 0 to 70% ethyl acetate in dichloromethane. The fractions containing the desired compound were evaporated to dryness to afford tert-butyl 4-[4-[6-amino-5-(1,3-benzoxazol-2-yl)-3-pyridyl]-3-ethoxy-pyrazol-1-yl]piperidine-1-carboxylate (168 mg, eluting first) and tert-butyl 4-[4-[6-amino-5-(1,3-benzoxazol-2-yl)-3-pyridyl]-5-ethoxy-pyrazol-1-yl]piperidine-1-carboxylate (47 mg, eluting second).

The N-tert-butoxycarbonyl group on tert-butyl 4-[4-[6-amino-5-(1,3-benzoxazol-2-yl)-3-pyridyl]-3-ethoxy-pyrazol-1-yl]piperidine-1-carboxylate (123 mg) was removed by treatment with 4N hydrogen chloride in dioxane. The derived product so obtained (74 mg) gave the following characterising data. NMR Spectrum: (CDCl3) 1.47 (t, 3H), 1.91-2.01 (m, 2H), 2.19-2.26 (m, 2H), 2.79-2.88 (m, 2H), 3.59-3.73 (m, 2H), 4.06-4.14 (m, 1H), 4.35 (q, 2H), 6.81 (bs, 2H), 7.33-7.40 (m, 2H), 7.54 (s, 1H), 7.56-7.61 (m, 1H), 7.72-7.77 (m, 1H), 8.52-8.57 (m, 2H); Mass spectrum: M+H+ 405.

The 4:1 mixture of tert-butyl 4-(4-bromo-3-ethoxy-pyrazol-1-yl)piperidine-1-carboxylate and tert-butyl 4-(4-bromo-5-ethoxy-pyrazol-1-yl)piperidine-1-carboxylate used as starting material was made as follows:

According to the procedure described for the starting material in [2] above, 1-acetyl-2H-pyrazol-3-one (1.42 g) was reacted with diethyl sulphate to give 3-ethoxypyrazole (1.15 g); NMR Spectrum: (CDCl$_3$) 1.40 (t, 3H), 4.21 (q, 2H), 5.73 (d, 1H), 7.36 (d, 1H), 9.21 (bs, 1H) 3-Ethoxypyrazole was reacted according to the procedure described in [2] and the following intermediates were successively isolated:

4-Bromo-3-ethoxypyrazole, hydrochloride salt: 710 mg; NMR Spectrum: (DMSO) 1.30 (t, 3H), 4.17 (q, 2H), 4.91 (bs, 2H), 4.76 (s, 1H) tert-butyl 4-(4-bromo-3-ethoxy-pyrazol-1-yl)piperidine-1-carboxylate and tert-butyl 4-(4-bromo-5-ethoxy-pyrazol-1-yl)piperidine-1-carboxylate; isolated as a 4:1 mixture (579 mg), colourless oil, after chromatography on silica gel eluting with 0 to 20% ethyl acetate in petroleum ether. Major isomer NMR Spectrum: (CDCl3): 1.40 (t, 3H), 1.47 (s, 9H), 1.77 (d, 1H), 1.82 (d, 1H), 2.03-2.09 (m, 2H), 2.80-2.91 (m, 2H), 3.99-4.06 (m, 1H), 4.22 (bs, 2H), 4.26 (q, 2H), 7.23 (s, 1H); Minor isomer NMR Spectrum: (CDCl3) 1.41 (t, 3H), 1.47 (s, 9H), 1.77 (d, 1H), 1.82 (d, 1H), 2.03-2.09 (m, 2H), 2.80-2.91 (m, 2H), 3.99-4.06 (ms, 1H), 4.22 (bs, 2H), 4.38 (q, 2H), 7.31 (s, 1H)

[4] The N-tert-butoxycarbonyl group on tert-butyl 4-[4-[6-amino-5-(1,3-benzoxazol-2-yl)-3-pyridyl]-5-ethoxy-pyrazol-1-yl]piperidine-1-carboxylate (47 mg, isolated in [3] above) was removed by conventional treatment with 4N hydrogen chloride in dioxane. The derived product so obtained (18 mg) gave the following characterising data. NMR Spectrum: (CDCl3) 1.38 (t, 3H), 1.93-2.01 (m, 2H), 2.10 (dd, 1H), 2.16 (dd, 1H), 2.78-2.87 (m, 2H), 2.28-2.37 (m, 2H), 4.03 (q, 2H), 4.26-4.34 (m, 1H), 6.89 (bs, 2H), 7.34-7.41 (m, 2H), 7.56-7.64 (m, 2H), 7.72-7.78 (m, 1H), 8.40 (d, 1H), 8.45 (d, 1H); Mass spectrum: M+H+ 405.

[5] Compound [5] was prepared as follows. 3-(1,3-benzoxazol-2-yl)-5-(4,4,5,5-tetramethyl-1,3,2-dioxaborolan-2-yl) pyridin-2-amine (150 mg), 1-(5-bromothiazol-2-yl)-4-methyl-piperazine (117 mg), bis(triphenylphosphine) palladium (II) chloride (15.61 mg) and caesium fluoride (169 mg) were weighed out in a microwave vial and sealed. Methanol (1.5 ml) was added and argon was bubbled in the resulting suspension for 10 minutes. The resulting mixture was heated in the 300 W microwave at 120° C. for 20 minutes. The crude product was purified by flash chromatography on silica gel eluting with 0 to 3% methanol in dichloromethane then 3% to 5% methanolic ammonia 7N in dichloromethane. The solvent was evaporated to dryness to afford the product, which was stirred at room temperature for 1 h in acetonitrile (3 ml), collected by filtration, washed with acetonitrile and dried under vacuum at 40° C., to give 3-(1,3-benzoxazol-2-yl)-5-[2-(4-methylpiperazin-1-yl)thiazol-5-yl]pyridin-2-amine (80 mg). NMR Spectrum: (CDCl3) 2.39 (s, 3H), 2.54-2.65 (m, 4H), 3.56-3.65 (m, 4H), 6.96 (m, 2H), 7.35 (s, 1H), 7.36-7.40 (m, 2H), 7.61 (dd, 1H), 7.74 (dd, 1H), 8.31-8.35 (m, 2H); Mass spectrum: M+H$^+$ 393. There was no deprotection step.

[6] Compound [6] was prepared as follows. 3-oxazolo[4,5-b]pyridin-2-yl-5-(4,4,5,5-tetramethyl-1,3,2-dioxaborolan-2-yl)pyridin-2-amine (138 mg), 1-(4-bromo-3-methoxy-phenyl)-4-methyl-piperazine (97 mg), bis(triphenylphosphine) palladium (II) chloride (50.1 mg) and sodium carbonate (50.5 mg) were weighed out and sealed in a tube. DME (3 ml) and water (0.3 ml) were added. Argon was bubbled in the resulting mixture for 10 minutes then it was stirred at 100° C. for 1 hour. After cooling, the reaction mixture was diluted with ethyl acetate (5 ml), filtered, and purified by flash chromatography on silica gel eluting with 0 to 5% methanol in dichloromethane/ethyl acetate (1/1) then 5% methanolic ammonia 7N in dichloromethane/ethyl acetate (1/1). The solvent was evaporated to dryness and the product was triturated in acetonitrile (4 ml), collected by filtration, washed with Acetonitrile and dried under vacuum at 40° C., to give 5-[2-methoxy-4-(4-methylpiperazin-1-yl)phenyl]-3-oxazolo[4,5-b]pyridin-2-yl-pyridin-2-amine (78 mg). NMR Spectrum: (CDCl3) 2.40 (s, 3H), 2.61-2.69 (m, 4H), 3.27-3.36 (m, 4H), 3.85 (s, 3H), 6.58 (d, 1H), 6.62 (dd, 1H), 6.91 (bs, 2H), 7.25 (d, 1H), 7.30 (dd, 1H), 7.85 (dd, 1H), 8.46 (d, 1H), 8.47 (d, 1H), 8.56 (dd, 1H); Mass spectrum: M+H$^+$ 417. There was no deprotection step.

The 3-oxazolo[4,5-b]pyridin-2-yl-5-(4,4,5,5-tetramethyl-1,3,2-dioxaborolan-2-yl)pyridin-2-amine used as starting material was prepared as follows:

5-bromo-3-oxazolo[4,5-b]pyridin-2-yl-pyridin-2-amine (50 mg), potassium acetate (52.3 mg), 1,1'-bis(diphenylphosphino)ferrocenedichloropalladium(II)-dichloromethane adduct (6.94 mg) and 4,4,4',4',5,5,5',5'-octamethyl-2,2'-bi(1,3,2-dioxaborolane) (48.0 mg) were suspended in dioxane (800 µL) and degassed several times with argon. Argon stream was bubbled in the suspension at 25° C. for 15 minutes. The resulting suspension was sealed and stirred at 80° C. overnight. The reaction mixture was diluted with chloroform (800 µL) and filtered. The residue was taken up into ethyl acetate (3 ml), collected by filtration to give 3-oxazolo[4,5-b]pyridin-2-yl-5-(4,4,5,5-tetramethyl-1,3,2-dioxaborolan-2-yl)pyridin-2-amine (37.0 mg). NMR Spectrum: (CDCl3) 1.31 (s, 12H), 5.97 (bs, 2H), 7.24 (dd, 1H), 7.70 (dd, 1H), 8.49 (dd, 1H), 8.55 (d, 1H), 8.65 (d, 1H); Mass spectrum: M+H$^+$ 339

The 1-(4-bromo-3-methoxy-phenyl)-4-methyl-piperazine used as starting material was prepared as follows:

Sodium triacetoxyhydroborate (25.9 mg) was added to 1-(4-bromo-3-methoxy-phenyl)piperazine (30 mg), N-ethyl-N-isopropyl-propan-2-amine (0.030 ml) and 37% aqueous formaldehyde (8.01 µl) dissolved in dichloromethane (1 ml). The resulting mixture was stirred at 25° C. for 2 hours. The reaction mixture was quenched with a saturated aqueous solution of sodium hydrogencarbonate (5 ml) and extracted with ethyl acetate (2×10 ml). The combined organic phases were dried over magnesium sulfate and concentrated to afford the crude 1-(4-bromo-3-methoxy-phenyl)-4-methyl-piperazine (25.00 mg). NMR Spectrum: (CDCl3) 2.38 (s, 3H), 2.60 (bs, 4H), 3.17-3.28 (m, 4H), 3.88 (s, 3H), 6.41 (dd, 1H), 6.47 (d, 1H), 7.36 (d, 1H); Mass spectrum: M+H$^+$ 286

The 1-(4-bromo-3-methoxy-phenyl)piperazine used as starting material was prepared according to Page 88 of Pennel, et al. PCT Int WO 2005056015.

[7] Compound [7] was prepared according to the procedure described in [6] using 1-(4-bromophenyl)-4-methyl-piperazine. The derived product so obtained (37 mg) gave the following characterising data. NMR Spectrum: (CDCl3) 2.39 (s, 3H), 2.57-2.70 (m, 4H), 3.24-3.38 (m, 4H), 6.88 (bs, 2H), 7.04 (d, 2H), 7.33 (dd, 1H), 7.51 (d, 2H), 7.88 (dd, 1H), 8.50 (d, 1H), 8.52 (d, 1H), 8.58 (dd, 1H); Mass spectrum: M+H$^+$ 387

[8] Compound [8] was prepared according to the procedure described in [6] above. The N-tert-butoxycarbonyl group on the resultant product was removed by conventional treatment with 4N hydrogen chloride in dioxane. The derived product so obtained (72 mg) gave the following characterising data. NMR Spectrum: (CDCl3) 3.04-3.14 (m, 4H), 3.20-3.28 (m, 4H), 3.85 (s, 3H), 6.58 (d, 1H), 6.62 (dd, 1H), 6.93 (bs, 2H), 7.25 (d, 1H), 7.30 (dd, 1H), 7.85 (dd, 1H), 8.46 (d, 1H), 8.48 (d, 1H), 8.56 (dd, 1H); Mass spectrum: M+H$^+$ 403

The tert-butyl 4-(4-bromo-3-methoxy-phenyl)piperazine-1-carboxylate used as starting materials were made as follows:

Bromine (0.715 ml) was added dropwise to tert-butyl 4-(3-methoxyphenyl)piperazine-1-carboxylate (3.4 g) dissolved in cold acetic acid (25 ml) under argon. The resulting solution was stirred at room temperature for 90 minutes. The reaction mixture was concentrated to dryness and diluted with ethyl acetate, dichloromethane and a saturated aqueous solution of sodium bicarbonate. The phases were stirred, separated and the organic phase was dried over magnesium sulfate and concentrated in the presence of silica gel. The crude product was purified by flash chromatography on silica gel eluting with 10 to 20% ethyl acetate in petroleum ether. The solvent was evaporated to dryness to afford tert-butyl 4-(4-bromo-3-methoxy-phenyl)piperazine-1-carboxylate (1.770 g, 41.0%). NMR Spectrum: (CDCl3) 1.48 (s, 9H), 3.08-3.17 (m, 4H), 3.54-3.62 (m, 4H), 3.88 (s, 3H), 6.40 (dd, 1H), 6.47 (d, 1H), 7.37 (d, 1H)

[9] Compound [9] was prepared according to the procedure described in [6] above. The N-tert-butoxycarbonyl group on the resultant product was removed by conventional treatment with 4N hydrogen chloride in dioxane. Tert-butyl 4-(4-bromophenyl)piperazine-1-carboxylate was used as starting material. The product so obtained (35 mg) gave the following characterising data. NMR Spectrum: (CDCl3) 3.03-3.13 (m, 4H), 3.18-3.26 (m, 4H), 6.94 (bs, 2H), 7.03 (d, 2H), 7.33 (dd, 1H), 7.51 (d, 2H), 7.89 (d, 1H), 8.50 (d, 1H), 8.52 (d, 1H), 8.58 (d, 1H); Mass spectrum: M+H$^+$ 373

[10] Compound [10] was prepared according to the procedure described in [5] above using 3-oxazolo[5,4-b]pyridin-2-yl-5-(4,4,5,5-tetramethyl-1,3,2-dioxaborolan-2-yl)pyridin-2-amine and 1-(4-bromophenyl)-4-methyl-piperazine. There was no deprotection step and the product so obtained (72 mg) gave the following characterising data. NMR Spectrum: (CDCl3) 2.39 (s, 3H), 2.59-2.67 (m, 4H), 3.26-3.35 (m, 4H), 6.88 (bs, 2H), 7.04 (d, 2H), 7.37 (dd, 1H), 7.52 (d, 2H), 8.04 (dd, 1H), 8.36 (dd, 1H), 8.50 (d, 1H), 8.57 (d, 1H); Mass spectrum: M+H$^+$ 387

The 3-oxazolo[5,4-b]pyridin-2-yl-5-(4,4,5,5-tetramethyl-1,3,2-dioxaborolan-2-yl)pyridin-2-amine used as starting materials were made as follows:

5-bromo-3-oxazolo[5,4-b]pyridin-2-yl-pyridin-2-amine (1 g), potassium acetate (1.045 g), Pd(dppf)Cl$_2$ (0.139 g) and 4,4,4',4',5,5,5',5'-octamethyl-2,2'-bi(1,3,2-dioxaborolane) (0.960 g) were suspended in dioxane (15 ml) and degassed several times with argon. The resulting suspension was sealed and stirred at 80° C. overnight. The reaction mixture was diluted with chloroform (15 ml), filtered and concentrated. The residue was taken up into ethyl acetate (10 ml), collected by filtration, washed with ethyl acetate (10 ml) to give 3-oxazolo[5,4-b]pyridin-2-yl-5-(4,4,5,5-tetramethyl-1,3,2-dioxaborolan-2-yl)pyridin-2-amine (782 mg). NMR Spectrum:

(CDCl3) 1.37 (s, 12H), 5.98 (bs, 2H), 7.35 (dd, 1H), 8.01 (dd, 1H), 8.35 (dd, 1H), 8.60 (d, 1H), 8.81 (d, 1H); Mass spectrum: M+H+ 339

[11] Compound [11] was prepared according to the procedure described in [5] above using tert-butyl 4-(4-bromophenyl)piperazine-1-carboxylate. The N-tert-butoxycarbonyl group on the resultant product was removed by conventional treatment with 4N hydrogen chloride in dioxane. The derived product so obtained (75 mg) gave the following characterising data. NMR Spectrum: (CDCl3) 3.04-3.11 (m, 4H), 3.19-3.26 (m, 4H), 6.87 (bs, 2H), 7.04 (d, 2H), 7.37 (dd, 1H), 7.52 (d, 2H), 8.04 (d, 1H), 8.36 (d, 1H), 8.51 (d, 1H), 8.57 (d, 1H); Mass spectrum: M+H+ 373

[12] Compound [12] was prepared according to the procedure described in [5] above. There was no deprotection step. The derived product so obtained (22 mg) gave the following characterising data. NMR Spectrum: (CDCl3) 2.38 (s, 3H), 2.52-2.64 (m, 4H), 3.54-3.63 (m, 4H), 6.91 (bs, 2H), 7.36 (s, 1H), 7.38 (dd, 1H), 8.05 (dd, 1H), 8.35-8.39 (m, 2H), 8.40 (d, 1H); Mass spectrum: M+H+ 394

[13] Compound [13] was prepared according to the first portion of the procedure described in Example 24 using tert-butyl 4-[4-bromo-3-(hydroxymethyl)pyrazol-1-yl]piperidine-1-carboxylate and 3-(1,3-benzoxazol-2-yl)-5-(4,4,5,5-tetramethyl-1,3,2-dioxaborolan-2-yl)pyridin-2-amine except that the reaction was carried out at 120° C. The N-tert-butoxycarbonyl group on the resultant product was removed by conventional treatment with 4N hydrogen chloride in dioxane. The derived product so obtained (15 mg) gave the following characterising data. NMR Spectrum: (CDCl3) 1.92 (dd, 1H), 1.96 (dd, 1H), 2.17-2.25 (m, 2H), 2.27 (bs, 1H), 2.74-2.85 (m, 2H), 3.22-3.32 (m, 2H), 4.19-4.29 (m, 1H), 4.80 (s, 2H), 6.92 (bs, 2H), 7.33-7.41 (m, 2H), 7.55-7.62 (m, 2H), 7.71-7.78 (m, 1H), 8.36 (d, 1H), 8.44 (d, 1H); Mass spectrum: M+H+ 391.

The tert-butyl 4-[4-bromo-3-(hydroxymethyl)pyrazol-1-yl]piperidine-1-carboxylate used as starting materials were made as follows:

Sodium tetrahydroborate (35.7 mg) was added to 4-bromo-2H-pyrazole-3-carbaldehyde (150 mg) suspended in 2-propanol (10 ml). The resulting suspension was stirred at 25° C. for 1 hour. A few drops of acetic acid were added and the solution was concentrated to dryness. The crude product was purified by flash chromatography on silica gel eluting with 100% ethyl acetate. The solvent was evaporated to dryness to afford (4-bromo-2H-pyrazol-3-yl)methanol (110 mg). NMR Spectrum: (DMSO-d6+TFAd) 4.44 (s, 2H), 7.69 (s, 1H); Mass spectrum: M+H+ 177-179.

Sodium hydride (0.271 g, 60% dispersion in oil) was added to (4-bromo-2H-pyrazol-3-yl)methanol (1 g) dissolved in degassed DMF (20 ml) under nitrogen. The resulting solution was stirred at room temperature for 10 minutes. Tert-butyl 4-methylsulphonyloxypiperidine-1-carboxylate (1.578 g) was added and the resulting solution was stirred at 90° C. under nitrogen. Additional sodium hydride (0.068 g, 60% in oil) was added at 40° C. and the mixture was stirred 2 hours at 90° C. The reaction mixture was allowed to cool to room temperature under stirring, quenched with water and diluted with ethyl acetate. The aqueous phase was extracted with ethyl acetate. The combined organic phases were washed with a saturated aqueous solution of brine and concentrated in presence of dicalite speed plus to afford the crude, which was purified by flash chromatography on silica gel eluting with 0 to 90% ethyl acetate in petroleum ether. The solvent was evaporated to dryness to afford the products: the minor isomer, tert-butyl 4-[4-bromo-5-(hydroxymethyl)pyrazol-1-yl]piperidine-1-carboxylate (0.468 g) (NMR Spectrum: (DMSOd6) 1.41 (s, 9H), 1.73-1.94 (m, 4H), 2.87 (bs, 2H), 3.98-4.11 (m, 2H), 4.52 (d, 2H), 4.52-4.58 (m, 1H), 5.43 (t, 1H), 7.53 (s, 1H)) and the major isomer, tert-butyl 4-[4-bromo-3-(hydroxymethyl)pyrazol-1-yl]piperidine-1-carboxylate (0.856 g) (NMR Spectrum: (DMSOd6) 1.41 (s, 9H), 1.71 (dd, 1H), 1.76 (dd, 1H), 1.92-2.01 (m, 2H), 2.87 (bs, 2H), 4.02 (bs, 2H), 4.25-4.37 (m, 1H), 4.34 (d, 2H), 5.01 (t, 1H), 7.98 (s, 1H))

Compound [13] can also be prepared using the following method:

Sodium tetrahydroborate (42.6 mg) and tert-butyl 4-[4-[6-amino-5-(1,3-benzoxazol-2-yl)-3-pyridyl]-3-formyl-pyrazol-1-yl]piperidine-1-carboxylate (550 mg) in methanol (10 ml) were stirred at room temperature for 1 hour. The reaction was incomplete and further sodium tetrahydroborate (42.6 mg) was added at room temperature and the reaction mixture was stirred at room temperature for 1 hour. The reaction mixture was diluted with dichloromethane (100 ml) and washed with water (2×20 ml), dried over magnesium sulfate and concentrated to dryness. The residue was dissolved in dichloromethane (2 ml) and the solution was cooled to 0° C. and treated with trifluoroacetic acid (3 ml). The resulting solution was allowed to stir at room temperature for 1 hour and then concentrated to dryness. The residue was re-dissolved in methanolic ammonia (7N, 5 ml) and absorbed onto silica and purified by flash chromatography on silica gel eluting with 0 to 15% methanolic ammonia (7 N) in dichloromethane. The solvent was evaporated to dryness to afford [4-[6-amino-5-(1,3-benzoxazol-2-yl)-3-pyridyl]-1-(4-piperidyl)pyrazol-3-yl]methanol (440 mg) as a solid. The tert-butyl 4-[4-[6-amino-5-(1,3-benzoxazol-2-yl)-3-pyridyl]-3-formyl-pyrazol-1-yl]piperidine-1-carboxylate used as starting material was prepared as follows: 4-bromo-2H-pyrazole-3-carbaldehyde (3 g), potassium carbonate (3.32 g) and tert-butyl 4-methylsulfonyloxypiperidine-1-carboxylate (6.23 g) in acetonitrile (150 ml) were stirred at reflux overnight. The resulting precipitate was removed by filtration and the filtrate was concentrated and purified by flash chromatography on silica gel eluting with 0 to 20% ethyl acetate in petroleum ether. The solvent was evaporated to dryness to yield tert-butyl 4-(4-bromo-3-formyl-pyrazol-1-yl)piperidine-1-carboxylate (4.10 g) as a clear colourless oil which crystallised on standing. NMR Spectrum: (CDCl3) 1.48 (s, 9H), 1.92 (dd, 1H), 1.96 (dd, 1H), 2.10-2.18 (m, 2H), 2.81-2.97 (m, 2H), 4.27 (bs, 2H), 4.28-4.38 (m, 1H), 7.543 (s, 1H), 9.96 (s, 1H); Mass spectrum: M+H+ 360.

A suspension of 3-(1,3-benzoxazol-2-yl)-5-(4,4,5,5-tetramethyl-1,3,2-dioxaborolan-2-yl)pyridin-2-amine (0.3 g), tert-butyl 4-(4-bromo-3-formyl-pyrazol-1-yl)piperidine-1-carboxylate (0.362 g), potassium carbonate (0.335 g) and tetrakis(triphenylphosphine) palladium (0.093 g) in degassed acetonitrile (50 mL) was stirred at reflux overnight. The resulting suspension was cooled to ambient temperature, filtered, washed with dichloromethane (3×20 ml) and the filtrate was concentrated. The crude product was purified by flash chromatography on silica gel eluting with 5 to 90% ethyl acetate in petroleum ether. The solvent was evaporated to dryness to afford tert-butyl 4-[4-[6-amino-5-(1,3-benzoxazol-2-yl)-3-pyridyl]-3-formyl-pyrazol-1-yl]piperidine-1-carboxylate (0.370 g) as a solid. NMR Spectrum: (DMSOd6) 1.44 (s, 9H), 1.87 (dd, 1H), 1.92 (dd, 1H), 2.09-2.18 (m, 2H), 2.97 (bs, 2H), 4.04-4.16 (m, 2H), 4.52-4.61 (m, 1H), 7.41-7.49 (m, 2H), 7.80 (dd, 1H), 7.82 (bs, 2H), 7.85 (dd, 1H), 8.48 (s, 1H), 8.56 (d, 1H), 8.65 (d, 1H), 9.99 (s, 1H); Mass spectrum: M+H+ 489.

Compound [13] can also be prepared using the following method:

Tert-butyl N-[3-(1,3-benzoxazol-2-yl)-5-(4,4,5,5-tetramethyl-1,3,2-dioxaborolan-2-yl)-2-pyridyl]-N-tert-butoxycarbonyl-carbamate (237 mg), tert-butyl 4-(4-bromo-3-(hydroxymethyl)-1H-pyrazol-1-yl)piperidine-1-carboxylate (159 mg), potassium phosphate (225 mg) and trisdibenzilideneacetone dipalladium (20.19 mg) and tricyclohexylphosphine (12.37 mg) were weighed out in a microwave vial, sealed and 1,4-dioxane (4 ml) and water (400 μl) were added. Argon was bubbled through the suspension at 25° C. for 5 minutes. The mixture was stirred at 120° C. for 2 hours. The reaction mixture was allowed to cool down, Dicalite Speed Plus (Acros Chemicals) was added and the mixture was concentrated. The crude product was purified by flash chromatography on silica gel eluting with 50 to 100% ethyl acetate in petroleum ether. The solvent was evaporated to dryness to afford tert-butyl 4-[4-[5-(1,3-benzoxazol-2-yl)-6-(bis(tert-butoxycarbonyl)amino)-3-pyridyl]-3-(hydroxymethyl)pyrazol-1-yl]piperidine-1-carboxylate (150 mg). The N-tert-butoxycarbonyl groups on the resultant product were removed by conventional treatment with trifluoroacetic acid to afford [4-[6-amino-5-(1,3-benzoxazol-2-yl)-3-pyridyl]-1-(4-piperidyl)pyrazol-3-yl]methanol (49.0 mg) as a solid.

The tert-butyl N-[3-(1,3-benzoxazol-2-yl)-5-(4,4,5,5-tetramethyl-1,3,2-dioxaborolan-2-yl)-2-pyridyl]-N-tert-butoxycarbonyl-carbamate used as starting material was prepared as follows: N,N-dimethylpyridin-4-amine (42.1 mg) was added to 3-(1,3-benzoxazol-2-yl)-5-bromo-pyridin-2-amine (500 mg) and di-tert-butyl dicarbonate (1.069 g) suspended in DMF (5 ml). The resulting mixture was stirred at 25° C. for 48 hours. The reaction mixture was quenched with a saturated aqueous solution of sodium hydrogencarbonate (15 ml). The resulting precipitate was collected by filtration, washed with water and dried. The crude was taken up into ethyl acetate and filtered through a pad of silica gel. The resulting filtrate was concentrated to afford tert-butyl N-[3-(1,3-benzoxazol-2-yl)-5-bromo-2-pyridyl]-N-tert-butoxycarbonyl-carbamate (710 mg) as a solid. NMR Spectrum: (CDCl3): 1.32 (s, 18H), 7.37-7.44 (m, 2H), 7.60 (dd, 1H), 7.80 (dd, 1H), 8.70 (d, 1H), 8.81 (d, 1H); Mass spectrum: M+H$^+$ 491;

Tert-butyl N-[3-(1,3-benzoxazol-2-yl)-5-bromo-2-pyridyl]-N-tert-butoxycarbonyl-carbamate (4.78 g), potassium acetate (2.97 g), PdCl$_2$(dppf) (0.394 g) and 4,4,5,5-tetramethyl-2-(4,4,5,5-tetramethyl-1,3,2-dioxaborolan-2-yl)-1,3,2-dioxaborolane (2.72 g) were suspended in dioxane (45 ml). The mixture was degassed with nitrogen at 25° C. The resulting suspension was stirred at 80° C. under nitrogen for 3 hours. The reaction mixture was diluted with ethyl acetate (45 ml). The insolubles were removed by filtration and the filtrate was concentrated. The black oil was sonicated in petroleum ether (90 ml) for 10 minutes. The resultant solid was collected by filtration, washed with petroleum ether and dried, to give crude tert-butyl N-[3-(1,3-benzoxazol-2-yl)-5-(4,4,5,5-tetramethyl-1,3,2-dioxaborolan-2-yl)-2-pyridyl]-N-tert-butoxycarbonyl-carbamate (5.10 g) as a solid. NMR Spectrum (CDCl3): 1.29 (s, 18H), 1.40 (s, 12H), 7.34-7.44 (m, 2H), 7.60 (dd, 1H), 7.80 (dd, 1H), 8.97 (d, 1H), 9.03 (d, 1H)

[14] Compound [14] was prepared according to the procedure described in Example 24 except that the reaction was carried out at 120° C. The N-tert-butoxycarbonyl group on the resultant product was removed by conventional treatment with 4N hydrogen chloride in dioxane. The derived product so obtained (15 mg) gave the following characterising data. NMR Spectrum: (CDCl3) 1.93 (dd, 1H), 1.98 (dd, 1H), 2.19-2.29 (m, 2H), 2.76-2.84 (m, 2H), 3.25-3.32 (m, 2H), 3.52 (s, 3H), 4.23-4.31 (m, 1H), 4.50 (s, 2H), 6.89 (bs, 2H), 7.34-7.40 (m, 2H), 7.54-7.59 (m, 1H), 7.61 (s, 1H), 7.73-7.77 (m, 1H), 8.38 (d, 1H), 8.51 (d, 1H); Mass spectrum: M+H$^+$ 405.

The tert-butyl 4-[4-bromo-3-(methoxymethyl)pyrazol-1-yl]piperidine-1-carboxylate used as starting materials were made as follows:

Sodium hydride (57.7 mg, 60% in oil) was added to tert-butyl 4-[4-bromo-3-(hydroxymethyl)pyrazol-1-yl]piperidine-1-carboxylate (200 mg) dissolved in degassed DMF (2 mL) under nitrogen. The resulting solution was stirred at room temperature for 10 minutes. Dimethyl sulfate (0.068 ml) was added and the resulting solution was stirred at 25° C. for 1 hour. The reaction mixture was quenched with water and diluted with ethyl acetate. The aqueous phase was extracted with ethyl acetate. The combined organic phases were washed with a saturated aqueous solution of brine, dried over magnesium sulfate and concentrated in presence of silica gel to afford the crude, which was purified by flash chromatography on silica gel eluting with 0 to 100% ethyl acetate in petroleum ether. The solvent was evaporated to dryness to afford tert-butyl 4-[4-bromo-3-(methoxymethyl)pyrazol-1-yl]piperidine-1-carboxylate (180 mg). NMR Spectrum: (DMSOd6) 1.41 (s, 9H), 1.71 (dd, 1H), 1.76 (dd, 1H), 1.96 (bs, 1H), 1.98 (bs, 1H), 2.87 (bs, 2H), 3.22 (3H), 4.02 (bs, 2H), 4.28 (s, 2H), 4.29-4.36 (m, 1H), 8.04 (s, 1H).

The solvent was evaporated to dryness to afford two products as white solids: the minor isomer was tert-butyl 4-[4-bromo-3-(methoxymethyl)pyrazol-1-yl]piperidine-1-carboxylate (0.468 g) NMR Spectrum: (DMSOd6) 1.41 (s, 9H), 1.73-1.94 (m, 4H), 2.87 (bs, 2H), 3.98-4.11 (m, 2H), 4.52 (d, 2H), 4.52-4.58 (m, 1H), 5.43 (t, 1H), 7.53 (s, 1H)

Compound [14] can also be prepared using the following method:

A mixture of tert-butyl N-[3-(1,3-benzoxazol-2-yl)-5-(4,4,5,5-tetramethyl-1,3,2-dioxaborolan-2-yl)-2-pyridyl]-N-tert-butoxycarbonyl-carbamate (808 mg), tert-butyl 4-(4-bromo-3-(methoxymethyl)-1H-pyrazol-1-yl)piperidine-1-carboxylate (439 mg), trisdibenzylideneacetone dipalladium (53.7 mg), dicyclohexyl-[2-(2,6-dimethoxyphenyl)phenyl]phosphane (48.2 mgl) and potassium phosphate (0.233 g) in a mixture of dioxane (14 ml) and water (350 μl) was degassed. The resulting suspension was stirred at 120° C. for 3 hours under argon. After the mixture was cooled to room temperature the solvent was concentrated, ethyl acetate (80 ml) and water (20 ml) were added. The organic layer was washed with brine, dried over magnesium sulphate, filtered and evaporated under reduce pressure. The crude product was purified by flash chromatography on silica gel eluting with 30 to 80% ethyl acetate in petroleum ether. The solvent was evaporated to dryness to afford tert-butyl 4-[4-[5-(1,3-benzoxazol-2-yl)-6-(bis(tert-butoxycarbonyl)amino)-3-pyridyl]-3-(methoxymethyl)pyrazol-1-yl]piperidine-1-carboxylate (616 mg). The N-tert-butoxycarbonyl groups on the resultant product were removed by conventional treatment with hydrogen chloride in isopropanol to afford 3-(1,3-benzoxazol-2-yl)-5-[3-(methoxymethyl)-1-(4-piperidyl)pyrazol-4-yl]pyridin-2-amine (300 mg).

[15] Compound [15] was prepared according to the procedure described in Example 24. The N-tert-butoxycarbonyl group on the resultant product was removed by conventional treatment with trifluoroacetic acid. The product so obtained gave the following characterising data: NMR Spectrum: (DMSOd6) 1.77 (dd, 1H), 1.82 (dd, 1H), 1.92-2.00 (m, 2H), 2.09 (s, 1H), 2.33 (s, 3H), 2.54-2.62 (m, 2H), 3.00-3.09 (m, 2H), 4.06-4.16 (m, 1H), 7.52 (dd, 1H), 7.67 (bs, 2H), 8.07 (s, 1H), 8.28 (d, 1H), 8.29 (s, 1H), 8.37-8.41 (m, 2H); Mass spectrum: M+H$^+$ 376.

[16] Compound [16] was prepared according to the procedure described in Example 24. The N-tert-butoxycarbonyl group on the resultant product was removed by conventional treatment with trifluoroacetic acid. The product so obtained gave the following characterising data: NMR Spectrum: (DMSOd6): 1.79 (dd, 1H), 1.84 (dd, 1H), 1.94-2.03 (m, 2H), 2.34 (s, 3H), 2.57-2.67 (m, 2H), 3.03-3.12 (m, 2H), 4.08-4.19 (m, 1H), 7.48 (dd, 1H), 7.68 (bs, 2H), 8.06 (s, 1H), 8.24 (dd, 1H), 8.31 (d, 1H), 841 (d, 1H), 8.56 (dd, 1H); Mass spectrum: M+H+ 376.

EXAMPLE 25A 3-(4-fluoro-1,3-benzoxazol-2-yl)-5-[3-methyl-1-(4-piperidyl)pyrazol-4-yl]pyridin-2-amine

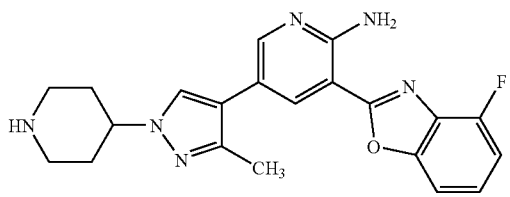

Example 25A was prepared according to the procedure described in Example 24 using 3-(4-fluoro-1,3-benzoxazol-2-yl)-5-(4,4,5,5-tetramethyl-1,3,2-dioxaborolan-2-yl)pyridin-2-amine and tert-butyl 4-(4-bromo-3-methyl-pyrazol-1-yl)piperidine-1-carboxylate as starting materials. The N-tert-butoxycarbonyl group on the resultant product was removed by conventional treatment with trifluoroacetic acid. The product so obtained gave the following characterising data: NMR Spectrum: (DMSOd6): 1.74-1.86 (m, 2H), 1.91-2.02 (m, 2H), 2.33 (s, 3H), 2.54-2.63 (m, 2H), 2.99-3.10 (m, 2H), 4.06-4.17 (m, 1H), 7.33 (dd, 1H), 7.47 (ddd, 1H), 7.61 (bs, 2H), 7.68 (d, 1H), 8.05 (s, 1H), 8.29 (d, 1H), 8.38 (d, 1H); Mass spectrum: M+H+ 393.

The 3-(4-fluoro-1,3-benzoxazol-2-yl)-5-(4,4,5,5-tetramethyl-1,3,2-dioxaborolan-2-yl)pyridin-2-amine used as starting material was prepared as follows:

2-amino-5-bromo-pyridine-3-carboxylic acid (1 g) and 2-amino-3-fluoro-phenol (0.586 g) in polyphosphoric acid were stirred at 200° C. for 22 hours. After cooling, water (75 ml) was added and the mixture was stirred for 30 min. The mixture was basified to pH 12 with concentrated sodium hydroxide solution (6N and 2N). The solid was filtered, washed with water (3×20 ml), and ether (3×10 ml). After drying under vacuum over phosphorus pentoxide; the desired compound 5-bromo-3-(4-fluoro-1,3-benzoxazol-2-yl)pyridin-2-amine (0.995 g) was obtained as a solid which was used without further purification in the next step. NMR Spectrum: (DMSOd6): 7.34 (dd, 1H), 7.50 (ddd, 1H), 7.68 (dd, 1H), 7.81 (bs, 2H), 8.35 (d, 1H), 8.38 (d, 1H); Mass spectrum: M+H+ 307-309

A mixture of 5-bromo-3-(4-fluoro-1,3-benzoxazol-2-yl)pyridin-2-amine (955 mg), potassium acetate (943 mg), PdCl2(dppf) (125 mg) and 4,4,5,5-tetramethyl-2-(4,4,5,5-tetramethyl-1,3,2-dioxaborolan-2-yl)-1,3,2-dioxaborolane (866 mg) was suspended in dioxane (15 ml). Argon was bubbled through the suspension at ambient temperature for 15 minutes. The resulting suspension was sealed and stirred at 80° C. for 15 hours. The reaction mixture was diluted with chloroform (50 ml) and stirred for 20 minutes at room temperature. The insolubles were removed by filtration, washed with chloroform- and dried. The filtrate was concentrated to give a gummy solid, which was taken up into ethyl acetate (30 mL) and stirred for 10 minutes. The resultant solid was collected by filtration, washed with ethyl acetate, diethyl ether and petroleum ether to afford after drying under vacuum at 50° C., 3-(4-fluoro-1,3-benzoxazol-2-yl)-5-(4,4,5,5-tetramethyl-1,3,2-dioxaborolan-2-yl)pyridin-2-amine (873 mg) as a solid. NMR Spectrum: (CDCl3): 1.37 (s, 12H), 5.97 (bs, 2H), 7.08 (dd, 1H), 7.31 (ddd, 1H), 7.39 (d, 1H), 8.59 (d, 1H), 8.69 (d, 1H); Mass spectrum: M+H+ 356

EXAMPLE 26

3-(1,3-benzoxazol-2-yl)-5-[1-(2-morpholinoethyl)pyrazol-4-yl]pyridin-2-amine

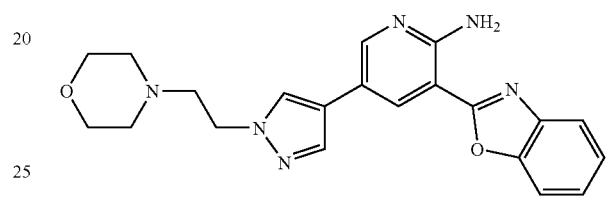

4-(2-Chloroethyl)morpholine hydrochloride (101 mg) was added to a stirred solution 3-(1,3-benzoxazol-2-yl)-5-(1H-pyrazol-4-yl)pyridin-2-amine (150 mg, 0.54 mol) and potassium carbonate (164 mg, 1.19 mol) dissolved in DMA (1 ml) over a period of 5 minutes. The resulting solution was stirred at 120° C. for 7 hours. The mixture was filtered. The reaction mixture was purified by preparative HPLC using a Waters X-Terra reverse-phase column (C-18, 5 microns silica, 19 mm diameter, 100 mm length, flow rate of 40 ml/minute) and decreasingly polar mixtures of water (containing 1% acetic acid) and acetonitrile as eluent. The fractions containing the desired compound were evaporated to dryness to afford 3-(1,3-benzoxazol-2-yl)-5-[1-(2-morpholinoethyl)pyrazol-4-yl]pyridin-2-amine (134 mg. NMR Spectrum: (CDCl3) 2.27-2.58 (m, 4H), 2.88 (t, 2H), 3.68-3.77 (m, 4H), 4.30 (t, 2H), 6.90 (bs, 2H), 7.34-7.41 (m, 2H), 7.58-7.63 (m, 1H), 7.73 (s, 1H), 7.74-7.77 (m, 1H), 7.79 (s, 1H), 8.38 (d, 1H), 8.39 (d, 1H); Mass spectrum: M+H+ 391.

The 3-(1,3-benzoxazol-2-yl)-5-(1H-pyrazol-4-yl)pyridin-2-amine was prepared as follows: Hydrogen chloride (16.26 ml, 4N in dioxane) was added to a stirred suspension 3-(1,3-benzoxazol-2-yl)-5-(1-tetrahydropyran-2-ylpyrazol-4-yl)pyridin-2-amine (4.7 g) dissolved in ethanol (30 ml). The resulting mixture was stirred at 25° C. for 2 hours. The reaction was evaporated under reduce pressure, adsorbed on silica gel and purified by flash chromatography on silica gel eluting with 20 to 80% methanolic ammonia (7 N) in dichloromethane. The solvent was evaporated to dryness to afford 3-(1,3-benzoxazol-2-yl)-5-(1H-pyrazol-4-yl)pyridin-2-amine (3.35 g). NMR Spectrum: (CDCl3) 7.39-7.50 (m, 2H), 7.65 (bs, 2H), 7.80 (dd, 1H), 7.84 (dd, 1H), 7.98 (bs, 1H), 8.24 (bs, 1H), 8.45 (d, 1H), 8.55 (d, 1H); Mass spectrum: M+H+ 278

EXAMPLES 27

Using an analogous procedure to that described in Example 26, 3-(1,3-benzoxazol-2-yl)-5-(1H-pyrazol-4-yl)pyridin-2-amine was reacted with an appropriate alkylating agent to give the compounds described in Table X. Unless otherwise stated, the required appropriate alkylating agents are commercially available.

TABLE X

![structure with R1-N-pyrazole attached to pyridine with NH2, and benzoxazole]

| No. & Note | R¹ |
|---|---|
| [1] | (1-methylpiperidin-3-yl)methyl |
| [2] | 3-pyrrolidin-1-ylpropyl |
| [3] | 2-pyrrolidin-1-ylethyl |
| [4] | 3-dimethylaminopropyl |
| [5] | 2-dimethylaminoethyl |
| [6] | (1S,5S)-8-methyl-8-azabicyclo[3.2.1]octan-3-yl |
| [7] | tetrahydropyran-4-yl |

[1] 3-(chloromethyl)-1-methyl-piperidine hydrochloride was used as the alkylating agent in the preparation of this product. The final product gave the following characterising data. NMR Spectrum: (CDCl3): 1.03-1.16 (m, 1H), 1.68-1.83 (m, 3H), 1.94-2.04 (m, 1H), 2.14 (bs, 1H), 2.35 (s, 3H), 2.39 (bs, 1H), 2.81-2.92 (m, 2H), 4.12 (d, 2H), 6.98 (bs, 2H), 7.35-7.41 (m, 2H), 7.59-7.64 (m, 1H), 7.67 (s, 1H), 7.73-7.77 (m, 1H), 7.78 (s, 1H), 8.37 (d, 1H), 8.40 (d, 1H); Mass spectrum: M+H⁺ 389.

[2] 1-(3-chloropropyl)pyrrolidine was used as the alkylating agent in the preparation of this product. The final product gave the following characterising data. NMR Spectrum: (CDCl3) 1.87-1.97 (m, 4H), 2.24-2.32 (m, 2H), 2.76 (t, 2H), 2.82-2.91 (m, 4H), 4.27 (t, 2H), 7.11 (bs, 2H), 7.35-7.42 (m, 2H), 7.58-7.76 (m, 1H), 7.71 (s, 1H), 7.73-7.77 (m, 1H), 7.78 (s, 1H), 8.35 (d, 1H), 8.41 (d, 1H); Mass spectrum: M+H⁺ 389.

[3] 1-(2-chloroethyl)pyrrolidine hydrochloride was used as the alkylating agent in the preparation of this product. The final product gave the following characterising data. NMR Spectrum: (CDCl3) 1.78-1.89 (m, 4H), 2.61-2.71 (m, 4H), 3.10 (t, 2H), 4.39 (t, 2H), 6.95 (bs, 2H), 7.34-7.42 (m, 2H), 7.58-7.63 (m, 1H), 7.73-7.78 (m, 2H), 7.80 (s, 1H), 8.38 (d, 1H), 8.40 (d, 1H); Mass spectrum: M+H⁺ 375.

[4] 3-chloro-N,N-dimethyl-propan-1-amine hydrochloride was used as the alkylating agent in the preparation of this product. The final product gave the following characterising data. NMR Spectrum: (CDCl3) 2.15-2.27 (m, 2H), 2.39 (s, 6H), 2.52 (t, 2H), 4.29 (t, 2H), 7.02 (bs, 2H), 7.34-7.41 (m, 2H), 7.58-7.63 (m, 1H), 7.70 (s, 1H), 7.73-7.77 (m, 1H), 7.79 (s, 1H), 8.36 (d, 1H), 8.40 (d, 1H); Mass spectrum: M+H⁺ 363.

[5] 2-chloro-N,N-dimethyl-ethanamine hydrochloride was used as the alkylating agent in the preparation of this product. The final product gave the following characterising data. NMR Spectrum: (DMSOd6) 2.12 (s, 6H), 2.63 (t, 2H), 4.14 (t, 2H), 7.34-7.42 (m, 2H), 7.58 (bs, 2H), 7.73 (dd, 1H), 7.78 (dd, 1H), 7.84 (s, 1H), 8.18 (s, 1H), 8.33 (d, 1H), 8.45 (d, 1H); Mass spectrum: M+H⁺ 349.

[6] [(1S,5S)-8-methyl-8-azabicyclo[3.2.1]octan-3-yl] methanesulphonate was used as the alkylating agent in the preparation of this product. The final product gave the following characterising data. NMR Spectrum: (DMSOd6) 1.39-1.46 (m, 1H), 1.64-1.72 (m, 1H), 1.78-1.87 (m, 2H), 1.97-2.05 (m, 1H), 2.07-2.15 (m, 1H), 2.17 (s, 1.5H), 2.25 (s, 1.5H), 2.27-2.34 (m, 1H), 2.45-2.53 (m partially hidden by DMSOd6, 1H), 3.08-3.13 (m, 1H), 3.18-3.23 (m, 1H), 4.31-4.37 (m, 0.5H), 4.43-4.52 (m, 0.5H), 7.41-7.49 (m, 2H), 7.64 (bs, 2H), 7.77-7.82 (m, 1H), 7.83-7.86 (m, 1H), 7.89 (s, 0.5H), 7.93 (s, 0.5H), 8.31 (s, 0.5H), 8.42 (d, 0.5H), 8.47 (d, 0.5H), 8.51 (d, 0.5H), 8.51 (s, 0.5H), 8.56 (d, 0.5H); Mass spectrum: M+H⁺ 401.

[7] tetrahydro-2H-pyran-4-yl methanesulphonate was used as the alkylating agent in the preparation of this product. The final product gave the following characterising data. NMR Spectrum: (DMSOd6) 1.93-2.08 (m, 4H), 3.45-3.54 (m, 2H), 3.95-4.03 (m, 2H), 4.37-4.46 (m, 1H), 7.41-7.49 (m, 2H), 7.65 (bs, 2H), 7.74-7.82 (m, 1H), 7.82-7.87 (m, 1H), 7.94 (s, 1H), 8.35 (s, 1H), 8.44 (d, 1H), 8.54 (d, 1H); Mass spectrum: M+H⁺ 362.

EXAMPLE 28

2-[4-[6-amino-5-(1,3-benzoxazol-2-yl)-3-pyridyl]pyrazol-1-yl]ethanol

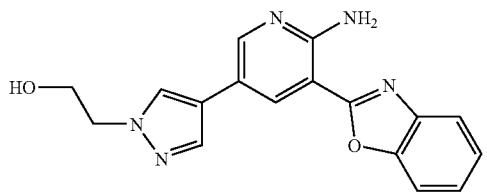

3-(1,3-benzoxazol-2-yl)-5-[1-(2-tert-butoxyethyl)pyrazol-4-yl]pyridin-2-amine (485 mg) was dissolved in TFA (3 ml). The resulting solution was stirred at 25° C. for 1 hour. A solution 7N of ammonia in methanol (20 ml) was added to the mixture and adsorbed on silica gel. The crude product was purified by flash chromatography on silica gel eluting with 1 to 5% methanolic ammonia (7 N) in dichloromethane. The solvent was evaporated to dryness to afford 2-[4-[6-amino-5-(1,3-benzoxazol-2-yl)-3-pyridyl]pyrazol-1-yl]ethanol (315 mg). NMR Spectrum: (DMSOd6) 3.75-3.81 (m, 2H), 4.17 (t, 2H), 4.94 (t, 1H), 7.40-7.49 (m, 2H), 7.64 (bs, 2H), 7.79-7.82 (m, 1H), 7.83-7.86 (m, 1H), 7.92 (s, 1H), 8.21 (s, 1H), 8.41 (d, 1H), 8.52 (d, 1H); Mass spectrum: M+H⁺ 322.

The 3-(1,3-benzoxazol-2-yl)-5-[1-(2-tert-butoxyethyl) pyrazol-4-yl]pyridin-2-amine used as starting material was prepared according to procedure in Example 26 using 2-(2-bromoethoxy)-2-methyl-propane as alkyl halide to give 500 mg solid. NMR Spectrum: (CDCl3) 1.14 (s, 9H), 3.75 (t, 2H), 4.30 (t, 2H), 7.04 (bs, 2H), 7.35-7.41 (m, 2H), 7.68-7.63 (m, 1H), 7.73-7.77 (m, 1H), 7.77 (s, 1H), 7.78 (s, 1H), 8.36 (d, 1H), 8.42 (d, 1H); Mass spectrum: M+H⁺ 378.

EXAMPLE 29

Using an analogous procedure to that described in Example 26, the appropriate pyrazole was reacted with an appropriate alkylating agent. As in Example 28, an O-Butyl or N-tert-butoxycarbonyl (N-Boc) protecting group was employed. Such protecting groups were removed using conventional treatment with trifluoroacetic acid as described in Example 28 to give the compounds described in Table XI. Unless otherwise stated, the required appropriate alkylating agents are commercially available.

TABLE XI

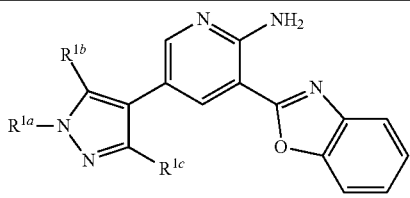

| No. & Note | R$^{1a}$ | R$^{1b}$ | R$^{1c}$ |
|---|---|---|---|
| [1] | 3-hydroxypropyl | H | H |
| [2] | azetidin-3-yl | H | H |
| [3] | pyrrolidin-3-yl | H | H |
| [4] | azetidin-3-ylmethyl | H | H |
| [5] | pyrrolidin-3-ylmethyl | H | H |
| [6] | piperidin-3-yl | H | H |
| [7] | piperidin-4-ylmethyl | H | H |
| [8] | piperidin-4-yl | methyl | methyl |

[1] 2-(3-bromopropoxy)-2-methyl-propane was used as the alkylating agent in the preparation of this product. The final product gave the following characterising data. NMR Spectrum: (DMSOd6) 1.93-2.00 (m, 2H), 3.40-3.45 (m, 2H), 4.19 (t, 2H), 4.62 (t, 1H), 7.41-7.48 (m, 2H), 7.65 (bs, 2H), 7.78-7.82 (m, 1H), 7.82-7.87 (m, 1H), 7.91 (s, 1H), 8.24 (s, 1H), 8.41 (d, 1H), 8.52 (d, 1H); Mass spectrum: M+H$^+$ 336

[2] tert-butyl 3-methylsulphonyloxyazetidine-1-carboxylate was used as the alkylating agent in the preparation of this product. The final product gave the following characterising data. NMR Spectrum: (DMSOd6) 3.72-3.79 (m, 2H), 3.91-3.99 (m, 2H), 5.14-5.23 (m, 1H), 7.41-7.49 (m, 2H), 7.66 (bs, 2H), 7.78-7.82 (m, 1H), 7.83-7.87 (m, 1H), 7.99 (s, 1H), 8.42 (s, 1H), 8.45 (d, 1H), 8.54 (d, 1H); Mass spectrum: M+H$^+$ 333

[3] tert-butyl 3-methylsulphonyloxypyrrolidine-1-carboxylate was used as the alkylating agent in the preparation of this product. The final product gave the following characterising data. NMR Spectrum: (DMSOd6) 2.02-2.11 (m, 1H), 2.16-2.26 (m, 1H), 2.74 (bs, 1H), 2.87 (ddd, 1H), 3.00 (dd, 1H), 3.07 (ddd, 1H), 3.16 (dd, 1H), 4.78-4.85 (m, 1H), 7.41-7.49 (m, 2H), 7.65 (m, 2H), 7.78-7.81 (m, 1H), 7.83-7.86 (m, 1H), 7.91 (d, 1H), 8.32 (d, 1H), 8.43 (d, 1H), 8.53 (d, 1H); Mass spectrum: M+H$^+$ 347

[4] tert-butyl 3-(methylsulphonyloxymethyl)azetidine-1-carboxylate was used as the alkylating agent in the preparation of this product. The final product gave the following characterising data. NMR Spectrum: (CDCl3) 3.24-3.32 (m, 1H), 3.47-3.52 (m, 2H), 3.77-3.82 (m, 2H), 4.42 (d, 2H), 6.88 (bs, 2H), 7.35-7.41 (m, 2H), 7.58-7.62 (m, 1H), 7.65 (s, 1H), 7.73-7.77 (m, 1H), 7.78 (s, 1H), 8.38 (d, 1H), 8.39 (d, 1H); Mass spectrum: M+H$^+$ 347

[5] tert-butyl 3-(methylsulphonyloxymethyl)pyrrolidine-1-carboxylate was used as the alkylating agent in the preparation of this product. The final product gave the following characterising data. NMR Spectrum: (DMSOd6) 1.34-1.45 (m, 1H), 1.69-1.70 (m, 1H), 2.51-2.58 (m, 2H), 2.67-2.79 (m, 2H), 2.79-2.87 (m, 1H), 4.06 (d, 2H), 7.40-7.49 (m, 2H), 7.66 (bs, 2H), 7.77-7.82 (m, 1H), 7.82-7.86 (m, 1H), 7.91 (s, 1H), 8.26 (s, 1H), 8.42 (d, 1H), 8.52 (d, 1H); Mass spectrum: M+H$^+$ 361

[6] tert-butyl 3-methylsulphonyloxypiperidine-1-carboxylate was used as the alkylating agent in the preparation of this product. The final product gave the following characterising data. NMR Spectrum: (DMSOd6) 1.46-1.57 (m, 1H), 1.69-1.77 (m, 1H), 1.87-1.98 (ddd, 1H), 2.10-2.18 (m, 1H), 2.33 (bs, 1H), 2.46 (dd, 1H), 2.76 (dd, 1H), 2.85-2.92 (m, 1H), 3.19 (dd, 1H), 4.09-4.18 (m, 1H), 7.40-7.50 (m, 2H), 7.65 (bs, 2H), 7.80 (dd, 1H), 7.85 (dd, 1H), 7.91 (s, 1H), 8.32 (s, 1H), 8.43 (d, 1H), 8.53 (d, 1H); Mass spectrum: M+H$^+$ 361

[7] tert-butyl 4-(bromomethyl)piperidine-1-carboxylate was used as the alkylating agent in the preparation of this product. The final product gave the following characterising data. NMR Spectrum: (CDCl3) 1.18-1.31 (m, 2H), 1.61-1.66 (bs partially hidden by H2O, 2H), 2.03-2.16 (m, 1H), 2.57-2.68 (m, 2H), 3.07-3.16 (m, 2H), 4.03 (d, 2H), 6.87 (bs, 2H), 7.34-7.41 (m, 2H), 7.58-7.63 (m, 1H), 7.64 (s, 1H), 7.73-7.77 (m, 1H), 7.80 (s, 1H), 8.38 (d, 1H), 8.39 (d, 1H); Mass spectrum: M+H$^+$ 375

[8] tert-butyl 4-(methylsulphonyloxy)piperidine-1-carboxylate was used as the alkylating agent in the preparation of this product. The final product gave the following characterising data. NMR Spectrum: (DMSOd6) 1.74-1.81 (m, 2H), 1.90 (dd, 1H), 1.95 (dd, 1H), 2.16 (s, 3H), 2.26 (s, 3H), 2.59-2.67 (m, 2H), 3.03-3.09 (m, 2H), 4.12-4.20 (m, 1H), 7.40-7.46 (m, 2H), 7.66 (bs, 2H), 7.75-7.79 (m, 1H), 7.82-7.86 (m, 1H), 8.09 (d, 1H), 8.15 (d, 1H); Mass spectrum: M+H$^+$ 389.

The 3-(1,3-benzoxazol-2-yl)-5-(3,5-dimethyl-1H-pyrazol-4-yl)pyridin-2-amine used as starting materials were made as follows:

Bis(triphenylphosphine) palladium (II) chloride (85 mg) and caesium fluoride (1.1 g) were added to a degassed solution of 3-(1,3-benzoxazol-2-yl)-5-bromo-pyridin-2-amine (700 mg) and 3,5-dimethyl-4-(4,4,5,5-tetramethyl-1,3,2-dioxaborolan-2-yl)-1H-pyrazole (563 mg) in Methanol (14 ml). The suspension was stirred at 140° C. for 2 hours in a 300 W microwave. The mixture was adsorbed on silica gel and purified by flash chromatography on silica gel eluting with 5 to 10% methanol in dichloromethane. The solvent was evaporated to dryness to afford 3-(1,3-benzoxazol-2-yl)-5-(3,5-dimethyl-1H-pyrazol-4-yl)pyridin-2-amine (120 mg). NMR Spectrum: (DMSOd6) 2.22 (s, 6H), 7.40-7.487 (m, 2H), 7.66 (bs, 2H), 7.76-7.81 (m, 1H), 7.82-7.87 (m, 1H), 8.13 (d, 1H), 8.18 (d, 1H); Mass spectrum: M+H$^+$ 306

EXAMPLE 30

3-(1,3-benzoxazol-2-yl)-5-[1-[2-(4-methylpiperazin-1-yl)ethyl]pyrazol-4-yl]pyridin-2-amine

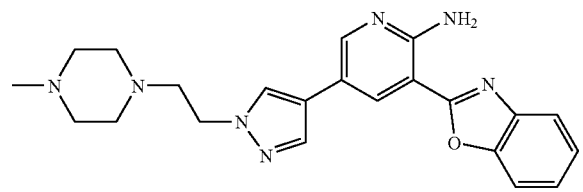

A solution of 1-methylpiperazine (0.115 ml) was added to 2-[4-[6-amino-5-(1,3-benzoxazol-2-yl)-3-pyridyl]pyrazol-1-yl]ethyl methanesulphonate (138 mg) dissolved DMF (5 ml). The resulting solution was stirred at 100° C. for 1 hour. The mixture was adsorbed on silica gel and purified by flash chromatography on silica gel eluting with 2 to 6% methanolic ammonia (7 N) in dichloromethane. The solvent was evaporated to dryness and the solid was triturated with hot acetonitrile to afford 3-(1,3-benzoxazol-2-yl)-5-[1-[2-(4-methylpiperazin-1-yl)ethyl]pyrazol-4-yl]pyridin-2-amine (109 mg) as a solid. NMR Spectrum: (DMSOd6) 2.14 (s, 3H), 2.30 (bs, 4H), 2.44 (bs, 4H), 2.74 (t, 2H), 4.23 (s, 2H), 7.40-7.50

(m, 2H), 7.65 (bs, 2H), 7.77-7.82 (m, 1H), 7.82-7.87 (m, 1H), 7.90 (s, 1H), 8.24 (s, 1H), 8.40 (d, 1H), 8.51 (d, 1H); Mass spectrum: M+H⁺ 404.

The 2-[4-[6-amino-5-(1,3-benzoxazol-2-yl)-3-pyridyl]pyrazol-1-yl]ethyl methanesulphonate used as starting material was prepared as follows:

A solution of methanesulphonyl chloride (0.072 ml) was added to 2-[4-[6-amino-5-(1,3-benzoxazol-2-yl)-3-pyridyl]pyrazol-1-yl]ethanol (150 mg, Example 28), triethylamine (0.130 ml) dissolved dichloromethane (5 ml) at 0° C. The resulting suspension was stirred at 0° C. for 2 hours. The mixture was adsorbed on silica gel and purified by flash chromatography on silica gel eluting with 1 to 4% methanolic ammonia (7 N) in dichloromethane. The solvent was evaporated to dryness to afford 2-[4-[6-amino-5-(1,3-benzoxazol-2-yl)-3-pyridyl]pyrazol-1-yl]ethyl methanesulphonate (150 mg) as a solid. NMR Spectrum: (CDCl3) 3.11 (s, 3H), 4.49 (t, 2H), 4.62 (t, 2H), 7.41-7.49 (m, 2H), 7.68 (bs, 2H), 7.78-7.82 (m, 1H), 7.83-7.87 m, 1H), 8.01 (d, 1H), 8.31 (d, 1H), 8.43 (d, 1H), 8.53 (d, 1H); Mass spectrum: M+H⁺ 400.

EXAMPLE 31

Using analogous procedures to those described in Example 30, the appropriate ethyl or propyl methanesulphonate was reacted with an appropriate heterocycle to give the compounds described in Table XII. Unless otherwise stated, the required appropriate heterocycles are commercially available.

TABLE XII

| No. & Note | R¹ |
|---|---|
| [1] | 3-(3-hydroxypyrrolidin-1-yl)propyl |
| [2] | 3-[(2R)-2-(hydroxymethyl)pyrrolidin-1-yl]propyl |
| [3] | 3-(4-hydroxypiperidin-1-yl)propyl |
| [4] | 3-morpholinopropyl |
| [5] | 3-(4-methylpiperazin-1-yl)propyl |
| [6] | 3-(azeitidin-1-yl)propyl |
| [7] | 2-(3-hydroxypyrrolidin-1-yl)ethyl |
| [8] | 2-[(2R)-2-(hydroxymethyl)pyrrolidin-1-yl]ethyl |
| [9] | 2-(4-hydroxypiperidin-1-yl)ethyl |
| [10] | 2-(azetidin-1-yl)ethyl |

[1] pyrrolidin-3-ol was used in the preparation of this product. The final product gave the following characterising data. NMR Spectrum: (DMSOd6) 1.49-1.58 (m, 1H), 1.92-2.03 (m, 3H), 2.29 (dd, 1H), 2.32-2.43 (m, 3H), 2.50-2.58 (m partially hidden by DMSOd5, 1H), 2.68 (dd, 1H), 4.12-4.22 (m, 3H), 4.67 (d, 1H), 7.40-7.49 (m, 2H), 7.65 (bs, 2H), 7.77-7.82 (m, 1H), 7.82-7.87 (m, 1H), 7.91 (s, 1H), 8.25 (s, 1H), 8.41 (d, 1H), 8.52 (d, 1H); Mass spectrum: M+H⁺ 405

The 3-[4-[6-amino-5-(1,3-benzoxazol-2-yl)-3-pyridyl]pyrazol-1-yl]propyl methanesulphonate used as starting material was prepared as follows:

A solution of methanesulphonyl chloride (0.577 ml) was added to 3-[4-[6-amino-5-(1,3-benzoxazol-2-yl)-3-pyridyl]pyrazol-1-yl]propan-1-ol (1.25 g, Example 29-1), triethylamine (1.559 ml) dissolved dichloromethane (20 ml) and THF (20 ml) at 0° C. The resulting suspension was stirred at 25° C. for 2 hours. The suspension was filtered and washed with water (3 time) and dried over night on reduce pressure to afford 3-[4-[6-amino-5-(1,3-benzoxazol-2-yl)-3-pyridyl]pyrazol-1-yl]propyl methanesulphonate (0.988 g). NMR Spectrum: (DMSOd6) 2.21-2.32 (m, 2H), 3.23 (s, 3H), 4.21-4.33 (m, 4H), 7.42-7.51 (m, 2H), 7.68 (bs, 2H), 7.81 (d, 1H), 7.86 (d, 1H), 7.98 (s, 1H), 8.30 (s, 1H), 8.44 (s, 1H), 8.54 (s, 1H)

[2] (R)-pyrrolidin-2-ylmethanol was used in the preparation of this product. The final product gave the following characterising data. NMR Spectrum: (DMSOd6) 1.54-1.62 (m, 1H), 1.62-1.71 (m, 2H), 1.75-1.84 (m, 1H), 1.91-2.05 (m, 2H), 2.07-2.15 (m, 1H), 2.20-2.29 (m, 1H), 2.35-2.43 (m, 1H), 2.71-2.80 (m, 1H), 3.04-3.11 (m, 1H), 3.19-3.26 (m, 1H), 3.35-3.41 (m partially hidden by H2O, 1H), 4.18 (t, 2H), 4.38 (t, 1H), 7.42. 7.50 (m, 2H), 7.66 (bs, 2H), 7.79-7.83 (m, 1H), 7.83-7.88 (m, 1H), 7.92 (s, 1H), 8.26 (s, 1H), 8.43 (d, 1H), 8.53 (d, 1H); Mass spectrum: M+H⁺ 419

3-[4-[6-amino-5-(1,3-benzoxazol-2-yl)-3-pyridyl]pyrazol-1-yl]propyl methanesulphonate was used as starting material.

[3] piperidin-4-ol was used in the preparation of this product. The final product gave the following characterising data. NMR Spectrum: (DMSOd6) 1.33-1.46 (m, 2H), 1.66-1.76 (m, 2H), 1.91-2.04 (m, 4H), 2.24 (t, 2H), 2.64-2.74 (m, 2H), 3.37-3.49 (m, 1H), 4.14 (t, 2H), 4.54 (d, 1H), 7.40-7.50 (m, 2H), 7.65 (bs, 2H), 7.77-7.82 (m, 1H), 7.82-7.87 (m, 1H), 7.91 (s, 1H), 8.24 (s, 1H), 8.41 (d, 1H), 8.52 (d, 1H); Mass spectrum: M+H⁺ 419

3-[4-[6-amino-5-(1,3-benzoxazol-2-yl)-3-pyridyl]pyrazol-1-yl]propyl methanesulphonate was used as starting material

[4] morpholine was used in the preparation of this product. The final product gave the following characterising data. NMR Spectrum: (DMSOd6) 1.94-2.03 (m, 2H), 2.28 (t, 2H), 2.34 (bs, 4H), 3.55-3.62 (m, 4H), 4.16 (t, 2H), 7.41-7.49 (m, 2H), 7.65 (bs, 2H), 7.77-7.82 (m, 1H), 7.82-7.87 (m, 1H), 7.91 (s, 1H), 8.25 (s, 1H), 8.41 (d, 1H), 8.52 (d, 1H); Mass spectrum: M+H⁺ 405

3-[4-[6-amino-5-(1,3-benzoxazol-2-yl)-3-pyridyl]pyrazol-1-yl]propyl methanesulphonate was used as starting material

[5] 1-methylpiperazine was used in the preparation of this product. The final product gave the following characterising data. NMR Spectrum: (DMSOd6) 1.92-2.01 (m, 2H), 2.14 (s, 3H), 2.27 (t, 2H), 2.32 (bs, 8H), 4.14 (t, 2H), 7.41-7.49 (m, 2H), 7.65 (bs, 2H), 7.77-7.82 (m, 1H), 7.82-7.86 (m, 1H), 7.91 (s, 1H), 8.24 (s, 1H), 8.41 (d, 1H), 8.52 (d, 1H); Mass spectrum: M+H⁺ 418

3-[4-[6-amino-5-(1,3-benzoxazol-2-yl)-3-pyridyl]pyrazol-1-yl]propyl methanesulphonate was used as starting material

[6] azetidine was used as in the preparation of this product. The final product gave the following characterising data. NMR Spectrum: (DMSOd6) 1.75-1.83 (m, 2H), 1.91-1.99 (m, 2H), 2.31 (t, 2H), 3.07 (t, 4H), 4.12 (t, 2H), 7.41-7.49 (m, 2H), 7.65 (bs, 2H), 7.78-7.82 (m, 1H), 7.82-7.86 (m, 1H), 7.91 (s, 1H), 8.23 (s, 1H), 8.41 (d, 1H), 8.52 (d, 1H); Mass spectrum: M+H⁺ 375

3-[4-[6-amino-5-(1,3-benzoxazol-2-yl)-3-pyridyl]pyrazol-1-yl]propyl methanesulphonate was used as starting material

[7] pyrrolidin-3-ol was used in the preparation of this product. The final product gave the following characterising data. NMR Spectrum: (DMSOd6) 1.48-1.57 (m, 1H), 1.90-1.99 (m, 1H), 2.34 (dd, 1H), 0.47 (dd, 1H), 2.58-2.63 (m, 1H), 2.74

(dd, 1H), 2.85 (t, 2H), 4.14-4.20 (m, 1H), 4.21 (t, 2H), 4.69 (d, 1H), 7.41-7.48 (m, 2H), 7.77-7.82 (m, 1H), 7.82-7.86 (m, 1H), 7.91 (s, 1H), 8.26 (s, 1H), 8.41 (d, 1H), 8.52 (d, 1H); Mass spectrum: M+H+ 391

[8] (R)-pyrrolidin-2-ylmethanol was used in the preparation of this product. The final product gave the following characterising data. NMR Spectrum: (DMSOd6) 1.45-1.54 (m, 1H), 1.56-1.71 (m, 2H), 1.74-1.83 (m, 1H), 2.20-2.27 (m, 1H), 2.51-2.56 (m partially hidden by dMSOd5, 1H), 2.69-2.77 (m, 1H), 3.00-3.07 (m, 1H), 3.15-3.22 (m, 1H), 3.23-3.30 (m, 1H), 3.33-3.37 (m partially hidden by H2O, 1H), 4.21 (t, 2H), 4.33 (t, 1H), 7.41-7.49 (m, 2H), 7.65 (bs, 2H), 7.77-7.82 (m, 1H), 7.82-7.87 (m, 1H), 7.91 (s, 1H), 8.27 (s, 1H), 8.41 (d, 1H), 8.51 (d, 1H); Mass spectrum: M+H+ 405

[9] piperidin-4-ol was used in the preparation of this product. The final product gave the following characterising data. NMR Spectrum: (DMSO-d6) 1.31-1.43 (m, 2H), 1.65-1.74 (m, 2H), 2.06-2.15 (m, 2H), 2.69-2.79 (m, 4H), 3.39-3.48 (m, 1H), 4.21 (t, 2H), 4.52 (d, 1H), 7.41-7.49 (m, 2H), 7.65 (bs, 2H), 7.77-7.82 (m, 1H), 7.82-7.86 (m, 1H), 7.90 (s, 1H), 8.24 (s, 1H), 8.40 (d, 1H), 8.51 (d, 1H); Mass spectrum: M+H+ 405

[10] azetidine was used in the preparation of this product. The final product gave the following characterising data. NMR Spectrum: (DMSOd6) 1.89-1.98 (m, 2H), 2.77 (t, 2H), 3.09 (t, 4H), 4.04 (t, 2H), 7.41-7.49 (m, 2H), 7.65 (bs, 2H), 7.78-7.82 (m, 1H), 7.82-7.86 (m, 1H), 7.90 (s, 1H), 8.22 (s, 1H), 8.41 (d, 1H), 8.52 (d, 1H); Mass spectrum: M+H+ 361

EXAMPLE 32

3-(1,3-benzoxazol-2-yl)-5-[1-(2-piperazin-1-ylethyl)pyrazol-4-yl]pyridin-2-amine

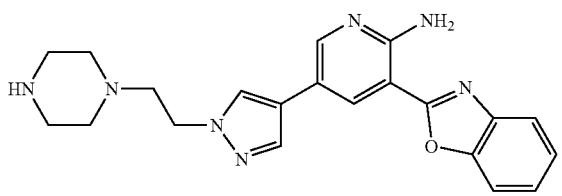

A solution of tert-butyl 4-[2-[4-[6-amino-5-(1,3-benzoxazol-2-yl)-3-pyridyl]pyrazol-1-yl]ethyl]piperazine-1-carboxylate (90 mg) in TFA (3 ml) was stirred at 25° C. for 1 hour. A solution 7N ammonia in methanol (20 ml) was added to the mixture and adsorbed on silica gel. The crude product was purified by flash chromatography on silica gel eluting with 2 to 8% methanolic ammonia (7 N) in dichloromethane. The solvent was evaporated to dryness to afford 3-(1,3-benzoxazol-2-yl)-5-[1-(2-piperazin-1-ylethyl)pyrazol-4-yl]pyridin-2-amine (49.0 mg). NMR Spectrum: (DMSOd6) 2.29-2.42 (m, 4H), 2.64-2.70 (m, 4H), 2.71 (t, 2H), 4.23 (t, 2H), 7.41-7.49 (m, 2H), 7.65 (bs, 2H), 7.77-7.82 (m, 1H), 7.82-7.87 (m, 1H), 7.90 (s, 1H), 8.24 (s, 1H), 8.40 (d, 1H), 8.51 (d, 1H); Mass spectrum: M+H+ 390.

The tert-butyl 4-[2-[4-[6-amino-5-(1,3-benzoxazol-2-yl)-3-pyridyl]pyrazol-1-yl]ethyl]piperazine-1-carboxylate used as starting material was prepared using the procedure described in example 30 using tert-butyl piperazine-1-carboxylate as secondary amine to give 90 mg of product. NMR Spectrum: (CDCl3) 1.46 (s, 9H), 2.49 (bs, 4H), 2.92 (t, 2H), 3.45 (bs, 4H), 4.33 (t, 2H), 6.90 (bs, 2H), 7.45-7.41 (m, 2H), 7.58-7.63 (m, 1H), 7.72-7.77 (m, 2H), 7.79 (s, 1H), 8.38 (d, 1H), 8.39 (d, 1H); Mass spectrum: M+H+ 490.

EXAMPLE 33

1-[4-[4-[6-amino-5-(1,3-benzoxazol-2-yl)-3-pyridyl]pyrazol-1-yl]-1-piperidyl]-2-methoxy-ethanone

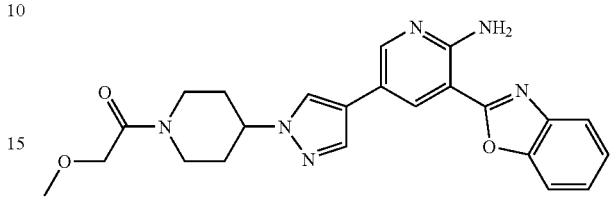

2-methoxyacetyl chloride (0.033 ml) was added in one portion to a stirred ice-cooled suspension of 3-(1,3-benzoxazol-2-yl)-5-[1-(4-piperidyl)pyrazol-4-yl]pyridin-2-amine (100 mg) and N-benzyl-N-isopropyl-propan-2-amine on polystyrene (185 mg, 3 mmol/g) in dichloromethane (5 ml) and THF (5 ml). The resulting suspension was stirred at room temperature for 2 hours. The resin was filtered, rinsed with dichloromethane/methanol. The filtrate was concentrated to dryness. The crude product was purified by flash chromatography on silica gel eluting with 0 to 4% methanol in dichloromethane. After evaporation of the solvents, the resulting solid was triturated in acetonitrile to give the title compound (79 mg). NMR Spectrum: (CDCl3): 1.97-2.11 (m, 2H), 2.22-2.35 (m, 2H), 2.80-2.91 (m, 1H), 3.17-3.29 (m, 1H), 3.46 (s, 3H), 4.06-4.23 (m, 3H), 4.38-4.47 (m, 1H), 4.69-4.80 (m, 1H), 7.08 (bs, 2H), 7.35-7.42 (m, 2H), 7.58-7.63 (m, 1H), 7.69 (s, 1H), 7.73-7.78 (m, 1H), 7.80 (s, 1H), 8.35 (d, 1H), 8.41 (d, 1H); Mass spectrum: M+H+ 433.

EXAMPLE 34

Using analogous procedures to those described in Example 33, 3-(benzo[d]oxazol-2-yl)-5-(1-(piperidin-4-yl)-1H-pyrazol-4-yl)pyridin-2-amine was reacted with an appropriate acid chloride to give the compounds described in Table XIII. Unless otherwise stated, the required appropriate acid chlorides are commercially available.

TABLE XIII

| No. & Note | K |
|---|---|
| [1] | Acetyl |
| [2] | 2-hydroxyacetyl |
| [3] | (S)-2-hydroxypropionyl |

[1] Acetyl chloride was used as the acid chloride in the preparation of this product. The final product gave the following characterising data. NMR Spectrum: (CDCl3) 1.94-2.09 (m, 2H), 2.16 (s, 3H), 2.19-2.34 (m, 2H), 2.75-2.85 (m, 1H), 3.23-3.33 (m, 1H), 3.96-4.05 (m, 1H), 4.37-4.45 (m, 1H), 4.75-4.82 (m, 1H), 7.08 (bs, 2H), 7.36-7.42 (m, 2H), 7.59-7.63 (m, 1H), 7.69 (s, 1H), 7.74-7.78 (m, 1H), 7.80 (s, 1H), 8.35 (d, 1H), 8.42 (d, 1H). Mass spectrum: M+H$^+$ 403.

[2] (2-chloro-2-oxo-ethyl)acetate was used as the acid chloride in the preparation of this product. The resultant product was deprotected using lithium hydroxide hydrate (20.5 mg, 1.1 eq.) in methanol (6 ml)-water (1 ml); the reaction mixture was stirred at room temperature for 1 hour and quenched with acetic acid (0.033 ml, 1.3 eq.). Concentration to dryness, purification by chromatography on silica gel eluting with 0 to 4% methanol in dichloromethane; followed by trituration of the resulting solid gave the expected product (143 mg). NMR Spectrum: (CDCl3) 2.00-2.13 (m, 2H), 2.24-2.36 (m, 2H), 2.93-3.04 (m, 1H), 3.15-3.27 (m, 1H), 3.66-3.77 (m, 2H), 4.21 (d, 1H), 4.25 (d, 1H), 4.39-4.49 (m, 1H), 4.69-4.77 (m, 1H), 6.98 (bs, 2H), 7.35-7.42 (m, 2H), 7.57-7.63 (m, 1H), 7.69 (s, 1H), 7.73-7.78 (m, 1H), 7.80 (s, 1H), 8.36 (d, 1H), 8.39 (d, 1H). Mass spectrum: M+H$^+$ 419.

[3] The acid chloride used was (S)-(2-chloro-1-methyl-2-oxo-ethyl)acetate. The resultant product was deprotected as described in Example 34.2. NMR Spectrum: (CDCl3) 1.36 (d, 1.5H), 1.39 (d, 1.5H), 2.00-2.13 (m, 2H), 2.24-2.37 (m, 2H), 2.88-3.03 (m, 1H), 3.20-3.31 (m, 1H), 3.85 (bs, 1H), 3.88-3.97 (m, 1H), 4.39-4.49 (m, 1H), 4.52 (q, 1H), 4.75 (dd, 1H), 6.98 (bs, 2H), 7.38-7.42 (m, 2H), 7.58-7.63 (m, 1H), 7.67-7.72 (m, 1H), 7.73-7.78 (m, 1H), 7.81 (s, 1H), 8.36 (d, 1H), 8.40 (d, 1H). Mass spectrum: M+H$^+$ 433.

EXAMPLE 35

3-(6-methoxy-1,3-benzoxazol-2-yl)-5-[1-(1-methyl-4-piperidyl)pyrazol-4-yl]pyridin-2-amine

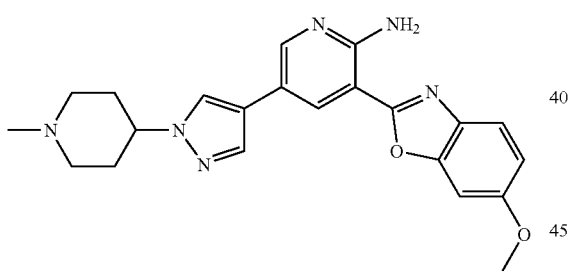

To a solution of 2-amino-N-(2-hydroxy-4-methoxy-phenyl)-5-[1-(1-methyl-4-piperidyl)pyrazol-4-yl]pyridine-3-carboxamide (110 mg) in acetic acid (1.8 ml) was added TFA (1.8 ml). The clear mixture was sealed into a microwave tube. The reaction was heated to 200° C. a 300 W microwave for 20 minutes. The solvents were evaporated. The residue was trituratred in diethyl ether, dried to give a yellow solid. The solid was dissolved in DMF (1.5 ml) and two drops of a 30% aqueous ammonia solution. The precipitate was filtered, washed with Ether and dried at 50° C. for 48 h to afford 3-(6-methoxy-1,3-benzoxazol-2-yl)-5-[1-(1-methyl-4-piperidyl)pyrazol-4-yl]pyridin-2-amine (25.00 mg). NMR Spectrum: (DMSOd6) 1.93-2.12 (m, 6H), 2.22 (s, 3H), 2.94-2.91 (m, 2H), 3.86 (s, 3H), 4.07-4.16 (m, 1H), 7.03 (dd, 1H), 7.40 (d, 1H), 7.57 (bs, 2H), 7.72 (d, 1H), 7.89 (d, 1H), 8.30 (s, 1H), 8.36 (d, 1H), 8.49 (d, 1H). Mass spectrum: M+H$^+$ 405.

The 2-amino-N-(2-hydroxy-4-methoxy-phenyl)-5-[1-(1-methyl-4-piperidyl)pyrazol-4-yl]pyridine-3-carboxamide used as starting material was prepared as follows:

Potassium hydroxide (0.773 g) was added to a cold solution of methyl 2-amino-5-[1-(1-methyl-4-piperidyl)pyrazol-4-yl]pyridine-3-carboxylate (2.172 g) in methanol (50 ml) and water (5 ml). The resulting mixture was stirred at room temperature during 48 hours. A 2N aqueous hydrochloric acid solution (6.89 ml) was added. The mixture was evaporated to dryness, dried, diluted with water (50 ml) and purified on OASIS resine (ion exchange resin Oasis, HLB 30 μM, Waters) (150 ml). The salts were eluted with water and the product was eluted with 50% Methanol/water. The solvents were evaporated to dryness. The residue was dried at 50° C. to give 2-amino-5-[1-(1-methyl-4-piperidyl)pyrazol-4-yl]pyridine-3-carboxylic acid (1.600 g). NMR Spectrum: (DMSO-d6) 2.02-2.13 (m, 4H), 2.27-2.38 (m, 2H), 2.35 (s, 3H), 2.97-3.06 (m, 2H), 4.13-4.22 (m, 1H), 7.21 (bs, 2H), 7.80 (s, 1H), 8.18 (s, 1H), 8.19 (d, 1H), 8.39 (d, 1H); Mass spectrum: M+H$^+$ 302

2-amino-5-methoxy-phenol hydrochloride (210 mg), N-ethyl-N-isopropyl-propan-2-amine (0.208 ml) and 2-hydroxypyridine-1-oxide (221 mg) were added to a stirred solution of 2-amino-5-[1-(1-methyl-4-piperidyl)pyrazol-4-yl]pyridine-3-carboxylic acid (300 mg) dissolved in DMF (5 ml) under nitrogen. 3-(ethyliminomethyleneamino)-N,N-dimethyl-propan-1-amine hydrochloride (382 mg) was added portionwise to this mixture and the resulting solution was stirred at 25° C. for 48 hours. The reaction mixture was purified by preparative HPLC using a Waters X-Terra reverse-phase column and decreasingly polar mixtures of water (containing 0.2% ammonium carbonate) and acetonitrile as eluent. The fractions containing the desired compound were evaporated to dryness to afford 2-amino-N-(2-hydroxy-4-methoxy-phenyl)-5-[1-(1-methyl-4-piperidyl)pyrazol-4-yl]pyridine-3-carboxamide (190 mg). NMR Spectrum: (DMSOd6) 1.88-2.10 (m, 6H), 2.20 (s, 3H), 2.82-2.90 (m, 2H), 3.71 (s, 3H), 4.06-4.15 (m, 1H), 6.42 (dd, 1H), 6.49 (d, 1H), 6.99 (bs, 2H), 7.26 (d, 1H), 7.85 (s, 1H), 8.16 (s, 1H), 8.30 (d, 1H), 8.39 (d, 1H), 9.51 (bs, 1H), 9.58 (bs, 1H) Mass spectrum: M+H$^+$ 423

EXAMPLE 35A 3-(5-methoxy-1,3-benzoxazol-2-yl)-5-[1-(1-methyl-4-piperidyl)pyrazol-4-yl]pyridin-2-amine

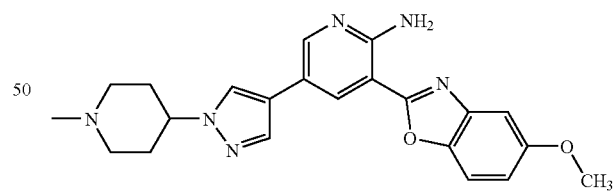

Compound 35A was prepared according to the procedure described for Example 35 using 2-amino-N-(2-hydroxy-5-methoxy-phenyl)-5-[1-(1-methyl-4-piperidyl)pyrazol-4-yl]pyridine-3-carboxamide as a starting material. The product gave the following characterising data: NMR Spectrum: (DMSOd6): 1.93-2.11 (m, 6H), 2.22 (s, 3H), 2.82-2.91 (m, 2H), 3.84 (s, 3H), 4.06-4.16 (m, 1H), 7.02 (dd, 1H), 7.40 (d, 1H), 7.63 (bs, 2H), 7.68 (d, 1H), 7.91 (s, 1H), 8.31 (s, 1H), 8.40 (d, 1H), 8.51 (d, 1H); Mass spectrum: M+H$^+$ 405

The 2-amino-N-(2-hydroxy-5-methoxy-phenyl)-5-[1-(1-methyl-4-piperidyl)pyrazol-4-yl]pyridine-3-carboxamide used as starting material was prepared as follows: 2-amino- 4-methoxy-phenol (87 mg), N-ethyl-N-isopropyl-propan-2-amine (0.206 ml) and 2-hydroxypyridine 1-oxide (132 mg) were added to a stirred solution of 2-amino-5-[1-(1-methylpiperidin-4-yl)pyrazol-4-yl]pyridine-3-carboxylic acid hydrochloride (200 mg) dissolved in DMA (4 ml) under nitrogen. After 10 minutes at room temperature, 3-(ethyliminomethyleneamino)-N,N-dimethyl-propan-1-amine hydrochloride (227 mg) was added portionwise to this mixture and the resulting solution was stirred at 25° C. for 36 hours. The reaction mixture was purified by preparative HPLC using a Waters X-Terra reverse-phase column and decreasingly polar mixtures of water (containing 0.2% ammonium carbonate) and acetonitrile as eluent. The fractions containing the desired compound were evaporated and repurified by preparative HPLC using a Waters X-Terra reverse-phase column and decreasingly polar mixtures of water (containing 1% acetic acid) and acetonitrile as eluent. The solvent was evaporated to give 2-amino-N-(2-hydroxy-5-methoxy-phenyl)-5-[1-(1-methyl-4-piperidyl)pyrazol-4-yl]pyridine-3-carboxamide (200 mg) as a solid that was sufficiently pure for use.

Mass spectrum: M+H+ 423; RT 1.08 min.

EXAMPLE 36

3-(7-methyl-1,3-benzoxazol-2-yl)-5-[1-(1-methyl-4-piperidyl)pyrazol-4-yl]pyridin-2-amine

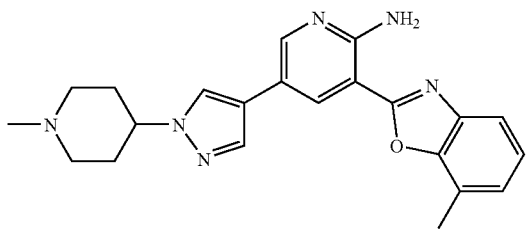

To a solution of 2-amino-N-(2-hydroxy-3-methyl-phenyl)-5-[1-(1-methyl-4-piperidyl)pyrazol-4-yl]pyridine-3-carboxamide (80 mg) in acetic acid (1.3 ml) was added TFA (1.3 ml). The clear mixture was sealed into a microwave tube. The reaction was heated to 200° C. in a 300 W microwave for 20 minutes. The solvents were evaporated. The residue purified by preparative HPLC using a Waters X-Terra reverse-phase column and decreasingly polar mixtures of water (containing 1% acetic acid) and acetonitrile as eluent. The fractions containing the desired compound were evaporated to dryness to afford 3-(7-methyl-1,3-benzoxazol-2-yl)-5-[1-(1-methyl-4-piperidyl)pyrazol-4-yl]pyridin-2-amine (44.0 mg) NMR Spectrum: (DMSOd6) 1.94-2.10 (m, 6H), 2.22 (s, 3H), 2.62 (s, 3H), 2.84-2.92 (m, 2H), 4.09-4.17 (m, 1H), 7.27 (d, 1H), 7.32 (dd, 1H), 7.63 (bs, 2H), 7.64 (d, 1H), 7.93 (s, 1H), 8.30 (s, 1H), 8.44 (d, 1H), 8.52 (d, 1H); Mass spectrum: M+H+ 389.

The 2-amino-N-(2-hydroxy-3-methyl-phenyl)-5-[1-(1-methyl-4-piperidyl)pyrazol-4-yl]pyridine-3-carboxamide used as a starting material was prepared as follows: 2-amino-6-methyl-phenol (57.4 mg), N-ethyl-N-isopropyl-propan-2-amine (0.155 ml) and 2-hydroxypyridine 1-oxide (99 mg) were added to a stirred solution of 2-amino-5-[1-(1-methylpiperidin-1-ium-4-yl)pyrazol-4-yl]pyridine-3-carboxylic acid chloride (150 mg) dissolved in DMA (3 ml) under nitrogen. After 10 minutes at room temperature, 3-(ethyliminomethyleneamino)-N,N-dimethyl-propan-1-amine hydrochloride (170 mg) was added portionwise to this mixture and the resulting solution was stirred at 25° C. for 36 h. The reaction mixture was purified by preparative HPLC using a Waters X-Terra reverse-phase column and decreasingly polar mixtures of water (containing 0.2% ammonium carbonate) and acetonitrile as eluent. The fractions containing the desired compound were evaporated to dryness to afford 2-amino-N-(2-hydroxy-3-methyl-phenyl)-5-[1-(1-methyl-4-piperidyl)pyrazol-4-yl]pyridine-3-carboxamide (68 mg). NMR Spectrum: (DMSOd6) 1.90-2.12 (m, 6H), 2.21 (s, 3H), 2.22 (s, 3H), 2.83-2.90 (m, 2H), 4.07-4.15 (m, 1H), 6.78 (dd, 1H), 6.97 (bs, 2H), 7.01 (dd, 1H), 7.20 (dd, 1H), 7.86 (s, 1H), 8.18 (s, 1H), 8.32 (d, 1H), 8.42 (d, 1H), 8.76 (s, 1H); Mass spectrum: M+H+ 407.

EXAMPLE 37

3-(6-fluorooxazolo[4,5-b]pyridin-2-yl)-5-[1-(4-piperidyl)pyrazol-4-yl]pyridin-2-amine

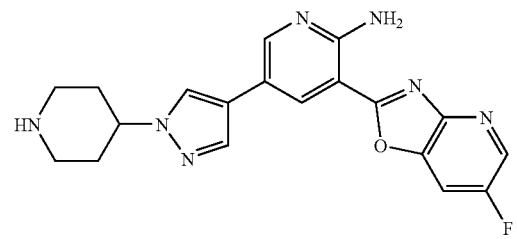

Tert-butyl 4-[4-(4,4,5,5-tetramethyl-1,3,2-dioxaborolan-2-yl)pyrazol-1-yl]piperidine-1-carboxylate (222 mg) and 5-bromo-3-(6-fluorooxazolo[4,5-b]pyridin-2-yl)pyridin-2-amine (140 mg), bis(triphenylphosphine) palladium (II) chloride (15.9 mg) and caesium fluoride (172 mg) were weighed out in a microwave vial and sealed. Methanol (2 ml) was added and nitrogen was bubbled in the resulting suspension. The resulting mixture was heated in a 300 W microwave at 120° C. for 20 minutes. The crude product was purified by flash chromatography on silica gel (dried deposit with silica gel) eluting with 0 to 5% methanol in dichloromethane. The solvent was evaporated to dryness to afford tert-butyl 4-[4-[6-amino-5-(6-fluorooxazolo[4,5-b]pyridin-2-yl)-3-pyridyl]pyrazol-1-yl]piperidine-1-carboxylate (190 mg). NMR Spectrum: (CDCl3) 1.49 (s, 9H), 1.94-2.03 (m, 2H), 2.16-2.24 (m, 2H), 2.84-3.00 (m, 2H), 3.28 (bs, 2H), 3.29-3.37 (m, 1H), 6.94 (bs, 2H), 7.66 (dd, 1H), 7.68 (s, 1H), 7.79 (s, 1H), 8.35 (d, 1H), 8.45 (d, 1H), 8.48 (dd, 1H); Mass spectrum: M+H+ 480.

A suspension of tert-butyl 4-[4-[6-amino-5-(6-fluorooxazolo[4,5-b]pyridin-2-yl)-3-pyridyl]pyrazol-1-yl]piperidine-1-carboxylate (190 mg) and hydrogen chloride (4M solution in dioxane) (4.95 ml) in dichloromethane (2 ml) was stirred at room temperature for 2 hours. The resulting precipitate was collected by filtration, washed with diethyl ether and dried to afford a solid, which was taken up into 5% methanolic ammonia (7 N) in dichloromethane (20 ml) and stirred for 10 minutes. The suspension was filtered, concentrated and the resulting solid was stirred in acetonitrile (2 ml) for 2 hours at room temperature. It was collected by filtration and dried to a constant weight to afford 3-(6-fluorooxazolo[4,5-b]pyridin-2-yl)-5-[1-(4-piperidyl)pyrazol-4-yl]pyridin-2-amine (110 mg). NMR Spectrum: (CDCl3) 1.88-2.03 (m, 2H), 2.18-2.27 (m, 2H), 2.76-2.84 (m, 2H), 3.23-3.33 (m, 2H), 4.23-4.33 (m, 1H), 6.86 (bs, 2H), 7.67 (dd, 1H), 7.70 (s, 1H), 7.78 (s, 1H), 8.36 (d, 1H), 8.44 (d, 1H), 8.48 (dd, 1H); Mass spectrum: M+H+ 380.

The 5-bromo-3-(6-fluorooxazolo[4,5-b]pyridin-2-yl)pyridin-2-amine used as starting material was prepared as follows:

A suspension of sodium 5-fluoro-2-nitro-pyridin-3-olate (7.3 g) and platinum(IV) oxide (0.092 g) in ethanol (20 ml) at 25° C., was hydrogenated under 3.5 atm at 25° C. for 30 minutes. The resulting black suspension was filtered through a pad of Dicalite Speed Plus (Acros Chemicals) and hydrogen chloride 4M in dioxane (4.26 ml) was added to the filtrate. The suspension was filtered and concentrated to a black oil, which was triturated in diethyl ether, the precipitate was collected by filtration and dried to afford the crude 2-amino-5-fluoro-pyridin-3-ol (0.607 g) hydrochloride salt. NMR Spectrum: (DMSOd6) 7.23 (dd, 1H), 7.65 (dd, 1H), 7.82 (bs, 2H), 12.23 (bs, 1H).

Sodium 5-fluoro-2-nitro-pyridin-3-olate was synthesized according to Kamenecka et al., PCT. Int. Appl. WO 2005021529.

2-amino-5-bromo-pyridine-3-carboxylic acid (797 mg) and 2-amino-5-fluoro-pyridin-3-ol, hydrochloride (400 mg) powders were mixed together and the resulting mixture was portionwise added in trimethylsilyl polyphosphate (4.5 g) stirred at 100° C. The mixture was stirred at 140° C. overnight. After cooling, water (20 ml) was added. The resulting precipitate was collected by filtration, washed with a 2N aqueous solution of HCl and water. The resulting solid was triturated in Ethyl acetate, collected by filtration to afford 5-bromo-3-(6-fluorooxazolo[4,5-b]pyridin-2-yl)pyridin-2-amine (150 mg). NMR Spectrum: (DMSO-$d_6$) 7.10 (bs, 2H), 7.66 (dd, 1H), 8.31 (d, 1H), 8.39 (d, 1H), 8.49 (dd, 1H); Mass spectrum: M+H$^+$ 309-311.

EXAMPLE 38

The compounds described in table XIV were prepared using analogous procedures to those described in Example 37.

TABLE XIV

| No. & Note | G$_1$ | R$^{3a}$ | R$^{3b}$ | R$^{3c}$ |
|---|---|---|---|---|
| [1] | CH | H | F | F |
| [2] | CH | F | H | H |
| [3] | CH | H | H | F |
| [4] | N | methyl | H | H |
| [5] | CH | H | H | methoxy |

[1] Compound [1] was prepared according to the procedure described in Example 37 except that sodium carbonate was used as the base in place of caesium fluoride and a 10/1 butanol/water solvent mixture was employed. The N-tert-butoxycarbonyl group on the resultant product was removed by conventional treatment with TFA in dichloromethane instead of 4N hydrogen chloride in dioxane. The derived product so obtained (155 mg) gave the following characterising data. NMR Spectrum: (DMSOd6) 1.80 (dd, 1H), 1.84 (dd, 1H), 1.95-2.03 (m, 2H), 2.55-2.66 (m, 2H), 3.01-3.10 (m, 2H), 4.15-4.24 (m, 1H), 7.54 (ddd, 1H), 7.60 (bs, 2H), 7.70 (dd, 1H), 7.93 (s, 1H), 8.33 (s, 1H), 8.41 (d, 1H), 8.57 (d, 1H); Mass spectrum: M+H$^+$ 397

The 5-bromo-3-(6,7-difluoro-1,3-benzoxazol-2-yl)pyridin-2-amine used as starting material was prepared as follows:

To a mixture of 2-amino-5-bromo-pyridine-3-carboxylic acid (1 g) and 6-amino-2,3-difluoro-phenol (0.669 g) placed in a round bottom flask was added polyphosphoric acid (10 g). The mixture was heated at 200° C. for 5 hours. A homogenous black mixture was obtained. The mixture was diluted in water and neutralizing to pH 8 with NaOH 2N. The heterogeneous mixture was diluted with dichloromethane. The insoluble was filtered. The organic phase was separated. The aqueous phase was extracted twice with dichloromethane. The combined organic phases were washed with brine, dried on sodium sulfate, evaporated and dried to afford 5-bromo-3-(6,7-difluoro-1,3-benzoxazol-2-yl)pyridin-2-amine (0.338 g). NMR Spectrum: (DMSOd6) 7.54 (ddd, 1H), 7.70 (ddd, 1H), 7.79 (bs, 2H), 8.34 (d, 1H), 8.38 (d, 1H); Mass spectrum: M+H$^+$ 326-328

[2] Compound [2] was prepared according to the procedure described in Example 37. The N-tert-butoxycarbonyl group on the resultant product was removed by conventional treatment with TFA in dichloromethane instead of 4N hydrogen chloride in dioxane. The derived product so obtained (445 mg) gave the following characterising data. NMR Spectrum: (DMSO-d6): 1.75-1.86 (m, 2H), 1.95-2.03 (m, 2H), 2.55-2.64 (m, 2H), 3.01-3.09 (m, 2H), 4.14-4.23 (m, 1H), 7.31 (ddd, 1H), 7.63 (bs, 2H), 7.73 (dd, 1H), 7.82 (dd, 1H), 7.90 (s, 1H), 8.30 (s, 1H), 8.42 (d, 1H), 8.55 (d, 1H)

Mass spectrum: M+H$^+$ 379

The 5-bromo-3-(5-fluoro-1,3-benzoxazol-2-yl)pyridin-2-amine used as starting material was prepared as follows:

To a mixture of 2-amino-5-bromo-pyridine-3-carboxylic acid (1 g) and 2-amino-4-fluoro-phenol (0.586 g) placed in a round bottom flask was added polyphosphoric acid (10 g). The mixture was heated at 200° C. for 16 hours. After cooling, water (75 ml) was added and the mixture was stirred for 30 min. The mixture was basified to pH 12 with concentrated sodium hydroxide solution (6N and 2N). The solid was filtered, washed with water (150 ml×2), and ether (50 ml×2) to afford 5-bromo-3-(5-fluoro-1,3-benzoxazol-2-yl)pyridin-2-amine (1.0 g). NMR Spectrum: (DMSOd6) 7.53 (ddd, 1H), 7.93 (dd, 1H), 7.99-8.06 (m, 3H), 8.52 (d, 1H), 8.56 (d, 1H); Mass spectrum: M+H$^+$ 308-310

[3] Compound [3] was prepared according to the procedure described in Example [1] above. The N-tert-butoxycarbonyl group on the resultant product was removed by conventional treatment with TFA in dichloromethane instead of 4N hydrogen chloride in dioxane. The derived product so obtained (350 mg) gave the following characterising data. NMR Spectrum: (DMSOd6) 1.76-1.87 (m, 2H), 1.95-2.03 (m, 2H), 2.12 (bs, 1H), 2.55-2.63 (m, 2H), 3.01-3.09 (m, 2H), 4.15-4.23 (m, 1H), 7.36-7.47 (m, 2H), 7.63 (m, 2H), 7.69 (dd, 1H), 7.92 (s, 1H), 8.32 (s, 1H), 8.42 (d, 1H), 8.56 (d, 1H); Mass spectrum: M+H$^+$ 379

The 5-bromo-3-(7-fluoro-1,3-benzoxazol-2-yl)pyridin-2-amine used as starting material was prepared as follows:

A mixture of 2-amino-5-bromo-pyridine-3-carboxylic acid (1 g), 2-amino-6-fluoro-phenol (0.586 g) and polyphosphoric acid (10 g) was stirred at 200° C. for 5 hours. The resulting mixture was cooled to room temperature, diluted with water (4 ml) and basified to pH 12 with aqueous NaOH 10N, then 2N. The precipitate was filtered, washed with water, diethyl ether, and dried. The compound was stirred in THF during 2 days, the insoluble was filtered, the filtrate was concentrated to dryness and dried under vacuum to give 5-bromo-3-(7-fluoro-1,3-benzoxazol-2-yl)pyridin-2-amine (0.475 g). NMR Spectrum: (DMSOd6) 7.37-7.48 (m, 2H), 7.69 (dd, 1H), 7.83 (bs, 2H), 8.34 (d, 1H), 8.38 (d, 1H); Mass spectrum: M+H$^+$ 307-309

[4] Compound [4] was prepared according to the procedure described in Example [1] above. The N-tert-butoxycarbonyl group on the resultant product was removed by conventional treatment with TFA in dichloromethane instead of 4N hydrogen chloride in dioxane. The derived product so obtained (320 mg) gave the following characterising data. NMR Spectrum: (DMSOd6) 1.78 (dd, 1H), 1.83 (dd, 1H), 1.96-2.02 (m, 2H), 2.16 (bs, 1H), 2.58 (dd, 1H), 2.60 (s, 2H), 2.62 (dd, 1H), 3.02-3.08 (m, 2H), 4.15-4.22 (m, 1H), 7.34 (d, 1H), 7.65 (bs, 2H), 7.91 (s, 1H), 8.10 (d, 1H), 8.30 (s, 1H), 8.44 (d, 1H), 8.57 (d, 1H); Mass spectrum: M+H$^+$ 376.

The 5-bromo-3-(5-methyloxazolo[4,5-b]pyridin-2-yl)pyridin-2-amine used as starting material was prepared as follows:

A mixture of 2-amino-5-bromo-pyridine-3-carboxylic acid (1 g), 2-amino-6-methyl-pyridin-3-ol (1.4 g) and polyphosphoric acid (10 g) was stirred at 200° C. for 5 hours. The resulting mixture was cooled to room temperature, diluted with water (4 ml) and basified to pH 12 with aqueous NaOH 10N, then 2N. The reaction mixture was extracted with dichloromethane/acetonitrile, the organic phase was washed with water, a saturated aqueous solution of brine, dried over magnesium sulfate and concentrated to afford the crude product 5-bromo-3-(5-methyloxazolo[4,5-b]pyridin-2-yl)pyridin-2-amine (0.500 g) as a solid. NMR Spectrum: (DMSOd6) 2.60 (s, 3H), 7.35 (d, 1H), 7.85 (bs, 2H), 8.10 (d, 1H), 8.35 (d, 1H), 8.37 (d, 1H); Mass spectrum: M+H$^+$ 304-306.

[5] Compound [5] was prepared according to the procedure described in Example 37 except that the N-tert-butoxycarbonyl group on the resultant product was removed by conventional treatment with TFA in dichloromethane instead of 4N hydrogen chloride in dioxane. The product so obtained (90 mg) gave the following characterising data. NMR Spectrum: (DMSOd6): 1.79 (dd, 1H), 1.85 (dd, 1H), 1.95-2.03 (m, 2H), 2.14 (bs, 1H), 2.55-2.63 (m, 2H), 3.01-3.09 (m, 2H), 4.03 (s, 3H), 4.14-4.24 (m, 1H), 7.10 (d, 1H), 7.35 (dd, 1H), 7.41 (dd, 1H), 7.62 (bs, 2H), 7.90 (s, 1H), 8.30 (s, 1H), 8.32 (d, 1H), 8.52 (d, 1H); Mass spectrum: M+H$^+$ 391.

The 5-bromo-3-(7-methoxy-1,3-benzoxazol-2-yl)pyridine-2-amine used as starting material was prepared as follows:

A mixture of 2-aminonicotinic acid (9.4 g), 2-amino-6-fluoro-phenol (8.65 g) and polyphosphoric acid (90 g) was stirred at 200° C. for 16 hours. The reaction mixture was allowed to cool to room temperature, quenched with water and basified with sodium hydroxide solution 6N until pH 12 to give a solid which was collected by filtration and dried under vacuum; The resultant product was diluted in dichloromethane/methanol and filtered through a plug of silica gel and washed with ethyl acetate. The filtrate was concentrated to dryness to give 3-(7-fluoro-1,3-benzoxazol-2-yl)pyridin-2-amine (7.5 g) as a solid. NMR Spectrum: (DMSOd6) 6.76 (dd, 1H), 7.33-7.46 (m, 2H), 7.66 (bs, 2H), 7.68 (dd, 1H), 8.26 (dd, 1H), 8.30 (dd, 1H); Mass spectrum: M+H$^+$ 230.

Sodium hydride (3.76 g) was added portionwise to a stirred solution of methanol (3.82 ml) dissolved in NMP (100 ml) under nitrogen. 3-(7-fluoro-1,3-benzoxazol-2-yl)pyridin-2-amine (5.39 g) was added to the stirred mixture. The resulting suspension was stirred at 70° C. for 16 hours. After dilution with water (220 ml) the mixture was extracted with ethyl acetate (3×150 ml. The organic phases were washed with brine, dried over magnesium sulphate and concentrated. The crude product was purified by flash chromatography on silica gel eluting with 10 to 50% ethyl acetate in dichloromethane. The solvent was evaporated to dryness to afford 3-(7-methoxy-1,3-benzoxazol-2-yl)pyridin-2-amine (2.13 g) as a solid. NMR Spectrum: (DMSOd6) 4.01 (s, 3H), 6.77 (dd, 1H), 7.08 (d, 1H), 7.34 (dd, 1H), 7.40 (dd, 1H), 7.64 (bs, 1H), 8.23 (dd, 1H), 8.27 (dd, 1H); Mass spectrum: M+H$^+$ 242.

A mixture of 3-(7-methoxy-1,3-benzoxazol-2-yl)pyridin-2-amine (85 mg) and 1-bromopyrrolidine-2,5-dione (69.0 mg) in THF (2 ml) was stirred at 25° C. for 1 hour. The reaction mixture was concentrated to dryness and the resulting solid was triturated with water to give a solid which was collected by filtration and dried under vacuum to give 5-bromo-3-(7-methoxy-1,3-benzoxazol-2-yl)pyridin-2-amine (120 mg) as a solid.

NMR Spectrum: (DMSO-d6) 4.02 (s, 3H), 7.11 (d, 1H), 7.36 (dd, 1H), 7.41 (dd, 1H), 7.82 (bs, 1H), 8.30 (dd, 1H), 8.32 (dd, 1H); Mass spectrum: M+H$^+$ 319-321

EXAMPLE 38A

The compounds described in Table XIVa were prepared using analogous procedures to those described in Example 37.

TABLE XIVa

| No. & Note | n | R$^3$ |
|---|---|---|
| [1] | 1 | 4-methoxy |
| [2] | 1 | 4-fluoro |
| [3] | 1 | 4-cyano |

[1] Compound [1] was prepared according to the procedure described in Example 37 except that the N-tert-butoxycarbonyl group on the resultant product was removed by treatment with TFA in dichloromethane instead of 4M hydrogen chloride in dioxane. NMR Spectrum: (CDCl3): 1.92 (dd, 1H), 1.97 (dd, 1H), 2.18-2.26 (m, 2H), 2.75-2.84 (m, 2H), 3.24-3.31 (m, 2H), 4.09 (s, 3H), 4.24-4.32 (m, 1H), 6.85 (d, 1H), 6.90 (bs, 2H), 7.23 (d, 1H), 7.31 (dd, 1H), 7.70 (s, 1H), 7.78 (s, 1H), 8.37 (s, 2H); Mass spectrum: M+H$^+$ 397

The 5-bromo-3-(4-methoxy-1,3-benzoxazol-2-yl)pyridin-2-amine used as starting material was prepared as follows:

PPA (10 ml) at 50° C. was added to a stirred mixture of 2-aminonicotinic acid (2 g) and 2-amino-3-fluoro-phenol (1.841 g). The resulting suspension was stirred at 200° C. for 16 hours. The mixture was cooled and quenched with ice and water (100 ml) and the pH was adjusted to 12 with an aqueous solution of sodium hydroxide (6N then 2N). The resultant solid was filtered and washed with water. The solid was dried under reduce pressure with phosphorus pentoxide. The solid was adsorbed on silica gel with methylene chloride (100 ml) and methanol (10 ml) and purified by flash chromatography on silica gel eluting with 20 to 30% ethyl acetate in dichloromethane. The solvent was evaporated to dryness to afford 3-(4-fluoro-1,3-benzoxazol-2-yl)pyridin-2-amine (2.060 g) as a solid. NMR Spectrum: (CDCl3): 6.78 (dd, 1H), 6.97 (bs, 2H), 7.09 (dd, 1H), 7.31 (ddd, 1H), 7.38 (d, 1H), 8.30 (d, 1H), 8.33 (bs, 1H); Mass spectrum: M+H$^+$ 230

Sodium hydride (1.08 g, 60% in mineral oil) was added to a stirred solution of (2,4-dimethoxyphenyl)methanol (4.54 g) dissolved in tetrahydrofuran (150 ml) over a period of 5 minutes at 0° C. After 30 minutes, 3-(4-fluoro-1,3-benzoxazol-2-yl)pyridin-2-amine (1.547 g) was added and the mixture was heated to reflux for 16 hours. The THF was evaporated, water was added and the resultant solid was filtered and washed with water. The solid was then triturated with diethyl ether and dried with phosphorus pentoxide under reduced pressure to afford 3-[4-[(2,4-dimethoxyphenyl)methoxy]-1,3-benzoxazol-2-yl]pyridin-2-amine (2.32 g) as a solid. NMR Spectrum: (CDCl3) 3.82 (s, 3H), 3.86 (s, 3H), 5.41 (s, 2H), 6.50 (dd, 1H), 6.51 (s, 1H), 6.75 (dd, 1H), 6.91 (d, 1H), 6.96 (bs, 2H), 7.17 (d, 1H), 7.24 (d, 1H), 7.41 (d, 1H), 8.20 (dd, 1H), 8.29 (dd, 1H); Mass spectrum: M+H$^+$ 378

1-bromopyrrolidine-2,5-dione (2.188 g) was added to a stirred suspension of -[4-[(2,4-dimethoxyphenyl)methoxy]-1,3-benzoxazol-2-yl]pyridin-2-amine (2.32 g) dissolved in tetrahydrofuran (150 ml) over a period of 5 minutes. The resulting solution was stirred at 25° C. for 3 hours. The solvent was evaporated and the mixture was washed with water and dried over phosphorus pentoxide under reduced pressure to afford 5-bromo-3-[4-[(2,4-dimethoxyphenyl) methoxy]-1,3-benzoxazol-2-yl]pyridin-2-amine in admixture with 5-bromo-3-[4-[(5-bromo-2,4-dimethoxy-phenyl) methoxy]-1,3-benzoxazol-2-yl]pyridin-2-amine (2.80 g) as a solid.

TFA (20 ml) was added to the mixture. The resulting solution was stirred at 25° C. for 2 hours. The TFA was evaporated and the mixture was basified with a solution 7N of ammonia in methanol. The mixture was adsorbed on silica gel. The crude product was purified by flash chromatography on silica gel eluting with 1 to 2% methanol in dichloromethane. The solvent was evaporated to dryness to afford 2-(2-amino-5-bromo-3-pyridyl)-1,3-benzoxazol-4-ol (1.040 g) as a solid. NMR Spectrum: (DMSOd6) 6.81 (d, 1H), 7.18 (d, 1H), 7.25 (dd, 1H), 7.94 (bs, 2H), 8.28 (d, 1H), 8.30 (d, 1H), 10.47 (bs, 1H); Mass spectrum: M+H$^+$ 306-308 Iodomethane (0.5 ml) was added to a stirred suspension 2-(2-amino-5-bromo-3-pyridyl)-1,3-benzoxazol-4-ol (820 mg) and potassium carbonate (1111 mg) in DMF (5 ml). The resulting suspension was stirred at 25° C. for 3 hours. The DMF was evaporated under reduce pressure. The mixture was adsorbed on silica gel. The crude product was purified by flash chromatography on silica gel eluting with 20 to 50% ethyl acetate in dichloromethane. The solvent was evaporated to dryness to afford 5-bromo-3-(4-methoxy-1,3-benzoxazol-2-yl)pyridin-2-amine (480 mg) as a solid. NMR Spectrum: (CDCl3) 4.08 (s, 3H), 6.84 (d, 1H), 6.93 (bs, 2H), 7.20 (d, 1H), 7.31 (dd, 1H), 8.23 (d, 1H), 8.38 (d, 1H); Mass spectrum: M+H$^+$ 319-321

[2] Compound [2] was prepared according to the procedure described in Example 37, except that the N-tert-butoxycarbonyl group on the resultant product was removed by treatment with 4M hydrogen chloride in isopropanol instead of 4M hydrogen chloride in dioxane. NMR Spectrum: (CDCl3) 1.93 (dd, 1H), 1.98 (dd, 1H), 2.18-2.26 (m, 2H), 2.75-2.84 (m, 2H), 3.24-3.32 (m, 2H), 4.24-4.32 (m, 1H), 6.90 (bs, 2H), 7.10 (s, 1H), 7.33 (ddd, 1H), 7.42 (d, 1H), 7.71 (s, 1H), 7.79 (s, 1H), 8.37 (d, 1H), 8.40 (d, 1H); Mass spectrum: M+H$^+$ 379

The 5-Bromo-3-(4-fluoro-1,3-benzoxazol-2-yl)pyridin-2-amine used as a starting material was prepared as follows:

1-bromopyrrolidine-2,5-dione (427 mg) was added to a stirred solution of 3-(4-fluoro-1,3-benzoxazol-2-yl)pyridin-2-amine (500 mg) dissolved in tetrahydrofuran (20 ml) over a period of 5 minutes. The resulting solution was stirred at 25° C. for 2 hours. The solvent was evaporated and the residue was washed with water and dried over P$_2$O$_5$ under reduced pressure to afford 5-bromo-3-(4-fluoro-1,3-benzoxazol-2-yl) pyridin-2-amine (637 mg) as a solid. Mass spectrum: M+H$^+$ 307-309, R.T. 3.95 min.

[3] Compound [3] was prepared according to the procedure described in Example 37. The N-tert-butoxycarbonyl group on the resultant product was removed by treatment with TFA in dichloromethane instead of 4M hydrogen chloride in dioxane. NMR Spectrum: (CDCl3): 1.93 (dd, 1H), 1.98 (dd, 1H), 2.18-2.26 (m, 2H), 2.76-2.85 (m, 2H), 3.25-3.32 (m, 2H), 4.24-4.33 (m, 1H), 6.92 (bs, 2H), 7.45 (dd, 1H), 7.69 (d, 1H), 7.71 (s, 1H), 7.79 (s, 1H), 7.83 (d, 1H), 8.37 (d, 1H), 8.45 (d, 1H); Mass spectrum: M+H$^+$ 386

The 2-(2-amino-5-bromo-3-pyridyl)-1,3-benzoxazole-4-carbonitrile used as starting material was prepared as follows:

TFA (10 ml) was added to 3-[4-[(2,4-dimethoxyphenyl) methoxy]-1,3-benzoxazol-2-yl]pyridin-2-amine (1.4 g). The resulting solution was stirred at 25° C. for 2 hours. The TFA was evaporated under reduced pressure. Toluene was added and the mixture was evaporated. The solid was triturated with water. The pH was adjusted to 7 with a 30% solution of ammonia. The solid was filtered and washed with water, diethyl ether and dried under reduced pressure to afford 2-(2-amino-3-pyridyl)-1,3-benzoxazol-4-ol (617 mg) as a solid. NMR Spectrum: (DMSOd6): 6.74-6.83 (m, 2H), 7.18 (d, 1H), 7.23 (dd, 1H), 7.84 (bs, 2H), 8.20 (d, 1H), 8.26 (d, 1H), 10.43 (s, 1H); Mass spectrum: M+H$^+$ 228

1,1,1-trifluoro-N-phenyl-N-(trifluoromethylsulfonyl) methanesulfonamide (998 mg, 2.79 mmol) was added to a stirred suspension 2-(2-amino-3-pyridyl)-1,3-benzoxazol-4-ol (577 mg) and potassium carbonate (1053 mg) dissolved in dichloromethane (20 ml). The resulting suspension was stirred at 25° C. for 2 hours. The mixture was adsorbed on silica gel. The crude product was purified by flash chromatography on silica gel eluting with 20 to 40% ethyl acetate in petroleum ether. The solvent was evaporated to dryness to afford [2-(2-amino-3-pyridyl)-1,3-benzoxazol-4-yl]trifluoromethanesulfonate (559 mg) as a solid. NMR Spectrum: (DMSOd6): 6.81 (dd, 1H), 6.56-6.63 (m, 2H), 7.71 (bs, 2H), 7.96 (dd, 1H), 8.29 (dd, 1H), 8.31 (d, 1H); Mass spectrum: M+H$^+$ 360

Tris(dibenzylideneacetone)dipalladium (31.9 mg) was added to a stirred degassed suspension of [2-(2-amino-3-pyridyl)-1,3-benzoxazol-4-yl]trifluoromethanesulfonate (500 mg) and dicyanozinc (0.132 ml) and zinc (9.10 mg), and (9,9-dimethyl-9H-xanthene-4,5-diyl)bis(diphenylphosphine) (81 mg) dissolved in acetonitrile (10 ml). The resulting suspension was stirred at 100° C. for 15 hours. The mixture was adsorbed on silica gel. The crude product was purified by flash chromatography on silica gel eluting with 20 to 40% ethyl acetate in petroleum ether. The solvent was evaporated to dryness to afford 2-(2-amino-3-pyridyl)-1,3-benzoxazole-4-carbonitrile (210 mg) as a solid. Mass spectrum: M+H$^+$ 237; RT 2.90 min 1-Bromopyrrolidine-2,5-dione (199 mg) was added to a stirred solution of 2-(2-amino-3-pyridyl)-1,3-benzoxazole-4-carbonitrile (240 mg) dissolved in tetrahydrofuran (5 ml) over a period of 5 minutes. The resulting solution was stirred at 25° C. for 2 hours. The solvent was evaporated and the residue was washed with water. The residue was basified with 7 M ammonia in methanol and adsorbed on silica gel with methylene chloride. The crude product was purified by flash chromatography on silica gel eluting with 1 to 2% methanol in dichloromethane. The solvent was evaporated to dryness to afford 2-(2-amino-5-bromopyridin-3-yl)benzo[d]oxazole-4-carbonitrile (205 mg) as a solid. NMR Spectrum: (CDCl3):

7.47 (dd, 1H), 7.70 (dd, 1H), 7.82 (dd, 1H), 7.97 (bs, 2H), 8.31 (d, 1H), 8.41 (d, 1H); Mass spectrum: M+H⁺ 315-317

EXAMPLE 39

(2S,4R)-4-[4-[6-amino-5-(1,3-benzoxazol-2-yl)-3-pyridyl]pyrazol-1-yl]-N,1-dimethyl-pyrrolidine-2-carboxamide

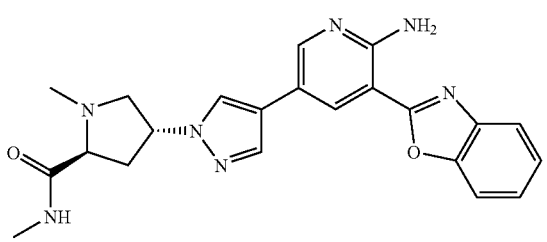

TFA (5 ml) was added to (2S,4R)-tert-butyl 4-[4-[6-amino-5-(1,3-benzoxazol-2-yl)-3-pyridyl]pyrazol-1-yl]-2-(methylcarbamoyl)pyrrolidine-1-carboxylate under argon. The resulting solution was stirred at 25° C. for 1 hour. The solution was evaporated under reduced pressure, adsorbed with ammonia in methanol solution. The crude product was purified by flash chromatography on silica gel eluting with 1 to 6% methanolic ammonia (7 N) in dichloromethane. The solvent was evaporated to dryness to afford (2S,4R)-4-[4-[6-amino-5-(1,3-benzoxazol-2-yl)-3-pyridyl]pyrazol-1-yl]-N-methyl-pyrrolidine-2-carboxamide (38 mg) as a pale yellow solid. 37% Aqueous formaldehyde (8.42 µl) at 0° C. was added to a stirred solution 4-[4-[6-amino-5-(1,3-benzoxazol-2-yl)-3-pyridyl]pyrazol-1-yl]-N-methyl-pyrrolidine-2-carboxamide (38 mg) dissolved in methanol (2 ml) and dichloromethane (2 ml) over a period of 5 minutes under argon. The resulting solution was stirred at 0° C. for 5 minutes. Sodium triacetoxyhydroborate (23.96 mg, 0.11 mmol) was added and the mixture was stirred 5 minutes at 25° C. A solution of ammonia in methanol 7N (1 ml) was added and the mixture was adsorbed on silica gel. The crude product was purified by flash chromatography on silica gel eluting with 1 to 6% methanolic ammonia (7 N) in dichloromethane. The solvent was evaporated to dryness to afford (2S,4R)-4-[4-[6-amino-5-(1,3-benzoxazol-2-yl)-3-pyridyl]pyrazol-1-yl]-N,1-dimethyl-pyrrolidine-2-carboxamide (30 mg) after overnight stirring in acetonitrile as a solid. NMR Spectrum: (DMSOd6) 2.23-2.32 (m, 1H), 2.35 (s, 3H), 2.47-2.56 (m partially hidden by DMSOd5, 1H), 2.65 (d, 3H), 2.76-2.84 (m, 1H), 3.19-3.27 (m, 1H), 3.47-3.56 (m, 1H), 4.89-4.99 (m, 1H), 7.41-7.50 (m, 2H), 7.67 (bs, 2H), 7.77-7.82 (m, 1H), 7.83-7.87 (m, 1H), 7.90 (q, 1H), 7.97 (s, 1H), 8.37 (s, 1H), 8.44 (d, 1H), 8.53 (d, 1H) Mass spectrum: M+H⁺ 418

The (2S,4R)-tert-butyl 4-[4-[6-amino-5-(1,3-benzoxazol-2-yl)-3-pyridyl]pyrazol-1-yl]-2-(methylcarbamoyl)pyrrolidine-1-carboxylate used as starting material was prepared as follows.

(2S,4R)—O1-tert-butyl O2-methyl 4-[4-[6-amino-5-(1,3-benzoxazol-2-yl)-3-pyridyl]pyrazol-1-yl]pyrrolidine-1,2-dicarboxylate was prepared according to the procedure described in Example 26 except that caesium carbonate was used, using (2S,4S)—O1-tert-butyl O2-methyl 4-methylsulphonyloxypyrrolidine-1,2-dicarboxylate (Siddiqui et al., PCT. Int. Appl. US2007/0167426) as alkylating agent to give 442 mg of solid. NMR Spectrum: (CDCl3) 1.45 (s, 5.4H), 1.48 (s, 3.6H), 2.44-2.52 (m, 1H). 2.82-2.96 (m, 1H), 3.79 (s, 1.8H), 3.80 (s, 1.2H), 3.82-3.89 (m, 0.4H), 3.92-3.98 (m, 0.6H), 4.03-4.11 (m, 1H), 4.49-4.55 (m, 0.6H), 4.60-4.65 (m, 0.4H), 4.99-5.10 (m, 1H), 7.05 (bs, 2H), 7.35-7.42 (m, 2H), 7.59-7.63 (m, 1H), 7.68 (s, 1H), 7.74-7.78 (m, 1H), 7.81 (d, 1H), 8.35 (d, 1H), 8.40 (d, 1H) Mass spectrum: M+H⁺ 505 A solution of potassium hydroxide (1.249 ml, 2N) was added to (2S,4R)—O1-tert-butyl O2-methyl 4-[4-[6-amino-5-(1,3-benzoxazol-2-yl)-3-pyridyl]pyrazol-1-yl]pyrrolidine-1,2-dicarboxylate (420 mg) dissolved in methanol (10 ml) over a period of 10 minutes under argon. The resulting solution was stirred at 50° C. for 2 hours. The methanol was evaporated and the pH was adjusted to 5.5 with HCl 6N. The mixture was evaporated on reduce pressure. The reaction mixture was purified by preparative HPLC using a Waters X-Terra reverse-phase column (C-18, 5 microns silica, 19 mm diameter, 100 mm length, flow rate of 40 ml/minute) and decreasingly polar mixtures of water (containing 0.2% ammonium carbonate) and acetonitrile as eluent. The fractions containing the desired compound were evaporated to dryness to afford (2S, 4R)-4-[4-[6-amino-5-(1,3-benzoxazol-2-yl)-3-pyridyl]pyrazol-1-yl]-1-tert-butoxycarbonyl-pyrrolidine-2-carboxylic acid (195 mg) as a solid. NMR Spectrum: (DMSOd6) 1.35 (s, 5.4H), 1.39 (s, 3.6H), 2.32-2.43 (m, 1H), 2.66-2.82 (m, 1H), 3.63-3.71 (m, 1H), 3.80-3.89 (m, 1H), 4.28-4.36 (m, 1H), 4.96-5.06 (m, 1H), 7.40-7.49 (m, 2H), 7.67 (bs, 2H), 7.77-7.81 (m, 1H), 7.82-7.86 (m, 1H), 7.97 (s, 1H), 8.36 (s, 0.6H), 8.39 (s, 0.4H), 8.41-8.46 (m, 1H), 8.50-8.55 (m, 1H); Mass spectrum: M+H⁺ 491

A slurry of benzotriazol-1-yl-[bis(dimethylamino)methylene]oxonium tetrafluoroborate (149 mg) was added to methylamine (0.892 ml, 2M in methanol) and (2S,4R)-4-[4-[6-amino-5-(1,3-benzoxazol-2-yl)-3-pyridyl]pyrazol-1-yl]-1-tert-butoxycarbonyl-pyrrolidine-2-carboxylic acid (175 mg) and triethylamine (0.883 ml) dissolved in DMF (8 ml) over a period of 10 minutes. The resulting solution was stirred at 25° C. overnight. The mixture was evaporated and a saturated solution of NaHCO₃ (50 ml) was added to the mixture, extracted with methylene chloride (50 ml×2), dried over Magnesium sulphate, filtered and evaporated in reduce pressure. The reaction mixture was purified by preparative HPLC using a Waters X-Terra reverse-phase column (C-18, 5 microns silica, 19 mm diameter, 100 mm length, flow rate of 40 ml/minute) and decreasingly polar mixtures of water (containing 0.2% ammonium carbonate) and acetonitrile as eluent. The fractions containing the desired compound were evaporated to dryness to afford (2S,4R)-tert-butyl 4-[4-[6-amino-5-(1,3-benzoxazol-2-yl)-3-pyridyl]pyrazol-1-yl]-2-(methylcarbamoyl)pyrrolidine-1-carboxylate (60 mg) as a solid. Retention time: 3.44 min Mass spectrum: M+H⁺ 504

Analytical LC-MS was carried out using a Waters Alliance HT (2695) fitted with a Waters ZQ or ZMD ESCi mass spectrometer and a Sunfire 3.5 µm C-18 column (4.6×50 mm) at a flow rate of 2.5 ml/min, using a solvent system of 95% A+5% C to 95% B+5% C over 4 minutes, where A=water, B=acetonitrile, C=5% HCOOH in Methanol; retention time of each product is quoted in minutes.

EXAMPLE 40

3-(1,3-benzoxazol-2-yl)-5-[1-(4-piperidyl)triazol-4-yl]pyridin-2-amine

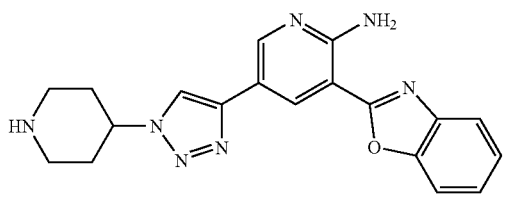

TFA (0.771 ml) was added to a stirred suspension of tert-butyl 4-[4-[6-amino-5-(1,3-benzoxazol-2-yl)-3-pyridyl]triazol-1-yl]piperidine-1-carboxylate (231 mg) dissolved in dichloromethane (5 ml) at room temperature. The resulting solution was stirred for 2 hours. Excess TFA was removed by azeotropic concentration with toluene. The residue was taken off with dichloromethane-methanol and treated with methanolic ammonia (7 M). The mixture was concentrated to dryness and the resulting solid was triturated with diethyl ether. The resultant solid was collected by filtration, washed with diethyl ether followed by petroleum ether and dried under vacuum at 60° C. to give 3-(1,3-benzoxazol-2-yl)-5-[1-(4-piperidyl)triazol-4-yl]pyridin-2-amine (180 mg) as a solid; NMR Spectrum: (DMSOd6+TFAd) 2.20-2.32 (m, 2H), 2.38-2.48 (m, 2H), 3.7-3.30 (m, 2H), 3.47-3.58 (m, 2H), 4.92-5.02 (m, 1H), 7.54 (ddd, 1H), 7.59 (ddd, 1H), 7.90 (d, 1H), 7.95 (dd, 1H), 8.84 (d, 1H), 8.96 (s, 1H), 9.24 (d, 1H); Mass spectrum: M+H$^+$: 362

The tert-butyl 4-[4-[6-amino-5-(1,3-benzoxazol-2-yl)-3-pyridyl]triazol-1-yl]piperidine-1-carboxylate used as a reagent was prepared as follows:

A suspension of 3-(1,3-benzoxazol-2-yl)-5-bromo-pyridin-2-amine (3.5 g), triethylamine (15 ml) and ethynyltrimethylsilane (5.11 ml) in DMA (50 ml) at room temperature was deoxygenated with a stream of argon. Pd(dppf)Cl$_2$ (0.488 g) was added to the slurry, the vial was sealed and the resulting suspension was then heated by microwave irradiation to 125° C. for 2 hours. After concentration, the crude product was purified twice by flash chromatography on silica gel eluting with 0 to 10% ethyl acetate in dichloromethane for the first column and 0 to 10% ethyl acetate in petroleum ether for the second column to afford after evaporation 3-(1,3-benzoxazol-2-yl)-5-(2-trimethylsilylethynyl)pyridin-2-amine (0.969 g) as a solid; NMR Spectrum: (DMSOd6) 0.25 (s, 9H), 7.41-7.51 (ms, 2H), 7.79 (d, 1H), 7.85 (d, 1H), 8.06 (bs, 2H), 8.28 (d, 1H), 8.33 (d, 1H); Mass spectrum: M+H$^+$: 308

Tetrabutylammonium fluoride 1.0M in THF (0.629 ml) was added to a stirred solution of 3-(1,3-benzoxazol-2-yl)-5-(2-trimethylsilylethynyl)pyridin-2-amine (0.370 g) in THF (10 ml) at room temperature. The resulting solution was stirred for 1 hour. A yellow precipitate appeared during the reaction. After concentration, the crude product was purified by flash chromatography on silica gel eluting with 0 to 15% ethyl acetate in dichloromethane to afford 3-(1,3-benzoxazol-2-yl)-5-ethynyl-pyridin-2-amine (225 mg) as a solid; NMR Spectrum: (DMSOd6) 4.20 (s, 1H), 7.42-7.51 (m, 2H), 7.80 (dd, 1H), 7.85 (dd, 1H), 8.04 (bs, 2H), 8.31 (d, 1H), 8.36 (d, 1H); Mass spectrum: M+H$^+$: 236

Sodium (R)-2-((S)-1,2-dihydroxyethyl)-4-hydroxy-5-oxo-2,5-dihydrofuran-3-olate (211 mg) and tris((1-benzyl-1H-1,2,3-triazol-4-yl)methyl)amine (90 mg) were added to a stirred solution of 3-(1,3-benzoxazol-2-yl)-5-ethynyl-pyridin-2-amine (125 mg) in THF (15 ml) at room temperature. To the reaction mixture was then added water (5 ml), tert-butyl 4-azidopiperidine-1-carboxylate (180 mg) in THF (1 ml) and tetrakis(acetonitrile)copper(I) hexafluorophosphate (9.9 mg). The resulting solution was stirred overnight: a precipitate appeared. The precipitate was filtered, washed successively with water, THF, diethyl ether and petroleum ether, and dried under vacuum at 50° C. to afford tert-butyl 4-[4-[6-amino-5-(1,3-benzoxazol-2-yl)-3-pyridyl]triazol-1-yl]piperidine-1-carboxylate (218 mg) as a solid; NMR Spectrum: (DMSOd6) 1.44 (s, 9H), 1.82-1.96 (m, 2H), 2.07-2.21 (m, 2H), 3.01 (bs, 2H), 3.99-4.20 (m, 2H), 4.72-4.85 (m, 1H), 7.40-7.53 (m, 2H), 7.80-8.04 (m, 4H), 8.72 (s, 2H), 8.78 (s, 1H); Mass spectrum: M+H$^+$: 462

EXAMPLE 41

Using analogous procedures to that described in Example 23, an NH group in an appropriate heterocyclyl-substituted pyrazole or triazole was reacted with 37% aqueous formaldehyde in a reductive amination reaction to give the corresponding NMe substituted heterocyclyl.

TABLE XV

| N° & Note | Structure | Name | Mass spectrum |
|---|---|---|---|
| [1] | 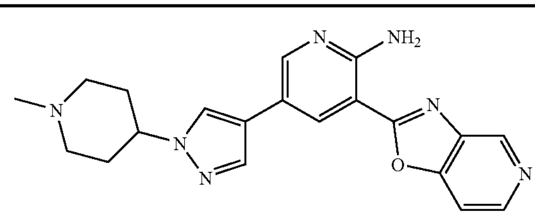 | 5-[1-(1-methyl-4-piperidyl)pyrazol-4-yl]-3-oxazolo[4,5-c]pyridin-2-yl-pyridin-2-amine | M + H$^+$ 376 |

TABLE XV-continued

| N° & Note | Structure | Name | Mass spectrum |
|---|---|---|---|
| [2] | 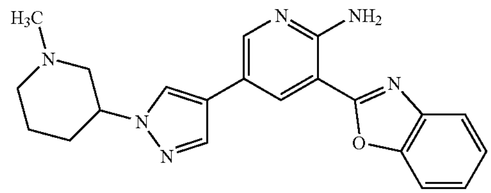 | 3-(1,3-benzoxazol-2-yl)-5-[1-(1-methyl-3-piperidyl)pyrazol-4-yl]pyridin-2-amine | M + H⁺ 375 |
| [3] | 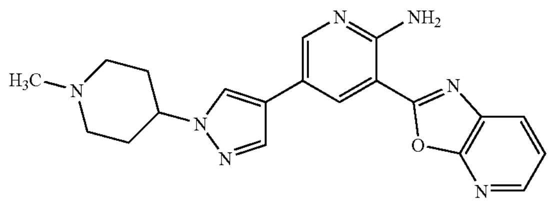 | 5-[1-(1-methyl-4-piperidyl)pyrazol-4-yl]-3-oxazolo[5,4-b]pyridin-2-yl-pyridin-2-amine | M + H⁺ 376 |
| [4] | 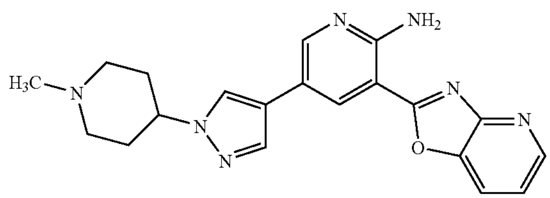 | 5-[1-(1-methyl-4-piperidyl)pyrazol-4-yl]-3-oxazolo[4,5-b]pyridin-2-yl-pyridin-2-amine | M + H⁺ 376 |
| [5] | 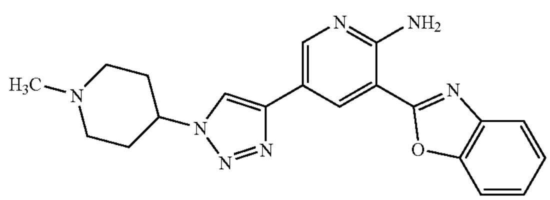 | 3-(1,3-benzoxazol-2-yl)-5-[1-(1-methyl-4-piperidyl)triazol-4-yl]pyridin-2-amine | M + H⁺ 376 |
| [6] | 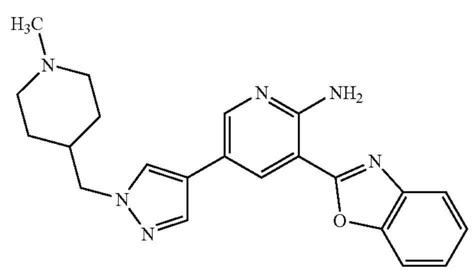 | 3-(1,3-benzoxazol-2-yl)-5-[1-[(1-methyl-4-piperidyl)methyl]pyrazol-4-yl]pyridin-2-amine | M + H⁺ 389 |
| [7] | 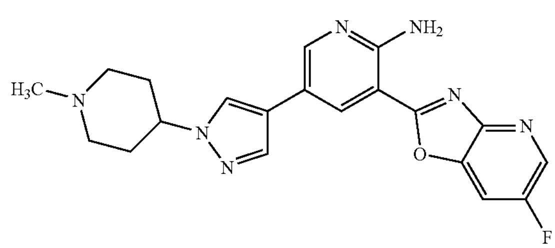 | 3-(6-fluoroxazolo[4,5-b]pyridin-2-yl)-5-[1-(1-methyl-4-piperidyl)pyrazol-4-yl]pyridin-2-amine | M + H⁺ 394 |
| [8] | 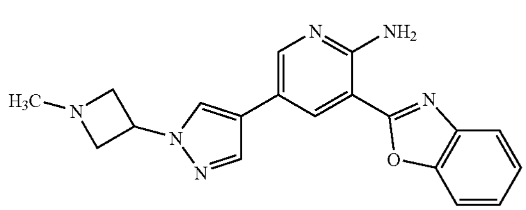 | 3-(1,3-benzoxazol-2-yl)-5-[1-(1-methylazetidin-3-yl)pyrazol-4-yl]pyridin-2-amine | M + H⁺ 347 |

TABLE XV-continued

| N° & Note | Structure | Name | Mass spectrum |
|---|---|---|---|
| [9] | 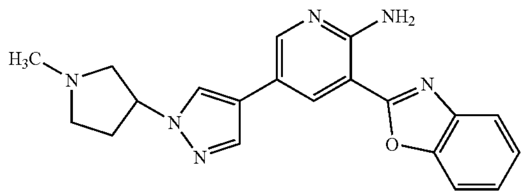 | 3-(1,3-benzoxazol-2-yl)-5-[1-(1-methylpyrrolidin-3-yl)pyrazol-4-yl]pyridin-2-amine | M + H⁺ 361 |
| [10] | 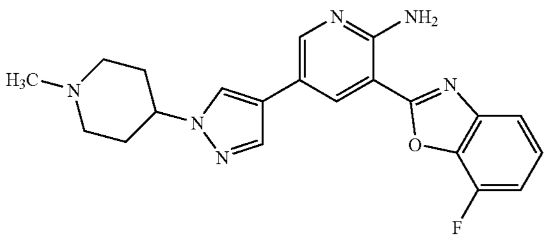 | 3-(7-fluoro-1,3-benzoxazol-2-yl)-5-[1-(1-methyl-4-piperidyl)pyrazol-4-yl]pyridin-2-amine | M + H⁺ 393 |
| [11] | 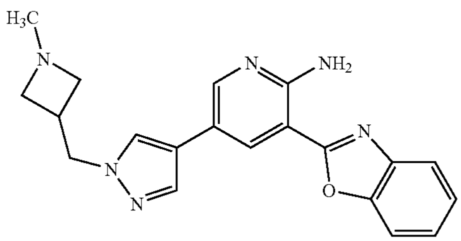 | 3-(1,3-benzoxazol-2-yl)-5-[1-[(1-methylazetidin-3-yl)methyl]pyrazol-4-yl]pyridin-2-amine | M + H⁺ 361 |
| [12] | 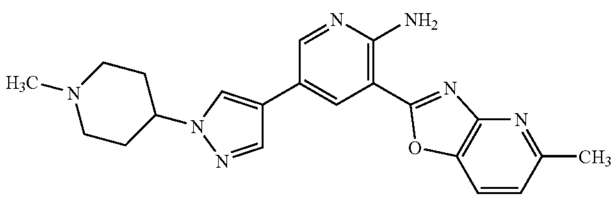 | 3-(5-methyloxazolo[4,5-b]pyridin-2-yl)-5-[1-(1-methyl-4-piperidyl)pyrazol-4-yl]pyridin-2-amine | M + H⁺ 390 |
| [13] | 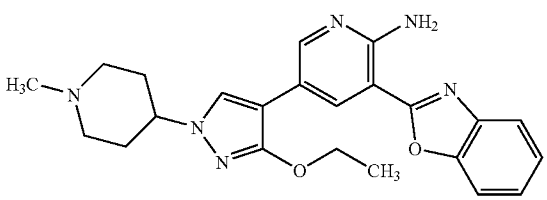 | 3-(1,3-benzoxazol-2-yl)-5-[3-ethoxy-1-(1-methyl-4-piperidyl)pyrazol-4-yl]pyridin-2-amine | M + H⁺ 419 |
| [14] | 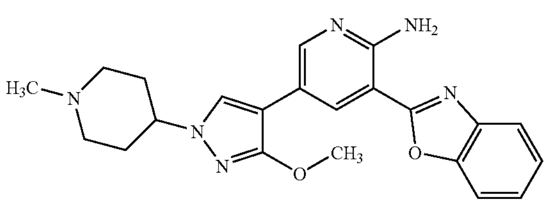 | 3-(1,3-benzoxazol-2-yl)-5-[3-methoxy-1-(1-methyl-4-piperidyl)pyrazol-4-yl]pyridin-2-amine | M + H⁺ 405 |
| [15] | 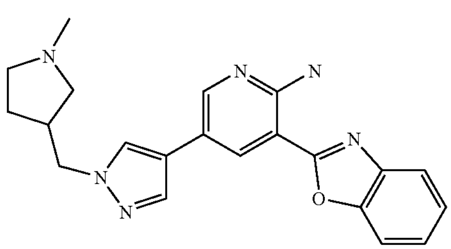 | 3-(1,3-benzoxazol-2-yl)-5-[1-[(1-methylpyrrolidin-3-yl)methyl]pyrazol-4-yl]pyridin-2-amine | M + H⁺ 375 |

TABLE XV-continued

| N° & Note | Name | Mass spectrum |
|---|---|---|
| [16] | 3-(6,7-difluoro-1,3-benzoxazol-2-yl)-5-[1-(1-methyl-4-piperidyl)pyrazol-4-yl]pyridin-2-amine | M + H+ 411 |
| [17] | 3-(1,3-benzoxazol-2-yl)-5-[3,5-dimethyl-1-(1-methyl-4-piperidyl)pyrazol-4-yl]pyridin-2-amine | M + H+ 403 |
| [18] | 3-(1,3-benzoxazol-2-yl)-5-[5-methyl-1-(1-methyl-4-piperidyl)pyrazol-4-yl]pyridin-2-amine | M + H+ 389 |
| [19] | [4-[6-amino-5-(1,3-benzoxazol-2-yl)-3-pyridyl]-1-(1-methyl-4-piperidyl)pyrazol-3-yl]methanol | M + H+ 405 |
| [20] | 5-[3-methyl-1-(1-methyl-4-piperidyl)pyrazol-4-yl]-3-oxazolo[5,4-b]pyridin-2-yl-pyridin-2-amine | M + H+ 390 |
| [21] | 3-(1,3-benzoxazol-2-yl)-5-[3-methyl-1-(1-methyl-4-piperidyl)pyrazol-4-yl]pyrazin-2-amine | M + H+ 390 |
| [22] | 5-[3-methyl-1-(1-methyl-4-piperidyl)pyrazol-4-yl]-3-oxazolo[4,5-b]pyridin-2-yl-pyridin-2-amine | M + H+ 390 |

TABLE XV-continued

| N° & Note | Structure | Name | Mass spectrum |
|---|---|---|---|
| [23] | 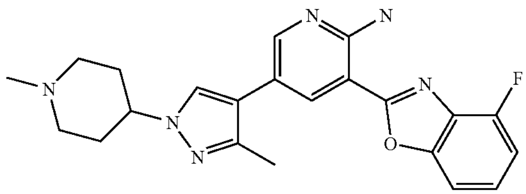 | 3-(4-fluoro-1,3-benzoxazol-2-yl)-5-[3-methyl-1-(1-methyl-4-piperidyl)pyrazol-4-yl]pyridin-2-amine | M + H$^+$ 407 |
| [24] | 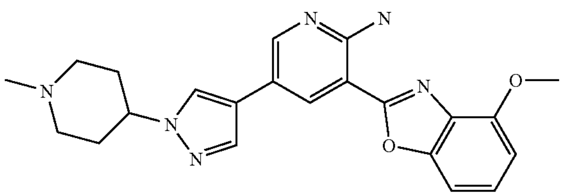 | 3-(4-methoxy-1,3-benzoxazol-2-yl)-5-[1-(1-methyl-4-piperidyl)pyrazol-4-yl]pyridin-2-amine | M + H$^+$ 405 |
| [25] | 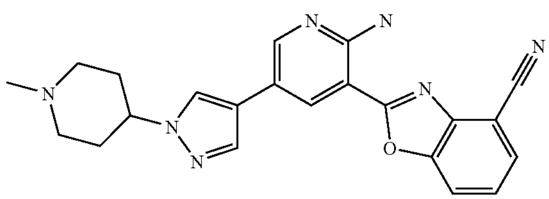 | 2-[2-amino-5-[1-(1-methyl-4-piperidyl)pyrazol-4-yl]-3-pyridyl]-1,3-benzoxazole-4-carbonitrile | M + H$^+$ 400 |
| [26] | 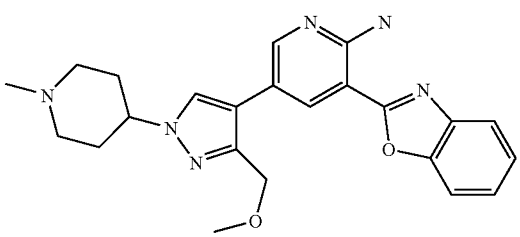 | 3-(1,3-benzoxazol-2-yl)-5-[3-(methoxymethyl)-1-(1-methyl-4-piperidyl)pyrazol-4-yl]pyridin-2-amine | M + H$^+$ 419 |
| [27] | 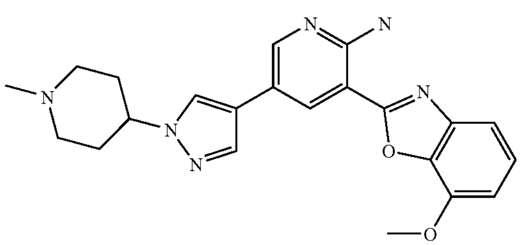 | 3-(7-methoxy-1,3-benzoxazol-2-yl)-5-[1-(1-methyl-4-piperidyl)pyrazol-4-yl]pyridin-2-amine | M + H$^+$ 405 |
| [28] | 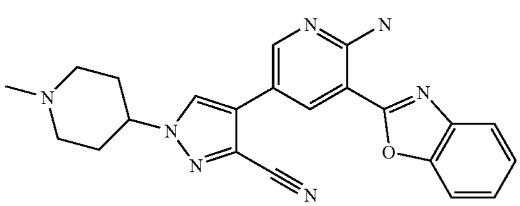 | 4-[6-amino-5-(1,3-benzoxazol-2-yl)-3-pyridyl]-1-(1-methyl-4-piperidyl)pyrazole-3-carbonitrile | M + H$^+$ 400 |
| [29] | 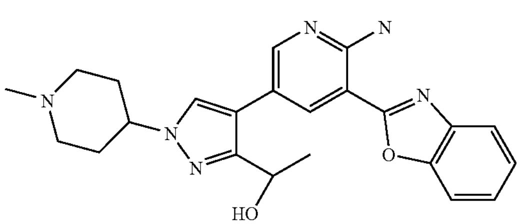 | 1-[4-[6-amino-5-(1,3-benzoxazol-2-yl)-3-pyridyl]-1-(1-methyl-4-piperidyl)pyrazol-3-yl]ethanol | M + H$^+$ 419 |

TABLE XV-continued

| N° & Note | Structure | Name | Mass spectrum |
|---|---|---|---|
| [30] | 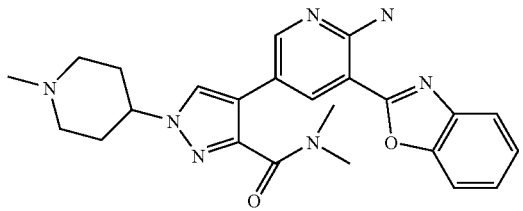 | 4-[6-amino-5-(1,3-benzoxazol-2-yl)-3-pyridyl]-N,N-dimethyl-1-(1-methyl-4-piperidyl)pyrazole-3-carboxamide | M + H$^+$ 446 |
| [31] | 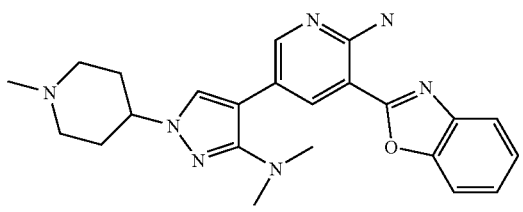 | 3-(1,3-benzoxazol-2-yl)-5-[3-dimethylamino-1-(1-methyl-4-piperidyl)pyrazol-4-yl]pyridin-2-amine | M + H$^+$ 418 |
| [32] | 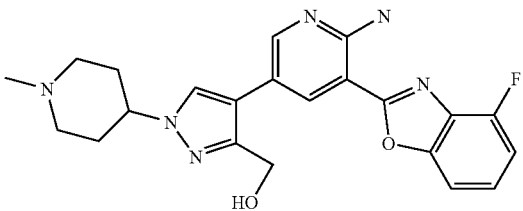 | [4-[6-amino-5-(4-fluoro-1,3-benzoxazol-2-yl)-3-pyridyl]-1-(1-methyl-4-piperidyl)pyrazol-3-yl]methanol | M + H$^+$ 423 |
| [33] | 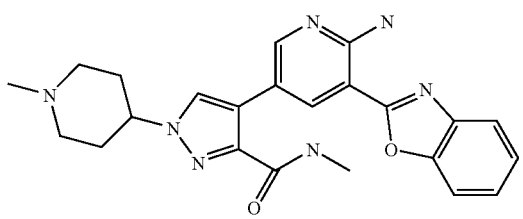 | 4-[6-amino-5-(1,3-benzoxazol-2-yl)-3-pyridyl]-N-methyl-1-(1-methyl-4-piperidyl)pyrazole-3-carboxamide | M + H$^+$ 432 |
| [34] | 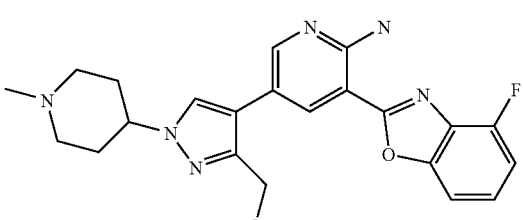 | 3-(4-fluoro-1,3-benzoxazol-2-yl)-5-[3-(methoxymethyl)-1-(1-methyl-4-piperidyl)pyrazol-4-yl]pyridin-2-amine | M + H$^+$ 437 |
| [35] | 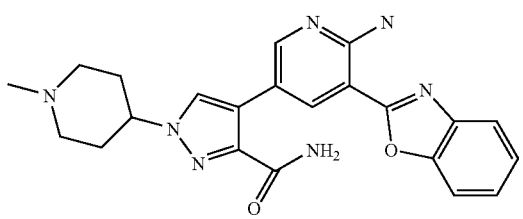 | 4-[6-amino-5-(1,3-benzoxazol-2-yl)-3-pyridyl]-1-(1-methyl-4-piperidyl)pyrazole-3-carboxamide | M + H$^+$ 418 |

TABLE XV-continued

| N° & Note | Structure | Name | Mass spectrum |
|---|---|---|---|
| [36] | 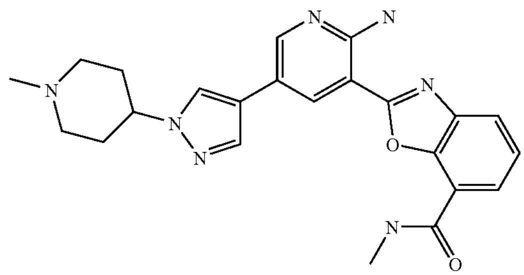 | 2-[2-amino-5-[1-(1-methyl-4-piperidyl)pyrazol-4-yl]-3-pyridyl]-N-methyl-1,3-benzoxazole-7-carboxamide | M + H⁺ 432 |
| [37] | 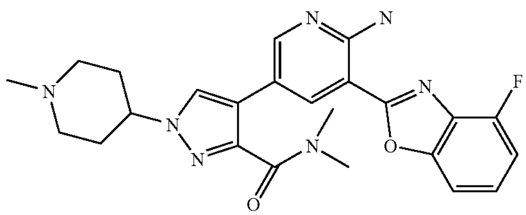 | 4-[6-amino-5-(4-fluoro-1,3-benzoxazol-2-yl)-3-pyridyl]-N,N-dimethyl-1-(1-methyl-4-piperidyl)pyrazole-3-carboxamide | M + H⁺ 464 |
| [38] | 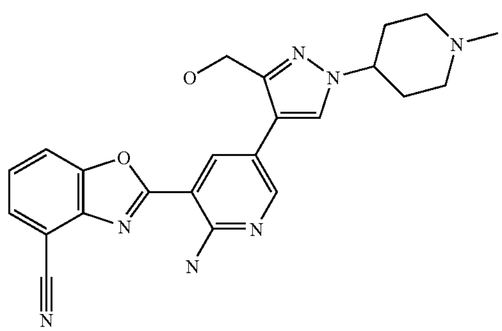 | 2-[2-amino-5-[3-(hydroxymethyl)-1-(1-methyl-4-piperidyl)pyrazol-4-yl]-3-pyridyl]-1,3-benzoxazole-4-carbonitrile | M + H⁺ 430 |
| [39] | 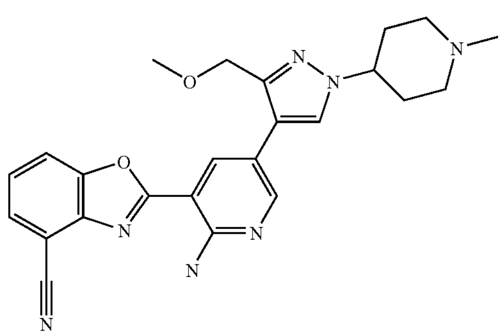 | 2-[2-amino-5-[3-(methoxymethyl)-1-(1-methyl-4-piperidyl)pyrazol-4-yl]-3-pyridyl]-1,3-benzoxazole-4-carbonitrile | M + H⁺ 444 |
| [40] | 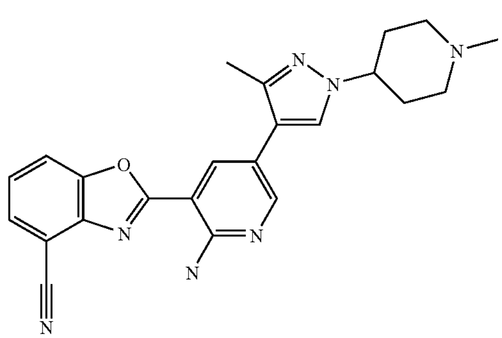 | 2-[2-amino-5-[3-methyl-1-(1-methyl-4-piperidyl)pyrazol-4-yl]-3-pyridyl]-1,3-benzoxazole-4-carbonitrile | M + H⁺ 414 |

TABLE XV-continued

| N° & Note | Structure | Name | Mass spectrum |
|---|---|---|---|
| [41] | 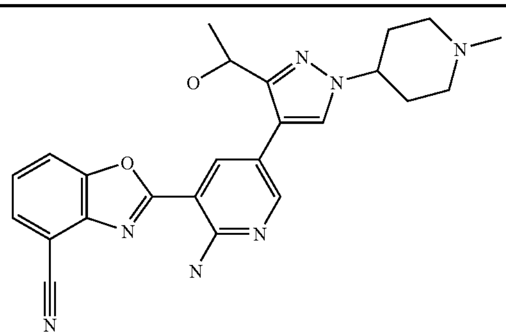 | 2-[2-amino-5-[3-(1-hydroxyethyl)-1-(1-methyl-4-piperidyl)pyrazol-4-yl]-3-pyridyl]-1,3-benzoxazole-4-carbonitrile | M + H⁺ 444 |
| [42] | 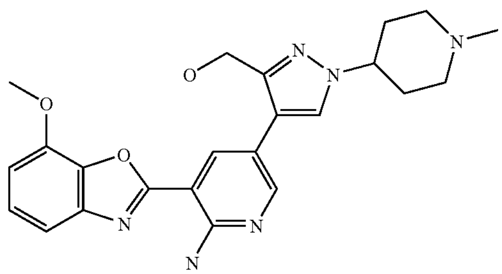 | [4-[6-amino-5-(7-methoxy-1,3-benzoxazol-2-yl)-3-pyridyl]-1-(1-methyl-4-piperidyl)pyrazol-3-yl]methanol | M + H⁺ 435 |
| [43] | 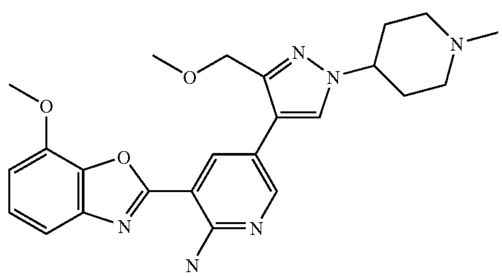 | 3-(7-methoxy-1,3-benzoxazol-2-yl)-5-[3-(methoxymethyl)-1-(1-methyl-4-piperidyl)pyrazol-4-yl]pyridin-2-amine | M + H⁺ 449 |
| [44] | 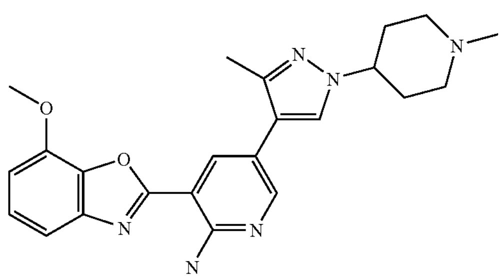 | 3-(7-methoxy-1,3-benzoxazol-2-yl)-5-[3-methyl-1-(1-methyl-4-piperidyl)pyrazol-4-yl]pyridin-2-amine | M + H⁺ 419 |

The products gave the following characterising data:

[1] NMR Spectrum: (DMSOd6) 1.94-2.12 (m, 6H), 2.21 (s, 3H), 2.83-2.92 (m, 2H), 4.06-4.17 (m, 1H), 7.67 (bs, 2H), 7.89 (d, 1H), 7.93 (s, 1H), 8.33 (s, 1H), 8.45 (d, 1H), 8.57 (d, 1H), 8.61 (d, 1H), 9.13 (s, 1H)

[2] NMR Spectrum: (DMSOd6) 1.56-1.68 (m, 1H), 1.72-1.84 (m, 2H), 1.91-1.99 (m, 1H), 2.03-2.11 (m, 1H), 2.23 (s, 3H), 2.24-2.28 (m, 1H), 2.69-2.77 (m, 1H), 3.03 (dd, 1H), 4.24-4.33 (m, 1H), 7.41-7.50 (m, 2H), 7.60 (bs, 2H), 7.80 (dd, 1H), 7.84 (dd, 1H), 7.92 (s, 1H), 8.34 (s, 1H), 8.43 (d, 1H), 8.52 (d, 1H)

[3] NMR Spectrum: (DMSOd6) 1.97-2.12 (m, 6H), 2.22 (s, 3H), 2.83-2.93 (m, 2H), 4.07-4.17 (m, 1H), 7.53 (dd, 1H), 7.68 (bs, 2H), 7.96 (s, 1H), 8.29 (dd, 1H), 8.38 (s, 1H), 8.40 (dd, 1H), 8.46 (d, 1H), 8.56 (d, 1H)

[4] NMR Spectrum: (DMSOd6) 1.93-2.12 (m, 6H), 2.22 (s, 3H), 2.84-2.92 (m, 2H), 4.07-4.17 (m, 1H), 7.86 (dd, 1H), 7.68 (bs, 2H), 7.93 (s, 1H), 8.23 (dd, 1H), 8.34 (s, 1H), 8.47 (d, 1H), 8.56 (dd, 1H), 8.59 (d, 1H)

[5] NMR Spectrum: (DMSOd6) 1.99-2.17 (m, 6H), 2.23 (s, 3H), 2.85-2.94 (m, 2H), 4.46-4.54 (m, 1H), 7.41-7.51 (m, 2H), 7.70-8.00 (m, 4H), 8.72 (d, 1H), 8.73 (d, 1H), 8.75 (s, 1H)

[6] NMR Spectrum: (CDCl3) 1.34-1.45 (m, 2H), 1.61-1.69 (m, 2H), 1.89-1.99 (m, 3H), 2.28 (s, 3H), 2.84-2.91 (m, 2H), 4.04 (d, 2H), 6.90 (bs, 2H), 7.34-7.40 (m, 2H), 7.57-7.62 (m, 1H), 7.63 (s, 1H), 7.72-7.77 (m, 1H), 7.79 (s, 1H), 8.38 (s, 2H)

[7] NMR Spectrum: (CDCl3) 2.05-2.27 (m, 6H), 2.35 (s, 3H), 2.97-3.07 (m, 2H), 4.13-4.23 (m, 1H), 6.86 (bs, 2H), 7.86 (dd, 1H), 7.69 (s, 1H), 7.77 (s, 1H), 8.35 (d, 1H), 8.44 (d, 1H), 8.48 (dd, 1H)

[8] NMR Spectrum: (DMSOd6) 2.35 (s, 3H), 3.38-3.44 (m, 2H), 3.69-3.75 (m, 2H), 4.91-4.99 (m, 1H), 7.41-7.50 (m, 2H), 7.67 (bs, 2H), 7.78-7.82 (m, 1H), 7.83-7.87 (m, 1H), 7.99 (s, 1H), 8.43 (s, 1H), 8.45 (d, 1H), 8.54 (d, 1H)

[9] NMR Spectrum: (DMSOd6) 2.11-2.19 (m, 1H), 2.31 (s, 3H), 2.34-2.43 (m, 1H), 2.51-2.56 (m partially hidden by DMSO-d$_6$, 1H), 2.73-2.81 (m, 2H), 2.88 (dd, 1H), 4.87-4.94 (m, 1H), 7.41-7.49 (m, 2H), 7.65 (bs, 2H), 7.79-7.82 (m, 1H), 7.83-7.87 (m, 1H), 7.92 (s, 1H), 8.31 (s, 1H), 8.43 (d, 1H), 8.53 (d, 1H)

[10] NMR Spectrum: (CDCl3) 2.06-2.28 (m, 6H), 2.35 (s, 3H), 2.97-3.06 (m, 2H), 4.14-4.23 (m, 1H), 6.85 (bs, 2H), 7.13 (dd, 1H), 7.28-7.34 (m, 2H), 7.53 (d, 1H), 7.72 (s, 1H), 7.79 (s, 1H), 8.41 (s, 2H)

[11] NMR Spectrum: (CDCl3) 2.33 (s, 3H), 2.95-3.03 (m, 1H), 3.05-3.12 (m, 2H), 3.35-3.42 (m, 2H), 4.39 (d, 2H), 6.88 (bs, 2H), 7.34-7.41 (m, 2H), 7.58-7.63 (m, 1H), 7.65 (s, 1H), 7.73-7.77 (m, 1H), 7.78 (s, 1H), 8.36-8.40 (m, 2H)

[12] NMR Spectrum: (DMSOd6) 1.93-2.10 (m, 6H), 2.21 (s, 3H), 2.60 (s, 3H), 2.83-2.91 (m, 2H), 4.07-4.16 (m, 1H), 7.34 (d, 1H), 7.66 (bs, 2H), 7.92 (s, 1H), 8.10 (d, 1H), 8.32 (s, 1H), 8.43 (d, 1H), 8.57 (d, 1H)

[13] NMR Spectrum: (CDCl3) 1.47 (t, 3H), 2.00-2.13 (m, 2H), 2.13-2.29 (m, 4H), 2.37 (s, 3H), 2.95-3.09 (m, 2H), 3.92-4.04 (m, 1H), 4.35 (q, 2H), 6.80 (bs, 2H), 7.33-7.39 (m, 2H), 7.52 (s, 1H), 7.56-7.62 (m, 1H), 7.71-7.77 (m, 1H), 8.54 (d, 1H), 8.55 (d, 1H)

[14] NMR Spectrum: (CDCl3) 2.01-2.13 (m, 2H), 2.13-2.28 (m, 4H), 2.36 (s, 3H), 2.96-3.10 (m, 2H), 3.94-4.04 (m, 1H), 4.03 (s, 3H), 6.82 (bs, 2H), 7.33-7.40 (m, 2H), 7.52 (s, 1H), 7.57-7.64 (m, 1H), 7.71-7.67 (m, 1H), 8.48 (d, 1H), 8.50 (d, 1H)

[15] NMR Spectrum: (DMSOd6) 1.46-1.56 (m, 1H), 1.81-1.91 (m, 1H), 2.23 (s, 3H), 2.28-2.33 (m, 1H), 2.33-240 (m, 1H), 2.40-2.45 (m, 1H), 2.50-2.56 (m, 1H), 2.64-2.73 (m, 1H), 4.05 (dd, 1H), 4.09 (dd, 1H), 7.40-7.49 (m, 2H), 7.65 (bs, 2H), 7.77-7.82 (m, 1H), 7.82-7.87 (m, 1H), 7.91 (s, 1H), 8.28 (s, 1H), 8.42 (d, 1H), 8.52 (d, 1H)

[16] NMR Spectrum: (DMSOd6) 1.93-2.11 (m, 6H), 2.21 (s, 3H), 2.83-2.91 (m, 2H), 4.07-4.16 (m, 1H), 7.53 (ddd, 1H), 7.61 (bs, 2H), 7.70 (ddd, 1H), 7.94 (s, 1H), 8.35 (s, 1H), 8.41 (d, 1H), 8.56 (d, 1H)

[17] NMR Spectrum: (DMSOd6) 1.77-1.84 (m, 2H), 2.00-2.11 (m, 4H), 2.15 (s, 3H), 2.21 (s, 3H), 2.25 (s, 3H), 2.84-0.291 (m, 2H), 4.01-4.11 (m, 1H), 7.39-7.47 (m, 2H), 7.67 (bs, 2H), 7.75-7.79 (m, 1H), 7.81-7.87 (m, 1H), 8.10 (d, 1H), 8.14 (d, 1H)

[18] NMR Spectrum: (DMSOd6) 1.78-1.87 (m, 2H), 2.02-2.13 (m, 4H), 2.22 (s, 3H), 2.40 (s, 3H), 2.84-2.94 (m, 2H), 4.10-4.19 (m, 1H), 7.40-7.48 (m, 2H), 7.65 (s, 1H), 7.67 (bs, 2H), 7.79 (dd, 1H), 7.84 (dd, 1H), 7.21 (d, 1H), 7.28 (d, 1H)

[19] NMR Spectrum: (CDCl3) 2.04-2.71 (m, 9H), 3.2 (bs, 2H), 4.28 (bs, 1H), 4.79 (s, 2H), 6.95 (bs, 2H), 7.35-7.42 (m, 2H), 7.56-7.61 (m, 1H), 7.62 (s, 1H), 7.72-7.77 (m, 1H), 8.36 (d, 1H), 8.43 (d, 1H)

[20] NMR Spectrum: (DMSOd6) 1.91-2.09 (m, 6H), 2.21 (s, 3H), 2.33 (s, 3H), 2.82-2.90 (m, 2H), 3.98-4.08 (m, 1H), 7.52 (dd, 1H), 7.68 (bs, 2H), 8.09 (s, 1H), 8.28 (dd, 1H), 8.28 (s, 1H), 8.36-8.42 (m, 2H)

[21] NMR Spectrum: (DMSOd6) 1.92-2.12 (m, 6H), 2.22 (s, 3H), 2.54 (s, 3H), 2.84-2.92 (m, 2H), 4.03-4.13 (m, 1H), 7.44-7.53 (m, 2H), 7.80 (bs, 2H), 7.86 (d, 1H), 7.90 (d, 1H), 8.28 (s, 1H), 8.57 (s, 1H)

[22] NMR Spectrum: (DMSOd6) 1.91-2.10 (m, 6H), 2.20 (s, 3H), 2.33 (s, 3H), 2.82-2.91 (m, 2H), 3.99-4.07 (m, 1H), 7.47 (dd, 1H), 7.68 (bs, 2H), 8.07 (s, 1H), 8.23 (dd, 1H), 8.31 (d, 1H), 8.41 (d, 1H), 8.55 (dd, 1H)

[23] NMR Spectrum: (DMSOd6) 1.90-2.09 (m, 6H), 2.21 (s, 3H), 2.32 (s, 3H), 2.82-2.91 (m, 2H), 3.98-4.08 (m, 1H), 7.32 (dd, 1H), 7.47 (ddd, 1H), 7.61 (bs, 2H), 7.67 (d, 1H), 8.07 (s, 1H), 8.28 (d, 1H), 8.37 (d, 1H)

[24] NMR Spectrum: (CDCl3) 2.06-2.30 (m, 6H), 2.37 (s, 3H), 2.99-3.08 (m, 2H), 4.09 (s, 3H), 4.14-4.25 (m, 1H), 6.85 (d, 1H), 6.90 (bs, 2H), 7.24 (d, 1H), 7.30 (dd, 1H), 7.70 (s, 1H), 7.78 (s, 1H), 8.36 (s, 2H)

[25] NMR Spectrum: (CDCl3) 2.05-2.27 (m, 6H), 2.35 (s, 3H), 2.98-3.06 (m, 2H), 4.14-4.24 (m, 1H), 6.94 (bs, 2H), 7.45 (dd, 1H), 7.68 (dd, 1H), 7.70 (s, 1H), 7.78 (s, 1H), 7.83 (dd, 1H), 8.37 (d, 1HO, 8.44 (d, 1H)

[26] NMR Spectrum: (DMSOd6): 1.93-2.10 (m, 6H), 2.21 (s, 3H), 2.83-2.91 (m, 2H), 3.40 (s, 3H), 4.06-4.15 (m, 1H), 4.40 (m, 2H), 7.40-7.48 (m, 2H), 7.65 (bs, 2H), 7.78 (dd, 1H), 7.84 (dd, 1H), 8.21 (s, 1H), 8.43 (d, 1H), 8.50 (d, 1H)

[27] NMR Spectrum: (DMSOd6) 1.94-2.10 (m, 6H), 2.22 (s, 3H), 2.82-2.93 (m, 2H), 4.03 (s, 3H), 4.07-4.17 (m, 1H), 7.10 (d, 1H), 7.36 (dd, 1H), 7.41 (d, 1H), 7.63 (bs, 2H), 7.91 (s, 1H), 8.32 (s, 1H), 8.35 (d, 1H), 8.52 (d, 1H)

[28] NMR Spectrum: (DMSOd6) 1.96-2.15 (m, 6H), 2.23 (s, 3H), 2.85-2.94 (m, 2H), 4.25-4.35 (m, 1H), 7.42-7.51 (m, 2H), 7.81 (dd, 1H), 7.87 (dd, 1H), 7.93 (bs, 2H), 8.56 (s, 2H), 8.64 (s, 1H)

[29] NMR Spectrum: (DMSOd6) 1.44 (d, 3H), 1.93-2.12 (m, 6H), 2.22 (s, 3H), 2.84-2.93 (m, 2H), 4.03-4.14 (m, 1H), 4.79-4.88 (m, 1H), 5.22 (d, 1H), 7.41-7.49 (m, 2H), 7.64 (bs, 2H), 7.78 (dd, 1H), 7.85 (dd, 1H), 8.08 (s, 1H), 8.51 (d, 1H), 8.57 (d, 1H)

[30] NMR Spectrum: (DMSOd6) 1.95-2.12 (m, 6H), 2.22 (s, 3H), 2.83-2.90 (m, 2H), 2.91 (s, 3H), 3.03 (s, 3H), 4.11-4.20 (m, 1H), 7.40-7.50 (m, 2H), 7.68 (bs, 2H), 7.79 (dd, 1H), −7.84 (dd, 1H), 8.32 (s, 1H), 8.33 (d, 1H), 8.35 (d, 1H)

[31] NMR Spectrum: (DMSOd6) 1.87-1.97 (m, 2H), 2.97-2.06 (m, 4H), 2.20 (s, 3H), 2.65 (s, 6H), 2.82-2.89 (m, 2H), 3.89-3.87 (bs, 1H), 7.40-7.48 (m, 2H), 7.62 (bs, 2H), 7.81 (dd, 1H), 7.84 (dd, 1H), 7.96 (s, 1H), 8.40 (d, 1H), 8.43 (d, 1H)

[32] NMR Spectrum: (DMSOd6) 1.93-2.10 (m, 6H), 2.22 (s, 3H), 2.84-2.92 (m, 2H), 4.04-4.13 (m, 1H), 4.50 (d, 2H), 6.25 (t, 1H), 7.32 (dd, 1H), 7.47 (ddd, 1H), 7.62 (bs, 2H), 7.65 (d, 1H), 8.17 (s, 1H), 4.55 (d, 1H), 8.56 (d, 1H)

[33] NMR Spectrum: (DMSOd6) 2.01-2.12 (m, 6H), 2.22 (s, 3H), 2.75 (d, 3H), 2.84-2.93 (m, 2H), 4.11-4.22 (m, 1H), 7.40-7.48 (m, 2H), 7.69 (bs, 2H), 7.80 (dd, 1H), 7.84 (dd, 1H), 8.06 (q, 1H), 8.22 (s, 1H), 8.44 (d, 1H), 8.59 (d, 1H)

[34] NMR Spectrum: (DMSOd6) 1.92-2.10 (m, 6H), 2.21 (s, 3H), 2.82-2.91 (m, 2H), 3.41 (s, 3H), 4.06-4.16 (m, 1H), 4.40 (s, 2H), 7.32 (dd, 1H), 7.46 (ddd, 1H), 7.62 (bs, 2H), 7.66 (d, 1H), 8.22 (s, 1H), 8.46 (d, 1H), 8.50 (d, 1H)

[35] NMR Spectrum: (DMSOd6) 2.01-2.11 (m, 6H), 2.22 (s, 3H), 2.84-2.94 (m, 2H), 4.12-4.21 (m, 1H), 7.26 (bs, 1H), 7.40-7.49 (m, 3H), 7.69 (bs, 2H), 7.77-7.81 (m, 1H), 7.82-7.86 (m, 1H), 8.22 (s, 1H), 8.45 (d, 1H), 8.60 (d, 1H)

[36] NMR Spectrum: (DMSOd6) 1.94-2.13 (m, 6H), 2.22 (s, 3H), 2.83-2.92 (m, 2H), 2.97 (d, 3H), 4.11-4.20 (m, 1H), 7.52 (dd, 1H), 7.65 (bs, 2H), 7.82 (dd, 1H), 7.92 (s, 1H), 7.98 (dd, 1H), 8.28 (s, 1H), 8.44 (q, 1H), 8.54 (d, 1H), 8.57 (d, 1H)

[37] NMR Spectrum: (DMSOd6): 1.94-2.13 (m, 6H), 2.22 (s, 3H), 2.83-2.91 (m, 2H), 2.92 (s, 3H), 3.03 (s, 3H), 4.11-4.20 (m, 1H), 7.32 (dd, 1H), 7.47 (ddd, 1H), 7.65 (bs, 2H), 7.67 (d, 1H), 8.33 (s, 1H), 8.35 (d, 1H), 8.36 (d, 1H).

[38] NMR Spectrum: (DMSOd6): 1.93-2.11 (m, 6H), 2.21 (s, 3H), 2.83-2.93 (m, 2H), 4.04-4.14 (m, 1H), 4.50 (d, 2H), 5.27 (t, 1H), 7.60 (dd, 1H), 7.70 (bs, 2H), 7.93 (d, 1H), 8.14 (d, 1H), 8.18 (s, 1H), 8.59 (s, 2H).

[39] NMR Spectrum: (DMSOd6): 1.93-2.11 (m, 6H), 2.21 (s, 3H), 2.83-2.92 (m, 2H), 3.41 (s, 3H), 4.05-4.15 (m, 1H), 4.41 (s, 2H), 7.60 (dd, 1H), 7.70 (bs, 2H), 7.93 (d, 1H), 8.16 (d, 1H), 8.23 (s, 1H), 8.50 (d, 1H), 8.52 (d, 1H).

[40] NMR Spectrum: (DMSOd6): 1.77-1.90 (m, 2H), 2.03-2.15 (m, 4H), 2.22 (s, 3H), 2.40 (s, 3H), 2.83-2.95 (m, 2H), 4.10-4.22 (m, 1H), 7.60 (dd, 1H), 7.66 (s, 1H), 7.72 (bs, 2H), 7.93 (d, 1H), 8.17 (d, 1H), 8.24 (d, 1H), 8.35 (d, 1H)

[41] NMR Spectrum: (DMSOd6): 1.43 (d, 3H), 1.92-2.10 (m, 6H), 2.21 (s, 3H), 2.82-2.91 (m, 2H), 4.03-4.12 (m, 1H), 4.78-4.86 (m, 1H), 5.24 (d, 1H), 7.59 (dd, 1H), 7.70 (bs, 2H), 7.93 (d, 1H), 8.09 (s, 1H), 8.14 (d, 1H), 8.58 (d, 1H), 8.60 (d, 1H).

[42] NMR Spectrum: (DMSOd6): 1.94-2.08 (m, 6H), 2.22 (s, 3H), 2.85-2.91 (m, 2H), 4.03 (s, 3H), 4.05-4.13 (m, 1H), 4.48 (d, 2H), 5.22 (t, 1H), 7.08 (dd, 1H), 7.34 (dd, 1H), 7.41 (dd, 1H), 7.62 (bs, 2H), 8.16 (s, 1H), 8.49 (d, 1H), 8.52 (d, 1H).

[43] NMR Spectrum: (DMSOd6): 1.90-2.12 (m, 6H), 2.22 (s, 3H), 2.83-2.92 (m, 2H), 3.43 (s, 3H), 4.01 (s, 3H), 4.06-4.18 (m, 1H), 4.40 (s, 2H), 7.09 (d, 1H), 7.35 (dd, 1H), 7.41 (d, 1H), 7.63 (bs, 2H), 8.21 (s, 1H), 8.44 (s, 1H), 8.50 (s, 1H).

[44] NMR Spectrum: (DMSOd6): 1.78-1.88 (m, 2H), 2.02-2.14 (m, 4H), 2.22 (s, 3H), 2.39 (s, 3H), 2.83-2.94 (m, 2H), 4.02 (s, 3H), 4.09-4.19 (m, 1H), 7.08 (dd, 1H), 7.35 (dd, 1H), 7.41 (dd, 1H), 7.63 (bs, 2H), 7.64 (s, 1H), 8.16 (d, 1H), 8.27 (d, 1H).

EXAMPLE 42

3-oxazolo[5,4-b]pyridin-2-yl-5-[4-(3-pyrrolidin-1-ylpropoxy)phenyl]pyridin-2-amine

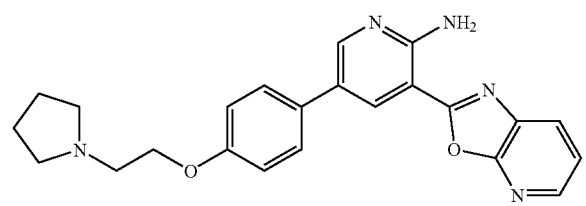

A solution of di-tert-butyl azodicarboxylate (DTAD) (227 mg) in dichloromethane (1 ml) was added to a stirred solution of 4-(6-amino-5-oxazolo[5,4-b]pyridin-2-yl-3-pyridyl)phenol (100 mg), polystyrene bound triphenylphosphine (330 mg, 3 mmol/g) and 3-pyrrolidin-1-ylpropan-1-ol (64 mg) in DMF (2 ml) at room temperature under argon. The resulting suspension was stirred at room temperature for 2 hours. The mixture was filtered and the resulting solid was washed with methanol. The filtrates were combined, concentrated to dryness and diluted with DCM/TFA (1 ml: 1 ml). The mixture was stirred for 30 min and concentrated. The reaction mixture was purified by preparative HPLC using a Waters X-Bridge reverse-phase column (C-18, 5 micron silica, 19 mm diameter, 100 mm length, flow rate of 40 ml/minute) and decreasingly polar mixtures of water (containing 1% acetic acid) and Methanol as eluent. The fractions containing the desired compound were evaporated to dryness to afford 3-oxazolo[5,4-b]pyridin-2-yl-5-[4-(3-pyrrolidin-1-ylpropoxy)phenyl]pyridin-2-amine (36 mg) as a solid. NMR Spectrum: (DMSOd6) 1.86 (bs, 4H), 2.03-2.15 (m, 2H), 3.02-3.33 (m partially hidden by H2O, 6H), 4.11 (t, 2H), 7.06 (d, 2H), 7.53 (dd, 1H), 7.68 (d, 2H), 7.77 (bs, 2H), 8.30 (dd, 1H), 8.40 (dd, 1H), 8.46 (d, 1H), 8.58 (d, 1H); Mass spectrum: M+H+ 416. The 4-(6-amino-5-oxazolo[5,4-b]pyridin-2-yl-3-pyridyl)phenol used as starting material was made as follows:

A mixture of 5-bromo-3-oxazolo[5,4-b]pyridin-2-yl-pyridin-2-amine (1 g, Example 9 starting material), 4-(4,4,5,5-tetramethyl-1,3,2-dioxaborolan-2-yl)phenol (0.794 g), bis (triphenylphosphine) palladium(II) chloride (0.121 g) and caesium fluoride (1.56 g) in methanol (17 ml) was heated at 120° C. for 20 min in a microwave oven. The reaction was repeated and the reaction mixtures were combined. The resulting mixture was concentrated, then diluted with water (400 ml) and stirred for 30 min. The resulting solid was filtered, washed with water (4×150 ml), dried, washed with diethyl ether (4×150 ml) and dried overnight to give 4-(6-amino-5-oxazolo[5,4-b]pyridin-2-yl-3-pyridyl)phenol (12.3 g) as a solid. NMR Spectrum: (DMSOd6) 6.88 (d, 2H), 7.50-7.57 (m, 3H), 7.72 (bs, 2H), 8.28 (dd, 1H), 8.37-8.42 (m, 2H), 8.53 (d, 1H), 8.55 (bs, 1H); Mass spectrum: M+H+ 355

EXAMPLE 43A

Using an analogous procedure to that described in Example 42, the following examples were prepared by reacting 4-(6-amino-5-oxazolo[5,4-b]pyridin-2-yl-3-pyridyl)phenol with an appropriate alcohol:

TABLE XVI

| No. & Note | R1 | G1 | G4 | RT (min) | MS (M + H+) |
|---|---|---|---|---|---|
| [A1] | 3-(4-methylpiperazin-1-yl)propoxy | CH | N | 1.72 | 431 |
| [A2] | 2-(morpholin-4-yl)ethoxy | CH | N | 2.08 | 418 |
| [A3] | 2-(pyrrolidin-1-yl)ethoxy | CH | N | 1.70 | 402 |

[2] NMR Spectrum: (DMSOd6) 2.32-2.93 (m, 6H), 3.65 (bs, 4H), 4.32 (bs, 2H), 7.08 (d, 2H), 7.53 (dd, 1H), 7.67 (d, 2H), 7.77 (bs, 2H), 8.29 (dd, 1H), 8.39 (dd, 1H), 8.45 (d, 1H), 8.58 (d, 1H)

EXAMPLE 43B

The following examples were prepared by reacting 4-(6-amino-5-oxazolo[4,5-b]pyridin-2-yl-3-pyridyl)phenol with the appropriate alcohol using the following procedure: di-tert-butyl azodicarboxylate (DTAD) (227 mg) in dichloromethane (2 ml) was added to a stirred suspension of the appropriate alcohol (0.66 mol), 4-(6-amino-5-oxazolo[4,5-b] pyridin-2-yl-3-pyridyl)phenol (100 mg) and polystyrene bound triphenylphosphine (329 mg, 3 mmol/g) dissolved in THF (3 ml) at room temperature. The resulting suspension was stirred at room temperature for 18 hours. The mixture was filtered. The resulting solution was concentrated to dryness. TFA/DCM (2 ml, 1:1) was added. The mixture was stirred at room temperature for 2 hours and concentrated to dryness. The residue was dissolved in DMF (1.5 ml) and purified by preparative HPLC using a Waters X-Bridge reverse-phase column (C-18, 5 microns silica, 19 mm diameter, 100 mm length, flow rate of 40 ml/minute) and decreasingly polar mixtures of water (containing 1% acetic acid) and acetonitrile as eluent. The fractions containing the desired compound were evaporated to dryness. The residue was dissolved in a mixture of methanol (10 ml), water (10 ml) and 30% aqueous ammonia (1 ml) and concentrated to dryness to give the title compound.

The 4-(6-amino-5-oxazolo[4,5-b]pyridin-2-yl-3-pyridyl)phenol used as starting material was made from 5-bromo-3-(oxazolo[4,5-b]pyridin-2-yl)pyridin-2-amine (Example 10, starting material) and 4-(4,4,5,5-tetramethyl-1,3,2-dioxaborolan-2-yl)phenol in several batches (using about 1 g of 5-bromo-3-(oxazolo[4,5-b]pyridin-2-yl)pyridin-2-amine each time) according to the starting material portion of the procedure described in Example 42. The different batches were combined. The reaction mixture was concentrated, diluted with water (400 ml) and stirred for 30 min. The resulting solid was filtered, washed with water, dried, washed with diethyl ether and dried overnight. The resulting solid was suspended in THF and heated at 70° C. during 10 minutes. The mixture was filtered and washed with THF. The solid was triturated in diethyl ether, filtered and dried to give 4-(6-amino-5-(oxazolo[4,5-b]pyridin-2-yl)pyridin-3-yl)phenol (10.34 g) as a solid. NMR Spectrum (DMSOd6): 6.87 (d, 2H), 7.49 (dd, 1H), 7.52 (d, 2H), 7.71 (bs, 2H), 8.24 (dd, 1H), 8.43 (d, 1H), 8.53-8.58 (m, 2H), 9.55 (s, 1H); Mass spectrum: M+H⁺ 305.

TABLE XVII

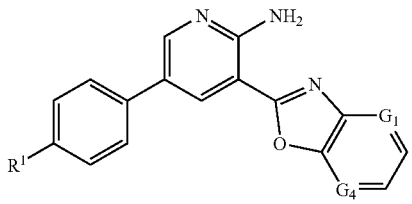

| No. & Note | R¹ | G₁ | G₄ | RT (min) | MS (M + H⁺) |
|---|---|---|---|---|---|
| [B1] | 2-(pyrrolidin-1-yl)ethoxy | N | CH | 1.70 | 402 |
| [B2] | 2-dimethylaminoethoxy | N | CH | 1.59 | 376 |
| [B3] | 2-diethylaminoethoxy | N | CH | 1.75 | 404 |
| [B4] | (1-methylpyrrolidin-3-yl)oxy | N | CH | 1.67 | 388 |
| [B5] | [(2S)-1-methylpyrrolidin-2-yl]methoxy | N | CH | 1.74 | 402 |
| [B6] | 2-morpholinoethoxy | N | CH | 1.82 | 418 |
| [B7] | 2-(4-methylpiperazin-1-yl)ethoxy | N | CH | 1.75 | 431 |
| [B8] | 2-(piperidin-1-yl)ethoxy | N | CH | 1.80 | 416 |
| [B9] | (1-methylpiperidin-3-yl)oxy | N | CH | 1.74 | 402 |
| [B10] | 3-dimethylaminopropoxy | N | CH | 1.74 | 390 |
| [B11] | (1-methylpiperidin-4-yl)oxy | N | CH | 1.75 | 402 |
| [B12] | (1-methylpiperidin-3-yl)methoxy | N | CH | 1.87 | 416 |
| [B13] | 2-(1-methylpiperidin-2-yl)ethoxy | N | CH | 1.90 | 430 |
| [B14] | 3-(4-methylpiperazin-1-yl)propoxy | N | CH | 1.80 | 445 |
| [B15] | 3-(4-methylsulphonylpiperazin-1-yl)propoxy | N | CH | 2.08 | 509 |
| [B16] | 3-(1,1-dioxo-1,4-thiazinan-4-yl)propoxy | N | CH | 3.00 | 480 |
| [B17] | 2-(1-methylpyrrolidin-2-yl)ethoxy | N | CH | 1.84 | 416 |
| [B18] | 3-(pyrrolidin-1-yl)propoxy | N | CH | 1.83 | 416 |
| [B19] | 3-morpholinopropoxy | N | CH | 1.82 | 432 |
| [B20] | 3-diethylaminopropoxy | N | CH | 1.87 | 418 |
| [B21] | [(1R,5S)-8-methyl-8-azabicyclo[3.2.1]octan-3-yl]oxy | N | CH | 1.80 | 428 |
| [B22] | 2-(2-morpholinoethoxy)ethoxy | N | CH | 1.83 | 462 |
| [B23] | 4-(1,1-dioxo-1,4-thiazinan-4-yl)but-2-ynoxy | N | CH | 3.24 | 490 |
| [B24] | 3-(4-methylpiperazin-1-yl)sulphonylpropoxy | N | CH | 2.05 | 509 |
| [B25] | 2-aminoethoxy | N | CH | 1.57 | 348 |
| [B26] | 2-methylaminoethoxy | N | CH | 1.61 | 362 |
| [B27] | pyrrolidin-3-yloxy | N | CH | 1.68 | 374 |
| [B28] | [(2R)-pyrrolidin-2-yl]methoxy | N | CH | 1.74 | 388 |

TABLE XVII-continued

| No. & Note | R¹ | G₁ | G₄ | RT (min) | MS (M + H⁺) |
|---|---|---|---|---|---|
| [B29] | 2-(piperazin-1-yl)ethoxy | N | CH | 1.74 | 417 |
| [B30] | piperidin-3-yloxy | N | CH | 1.75 | 388 |
| [B31] | 3-aminopropoxy | N | CH | 1.67 | 362 |
| [B32] | 3-methylaminopropoxy | N | CH | 1.72 | 376 |
| [B33] | 4-piperidyloxy | N | CH | 1.77 | 388 |
| [B34] | 4-aminobutoxy | N | CH | 1.80 | 376 |
| [B35] | 2-(piperidin-4-yl)ethoxy | N | CH | 1.96 | 416 |
| [B36] | piperidin-4-ylmethoxy | N | CH | 1.85 | 402 |
| [B37] | 2-(piperidin-4-yloxy)ethoxy | N | CH | 1.83 | 432 |
| [B38] | 3-(piperazin-1-yl)propoxy | N | CH | 1.73 | 431 |
| [B39] | 2-(azetidin-3-yloxy)ethoxy | N | CH | 1.75 | 404 |
| [B40] | 2-(piperidin-2-yl)ethoxy | N | CH | 1.89 | 416 |
| [B41] | piperidin-3-ylmethoxy | N | CH | 1.87 | 402 |
| [B42] | 3-[(3R,5S)-3,5-dimethylpiperazin-1-yl]propoxy | N | CH | 1.85 | 459 |
| [B43] | 2-(2-piperazin-1-ylethoxy)ethoxy | N | CH | 1.74 | 461 |

The products gave the following characterising data:

[B1] NMR Spectrum (DMSOd6): 1.83-1.90 (m, 4H), 2.72 (bs, 4H), 2.96-3.02 (m, 2H), 4.29 (t, 2H), 7.22 (d, 2H), 7.66 (dd, 1H), 7.81 (d, 2H), 7.91 (bs, 2H), 8.42 (dd, 1H), 8.64 (d, 1H), 8.72 (dd, 1H), 8.76 (d, 1H)

[B2] NMR Spectrum: (DMSO-d6+TFAd) 2.90 (s, 6H), 3.57 (t, 2H), 4.40 (t, 2H), 7.17 (d, 2H), 7.58 (dd, 1H), 7.80 (d, 2H), 8.31 (dd, 1H), 8.65 (dd, 1H), 8.67 (d, 1H), 9.00 (d, 1H)

[B15] 3-(4-methylsulphonylpiperazin-1-yl)propan-1-ol used as starting material was made according to AstraZeneca, PCT Int Appl WO2002012228 p 103.

[B16] 3-(1,1-dioxido-1,4-thiazinan-4-yl)propan-1-ol used as starting material was made according to AstraZeneca, PCT Int Appl WO2002012228 p 86.

[B18] 3-(Pyrrolidin-1-yl)propan-1-ol used as starting material was made according to AstraZeneca, PCT Int Appl WO2002012228 p 81.

[B22] 2-(2-morpholinoethoxy)ethanol (Calderon, S. et al., J. Med. Chem., 1994, 37, 2285) was used as starting material

[B23] The 4-(1,1-dioxo-1,4-thiazinan-4-yl)but-2-yn-1-ol used as starting material was made as follows: 4-aminobut-2-yn-1-ol (500 mg, Juenge E., J. Org. Chem., 1964, 24, 226) and 1-vinylsulphonylethylene (0.71 ml) were stirred at 110° C. for 1 hour and at 125° C. for 2 hours. The residue was purified by chromatography on silica gel (eluent: 2% to 5% methanol in DCM) to give 4-(1,1-dioxo-1,4-thiazinan-4-yl)but-2-yn-1-ol (512 mg). Mass spectrum: MH⁺ 204

[B24] 3-(4-methylpiperazin-1-yl)sulphonylpropan-1-ol (Miyake A., Eur. Pat. EP5 62440 (1993)) was used as starting material

[B25] BOC-glycinol was used as starting material.

[B26] tert-butyl N-(3-hydroxypropyl)carbamate was used as starting material.

[B27] tert-butyl 3-hydroxypyrrolidine-1-carboxylate was used as starting material.

[B28] BOC-D-prolinol was used as starting material.

[B29] tert-butyl 4-(2-hydroxyethyl)piperazine-1-carboxylate was used as starting material.

[B30] tert-butyl 3-hydroxypiperidine-1-carboxylate was used as starting material.

[B31] tert-butyl (3-hydroxypropyl)carbamate was used as starting material.

[B32] tert-butyl N-(4-hydroxybutyl)carbamate was used as starting material.

[B33] tert-butyl 4-hydroxypiperidine-1-carboxylate was used as starting material.

[B34] tert-butyl N-(4-hydroxybutyl)carbamate was used as starting material.

[B35] tert-butyl 4-(2-hydroxyethyl)piperidine-1-carboxylate was used as starting material.

[B36] tert-butyl 4-(hydroxymethyl)piperidine-1-carboxylate was used as starting material.

[B37] tert-butyl 4-(2-hydroxyethoxy)piperidine-1-carboxylate (Hennequin et al., PCT Int. Appl. WO2000047212) was used as starting material.

[B38] tert-butyl 4-(3-hydroxypropyl)piperazine-1-carboxylate was used as starting material.

[B39] tert-butyl 3-(2-hydroxyethoxy)azetidine-1-carboxylate used as starting material was made as follows:

Sodium hydride (2.03 g, 60% in oil) was added portionwise to a ice-cooled solution of tert-butyl 3-hydroxyazetidine-1-carboxylate (8 g) in DMF (20 ml). The mixture was stirred at 0° C. for 20 minutes and benzyl 2-bromoethyl ether (8.03 ml) was added. The mixture was heated at 80° C. for 18 hours. After cooling, the mixture was diluted in water and extracted with ethyl acetate. The organic layer was washed with brine and dried over magnesium sulfate. Evaporation of the solvent and chromatography on silica gel (eluting with 20% to 50% ethyl acetate in petroleum ether gave tert-butyl 3-(2-benzyloxyethoxy)azetidine-1-carboxylate (9.15 g).

tert-butyl 3-(2-benzyloxyethoxy)azetidine-1-carboxylate (7.1 g) in ethanol (200 ml) was hydrogenated for 3 hours in the presence of 10% palladium on charcoal at a 60 PSI pressure to give tert-butyl 4-(3-hydroxypropyl)piperazine-1-carboxylate (4.62 g); NMR Spectrum: (CDCl$_3$) 1.44 (s, 9H), 3.49 (m, 2H), 3.76 (m, 2H), 3.84 (m, 2H), 4.08 (m, 2H), 4.27 (m, 1H).

[B42] 3-[(3R,5S)-3,5-dimethylpiperazin-1-yl]propan-1-ol (Hennequin et al., PCT Int. Appl. WO2002016352) was used as starting material.

EXAMPLE 43C

The following examples were prepared using analogous procedures to those described in Example 43B. Compounds [C3] to [C38] were prepared using analogous procedures to that described for compound [C2].

TABLE XVIII

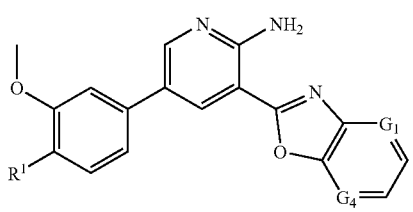

| No. & Note | R$^1$ | G$_1$ | G$_4$ | RT (min) | MS (M + H$^+$) |
|---|---|---|---|---|---|
| [C1] | 2-(pyrrolidin-1-yl)ethoxy | CH | N | 1.76 | 432 |
| [C2] | 2-morpholinoethoxy | N | CH | 1.85 | 448 |
| [C3] | 2-dimethylaminoethoxy | N | CH | 1.66 | 406 |

TABLE XVIII-continued

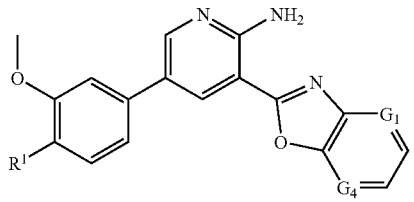

| No. & Note | R$^1$ | G$_1$ | G$_4$ | RT (min) | MS (M + H$^+$) |
|---|---|---|---|---|---|
| [C4] | 2-diethylaminoethoxy | N | CH | 1.76 | 434 |
| [C5] | 2-pyrrolidin-1-ylethoxy | N | CH | 1.72 | 432 |
| [C6] | [(2S)-1-methylpyrrolidin-2-yl]methoxy | N | CH | 1.76 | 432 |
| [C7] | 2-(4-methylpiperazin-1-yl)ethoxy | N | CH | 1.74 | 461 |
| [C8] | 2-(piperidin-1-yl)ethoxy | N | CH | 1.82 | 446 |
| [C9] | (1-methylpiperidin-3-yl)oxy | N | CH | 1.76 | 432 |
| [C10] | 3-dimethylaminopropoxy | N | CH | 1.73 | 420 |
| [C11] | (1-methyl-4-piperidyl)oxy | N | CH | 1.73 | 432 |
| [C12] | (1-methyl-3-piperidyl)methoxy | N | CH | 1.84 | 446 |
| [C13] | 2-(1-methyl-2-piperidyl)ethoxy | N | CH | 1.9 | 460 |
| [C14] | 3-(4-methylpiperazin-1-yl)propoxy | N | CH | 1.76 | 475 |
| [C15] | 3-(4-methylsulfonylpiperazin-1-yl)propoxy | N | CH | 2.09 | 539 |
| [C16] | 3-(1,1-dioxo-1,4-thiazinan-4-yl)propoxy | N | CH | 2.91 | 510 |
| [C17] | 3-morpholinopropoxy | N | CH | 1.81 | 462 |
| [C18] | 3-diethylaminopropoxy | N | CH | 1.85 | 448 |
| [C19] | [(1R,5R)-8-methyl-8-azabicyclo[3.2.1]octan-3-yl]oxy | N | CH | 1.76 | 458 |
| [C20] | 4-(1,1-dioxo-1,4-thiazinan-4-yl)but-2-ynoxy | N | CH | 3.11 | 520 |
| [C21] | 2-aminoethoxy | N | CH | 1.62 | 378 |
| [C22] | 2-methylaminoethoxy | N | CH | 1.64 | 392 |
| [C23] | pyrrolidin-3-yloxy | N | CH | 1.67 | 404 |
| [C24] | [(2R)-pyrrolidin-2-yl]methoxy | N | CH | 1.74 | 418 |
| [C25] | 2-piperazin-1-ylethoxy | N | CH | 1.71 | 447 |
| [C26] | 3-piperidyloxy | N | CH | 1.77 | 418 |
| [C27] | 3-aminopropoxy | N | CH | 1.68 | 392 |
| [C28] | 3-methylaminopropoxy | N | CH | 1.72 | 406 |
| [C29] | 4-piperidyloxy | N | CH | 1.74 | 418 |
| [C30] | 4-aminobutoxy | N | CH | 1.78 | 406 |
| [C31] | 2-(4-piperidyl)ethoxy | N | CH | 1.87 | 446 |
| [C32] | 3-piperazin-1-ylpropoxy | N | CH | 1.7 | 461 |
| [C33] | 3-piperidylmethoxy | N | CH | 1.83 | 432 |
| [C34] | 3-[(3R,5S)-3,5-dimethylpiperazin-1-yl]propoxy | N | CH | 1.8 | 489 |
| [C35] | 2-(2-piperazin-1-ylethoxy)ethoxy | N | CH | 1.74 | 491 |
| [C36] | [(3S,5R)-5-(methoxymethyl)pyrrolidin-3-yl]oxy | N | CH | 1.78 | 448 |
| [C37] | [(3S,4R)-3-methylaminotetrahydropyran-4-yl]oxy | N | CH | 1.73 | 448 |
| [C38] | azepan-4-yloxy | N | CH | 1.79 | 432 |

[C1] A solution of di-tert-butyl azodicarboxylate (37.9 mg) in dichloromethane (1 ml) was added to a stirred suspension of 4-(6-amino-5-(oxazolo[5,4-b]pyridin-2-yl)pyridin-3-yl)-2-methoxyphenol (50 mg), triphenylphosphine (43 mg) and 2-(pyrrolidin-1-yl)ethanol (19 mg) dissolved in dichloromethane (4 ml) under nitrogen. The resulting suspension was stirred at room temperature for 1 hour. Triphenylphosphine (43 mg) and a solution of DTAD (37.9 mg) in dichloromethane (1 ml) were added. The resulting mixture was stirred at room temperature for 20 minutes. After evaporation of the solvents, the residue was purified by flash chromatography on silica gel eluting with 5% methanol in dichloromethane and methanolic ammonia (7 N) in dichloromethane. After collection of the desired fractions and evaporation of the solvents, the resulting solid was triturated with acetonitrile to give 5-[3-methoxy-4-(2-pyrrolidin-1- ylethoxy)phenyl]-3-oxazolo[5,4-b]pyridin-2-yl-pyridin-2-amine (20 mg) as a solid. NMR Spectrum: (DMSOd6) 1.66-1.73 (m, 4H), 2.51-2.58 (m, 4H), 2.81 (t, 2H), 3.88 (s, 3H), 4.09 (t, 2H), 7.07 (d, 1H), 7.21 (dd, 1H), 7.28 (d, 1H), 7.53 (dd, 1H), 7.78 (bs, 2H), 8.30 (dd, 1H), 8.40 (dd, 1H), 8.47 (d, 1H), 8.60 (d, 1H)

The 4-(6-amino-5-oxazolo[5,4-b]pyridin-2-yl-3-pyridyl)-2-methoxy-phenol used as starting material was made as follows:

Using the procedure described in the starting material portion of Example 41, 5-bromo-3-oxazolo[5,4-b]pyridin-2-yl-pyridin-2-amine (1 g, Example 9 starting material) and 2-methoxy-4-(4,4,5,5-tetramethyl-1,3,2-dioxaborolan-2-yl)phenol (902 mg) were reacted to afford 4-(6-amino-5-oxazolo[5,4-b]pyridin-2-yl-3-pyridyl)-2-methoxy-phenol (940 mg) as a solid. NMR Spectrum: (DMSOd6) 3.89 (s, 3H), 6.87 (d, 1H), 7.11 (dd, 1H), 7.25 (d, 1H), 7.53 (dd, 1H), 7.74 (bs, 2H), 8.29 (dd, 1H), 8.39 (dd, 1H), 8.44 (d, 1H), 8.57 (d, 1H), 9.11 (bs, 1H); Mass spectrum: $M+H^+$ 335.

[C2] A solution of di-tert-butyl azodicarboxylate (241 mg) in dichloromethane (1 ml), was added dropwise to a stirred suspension of 4-(6-amino-5-(oxazolo[4,5-b]pyridin-2-yl)pyridin-3-yl)-2-methoxyphenol (130 mg), 2-morpholinoethanol (0.054 ml) and triphenylphosphine polymer bound (350 mg, 1.05 mmol) dissolved in dichloromethane (3 ml). The resulting suspension was stirred at room temperature for 2 hours. The mixture was filtered, washed with dichloromethane (1 ml) and methanol (1 ml). The solvent was evaporated. The resulting residue was diluted with 1 ml of dichloromethane and 1 ml of TFA; the mixture was stirred overnight and concentrated. The reaction mixture was purified by preparative HPLC using a Waters X-Bridge reverse-phase column (C-18, 5 microns silica, 19 mm diameter, 100 mm length, flow rate of 40 ml/minute) and decreasingly polar mixtures of water (containing 0.2% ammonium carbonate) and acetonitrile as eluent. The fractions containing the desired compound were evaporated to dryness to afford 5-[3-methoxy-4-(2-morpholinoethoxy)phenyl]-3-oxazolo[4,5-b]pyridin-2-yl-pyridin-2-amine (70 mg) as a solid. The 4-(6-amino-5-oxazolo[4,5-b]pyridin-2-yl-3-pyridyl)-2-methoxy-phenol used as starting material was made as follows:

A mixture of 2-methoxy-4-(4,4,5,5-tetramethyl-1,3,2-dioxaborolan-2-yl)phenol (90 mg), 5-bromo-3-oxazolo[4,5-b]pyridin-2-yl-pyridin-2-amine (100 mg), caesium fluoride (0.038 g) and bis(triphenylphosphine) palladium chloride (12.06 mg) were suspended in methanol (2 ml) and sealed into a microwave tube. The reaction was degassed, purged with nitrogen and heated to 120° C. over a period of 20 minutes in the microwave reactor. The solvent was removed; the residue was diluted with water (20 ml) and stirred for 30 min. The mixture was filtered, washed with water (3×10 ml), dried; and washed with diethyl ether (4×15 ml) and dichloromethane/diethyl ether (10 ml) and dried overnight to give 4-(6-amino-5-(oxazolo[4,5-b]pyridin-2-yl)pyridin-3-yl)-2-methoxyphenol (100 mg); NMR Spectrum: (DMSOd6) 3.88 (s, 3H), 6.87 (d, 1H), 7.09 (dd, 1H), 7.24 (d, 1H), 7.48 (dd, 1H), 7.73 (bs, 2H), 8.25 (dd, 1H), 8.46 (d, 1H), 8.55 (dd, 1H), 8.60 (d, 1H), 9.09 (s, 1H); Mass spectrum: $M+H^+$ 335.

[C36] The tert-butyl (2R,4R)-4-hydroxy-2-(methoxymethyl)pyrrolidine-1-carboxylate used as starting material was prepared as follows:

Iodomethane (4.17 ml) was added to (2R,4R)-1-tert-butoxycarbonyl-4-hydroxy-pyrrolidine-2-carboxylic acid (15.00 g) in DMF (100 ml) at 0° C. Caesium carbonate (25.4 g) was added in one portion and the resulting mixture stirred at 20° C. for 16 hours. The reaction mixture was diluted with water (150 ml) and extracted with dichloromethane (2×150 ml). The combined organics were washed with brine (100 ml), dried over Magnesium sulphate, filtered and evaporated to dryness to give O1-tert-butyl O2-methyl (2R,4R)-4-hydroxypyrrolidine-1,2-dicarboxylate (13.83 g) as a yellow oil. 1 NMR Spectrum: (DMSOd6) 1.32 (9H, s); 1.77-1.85 (1H, m); 2.24-2.38 (1H, m); 3.07-3.15 (1H, m); 3.47 (1H, q); 3.63 (3H, t); 4.16-4.23 (2H, m); 4.92-4.98 (1H, m).

Tert-Butyldimethylsilylchloride (9.36 g) was added to a mixture of O1-tert-butyl O2-methyl (2R,4R)-4-hydroxypyrrolidine-1,2-dicarboxylate (13.83 g) and imidazole (9.61 g) in DMF (100 ml). The reaction was stirred at 20° C. for 19 hours and then evaporated to dryness. The residues were slurried in diethyl ether and filtered. The filtrate was evaporated to dryness and the residues purified by flash chromatography on silica eluting with increasingly polar mixtures of methanol/dichloromethane (0/100-5/95). Fractions containing the desired product were combined and evaporated to dryness to give O1-tert-butyl O2-methyl (2R,4R) 4-(tert-butyl-dimethyl-silyl)oxypyrrolidine-1,2-dicarboxylate (10.35 g) as a colourless oil. NMR Spectrum: (DMSOd6) 0.00 (6H, s); 0.80 (9H, s); 1.32-1.38 (9H, m); 1.84-1.89 (1H, m); 2.30-2.35 (1H, m); 3.06-3.10 (1H, m); 3.49 (1H, q); 3.59 (3H, d); 4.22-4.26 (1H, m); 4.37 (1H, d).

2M Lithium borohydride in THF (15.06 ml) was added slowly to a stirred solution of O1-tert-butyl O2-methyl (2R, 4R) 4-(tert-butyl-dimethyl-silyl)oxypyrrolidine-1,2-dicarboxylate (10.35 g) in THF (100 ml) at 0° C. The resulting mixture was allowed to warm to 20° C. and stirred for a further 18 hours. The reaction mixture was quenched with water and evaporated to remove THF. The aqueous residues were extracted with DCM (250 ml). The organic phase was washed sequentially with water (250 ml) and saturated brine (250 ml), dried over Magnesium sulphate, filtered and evaporated to give tert-butyl (2R,4R) 4-(tert-butyl-dimethyl-silyl)oxy-2-(hydroxymethyl)pyrrolidine-1-carboxylate (9.32 g). NMR Spectrum: (DMSOd6) 0.01 (6H, s); 0.80-0.82 (9H, m); 1.34 (9H, s); 1.84-1.89 (1H, m); 1.99 (1H, m); 3.00 (1H, m); 3.53-3.57 (4H, m); 4.28 (1H, s); 4.48-4.49 (1H, m).

A solution of tert-butyl (2R,4R) 4-(tert-butyl-dimethyl-silyl)oxy-2-(hydroxymethyl)pyrrolidine-1-carboxylate (9.32 g) in DMF (15 ml) was added to a stirred suspension of sodium hydride (60% dispersion) (1.37 g) in DMF 100 ml) at −10° C. Iodomethane (2.13 ml) was added and the reaction allowed to warm to 20° C. The reaction mixture was quenched carefully with water and evaporated to dryness. The crude material was partitioned between ethyl acetate (250 ml) and water (100 ml). The organic layer was washed with brine (100 ml), dried over Magnesium sulphate, filtered and evaporated to give tert-butyl (2R,4R) 4-(tert-butyl-dimethyl-silyl)oxy-2-(methoxymethyl)pyrrolidine-1-carboxylate (6.68 g) as a colourless oil. NMR Spectrum: (DMSOd6) 0.02 (6H, s); 0.83-0.84 (9H, s); 1.36 (9H, s); 1.78 (1H, d); 1.99 (1H, s); 2.99 (1H, d); 3.19 (3H, d); 3.23-3.48 (3H, m); 3.80 (1H, s); 4.33 (1H, s).

Tetrabutyl ammonium fluoride (21.3 ml) was added to a stirred solution of tert-butyl (2R,4R) 4-(tert-butyl-dimethyl-silyl)oxy-2-(methoxymethyl)pyrrolidine-1-carboxylate (6.68 g) in THF (150 ml). The resulting mixture was stirred at 20° C. for 18 hours. The reaction mixture was evaporated to dryness and the residue was purified by flash chromatography on silica eluting with increasingly polar mixtures of methanol/dichloromethane (0/100-5/95). Fractions containing the desired product were combined and evaporated to give tert-butyl (2R,4R) 4-hydroxy-2-(methoxymethyl)pyrrolidine-1-carboxylate (3.32 g) as a solid. NMR Spectrum: (DMSOd6)

1.44 (9H, s); 1.81-1.86 (1H, m); 2.05 (1H, d); 3.09 (1H, d); 3.43-3.49 (3H, s); 3.52 (3H, m); 3.83 (1H, d); 4.20-4.25 (1H, m); 4.94 (1H, d).

[C37] Tert-butyl N-[(3S,4S)-4-hydroxytetrahydropyran-3-yl]-N-methyl-carbamate was used as a starting material.

[C38] Tert-butyl 4-hydroxyazepane-1-carboxylate was used as starting material.

EXAMPLE 44

4-(6-amino-5-(oxazolo[5,4-b]pyridin-2-yl)pyridin-3-yl)-N-(2-(dimethylamino)ethyl)benzamide

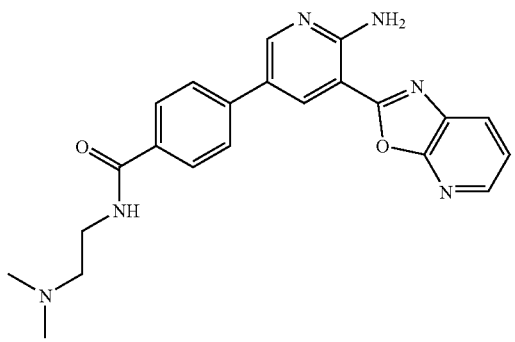

A mixture of 4-(6-amino-5-oxazolo[5,4-b]pyridin-2-yl-3-pyridyl)benzoic acid (100 mg) N,N-dimethylethane-1,2-diamine (0.036 ml), 2-(1H-benzo[d][1,2,3]triazol-1-yl)-1,1,3,3-tetramethylisouronium tetrafluoroborate (145 mg) and 4-methylmorpholine (0.066 ml) in NMP (1 ml) was stirred at room temperature for 15 hours. The reaction mixture was purified by preparative HPLC using a Waters X-Bridge reverse-phase column (5 microns silica, 30 mm diameter, 150 mm length) and decreasingly polar mixtures of water (containing 0.2% ammonium carbonate) and acetonitrile as eluent. The fractions were evaporated to dryness to afford the title compound (38 mg) as a solid; NMR Spectrum: (DMSOd6) 2.19 (s, 6H), 2.42 (t, 2H), 3.35-3.42 (m, 2H), 7.54 (dd, 1H), 7.86 (d, 2H), 7.93 (bs, 2H), 7.95 (d, 2H), 8.30 (dd, 1H), 8.41 (dd, 1H), 8.45 (t, 1H), 8.59 (d, 1H), 8.71 (d, 1H); Mass spectrum: M+H$^+$: 403. RT: 1.73

The 4-(6-amino-5-oxazolo[5,4-b]pyridin-2-yl-3-pyridyl) benzoic acid used as starting material was prepared as follows:

Bis(triphenylphosphine) palladium (II) chloride (0.121 g) and caesium fluoride (1.56 g) were added to a degassed solution of 5-bromo-3-oxazolo[5,4-b]pyridin-2-yl-pyridin-2-amine (1 g) and 4-boronobenzoic acid (0.570 g) in methanol (15 ml) under nitrogen atmosphere. The suspension was stirred at 120° C. for 20 min in a 300 W microwave reactor. The reaction mixture was then stirred at 130° C. for 20 minutes in a 300 W microwave reactor. The mixture was diluted with water (25 ml) and stirred for 30 min. The yellow suspension was filtered, washed with water (4×15 ml), washed with diethyl ether (4×15 ml) and dried overnight to give 4-(6-amino-5-oxazolo[5,4-b]pyridin-2-yl-3-pyridyl)benzoic acid (1.090 g, 95%). NMR Spectrum: (DMSOd6) 7.54 (dd, 1H), 7.89 (d, 2H), 7.95 (bs, 2H), 8.03 (d, 2H), 8.30 (dd, 1H), 8.41 (dd, 1H), 8.60 (d, 1H), 8.71 (d, 1H); Mass spectrum: M+H$^+$ 333

EXAMPLE 45A

Using an analogous procedure to that described in Example 44, the following examples were prepared by reacting 4-(6-amino-5-(oxazolo[5,4-b]pyridin-2-yl)pyridin-3-yl) benzoic acid with an appropriate amine.

TABLE XIX

| No. & Note | K$^1$ | RT (min) | MS (M + H$^+$) |
|---|---|---|---|
| [1] | 4-dimethylaminopiperidin-1-yl | 1.67 | 443 |
| [2] | 4-dimethylaminobutylamino | 1.74 | 431 |
| [3] | N-methyl-N-(1-methylpyrrolidin-3-yl)amino | 1.72 | 429 |
| [4] | quinuclidin-3-ylamino | 1.77 | 441 |
| [5] | 2-(1-methylpyrrolidin-2-yl)ethylamino | 1.78 | 443 |
| [6] | 3-pyrrolidin-1-ylpropylamino | 1.78 | 443 |
| [7] | 2-imidazol-1-ylethylamino | 1.83 | 426 |
| [8] | 2-(piperidin-1-ylmethyl)piperidin-1-yl | 2.08 | 497 |
| [9] | 3-(piperidin-1-yl)propylamino | 1.83 | 457 |
| [10] | [1-(2-methoxyethyl)piperidin-4-yl]amino | 1.84 | 473 |
| [11] | N-methyl-N-(2-pyrrolidin-1-ylcyclohexyl)amino | 2.03 | 497 |
| [12] | 2-(1,1-dioxo-1,4-thiazinan-4-yl)ethylamino | 2.88 | 493 |
| [13] | 2-[(3R)-3-fluoropyrrolidin-1-yl]ethylamino | 1.82 | 447 |
| [14] | 4-(2-dimethylaminoethyl)piperidin-1-yl | 1.85 | 471 |
| [15] | 2-(1-methylpiperidin-2-yl)pyrrolidin-1-yl | 2.01 | 483 |
| [16] | 2-(morpholinomethyl)pyrrolidin-1-yl | 2.1 | 485 |
| [17] | 2-(azepan-1-ylmethyl)pyrrolidin-1-yl | 2.1 | 497 |
| [18] | 2-[(2-methylpiperidin-1-yl)methyl]pyrrolidin-1-yl | 2.07 | 497 |
| [19] | (1-methylpiperidin-3-yl)amino | 1.79 | 429 |
| [20] | 3-dimethylaminopiperidin-1-yl | 1.75 | 443 |
| [21] | 2-(morpholinomethyl)piperidin-1-yl | 2.58 | 499 |
| [22] | (3S)-3-pyrroliin-1-ylpyrrolidin-1-yl | 1.76 | 455 |
| [23] | 2-(pyrrolidin-1-ylmethyl)piperidin-1-yl | 2 | 483 |
| [24] | (4-dimethylaminocyclohexyl)amino | 1.83 | 457 |
| [25] | (1-methylpiperidin-4-yl)methylamino | 1.76 | 443 |
| [26] | (1-methylpiperidin-2-yl)methylamino | 1.82 | 443 |
| [27] | (1-methylpyrrolidin-3-yl)methylamino | 1.74 | 429 |
| [28] | (4-methylmorpholin-2-yl)methylamino | 1.82 | 445 |
| [29] | 2-(2-pyrrolidin-1-ylethyl)piperidin-1-yl | 2.04 | 497 |
| [30] | (1-methylazetidin-3-yl)amino | 1.7 | 401 |
| [31] | methyl-(1-methylpiperidin-4-yl)amino | 1.71 | 443 |
| [32] | 2-(azepan-1-yl)ethylamino | 1.96 | 457 |
| [33] | 3-diethylaminopyrrolidin-1-yl | 1.8 | 457 |
| [34] | methyl-[(1R,2R)-2-pyrrolidin-1-ylcyclohexyl]amino | 2.03 | 497 |
| [35] | [(3R)-quinuclidin-3-yl]amino | 1.78 | 441 |
| [36] | [(2R)-1-ethylpyrrolidin-2-yl]methylamino | 1.83 | 443 |

TABLE XIX-continued

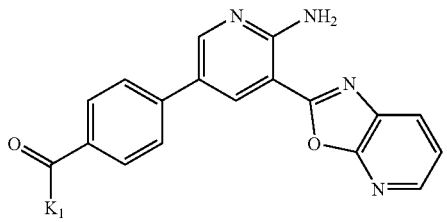

| No. & Note | K¹ | RT (min) | MS (M + H⁺) |
|---|---|---|---|
| [37] | 2-(3,3-difluoropyrrolidin-1-yl)ethylamino | 2.94 | 465 |
| [38] | 2-[(3S)-3-fluoropyrrolidin-1-yl]ethylamino | 1.83 | 447 |
| [39] | 3-[(3R)-3-fluoropyrrolidin-1-yl]propylamino | 1.81 | 461 |
| [40] | 3-[(3S)-3-fluoropyrrolidin-1-yl]propylamino | 1.78 | 461 |
| [41] | (1-dimethylaminocyclohexyl)methylamino | 1.99 | 471 |
| [42] | (1-isopropylpyrrolidin-3-yl)methyl-methyl-amino | 1.9 | 471 |
| [43] | [(2S)-1-isopropylpyrrolidin-2-yl]methylamino | 1.94 | 457 |
| [44] | (1-methyl-3,4,4a,5,6,7,8,8a-octahydro-2H-quinolin-4-yl)amino | 2.01 | 483 |
| [45] | 2-[(2R,6S)-2,6-dimethylmorphorlin-4-yl]ethylamino | 2.1 | 473 |
| [46] | 3-(4-methylpiperidin-1-yl)propylamino | 1.99 | 471 |
| [47] | (1-ethylpiperidin-4-yl)methylamino | 1.82 | 457 |
| [48] | 2-dimethylaminoethyl-methyl-amino | 1.73 | 417 |
| [49] | 4-methylpiperazin-1-yl | 1.78 | 415 |
| [50] | 4-(2-dimethylaminoethyl)piperazin-1-yl | 1.79 | 472 |
| [51] | 2-morpholinoethylamino | 1.91 | 445 |
| [52] | 4-(1-piperidyl)piperidin-1-yl | 1.94 | 483 |
| [53] | 3-imidazo1-1-ylpropylamino | 1.86 | 440 |
| [54] | 3-dimethylaminopropyl-methyl-amino | 1.76 | 431 |
| [55] | 2-pyrrolidin-1-ylethylamino | 1.76 | 429 |
| [56] | 2-(piperidin-1-yl)ethylamino | 1.85 | 443 |
| [57] | 3-morpholinopropylamino | 1.82 | 459 |
| [58] | 3-(4-methylpiperazin-1-yl)propylamino | 1.76 | 472 |
| [59] | 4-(2-methoxyethyl)piperazin-1-yl | 2.11 | 459 |
| [60] | 4-(2-pyridylmethyl)piperazin-1-yl | 2.65 | 492 |
| [61] | 4-(3-pyridylmethyl)piperazin-1-yl | 2.68 | 492 |
| [62] | 4-(4-pyridylmethyl)piperazin-1-yl | 2.76 | 492 |
| [63] | 4-pyrrolidin-1-ylpiperidin-1-yl | 1.77 | 469 |
| [64] | 4-morpholinopiperidin-1-yl | 1.96 | 485 |
| [65] | 4-methyl-1,4-diazepan-1-yl | 1.7 | 429 |
| [66] | (2S)-2-(pyrrolidin-1-ylmethyl)pyrrolidin-1-yl | 1.96 | 469 |
| [67] | 4-(2-dimethylamino-2-oxo-ethyl)piperazin-1-yl | 2.3 | 486 |
| [68] | 4-(2-pyrrolidin-1-ylethyl)piperazin-1-yl | 1.84 | 497.9 |
| [69] | (1-methylpiperidin-4-yl)amino | 1.72 | 429 |
| [70] | methyl-(2-pyrrolidin-1-ylethyl)amino | 1.78 | 443 |
| [71] | 4-(3-amino-3-oxo-propyl)piperazin-1-yl | 1.89 | 472 |
| [72] | (1-ethylpyrrolidin-2-yl)methylamino | 1.86 | 443 |
| [73] | 2-(4-methylpiperazin-1-yl)ethylamino | 1.79 | 458 |

TABLE XIX-continued

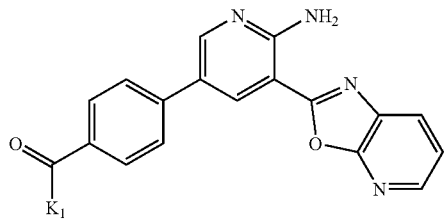

| No. & Note | K¹ | RT (min) | MS (M + H⁺) |
|---|---|---|---|
| [74] | 3,4,6,7,8,8a-hexahydro-1H-pyrrolo[2,1-c]pyrazin-2-yl | 1.89 | 441 |
| [75] | (2S)-2-(dimethylcarbamoyl)pyrrolidin-1-yl | 2.94 | 457 |
| [76] | (3R)-3-dimethylaminopyrrolidin-1-yl | 1.76 | 429 |
| [77] | (3S)-3-dimethylaminopyrrolidin-1-yl | 1.76 | 429 |
| [78] | 4-(aminomethyl)-1-piperidyl | 1.89 | 429 |
| [79] | 3-aminopyrrolidin-1-yl | 1.65 | 401 |
| [80] | 3-methylaminopyrrolidin-1-yl | 1.64 | 415 |
| [81] | 3-methylaminopropylamino | 1.74 | 403 |
| [82] | 1,4-diazepan-1-yl | 1.68 | 415 |
| [83] | 2-piperazin-1-ylethylamino | 1.67 | 444 |
| [84] | 3-piperidylamino | 1.81 | 416 |
| [85] | methyl-(2-methylaminoethyl)amino | 1.71 | 403 |
| [86] | 4-(4-piperidyl)-1-piperidyl | 1.92 | 483 |
| [87] | 3,8-diazaspiro[5.5]undecan-3-yl | 1.93 | 469 |
| [88] | (3S)-3-amino-1-piperidyl | 1.77 | 415 |
| [89] | 2,8-diazaspiro[4.5]decan-8-yl | 1.77 | 455 |
| [90] | [(2S)-pyrrolidin-2-yl]methylamino | 1.74 | 415 |
| [91] | 4,9-diazaspiro[5.5]undecan-4-yl | 1.87 | 469 |
| [92] | (3R)-3-(2-aminoethyl)-1-piperidyl | 1.87 | 443 |
| [93] | [(3S)-3-piperidyl]methylamino | 1.82 | 429 |
| [94] | 3,3a,4,5,6,6a-hexahydro-1H-pyrrolo[3,4-c]pyrrol-2-yl | 1.66 | 427 |
| [95] | 4-aminoazepan-1-yl | 1.97 | 429 |
| [96] | methyl-(4-piperidyl)amino | 1.7 | 429 |
| [97] | 4-methylamino-1-piperidyl | 1.7 | 429 |
| [98] | 4-(piperazin-1-ylmethyl)piperidin-1-yl | 1.7 | 498 |
| [99] | Trans (4-methylaminocyclohexyl)amino | 1.83 | 443 |
| [100] | 3,9-diazaspiro[5.5]undecan-3-yl | 1.79 | 469 |
| [101] | 3-piperazin-1-ylpropylamino | 1.57 | 458 |
| [102] | (1S,4S)-3,6-diazabicyclo[2.2.1]heptan-1-yl | 1.64 | 413 |
| [103] | 4-piperidylamino | 1.76 | 415 |
| [104] | 2-piperidylmethylamino | 1.85 | 429 |
| [105] | 3-aminoazetidin-1-yl | 1.65 | 387 |
| [106] | pyrrolidin-3-ylamino | 1.76 | 401 |
| [107] | 4-amino-1-piperidyl | 1.68 | 415 |

[48] NMR Spectrum: (DMSOd6 at 323° K) 2.13 (bs, 6H), 2.45 (bs 2H), 2.98 (s, 3H), 3.46 (bs, 2H), 7.47 (d, 2H), 7.52 (dd, 1H), 7.77 (bs, 2H), 7.80 (d, 2H), 8.27 (dd, 1H), 8.39 (dd, 1H), 8.55 (d, 1H), 8.66 (d, 1H).

[78] Compound [78] was prepared using an analogous procedure to that described in Example 44. The N-tert-butoxycarbonyl group on the resultant product was removed by conventional treatment with trifluoroacetic acid. Tert-butyl N-(4-piperidylmethyl)carbamate was used as starting material.

[79] Compound [79] was prepared using an analogous procedure to that described in Example 44. The N-tert-butoxycarbonyl group on the resultant product was removed by treatment with trifluoroacetic acid. Tert-butyl N-pyrrolidin-3-ylcarbamate was used as starting material.

[80] Compound [80] was prepared using an analogous procedure to that described in Example 44. The N-tert-butoxycarbonyl group on the resultant product was removed by treatment with trifluoroacetic acid. Tert-butyl N-methyl-N-pyrrolidin-3-yl-carbamate was used as starting material.

[81] Compound [81] was prepared using an analogous procedure to that described in Example 44. The N-tert-butoxycarbonyl group on the resultant product was removed by treatment with trifluoroacetic acid. Tert-butyl N-(3-aminopropyl)-N-methyl-carbamate was used as starting material.

[82] Compound [82] was prepared using an analogous procedure to that described in Example 44. The N-tert-butoxycarbonyl group on the resultant product was removed by treatment with trifluoroacetic acid. Tert-butyl 1,4-diazepane-1-carboxylate was used as starting material.

[83] Compound [83] was prepared using an analogous procedure to that described in Example 44. The N-tert-butoxycarbonyl group on the resultant product was removed by treatment with trifluoroacetic acid. Tert-butyl 4-(2-aminoethyl)piperazine-1-carboxylate was used as starting material.

[84] Compound [84] was prepared using an analogous procedure to that described in Example 44. The N-tert-butoxycarbonyl group on the resultant product was removed by treatment with trifluoroacetic acid. Tert-butyl 3-aminopiperidine-1-carboxylate was used as starting material.

[85] Compound [85] was prepared using an analogous procedure to that described in Example 44. The N-tert-butoxycarbonyl group on the resultant product was removed by treatment with trifluoroacetic acid. Tert-butyl N-methyl-N-(2-methylaminoethyl)carbamate (Kleeman, H.-W. et al.; J. Med. Chem. 1992, 35, 559) was used as starting material.

[86] Compound [86] was prepared using an analogous procedure to that described in Example 44. The N-tert-butoxycarbonyl group on the resultant product was removed by treatment with trifluoroacetic acid. Tert-butyl 4-(4-piperidyl)piperidine-1-carboxylate was used as starting material.

[87] Compound [87] was prepared using an analogous procedure to that described in Example 44. The N-tert-butoxycarbonyl group on the resultant product was removed by treatment with trifluoroacetic acid. Tert-butyl 4,9-diazaspiro[5.5]undecane-4-carboxylate (Fisher, M.; PCT Int Appl WO 1997011940) was used as starting material.

[88] Compound [88] was prepared using an analogous procedure to that described in Example 44. The N-tert-butoxycarbonyl group on the resultant product was removed by treatment with trifluoroacetic acid. Tert-butyl N-((3S)-3-piperidyl)carbamate was used as starting material.

[89] Compound [89] was prepared using an analogous procedure to that described in Example 44. The N-tert-butoxycarbonyl group on the resultant product was removed by treatment with trifluoroacetic acid. Tert-butyl 3,8-diazaspiro[4.5]decane-3-carboxylate was used as starting material.

[90] Compound [90] was prepared using an analogous procedure to that described in Example 44. The N-tert-butoxycarbonyl group on the resultant product was removed by treatment with trifluoroacetic acid. Tert-butyl (2S)-2-(aminomethyl)pyrrolidine-1-carboxylate was used as starting material.

[91] Compound [91] was prepared using an analogous procedure to that described in Example 44. The N-tert-butoxycarbonyl group on the resultant product was removed by treatment with trifluoroacetic acid. Tert-butyl 3,8-diazaspiro[5.5]undecane-3-carboxylate (Shipps, G.; PCT Int Appl WO2008054702) was used as starting material.

[92] Compound [92] was prepared using an analogous procedure to that described in Example 44. The N-tert-butoxycarbonyl group on the resultant product was removed by treatment with trifluoroacetic acid. Tert-butyl N-[2-[(3R)-3-piperidyl]ethyl]carbamate was used as starting material.

[93] Compound [93] was prepared using an analogous procedure to that described in Example 44. The N-tert-butoxycarbonyl group on the resultant product was removed by treatment with trifluoroacetic acid. Tert-butyl (3S)-3-(aminomethyl)piperidine-1-carboxylate was used as starting material.

[94] Compound [94] was prepared using an analogous procedure to that described in Example 44. The N-tert-butoxycarbonyl group on the resultant product was removed by treatment with trifluoroacetic acid. Tert-butyl 3,3a,4,5,6,6a-hexahydro-1H-pyrrolo[3,4-c]pyrrole-2-carboxylate was used as starting material.

[95] Compound [95] was prepared using an analogous procedure to that described in Example 44. The N-tert-butoxycarbonyl group on the resultant product was removed by treatment with trifluoroacetic acid. Tert-butyl N-(azepan-4-yl)carbamate was used as starting material.

[96] Compound [96] was prepared using an analogous procedure to that described in Example 44. The N-tert-butoxycarbonyl group on the resultant product was removed by conventional treatment with trifluoroacetic acid. Tert-butyl 4-methylaminopiperidine-1-carboxylate was used as starting material.

[97] Compound [97] was prepared using an analogous procedure to that described in Example 44. The N-tert-butoxycarbonyl group on the resultant product was removed by treatment with trifluoroacetic acid. Tert-butyl N-methyl-N-(4-piperidyl)carbamate was used as starting material.

[98] Compound [98] was prepared using an analogous procedure to that described in Example 44. The N-tert-butoxycarbonyl group on the resultant product was removed by treatment with trifluoroacetic acid. The tert-butyl 4-(4-piperidylmethyl)piperazine-1-carboxylate used as starting material was prepared as follows:

To a solution of benzyl 4-formylpiperidine-1-carboxylate (3 g) and tert-butyl piperazine-1-carboxylate (2.2 g) in dichloromethane (100 ml) was added sodium triacetoxyborohydride ((2.6 g). The resulting solution was stirred at room temperature for 18 hours and then washed with 2M sodium hydroxide (2×50 ml) and 2M hydrochloric acid (2×50 ml), dried over Magnesium sulphate, filtered and evaporated to afford tert-butyl 4-[(1-benzyloxycarbonyl-4-piperidyl)methyl]piperazine-1-carboxylate (4.9 g) as an oil. Tert-butyl 4-[(1-benzyloxycarbonyl-4-piperidyl)methyl]piperazine-1-carboxylate (4.9 g) was dissolved in ethanol and purged with argon. 20% Palladium hydroxide on carbon (500 mg) was added. The reaction mixture was purged with argon, evacuated and filled with hydrogen from a balloon. The reaction mixture was stirred at room temperature for 2 hours. A white solid precipitate formed. The reaction mixture was warmed to 40° C. and stirred at this temperature for a further 1 hour until the precipitate dissolved. The reaction mixture was allowed to cool to room temperature and stirred for a further 18 hours. The reaction mixture was purged with argon, filtered through celite and evaporated to afford tert-butyl 4-(4-piperidylmethyl)piperazine-1-carboxylate (3.2 g) as a solid. Mass spectrum: M+H$^+$ 284

[99] Compound [99] was prepared using an analogous procedure to that described in Example 44. The N-tert-butoxycarbonyl group on the resultant product was removed by treatment with trifluoroacetic acid. Trans-tert-butyl N-(4-aminocyclohexyl)-N-methyl-carbamate was used as starting material.

[100] Compound [100] was prepared using an analogous procedure to that described in Example 44. The N-tert-butoxycarbonyl group on the resultant product was removed by treatment with trifluoroacetic acid. Tert-butyl 3,9-diazaspiro [5.5]undecane-3-carboxylate was used as starting material.

[101] Compound [101] was prepared using an analogous procedure to that described in Example 44. The N-tert-butoxycarbonyl group on the resultant product was removed by treatment with trifluoroacetic acid. Tert-butyl 4-(3-aminopropyl)piperazine-1-carboxylate was used as starting material.

[102] Compound [102] was prepared using an analogous procedure to that described in Example 44. The N-tert-butoxycarbonyl group on the resultant product was removed by treatment with trifluoroacetic acid. Tert-butyl (1S,4S)-2,5-diazabicyclo[2.2.1]heptane-5-carboxylate was used as starting material.

[103] Compound [103] was prepared using an analogous procedure to that described in Example 44. The N-tert-butoxycarbonyl group on the resultant product was removed by treatment with trifluoroacetic acid. Tert-butyl 4-aminopiperidine-1-carboxylate was used as starting material.

[104] Compound [104] was prepared using an analogous procedure to that described in Example 44. The N-tert-butoxycarbonyl group on the resultant product was removed by treatment with trifluoroacetic acid. Tert-butyl 2-(aminomethyl)piperidine-1-carboxylate was used as starting material.

[105] Compound [105] was prepared using an analogous procedure to that described in Example 44. The N-tert-butoxycarbonyl group on the resultant product was removed by treatment with trifluoroacetic acid. Tert-butyl N-(azetidin-3-yl)carbamate was used as starting material.

[106] Compound [106] was prepared using an analogous procedure to that described in Example 44. The N-tert-butoxycarbonyl group on the resultant product was removed by treatment with trifluoroacetic acid. Tert-butyl 3-aminopyrrolidine-1-carboxylate was used as starting material.

[107] Compound [107] was prepared using an analogous procedure to that described in Example 44. The N-tert-butoxycarbonyl group on the resultant product was removed by treatment with trifluoroacetic acid. Tert-butyl N-(4-piperidyl) carbamate was used as starting material.

EXAMPLE 45B

Using an analogous procedure to that described in Example 44, the following examples were prepared by reacting 4-(6-amino-5-oxazolo[4,5-b]pyridin-2-yl-3-pyridyl)benzoic acid with an appropriate amine.

TABLE XX

| No. & Note | $K^1$ | RT (min) | MS (M + H$^+$) |
|---|---|---|---|
| [1] | N-(2-dimethylaminoethyl)-N-methyl-amino | 1.47 | 417 |
| [2] | 4-methylpiperazin-1-yl | 1.54 | 415 |
| [3] | 2-morpholinoethylamino | 1.68 | 445 |
| [4] | 4-(2-pyridylmethyl)piperazin-1-yl | 2.23 | 491 |
| [5] | 4-pyrrolidin-1-yl-1-piperidyl | 1.54 | 469 |

TABLE XX-continued

| No. & Note | $K^1$ | RT (min) | MS (M + H$^+$) |
|---|---|---|---|
| [6] | 4-(2-dimethylamino-2-oxo-ethyl)piperazin-1-yl | 1.98 | 486 |

The 4-(6-amino-5-oxazolo[4,5-b]pyridin-2-yl-3-pyridyl)benzoic acid used as starting material was prepared as follows:

A mixture of 5-bromo-3-(oxazolo[4,5-b]pyridin-2-yl)pyridin-2-amine, 4-boronobenzoic acid (0.57 g), bistriphenylphosphine palladium chloride (0.121 g) and caesium fluoride (0.380 g) in MeOH (15 ml) were stirred at 120° C. for 20 mins under microwaves in a 300 W microwave oven.

The mixture was diluted with water (250 ml) and stirred for 30 min. The yellow mixture was filtered. The solid was washed with water (4×150 ml), washed with diethylether (4×150 ml) and dried overnight to give 4-(6-amino-5-oxazolo[4,5-b]pyridin-2-yl-3-pyridyl)benzoic acid (0.786 g) NMR Spectrum: (DMSOd6) 7.50 (dd, 1H), 7.87 (d, 2H), 7.94 (bs, 2H), 8.03 (d, 2H), 8.27 (d, 1H), 8.57 (d, 1H), 8.62 (d, 1H), 8.74 (d, 1H); Mass spectrum: M+H$^+$ 333

EXAMPLE 46

3-(1,3-Benzoxazol-2-yl)-5-[3-[2-(4-piperidyl)ethylsulphonyl]phenyl]pyridin-2-amine

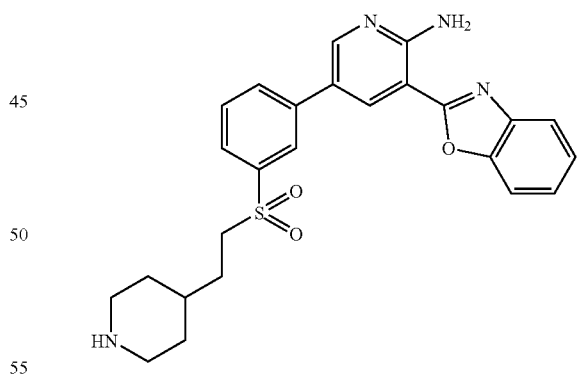

Dichlorobis(triphenylphosphine)palladium(II) (0.008 g) was added to 2-[2-(2,5-dimethylpyrrol-1-yl)-5-(4,4,5,5-tetramethyl-1,3,2-dioxaborolan-2-yl)-3-pyridyl]-1,3-benzoxazole (0.10 g), tert-butyl 4-[2-(3-bromophenyl)sulphonylethyl]piperidine-1-carboxylate (0.10 g) and sodium carbonate (0.241 ml) in DMF:DME:ethanol:water 2:7:2:1 (100 ml) at ambient temperature. The resulting mixture was stirred at 70° C. for 20 minutes. The reaction was filtered and evaporated to dryness, then added to TFA (3 ml) and water (0.3 ml). The resulting solution was stirred at ambient temperature for 1 hour, then concentrated under reduced pressure and purified by SCX ion exchange chromatography. The desired product was eluted from the column using 7M ammonia in methanol. Pure fractions were evaporated to dryness and triturated with diethyl ether. There was thus obtained 3-(1,3-benzoxazol-2-yl)-5-[3-[2-(4-piperidyl)ethylsulphonyl]phenyl]pyridin-2-amine (0.048 g); Mass Spectrum: M+H+ 463; RT 2.33 min; NMR Spectrum: (DMSOd6) 8.71 (1H, d), 8.62 (1H, d), 8.22 (1H, d), 8.14 (1H, d), 7.91 (1H, br s), 7.84-7.89 (3H, m), 7.77 (1H, t), 7.45-7.50 (2H, m), 3.50 (1H, s), 3.47 (2H, d), 3.35 (2H, s), 3.16 (2H, d), 2.68-2.73 (2H, m), 1.77 (2H, d), 1.57 (3H, t), 1.16-1.19 (2H, m).

The 2-[2-(2,5-dimethylpyrrol-1-yl)-5-(4,4,5,5-tetramethyl-1,3,2-dioxaborolan-2-yl)-3-pyridyl]-1,3-benzoxazole used as starting materials were prepared as follows: Acetonylacetone (40.6 ml) was added to para-toluenesulphonic acid (0.594 g) and 3-(1,3-benzoxazol-2-yl)-5-bromo-pyridin-2-amine (10.0 g) in toluene (250 ml). The resulting solution was stirred at 180° C. with continuous water extraction conditions using a Dean-Stark apparatus for 24 hours. The reaction mixture was cooled and diluted with ethyl acetate (150 ml) and washed with saturated sodium hydrogen carbonate (2×100 ml). The organic layer was washed with brine (50 ml) dried over magnesium sulfate, filtered and evaporated under reduced pressure. The crude product was purified by flash silica chromatography, using an elution gradient 0 to 25% ethyl acetate in isohexane. Pure fractions were evaporated to dryness. There was thus obtained 2-[5-bromo-2-(2,5-dimethylpyrrol-1-yl)-3-pyridyl]-1,3-benzoxazole (7.55 g); Mass Spectrum: M+H+ 370; RT 3.4 min; NMR Spectrum: (DMSOd6) 9.01 (1H, d), 8.88 (1H, d), 7.78-7.80 (1H, m), 7.56-7.59 (1H, m), 7.39-7.46 (2H, m), 5.79 (2H, s), 1.86 (6H, s).

{1,1'-Bis(diphenylphosphene)ferrocene}palladium chloride dichloromethane adduct (0.066 g) was added to a mixture of 2-[5-bromo-2-(2,5-dimethylpyrrol-1-yl)-3-pyridyl]-1,3-benzoxazole (0.600 g), potassium acetate (0.496 g) and 4,4,4',4',5,5,5',5'-octamethyl-2,2'-bi(1,3,2-dioxaborolane) (0.497 g) in dioxane (15 ml) which had been degassed with bubbling nitrogen for 20 minutes. The resulting mixture was stirred at 80° C. under an atmosphere of nitrogen for 1 hour. The reaction was filtered and then evaporated. The crude product was purified by flash silica chromatography (elution gradient 10 to 60% ethyl acetate in isohexane). Pure fractions were evaporated to dryness and triturated with isohexane. There was thus obtained 2-[2-(2,5-dimethylpyrrol-1-yl)-5-(4,4,5,5-tetramethyl-1,3,2-dioxaborolan-2-yl)-3-pyridyl]-1,3-benzoxazole (0.500 g); Mass Spectrum: M+H+ 416; RT 1.56 min; NMR Spectrum: (DMSOd6) 8.98 (1H, s), 8.86 (1H, d), 7.76-7.79 (1H, m), 7.56-7.58 (1H, m), 7.38-7.44 (2H, m), 5.81 (2H, s), 1.85 (6H, s), 1.39 (12H, s).

The tert-butyl 4-[2-(3-bromophenyl)sulphonylethyl]piperidine-1-carboxylate used as a starting material was prepared as follows:

tert-Butyl 4-(2-hydroxyethyl)piperidine-1-carboxylate (20 g) was added to a solution of triethylamine (12.2 ml) in DCM (100 ml) at 0° C. 4-Methylbenzene-sulphonyl chloride (16.6 g) was added in portions over a period of 20 minutes. The reaction was then allowed to warm to ambient temperature and stirred for 16 hours, then washed with 2N sodium hydrogen carbonate (2×100 ml), dried over magnesium sulfate and concentrated under reduced pressure. The mixture was purified by silica gel chromatography (eluting with a solvent gradient from hexane to 40% ethyl acetate and hexane). There was thus obtained tert-butyl 4-[2-(4-methylphenyl)sulphonyloxyethyl]piperidine-1-carboxylate (29 g).

60% Sodium hydride (1.3 g) was suspended in DMF (150 ml) and cooled to 0° C. 3-bromobenzenethiol (5 g) was dissolved in DMF (50 ml) and added to the sodium hydride solution over a period of 10 minutes. The resultant mixture was stirred at 0° C. for 30 minutes. tert-Butyl 4-[2-(4-methylphenyl)sulphonyloxyethyl]piperidine-1-carboxylate (10.1 g) was then added and the resultant mixture was stirred at ambient temperature overnight. The mixture was then concentrated under reduced pressure and the residue dissolved in DCM (150 ml) and washed with saturated ammonium chloride (2×100 ml). The resultant mixture was then dried over magnesium sulfate and evaporated under reduced pressure.

The residue was redissolved in DCM (200 ml) and cooled to 0° C. Small portions of chloroperbenzoic acid (11.8 g) added slowly over a 10 minute period and the mixture was stirred at ambient temperature for 3 hours. The mixture was then washed sequentially with saturated sodium thiosulfate solution (2×50 ml), 2N sodium hydroxide solution (4×50 ml), then dried over magnesium sulfate and concentrated under reduced pressure. The residue was purified by silica gel chromatography (eluting with 10-30% ethyl acetate in isohexane). The fractions containing the desired compound were concentrated under reduced pressure, and triturated with isohexane. The resultant solid was filtered and dried under vacuum. There was thus obtained tert-butyl 4-[2-(3-bromophenyl)sulphonylethyl]piperidine-1-carboxylate (9.3 g); NMR Spectrum: (CDCl3) 8.05 (s, 1H), 7.78-7.85 (m, 2H), 7.46 (t, 1H), 4.07 (d, 2H), 3.07-3.13 (m, 2H), 2.64 (t, 2H), 1.56-1.73 (m, 5H), 1.44 (s, 9H), 1.01-1.16 (m, 2H).

EXAMPLE 47

3-(1,3-Benzoxazol-2-yl)-5-(3-morpholinosulphonylphenyl)pyridin-2-amine

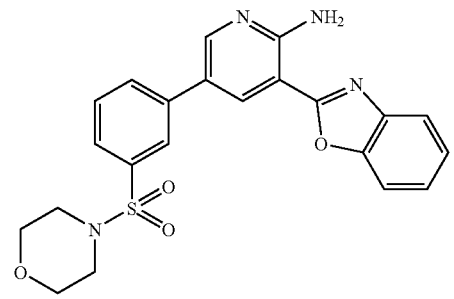

Morpholine (10.68 μl) was added in one portion to 3-[6-amino-5-(1,3-benzoxazol-2-yl)-3-pyridyl]benzenesulphonyl chloride (0.045 g), and N-ethyl-N-isopropylpropan-2-amine (30 μl) in THF (2 ml) at ambient temperature. The resulting mixture was stirred at ambient temperature for 20 hours, then evaporated to dryness under reduced pressure, dissolved in NMP (2 ml) and purified by preparative LCMS (Waters XBridge Prep C18 OBD column, 5μ silica, 19 mm diameter, 100 mm length), using decreasingly polar mixtures of water (containing 1% ammonia) and acetonitrile as eluents. Fractions containing the desired compound were evaporated to dryness and there was thus obtained 3-(1,3-benzoxazol-2-yl)-5-(3-morpholinosulphonylphenyl)pyridin-2-amine (0.020 g); Mass Spectrum: M+H+ 437.42; RT 2.61 min; NMR Spectrum: (DMSOd6) 8.68 (1H, d), 8.58 (1H, d), 8.13 (1H, dt), 7.98 (1H, t), 7.93 (2H, s), 7.84-7.88 (2H, m), 7.79 (1H, t), 7.73 (1H, dt), 7.43-7.50 (2H, m), 3.66 (4H, t), 2.97 (4H, t).

The 3-[6-amino-5-(1,3-benzoxazol-2-yl)-3-pyridyl]benzenesulphonyl chloride used as starting material was prepared as follows:

3-Aminophenylboronic acid (0.129 g), 2-[5-bromo-2-(2,5-dimethylpyrrol-1-yl)-3-pyridyl]-1,3-benzoxazole (0.315 g) and dichlorobis(triphenylphosphine)palladium (II) (0.006 g) were suspended in a mixture of DMF:DME:ethanol:water 2:7:2:1 (10 ml) and 2M sodium hydrogen carbonate solution (0.5 ml) and sealed into a microwave tube. The reaction was heated to 70° C. for 20 minutes in the microwave reactor. The mixture was allowed to cool, then filtered through a PTFE filter. The filtrate was evaporated to dryness, then redissolved in a mixture of ethyl acetate (75 ml) and water (20 ml), and washed sequentially with 0.5M HCl (20 ml), water (20 ml), and saturated brine (20 ml). The organic layer was dried over magnesium sulfate, filtered and concentrated under reduced pressure. There was thus obtained 3-[5-(1,3-benzoxazol-2-yl)-6-(2,5-dimethylpyrrol-1-yl)pyridin-3-yl]aniline (0.42 g); Mass Spectrum: M+H⁺ 381.21; RT 2.63 min; NMR Spectrum: (DMSOd6) 9.08 (1H, d), 8.79 (1H, d), 7.78-7.83 (1H, m), 7.57-7.59 (1H, m), 7.39-7.46 (2H, m), 7.25 (1H, t), 7.08-7.13 (2H, m), 6.74 (1H, ddd), 5.81 (2H, s), 5.52 (2H, s), 1.90 (6H, s).

Sulfur dioxide gas was bubbled through a mixture of copper (II) chloride dihydrate (0.1 g) and acetic acid (5 ml) at ambient temperature for 20 minutes, then cooled to 5° C. Separately, a solution of sodium nitrite (0.078 g) in water (2 ml) was added dropwise to a stirred solution of 3-[5-(1,3-benzoxazol-2-yl)-6-(2,5-dimethylpyrrol-1-yl)-3-pyridyl]aniline (0.400 g) in acetic acid (2.5 ml) and concentrated HCl (2.5 ml) at 5° C., over a period of 20 minutes. The temperature was maintained at <5° C., and after addition was complete, the mixture was stirred at 5° C. for 10 minutes. This mixture was then added dropwise to the copper chloride/sulfur dioxide mixture and the resultant mixture was stirred at 5° C. for a further 25 minutes, and then allowed to warm to ambient temperature and stirred for a further 1 hour. Ice water (10 ml) was then added to the mixture, and it was extracted with ethyl acetate (3×10 ml). The combined organic layers were washed with water, saturated sodium hydrogen carbonate solution and brine, then dried over magnesium sulfate, filtered and evaporated to dryness. There was thus obtained 3-[6-amino-5-(1,3-benzoxazol-2-yl)-3-pyridyl]benzenesulphonyl chloride (0.197 g); Mass Spectrum: M+H⁺ 386.09; RT 3.04 min.

EXAMPLE 48

3-[6-Amino-5-(1,3-benzoxazol-2-yl)-3-pyridyl]-N-ethyl-benzenesulphonamide

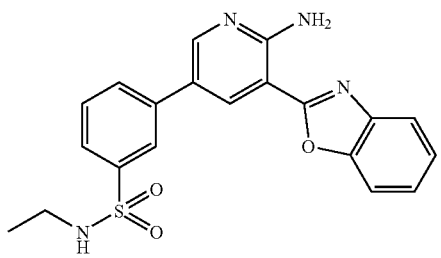

Ethylamine (2M in methanol, 0.117 ml) was added in one portion to a solution of 3-[6-amino-5-(1,3-benzoxazol-2-yl)-3-pyridyl]benzenesulphonyl chloride (0.045 g) and N-ethyl-N-isopropylpropan-2-amine (0.030 ml) in THF (2 ml) at ambient temperature, and the resultant mixture stirred for 20 hours. The mixture was then evaporated to dryness in vacuo and redissolved in NMP (2 ml), filtered and purified by preparative LCMS (Waters XBridge Prep C18 OBD column, 5μ silica, 21 mm diameter, 100 mm length), using decreasingly polar mixtures of water (containing 1% ammonia) and acetonitrile as eluents. Fractions containing the desired compound were evaporated to dryness to afford 3-[6-amino-5-(1,3-benzoxazol-2-yl)-3-pyridyl]-N-ethyl-benzenesulphonamide (0.007 mg); Mass Spectrum: M+H⁺ 395.13; RT 2.59 min.

EXAMPLE 49

3-(1,3-Benzothiazol-2-yl)-5-(3-morpholinophenyl)pyrazin-2-amine

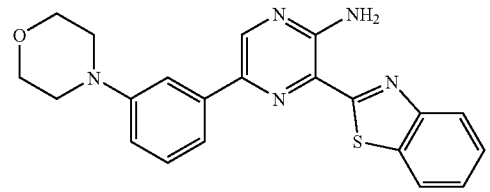

tert-Butyl N-[3-bromo-5-(3-morpholinophenyl)pyrazin-2-yl]-N-tert-butoxycarbonyl-carbamate (0.073 g), 1,3-benzothiazol-2-yl-tributyl-stannane (0.058 g) and bis(triphenylphosphine)palladium(II) chloride (0.004 g) were dissolved in DMA (5 ml) and sealed into a microwave tube. The reaction was heated at 140° C. for 1 hour in a microwave reactor and then cooled to ambient temperature. The reaction product was purified by ion exchange chromatography, using an SCX column. The desired product was eluted from the column using 7M ammonia in methanol and pure fractions were evaporated to dryness. The crude product was purified by preparative HPLC (Waters XBridge Prep C18 OBD column, 5μ silica, 19 mm diameter, 100 mm length), using decreasingly polar mixtures of water (containing 1% ammonia) and acetonitrile as eluents. Fractions containing the desired compound were evaporated to dryness and there was thus obtained 3-(1,3-benzothiazol-2-yl)-5-(3-morpholinophenyl)pyrazin-2-amine (0.019 g); Mass Spectrum: M+H⁺ 390; RT 2.97 min; NMR Spectrum: (DMSOd6) 8.90 (1H, s), 8.18-8.20 (2H, m), 7.63-7.64 (2H, m), 7.57-7.61 (1H, m), 7.50-7.54 (1H, m), 7.39 (1H, t), 7.01-7.03 (1H, m), 3.78-3.82 (4H, m), 3.23-3.27 (4H, m).

The tert-Butyl N-[3-bromo-5-(3-morpholinophenyl)pyrazin-2-yl]-N-tert-butoxycarbonyl-carbamate used as a reagent was prepared as follows:

Triethylamine (1.101 ml) was added to 3,5-dibromopyrazin-2-amine (1.03 g), di-tert-butyl dicarbonate (2.75 ml) and N,N-dimethylpyridin-4-amine (0.048 g) in a solution of THF (70 ml) under nitrogen. The resulting solution was stirred at 70° C. for 3 hours, then evaporated to dryness and redissolved in ethyl acetate (125 ml), and washed sequentially with water (125 ml) and saturated brine (125 ml). The organic layer was dried over sodium sulfate, filtered and evaporated under reduced pressure to afford crude product. The crude product was purified by flash silica chromatography, (elution gradient 10 to 20% ethyl acetate in isohexane). Pure fractions were evaporated to dryness and there was thus obtained tert-butyl N-tert-butoxycarbonyl-N-(3,5-dibromopyrazin-2-yl)carbamate (1.682 g); Mass Spectrum: M+Na⁺+CH₃CN 517; RT 2.98 min; NMR Spectrum: (DMSOd6) 8.52 (1H, s), 1.43 (18H, s). 4-(3-(4,4,5,5-tetramethyl-1,3,2-dioxaborolan-2-yl)phenyl)morpholine (0.907 g) was added to tert-butyl N-tert-butoxycarbonyl-N-(3,5-dibromopyrazin-2-yl)carbamate (1.672 g) and sodium carbonate (5.65 ml) in DMF (20 ml), ethylene glycol dimethyl ether (20 ml), ethanol (20 ml) and water (10 ml). The mixture was de-gassed and purged with nitrogen then bis(triphenylphosphine)palladium(II) chloride (0.110 g) was added. The resultant mixture was stirred at 70° C. for 1 hour, then concentrated under reduced pressure and diluted with ethyl acetate (300 ml), and washed sequentially with water (300 ml) and saturated brine (300 ml). The organic layer was dried over sodium sulfate, filtered and evaporated under reduced pressure, then purified by flash silica chromatography (elution gradient 30 to 40% ethyl acetate in isohexane). There was thus obtained tert-butyl N-[3-bromo-5-(3-morpholinophenyl)pyrazin-2-yl]-N-tert-butoxycarbonyl-carbamate (1.010 g); Mass Spectrum: M+CH$_3$CN 576, 578; RT 3.13 min; NMR Spectrum: (DMSOd6) 8.83 (1H, s), 7.61-7.62 (1H, m), 7.49-7.51 (1H, m), 7.41 (1H, t), 7.05 (1H, d), 3.88-3.92 (4H, m), 3.25-3.29 (4H, m), 1.44 (18H, s).

The 4-(3-(4,4,5,5-tetramethyl-1,3,2-dioxaborolan-2-yl) phenyl)morpholine used as a reagent was prepared as follows:

(1,1'-Bis(diphenylphosphino)ferrocene)-dichloropalladium(II) (1.373 g) was added to 4-(3-bromophenyl)morpholine (20.2 g), 4,4,5,5-tetramethyl-2-(4,4,5,5-tetramethyl-1,3,2-dioxaborolan-2-yl)-1,3,2-dioxaborolane (63.6 g) and potassium acetate (46.9 ml) in dioxane (550 ml) ambient temperature under an atmosphere of nitrogen. The resultant mixture was stirred at 80° C. for 18 hours. The reaction mixture was evaporated to dryness, then DCM (500 ml) was added. The mixture was stirred for 15 minutes, then filtered, and the filtrate was concentrated under reduced pressure. The crude product was purified by flash silica chromatography (elution gradient 8 to 20% ethyl acetate in isohexane). There was thus obtained 4-(3-(4,4,5,5-tetramethyl-1,3,2-dioxaborolan-2-yl)phenyl)morpholine (9.88 g); Mass Spectrum: M+H$^+$ 290; RT 1.93 min; NMR Spectrum: (DMSOd6) 7.24-7.28 (1H, m), 7.19 (1H, d), 7.14-7.16 (1H, m), 7.08-7.11 (1H, m), 3.72-3.76 (4H, m), 3.08-3.12 (4H, m), 1.30 (12H, s).

EXAMPLE 50

2-[3-[5-amino-6-(6-fluoro-1,3-benzoxazol-2-yl) pyrazin-2-yl]phenyl]acetic acid

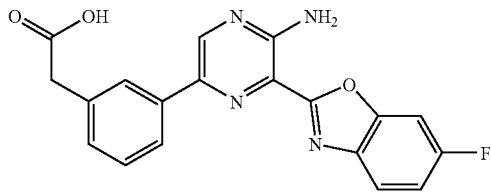

A mixture of 2-(3-(4,4,5,5-tetramethyl-1,3,2-dioxaborolan-2-yl)phenyl)acetic acid (85 mg), 5-bromo-3-(6-fluoro-1,3-benzoxazol-2-yl)pyrazin-2-amine (100 mg) in toluene-dioxane (1 ml-1.5 ml) and 2M aqueous sodium carbonate (5 ml) was degassed. Pd(dppf)Cl$_2$ (24 mg) was added. The resulting mixture was heated to 85° C. for 6 hours. 1-Butanol (5 ml) was added to the mixture and the mixture was washed with brine (3×5 ml). The resulting organic layer was concentrated and purified by chromatography on silica gel eluting with a gradient of methanol in ethyl acetate to give the title compound (15 mg) as a solid. NMR Spectrum: (DMSOd$_6$, 400 MHz) 7.25 (m, 2H), 7.30 (m, 1H), 7.40 (m, 1H), 7.90 (m, 6H), 8.80 (s, 1H); Mass spectrum: M+H$^+$ 365.

The 5-bromo-3-(6-fluoro-1,3-benzoxazol-2-yl)pyrazin-2-amine used as starting material was prepared as follows:

3-Aminopyrazine-2-carboxylic acid (5 g) and 2-amino-5-fluorophenol (5.9 g) were dissolved into DMF (30 ml). Triethylamine (5.8 g) and HATU (19.2 g) were added to the mixture. The resulting mixture was stirred at room temperature for 24 hours. Ethyl acetate (100 ml) was added to the mixture. The resulting mixture was washed with brine (20 ml×3). The organic phase was dried and concentrated. The resulting residue was purified by chromatography on silica gel to give 3-amino-N-(4-fluoro-2-hydroxyphenyl)pyrazine-2-carboxamide (6 g). NMR Spectrum: (DMSOd$_6$, 400 MHz) 6.60 (m, 2H), 7.50 (br s, 2H), 7.80 (s, 1H), 8.30 (m, 2H), 10.2 (s, 1H), 10.8 (s, 1H); Mass spectrum: MH$^+$ 249.

3-Amino-N-(4-fluoro-2-hydroxyphenyl)pyrazine-2-carboxamide (1.6 g) and triphenylphosphine (5.1 g) were dissolved into pyridine (20 ml). The mixture was cooled to 10° C. in a salt-ice bath. 2,2,2-Trichloroacetonitrile (2.79 g) was added slowly to the mixture. The mixture was warmed up to room temperature, and then heated to 130° C. for 13 hours. The resulting mixture was diluted with ethyl acetate/methanol (4/1, 100 ml). The mixture was filtered through Celite (diatomaceous earth), and the mixture was washed to pH 6 with 1 M hydrochloric acid. The organic layer was concentrated, and the residue was purified by chromatography on silica gel to give 3-(6-fluoro-1,3-benzoxazol-2-yl)pyrazin-2-amine (0.3 g). NMR Spectrum: (DMSOd$_6$, 400 MHz) 7.30 (m, 1H), 7.80 (m, 4H), 7.85 (m, 1H), 8.00 (s, 1H), 8.23 (s, 1H); Mass spectrum: M+H$^+$ 231

3-(6-Fluoro-1,3-benzoxazol-2-yl)pyrazin-2-amine (300 mg) was dissolved into DMF (15 ml) at 50° C. N-bromosuccimide (325 mg) was added. The mixture was stirred at 40° C. for 2 hours. The resulting mixture was diluted with ethyl acetate (15 ml), and washed with brine (10 ml×3). The organic layer was dried and concentrated to give 5-bromo-3-(6-fluoro-1,3-benzoxazol-2-yl)pyrazin-2-amine, which was used in the next reaction without further purification.

EXAMPLE 51

(2S,4R)-4-[4-[6-amino-5-(1,3-benzoxazol-2-yl)-3-pyridyl]pyrazol-1-yl]-N-methyl-pyrrolidine-2-carboxamide

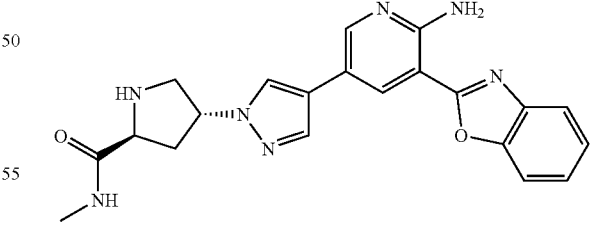

Trifluoroacetic acid (5 ml) was added to (2S,4R)-tert-butyl 4-[4-[6-amino-5-(1,3-benzoxazol-2-yl)-3-pyridyl]pyrazol-1-yl]-2-(methylcarbamoyl)pyrrolidine-1-carboxylate (70 mg) under argon. The resulting solution was stirred at 25° C. for 1 hour. The solution was evaporated under reduced pressure. The residue was basified with a solution of ammonia in methanol and the resultant mixture was adsorbed onto silica gel and purified by flash chromatography on silica gel eluting with 1 to 6% methanolic ammonia (7 N) in dichloromethane.

The solvent was evaporated to dryness to afford (2S,4R)-4-[4-[6-amino-5-(1,3-benzoxazol-2-yl)-3-pyridyl]pyrazol-1-yl]-N-methyl-pyrrolidine-2-carboxamide (55 mg) as a solid. NMR Spectrum: (CDCl3) 1.75 (bs, 1H), 2.48-2.58 (m, 1H), 2.68-2.76 (m, 1H), 2.85 (d, 1.5H), 2.87 (d, 1.5H), 3.08 (d, 0.5H), 3.10 (d, 0.5H), 3.43-3.46 (m, 0.5H), 3.46-3.49 (m, 0.5H), 4.11-4.17 (m, 1H), 4.79-4.85 (m, 1H), 6.95 (m, 2H), 7.34-7.42 (m, 2H), 7.58-7.62 (m, 1H), 7.63-7.68 (m, 1H), 7.69 (s, 1H), 7.73-7.78 (m, 2H), 8.36 (d, 1H), 8.38 (d, 1H); Mass spectrum: M+H⁺ 404.

EXAMPLE 52

5-[1-(1-ethyl-4-piperidyl)pyrazol-4-yl]-3-oxazolo[4,5-b]pyridin-2-yl-pyridin-2-amine

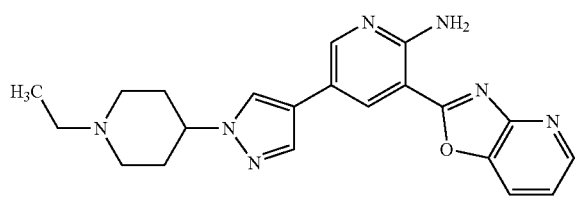

Bromoethane (0.019 ml) at 0° C. was added to a stirred mixture of 3-oxazolo[4,5-b]pyridin-2-yl-5-[1-(4-piperidyl)pyrazol-4-yl]pyridin-2-amine (90 mg) and potassium carbonate (68.8 mg) and DMF (1.5 mL) over a period of 5 minutes under argon. The resulting suspension was stirred at 25° C. for 20 hours. The solvent was evaporated. A solution of ammonia in methanol 7N (1 ml) was added and the mixture was adsorbed on silica gel. The crude product was purified by flash chromatography on silica gel eluting with 1 to 5% methanolic ammonia (7 N) in dichloromethane. The solvent was evaporated to dryness to afford 5-[1-(1-ethyl-4-piperidyl)pyrazol-4-yl]-3-oxazolo[4,5-b]pyridin-2-yl-pyridin-2-amine (60.0 mg) as a solid. NMR Spectrum: (DMSOd6) 1.03 (t, 3H), 1.91-2.10 (m, 6H), 2.38 (q, 2H), 2.94-3.01 (m, 2H), 4.09-4.18 (m, 1H), 7.48 (dd, 1H), 7.67 (bs, 2H), 7.92 (s, 1H), 8.23 (dd, 1H), 8.34 (s, 1H), 8.46 (d, 1H), 8.55 (dd, 1H), 8.58 (d, 1H); Mass spectrum: M+H⁺ 390.

EXAMPLE 53

Using an analogous procedure to that described in Example 52, the appropriate alkylating agent was used to give the compounds described in Table XXI.

TABLE XXI

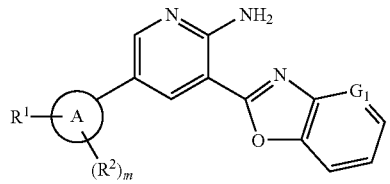

| No. & Note | R¹-A | m | R² | G₁ |
|---|---|---|---|---|
| [1] | 1-[1-(2-dimethylamino-2-oxo-ethyl)-4-piperidyl]pyrazol-4-yl | 0 | | N |

TABLE XXI-continued

| No. & Note | R¹-A | m | R² | G₁ |
|---|---|---|---|---|
| [2] | 1-[1-(2-methylamino-2-oxo-ethyl)-4-piperidyl]pyrazol-4-yl | 0 | | N |
| [3] | 1-[1-(2-amino-2-oxo-ethyl)-4-piperidyl]pyrazol-4-yl | 0 | | N |
| [4] | 1-(1-isopropyl-4-piperidyl)pyrazol-4-yl | 0 | | N |
| [5] | 1-[1-(2-hydroxyethyl)-4-piperidyl]pyrazol-4-yl | 0 | | N |
| [6] | 1-[1-(2-amino-2-oxo-ethyl)-4-piperidyl]pyrazol-4-yl | 0 | | CH |
| [7] | 1-[1-(2-methylamino-2-oxo-ethyl)-4-piperidyl]pyrazol-4-yl | 0 | | CH |
| [8] | 1-[1-(2-dimethylamino-2-oxo-ethyl)-4-piperidyl]pyrazol-4-yl | 0 | | CH |

[1] Compound [1] was prepared according to the procedure described in Example 52 using 2-chloro-N,N-dimethyl-acetamide as alkylating agent; The product gave the following characterizing data: NMR Spectrum: (CDCl3) 2.15-2.29 (m, 4H), 2.41-2.58 (m, 2H), 2.98 (s, 3H), 3.11 (s, 3H), 3.11-3.21 (m, 2H), 3.32 (s, 2H), 4.17-4.28 (m, 1H), 6.94 (bs, 2H), 7.33 (dd, 1H), 7.70 (s, 1H), 7.78 (s, 1H), 7.90 (dd, 1H), 8.39 (d, 1H), 8.43 (d, 1H), 8.58 (dd, 1H); Mass spectrum: M+H⁺ 447

[2] Compound [2] was prepared according to the procedure described in Example 52 using 2-chloro-N-methyl-acetamide as alkylating agent; The product gave the following characterizing data: NMR Spectrum: (CDCl3) 2.13-2.28 (m, 4H), 2.36-2.48 (m, 2H), 2.87 (d, 3H), 2.98-3.06 (m, 2H), 3.09 (s, 2H), 4.13-4.24 (m, 1H), 7.02 (bs, 2H), 7.19 (bs, 1H), 7.33 (dd, 1H), 7.71 (s, 1H), 7.80 (s, 1H), 7.89 (dd, 1H), 8.39 (d, 1H), 8.43 (d, 1H), 8.58 (dd, 1H); Mass spectrum: M+H⁺ 433

[3] Compound [3] was prepared according to the procedure described in Example 52 using 2-chloroacetamide as alkylating agent; The product gave the following characterizing data: NMR Spectrum: (CDCl3) 2.12-2.26 (m, 4H), 2.37-2.47 (m, 2H), 3.03-3.13 (m, 4H), 4.14-4.25 (m, 1H), 5.59 (bs, 1H), 6.95 (ns, 2H), 7.05 (bs, 1H), 7.33 (dd, 1H), 7.70 (s, 1H), 7.80 (s, 1H), 7.88 (dd, 1H), 8.38 (d, 1H), 8.43 (d, 1H), 8.57 (dd, 1H); Mass spectrum: M+H⁺ 419

[4] Compound [4] was prepared according to the procedure described in Example 52 using 2-iodopropane as alkylating agent; The product gave the following characterizing data: NMR Spectrum: (CDCl3) 1.09 (d, 6H), 1.99-2.13 (m, 2H), 2.19-2.30 (m, 2H), 2.30-2.41 (m, 2H), 2.76-2.90 (m, 1H), 2.98-3.11 (m, 2H), 4.12-4.24 (m, 1H), 6.95 (m, 2H), 7.32 (dd, 1H), 7.70 (s, 1H), 7.76 (s, 1H), (dd, 1H), 8.38 (d, 1H), 8.42 (d, 1H), 8.57 (dd, 1H); Mass spectrum: M+H⁺ 404

[5] Compound [5] was prepared according to the procedure described in Example 52 using 2-(2-bromoethoxy)-2-methyl-propane as alkylating agent; this was followed by deprotection of the tert-butyl protecting group on the alcohol using trifluoroacetic acid in dichloromethane. The product gave the following characterizing data: NMR Spectrum: (CDCl3) 2.11 (dd, 1H), 2.16 (dd, 1H), 2.20-2.29 (m, 2H), 2.30-2.42 (m, 2H), 2.61-2.69 (m, 2H), 2.80 (bs, 1H), 3.08-3.17 (m, 2H), 3.65-3.70 (m, 2H), 4.19-4.28 (m, 1H), 6.98 (bs, 2H), 7.32 (dd, 1H), 7.70 (s, 1H), 7.78 (s, 1H), 7.88 (dd, 1H), 8.38 (d, 1H), 8.43 (d, 1H), 8.57 (dd, 1H); Mass spectrum: M+H⁺ 406

[6] Compound [6] was prepared according to the procedure described in Example 52 using 2-chloroacetamide as alkylating agent and 3-(1,3-benzoxazol-2-yl)-5-[1-(4-piperidyl)pyrazol-4-yl]pyridin-2-amine; The product gave the following characterizing data: NMR Spectrum: (DMSOd6) 2.00-2.13 (m, 4H), 2.24-2.33 (m, 2H), 2.89-2.87 (m, 2H), 2.92 (s, 2H), 4.11-4.20 (m, 1H), 7.15 (bs, 1H), 7.22 (bs, 1H), 7.41-7.49 (m, 2H), 7.65 (bs, 2H), 7.80 (dd, 1H), 7.85 (dd, 1H), 7.92 (s, 1H), 8.32 (s, 1H), 8.43 (d, 1H), 8.53 (s, 1H); Mass spectrum: M+H⁺ 418

[7] Compound [7] was prepared according to the procedure described in Example 52 using 2-chloro-N-methyl-acetamide as alkylating agent and 3-(1,3-benzoxazol-2-yl)-5-[1-(4-piperidyl)pyrazol-4-yl]pyridin-2-amine; The product gave the following characterizing data: NMR Spectrum: (DMSOd6) 1.99-2.16 (m, 4H), 2.23-2.53 (m, 2H), 2.64 (d, 3H), 2.86-2.93 (m, 2H), 2.96 (s, 2H), 4.11-4.21 (m, 1H), 7.41-7.49 (m, 2H), 7.65 (bs, 2H), 7.74 (q, 1H), 7.79 (dd, 1H), 7.85 (dd, 1H), 7.93 (s, 1H), 8.31 (s, 1H), 8.43 (d, 1H), 8.53 (d, 1H); Mass spectrum: M+H⁺ 432

[8] Compound [8] was prepared according to the procedure described in Example 52 using 2-chloro-N,N-dimethyl-acetamide as alkylating agent and 3-(1,3-benzoxazol-2-yl)-5-[1-(4-piperidyl)pyrazol-4-yl]pyridin-2-amine; The product gave the following characterizing data: NMR Spectrum: (DMSOd6): 1.93-2.07 (m, 4H), 2.21-2.30 (m, 2H), 2.82 (s, 3H), 2.91-2.99 (m, 2H), 3.05 (s, 3H), 3.19 (s, 2H), 4.10-4.19 (m, 1H), 7.41-7.49 (m, 2H), 7.64 (bs, 2H), 7.79 (dd, 1H), 7.84 (dd, 1H), 7.92 (s, 1H), 8.35 (s, 1H), 8.44 (d, 1H), 8.53 (d, 1H); Mass spectrum: M+H⁺ 446

EXAMPLE 54

2-methoxyethyl 4-[4-(6-amino-5-oxazolo[4,5-b]pyridin-2-yl-3-pyridyl)pyrazol-1-yl]piperidine-1-carboxylate

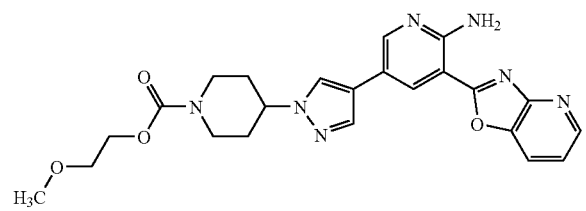

2-methoxyethyl chloroformate (0.035 ml) at 25° C. was added over a period of 5 minutes under argon to a stirred mixture of 3-oxazolo[4,5-b]pyridin-2-yl-5-[1-(4-piperidyl)pyrazol-4-yl]pyridin-2-amine (90 mg) and pyridine (5 ml). The resulting suspension was stirred at 25° C. for 2 hours. The solvent was evaporated. A solution of ammonia in methanol 7N (1 ml) was added and the mixture was adsorbed on silica gel. The crude product was purified by flash chromatography on silica gel eluting with 1 to 5% methanolic ammonia (7 N) in dichloromethane. The solvent was evaporated to dryness to afford 2-methoxyethyl 4-[4-(6-amino-5-oxazolo[4,5-b]pyridin-2-yl-3-pyridyl)pyrazol-1-yl]piperidine-1-carboxylate (75 mg) as a solid. NMR Spectrum: (CDCl3): 1.95-2.07 (m, 2H), 2.17-2.26 (m, 2H), 3.01 (bs, 2H), 3.40 (s, 3H), 3.63 (t, 2H), 4.28 (bs, 2H), 4.29-4.44 (m, 3H), 7.02 (bs, 2H), 7.35 (dd, 1H), 7.69 (s, 1H), 7.79 (s, 1H), 7.90 (dd, 1H), 8.41 (d, 1H), 8.42 (d, 1H), 8.59 (dd, 1H); Mass spectrum: M+H⁺ 464.

EXAMPLE 55

Using an analogous procedure to that described in Example 54, the appropriate reagent was reacted with 3-oxazolo[4,5-b]pyridin-2-yl-5-[1-(4-piperidyl)pyrazol-4-yl]pyridin-2-amine to give the compounds described in Table XXII.

TABLE XXII

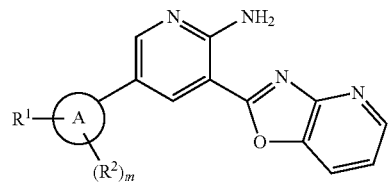

| No. & Note | R¹-A | m | R² |
|---|---|---|---|
| [1] | 1-(1-methylsulfonyl-4-piperidyl)pyrazol-4-yl | 0 | |
| [2] | 1-(1-cyclopropylsulfonyl-4-piperidyl)pyrazol-4-yl | 0 | |
| [3] | 1-(1-methoxycarbonyl-4-piperidyl)pyrazol-4-yl | 0 | |

[1] Compound [1] was prepared according to the procedure described in Example 54 using methanesulfonyl chloride; The product gave the following characterizing data: NMR Spectrum: (CDCl3) 2.18 (dd, 1H), 2.23 (dd, 1H), 2.29-2.38 (m, 2H), 2.87 (s, 3H), 2.93-3.02 (m, 2H), 3.93-4.01 (m, 2H), 4.30-4.39 (m, 1H), 7.20 (m, 2H), 7.35 (dd, 1H), 7.70 (s, 1H), 7.80 (s, 1H), 7.91 (dd, 1H), 8.41 (d, 1H), 8.42 (d, 1H), 8.59 (dd, 1H); Mass spectrum: M+H⁺ 440

[2] Compound [2] was prepared according to the procedure described in Example 54 using cyclopropanesulfonyl chloride; The product gave the following characterizing data: NMR Spectrum: (CDCl3): 0.79-0.91 (m, 1H), 1.01-1.08 (m, 2H), 1.18-1.24 (m, 2H), 2.17 (dd, 1H), 2.22 (dd, 1H), 2.28-2.37 (m, 2H), 3.03-3.11 (m, 2H), 3.95-4.03 (m, 2H), 4.30-4.38 (m, 1H), 7.01 (bs, 2H), 7.34 (dd, 1H), 7.71 (s, 1H), 7.79 (s, 1H), 7.90 (dd, 1H), 8.39 (dd, 1H), 8.43 (d, 1H), 8.58 (d, 1H); Mass spectrum: M+H⁺ 466

[3] Compound [3] was prepared according to the procedure described in Example 54 using methyl chloroformate; The product gave the following characterizing data: NMR Spectrum: (CDCl3) 1.94-2.08 (m, 2H), 2.16-2.27 (m, 2H), 2.90-3.08 (m, 2H), 3.74 (s, 3H), 4.31 (bs, 2H), 4.31-4.40 (m, 1H), 7.01 (bs, 2H), 7.34 (dd, 1H), 7.79 (s, 1H), 7.79 (s, 1H), 7.90 (dd, 1H), 8.39 (d, 1H), 8.42 (d, 1H), 8.58 (dd, 1H); Mass spectrum: M+H+ 420

EXAMPLE 56

1-[4-[4-(6-amino-5-oxazolo[4,5-b]pyridin-2-yl-3-pyridyl)pyrazol-1-yl]-1-piperidyl]-2-methoxy-ethanone

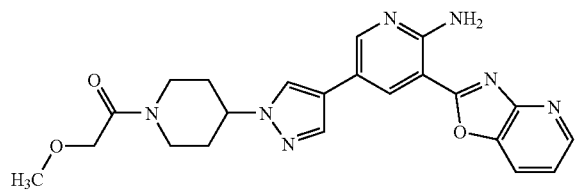

2-methoxyacetyl chloride (0.023 ml) was added in one portion to a stirred solution of 3-oxazolo[4,5-b]pyridin-2-yl-5-[1-(4-piperidyl)pyrazol-4-yl]pyridin-2-amine (90 mg) and triethylamine (0.069 ml) in THF (40 ml). The resulting mixture was stirred at 23° C. for 2 hours and concentrated to dryness. The product was purified by preparative HPLC using a Waters X-Bridge reverse-phase column (5 microns silica, 30 mm diameter, 150 mm length) and decreasingly polar mixtures of water (containing 0.2% ammonium carbonate) and acetonitrile as eluent. The fractions were evaporated to dryness and the resulting solid was triturated overnight with acetonitrile, filtered and dried under vacuum at 50° C. overnight to afford 1-[4-[4-(6-amino-5-oxazolo[4,5-b]pyridin-2-yl-3-pyridyl)pyrazol-1-yl]-1-piperidyl]-2-methoxy-ethanone (80 mg) as a solid. Mass spectrum: M+H+ 434; RT 2.23 min

EXAMPLE 57

Using an analogous procedure to that described in Example 56, the appropriate reagent was used to give the compounds described in Table XXIII.

TABLE XXIII

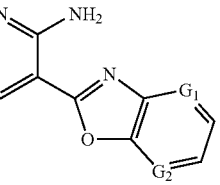

| No. & Note | R¹-A | m | R² | G₁ | G₂ |
|---|---|---|---|---|---|
| [1] | 1-(1-acetyl-4-piperidyl)pyrazol-4-yl | 0 | | N | CH |
| [2] | 1-[1-(2-hydroxyacetyl)-4-piperidyl]pyrazol-4-yl | 0 | | N | CH |
| [3] | 1-[1-[(2S)-2-hydroxypropanoyl]-4-piperidyl]pyrazol-4-yl | 0 | | N | CH |
| [4] | 1-(1-acetyl-4-piperidyl)pyrazol-4-yl | 0 | | CH | N |
| [5] | 1-[1-(2-methoxyacetyl)-4-piperidyl]pyrazol-4-yl | 0 | | CH | N |
| [6] | 1-[1-(2-hydroxyacetyl)-4-piperidyl]pyrazol-4-yl | 0 | | CH | N |
| [7] | 1-[1-[(2S)-2-hydroxypropanoyl]-4-piperidyl]pyrazol-4-yl | 0 | | CH | N |

[1] Compound [1] was prepared according to the procedure described in Example 56 using acetyl chloride and polystyrene supported-diisopropylethylamine resin as base; The product gave the following characterizing data: NMR Spectrum: (DMSOd6): 1.73-1.84 (m, 1H), 1.87-1.98 (m, 1H), 2.06 (s, 3H), 2.06-2.14 (m, 2H), 2.71-2.80 (m, 1H), 3.19-3.28 (m, 1H), 3.89-3.97 (m, 1H), 4.40-4.51 (m, 2H), 7.48 (dd, 1H), 7.68 (bs, 2H), 7.94 (s, 1H), 8.22 (d, 1H), 8.36 (s, 1H), 8.46 (d, 1H), 8.55 (d, 1H), 8.59 (d, 1H); Mass spectrum: M+H+ 404.

[2] Compound [2] was prepared according to the procedure described in Example 56 using (2-chloro-2-oxo-ethyl)acetate; the intermediate ester was deprotected as described in Example 34.2; The product gave the following characterizing data: Mass spectrum: M+H+ 420; RT 2.08 min.

[3] Compound [3] was prepared according to the procedure described in Example 56 using (2-chloro-1-methyl-2-oxo-ethyl)acetate; the intermediate ester was deprotected as described in Example 34.2; The product gave the following characterizing data: Mass spectrum: M+H+ 434; RT 2.18 min.

[4] Compound [4] was prepared according to the procedure described in Compound [1] using 3-oxazolo[5,4-b]pyridin-2-yl-5-[1-(4-piperidyl)pyrazol-4-yl]pyridin-2-amine as starting material; The product gave the following characterizing data: Mass spectrum: M+H+ 404; RT 2.44 min.

[5] Compound [5] was prepared according to the procedure described in Example 56 using 3-oxazolo[5,4-b]pyridin-2-yl-5-[1-(4-piperidyl)pyrazol-4-yl]pyridin-2-amine as starting material. The product gave the following characterizing data: Mass spectrum: M+H+ 434; RT 2.33 min.

[6] Compound [6] was prepared according to the procedure described in Compound [2] using 3-oxazolo[5,4-b]pyridin-2-yl-5-[1-(4-piperidyl)pyrazol-4-yl]pyridin-2-amine as starting material. The product gave the following characterizing data: Mass spectrum: M+H+ 420; RT 2.30 min.

[7] Compound [7] was prepared according to the procedure described in Compound [3] using 3-oxazolo[5,4-b]pyridin-2-yl-5-[1-(4-piperidyl)pyrazol-4-yl]pyridin-2-amine as start-

EXAMPLE 58

1-[4-[4-(6-amino-5-oxazolo[4,5-b]pyridin-2-yl-3-pyridyl)pyrazol-1-yl]-1-piperidyl]-2-dimethylamino-ethanone

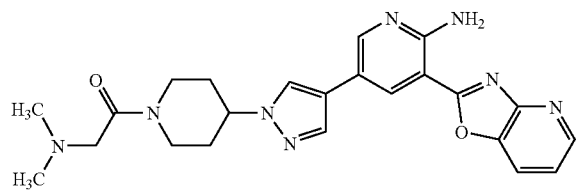

Benzotriazol-1-yl-[bis(dimethylamino)methylene]oxonium tetrafluoroborate (96 mg) was added to a stirred suspension of 3-oxazolo[4,5-b]pyridin-2-yl-5-[1-(4-piperidyl)pyrazol-4-yl]pyridin-2-amine (90 mg), 2-dimethylaminoacetic acid (27.0 mg) and 4-methylmorpholine (0.055 ml) in NMP (1 ml) at 25° C. The resulting solution was stirred at 25° C. for 2 hours. The reaction mixture was purified by preparative HPLC using a Waters OBD reverse-phase column (C-18, 5 microns silica, 19 mm diameter, 100 mm length, flow rate of 40 ml/minute) and decreasingly polar mixtures of water (containing 0.2% ammonium carbonate) and acetonitrile as eluent. The fractions containing the desired compound were evaporated to dryness, the solid was taken up in dichloromethane, dried over Magnesium sulphate, filtered and concentrated. A precipitate appeared which was diluted with diethyl ether, the solid was collected by filtration, washed with petroleum ether then triturated several hours with acetonitrile, filtered and dried under vacuum at 50° C. overnight to afford 1-[4-[4-(6-amino-5-oxazolo[4,5-b]pyridin-2-yl-3-pyridyl)pyrazol-1-yl]-1-piperidyl]-2-dimethylamino-ethanone (50.0 mg) as a solid. NMR Spectrum: (DMSOd6) 1.74-1.85 (m, 1H), 1.86-1.97 (m, 1H), 2.05-2.15 (m, 2H), 2.21 (s, 6H), 2.72-2.83 (m, 1H), 3.01-3.10 (m, 1H), 3.12-3.23 (m, 2H), 4.14-4.25 (m, 1H), 4.39-4.52 (m, 2H), 7.48 (dd, 1H), 7.68 (bs, 2H), 7.95 (s, 1H), 8.23 (dd, 1H), 8.36 (s, 1H), 8.47 (d, 1H), 8.56 (dd, 1H), 8.59 (d, 1H); Mass spectrum: M+H$^+$ 447;

EXAMPLE 59

Using an analogous procedure to that described in Example 58, the appropriate reagent was used to give the compounds described in Table XXIV.

TABLE XXIV

| No. & Note | R$^1$-A | m | R$^2$ | G1 | G2 |
|---|---|---|---|---|---|
| [1] | 1-[1-(3-methoxypropanoyl)-4-piperidyl]pyrazol-4-yl | 0 | | N | CH |
| [2] | 1-[1-[(2R)-2-methoxypropanoyl]-4-piperidyl]pyrazol-4-yl | 0 | | N | CH |
| [3] | 1-[1-(2-acetamidoacetyl)-4-piperidyl]pyrazol-4-yl | 0 | | N | CH |
| [4] | 1-[1-(3-acetamidopropanoyl)-4-piperidyl]pyrazol-4-yl | 0 | | N | CH |
| [5] | 1-[1-[2-(2-methoxyethoxy)acetyl]-4-piperidyl]pyrazol-4-yl | 0 | | N | CH |
| [6] | 1-[1-(3-dimethylaminopropanoyl)-4-piperidyl]pyrazol-4-yl | 0 | | N | CH |
| [7] | 1-[1-(2-dimethylaminoacetyl)-4-piperidyl]pyrazol-4-yl | 0 | | CH | N |
| [8] | 1-[1-(3-methoxypropanoyl)-4-piperidyl]pyrazol-4-yl | 0 | | CH | N |
| [9] | 1-[1-[(2R)-2-methoxypropanoyl]-4-piperidyl]pyrazol-4-yl | 0 | | CH | N |
| [10] | 1-[1-(2-acetamidoacetyl)-4-piperidyl]pyrazol-4-yl | 0 | | CH | N |
| [11] | 1-[1-(3-acetamidopropanoyl)-4-piperidyl]pyrazol-4-yl | 0 | | CH | N |
| [12] | 1-[1-[2-(2-methoxyethoxy)acetyl]-4-piperidyl]pyrazol-4-yl | 0 | | CH | N |
| [13] | 1-[1-(3-dimethylaminopropanoyl)-4-piperidyl]pyrazol-4-yl | 0 | | CH | N |

[1] Compound [1] was prepared according to the procedure described in Example 58 using 3-methoxypropanoic acid; The product gave the following characterizing data: Mass spectrum: M+H$^+$ 448; RT 2.35 min

[2] Compound [2] was prepared according to the procedure described in Example 58 using (R)-(+)-2-methoxypropanoic acid; The product gave the following characterizing data: Mass spectrum: M+H$^+$ 448; RT 2.35 min

[3] Compound [3] was prepared according to the procedure described in Example 58 using 2-acetamidoacetic acid; The product gave the following characterizing data: Mass spectrum: M+H$^+$ 461; RT 2.08 min

[4] Compound [4] was prepared according to the procedure described in Example 58 using 3-acetamidopropanoic acid; The product gave the following characterizing data: Mass spectrum: M+H$^+$ 475; RT 2.13 min

[5] Compound [5] was prepared according to the procedure described in Example 58 using 2-(2-methoxyethoxy)acetic acid; The product gave the following characterizing data: Mass spectrum: M+H$^+$ 478; RT 2.30 min

[6] Compound [6] was prepared according to the procedure described in Example 58 using 3-dimethylaminopropanoic acid hydrochloride; The product gave the following characterizing data: Mass spectrum: M+H$^+$ 461; RT 1.30 min

[7] Compound [7] was prepared according to the procedure described in Example 58 using 3-oxazolo[5,4-b]pyridin-2-yl-5-[1-(4-piperidyl)pyrazol-4-yl]pyridin-2-amine as starting material; The product gave the following characterizing data: Mass spectrum: M+H$^+$ 447; RT 1.35 min

[8] Compound [8] was prepared according to the procedure described in Compound [1] using 3-oxazolo[5,4-b]pyridin-2-yl-5-[1-(4-piperidyl)pyrazol-4-yl]pyridin-2-amine as starting material; The product gave the following characterizing data: Mass spectrum: M+H$^+$ 448; RT 2.55 min

[9] Compound [9] was prepared according to the procedure described in Compound [2] using 3-oxazolo[5,4-b]pyridin-2-yl-5-[1-(4-piperidyl)pyrazol-4-yl]pyridin-2-amine as starting material; The product gave the following characterizing data: Mass spectrum: M+H⁺ 448; RT 2.57 min

[10] Compound [10] was prepared according to the procedure described in Compound [3] using 3-oxazolo[5,4-b]pyridin-2-yl-5-[1-(4-piperidyl)pyrazol-4-yl]pyridin-2-amine as starting material; The product gave the following characterizing data: Mass spectrum: M+H⁺ 461 RT 2.28 min

[11] Compound [11] was prepared according to the procedure described in Compound [4] using 3-oxazolo[5,4-b]pyridin-2-yl-5-[1-(4-piperidyl)pyrazol-4-yl]pyridin-2-amine as starting material; The product gave the following characterizing data: Mass spectrum: M+H⁺ 475; RT 2.32 min

[12] Compound [12] was prepared according to the procedure described in Compound [5] using 3-oxazolo[5,4-b]pyridin-2-yl-5-[1-(4-piperidyl)pyrazol-4-yl]pyridin-2-amine as starting material; The product gave the following characterizing data: Mass spectrum: M+H⁺ 478; RT 2.52 min

[13] Compound [13] was prepared according to the procedure described in Compound [6] using 3-oxazolo[5,4-b]pyridin-2-yl-5-[1-(4-piperidyl)pyrazol-4-yl]pyridin-2-amine as starting material; The product gave the following characterizing data: Mass spectrum: M+H⁺ 461; RT 1.30 min

EXAMPLE 60

1-[4-[6-amino-5-(1,3-benzoxazol-2-yl)-3-pyridyl]-1-(4-piperidyl)pyrazol-3-yl]ethanol

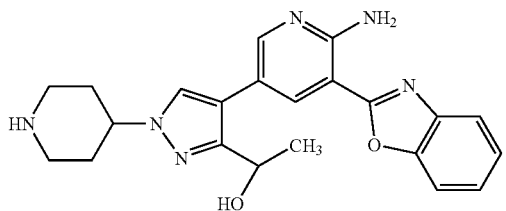

Tert-butyl 4-[4-[6-amino-5-(1,3-benzoxazol-2-yl)-3-pyridyl]-3-(1-hydroxyethyl)pyrazol-1-yl]piperidine-1-carboxylate (0.17 g) dissolved in dichloromethane (1 ml) was treated with trifluoroacetic acid (2 ml) and stirred at room temperature for 2 hours. The resulting mixture was evaporated to dryness and the residual trifluoroacetic acid was removed by azeotropic distillation with toluene under vacuum to afford the crude product. The crude product was purified by flash chromatography on silica gel eluting with 0 to 10% methanolic ammonia (7 N) in dichloromethane. The solvent was evaporated to dryness and the yellow foam was triturated with acetonitrile and re-evaporated to dryness to afford 1-[4-[6-amino-5-(1,3-benzoxazol-2-yl)-3-pyridyl]-1-(4-piperidyl)pyrazol-3-yl]ethanol (0.110 g) as a solid. NMR Spectrum: (DMSOd6): 1.43 (d, 1.5H), 1.44 (d, 1.5H), 1.74-1.86 (m, 1H), 1.93-2.03 (m, 2H), 2.03-2.09 (m, 1H), 2.09-2.17 (m, 1H), 2.56-2.64 (m, 1H), 3.01-3.08 (m, 1H), 3.10-3.18 (m, 1H), 4.10-4.20 (m, 1H), 4.78-4.87 (m, 1H), 5.21 (d, 0.5H), 5.22 (d, 0.5H), 7.40-7.48 (m, 2H), 7.63 (bs, 2H), 7.77 (dd, 1H), 7.84 (dd, 1H), 8.04 (s, 0.5H), 8.11 (s, 0.5H), 7.51 (d, 0.5H), 7.52 (d, 0.5H), 7.56 (d, 0.5H), 7.57 (d, 0.5H); Mass spectrum: M+H⁺ 405.

The tert-butyl 4-[4-[6-amino-5-(1,3-benzoxazol-2-yl)-3-pyridyl]-3-(1-hydroxyethyl)pyrazol-1-yl]piperidine-1-carboxylate used as starting material was prepared as follows:

4-bromo-2H-pyrazole-3-carbaldehyde (3 g), potassium carbonate (3.32 g) and tert-butyl 4-methylsulfonyloxypiperidine-1-carboxylate (6.23 g) in acetonitrile (150 ml) were stirred at reflux overnight. The resulting precipitate was removed by filtration and the filtrate was concentrated and purified by flash chromatography on silica gel eluting with 0 to 20% ethyl acetate in petroleum ether. The solvent was evaporated to dryness tert-butyl 4-(4-bromo-3-formyl-pyrazol-1-yl)piperidine-1-carboxylate (4.10 g) as a clear colourless oil which crystallised on standing. NMR Spectrum: (CDCl3) 1.48 (s, 9H), 1.92 (dd, 1H), 1.96 (dd, 1H), 2.10-2.18 (m, 2H), 2.81-2.97 (m, 2H), 4.27 (bs, 2H), 4.28-4.38 (m, 1H), 7.543 (s, 1H), 9.96 (s, 1H); Mass spectrum: M+H⁺ 360.

A suspension of 3-(1,3-benzoxazol-2-yl)-5-(4,4,5,5-tetramethyl-1,3,2-dioxaborolan-2-yl)pyridin-2-amine (0.3 g), tert-butyl 4-(4-bromo-3-formyl-pyrazol-1-yl)piperidine-1-carboxylate (0.362 g), potassium carbonate (0.335 g) and tetrakis(triphenylphosphine) palladium (0.093 g) in degassed acetonitrile (50 mL) was stirred at reflux overnight. The resulting suspension was cooled to room temperature, filtered, washed with dichloromethane (3×20 ml) and the filtrate concentrated and the crude product was purified by flash chromatography on silica gel eluting with 5 to 90% ethyl acetate in petroleum ether. The solvent was evaporated to dryness to afford tert-butyl 4-[4-[6-amino-5-(1,3-benzoxazol-2-yl)-3-pyridyl]-3-formyl-pyrazol-1-yl]piperidine-1-carboxylate (0.370 g) as a solid. NMR Spectrum: (DMSOd6) 1.44 (s, 9H), 1.87 (dd, 1H), 1.92 (dd, 1H), 2.09-2.18 (m, 2H), 2.97 (bs, 2H), 4.04-4.16 (m, 2H), 4.52-4.61 (m, 1H), 7.41-7.49 (m, 2H), 7.80 (dd, 1H), 7.82 (bs, 2H), 7.85 (dd, 1H), 8.48 (s, 1H), 8.56 (d, 1H), 8.65 (d, 1H), 9.99 (s, 1H); Mass spectrum: M+H⁺ 489.

Over a period of 1 minute at −10° C. under nitrogen, a solution of methylmagnesium bromide (1.287 ml, 1.4M in toluene) was added portionwise to a stirred solution of tert-butyl 4-[4-[6-amino-5-(1,3-benzoxazol-2-yl)-3-pyridyl]-3-formyl-pyrazol-1-yl]piperidine-1-carboxylate (0.44 g), dissolved in tetrahydrofuran (10 ml). The resulting solution was stirred at room temperature for 1 hour. The reaction mixture was allowed to warm to room temperature under stirring over a period of 1 hour, quenched with a saturated aqueous solution of ammonium chloride and extracted with dichloromethane (2×50 ml). The combined organic phases were washed with water (2×10 ml), dried over magnesium sulfate and concentrated to afford the crude product as a dark orange oil which solidified on standing. The product was purified by flash chromatography on silica gel eluting with 30 to 100% ethyl acetate in petroleum ether. The solvent was evaporated to dryness to afford tert-butyl 4-[4-[6-amino-5-(1,3-benzoxazol-2-yl)-3-pyridyl]-3-(1-hydroxyethyl)pyrazol-1-yl]piperidine-1-carboxylate (0.120 g) as a solid. NMR Spectrum: (DMSOd6) 1.42 (d, 3H), 1.43 (s, 9H), 1.79 (dd, 1H), 1.85 (dd, 1H), 2.01-2.08 (m, 2H), 2.93 (bs, 2H), 4.06 (bs, 2H), 4.28-4.38 (m, 1H), 4.77-4.87 (m, 1H), 5.22 (d, 1H), 7.40-7.48 (m,

EXAMPLE 61

[4-[6-amino-5-(1,3-benzoxazol-2-yl)-3-pyridyl]-2-(4-piperidyl)pyrazol-3-yl]methanol

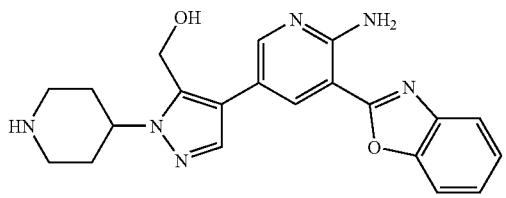

Tert-butyl N-[3-(1,3-benzoxazol-2-yl)-5-(4,4,5,5-tetramethyl-1,3,2-dioxaborolan-2-yl)-2-pyridyl]-N-tert-butoxycarbonyl-carbamate (250 mg), tert-butyl 4-(4-bromo-5-(hydroxymethyl)pyrazol-1-yl)piperidine-1-carboxylate (131 mg), bis(triphenylphosphine) palladium chloride (12.73 mg) and caesium fluoride (165 mg) were weighed out in a microwave vial and sealed. Methanol (3 ml) was added and argon was let to bubble in the resulting suspension for 5 minutes. The resulting mixture was heated in the microwave at 120° C. for 20 minutes. Insolubles were removed by filtration and the filtrate was concentrated. Hydrogen chloride (5N in isopropanol) (1.814 ml) was added and the mixture was heated at reflux for 2 hours. The resulting precipitate was collected by filtration, washed with isopropanol. The solid was taken up into methanolic ammonia (7N-2 mL) and dicalite speed plus. The crude product was purified by flash chromatography on silica gel eluting with 5 to 10% methanolic ammonia (7 N) in dichloromethane. The solvent was evaporated to dryness to afford [4-[6-amino-5-(1,3-benzoxazol-2-yl)-3-pyridyl]-2-(4-piperidyl)pyrazol-3-yl]methanol (60 mg). NMR Spectrum: (DMSOd6) 1.80-1.89 (m, 2H), 1.93 (dd, 1H), 1.98 (dd, 1H), 2.25 (bs, 1H), 2.57-2.67 (m, 2H), 3.03-3.11 (m, 2H), 4.37-4.46 (m, 1H), 4.56 (d, 2H), 5.46 (t, 1H), 7.41-7.48 (m, 2H), 7.70 (bs, 2H), 7.71 (s, 1H), 7.79 (dd, 1H), 7.85 (dd, 1H), 8.35 (d, 1H), 8.36 (d, 1H). Mass spectrum: M+H+ 391;

The tert-butyl N-[3-(1,3-benzoxazol-2-yl)-5-(4,4,5,5-tetramethyl-1,3,2-dioxaborolan-2-yl)-2-pyridyl]-N-tert-butoxycarbonyl-carbamate used as starting material was prepared as follows: N,N-dimethylpyridin-4-amine (42.1 mg) was added to 3-(1,3-benzoxazol-2-yl)-5-bromo-pyridin-2-amine (500 mg) and di-tert-butyl dicarbonate (1.069 g) suspended in DMF (5 ml). The resulting mixture was stirred at 25° C. for 48 hours. The reaction mixture was quenched with a saturated aqueous solution of sodium hydrogencarbonate (15 ml). The resulting precipitate was collected by filtration, washed with water and dried. The crude was taken up into ethylacetate and filtered through a pad of silica gel. The resulting filtrate was concentrated to afford tert-butyl N-[3-(1,3-benzoxazol-2-yl)-5-bromo-2-pyridyl]-N-tert-butoxycarbonyl-carbamate (710 mg) as a brown solid. NMR Spectrum: (CDCl3): 1.32 (s, 18H), 7.37-7.44 (m, 2H), 7.60 (dd, 1H), 7.80 (dd, 1H), 8.70 (d, 1H), 8.81 (d, 1H); Mass spectrum: M+H+ 491;

Tert-butyl N-[3-(1,3-benzoxazol-2-yl)-5-bromo-2-pyridyl]-N-tert-butoxycarbonyl-carbamate (4.78 g), potassium acetate (2.97 g), PdCl2(dppf) (0.394 g) and 4,4,5,5-tetramethyl-2-(4,4,5,5-tetramethyl-1,3,2-dioxaborolan-2-yl)-1,3,2-dioxaborolane (2.72 g) were suspended in dioxane (45 ml). The mixture was degassed with nitrogen at 25° C. The resulting suspension was stirred at 80° C. under nitrogen for 3 h. The reaction mixture was diluted with ethyl acetate (45 ml). The insolubles were removed by filtration and the filtrate was concentrated. The black oil was sonicated in petroleum ether (90 ml) for 10 minutes. The solid was collected by filtration, washed with petroleum ether and dried, to give crude tert-butyl N-[3-(1,3-benzoxazol-2-yl)-5-(4,4,5,5-tetramethyl-1,3,2-dioxaborolan-2-yl)-2-pyridyl]-N-tert-butoxycarbonyl-carbamate (5.10 g) as a beige solid. NMR Spectrum (CDCl3): 1.29 (s, 18H), 1.40 (s, 12H), 7.34-7.44 (m, 2H), 7.60 (dd, 1H), 7.80 (dd, 1H), 8.97 (d, 1H), 9.03 (d, 1H)

EXAMPLE 62

Using analogous procedures to those described in Example 61, unless otherwise stated, the appropriate reactants were used to give the compounds described in Table XXV.

TABLE XXV

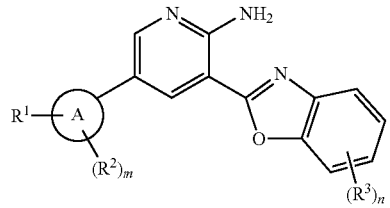

| No. & Note | R1-A | m | R2 | n | R3 |
|---|---|---|---|---|---|
| [1] | 1-(piperidin-4-yl)pyrazol-4-yl | 1 | 3-cyano | 0 | |
| [2] | 1-(piperidin-4-yl)pyrazol-4-yl | 1 | 3-dimethylcarbamoyl | 0 | |
| [3] | 1-(piperidin-4-yl)pyrazol-4-yl | 1 | 3-dimethylamino | 0 | |
| [4] | 1-(piperidin-4-yl)pyrazol-4-yl | 1 | 3-methylcarbamoyl | 0 | |
| [5] | 1-(piperidin-4-yl)pyrazol-4-yl | 1 | 3-carbamoyl | 0 | |
| [6] | 1-(piperidin-4-yl)pyrazol-4-yl | 1 | 3-hydroxymethyl | 1 | 4-fluoro |
| [7] | 1-(piperidin-4-yl)pyrazol-4-yl | 1 | 3-methoxymethyl | 1 | 4-fluoro |
| [8] | 1-(piperidin-4-yl)pyrazol-4-yl | 1 | 3-dimethylcarbamoyl | 1 | 4-fluoro |
| [9] | 1-(piperidin-4-yl)pyrazol-4-yl | 1 | 3-hydroxymethyl | 1 | 4-cyano |
| [10] | 1-(piperidin-4-yl)pyrazol-4-yl | 1 | 3-methoxymethyl | 1 | 4-cyano |

TABLE XXV-continued

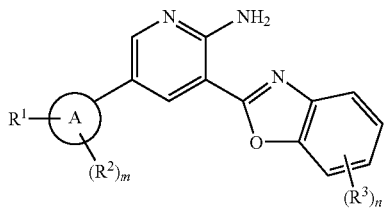

| No. & Note | R¹-A | m | R² | n | R³ |
|---|---|---|---|---|---|
| [11] | 1-(piperidin-4-yl)pyrazol-4-yl | 1 | 3-methyl | 1 | 4-cyano |
| [12] | 1-(piperidin-4-yl)pyrazol-4-yl | 1 | 3-(1-hydroxyethyl) | 1 | 4-cyano |
| [13] | 1-(piperidin-4-yl)pyrazol-4-yl | 1 | 3-hydroxymethyl | 1 | 7-methoxy |
| [14] | 1-(piperidin-4-yl)pyrazol-4-yl | 1 | 3-methoxymethyl | 1 | 7-methoxy |
| [15] | 1-(piperidin-4-yl)pyrazol-4-yl | 1 | 3-methyl | 1 | 7-methoxy |

[1] Compound [1] was prepared using the following procedure: A mixture of tert-butyl N-[3-(1,3-benzoxazol-2-yl)-5-(4,4,5,5-tetramethyl-1,3,2-dioxaborolan-2-yl)-2-pyridyl]-N-tert-butoxycarbonyl-carbamate (291 mg), tert-butyl 4-(4-bromo-3-cyanopyrazol-1-yl)piperidine-1-carboxylate (150 mg), tris(dibenzylideneacetone)dipalladium (19.33 mg), dicyclohexyl-[2-(2,6-dimethoxyphenyl)phenyl]phosphine (17.34 mg) and potassium phosphate (0.084 g) in a mixture of dioxane (5 ml) and water (150 µl) was degassed. The resulting suspension was stirred and heated to 120° C. for 3 hours under argon. After the mixture was cooled to room temperature the solvent was concentrated, ethyl acetate (80 ml) and water (20 ml) were added. The organic layer was washed with brine, dried over Magnesium sulphate, filtered and evaporated under reduce pressure. The crude product was purified by flash chromatography on silica gel eluting with 20 to 75% ethyl acetate in petroleum ether. The solvent was evaporated to dryness to afford tert-butyl 4-[4-[5-(1,3-benzoxazol-2-yl)-6-(bis(tert-butoxycarbonyl)amino)-3-pyridyl]-3-cyano-pyrazol-1-yl]piperidine-1-carboxylate (251 mg) as pale pink foam. The N-tert-butoxycarbonyl groups on the resultant product were removed using the procedure described for example 61. The product gave the following characterizing data: NMR Spectrum: (DMSOd6) 1.82 (dd, 1H), 1.87 (dd, 1H), 2.01-2.09 (m, 2H), 2.58-2.67 (m, 2H), 3.04-3.12 (m, 2H), 4.34-4.42 (m, 1H), 7.43-7.52 (m, 2H), 7.81 (dd, 1H), 7.87 (dd, 1H), 7.92 (bs, 2H), 8.58 (s, 2H), 8.51 (s, 1H); Mass spectrum: M+H⁺ 386.

The tert-butyl 4-(4-bromo-3-cyanopyrazol-1-yl)piperidine-1-carboxylate used as a starting material was prepared as follows:

4-bromo-2H-pyrazole-3-carbonitrile (500 mg), potassium carbonate (522 mg) and tert-butyl 4-methylsulfonyloxypiperidine-1-carboxylate (975 mg) in acetonitrile (15 ml) were stirred at 90° C. overnight. The mixture was concentrated and the residue was dissolved in ethylacetate, washed with water and brine, dried over magnesium sulfate and concentrated. The crude product was purified by flash chromatography on silica gel eluting with 10 to 50% ethyl acetate in petroleum ether. The solvent was evaporated to dryness to afford. tert-butyl 4-(4-bromo-3-cyano-pyrazol-1-yl)piperidine-1-carboxylate (627 mg) The product gave the following characterizing data: NMR Spectrum: (DMSOd6) 1.41 (s, 9H), 1.74 (dd, 1H), 1.78 (dd, 1H), 1.98-2.08 (m, 2H), 2.90 (bs, 2H), 3.95-4.11 (m, 2H), 4.46-4.57 (m, 1H), 8.45 (s, 1H).

[2] Compound [2] was prepared according to the procedure described for compound [1]; NMR Spectrum: (DMSOd6) 1.80 (dd, 1H), 1.85 (dd, 1H), 1.98-2.06 (m, 2H), 2.56-2.64 (m, 2H), 2.91 (s, 3H), 3.03 (s, 3H), 3.03-3.09 (m, 2H), 4.18-4.28 (m, 1H), 7.40-2.49 (m, 2H), 7.68 (bs, 2H), 7.79 (dd, 1H), 7.84 (dd, 1H), 8.30 (s, 1H), 8.34 (d, 1H), 8.35 (d, 1H); Mass spectrum: M+H⁺ 432.

The tert-butyl 4-[4-bromo-3-(dimethylcarbamoyl)pyrazol-1-yl]piperidine-1-carboxylate used as starting material was prepared as follows:

di(imidazol-1-yl)methanone (1910 mg) was added portionwise to a suspension of 4-bromo-1H-pyrazole-3-carboxylic acid (900 mg) in DCM (18 ml).After 2 hours dimethylamine 2M in THF (9.42 ml) was added portionwise and the mixture was stirred overnight. The reaction mixture was purified by preparative HPLC using a Waters X-Bridge reverse-phase column (5 microns silica, 30 mm diameter, 150 mm length) and decreasingly polar mixtures of water (containing 0.2% ammonium carbonate) and acetonitrile as eluent. The fractions were evaporated to dryness to afford 4-bromo-N,N-dimethyl-1H-pyrazole-3-carboxamide (471 mg) as a solid. NMR Spectrum: (DMSOd6): 2.95 (s, 3H), 2.98 (s, 3H), 7.99 (s, 1H); Mass spectrum: M+H⁺ 220.

4-bromo-N,N-dimethyl-1H-pyrazole-3-carboxamide (450 mg), potassium carbonate (456 mg) and tert-butyl 4-(methylsulfonyloxy)piperidine-1-carboxylate (900 mg) in acetonitrile (13 mL) were stirred at 90° C. overnight. The mixture was concentrated and the residue was dissolved in ethylacetate, washed with water, brine dried over magnesium sulfate and concentrated. The crude product was purified by flash chromatography on silica gel eluting with 50 to 90% ethyl acetate in petroleum ether. The solvent was evaporated to dryness to afford tert-butyl 4-[4-bromo-3-(dimethylcarbamoyl)pyrazol-1-yl]piperidine-1-carboxylate (340 mg). NMR Spectrum: (DMSOd6) 1.41 (s, 9H), 1.73 (dd, 1H), 1.78 (dd, 1H), 1.96-1.05 (m, 2H), 2.89 (bs, 2H), 2.95 (s, 3H), 2.87 (s, 3H), 3.92-4.10 (m, 2H), 4.33-4.44 (m, 1H), 8.15 (s, 1H); Mass spectrum: M+H⁺ 401-403

[3] Compound [3] was prepared according to the procedure described for compound [1]; The product gave the following characterizing data: NMR Spectrum: (DMSOd6) 1.72 (dd, 1H), 1.78 (dd, 1H), 1.91-2.00 (m, 2H), 2.12 (bs, 1H), 2.53-2.61 (m, 2H), 2.65 (s, 6H), 2.99-3.08 (m, 2H), 3.97-4.05 (m, 1H), 7.40-7.48 (m, 2H), 7.62 (bs, 2H), 7.81 (dd, 1H), 7.84 (dd, 1H), 7.93 (s, 1H), 8.41 (d, 1H), 8.43 (d, 1H); Mass spectrum: M+H⁺ 404.

The tert-butyl 4-(4-bromo-3-dimethylamino-pyrazol-1-yl)piperidine-1-carboxylate used as starting material was prepared as follows:

Dibromine (6.49 ml) in glacial acetic acid (12 ml) was added to a stirred solution of 1H-pyrazol-3-amine (5.26 g) in glacial acetic acid (12 ml) at 0° C. over 30 mins. At the end of the addition, carbon tetrachloride (6 ml) was added and the resulting mixture was stirred at 25° C. for 1 hour.

The precipitate was filtered and washed with carbon tetrachloride, the solid so obtained was suspended in ethyl acetate, a saturated aqueous solution of sodium hydrogencarbonate was added until neutral, the reaction mixture was extracted with ethyl acetate, the organic phases were combined, washed with brine, dried over magnesium sulfate and concentrated to afford the a dark black-brown solid.

The crude product was purified by flash chromatography on silica gel eluting with 10 to 60% ethyl acetate in dichloromethane. The solvent was evaporated to dryness to afford 4-bromo-1H-pyrazol-3-amine hydrobromide (6.17 g); NMR Spectrum: (DMSO-d6+TFAd) 8.13 (s, 1H); Mass spectrum: M+H$^+$ 162-164.

37% Aqueous formaldehyde (1.453 ml) was added to a stirred solution of 4-bromo-1H-pyrazol-3-amine hydrobromide (1.58 g) in methanol (50 ml) and water (5 ml) at 23° C. At the end of the addition, a precipitate appeared. The resulting suspension was stirred at 23° C. for 15 minutes and sodium cyanotrihydroborate (0.613 g) was added portionwise.

The solution was stirred at 25° C. for 1 hour, diluted with dichloromethane, washed with saturated aqueous sodium bicarbonate, water, and brine. The organic phase was dried with magnesium sulphate, filtered and concentrated. The crude product was purified by flash chromatography on silica gel eluting with 0 to 25% ethyl acetate in dichloromethane. The solvent was evaporated to dryness to afford 4-bromo-N,N-dimethyl-1H-pyrazol-3-amine (0.670 g) as a clear yellow oil which crystallised on standing. NMR Spectrum: (DMSOd6) 2.75 (s, 6H), 7.75 (s, 1H); Mass spectrum: M+H$^+$ 190-192

Sodium hydride (0.498 g, 60% in mineral oil) was added to a stirred solution of 4-bromo-N,N-dimethyl-1H-pyrazol-3-amine (1.97 g) dissolved in DMF (20 ml) under argon. The resulting mixture was stirred at 23° C. for 30 minutes. A solution of Tert-butyl 4-methylsulfonyloxypiperidine-1-carboxylate (3.19 g) in DMF (10 ml) was added and the reaction mixture was stirred at 95° C. for 5 hours and left at 23° C. overnight. DMF was evaporated and the residue was taken up in dichloromethane, washed with H$_2$O and sat NaCl. The organic was dried (magnesium sulphate), filtered and concentrated. The residue was purified by flash chromatography on silica gel eluting with 0 to 30% ethyl acetate in petroleum ether. The solvent was evaporated to afford tert-butyl 4-(4-bromo-3-dimethylamino-pyrazol-1-yl)piperidine-1-carboxylate (1.700 g) as a clear colorless oil which crystallised on standing. NMR Spectrum: (DMSOd6) 1.40 (s, 9H), 1.65 (d, 1H), 1.71 (d, 1H), 1.89-1.87 (m, 2H), 2.74 (s, 6H), 2.85 (bs, 2H), 3.93-4.06 (m, 2H), 4.09-4.17 (m, 1H), 7.82 (s, 1H); Mass spectrum: M+H$^+$ 373-375

[4] Compound [4] was prepared according to the procedure described for compound [1]; The product gave the following characterizing data: NMR Spectrum: (DMSOd6) 1.84 (dd, 1H), 1.89 (dd, 1H), 1.99-2.07 (m, 2H), 2.55-2.66 (m, 2H), 2.75 (d, 3H), 3.03-3.12 (m, 2H), 4.19-4.29 (m, 1H), 7.40-7.48 (m, 2H), 7.69 (bs, 2H), 7.80 (dd, 1H), 7.84 (dd, 1H), 8.04 (q, 1H), 8.20 (s, 1H), 8.44 (d, 1H), 8.59 (d, 1H); Mass spectrum: M+H$^+$ 418.

The tert-butyl 4-[4-bromo-3-(methylcarbamoyl)pyrazol-1-yl]piperidine-1-carboxylate used as starting material was prepared as follows:

4-bromo-1H-pyrazole-3-carboxylic acid (815 mg) was suspended in thionylchloride (9749 μl) and heated to 90° C. for 3 hours. The mixture was concentrated.

The residue was dried under vacuum, suspended in THF (1 ml). Methylamine 2M in THF (12.84 ml) was added. The mixture was stirred overnight. The reaction mixture was concentrated and purified by preparative HPLC using a Waters X-Bridge reverse-phase column (5 microns silica, 30 mm diameter, 150 mm length) and decreasingly polar mixtures of water (containing 0.2% ammonium carbonate) and acetonitrile as eluent. The fractions were evaporated to dryness to afford 4-bromo-N-methyl-1H-pyrazole-3-carboxamide (579 mg) as a solid; NMR Spectrum: (DMSOd6) 2.72 (d, 3H), 8.02 (s, 1H), 8.09 (q, 1H); Mass spectrum: M+H$^+$ 206.

4-bromo-N-methyl-1H-pyrazole-3-carboxamide (550 mg), potassium carbonate (579 mg) and tert-butyl 4-methylsulfonyloxypiperidine-1-carboxylate (1081 mg) in acetonitrile (20 mL) were stirred at 90° C. overnight. The mixture was concentrated and the residue was dissolved in ethyl acetate, washed with water, brine dried over magnesium sulfate and concentrated. The crude product was purified by flash chromatography on silica gel eluting with 40 to 70% ethyl acetate in petroleum ether. The solvent was evaporated to dryness to afford tert-butyl 4-[4-bromo-3-(methylcarbamoyl) pyrazol-1-yl]piperidine-1-carboxylate (436 mg) as a off-white solid. The product gave the following characterizing data: NMR Spectrum: (DMSOd6) 1.42 (s, 9H), 1.79 (dd, 1H), 1.84 (dd, 1H), 1.97-2.05 (m, 2H), 2.71 (d, 3H), 2.91 (bs, 2H), 3.97-4.13 (m, 2H), 4.33-4.43 (m, 1H), 8.05 (q, 1H), 8.15 (s, 1H); Mass spectrum: M+H$^+$ 386-388.

[5] Compound [5] was prepared according to the procedure described for compound [1]; The product gave the following characterizing data: NMR Spectrum: (DMSOd6) 1.83 (dd, 1H), 1.89 (dd, 1H), 1.99-2.07 (m, 2H), 2.27 (bs, 1H), 2.56-2.65 (m, 2H), 3.03-3.11 (m, 2H), 4.20-4.29 (m, 1H), 7.26 (bs, 1H), 7.40-7.49 (m, 3H), 7.78 (bs, 2H), 7.80 (dd, 1H), 7.84 (dd, 1H), 8.20 (s, 1H), 8.45 (d, 1H), 8.59 (d, 1H); Mass spectrum: M+H$^+$ 404.

The tert-butyl 4-[4-bromo-3-carbamoyl-pyrazol-1-yl]piperidine-1-carboxylate used as starting material was prepared as follows:

4-bromo-1H-pyrazole-3-carboxylic acid (815 mg) was suspended in thionyl chloride (9749 μl) and heated to 90° C. for 3 hours. The mixture was concentrated. The residue was dried under vacuum, suspended in THF (1 ml). Ammonia 2M in THF (12.8 ml) was added. The mixture was stirred overnight. The reaction mixture was concentrated and purified by preparative HPLC using a Waters X-Bridge reverse-phase column (5 microns silica, 30 mm diameter, 150 mm length) and decreasingly polar mixtures of water (containing 0.2% ammonium carbonate) and acetonitrile as eluent. The fractions were evaporated to dryness to afford 4-bromo-1H-pyrazole-3-carboxamide (452 mg) as a white solid. NMR Spectrum: (DMSOd6) 7.34 (bs, 1H), 7.48 (bs, 1H), 8.00 (s, 1H); Mass spectrum: M+H$^+$ 190.

4-bromo-1H-pyrazole-3-carboxamide (673 mg), potassium carbonate (636 mg) and tert-butyl 4-methylsulfonyloxypiperidine-1-carboxylate (1187 mg) in acetonitrile (20 ml) were stirred at 90° C. overnight. The mixture was concentrated and the residue was dissolved in ethyl acetate, washed with water, brine, dried over magnesium sulfate and concentrated. The crude product was purified by flash chromatography on silica gel eluting with 55 to 100% ethyl acetate in petroleum ether. The solvent was evaporated to dryness to afford tert-butyl 4-(4-bromo-3-carbamoyl-pyrazol-1-yl)piperidine-1-carboxylate (489 mg) as a solid. NMR Spectrum: (DMSOd6): 1.41 (s, 9H), 1.78 (dd, 1H), 1.83 (dd, 1H), 1.96-

2.04 (m, 2H), 2.90 (bs, 2H), 4.03 (m, 2H), 4.33-4.41 (m, 1H), 7.30 (s, 1H), 7.44 (s, 1H), 8.14 (s, 1H)

[6] Compound [6] was prepared according to the procedure described for compound [1]; The product gave the following characterizing data: NMR Spectrum: (CDCl3) 2.02-2.25 (m, 6H), 3.16-3.26 (m, 2H), 4.09-4.21 (m, 1H), 4.80 (s, 2H), 6.90 (bs, 2H), 7.09 (dd, 1H), 7.31 (ddd, 1H), 7.39 (d, 1H), 7.61 (s, 1H), 8.38 (d, 1H), 8.44 (d, 1H); Mass spectrum: M+H$^+$ 0.409 The tert-butyl N-tert-butoxycarbonyl-N-[3-(4-fluoro-1,3-benzoxazol-2-yl)-5-(4,4,5,5-tetramethyl-1,3,2-dioxaborolan-2-yl)-2-pyridyl]carbamate used as starting material was prepared as follows:

N,N-dimethylpyridin-4-amine (0.190 g), was added to a stirred suspension of 5-bromo-3-(4-fluoro-1,3-benzoxazol-2-yl)pyridin-2-amine (2.4 g) and di-tert-butyl carbonate (4.83 g) in DMF (50 ml) at 25° C. under nitrogen. The resulting suspension was stirred at 25° C. for 45 hours. The DMF was evaporated under reduce pressure. The mixture was adsorbed on silica gel. The crude product was purified by flash chromatography on silica gel eluting with 0 to 2% methanol in dichloromethane. The solvent was evaporated to dryness to afford tert-butyl N-[5-bromo-3-(4-fluoro-1,3-benzoxazol-2-yl)-2-pyridyl]-N-tert-butoxycarbonyl-carbamate (3.54 g, 89%) as a pale orange solid. NMR Spectrum: (CDCl3) 1.35 (s, 18H), 7.12 (dd, 1H), 7.38 (ddd, 1H), 7.42 (d, 1H), 8.72 (d, 1H), 8.85 (d, 1H); Mass spectrum: M+H$^+$ 508-510 PdCl$_2$dppf (0.278 g), potassium acetate (2.095 ml) and 4,4,5,5-tetramethyl-2-(4,4,5,5-tetramethyl-1,3,2-dioxaborolan-2-yl)-1,3,2-dioxaborolane (1.923 g) were added over a period of 10 minutes, to a stirred solution tert-butyl N-[5-bromo-3-(4-fluoro-1,3-benzoxazol-2-yl)-2-pyridyl]-N-tert-butoxycarbonyl-carbamate (3.5 g) dissolved in dioxane (30 ml) degazed and under argon. The resulting mixture was stirred at 80° C. for 3 hours. The salts were filtered; The mixture was evaporated under reduce pressure. The crude product was purified by flash chromatography on silica gel eluting with 30 to 40% ethyl acetate in petroleum ether. The solvent was evaporated to dryness to afford tert-butyl N-tert-butoxycarbonyl-N-[3-(4-fluoro-1,3-benzoxazol-2-yl)-5-(4,4,5,5-tetramethyl-1,3,2-dioxaborolan-2-yl)-2-pyridyl]carbamate (3.26 g) as a pale orange solid. NMR Spectrum: (CDCl3) 1.33 (s, 18H), 1.39 (s, 12H), 7.10 (dd, 1H), 7.34 (ddd, 1H), 7.42 (d, 1H), 8.99 (d, 1H), 9.08 (d, 1H); Mass spectrum: M-(boc+pinacol)+H$^+$ 374

[7] Compound [7] was prepared according to the procedure described for compound [1]; The product gave the following characterizing data: NMR Spectrum: (DMSOd6) 1.78 (dd, 1H), 1.84 (dd, 1H), 1.95-2.02 (m, 2H), 2.10 (bs, 1H), 2.55-2.63 (m, 2H), 3.01-3.09 (m, 2H), 3.40 (s, 3H), 4.13-4.23 (m, 1H), 4.40 (s, 2H), 7.32 (dd, 1H), 7.46 (ddd, 1H), 7.62 (bs, 2H), 7.66 (d, 1H), 8.19 (s, 1H), 8.46 (d, 1H), 8.50 (d, 1H); Mass spectrum: M+H$^+$ 423.

[8] NMR Spectrum: (DMSOd6): 1.81 (dd, 1H), 1.86 (dd, 1H), 1.99-2.06 (m, 2H), 2.57-2.65 (m, 2H), 2.92 (s, 3H), 3.04 (s, 3H), 3.04-3.10 (m, 2H), 4.20-4.28 (m, 1H), 7.33 (dd, 1H), 7.48 (ddd, 1H), 7.65 (bs, 2H), 7.68 (d, 1H), 8.31 (s, 1H), 8.36 (d, 1H), 8.37 (d, 1H); Mass spectrum: M+H$^+$ 450.

[9] NMR Spectrum: 1.97 (dd, 1H), 2.02 (dd, 1H), 2.08-2.16 (m, 2H), 2.81-2.90 (m, 2H), 3.21-3.28 (m, 2H), 4.28-4.36 (m, 1H), 4.51 (s, 2H), 5.29 (bs, 1H), 7.60 (dd, 1H), 7.71 (bs, 2H), 7.93 (d, 1H), 8.14 (d, 1H), 8.17 (s, 1H), 8.59 (s, 2H); Mass spectrum: M+H$^+$ 416. The tert-butyl N-tert-butoxycarbonyl-N-[3-(4-cyano-1,3-benzoxazol-2-yl)-5-(4,4,5,5-tetramethyl-1,3,2-dioxaborolan-2-yl)-2-pyridyl]carbamate used as starting material was prepared as follows:

N,N-dimethylpyridin-4-amine (0.147 g), was added to a stirred suspension of 5-bromo-3-(4-cyano-1,3-benzoxazol-2-yl)-pyridin-2-amine (1.9 g) and di-tert-butyl dicarbonate (3.55 g) in DMF (50 ml) at 25° C. under nitrogen. The resulting suspension was stirred at 25° C. for 45 hours. The DMF was evaporated under reduce pressure. The mixture was adsorbed on silica gel. The crude product was purified by flash chromatography on silica gel eluting with 0 to 2% methanol in dichloromethane. The solvent was evaporated to dryness to afford tert-butyl N-[5-bromo-3-(4-cyano-1,3-benzoxazol-2-yl)-2-pyridyl]-N-tert-butoxycarbonyl-carbamate (2.67 g) as a pale yellow solid. NMR Spectrum: (CDCl3) 1.42 (s, 18H), 7.51 (dd, 1H), 7.74 (dd, 1H), 7.86 (dd, 1H), 8.77 (d, 1H), 8.87 (d, 1H); Mass spectrum: M(−Boc)+H$^+$ 417.

PdCl$_2$dppf (0.208 g), potassium acetate (1.564 g) and 4,4,5,5-tetramethyl-2-(4,4,5,5-tetramethyl-1,3,2-dioxaborolan-2-yl)-1,3,2-dioxaborolane (1.436 g) were added to a stirred degassed solution of tert-butyl N-[5-bromo-3-(4-cyano-1,3-benzoxazol-2-yl)-2-pyridyl]-N-tert-butoxycarbonyl-carbamate (2.65 g) dissolved in dioxane (30 ml) over a period of 10 minutes. The resulting mixture was stirred at 80° C. for 3 hours under argon. The salts were filtered. The mixture was evaporated under reduced pressure. The crude product was purified by flash chromatography on silica gel eluting with 20 to 40% ethyl acetate in petroleum ether. The solvent was evaporated to dryness to afford tert-butyl N-tert-butoxycarbonyl-N-[3-(4-cyano-1,3-benzoxazol-2-yl)-5-(4,4,5,5-tetramethyl-1,3,2-dioxaborolan-2-yl)-2-pyridyl]carbamate (2.60 g) as a pale beige solid. NMR Spectrum: (CDCl3) 1.39 (s, 18H), 1.40 (s, 12H), 7.48 (dd, 1H), 7.71 (dd, 1H), 7.85 (dd, 1H), 9.03 (d, 1H), 9.09 (d, 1H); Mass spectrum: M(−Boc-pinacol)+H$^+$ 380.

[10] NMR Spectrum: (DMSOd6): 1.79 (dd, 1H), 1.84 (dd, 1H), 1.94-2.04 (m, 2H), 2.55-2.64 (m, 2H), 3.01-3.10 (m, 2H), 3.41 (s, 3H), 4.13-4.23 (m, 1H), 4.41 (s, 2H), 7.60 (dd, 1H), 7.70 (bs, 2H), 7.93 (d, 1H), 8.16 (d, 1H), 8.20 (s, 1H), 8.50 (d, 1H), 8.53 (d, 1H); Mass spectrum: M+H$^+$ 430

[11] NMR Spectrum: 1.74-1.83 (m, 2H), 1.89 (dd, 1H), 1.94 (dd, 1H), 2.40 (s, 3H), 2.58-2.68 (m, 2H), 3.01-3.10 (m, 2H), 4.18-4.29 (m, 1H), 7.60 (dd, 1H), 7.71 (bs, 2H), 7.93 (d, 1H), 8.16 (d, 1H), 8.24 (d, 1H), 8.35 (d, 1H); Mass spectrum: M+H$^+$ 400.

[12] NMR Spectrum: (DMSOd6): 1.43 (d, 3H), 1.77 (dd, 1H), 1.82 (dd, 1H), 1.94-2.01 (m, 2H), 2.55-2.62 (m, 2H), 3.01-3.08 (m, 2H), 4.11-4.20 (m, 1H), 4.78-4.86 (m, 1H), 5.24 (d, 1H), 7.60 (dd, 1H), 7.69 (bs, 2H), 7.93 (d, 1H), 8.06 (s, 1H), 8.14 (d, 1H), 8.58 (d, 1H), 8.60 (d, 1H); Mass spectrum: M+H$^+$ 430

[13] NMR Spectrum: (DMSOd6): 1.80 (dd, 1H), 1.85 (dd, 1H), 1.95-2.02 (m, 2H), 2.10 (bs, 1H), 2.56-2.63 (m, 2H), 3.02-3.10 (m, 2H), 3.43 (s, 3H), 4.01 (s, 3H), 4.13-4.21 (m, 1H), 4.48 (d, 2H) 5.22 (t, 1H), 7.08 (d, 1H), 7.35 (dd, 1H), 7.41 (dd, 1H), 7.62 (bs, 2H), 8.13 (s, 1H), 8.49 (d, 1H), 8.52 (d, 1H); Mass spectrum: M+H$^+$ 421.

The tert-butyl N-tert-butoxycarbonyl-N-[3-(7-methoxy-1,3-benzoxazol-2-yl)-5-(4,4,5,5-tetramethyl-1,3,2-dioxaborolan-2-yl)-2-pyridyl]carbamate used as starting material was prepared as follows:

N,N-dimethylpyridin-4-amine (0.153 g) was added to a stirred suspension of 5-bromo-3-(7-methoxy-1,3-benzoxazol-2-yl)pyridin-2-amine (2 g) and di-tert-butyl dicarbonate (3.88 g) dissolved in DMF (20 ml) under nitrogen. The reaction was incomplete and further di-tert-butyl dicarbonate (3.88 g) and N,N-dimethylpyridin-4-amine (0.153 g) were added at 25° C. and the reaction mixture was stirred at 25° C. for 16 hours. The resulting suspension was stirred at 25° C. for a total of 90 hours. The reaction mixture was diluted with ethyl acetate (500 ml) and washed with water (10×50 ml), dried over magnesium sulfate and concentrated to afford a pale orange oil. This product was purified by flash chromatography on silica gel eluting with 5 to 20% ethyl acetate in petroleum ether. The solvent was evaporated to dryness to afford tert-butyl N-[5-bromo-3-(7-methoxy-1,3-benzoxazol-2-yl)-2-pyridyl]-N-tert-butoxycarbonyl-carbamate (2.1 g, 64.6%) as a white solid. NMR Spectrum: (DMSOd6) 1.34 (s, 18H), 4.06 (s, 3H), 6.93 (d, 1H), 7.30 (dd, 1H), 7.40 (d, 1H), 8.70 (d, 1H), 8.82 (d, 1H); Mass spectrum: M(-Boc)+H+ 420;

PdCl$_2$dppf (0.201 g), potassium acetate (1.514 g) and 4,4,5,5-tetramethyl-2-(4,4,5,5-tetramethyl-1,3,2-dioxaborolan-2-yl)-1,3,2-dioxaborolane (1.39 g) were added over a period of 10 minutes to a stirred solution of tert-butyl N-[5-bromo-3-(7-methoxy-1,3-benzoxazol-2-yl)-2-pyridyl]-N-tert-butoxycarbonyl-carbamate (2.59 g) dissolved in dioxane (30 ml) that had been degassed. Under argon, the resulting mixture was stirred at 80° C. for 3 hours. The mixture was filtered and the filtrate was evaporated under reduced pressure. The residue was purified by flash chromatography on silica gel eluting with 20 to 80% ethyl acetate in petroleum ether. The solvent was evaporated to dryness to afford tert-butyl N-tert-butoxycarbonyl-N-[3-(7-methoxy-1,3-benzoxazol-2-yl)-5-(4,4,5,5-tetramethyl-1,3,2-dioxaborolan-2-yl)-2-pyridyl]carbamate (1.89 g) as a solid. NMR Spectrum: (CDCl3) 1.30 (s, 18H), 1.39 (s, 12H), 4.08 (s, 3H), 6.90 (d, 1H), 7.28 (dd, 1H), 7.40 (d, 1H), 8.96 (d, 1H), 9.02 (d, 1H); Mass spectrum: M(-Boc-pinacol)+H+ 386.

[14] NMR Spectrum: (DMSOd6): 1.79 (dd, 1H), 1.84 (dd, 1H), 1.95-2.02 (m, 2H), 2.10 (bs, 1H), 2.55-2.63 (m, 2H), 3.01-3.10 (m, 2H), 3.43 (s, 3H), 4.01 (s, 3H), 4.14-4.22 (m, 1H), 4.39 (s, 2H) 7.08 (dd, 1H), 7.34 (dd, 1H), 7.41 (dd, 1H), 7.62 (bs, 2H), 8.19 (s, 1H), 8.43 (d, 1H), 8.49 (d, 1H); Mass spectrum: M+H+ 435.

[15] NMR Spectrum: (DMSOd6): 1.74-1.84 (m, 2H), 1.89 (dd, 1H), 1.94 (dd, 1H), 2.06 (bs, 1H), 2.36 (s, 3H), 2.58-2.67 (m, 2H), 3.01-3.10 (m, 2H), 4.02 (s, 3H), 4.18-4.27 (m, 1H), 7.08 (d, 1H), 7.35 (dd, 1H), 7.40 (dd, 1H), 7.62 (bs, 2H), 7.64 (s, 1H), 8.17 (d, 1H), 8.27 (d, 1H); Mass spectrum: M+H+ 405.

EXAMPLE 63

1-[4-[4-[6-amino-5-(1,3-benzoxazol-2-yl)-3-pyridyl]-3-(methylaminomethyl)pyrazol-1-yl]-1-piperidyl]ethanone

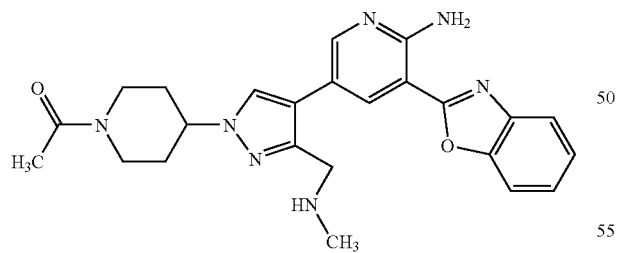

Over a period of 5 minutes, a solution of 1-(1-acetylpiperidin-4-yl)-4-(6-amino-5-(1,3-benzoxazol-2-yl)pyridin-3-yl)-1H-pyrazole-3-carbaldehyde (132 mg) in MeOH/dichloromethane (1:1) that had been cooled to 0° C., was added to a stirred solution of methylamine (0.153 ml, 0.31 mmol) dissolved in dichloromethane (6 ml) and methanol (6 ml). The resulting solution was stirred at 0° C. for 20 minutes. Sodium triacetoxyhydroborate (78 mg) was added at 0° C. to the mixture and stirred at 0° C. for 5 hours. The mixture was evaporated. A saturated solution of sodium bicarbonate was added and the mixture was extracted with methylene chloride, dried over magnesium sulphate, filtered and evaporated under reduced pression. The reaction mixture was purified by preparative HPLC using a Waters X-Bridge reverse-phase column (5 micron silica, 19 mm diameter, 100 mm length) and decreasingly polar mixtures of water (containing 0.2% ammonium carbonate) and acetonitrile as eluent. The fractions were evaporated to dryness, tritured with hot acetonitrile, filtered and dried under reduce pressure to afford 1-[4-[4-[6-amino-5-(1,3-benzoxazol-2-yl)-3-pyridyl]-3-(methylaminomethyl)pyrazol-1-yl]-1-piperidyl]ethanone (23 mg) as a solid. NMR Spectrum: (CDCl3) 1.86-2.11 (m, 2H), 2.15 (s, 3H), 2.13-2.24 (m, 1H), 2.24-2.33 (m, 1H), 2.60 (s, 3H), 2.73-2.84 (m, 1H), 3.21-3.32 (m, 1H), 3.96 (s, 2H), 3.97-4.06 (m, 1H), 4.31-4.42 (m, 1H), 4.70-4.85 (m, 1H), 6.97 (bs, 2H), 7.32-7.41 (m, 2H), 7.54 (s, 1H), 7.57 (dd, 1H), 7.73 (dd, 1H), 8.32 (s, 1H), 8.42 (s, 1H); Mass spectrum: M+H+ 446;

The 1-(1-acetyl-4-piperidyl)-4-[6-amino-5-(1,3-benzoxazol-2-yl)-3-pyridyl]pyrazole-3-carbaldehyde used as starting material was prepared as follows:

A solution of hydrogen chloride in 2-propanol (2047 μl, 8.19 mmol) at 25° C. was added to tert-butyl 4-[4-[6-amino-5-(1,3-benzoxazol-2-yl)-3-pyridyl]-3-formyl-pyrazol-1-yl]piperidine-1-carboxylate (200 mg). The resulting mixture was stirred at 25° C. for 2 hours. The solid was filtered and washed with isopropanol to afford 4-[6-amino-5-(1,3-benzoxazol-2-yl)-3-pyridyl]-1-(4-piperidyl)pyrazole-3-carbaldehyde hydrochloride (170 mg). A solution of triethylamine (0.171 ml) was added to 4-[6-amino-5-(1,3-benzoxazol-2-yl)-3-pyridyl]-1-(4-piperidyl)pyrazole-3-carbaldehyde hydrochloride (174 mg) dissolved in CH$_2$Cl$_2$ (10 ml) at 0° C. The resulting solution was stirred at 0° C. for 10 minutes. Acetyl chloride (0.032 ml) was added to the mixture at 0° C., then the mixture was stirred at 25° C. for 40 minutes. The mixture was adsorbed on silica gel. The crude product was purified by flash chromatography on silica gel eluting with 1 to 4% methanol in dichloromethane. The solvent was evaporated to dryness to afford 1-(1-acetyl-4-piperidyl)-4-[6-amino-5-(1,3-benzoxazol-2-yl)-3-pyridyl]pyrazole-3-carbaldehyde (148 mg) as a pale beige foam. NMR Spectrum: (CDCl3): 2.02-2.15 (m, 2H), 2.17 (s, 3H), 2.23-2.38 (m, 2H), 2.78-2.88 (m, 1H), 3.25-3.36 (m, 1H), 3.99-4.10 (m, 1H), 4.43-4.55 (m, 1H), 4.76-4.87 (m, 1H), 6.92 (bs, 2H), 7.34-7.41 (m, 2H), 7.59 (dd, 1H), 7.65 (s, 1H), 7.74 (dd, 1H), 8.42 (d, 1H), 8.64 (d, 1H), 10.09 (s, 1H); Mass spectrum: M+H+ 431;

EXAMPLE 64

2-[2-amino-5-[1-(1-methyl-4-piperidyl)pyrazol-4-yl]-3-pyridyl]-1,3-benzoxazole-7-carbonitrile

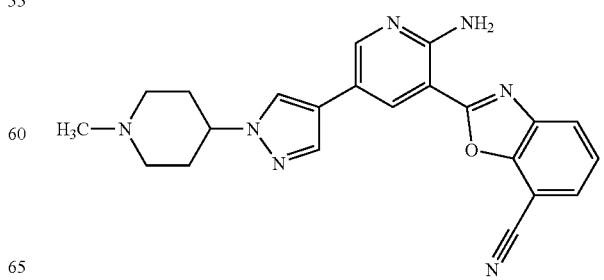

tert-butyl 4-[4-[6-amino-5-(7-cyano-1,3-benzoxazol-2-yl)-3-pyridyl]pyrazol-1-yl]piperidine-1-carboxylate (56 mg) was dissolved in trifluoroacetic acid (1955 µl) at 25° C. and the mixture was stirred for 2 hours. After concentration the residue was dissolved in 7N methanolic ammonia and concentrated. The resultant residue was dissolved in methanol (900 µl) and dichloromethane (900 µl), 37% aqueous formaldehyde (10.3 µl) was added and the mixture was stirred for 10 min. Sodium triacetoxyhydroborate (29.3 mg) was added and the mixture was stirred for 1 hour.

A solution of 7N methanolic ammonia (1 ml) was added and the mixture was adsorbed on silica. The crude product was purified by flash chromatography on silica gel eluting with 3 to 12% methanolic ammonia (7 N) in dichloromethane. After concentration the residue was triturated in methanol. A solid was obtained 2-[2-amino-5-[1-(1-methyl-4-piperidyl)pyrazol-4-yl]-3-pyridyl]-1,3-benzoxazole-7-carbonitrile (25.00 mg). NMR Spectrum: (DMSOd6) 1.95-2.11 (m, 6H), 2.22 (s, 3H), 2.84-2.92 (m, 2H), 4.09-4.20 (m, 1H), 7.60 (dd, 1H), 7.67 (bs, 2H), 7.92 (s, 1H), 7.94 (dd, 1H), 8.20 (dd, 1H), 8.32 (s, 1H), 8.38 (d, 1H), 8.57 (d, 1H); Mass spectrum: M+H+ 400;

The tert-butyl 4-[4-[6-amino-5-(7-cyano-1,3-benzoxazol-2-yl)-3-pyridyl]pyrazol-1-yl]piperidine-1-carboxylate used as starting material was prepared as follows:

A mixture of 2-aminopyridine-3-carbaldehyde (300 mg) and 3-amino-2-hydroxy-benzonitrile (330 mg) in methanol (10 ml) was stirred at 50° C. for overnight. The resulting suspension was concentrated to dryness to afford 2-(2-amino-3-pyridyl)-2,3-dihydro-1,3-benzoxazole-7-carbonitrile (585 mg) as a pale brown solid, which was used without further purification. 2-(2-amino-3-pyridyl)-2,3-dihydro-1,3-benzoxazole-7-carbonitrile (585 mg) and manganese dioxide (4269 mg) in dichloromethane (50 ml) was stirred at room temperature for 2 hours. The reaction mixture was filtered and the filtrate was evaporated. The residue was purified by preparative HPLC using a Waters X-Terra reverse-phase column (5 micron silica, 19 mm diameter, 100 mm length) and decreasingly polar mixtures of water (containing 0.2% ammonium carbonate) and acetonitrile as eluent. The fractions were evaporated to dryness to afford 2-(2-amino-3-pyridyl)-1,3-benzoxazole-7-carbonitrile (59.0 mg) as a pale brown solid. NMR Spectrum: (DMSOd6) 6.82 (dd, 1H), 7.59 (dd, 1H), 7.67 (bs, 2H), 7.93 (dd, 1H), 8.18 (dd, 1H), 8.28 (dd, 1H), 8.32 (dd, 1H); Mass spectrum: M+H+ 237;

A mixture of 1-bromopyrrolidine-2,5-dione (44.5 mg) and 2-(2-amino-3-pyridyl)-1,3-benzoxazole-7-carbonitrile (59 mg) in tetrahydrofuran (5 ml) was stirred at room temperature for 1 hour. The reaction was incomplete and further 1-bromopyrrolidine-2,5-dione (44.5 mg) was added at room temperature and the reaction mixture was stirred at room temperature for 1 hour. The resulting precipitate was collected by filtration, washed with acetonitrile (2×2 ml) and dried to a constant weight to afford 2-(2-amino-5-bromo-3-pyridyl)-1,3-benzoxazole-7-carbonitrile (70.0 mg) as a pale brown solid. NMR Spectrum: (DMSOd6) 7.61 (dd, 1H), 7.85 (bs, 2H), 7.96 (dd, 1H), 8.20 (dd, 1H), 8.37 (d, 1H), 8.39 (d, 1H); Mass spectrum: M(+CH₃CN)+H+ 356-358.

2-(2-amino-5-bromo-3-pyridyl)-1,3-benzoxazole-7-carbonitrile (70 mg), tert-butyl 4-[4-(4,4,5,5-tetramethyl-1,3,2-dioxaborolan-2-yl)pyrazol-1-yl]piperidine-1-carboxylate (0.092 g), Bis(triphenylphosphine) palladium chloride (3.90 mg) and caesium fluoride (101 mg) in methanol (10 ml) were flushed with nitrogen and stirred at 120° C. under microwave irradition. The crude reaction mixture was cooled to room temperature and absorbed onto silica gel and purified by flash chromatography on silica gel eluting with 5 to 40% ethyl acetate in petroleum ether. The solvent was evaporated to dryness to afford tert-butyl 4-[4-[6-amino-5-(7-cyano-1,3-benzoxazol-2-yl)-3-pyridyl]pyrazol-1-yl]piperidine-1-carboxylate (0.055 g) as an orange solid. NMR Spectrum: (CDCl3) 1.49 (s, 9H), 1.99-2.05 (m, 2H), 2.18-2.25 (m, 2H), 2.92 (bs, 2H), 4.26-4.40 (m, 3H), 7.51 (dd, 1H), 7.71 (d, 1H), 7.78 (s, 1H), 7.81 (s, 1H), 8.02 (d, 1H), 8.36 (s, 1H), 8.53 (s, 1H); Mass spectrum: M+H+ 486.

EXAMPLE 65

[2-[2-amino-5-[1-(1-methyl-4-piperidyl)pyrazol-4-yl]-3-pyridyl]-1,3-benzoxazol-7-yl]methanol

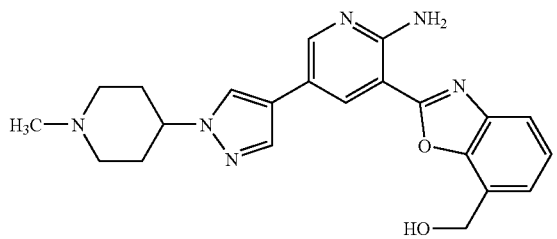

37% Aqueous formaldehyde (0.015 ml) at 0° C., was added to a stirred solution [2-[2-amino-5-[1-(4-piperidyl)pyrazol-4-yl]-3-pyridyl]-1,3-benzoxazol-7-yl]methanol (46 mg) dissolved in dichloromethane (2 ml) and methanol (2 ml) over a period of 5 minutes. The resulting solution was stirred at 0° C. for 10 minutes. Sodium triacetoxyhydroborate (30.0 mg) was added at 0° C. to the mixture and stirred at 0° C. for 1 hour. A solution 7N of ammonia in methanol (20 ml) was added to the mixture and adsorbed on silica gel. The crude product was purified by flash chromatography on silica gel eluting with 4 to 8% methanolic ammonia (7 N) in dichloromethane. The solvent was evaporated to dryness and the product was recrystallized from acetonitrile to afford [2-[2-amino-5-[1-(1-methyl-4-piperidyl)pyrazol-4-yl]-3-pyridyl]-1,3-benzoxazol-7-yl]methanol (37.0 mg) as a solid. NMR Spectrum: (CDCl3) 2.05-2.29 (m, 6H), 2.36 (s, 3H), 2.98-3.08 (m, 2H), 4.12-4.23 (m, 1H), 5.09 (s, 2H), 6.88 (bs, 2H), 7.37 (dd, 1H), 7.43 (d, 1H), 7.66 (d, 1H), 7.67 (s, 1H), 7.74 (s, 1H), 8.30 (d, 1H), 8.32 (d, 1H); Mass spectrum: M+H+ 405;

The [2-[2-amino-5-[1-(4-piperidyl)pyrazol-4-yl]-3-pyridyl]-1,3-benzoxazol-7-yl]methanol used as starting material was prepared as follows:

A 2-aminopyridine-3-carbaldehyde (650 mg) was added to a stirred solution of methyl 3-amino-2-hydroxy-benzoate (890 mg) in methanol (10 ml) and dichloromethane (5 ml). The resulting solution was stirred at 50° C. for 10 hours. The crude product was purified by flash chromatography on silica gel eluting with 1 to 2% methanol in dichloromethane. The solvent was evaporated to dryness to afford methyl 2-(2-amino-3-pyridyl)-2,3-dihydro-1,3-benzoxazole-7-carboxylate (400 mg) as a pale yellow solid. Manganese(IV) oxide (4629 mg) was added to a solution of this yellow solid (400 mg) in dichloromethane (5 ml) and tetrahydrofuran (10 ml), the mixture was stirred at 25° C. for 15 hours. The mixture was filtered and the filtrate was adsorbed on silica gel and purified by flash chromatography on silica gel eluting with 30 to 50% ethyl acetate in petroleum ether. The solvent was evaporated to dryness to afford methyl 2-(2-amino-3-pyridyl)-1,3-benzoxazole-7-carboxylate (345 mg) as a pale yellow solid. NMR Spectrum: (CDCl3) 4.06 (s, 3H), 6.79 (dd, 1H), 6.89 (bs, 2H), 7.43 (dd, 1H), 7.92 (dd, 1H), 8.00 (dd, 1H), 8.26 (dd, 1H), 8.44 (dd, 1H); Mass spectrum: M+H⁺ 270;

1-bromopyrrolidine-2,5-dione (233 mg) was added to a stirred solution of methyl 2-(2-amino-3-pyridyl)-1,3-benzoxazole-7-carboxylate (335 mg) dissolved in tetrahydrofuran (10 ml) over a period of 5 minutes. The resulting solution was stirred at 25° C. for 2 hours. The solvent was evaporated and the mixture was washed with water and dried over phosphorus pentoxide under reduce pressure to afford a brown solid. The mixture was adsorbed on silica gel with chloroform and methanolic ammonia (7N). The crude product was purified by flash chromatography on silica gel eluting with 0 to 2% methanol in dichloromethane. The solvent was evaporated to dryness to afford methyl 2-(2-amino-5-bromo-3-pyridyl)-1,3-benzoxazole-7-carboxylate (405 mg) as a pale brown solid. NMR Spectrum: (DMSOd6) 3.99 (s, 3H), 7.56 (dd, 1H), 7.85 (bs, 2H), 7.97 (d, 1H), 8.12 (d, 1H), 8.29 (s, 1H), 8.35 (s, 1H); Mass spectrum: M+H⁺ 348-350.

A mixture of bis(triphenylphosphine)palladium chloride (17.69 mg) was added to tert-butyl 4-[4-(4,4,5,5-tetramethyl-1,3,2-dioxaborolan-2-yl)pyrazol-1-yl]piperidine-1-carboxylate (380 mg), methyl 2-(2-amino-5-bromo-3-pyridyl)-1,3-benzoxazole-7-carboxylate (390 mg) and caesium fluoride (459 mg) dissolved in degassed methanol (5 ml) under argon. The resulting slurry was heated at 120° C. in the microwave for 30 minutes. The mixture was adsorbed on silica gel. The crude product was purified by flash chromatography on silica gel eluting with 1 to 4% methanol in dichloromethane. The solvent was evaporated to dryness to afford methyl 2-[2-amino-5-[1-(1-tert-butoxycarbonyl-4-piperidyl)pyrazol-4-yl]-3-pyridyl]-1,3-benzoxazole-7-carboxylate (365 mg) as a pale yellow solid. NMR Spectrum: (CDCl3) 1.49 (s, 9H), 1.97 (dd, 1H), 2.02 (dd, 1H), 2.16-2.23 (m, 2H), 2.84-3.01 (m, 2H), 4.06 (s, 3H), 4.19-4.40 (m, 3H), 6.88 (bs, 2H), 7.44 (dd, 1H), 7.70 (s, 1H), 7.80 (s, 1H), 7.94 (dd, 1H), 8.01 (dd, 1H), 8.40 (d, 1H), 8.48 (d, 1H); Mass spectrum: M+H⁺ 519;

Aluminium(III) lithium hydride (0.251 ml, 1M in THF) was added dropwise to methyl 2-[2-amino-5-[1-(1-tert-butoxycarbonyl-4-piperidyl)pyrazol-4-yl]-3-pyridyl]-1,3-benzoxazole-7-carboxylate (130 mg) dissolved in THF (5 ml). 7N Methanolic ammonia (15 ml) was added to the mixture and the solution was adsorbed on silica gel and the solvent was evaporated. The crude product was purified by flash chromatography on silica gel eluting with 1 to 4% methanol in dichloromethane. The solvent was evaporated to dryness to afford tert-butyl 4-[4-[6-amino-5-[7-(hydroxymethyl)-1,3-benzoxazol-2-yl]-3-pyridyl]pyrazol-1-yl]piperidine-1-carboxylate (56.0 mg) as a clear yellow solid. NMR Spectrum: (CDCl3): 1.49 (s, 9H), 1.96 (dd, 1H), 2.00 (dd, 1H), 2.13-2.24 (m, 2H), 2.84-3.01 (m, 2H), 4.17-4.44 (m, 3H), 5.09 (s, 2H), 6.98 (bs, 2H), 7.37 (dd, 1H), 7.43 (s, 1H), 7.66 (s, 1H), 7.67 (d, 1H), 7.76 (s, 1H), 8.28 (d, 1H), 8.33 (d, 1H); Mass spectrum: M+H⁺ 491;

7N Hydrogen chloride in propanol-2 (1083 µl) was added to tert-butyl 4-[4-[6-amino-5-[7-(hydroxymethyl)-1,3-benzoxazol-2-yl]-3-pyridyl]pyrazol-1-yl]piperidine-1-carboxylate (93 mg). The mixture was heated at 78° C. for 1 hour. The solvent was evaporated under reduced pressure. A solution of 7N methanolic ammonia was added to the mixture at 0° C. The mixture was adsorbed on silica gel. The crude product was purified by flash chromatography on silica gel eluting with 2 to 10% methanolic ammonia (7 N) in dichloromethane. The solvent was evaporated to dryness to afford [2-[2-amino-5-[1-(4-piperidyl)pyrazol-4-yl]-3-pyridyl]-1,3-benzoxazol-7-yl]methanol (46.0 mg) as a pale yellow solid. NMR Spectrum: (DMSOd6) 2.04-2.17 (m, 2H), 2.17-2.28 (m, 2H), 2.94-3.08 (m, 2H), 3.33-3.39 (m, 2H), 4.42-4.51 (m, 1H), 4.92 (d, 2H), 5.51 (t, 1H), 7.41 (dd, 1H), 7.46 (d, 1H), 7.65 (bs, 2H), 7.72 (d, 1H), 7.99 (s, 1H), 8.29 (s, 1H), 8.47 (d, 1H), 8.54 (d, 1H); Mass spectrum: M+H⁺ 391.

EXAMPLE 66

1-[4-[4-[6-amino-5-(1,3-benzoxazol-2-yl)-3-pyridyl]-3-(methoxymethyl)pyrazol-1-yl]-1-piperidyl]-2-hydroxy-ethanone

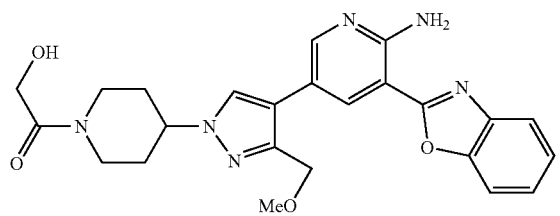

(2-chloro-2-oxo-ethyl)acetate (0.029 ml) was added in one portion to a stirred mixture of 3-(1,3-benzoxazol-2-yl)-5-[3-(methoxymethyl)-1-(4-piperidyl)pyrazol-4-yl]pyridin-2-amine (90 mg) and triethylamine (0.062 ml) in CH₂Cl₂ (5 ml) at 23° C. The resulting mixture was stirred at 23° C. for 2 hours and concentrated to dryness. Methanol (20 ml) and water (1 ml) were added to the residue followed by lithium hydroxide hydrateaqueous solution (0.334 g, 2M). The resulting solution was stirred at 23° C. After 4 hours the reaction mixture was concentrated and the crude product was purified by flash chromatography on silica gel eluting with 0 to 5% methanolic ammonia (7 N) in dichloromethane. The fractions were evaporated to dryness to afford 1-[4-[4-[6-amino-5-(1,3-benzoxazol-2-yl)-3-pyridyl]-3-(methoxymethyl)pyrazol-1-yl]-1-piperidyl]-2-hydroxy-ethanone (42.0 mg) as a solid. NMR Spectrum: (DMSOd6): 1.77-1.87 (m, 1H), 1.88-2.00 (m, 1H), 2.05-2.14 (m, 2H), 2.79-2.89 (m, 1H), 3.11-3.21 (m, 1H), 3.41 (s, 3H), 3.78-3.88 (m, 1H), 4.08-4.21 (m, 2H), 4.40 (s, 2H), 4.41-4.51 (m, 2H), 4.58 (t, 1H), 7.40-7.48 (m, 2H), 7.66 (bs, 2H), 7.78 (dd, 1H), 7.84 (dd, 1H), 8.23 (s, 1H), 8.42 (d, 1H), 8.50 (d, 1H); Mass spectrum: M+H⁺ 463.

EXAMPLE 67

Using an analogous procedure to that described in Example 66, the appropriate acid chloride was used to give the compounds described in Table XXVI.

TABLE XXVI

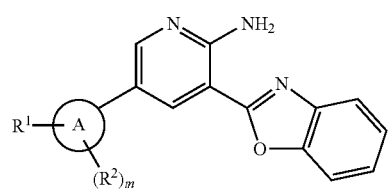

| No. & Note | R¹-A | m | R² |
|---|---|---|---|
| [1] | 1-[1-[(2S)-2-hydroxypropanoyl]-4-piperidyl]pyrazol-4-yl | 1 | 3-methoxymethyl |
| [2] | 1-[1-[(2S)-2-hydroxypropanoyl]-4-piperidyl]pyrazol-4-yl | 1 | 3-hydroxymethyl |

[1] The acid chloride used was (S)-(2-chloro-1-methyl-2-oxo-ethyl)acetate. The product gave the following characterising data: NMR Spectrum: (DMSOd6) 1.21 (d, 1.5H), 1.23 (d, 1.5H), 1.74-1.87 (m, 1H), 1.88-2.00 (m, 1H), 2.05-2.17 (m, 2H), 2.75-2.89 (m, 1H), 3.15-3.26 (m, 1H), 3.40 (s, 3H), 4.08-4.20 (m, 1H), 4.40 (s, 2H), 4.54 (m, 3H), 4.90-4.98 (m, 1H), 7.40-7.49 (m, 2H), 7.66 (bs, 2H), 7.78 (dd, 1H), 7.84 (dd, 1H), 8.24 (s, 1H), 8.42 (d, 1H), 8.50 (d, 1H); Mass spectrum: M+H+ 477.

[2] The acid chloride used was (S)-(2-chloro-1-methyl-2-oxo-ethyl)acetate. The product gave the following characterising data: NMR Spectrum: (DMSOd6) 1.21 (d, 1.5H), 1.23 (d, 1.5H), 1.74-1.87 (m, 1H), 1.88-1.99 (m, 1H), 2.05-2.16 (m, 2H), 2.74-2.87 (m, 1H), 3.13-3.26 (m, 1H), 4.09-4.20 (m, 1H), 4.39-4.53 (m, 3H), 4.51 (d, 2H), 4.90-4.97 (m, 1H), 5.25 (t, 1H), 7.40-7.49 (m, 2H), 7.66 (bs, 2H), 7.77 (dd, 1H), 7.84 (dd, 1H), 8.19 (d, 1H), 8.53 (d, 1H), 8.55 (d, 1H); Mass spectrum: M+H+ 463.

EXAMPLE 68

2-[4-[4-[6-amino-5-(1,3-benzoxazol-2-yl)-3-pyridyl]-3-(methoxymethyl)pyrazol-1-yl]-1-piperidyl]-N-methyl-acetamide

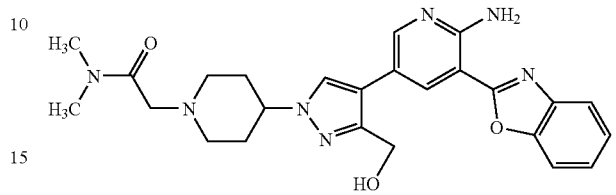

A solution of 2-chloro-N-methyl-acetamide (0.027 ml) in DMF (1 ml) was added to a stirred mixture of 3-(1,3-benzoxazol-2-yl)-5-[3-(methoxymethyl)-1-(4-piperidyl)pyrazol-4-yl]pyridin-2-amine (100 mg) and potassium carbonate (68 mg) in DMF (5 ml) at 25° C. under argon. The resulting solution was heated at 75° C. overnight. The DMF was evaporated and the residue was purified by preparative HPLC using a Waters X-Bridge reverse-phase column (5 microns silica, 30 mm diameter, 150 mm length) and decreasingly polar mixtures of water (containing 0.2% ammonium carbonate) and acetonitrile as eluent. The fractions were evaporated to afford 2-[4-[4-[6-amino-5-(1,3-benzoxazol-2-yl)-3-pyridyl]-3-(methoxymethyl)pyrazol-1-yl]-1-piperidyl]-N-methyl-acetamide (53.0 mg) as a solid. NMR Spectrum: (DMSOd6) 1.98-2.06 (m, 2H), 2.09 (dd, 1H), 2.14 (dd, 1H), 2.22-2.31 (m, 2H), 2.64 (d, 3H), 2.86-2.93 (m, 2H), 2.95 (s, 2H), 3.41 (s, 3H), 4.11-4.19 (m, 1H), 4.41 (s, 2H), 7.41-7.48 (m, 2H), 7.66 (bs, 2H), 7.75 (q, 1H), 7.78 (dd, 1H), 7.84 (dd, 1H), 8.19 (s, 1H), 8.43 (d, 1H), 8.50 (d, 1H); Mass spectrum: M+H+ 476.

EXAMPLE 69

2-[4-[4-[6-amino-5-(1,3-benzoxazol-2-yl)-3-pyridyl]-3-(hydroxymethyl)pyrazol-1-yl]-1-piperidyl]-N,N-dimethyl-acetamide

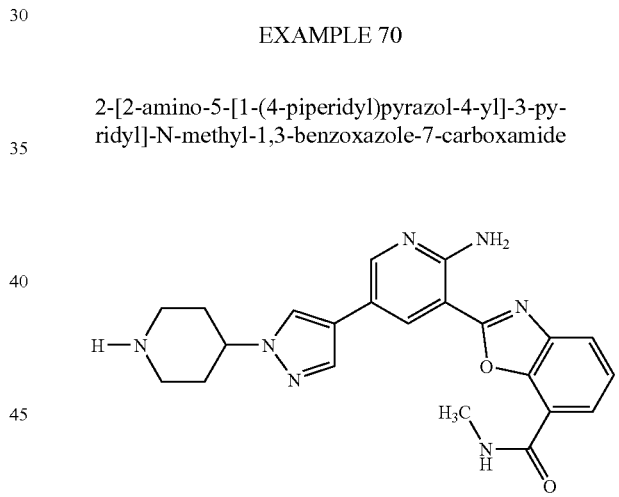

The title compound was prepared using an analogous procedure to that described in Example 68 except that 2-chloro-N,N-dimethylacetamide was used in place of 2-chloro-N-methylacetamide. The product gave the following characterising data: NMR Spectrum: (DMSOd6) 1.94-2.11 (m, 4H), 2.28 (bs, 2H), 2.83 (s, 3H), 2.90-3.04 (m, 2H), 3.04 (s, 3H), 3.24 (bs, 2H), 4.07-4.20 (m, 1H), 4.50 (d, 2H), 5.24 (t, 1H), 7.30-7.49 (m, 2H), 7.65 (bs, 2H), 7.77 (dd, 1H), 7.84 (dd, 1H), 8.19 (d, 1H), 8.53 (d, 1H), 8.56 (d, 1H); Mass spectrum: M+H+ 476.

EXAMPLE 70

2-[2-amino-5-[1-(4-piperidyl)pyrazol-4-yl]-3-pyridyl]-N-methyl-1,3-benzoxazole-7-carboxamide A 5M solution of hydrogen chloride in isopropanol (0.773 ml) was added to tert-butyl 4-[4-[6-amino-5-[7-(methylcarbamoyl)-1,3-benzoxazol-2-yl]-3-pyridyl]pyrazol-1-yl]piperidine-1-carboxylate (200 mg) dissolved in isopropanol (5 ml). The resulting solution was heated at 75° C. for 2 hours. The mixture was evaporated to dryness, diisopropylethyamine (1 ml) was added and the mixture was adsorbed on silica gel with 7N methanolic ammonia and dichloromethane. The crude product was purified by flash chromatography on silica gel eluting with 2 to 8% methanolic ammonia (7 N) in dichloromethane. The solvent was evaporated to dryness to afford 2-[2-amino-5-[1-(4-piperidyl)pyrazol-4-yl]-3-pyridyl]-N-methyl-1,3-benzoxazole-7-carboxamide (92 mg) as a solid.

NMR Spectrum: (DMSOd6) 1.81-1.92 (m, 1H), 1.94-2.11 (m, 3H), 2.11-2.20 (m, 1H), 2.64-2.72 (m, 1H), 2.96 (d, 3H), 3.07-3.17 (m, 2H), 4.17-4.31 (m, 1H), 7.51 (dd, 1H), 7.64 (bs, 2H), 7.82 (d, 1H), 7.92 (s, 1H), 7.98 (dd, 1H), 8.25 (s, 0.5H), 8.31 (s, 0.5H), 8.43 (q, 1H), 8.54 (d, 1H), 8.57 (d, 1H); Mass spectrum: M+H+ 418.

The tert-butyl 4-[4-[6-amino-5-[7-(methylcarbamoyl)-1,3-benzoxazol-2-yl]-3-pyridyl]pyrazol-1-yl]piperidine-1-carboxylate used as starting material was prepared as follows:

A 3N aqueous solution of sodium hydroxide (0.694 ml) was added to methyl 2-[2-amino-5-[1-(1-tert-butoxycarbonyl-4-piperidyl)pyrazol-4-yl]-3-pyridyl]-1,3-benzoxazole-7-carboxylate (360 mg) dissolved in methanol (5 ml). The resulting solution was heated at 50° C. for 2 hours. The mixture was evaporated to dryness. Water (30 ml) was added and the pH was adjusted to 5 with dilute hydrochloric acid. The resultant solid was filtered, washed with water and dried under reduced pressure to afford 2-[2-amino-5-[1-(1-tert-butoxycarbonyl-4-piperidyl)pyrazol-4-yl]-3-pyridyl]-1,3-benzoxazole-7-carboxylic acid (320 mg) as yellow solid. NMR Spectrum: (DMSOd6) 1.46 (s, 9H), 1.80 (dd, 1H), 1.85 (dd, 1H), 2.00-2.09 (m, 2H), 2.93 (bs, 2H), 3.98-4.12 (m, 2H), 4.35-4.44 (m, 1H), 7.52 (dd, 1H), 7.63 (bs, 2H), 7.83 (s, 1H), 7.92 (d, 1H), 8.06 (d, 1H), 8.27 (s, 1H), 8.33 (d, 1H), 8.52 (d, 1H); Mass spectrum: M+H+ 505.

A 2M solution of methylamine in methanol (0.535 ml) was added to a mixture of 2-[2-amino-5-[1-(1-tert-butoxycarbonyl-4-piperidyl)pyrazol-4-yl]-3-pyridyl]-1,3-benzoxazole-7-carboxylic acid (270 mg) and bis(dimethylamino)methylene-(triazolo[5,4-b]pyridin-3-yl)oxonium hexafluorophosphate (285 mg) dissolved in DMF (1 ml). The resulting solution was heated at 25° C. for 1 day. A 2N solution of methylamine (0.535 ml) in methanol was added and the mixture was stirred at 25° C. in a sealed tube for 3 days. The mixture was evaporated to dryness and adsorbed on silica gel. The crude product was purified by flash chromatography on silica gel eluting with 20 to 50% ethyl acetate in petroleum ether. The solvent was evaporated to dryness to afford tert-butyl 4-[4-[6-amino-5-[7-(methylcarbamoyl)-1,3-benzoxazol-2-yl]-3-pyridyl]pyrazol-1-yl]piperidine-1-carboxylate (210 mg) as a pale yellow solid. NMR Spectrum: (DMSOd6) 1.43 (s, 9H), 1.80 (dd, 1H), 1.85 (dd, 1H), 2.01-2.11 (m, 2H), 2.94 (bs, 2H), 2.96 (d, 3H), 4.00-4.13 (m, 2H), 4.36-4.46 (m, 1H), 7.51 (dd, 1H), 7.65 (bs, 2H), 7.82 (dd, 1H), 7.93 (s, 1H), 7.98 (dd, 1H), 8.30 (s, 1H), 8.43 (q, 1H), 8.54 (d, 1H), 8.57 (d, 1H); Mass spectrum: M+H+ 518.

EXAMPLE 71

1-[4-[4-[6-amino-5-(1,3-benzoxazol-2-yl)-3-pyridyl]-3-(methoxymethyl)pyrazol-1-yl]-1-piperidyl]-2-dimethylaminoethanone

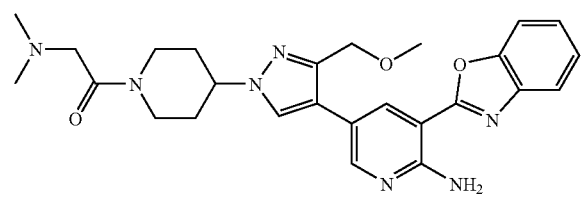

Benzotriazol-1-yl-[bis(dimethylamino)methylene]oxonium tetrafluoroborate (115 mg) was added to a stirred suspension of 3-(1,3-benzoxazol-2-yl)-5-[3-(methoxymethyl)-1-piperidin-4-ylpyrazol-4-yl]pyridin-2-amine] (121 mg), 2-(dimethylamino)acetic acid (32.4 mg) and 4-methylmorpholine (0.066 ml) in NMP (1.5 ml) at 25° C. The mixture was stirred at 25° C. for 5 hours and purified by preparative HPLC using a Waters OBD reverse-phase column (C-18, 5 microns silica, 30 mm diameter, 150 mm length, flow rate of 40 ml/minute) and decreasingly polar mixtures of water (containing 0.2% ammonium carbonate) and acetonitrile as eluent to provide the title compound (101 mg, 69.0%). NMR Spectrum: (DMSOd6) 1.73-1.85 (m, 1H), 1.87-1.98 (m, 1H), 2.04-2.16 (m, 2H), 2.21 (s, 6H), 2.72-2.82 (m, 1H), 3.08 (d, 1H), 3.13-3.22 (m, 2H), 3.41 (s, 3H), 4.15-4.23 (m, 1H), 4.41 (s, 2H), 4.41-4.51 (m, 2H), 7.40-7.48 (m, 2H), 7.66 (bs, 2H), 7.78 (dd, 1H), 7.84 (dd, 1H), 8.23 (s, 1H), 8.43 (d, 1H), 8.50 (d, 1H); Mass spectrum: M+H+ 490.

EXAMPLE 72

2-[4-[4-[6-amino-5-(1,3-benzoxazol-2-yl)-3-pyridyl]-3-(methoxymethyl)pyrazol-1-yl]-1-piperidyl]ethanol

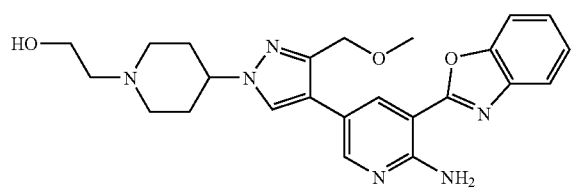

2-Bromoethanol (0.051 ml) was added to a stirred suspension of 3-(1,3-benzoxazol-2-yl)-5-[3-(methoxymethyl)-1-piperidin-4-ylpyrazol-4-yl]pyridin-2-amine] (145 mg) and potassium carbonate (124 mg) in DMF (2 ml) at 100° C. The mixture was stirred at 100° C. for 15 hours. The reaction mixture was then purified by preparative HPLC using a Waters OBD reverse-phase column (C-18, 5 microns silica, 30 mm diameter, 150 mm length, flow rate of 40 ml/minute) and decreasingly polar mixtures of water (containing 0.2% ammonium carbonate) and acetonitrile as eluent to afford the title compound as (90 mg) as a solid.

NMR Spectrum: (DMSOd6) 1.92-2.07 (m, 4H), 2.10-2.20 (m, 2H), 2.44 (t, 2H), 2.95-3.03 (m, 2H), 3.41 (s, 3H), 3.48-3.57 (m, 2H), 4.07-4.17 (m, 1H), 4.40 (s, 2H), 4.42 (bs, 1H), 7.40-7.48 (m, 2H), 7.65 (bs, 2H), 7.78 (dd, 1H), 7.84 (dd, 1H), 8.21 (s, 1H), 8.43 (d, 1H), 8.50 (d, 1H); Mass spectrum: M+H+ 449.

The invention claimed is:
1. A compound of Formula I

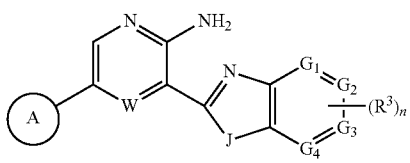

I wherein:
W is N;
n is 0
J is O;
each of $G_1$, $G_2$, $G_3$ and $G_4$ is CH or N provided that not more than two of $G_1$, $G_2$, $G_3$ and $G_4$ represent N;
Ring A is phenyl substituted by $R^1$;
$R^1$ is a group of the formula $Q^1$-$X^2$—;

wherein $X^2$ is a direct bond or is selected from O, SO, $SO_2$, $N(R^7)$, $N[C(O)R^7]$, $N[C(O)N(R^7)_2]$, $N[C(O)OR^7]$, $N[SO_2—N(R^7)_2]$, CO, $CON(R^7)$, $N(R^7)CO$, $SO_2N(R^7)$, $N(R^7)SO_2$, O—$SO_2$, $SO_2$—O, $C(R^7)_2O$, $OC(R^7)_2$, $C(R^7)_2$, $C(R^7)_2N(R^7)$ and $N(R^7)C(R^7)_2$, wherein each $R^7$ is independently hydrogen or (1-8C)alkyl;

and $Q^1$ is heterocyclyl, or heterocyclyl-(1-3C)alkyl, wherein said heterocyclyl or the heterocyclyl within the heterocyclyl-(1-3C)alkyl group is piperazinyl; and $R^3$ is hydrogen;

or a pharmaceutically acceptable salt thereof.

2. A compound according to claim 1, wherein:
n is O
W is N;
J is O;
$G_2$ is N or CH and $G_1$, $G_3$ and $G_4$ are CH;
Ring A is phenyl substituted by $R^1$;
$R^1$ is a group of the formula:

$Q^1$-$Q^2$- wherein $X^2$ is a direct bond or CO;

and $Q^1$ is heterocyclyl, or heterocyclyl-(1-3C)alkyl, wherein said heterocyclyl or the heterocyclyl within the heterocyclyl-(1-3C)alkyl group is piperazinyl; and $R^3$ is hydrogen;

or a pharmaceutically acceptable salt thereof.

3. A compound of Formula I according to claim 2 which is:
3-(1,3-benzoxazol-2-yl)-5 43-(4-methylpiperazin-1-yl) phenyl]pyrazin-2-amine;
3-(1,3-benzoxazol-2-yl)-5-(4-piperazin-1-ylphenyl) pyrazin-2-amine; or
3-(1,3-benzoxazol-2-yl)-5-(3-piperazin-1-ylphenyl) pyrazin-2-amine;

or a pharmaceutically acceptable salt of a foregoing compound.

4. A pharmaceutical composition, which comprises a compound of Formula I, or a pharmaceutically acceptable salt thereof, according to claim 1 in association with a pharmaceutically acceptable diluent or carrier.

* * * * *